(12) United States Patent
Thompson et al.

(10) Patent No.: US 9,222,094 B2
(45) Date of Patent: Dec. 29, 2015

(54) THERMOPHILIC AND THERMOACIDOPHILIC METABOLISM GENES AND ENZYMES FROM ALICYCLOBACILLUS ACIDOCALDARIUS AND RELATED ORGANISMS, METHODS

(71) Applicant: BATTELLE ENERGY ALLIANCE, LLC, Idaho Falls, ID (US)

(72) Inventors: Vicki S Thompson, Idaho Falls, ID (US); William A Apel, Jackson, WY (US); David William Reed, Idaho Falls, ID (US); Brady D Lee, Idaho Falls, ID (US); David N Thompson, Idaho Falls, ID (US); Francisco F Roberto, Highlands Ranch, CO (US); Jeffrey A Lacey, Idaho Falls, ID (US)

(73) Assignee: BATTELLE ENERGY ALLIANCE, LLC, Idaho Falls, ID (US)

( * ) Notice: Subject to any disclaimer, the term of this patent is extended or adjusted under 35 U.S.C. 154(b) by 0 days.

(21) Appl. No.: 14/226,573

(22) Filed: Mar. 26, 2014

(65) Prior Publication Data

US 2014/0227788 A1     Aug. 14, 2014

Related U.S. Application Data

(62) Division of application No. 12/380,551, filed on Feb. 26, 2009, now Pat. No. 8,728,803.

(60) Provisional application No. 61/032,339, filed on Feb. 28, 2008.

(51) Int. Cl.
| | |
|---|---|
| C12N 15/75 | (2006.01) |
| C07H 21/04 | (2006.01) |
| C12N 9/00 | (2006.01) |
| C12N 9/10 | (2006.01) |

(52) U.S. Cl.
CPC *C12N 15/75* (2013.01); *C12N 9/00* (2013.01); *C12N 9/1029* (2013.01)

(58) Field of Classification Search
CPC ........ C12N 15/75; C12N 9/00; C12N 9/1029; C12Q 1/34; C12Q 1/44; C12Q 1/61
See application file for complete search history.

(56) References Cited

U.S. PATENT DOCUMENTS

| | | | |
|---|---|---|---|
| 4,237,226 A | 12/1980 | Grethlein | |
| 4,581,333 A | 4/1986 | Kourilsky et al. | |
| 4,624,922 A | 11/1986 | Horikoshi et al. | |
| 5,098,825 A | 3/1992 | Tchen et al. | |
| 5,882,905 A | 3/1999 | Saha et al. | |
| 5,916,795 A | 6/1999 | Fukunaga et al. | |
| 5,948,667 A | 9/1999 | Cheng et al. | |
| 6,083,733 A | 7/2000 | Gronberg et al. | |
| 6,268,197 B1 | 7/2001 | Schulein et al. | |
| 6,426,211 B1 | 7/2002 | de Buyl et al. | |
| 6,506,585 B2 | 1/2003 | Danielsen et al. | |
| 6,777,212 B2 | 8/2004 | Asakura et al. | |
| 6,833,259 B2 | 12/2004 | Bhosle et al. | |
| 7,727,755 B2 | 6/2010 | Thompson et al. | |
| 7,858,353 B2 | 12/2010 | Thompson et al. | |
| 7,923,234 B2 | 4/2011 | Thompson et al. | |
| 7,960,534 B2 | 6/2011 | Thompson et al. | |
| 8,071,748 B2 | 12/2011 | Thompson et al. | |
| 8,202,716 B2 | 6/2012 | Thompson et al. | |
| 2003/0134395 A1 | 7/2003 | Shetty et al. | |
| 2003/0233674 A1 | 12/2003 | Gabor et al. | |
| 2003/0233675 A1 | 12/2003 | Cao et al. | |
| 2004/0029129 A1 | 2/2004 | Wang et al. | |
| 2005/0112742 A1 | 5/2005 | Thompson et al. | |
| 2006/0105442 A1 | 5/2006 | Wu et al. | |
| 2006/0211083 A1 | 9/2006 | Katzen et al. | |
| 2007/0082381 A1 | 4/2007 | Wilting et al. | |
| 2007/0134778 A1 | 6/2007 | Benning et al. | |
| 2007/0148728 A1 | 6/2007 | Johnson et al. | |
| 2009/0203107 A1 | 8/2009 | Thompson et al. | |
| 2009/0215168 A1 | 8/2009 | Lee et al. | |
| 2009/0221049 A1 | 9/2009 | Shaw, IV et al. | |
| 2009/0226978 A1 | 9/2009 | Thompson et al. | |
| 2009/0253205 A1 | 10/2009 | Thompson et al. | |
| 2009/0263859 A1 | 10/2009 | Thompson et al. | |
| 2009/0269827 A1 | 10/2009 | Thompson et al. | |
| 2010/0203583 A1 | 8/2010 | Thompson et al. | |
| 2010/0311110 A1 | 12/2010 | Thompson et al. | |
| 2011/0081683 A1 | 4/2011 | Thompson et al. | |

(Continued)

FOREIGN PATENT DOCUMENTS

| | | |
|---|---|---|
| DE | 19717893 A1 | 1/1999 |
| WO | 81/00577 A1 | 3/1981 |

(Continued)

OTHER PUBLICATIONS

Gessesse, Amare, "Purification and Properties of Two Thermostable Alkaline Xylanases from an Alkaliphilic *Bacillus* sp.," Applied and Environmental Microbiology, Sep. 1998, pp. 3533-3535.

Glenn et al., "Transformation of Acidiphilium by electroporation and conjugation," Can J Microbiol. May 1992;38 (5):387-93.

Goldstein et al., "The Hydrolysis of Cellulose with Superconcentrated Hydrochloric Acid," Biotechnology and Bioengineering Symp. No. 13, pp. 17-25 (1983).

Grassin et al., "Chapter 2.13, Fruit Juices," (T. Godfrey and S. West, eds.), Industrial Enzymology, 2nd Ed., pp. 227-264 (1996).

Grethlein, H. E., "Pretreatment for enhanced hydrolysis of cellulosic biomass," Biotechnol. Adv. 1984. 2:43-62.

Grethlein, Hans E., "Comparison of the Economics of Acid and Enzymatic Hydrolysis of Newsprint," Biotechnology and Bioengineering, vol. XX, pp. 503-525 (1978).

(Continued)

*Primary Examiner* — Padma V Baskar
(74) *Attorney, Agent, or Firm* — TraskBritt

(57) ABSTRACT

Isolated and/or purified polypeptides and nucleic acid sequences encoding polypeptides from *Alicyclobacillus acidocaldarius* are provided. Further provided are methods for modulating or altering metabolism in a cell using isolated and/or purified polypeptides and nucleic acid sequences from *Alicyclobacillus acidocaldarius*.

8 Claims, 141 Drawing Sheets

(56) References Cited

U.S. PATENT DOCUMENTS

2011/0275135 A1 11/2011 Lee et al.
2012/0015407 A1 1/2012 Thompson et al.

FOREIGN PATENT DOCUMENTS

| WO | 99/06584 A1 | 2/1999 |
|---|---|---|
| WO | 03/068926 A1 | 8/2003 |
| WO | 2005/066339 A1 | 7/2005 |
| WO | 2006/117247 A1 | 11/2006 |

OTHER PUBLICATIONS

Guateli, J. C. et al., 1990, PNAS. USA, 87: 1874-1878.
Hamelinck, CN, G van Hooijdonk, and APC Faaij, 2005, Ethanol from lignocellulosic biomass: techno-economic performance in short-, middle-, and long-term, Biomass Bioenergy, 28:384-410.
Hanselmann, K.W., "Lignochemicals," Experientia 38 (1982) pp. 176-189.
Houghton et al., "Fungal Upgrading of Wheat Straw for Straw-Thermoplastics Production," Applied Biochemistry and Biotechnology, vol. 113-116, 2004, pp. 71-93.
Hulsmann et al., "Maltose and maltodextrin transport in the thermoacidophilic gram-positive bacterium Alicyclobacillus acidocaldarius is mediated by a high-affinity transport system that includes a maltose binding protein tolerant to low pH," J. Bacteriology, Nov. 2000, p. 6292-6301.
Huygen, K. et al., 1996, Nature Medicine, 2(8): 893-898.
Ito et al., "Purification and properties of acid stable xylanases from Aspergillus kawachii," Bioscience Biotechnology and Biochemistry 56 (4):547-550, Apr. 1992.
Jeffries, 1996, Curr. Op. in Biotech., 7:337-342.
Jones et al., "Cloning and transcriptional analysis of the Thermoanaerobacter ethanolicus strain 39E maltose ABC transport system," Extremophiles 2002, 6:291-299.
Keller et al., "Microbial Pretreatment of Biomass: Potential for Reducing the Severity of Thermochemical Biomass Pretreatment," Applied Biochemistry and Biotechnology, vol. 105-108, 2003.
Kenealy et al., "Rapid 2,2'-bicinchoninic-based xylanase assay compatible with high throughput screening," Biotechnology Letters 25: 1619-1623, 2003.
Kievitis, T. et al., 1991, J. Virol. Methods, 35:273-286.
Knappert et al., "Partial Acid Hydrolysis of Cellulosic Materials as a Pretreatment for Enzymatic Hydrolysis," Biotechnolgy and Bioengineering, vol. XXII, pp. 1449-1463 (1980).
Kohler, G. et al., 1975, Nature, 256(5517): 495497.
Kulkarni et al., "Molecular an biotechnological aspects fo xylanases," FEMS Microbiology Reviews 23 (1999) 411-456.
Kwoh, D. Y. et al., 1989, PNAS, USA, 86: 1173-1177.
Lau et al., "PCR ligation mutagenesis in transformable streptococci: application and efficiency," Journal of Microbiolgical Methods 49 (2002) 193-205.
Lauro et al., "Characterization of a β-glycosidase from the thermacidophilic bacterium Alicyclobacillus acidocaldarius," Extremophiles (2006) 10:301-310.
Lauro et al., "Isolation and characterization of a new family 42 beta-glactosidase from the thermoacidaphilic bacterium Alicyclobacillus acidocaldarius: Identification of the active site residues," Biochimica et Biophysica Acta 1784 (2008) 292-301.
Lavarack et al., "The acid hydrolysis of sugarcane begasse hemicellulose to produce xylose, arabinose, glucose and other products," Biomass and Bioenergy 23 (2002) 367-380.
Lee et al., "Oxygen Effects on Thermophilic Microbial Populations in Biofilters Treating Nitric Oxide Containing Off-Gas Streams," Environmental Progress, vol. 20, No. 3, Oct. 2001.
Lin et al., "Purification, Characterization, and Gene Cloning of Thermopsin, a Thermostable Acid Protease from Sulfolobus acidocaldarius," The Journal of Biological Chemistry, 1990, vol. 265, No. 3, pp. 1490-1495.

Liu C, and CE Wyman, 2003, The effect of flow rate of compressed hot water on xylan, lignin, and total mass removal from corn stover, Ind. Eng. Chem. Res., 42:5409-5416.
Lucas et al., C4-Dicarboxylate Transporter/Malic Acid Transport Protein [Alicyclobacillus acidocaldarius LAA1], GenBank Direct Submission, Accession No. EED060659, Dec. 17, 2008 (Retrieved from the Internet Dec. 15, 2009: <URL:http://www.ncbl.nlm.nlh.gov/.
Luckow, V. A., 1993, Baculovirus systems for the expression of human gene products. Curr. Op. Biotechnology 4: 564-572.
Lynd et al., 2002, Micro. and Mol. Biol. Rev., vol. 66, No. 3, p. 506-577.
Lynd, Lee R., "Overview and Evaluation of Fuel Ethanol from Cellulosic Biomass: Technology, Ecnomics, the Environment, and Policy," Annu. Rev. Energy Environ. 1996, 21:403-65.
Mackenzie et al., "Multiple Chromosomes in Bacteria: The Yin and Yang of trp Gene Localization in Rhodobacter sphaeroides 2.4.1," Genetics 153: 525-538 (Oct. 1999).
Malherbe and Cloete, 2002, Re/View in Environmental Science and Bio/Technology, 1: 105-114.
Manchenko, Gennady P., "Handbook of Detection of Enzymes on Electrophoretic Gels," CRC Press, Inc. 1994, pp. 220-240.
Matthews, J. A. et al., 1988, Anal. Biochem., 169: 1-25.
McCoy, Michael, "Chemical Makers Try Biotech Paths," Chemcial Engineering News, Jun. 22, 1998, pp. 13-19.
Merrifield, R. D., 1966, J. Am. Chem. Soc., 88(21): 5051-5052.
Michel et al., "Specificity of the protein secretory apparatus: secretion of the heart-labile enterotoxin B subunit pentamers by different species of Gram bacteria," Gene 152 (1995) pp. 41-45.
Miele, E. A. et al., 1983, J. Mol. Biol., 171: 281-295.
Mielenz, 2001, Curr. Op. in Micro., 4:324-329.
Mosier et al., "Industrial Scale-Up of pH-Controlled Liquid Hot Water Pretreatment of Corn Fiber for Fuel Ethanol Production," Applied Biochemistry and Biotechnology, vol. 125, 2005, pp. 77-97.
Needleman and Wunsch, J. Mol. Biol. 48: 443 (1970).
Ng et al., 1981, Applied and Environmental Microbiology, 41(6):1337-1343.
Ohta et al., "Purification and Characterization of an Acidophilic Xylanase from *Aureobasidium pullulans* var. *melanigenum* and Sequence Analysis of the Encoding Gene," Journal of Bioscience and Bioengineering, vol. 92, No. 3, 262-270, 2001.
Olins, P. O., and Lee, S. C., 1993, Recent advances in heterologous gene expression in *E. coli*. Curr. Op. Biotechnology 4: 520-525.
Ooshima et al., "Simultaneous saccharification and fermentation of cellulose: Effect of ethanol on enzymatic saccharification of cellulose," Department of Applied Chemistry, Faculty of Engineering, Osaka City University, Osaka 558, Japan, Jun. 5, 1984.
Pajunen et al., Microbiology (2005) 151, 1209-1218.
Patel et al., (2006), "Medium and long-term opportunities and risks of the biotechnological production of bulk chemicals from renewable resources: The potential of white biotechnology". The Brew Project. Final Report prepared under the European Commission's GROWTH Programme (DG Research), (publica.fraunhofer.de/eprints/N-48834.pdf).
PCT International Search Report and Written Opinion of the International Searching Authority for PCT/US10/51095, dated Dec. 2, 2010, 11 pages.
Pearson and Lipman, Proc. Natl. Acad. Sci. (U.S.A.) 85: 2444 (1988).
Perlack et al., "Biomass as Feedstock for a Bioenergy and Bioproducts Industry: The Technical Feasibility of a Billion-Ton Annual Supply," USDA and DOE, Apr. 2005, 78 pages.
Peyton et al., "Biotransformation of Toxic Organic and Inorganic Contaminants by Halophilic Bacteria," Halophilic Microorganisms, Antionio Ventosa (Ed.), Springer, 2004, pp. 315-331.
Ragauskas et al., "The Path Forward for Biofuels and Biomaterials," Science, Jan. 27, 2006, vol. 311, pp. 484-4589.
Ramos et al., "Biomechanical and Biochemical Pulping of Sugarcane Bagasse with Ceriporiopsis subvermispora Fungal and Xylanase Pretreatments," J. Agric. Food Chem. 2001, 49, 1180-1186.
Saeman et al., "Quantitative Saccharification of Wood and Cellulose," Industrial and Engineering Chemistry, Jan. 1945, vol. 17, No. 1, pp. 35-37.

(56) References Cited

OTHER PUBLICATIONS

Saha et al., "Dilute Acid Pretreatment, Enzymatic Saccharification, and Fermentation of Rice Hulls to Ethanol," Biotechnol. Prog. 2005, 21, 816-822.
Sanchez-Pescador, R., 1988, J. Clin. Microbiol., 26(10): 1934-1938.
Sa-Pereira et al., "Rapid production of thermostable cellulose-free xylanase by a strain of Bacillus subtilis and its properties," Enzyme and Microbial Technology, 30 (2002) 924-933.
Schafer et al., "X-ray Structures of the Maltose-Maltodextrin-binding Protein of the Thermoacidophilic Bacterium Alicyclobacillus acidocaldarius Provide Insight into Acid Stability of Proteins," J. Mol. Biol. 2004, 335:261-274.
Schäffer, C. et al., 2001, Prokaryotic glycosylation. Proteomics, 1: 248-261.
Scheffel et al., "Functional reconstitution of a maltrose ATP-binding cassette transporter from the thermoacidophilic gram-positive bacterium Alicyclobacillus acidocaldarius," Biochem Biophy Acta, 2004, 1656(1):57-65.
Schell et al., "Dilute-Sulfuric Acid Pretreatment of Corn Stover in Pilot-Scale Reactor," Applied Biochemistry and Biotechnology, vol. 105-108, 2003, pp. 69-85.
Schneider, "Import of solutes by ABC transporters—the maltose system. ABC protein: from bacteria to man," Elsevier Science, London 2003, p. 157-185. [Retrieved from the Internet on Jan. 24, 2010; <http://www2.hu-berlin.de/biologie/baktphys/paper/1_ABC/r.
Schwarz, Wolfgang H., "A list of cellulolytic bacteria," Technische Universitat Munchen, Apr. 24, 2003, 8 pages.
Schwermann, B. et al., 1994, Purification, properties and structural aspects of a thermoacidophilic a-amylase from Alicyclobacillus acidocaldarius ATCC 27009, insight into acidostability of proteins. Eur. J. Biochem. 226: 981-991.
Seffernick et al. "Melamine Deaminase and Atrazine Chlorohydrolase: 98 Percent Identical but Functionally Different" Journal of Bacteriology vol. 183, No. 8, Apr. 2001 pp. 2045-2410 (6 pages).
Shallom et al., "Microbial hemicellulases," Current Opinion in Microbiology, Current Biology Ltd, GB, vol. 6, No. 3, Jun. 1, 2003, pp. 219-228.
Simpson et al., "An extremely Thermostable xylanase from the thermophilic eubacterium Thermotoga," Biochem. J. (1991) 277, 413-417.
Smook, G.A., "Handbook for Pulp & Paper Technologists," Tappi Pr; 2nd Ed. (Jun. 1992) pp. 65-88.
Subramaniyan et al., "Cellulase-free xylanases from Bacillus and other microorganisms," FEMS Microbiology Letters 183 (2000) 1-7.
Sunna et al., "Glycosyl hydrolases from hyperthermophiles," Extremophiles (1997) 12-13.
Techapun et al., "Production of a cellulose-free xylanase from agricultural waste materials by a thermotolerant Streptomyces sp.," Biotechnology Letters 23: 1685-1689, 2001.
Thompson et al., "Comparison of Pretreatment Methods on the Basis of Available Surface Area," Bioresource Technology 39 (1992) 155-163.
Thompson et al., "In Vitro Degradation of Natural Insoluble Lignin in Aqueous Media by the Extracellular Peroxidases of Phanerochaete chrysosporium," 1998 John Wiley & Sons, Inc. pp. 704-717.
Thompson et al., "Measurement of fumonsins in corn with a fiber-optic fluoroimmunosensor," SPIE vol. 2980, (2010) pp. 532-538.
Thompson et al., "Preliminary Investigation of Fungal Bioprocessing of Wheat Straw for Production of Straw-Thermoplastic Composites," Applied Biochemistry and Biotechnology, vol. 105-108, 2003, pp. 423-436.
Thompson et al., "Purification and Characterization of a Novel Thermo-Alkali-Stable Catalase from Thermus brockianus," Biotechnol. Prog. 2003, 19, 1292-1299.
Thompson et al., "Thermoacidophilic Cellulases and Hemicellulases from Alicyclobacillus acidocaldarius," Idaho National Laboratory, 2006, 1 page.
Thompson, et al., "Chapter 31: Changes in the Rate of Enzymatic Hydrolysis and Surface Area Available to Cellulase with Pretreatment Methods," Biotechnology in Pulp and Paper Manufacture: Applications and Fundamental Investigations. Proceedings of the Fourth International Conference on Biotechnology in the Pulp and Paper Industry (ICBPPI), May 16-19, 1989,Raleigh, NC and Myrtle Beach, SC, USA. Kirk, T.K. and Chang, H.M. (eds.). Butterworth-Heinemann, Boston, 1990, pp. 329-338.
Tsao, G.T., "Bacterial Hydrolysis: A Review," Anaerobic Digestion and Carbohydrate Hydrolysis of Waste, Ferrero et al. (eds.), Elsevier Applied Science Publishers, London, 1984, pp. 83-99.
Tsao, GT, MR Ladisch, and HR Bungay, 1987. Biomass Refining, In Advanced Biochemical Engineering, Wiley Interscience, N.Y., 79-101.
Turner et al., "Potential and utilization of thermophiles and thermostable enzymes in biorefining," Microbial Cell Factories, Biomed Central, London, NL, vol. 6, No. 1, Mar. 15, 2007, p. 9.
Uhl et al., "The first description of an archaeal hemicellulase: the xylanase from Thermococcus zilligii strain AN1," Extremophiles (1999) 3:263-267.
Uniprot Direct submission Q9RHZ5_ALIAC, "Putative maltose transport membrane protein malF," Nov. 13, 2007. [Retrieved from the Internet Jan. 22, 2010: <http://www.uniprot.org/uniprot/Q9RHZ5.txt?version=30?].
UniProtKB/TrEMBL Q9JRQ1 [online]. Oct. 1, 2000. Available on the Internet at <<URL://http://www.uniprot.org/uniprot/Q9JRQ1>>.
Upreti et al., 2003, Bacterial glycoproteins: Functions, biosynthesis and applications. Proteomics, 3: 363-379.
Urdea, M. S., 1988, Nucleic Acids Research, II: 4937-4957.
Vieille and Zeikus, 2001, Micro. and Mol. Biol. Rev., vol. 65, No. 1, p. 1-43.
Viikari et al., "Xylanases in bleaching: From an idea to the industry," FEMS Microbiology Reviews 13 (1994) 335-350.
Walker, G. T. et al., 1992, NAR 20: 1691-1696.
Walker, G.T. et al., 1992, PNAS. USA, 89:392-396.
Walseth, Curtis S., Occurrence of Cellulases in Enzyme Preparations from Microorganisms, TAPPI vol. 35, No. 5, May 1952, pp. 228-233.
Ward et al., "Characterization of a new bacteriophage which infects bacteria of the genus *Acidiphilium*," Journal of General Virology (1993) 74: 2419-2425.
Ward et al., "Electrotransformation of Acidophilic, Heterotrophic, Gram-negative Bacteria," Electrotransformation of Bacteria, Natalie Eynard, Justin Teissie (eds.), Springer (2000) pp. 94-103.
Whisstock et al. "Prediction of Protein Function from Protein Sequence and Structure" Quarlty Reviews of Biophysics 36, 3 (2003) pp. 307-340 (35 pages).
Witkowski et al. "Conversion of a β-Ketoacyl Synthase to a Malonyl Decarboxylase by Replacement of the Active-Site Cysteine with Glutamine" American Chemical Society, Biochemistry, vol. 38, No. 36, 1999 pp. 11643-11650 (8 pages).
Wright et al., "Ethanol from Biomass by Enzymatic Hydrolysis," Chemical Engineering Progress, Aug. 1988, pp. 62-74.
Yuan et al., Expression of acidophilic alpha-amylase from Alicyclobacillus acidocaldarius, Sheng Wu Gong Cheng Xue Bao, Jan. 2005, 21(1):78-83. Abstract only.
Database UniProt [Online]. Feb. 10, 2009. XP-002695727. Database accession No. B7DUZ1, 1 page.
Database UniProt [Online]. Feb. 10, 2009. XP-002698982. Database accession No. B7DRM6, 1 page.
Extended Supplementary European Search Report for EP 09 70 3173, dated Apr. 20, 2011, 7 pages.
Extended Supplementary European Search Report for EP 09 82 3952, dated Sep. 20, 2011, 7 pages.
Extended Supplementary European Search Report for EP 09 70 9191, dated Mar. 29, 2012, 6 pages.
Extended Supplementary European Search Report for EP 09 75 5307, dated Apr. 18, 2012, 4 pages.
Extended Supplementary European Search Report for EP 10 74 6882, dated Aug. 27, 2012, 9 pages.
Extended Supplementary European Search Report for EP 09 74 3132, dated Apr. 19, 2013, 4 pages.
Extended Supplementary European Search Report for EP 09 75 5308, dated Jun. 18, 2013, 3 pages.

(56) References Cited

OTHER PUBLICATIONS

International Search Report and Written Opinion of the International Search Authority for PCT/US09/32333, mailed Jun. 19, 2009, 9 pages.
International Search Report of the International Searching Authority for PCT/US06/42566, dated Jul. 25, 2008.
PCT International Search Report and Written Opinion of the International Search Authority for PCT/US11/34852, dated Oct. 21, 2011, 12 pages.
PCT International Search Report and Written Opinion of the International Searching Authority for PCT/US09/00442, dated May 18, 2009, 8 pages.
PCT International Search Report and Written Opinion of the International Searching Authority for PCT/US09/34701, dated Jan. 12, 2010, 10 pages.
PCT International Search Report and Written Opinion of the International Searching Authority for PCT/US09/35275, dated Feb. 25, 2010, 13 pages.
PCT International Search Report and Written Opinion of the International Searching Authority for PCT/US09/35331, dated Feb. 23, 2010, 10 pages.
PCT International Search Report and Written Opinion of the International Search Authority for PCT/US09/35307, dated Jun. 10, 2010, 10 pages.
PCT International Search Report and Written Opinion of the International Search Authority for PCT/US10/25521, dated Jul. 14, 2010, 12 pages.
Supplemental European Search Report for EP 06 82 7231, dated Nov. 12, 2009, 6 pages.
Auerbach et al., "Lactate dehydrogenase from the hyperthermophilic bacterium Thermotoga maritima: the crystal structure at 2.1 Å resolution reveals strategies for intrinsic protein stabilization," Structure (London, England:1993) 1998; 6(6):769-81.
Iwata et al., "T and R states in the crystals of bacterial L-lactate dehydrogenase reveal the mechanism for allosteric control," Nature Structural Biology 1, 176-185 (1994).
Olive et al., "The Crystal and Molecular Structure of Yeast L-Lactate Dehydrogenase (Cytochrome b2)" Int. J. of Peptide Protein Res, 5:219-228 (1973).
Uchikoba et al., "Crystal Structure of Non-Allosteric L-Lactate Dehydrogenase From Lactobacillus pentosus at 2.3 Å Resolution: Specific Interactions at Subunit Interfaces," Proteins: Structure, Function, and Genetics, 46:206-214 (2002).
EC-PDB Database. EC 3.2.1.23 Beta Galactosidase. Hydrolysis of terminal non-reducing beta-D-galactose residues in beta-D-galactosides, www.ebi.ac.uklthornton-srv/databases/cgi-bin/enzymes/GetPage.pl?ec_numbers=3.2.1.23, accessed Jan. 28, 2012.
EC-PDB Database, EC 3.2.1.55 Alpha-N-arabinofuranosidase, Hydrolysis of terminal non-reducing alpha-L-arabinofuranoside residues in alpha-L-arabinosides, www.ebi.ac.uklthornton-srv/databases/cgi-bin/enzymes/GetPage.pl?ec_number=3.2.1.55, accessed Jan. 28, 2012.
EC-PDB Database, EC 3.2.1.21 Beta Glucosidase, Hydrolysis of terminal, non-reducing beta-D-Giucosyl Residues with release of Beta-D-glucose, www.ebi.ac.uklthornton-srv/databases/cgi-bin/enzymes/GetPage.pl?ec_number=3.2.1.21, accessed Jan. 28, 2012.
EC-PDB Database, EC 3.2.1.91 Cellulose 1,4-beta-cellobiosidase (non-reducing end), Hydrolysis of (1>4)-beta-D-glucosidic linkages in cellulose and cellotetraose, releasing cellobiose from the non-reducing ends of the chains, www.ebi.ac.uklthornton-srv/databases/cgi-bin/enzymes/GetPage.pl?ec_number=3.2.1.91, accessed Jan. 28, 2012.
EC-PDB Database, EC 3.2.1.37 Xylan 1,4-beta-xylosidase, Hydrolysis of (1>4)-beta-D-xylans, to remove successive D-xylose residues from teh non-reducing termini, www.ebi.ac.uklthornton-srv/databases/cgi-bin/enzymes/GetPage.pl?ec_number=3.2.1.37, accessed Jan. 28, 2012.
Aden et al., "Lignocellulosic Biomass to Ethanol Process Design and Economics Utilizing Co-Current Dilute Acid Prehydrolysis and Enzymatic Hydrolysis for Corn Stover," NREL/TP-510-32438, National Renewable Energy Laboratory, Golden Colorado. Jun. 2002, pp. 1-88.
Avella et al., "A New Class of Biodegradable Materials: Poly-3-hydroxy-butyrate/Steam Exploded Straw Fiber Composites. I. Thermal and Impact Behaviour," Journal of Applied Polymer Science, vol. 49, 2091-2103 (1993).
Badger, P.C., "Ethanol from cellulose: A general review," In: J. Janick and A. Whipkey (eds.), Trands in new crops and new uses. ASHS Press, Alexandria, VA, 2002, pp. 17-21.
Bailey et al., "Interlaboratory testing of methods for assay of xylanase activity," Journal of Biotechnology, 23 (1992) 257-270.
Barany, F., 1991, PNAS. USA, 88: 189-193.
Bergquist et al., "Molecular diversity of thermophilic cellulolytic and hemicellulolytic bacteria," FEMS Microbiology Ecology 28 (1999) 99-110.
Bertoldo et al., 2004, Eng. Life Sci., 4, No. 6.
Bhatia et al., "Microbial beta-Glucosidases: Cloning, Properties, and Applications," Critical Reviews in Biotechnology, 22(4):375-407, Jan. 1, 2002.
Blast Search of Seq. ID. 36, accessed Apr. 22, 2009, 54 pages.
Blast Search of Seq. ID. 456, accessed Apr. 22, 2009, 48 pages.
Blast Search of Seq. ID. 458, accessed Apr. 22, 2009, 59 pages.
Blast Search of Seq. ID. 460, accessed Apr. 22, 2009, 37 pages.
Blast Search of Seq. ID. 462, accessed Apr. 22, 2009, 35 pages.
Blast Search of Seq. ID. 464, accessed Apr. 22, 2009, 45 pages.
Bork, Peer, "Powers and Pitfalls in Sequence Analysis: The 70% Hurdle," Genome Research, 2000, 10:398-400.
Borman, S., 2006, Glycosylation Engineering. Chem. Eng. News, 84(36): 13-22.
Bowie et al., "Deciphering the Message in Protein Sequences: Tolerance to Amino Acid Substitutions," Science, 1990, 247:1306-1310.
Breves et al., "Genes Encoding Two Different beta-Glucosidases of Thermoanaerobacter brockii Are Clustered in a Common Operon," Applied and Environmental Microbiology, vol. 63, No. 10, Oct. 1997, pp. 3902-3910.
Broun et al. "Catalytic Plasticity of Fatty Acid Modification Enzymes Underlying Chemical Diversity of Plant Lipids" Science vol. 282 Nov. 13, 1998 pp. 1315-1317 (4 pages).
Buckholz, R. G., 1993, Yeast systems for the expression of heterologous gene products. Curr. Op. Biotechnology 4:538-542.
Burg, J. L. et al., 1996, Mol. and Cell. Probes, 10: 257-271.
Chu, B. C. F. et al., 1986, NAR, 14: 5591-5603.
Collins et al., "Xylanaes, Xylanase Families and Extremophilic Xylanses," FEMS Microbiology Review, 2005, pp. 3-23.
Cowling, Ellis B., "Physical and Chemical Constrains in the Hydrolysis of Cellulose and Lignocellulosic Materials," Biotechnol. & Bioeng. Symposium No. 5, 163-181 (1975).
Crout et al., "Glycosidases and glycosyl transferases in glycoside and oligosaccharide synthesis," Current Opinion in Chemical Biology, Current Biology LTD, London, GB, vol. 2, No. 1, Feb. 1, 1998, pp. 98-111.
Dale, M. Clark, "Enzymatic simultaneous saccharification and fermentation (SSF) of biomass to ethanol in a pilot 130 liter multistage continuous reactor separator," Bio-Process Innovation, Inc., W. Lafayette, IN, 2005, 10 pages.
Database EMBL [Online]. Mar. 16, 2007. XP-002627757. Database accession No. ER073884, 1 page.
Database Geneseq [Online]. May 21, 1998. XP-002627734. Database accession No. AAW35004, 1 page.
Database UniProt [Online]. May 1, 1997. XP-002630045. Database accession No. P96090, 1 page.
Database UniProt [Online]. Oct. 1, 2001. XP-002627736. Database accession No. Q97U14, 1 page.
Database UniProt [Online]. Feb. 10, 2009. XP-000002659383. Database accession No. B7DT70, 1 page.
Database UniProt [Online]. Jun. 26, 2007. XP-002627735. Database accession No. A5IKZ4, 1 page.
Database UniProt [Online]. Nov. 3, 2009. XP-002627733. Database accession No. C8WTP2, 1 page.
Database Uniprot [Online]. Nov. 3, 2009. Database accession No. C8WVZ2, 2 pages.

(56) References Cited

OTHER PUBLICATIONS

Database UniProt [Online]. Feb. 10, 2009. XP-002674095. Database accession No. B7DM51, 1 page.
Devos et al. "Practical Limits of Functiona Prediction" Proteins: Structure, Function, and Genetics 41 (2000) pp. 98-107 (10 pages).
Duck, P. et al., 1990, Biotechniques, 9: 142-147.
Eckert et al., "A Thermoacidophilic Endoglucanase (CeIB), etc.," Eur. J. Biochem. 270, 2003, pp. 3593-3602.
Eckert et al., "Gene cloning, sequencing, and characterization of a family 9 endoglucanase (CelA) with an unusual pattern of activity from the theremoacidophile Alicyclobacillus acidocaldarius ATCC27009," Applied Microbiology and Biotechnology, vol. 60, pp. 428-436 (2002).
Eckert, Kelvin, "Dissertation, Cloning and Characterization of two glycosidases from the acidothermophile Alicyclobacillus acidocaldarius ATCC27009," Berlin, Dec. 18, 1971, 113 pages.
Edwards, C. P., and Aruffo, A., 1993, Current applications of COS cell based transient expression systems. Curr. Op. Biotechnology 4: 558-563.
Ehrman, Tina, "Standard Method for Determination of Total Solids in Biomass," Chemical Analysis and Testing Task, Laboratory Analytical Procedure, Oct. 28, 1994, 242 total pages.
EMBL Submission CP001728, Sep. 2009. [Retrieved from the internet: URL:http://www.ebi.ac.uk/Tools/dbfetch/embifetch?style=html&id=CP001728&Submit=Go], 51 pages.
Erlich, H.A., J Clin. Immunol., Nov. 1989; 9(6):437-47.
Fan et al., "The Nature of Lignocellulosics and Their Pretreatments for Enzymatic Hydrolysis," Advances in Biochemical Engineering/Biotechnology, 1982, vol. 23/1982, 157-187.
Flanagan, et al., "Development of gas phase bioreactors for the removal of nitrogen oxides from synthetic flue gas streams," Fuel 81 (2002) 1953-1961.
Fushinobu et al., "Crystallographic and mutational analyses of an extremely acidophilic and acid-stable xylanase: biased distribution of acidic residues and importance of Asp37 for catalysis at low pH," Protein Engineering vol. 11, No. 12, pp. 1121-1128, 1998.
Garrote, G, H Dominguez, and JC Parajo, 2001, Manufacture of xylose-based fermentation media from corncobs by posthydrolysis of autohydrolysis liquors, Appl. Biochem. Biotechnol., 95:195-207.
GenBank: E17054.1 Direct Submission Alicyclobacillus acidocaldarius genomic DNA clone pOP3 containing acyl carrier protein gene. Nov. 5, 2005 [Retrieved from the Internet Jan. 23, 2010: http://www.ncbi.nlm.nih.gov/nuccore/E17054.1?ordinalpos=2 &tool=Entr.
GenBank: AJ252161.1 Alicyclobacillus acidocaldarius maltose/maltodextrine transport gene region(malEFGR genese, cdaA gene and glcA gene), NCBI, Hulsmann, A. http://www.ncbi.nlm.nih.gov/nuccore/AJ252161 (Jan. 6, 2000).

FIG. 1A

```
ref|YP_359514.1|    ---DNFEALLQESRIFEPPAEFKEKAKVADLS----LYEWAERDFLGFWADAAKDIEWFL
ref|YP_516748.1|    MEEKNLEALLEEDRQFIPSEEFHKNALIQSAD----IYEQG--QSLGFWEEQAKQLSWLS
ref|YP_074710.1|    MDSKQFAALLNEDRRFPPPAEFAARANVADES----LYEQAARDREGFWAAQAERLHWFR
ref|YP_144514.1|    -----LESVLKEERVFYPSEEFRKQAHIKSEEEYQRLYEESVRDPEGFWGRVASELHWFE
ref|YP_643635.1|    -------------RTYDPPEEFASRANVRDPG----VYEEAARDYEGFWAERARKLHWFR
RAAC00079           MTPNDLDALLRETRTFAPSEEFRRQANYKDES----IYEEAARDPEGYWAKQAEHITWFH
                                  *  :  *.  **    .*       .         :**    .  :  *:*       *   :  *:

ref|YP_359514.1|    PFEKVLDDSDAPFYRWYTGGKLNVSYNCVDRHTKSFRRNKAALIFEG-EPGDSKILTYQE
ref|YP_516748.1|    PWEKTLEWN-PPFAQWFVGGKLNASANCLDRHLQDWHRNKAAIIFEG-ENGDSQVLTYQD
ref|YP_074710.1|    RWDKVLEWN-PPFAQWFLGGKLNVAYNCLDRHLQTHTRTKAAIIWEG-EPGDERVLTYLD
ref|YP_144514.1|    PWRKVLEGD-LPHPKWFVGGKTNLSYNALDRHVKTWRRNKAAIVWEG-EPGEERVLTYHD
ref|YP_643635.1|    EWDEVLRWD-PPEAQWFVGGKINASYNCLDYQVQQGRGDKRAIIWECDEPGENRTLTYSE
RAAC00079           EFESVCRWD-PPHAQWFIGGKINAAYNCVDRHTLTHRKNKAAIIWEG-EPGDSRVLTYDM
                      :  ..     .    *    :*:  *** *  :  *.:*     :                *  *::.:**  *::.: *** ref|YP_359514.1|    LYREVNKFANVLKKLGVQKGDRVTIYMPMIPEAVIAMLACTRIGAPHSVVFGGFSSQALK
ref|YP_516748.1|    LHREVSKFANVLKANGVNKGDRVTIYLPMIPEAVISMLACARIGAPHSVVFGGFSSEALR
ref|YP_074710.1|    LHREVCRFANVLRQMGVGKGDRVTIYLPMIPEAAIAMLACTRIGAIHSVVFGGFSAGALR
ref|YP_144514.1|    LWREVQRFANVLKRLGVKKGDRVTIYLPMIPEAAIAMLACTRIGAVHSVVFGGFSAGALA
ref|YP_643635.1|    LKAEVEKFANVLKGLGVRKGDAVSIYLPMIPELPIAMLACARIGAPHSVVFGAFSAQSLR
RAAC00079           LRREVDKAAHMLTQLGVKKGDRVTIYLPMVPELPIAMLACAKIGAMHSVVFGGFSAQALK
                      *   **  :   *::*       *  *:::       :::::*   ****.:  :* ref|YP_359514.1|    DRIDDAKAKLLITADGGYRRGSIVELKKNADAALEGETTIEKVVVVKRTGQ----EVPMT
ref|YP_516748.1|    DRVIDAQAKAVITSDGSFRRGNTIPLKDNTDIALDGVDCVEHVFVIQRTKQT--VQ--MK
ref|YP_074710.1|    DRINDSRSKVVVTADGGWRRGNIIRMKQIVNEAVVDCASVEKVIVVKRIGHESLVEHGWH
ref|YP_144514.1|    DRIKDAEAKVLITADGGFRRGGIVPLKQNADEALKDATSVEHVVVVRRTGE----EVPWT
ref|YP_643635.1|    DRINDCEAKVLVTADSGPRGGKRTPLKANADEALEDTPSIEKVVVVRRTGD----EVNMV
RAAC00079           DRILDAGSKLLITADGGWRRGKVIPLKQNADEAVVGTP-IEKVVVVQRIGEA--AQAAMD
                     **:   *.    :*    ::*:*..  *  *        :*    .: *: .          :*:*.*::*        .       :

ref|YP_359514.1|    EGRDYWYHELMADAALYCEP-EQCDAEDMLFILYSSGTTGKPKGIQHTTGGYLVGVHTTF
ref|YP_516748.1|    EERDLWYHEEMAKA-SPVCPAEPMDAEDMLFILYTSGTTGKPKGVVHTTGGYMVGVSTTH
ref|YP_074710.1|    PGRDEWYHTLMRNAPVT-CPVEEMDAEDPLFILYTSGSTGKPKGVLHTTGGYLTQVAATT
ref|YP_144514.1|    PGRDHWWHELMEAAPDRCDP-EPMEAEEPLFILYTSGSTGKPKGVLHTTCGYMTYVYYTT
ref|YP_643635.1|    EGRDLWWHELMREAEPE-CPAEFMDSEDILYILYSSGSTGKPKGIVHTTGGYLTHVNTTT
RAAC00079           PARDVWWHEAMQSAPTKPFPAEPMDAEDYLFLLYTSGTTGKPKGIVHSTGGYLVGVNTSM
                     * * *:*   *  *             *   *  :::*:   *::**:******:  *:****:.   *     :

ref|YP_359514.1|    KYIFDYREEDIYWCTADIGWITGHSYIVYGPLSNGATVVLYEGAPDWPQKDRFWEIIEKY
ref|YP_516748.1|    RWVFDLKEEDVYWCTADVGWITGHSYIVYGPLANGATVLMYEGSPDYPNRDRFWEIVEKY
ref|YP_074710.1|    KYVFDLKDEDVYWCSADIGWITGHSYVIYGPLANGATTLMYEGAPDYPDRGRIWEIIQKY
ref|YP_144514.1|    KLVFDLKDEDVYWCTADIGWVTGHSYIVYGPLLNGATTVMYEGAPNWPEPDRFWEIVDKY
ref|YP_643635.1|    DWVFDLKEDDVYWCTADIGWVTGHSYIVYGPLSNGATALMFEGTPSYPANDRWWDIIERH
RAAC00079           RTVFDLKDEDVFFCTADIGWITGHTYIVYGPLSAGATVVMYEGSPDYPDRDRYWAIVEKY
                     :**   :::*::*:.**:*:***  *** ****       ***.:::**:*.:      .* * *::::

ref|YP_359514.1|    RVNILYTAPTAIRTFMRWGEKWPKGRDLSSLRLLGTVGEPINPEAWIWYHEHIGGGRCPI
ref|YP_516748.1|    KVTILYTAPTAIRTFMKWGPQYPQSRDLSSLRLLGSVGEPINPEAWMWYYKYIGGERCPI
ref|YP_074710.1|    RVNIFYTAPTLIRSFMRWGEGWPGKHRLDSLRLLGTVGEPINPEAWMWYHKHIGGERCPI
ref|YP_144514.1|    GVTVFYTAPTAIRSFMKWGEGWPGKHRLDSLRLLGTVGEPINPEAWLWYYHVIGKGRCPI
ref|YP_643635.1|    GVTILYTAPTAIRAFMKQGPGPIEKHDLSSLRLLGSVGEPINPRAWEWYHFHVCCGRCPV
RAAC00079           GATILYTAPTSIRMFMKWGPQYVEKHDLSTLRLLGSVGEPINPEAWMWYHKYVGQERCPI
                    ..::****  **  **:    *       *  :****   ******:.**  **:.   :*    ***:
```

FIG. 1B

```
ref|YP_359514.1|    VDTWWQTETGMIMITPLPGVIPTKPGSATKPFPGVEADVVNDKGEPVP-PGQGGYLVLKK
ref|YP_516748.1|    VDTWWQTETGMIMMTPLPGITSLKPGSCTVPFPGVRIEVVDSAGHPVP-KGGGGYLAIKE
ref|YP_074710.1|    VDTWWQTETGAIMATPLPGVVHTKPGSTTRPFPGIEMAVVNEEGQEVP-PGAGGYLVVKS
ref|YP_144514.1|    VDTWWQTETGGIMITTLPGAHAMKPGHAGKPFFGVVPEILDGEHRPVENPDEGGHLCITR
ref|YP_643635.1|    VDTWWQTETGGIMISPLPGITRTKPGSATFPLPGIFAGIYDEEGNEIE-GPGVGNLVIKR
RAAC00079           VDTWWQTETGCAMIAPLPGIITTKPGSATKPVPGISVDILDDDGNPVP-PGHGGNLVITK
                    **********  *  :.***      ***    *. *:   : :   . :      *  * :.

ref|YP_359514.1|    PWPAMLRTLYGDPERYKNTYWSKFPG-WYFTGDGAKKDEDGYFWILGRVDDVINVSGHRI
ref|YP_516748.1|    PWPAMLRNIYGDPARFERTYFGNWPG-VYFPGDGAKWDKDGYFWILGRVDDVINVSGHRI
ref|YP_074710.1|    PWPSMLRTVWGDPDRYVSTYFGRFGHQVYFTGDGAKRDEDGYYWIIGRVDDVINVSGHRI
ref|YP_144514.1|    PWPSMLRTVWGDPERFLQQYFSQHPG-VYFSGDGAKRDKDGYYMILGRVDDVLNVAGHRL
ref|YP_643635.1|    PWPGMLRTLYKDPERFRETYWQKYGD-VYFSGDGARRDEDGYFWVTGRVDDVINVSGHRI
RAAC00079           PWPSMLRTVWGDDERFRKTYFEKFEG-IYLPGDGAYRDQDGYYWIVGRLDDVINVSGHRI
                    *** ***. :: *   *:    *:        *:.****  *:***: : **:***:**:***:

ref|YP_359514.1|    GTMEVESALVEHPLVAEAAVIGKSHEVKGQAIAAFVTLKEGVEGTPELVQELKQFVAQKI
ref|YP_516748.1|    GTMEVESALVDHPSVAEAAVIGKNHEVKGQALACFVTLKEGIEITPDLEDELKKHVAKKI
ref|YP_074710.1|    GTMEVESALVDHPLVAEAAVIGRSHAVKGQAITAFVTLKEGRRGTPDLVDELKQHVVTKI
ref|YP_144514.1|    GTMEIESALVAHPAVAEAAVVGRPDPVKGEAIVAFVTLKEGHTPSDALKEELRAHVAKVI
ref|YP_643635.1|    STAEVESALVAHPAVAEAAVIGRYDEDTGQAIVAYVILEGGREGNDELAQELRQQVRKVI
RAAC00079           GTAEVESALVAHPAVAEAAVIGRAHEVKGQAITAFVILKEGHTGSDDLVSELKQFVVEQI
                    .*  *:***  ******:*:    . *:*:...:* *: *    . *  .**:  *     * ref|YP_359514.1|    GALARPDDIFFTAELPKTRSGKIMRRLLRDIAEG--RALGDTTTLTDPAVINKIKEQYKD
ref|YP_516748.1|    GALARPDDIFFTAELPKTRSGKIMRRLLRDIAEG--RAIGDTTTLADASVVNTLKANYQE
ref|YP_074710.1|    GALARPEEIYFAADLPKTRSGKIMRRLLRDIAEG--RALGDTTTLADPNVVAQLRQQYES
ref|YP_144514.1|    GPIARPDEIRFTDALPKTRSGKIMRRLLRQIAAGEKEIKGDTSTLEDRSVVERLK-----
ref|YP_643635.1|    GAHARPQEIIFTPDLPKTRSGKIMRRILRSLSEG-RDDLGDTTTLADPGVVESLKEQ---
RAAC00079           GAMARPEEIIFTADLPKTRSGKIMRRLLRDIAEG-R-VVGDTTTLADPAVVEQLKSQYKD
                    *. ***::* *:    ************:**.:: *        ***:** *  *:   ::

ref|YP_359514.1|    E-
ref|YP_516748.1|    --
ref|YP_074710.1|    QE
ref|YP_144514.1|    --
ref|YP_643635.1|    --
RAAC00079           QE
```

FIG. 2

```
ref|NP_693902.1|      ----------------------------------------------------------------
ref|ZP_01725542.1|    ----------------------------------------------------------------
ref|YP_521150.1|      ----------------------------------------------------------------
ref|ZP_01666741.1|    ----------------------------------------------------------------
gb|ABE97159.1|        ----------------------------------------------------------------
RAAC00455             MRRTASTDPRRPQGLARTKFTSINKRRNRLMQLDMVKAIYDIAVALLLGLAAVGSGVGDG ref|NP_693902.1|      ----KTVEGIARQPELRGALQGTMFIGVALVEAIPIIAAVIAFMVM------
ref|ZP_01725542.1|    ----KTVEGIARQPEARGVLQTTMFIGVALVEALPIIAVVVAFIVM------
ref|YP_521150.1|      ----KTVEGIARQPEAKGALQSTMFIGVGLIEALPLLTWVLALLLMFTK---
ref|ZP_01666741.1|    ----KAIEGMARQPEAKGTILVNMLISVGLIESIPIIAAVIAIVLVF-----
gb|ABE97159.1|        ----RYLSGITRQPEAASQLLTSMFIGIALVEALPIIAVALGIIKLFSIGS-
RAAC00455             MVMSKYVEGVARQPEARGSIFGSALLGVALVEAFPVIALAFGIIILFTKGAF
                        : :.*::****   . :   . ::.:..*:*:*::*::: ...:: :
```

FIG. 3A

```
ref|YP_001127398.1|     --------------------------------LPQQDPQVFATIEQERKRQHAKIELIA
ref|YP_149222.1|        --------------------------------LPQQDPQVFAAIEQERKRQHAKIELIA
ref|NP_244632.1|        --------------------------------LQSKDPKVFEAVQQELGRQRDKIELIA
ref|ZP_00538452.1|      --------------------------------TYLKQQDEELFSAMRKELKRQRDNIELIA
ref|YP_361350.1|        ---------------------------LNLRLKDVDPEIFEAMEKELSRQREKIELIA
RAAC00461               MCAPCSNRKMNVNRGVLSHAALDERSCAGLTTLLQQVDPDVASAMQAELRRQQRNIELIA
                                                    *  . * .: ::. *  : :*** ref|YP_001127398.1|     SENFVSRAVMEAQGSVMTNKYAEGYPGRRYYGGCEYVDVVEDLARERAKQLFGAEHANVQ
ref|YP_149222.1|        SENFVSRAVMEAQGSVLTNKYAEGYPGRRYYGGCEYVDVVEDLARERAKQLFGAEHVNVQ
ref|NP_244632.1|        SENFVSEAVMEAQSSVLTNKYAEGYPGRRYYGGCEYVDIVEDLARDRAKEIFGGEHVNVQ
ref|ZP_00538452.1|      SENFVSQAVMEAQGSVLTNKYAEGYPGRRYYGGCEFVDLAENLARDRAKAIFCAEHVNVQ
ref|YP_361350.1|        SENFVSRAVMEAMGSHLTNKYAEGLPGKRYYGGCEYVDVVENIARERAKKLFGAEHVNVQ
RAAC00461               SENFVSEAVLEALGSVLTNKYAEGYPGRRYYGGCEYVDVVERIAIDRVKELFGAEYANVQ
                        ****.:**  .* :***** :****::*  :* :*.*  :**.*:.*** ref|YP_001127398.1|     PHSGAQANMAVYFTVLKPGDTVLGMNLSHGGHLTHGSPVNFSGVQYNFVEYGVDPETHVI
ref|YP_149222.1|        PHSGAQANMAVYFTVLEHGDTVLGMNLSHGGHLTHGSPVNFSGIQYNFVEYGVDPETHVI
ref|NP_244632.1|        PHSGAQANMAVYFTILEHGDTVLGMNLSHGGHLTHGSPVNFSGIQYNFVEYGVDKESQRI
ref|ZP_00538452.1|      PHSGAQANMAVYFTILNQGDTVLGMNLSHGGHLTHGSPVNFSGVQYNFVEYGVDPETEMI
ref|YP_361350.1|        PHSGAQANMAAYMAFLEPGDTVLGMNLAHGGHLTHGSPVNFSGKLYNFVSYCVEPDTEKI
RAAC00461               PHSGSQANMTVYFSVLKPGDTVLGMNLAHGGHLTHGSPVNFSGQLYKFVSYGVHPETHLI
                        **:**:.*:: .*: ******:***********.   *: .*  .  :. * ref|YP_001127398.1|     DYDDVREKARLHRPKLIVAGASAYPRVIDFAKFREIADEVGAYLMVDMAHIAGLVAAGLH
ref|YP_149222.1|        DYDDVREKARLHRPKLIVAGASAYPRIIDFAKFREIADEVGAYLMVDMAHIAGLVAACVH
ref|NP_244632.1|        DYEEVRRLAKEHQPKMIVAGASAYPREIDFAKTREIADEVGAYLMVDMAHIAGLVAAGLH
ref|ZP_00538452.1|      DYDVVAKLAEEHKPKLIVAGASAYPRVIDFKRFREIADSVGAYLMVDMAHIAGLVAAGLH
ref|YP_361350.1|        NYEKVFELAYKHKPKMIVAGASAYPRVIDFKHLKEIADEVGAYLMVDMAHIAGLVAAGLH
RAAC00461               DYDEVLKVAKEHRPKMIVAGASAYPRVIDFKRMREIADEVGAYLMVDMAHIAGLIAAGLH
                        :*:  *  . *  *::****** *  :::**.************:*:* ref|YP_001127398.1|     PNPVPYAHFVTTTTHKTLRGPRGGMILCQEQFAKQIDKSIFPGIQGGPLMHVIAAKAVAL
ref|YP_149222.1|        PNPVPYAHFVTTTTHKTLRGPRGGMILCQEQFAKQIDKAIFPGIQGGPLMHVIAAKAVAL
ref|NP_244632.1|        QNPVPHSHFVTTTTHKTLRGPRGGMIICNEEFAKQIDKSIFPGIQGGPLMHVIAAKAVAF
ref|ZP_00538452.1|      PNPVEHAHFVTTTTHKTLRGPRGGMILCKEEHAKAIDKSIFPGIQGGPLMHVIAAKAVAF
ref|YP_361350.1|        PSPIPYADVVTTTTHKTLRGPRGGVIFCKAEHAAKIDKTVFPGVQGGPLMHVIAAKAVAF
RAAC00461               PSPVPYAHFVTSTTHKTLRGPRGGFTLCQKDVAKLIDKTNFPGVQGGPLMHVIAAKAVAF
                         .*: ::..**:***********.*:*: : *   ***: ***:******************:

ref|YP_001127398.1|     GEALQDDFKVYAKRIIDNAQRLAAALQKEGFTLVSGGTDNHLLLVDLRPQQLTGKTAEKV
ref|YP_149222.1|        GEALQDDFKVYAKRVVENAKRLAAALQNECFTLISGGTDNHLLLVDLRPQQLTGKTAEKV
ref|NP_244632.1|        GEALQPEFKSYGEAIIRNAKRLGEKLTSEGIDLVSGGTDNELLLLDLRSLGLTGKVAEKA
ref|ZP_00538452.1|      AEEALAPEFKDYIEQVVANAKVLGEELTARGLRIVSGGTDNELLVDLQPLGITGKLAEHA
ref|YP_361350.1|        KEALSPEFREYQQQVVNNAKALAEELKKQGLRLVSGGTDNHLMLVDVRPVGLTGKRAEQL
RAAC00461               GEALKPEFKAYQEQIVKNAKALAEALKGYGFRLVSGGTDNHLMLIDVRSAGLTGKEAERR
                         ***  :*: *  : :: **: *.   *  *: ::*******:*:*:: .  :*** **:

ref|YP_001127398.1|     LDEVGITVNKNTIPYDPESPFVTSGIRIGTAAVTTRGFCLEEMDEIASLIGLVLKNIDNE
ref|YP_149222.1|        LDEVGITVNKNTIPYDPESPFVTSGIRIGTAAVTTRGFGLEEMDFTAATTGLVLKNVGSE
ref|NP_244632.1|        LDDVGITTNKNTIPFDPESPFVTSGIRIGTAAVTSRGLDEEAMDEIGATIALTLKNVDNE
ref|ZP_00538452.1|      LDEAGITVNKNTIPFDPASPFVTSGIRIGTAAMTSRGFKEAEMKQIAELIELVLKNPEDQ
ref|YP_361350.1|        LDEIGVTVNKNAIPYDPESPNVTSGIRIGTPAVTTRGMKEGEMAEIAEIIALVLKNPENE
RAAC00461               LDEIGITVNKNAIPFDPESPMVTSGIRVGTPAATSRGMDEGAMQEIAEIFKLVLLGDFSD
                        **:  *:*.***:**:** ** ******:**.*  *:*.   * :*.  : *.* .  .:
```

FIG. 3B

```
ref|YP_001127398.1|    QALEEARQRVVALTEKFPLY-------
ref|YP_149222.1|       QALEEARQRVAALTEKFPLY-------
ref|NP_244632.1|       EKMNEARERVDALTAKFPMYPNL----
ref|ZP_00538452.1|     ETLTSAHKQVLALTGRFPLYP------
ref|YP_361350.1|       DKHREAARKVRDLLNRFPLYDKLPY--
RAAC00461              EVKREARARVDSLTDRFPLYPTLSYVE
                       :  .*  :*   *  :**:*
```

FIG. 4

```
ref|ZP_01666099.1|    ----------YEFDGGIGIITINRPKALNALNGATMRELNELLDVIAQDPSVKVVIITGS
ref|YP_360429.1|      ----------FEKKDQVGITTTNRPQVLNALNSEVLEELDSLLDKIAEDESITVVILTGA
ref|NP_905294.1|      --------------KDGITTLTINKPETLNALSSEVLSELKSAIAVIATEK-PRVLIITGS
ref|YP_754604.1|      -------------EEKLAVLYINRPKAMNALNKDTLLEIKDAVTAVNDDPAVELLIITGS
ref|YP_384529.1|      ----------RHDDAIAVVSLARPESRNVLSRDLVLGLLSTFTSLKDDGRVKGIVVTGE
RAAC00481             MRNLTETFTTYRVEDHVAVLTLNRPQALNALSR-EVLSEIGAHLAMLDLKDVRVLVIRGE
                                .  :  : :  :*:    *.*.       :              :::  * ref|ZP_01666099.1|    GEKAFVAGADITEMQSMSAIEGRNWGKLGQAVFDKLENLPQPVIAAVNGFALGGGCEIAM
ref|YP_360429.1|      GEKSFVAGADISQMRNFTPRQARYFAKLGQKVLSKLERIPQPVIAAVNGFALGGGCEIAM
ref|NP_905294.1|      G-KAFVAGADIAEMQHLSAAEGKAFGGLGAEVFRRIEELPFPVIAAINGFALGGGCELAM
ref|YP_754604.1|      GDKSFVAGADIAFMQNLSAMEAREFGALGQKVFRLIEAMEKPVIAAVNGFALGGGCELAM
ref|YP_384529.1|      G-KSFCAGADISEMARMSPAEASSFAELGQRLMFAVERVGKPVVAAVNGHAFGGGLELAL
RAAC00481             G-RVFCAGADIGQMQHMSAVEAESMARLGQRVFQAIEQLPIPVIALIHGGAFGGGLELAL
                       *  : * ***** *  ::  ::       . **   ::  :* :  **:*  ::*.:*** *:*:

ref|ZP_01666099.1|    ACDIRIASDKAKFGQPEVTLGITPGFAGTQRLPRLVCKGRAKELLFTGDMIDAAEAYRIG
ref|YP_360429.1|      ACDFRIASTKAKFGQPEVGLGVTAGFGGTQRLPRLVGKGMAAELLYTGEMIDAQEALRIG
ref|NP_905294.1|      ACDIRIASAKAKFGQPEVGLGITPGFSGTQRLPRLVAPGIAKELIYTGRIIDAEEALRIG
ref|YP_754604.1|      CCDFRIAASNAKFGQPEVGLGITPGFCGTQRLPRLVGPGMAKQLLYIADVINADEAFRIG
ref|YP_384529.1|      ACDFIVAAESAVFAAPEVLLGVMPGFGGTQRLPRLIGKSRAKEMIFTGERINAAKAHSIG
RAAC00481             ACDFRIAAAGAVVGLPEVTLGVNPSFGGTYRLPRAIGFARALSMMLLGERIPVFKALEYG
                      .**: :*:    *  .. * : ..*. **  :.  .  ::.   * . :*        * ref|ZP_01666099.1|    LVNKVVPPEELMAAAKAMAQKIMSRAPMAVQLCKAAVNEGMDMDLQSAVAYEAEVFGLCF
ref|YP_360429.1|      LVNRVVEPEELMPTALEIAQKIAAKAKLAVFYSKAALNEGLNMDLERALAYEAEMFALCF
ref|NP_905294.1|      LVNRVTTPEELLPATMETAQLIASRSASAVSASKEAINRGTEMHIAEGIALEQNLFGLCF
ref|YP_754604.1|      LVNKVVQPEELLPEVKKIAGRILSKGQLAVRLSKAAANEGMQTDIDRAMSIEADAFGLCF
ref|YP_384529.1|      LVNRVVSDERLLAETVSLVKNICNRGLLSLRVAKEVIDAGAGIDLATACLMERDAFALCF
RAAC00481             LVNEVVAPDELEARGMDLARKLASQSSAAMAAIKRSAHHGFGQDPARAQAYEAAQFGLCF
                      ***.*.  ..:.*        . : :.   ::  *    .*   *     *. *** ref|ZP_01666099.1|    ATADQKEGMAAFVEKRKANF---
ref|YP_360429.1|      TTSDQKEGMDAFLNKRKPEF---
ref|NP_905294.1|      ATADQKEGMAAFLEKRKPAF---
ref|YP_754604.1|      ATQDQKEGMTAFLEKRKANF---
ref|YP_384529.1|      STDDQKEGMRAFMEKREPRF---
RAAC00481             ASGDAHEGMAAFKEKRQARFHED
                      :: * :*** **  :**:.  *
```

FIG. 5

```
ref|YP_146903.1|         ---------RRDLHQIPELGFQEFKTQQYLLRYIQSLPQERLQVRTWKTGIFVKVNGTSP
ref|YP_001125035.1|      ---------RRDLHKIPELGFQEFKTQQYLLNYIQSLPQERLDVRTWKTGIFVKVSGTAP
ref|YP_001646604.1|      -------QVRRDLHKIPEIGFKEWKTQQYILDYIGTLPNEYLEVKTWKTGVIVKVNGKNP
ref|YP_001375911.1|      -------QIRRDLHQIPELGFQEWKTQQYILNYIETLPNEHIEVKTWKTGVIVKVKGKNP
ref|ZP_01696300.1|       -METNLIAIRRDLHRIPELGYKEHKTQRYILDFISRLPKGHLEVKTWKTGVLVKVKGTCP
RAAC00529                MMEWDVYEARRALHQIPKPGFREFETQKLVLSYLQALPQEHLEIRTWETGVIALVKGHSP
                                     :*** *::* :**: :* :: : :::::**::.*.* * ref|YP_146903.1|         RKTIGYRADMDGLPIREETGLPYRSKHEGRMHACGHDVHMSIALGVLTHFAHHPLKDDLL
ref|YP_001125035.1|      RKTIGYRADIDGLPISEETGLPYRSEHAGQMHACGHDVHMSIALGVLTHFAHNPIRDDLL
ref|YP_001646604.1|      EKIIGYRADIDGLPITEETGYEYSSVHEGMMHACGHDLHATIGLGLLTAAVSERIDDDLV
ref|YP_001375911.1|      VKTIGYRADMDGLPIVEETGYEFASTHEGMMHACGHDFHTTIGLGLLTATVNDRIDDDLV
ref|ZP_01696300.1|       EKKIGYRTDIDGLPIKEETGFPFQSEHEGNMHACGHDFHMTIALGILSHFASRPVKDDLI
RAAC00529                KRRVGWRADMDGLPVAEETGVPYASRHPGMMHACCHDVHMAVALGLAQHFAHNPPPDDLV
                          : :*:*:*:****: **** : * * ******.* ::.**:    .   ***:

ref|YP_146903.1|         FVFQPAEEGPGGAKPMLESDIMREWKPDIIVALHIAPEYPVGTIATKEGLLFANTSELFI
ref|YP_001125035.1|      FIFQPAEEGPGGAKPMLESDIMREWKPDMIVALHIAPEYPVGTIATKEGLLFANTSELFI
ref|YP_001646604.1|      FIFQPAEEGPGGALPMLESDELKEWKPNMILGLHIAPEYSVGTIATKEGLLFANTSELYV
ref|YP_001375911.1|      FLFQPAEEGPGGALPMLESEELKEWKPNMILGLHIAPEYPVGTIATKEGLLFANTSELYI
ref|ZP_01696300.1|       FIFQPAEEGPGGAKMLEEVLHDEWQPDLVMALHVAPEYPACTVAVKKGLLFANTSELYI
RAAC00529                LVFQPAEEGPGGAQPMLASFAFQAVRPEMIFALHVQPDMAVGEIGIRPGVLFANTSELFI
                         ::**********  .**  .    :*::..**: *: ..* :. : *:*********::

ref|YP_146903.1|         DLKGKGGHAAFPHLANDMVVAACALVTQLQSIVARNVDPLDSAVITIGKIAGGTVQNVIA
ref|YP_001125035.1|      DLKGKGGHAAFPHLANDMVVAACALVTQLQSIVARNVDPLDSAVITIGKITSGTVQNVIA
ref|YP_001646604.1|      DLKGKGGHAAYPHTANDMIVAASHLVTQLQSVISRNVNPLDSAVITIGKITGGTVQNIIA
ref|YP_001375911.1|      DLKGKGGHAAYPHMANDMIVAASHLVTQLQSVISRNVNPLDSAVITIGKITGGTVQNIIA
ref|ZP_01696300.1|       DLEGKGGHAAYPQHTKDMVVAAAHLVTQLQSIISRNIDPLDSAVVTIGKITGGTVQNAIA
RAAC00529                HLVGQGGHAAYPHRANDMVVAGAHLVTALQTIVARNVDPLDSAVITVGRLESGTKMNIIA
                         .* *:*****:*:  :::.. *  :::::***:*:*:: .**  * ** ref|YP_146903.1|         EHARLEGTIRTLSTAAMQKVKRRIEAIVHGIEVAYECEASIDYGAMYHEVYNDPDLTAEF
ref|YP_001125035.1|      EHARLEGTIRTLSIDAMQAVKRRIEALVRGVEVAYECEAVIDYGAMYHEVYNNPALTTEF
ref|YP_001646604.1|      EKSRLEGTIRTLSVESMKRVKSRIEAIVGIEAAFQCEAVIDYGAMYHQVYNHEALTKEF
ref|YP_001375911.1|      EKSRLEGTIRTLSVESMKRVKDRIEAIVAGTEAAFQCEAVIDYGAMYHQVYNHEALTKEF
ref|ZP_01696300.1|       EHARLEGTIRTLSSEAMEKVKHRIEALTNGLSAGFECRAEIDYGCNYYQVFNHPEETARF
RAAC00529                ERARLEGTVRALNAATMPRLKNRIEAVVAGIERMFNCQAFIDYGANYYQVYNDERLTRGF
                         *::*****:*:*.  :*  :* ****:. *:.   ::*.* ****. *::*:*.   * * ref|YP_146903.1|         MKFAKAHGGVNVIRCKEAMTGEDFGYMLADIPGFMFWLGVASPYGLHHAKLAPNEEAIDR
ref|YP_001125035.1|      IQFAETHTDMNVIRCKEAMTGEDFGYMLAEIPGFMFWLGVDSPYGLHHAKLVPNEAAIDR
ref|YP_001646604.1|      MQFTREQTTMDVITCTEAMTGEDFGYMLREIPGFMFWLGVNSEYGLHHAKLKPDEEVIEK
ref|YP_001375911.1|      MEFASKDTNMNVVTCKEAMTGEDFGYMLRDIPGFMFWLGVDSEYGLHHAKLKPNEAAIDR
ref|ZP_01696300.1|       MDFVRSYEGAHLECREALTGEDFGYMLKEIPGFMFWLGVGSPYGLHHAKFAPDERALET
RAAC00529                MQFVEEAGLADVHEVPPAMTGEDFYFLREIPGFLFWLGAATPYGLHHEAKMLPDERCIDV
                         ::.*.    .:     *:*****:* :****:****. : ******: *:*    ::

ref|YP_146903.1|         AIAFLIDYFS------
ref|YP_001125035.1|      AIAFLISYFS------
ref|YP_001646604.1|      AIVFLNQY--------
ref|YP_001375911.1|      AIEFLNQY--------
ref|ZP_01696300.1|       AADLMIAY--------
RAAC00529                ALRVLIPYFAERRYEA
                         *  .: *
```

FIG. 6

```
ref|NP_846569.1|        -------MKQVQTKRD----WKKLAYDVVEEKMITKEDAIAILEADDTEVLEIMNAAYII
ref|ZP_00238879.1|      -------MKQVQTKRD----WKKLAYDVVEEKMITKEDATAILEADETEVLEIMNAAYII
ref|YP_896466.1|        -------MKQVQTKRD----WKKLAYDVVEEKMIAKEDAIAILEAEDTEVLEIMNAAYII
ref|YP_001376041.1|     -------MKQIQTKVD----WKKIAFEGIEGKRITKEDALAILEADDTEVLEIMNAAYMI
dbj|BAB39458.1|         -------GLETLVKKD----WKMLAENVIKGYKVTAEEALAIVQAPDNEVLEILNAAFLI
RAAC00552               ----MHEGALTMMKIDYQTNWIDLARRVLDGRGVTREEALDILRSSDDELLDLLAAAFLI
                                *  *    :*    :.    :: *:*: *:.: :  *:*:::  **::* ref|NP_846569.1|        RHHYFGKKVKLNMIINTKSGLCPEDCGYCSQSIISEAPIDKYAWLTQEKIVEGAHEAIRR
ref|ZP_00238879.1|      RHHHFGKKVKLNMIINTKSGLCPEDCGYCSQSIISEAPIDKYAWLTQEKIVEGAHEAIRR
ref|YP_896466.1|        RHHYFGKKVKLNMIINTKSGLCPEDCGYCSQSIISEAPIDKYAWLTQEKIVEGAHEAIRR
ref|YP_001376041.1|     RHHYFGKKVKLNMIINTKSGLCPEDCGYCSQSIVSEAPIDKYAWLTQEKIVEGAHEAVRR
dbj|BAB39458.1|         RQHYYGKKVKLNMIINTKSGLCPEDCGYCSQSIVSEAPIDKYAWLTKEKIVEGAQESIRR
RAAC00552               RRRYFGKKVKLNMIINAKSKMCPEDCAYCSQSAISKAPVSKYPLVSKEEIIAGAREAERR
                        *:::*********:**.:****.***** :*:**:.**. :::*:*: **:*: **

ref|NP_846569.1|        KAGTYCIVASGRRPTDKEVNHVIGAVKEIRETTDLKICCCLGFLNEDQAGRLAEAGVHRY
ref|ZP_00238879.1|      KAGTYCIVASGRRPTDKEVNHVIGAVKEIRETTDLKICCCLGFLNEDQAGRLAEAGVHRY
ref|YP_896466.1|        KAGTYCIVASGRRPTDKEVNHVIGAVKEIRETTDLKICCCLGFLNEDQAGRLAEAGVHRY
ref|YP_001376041.1|     KAGTYCIVASGRRPTDKEVNHVIGAVKEIKETTDLKICCCLGFLNEDQAKRLAEAGVHRY
dbj|BAB39458.1|         KAGTYCIVASGRRPTNREIDHVIFAVKEIRETTDLKICCCLGFLNETHASKLAEAGVHRY
RAAC00552               KAGTYCIVISGRRPSDREIERIAEAVEEIRATTTLKICCCLGLLTPAQADRLARAGVHRY
                        ****** ***:::*::::  ::  ******:*.  :*  :.**** ref|NP_846569.1|        NHNLNTHANNYESICSTHTYDDRVDTVQKAKQAGISPCSGAIFGMGETIEERAEIAFELQ
ref|ZP_00238879.1|      NHNLNTHANNYESICSTHTYDDRVDTVQKAKQAGISPCSGAIFGMGETIEERAEIAFELQ
ref|YP_896466.1|        NHNLNTHANNYENICSTHTYDDRVDTVQKAKQAGISPCSGAIFGMGETIEERAEIAFELQ
ref|YP_001376041.1|     NHNLNTHANHYDNICSTHTYDDRVDTVEKVKQAGISPCSGAIFGMGETKEERVEIAFELQ
dbj|BAB39458.1|         KHNLNTSQDNYKNITSTHTYEDRVDTVEAVKEAGMSPCSGAIFGMNESNEEAVEIALSLR
RAAC00552               NHNLNTSRDRYGDICTTHTYDDRVRTLEHVKEAGISPCSGVIFGMGESDEEAVDMAFALK
                        :***** :.* .* :****:*** *:: .*:**:*****.****.*: **  .::*: *:

ref|NP_846569.1|        RIDADSIPCNFLVAVKGTPLEGQKELTPVECLKVLAMMRFVNPTKEIRISGGREINLRSV
ref|ZP_00238879.1|      RIDADSIPCNFLVAVKGTPLEGQKELTPVECLKVLAMMRFVNPTKEIRISGGREINLRSV
ref|YP_896466.1|        RIDADSIPCNFLVAVKGTPLEGQKELTPVECLKVLAMMRFVNPTKEIRISGGREINLRSV
ref|YP_001376041.1|     RLDADSIPCNFLVSVKGTPFEGRKELTPVECLKILAMMRFVNPSKEIRISGGRELNLRSV
dbj|BAB39458.1|         SLDADSIPCNFLNAIDGTPLEGTSELTPTKCLKLISMMRFVNPSKEIRLAGGREVNLRSM
RAAC00552               EMDADSIPCNFLNPIPGTPLEGMETLNPRRCLKLLCMMRFVNPSKEIRIAGGRERNLRSL
                        :**********  .: ***:**  . *.* .***::.******:****:.**** ****:

ref|NP_846569.1|        QPIGLFAANSIFVGDYLTTAGQEPTADWGMIEDLGFEIEECAL
ref|ZP_00238879.1|      QPIGLFAANSIFVGDYLTTAGQEPTADWGMIEDLGFEIEECAL
ref|YP_896466.1|        QPIGLFAANSIFVGDYLTTAGQEPTADWGMIEDLGFEIEECAL
ref|YP_001376041.1|     QPLGLFAANSIFVGDYLTTVGQESTADWEMIQDLGFEIEECAL
dbj|BAB39458.1|         QPMALYAANSIFVGDYLTTAGQEPTADWGTIEDLGFEIEECAL
RAAC00552               QVLGLYPANSIFVGDYLTTPGQAPTEDWAMIEDIGFEIEECAL
                        *  :.*:.*********** **  * ** :*:**********
```

FIG. 7

```
ref|NP_833836.1|         ------------------MSGFFITATDTEVGKTVVAGAIAGVFRELGYNVGVYKPLQS
ref|ZP_00739346.1|       ------------------MSGFFITATDTEVGKTVVAGAIAGVFRELGYNVGVYKPLQS
ref|YP_085454.1|         ------------------MSGFFITATDTEVGKTVVAGALAGVFRELGYNIGVYKPLQS
ref|YP_001646745.1|      ------------------MSGFFITATDTEVGKTVVTGALAGIFRERGHNVGVYKPLQS
ref|YP_001376045.1|      ------------------MSGFFITATDTEVGKTVVTGAIAGGLRKLGHHIGVYKPLQS
RAAC00553                METISVSGRWRNLLHGRRTMKGLFITATDTEVGKTWVTGVLACALRHRGYDVGVCKPIQS
                                           *.*:***********  *:*.:*    :*. *::** **:**

ref|NP_833836.1|         GHVASNPEGDAARLKSLSGVPTQENEICPYSIEEPLAPRLAMKRAGRVVKLKEITDYYNG
ref|ZP_00739346.1|       GHVASNPEGDAARLKVLSGVPTQENEICPYSIEEPLAPRLAMKRAGRVVKLKEITDYYNE
ref|YP_085454.1|         GHVASNPEGDAARLKALSGVPTKEDEICPYSIEEPLAPRLAMKRAGRTVTLKDIIHHYNE
ref|YP_001646745.1|      GHVASNPEGDAARLKALSGVPTKEDEICPYSIEEPLAPRLAMKRAGRTVMLKEITAHYNE
ref|YP_001376045.1|      GHSASHPEGDAARLKMASGVETAVDKICPYSVEEPLAPRLAMQRAGRTVTLADITSYYNE
RAAC00553                GNHLDDPEGDAAKLKRLAGVSDSVSDICLCALPHPVAPQLALKLSGLDLFLDHVLSFVGQ
                         *:  ..******:** :**    ..**    ::  .*:**:**:: :*   : * .:  ..

ref|NP_833836.1|         LLKEFNSLFVEGAGGLAVPYTEDALVIDFAKELQLPLIVVARFTLGTVNHTVLTIAYAKA
ref|ZP_00739346.1|       LLKEFNSLFVEGAGGLAVPYTEDALVIDFAKELQLPLIVVARFTLGTVNHTVLTIAYAKA
ref|YP_085454.1|         RLKEFNSLFVEGAGGLAVPYTEDALVIDFAKELQLPLIVVARFTLGTVNHTVLTIAYAKA
ref|YP_001646745.1|      LLKEFNSLLVEGAGGLAVPYTEDALVIDFAKELQLPLIVVARFTLGTVNHTVLTISYAKA
ref|YP_001376045.1|      LMAEFDSLLVEGAGGLAVPYTEDALVVDFAKQLKLPLIIVARPTLGTVNHTVLTISYAKA
RAAC00553                AAKRHEWVFVEGAGGVAVPYLSDAWLVDVIQALNFPVLLVARAGLGTINHTILSIEYLNR
                          ..: ::******:**** .** ::*. : *::*:::***. ***:***:*:* * :

ref|NP_833836.1|         HGLTVAGVIL---------SGCKECEMERVQE--------------NKE----------
ref|ZP_00739346.1|       HGLTVAGVIL---------SGCKECEMERVQE--------------NKE----------
ref|YP_085454.1|         HGLTVAGVIL---------SGCKECEMERVQE--------------NKV----------
ref|YP_001646745.1|      HGLTVAGVIL---------SGCKECEKERVQE--------------NKE----------
ref|YP_001376045.1|      KGLQVAGVIL---------SGCKEDEKERVQE----------NKK-------------
RAAC00553                RGIRVLGVVLN--------RGSDTYADDAPDKQ--------ISFLLERTN-------SD
                         :*: * **:*         *..        :  ::

ref|NP_833836.1|         MIEELSGVPVLGLLPFFAGEFTKEEVLESAKEHI-----------------
ref|ZP_00739346.1|       MIEELSGVPVLGLLPFEGEFTKEEVLESAKEYI------------------
ref|YP_085454.1|         MIEELSGVPVLGLLPFFEGEFTKKEVLESAKEYI-----------------
ref|YP_001646745.1|      MIEELSGVPVLGLLPFLEGEFTKEELLESVKEHI-----------------
ref|YP_001376045.1|      MIEELSDVPVFGLFPKIREEYTRDELIKAAEESIQI---------------
RAAC00553                YIREATGVPVFGVLPNMSSCTVELEIVNAVEQNIDVLGIAKSMNAIYERPNV
                         *.* :.***:*:*   :       ..  *:::: :: *
```

FIG. 8

```
sp|P22806|BIOF_BACSH      ------------MNDRFRRELQVIEEQGLTRKLRL-FSTG-NESEVVMNGKKFLLFSSNN
dbj|BAB39457.1|           ------------------ELEKIKEGGLYRQLQT-VETMSDQGYAMVNGKKMMMFASNN
ref|NP_390900.1|          ----------------LNERLDRMKEAGVHRNLRS--MDGAPVPERNIDGENQTVWSSNN
ref|ZP_01667656.1|        ---------------VTEALAEIKRHGLYRQIPD--YDPVDAHVVEDGRRYLMLASNN
ref|YP_147981.1|          ------------MKTELTVKLHEWEQKAQKRQLRR---AEASGATVILNGKPMLNLASNN
RAAC00554                 ---------MLKSLESRIVNELFDLREAGRHRSLHS---TVVRGARMWLESKEVLHFSSND
                                             *   ..  *.:           :..       :**:

sp|P22806|BIOF_BACSH      YLGLATDSRLKKKATEGISKYGTGAGGSRLTTGNFDIHEQLESEIADFKKTEAAIVFSSG
dbj|BAB39457.1|           YLGIANDQRLIEASVQATQRFGTGSTGSRLTTGNTIVIIEKLEKRLAEFKQTDAAIVLNTG
ref|NP_390900.1|          YLGLASDRRLIDAAQTALQQFGTGSSCSRLTTGNSVWHEKLEKKIASFKLTEAALLFSSG
ref|ZP_01667656.1|        YLGLTHDPAVREAAAAAALRYGAGSGAARLTTGSHPLFAELERELAAFKGTEAALVFNTG
ref|YP_147981.1|          YLGLADDRRLIEAGCEAMRAYGAGAGASRLVVGNHPLYERAEAALKQWKKAEAALIFNSG
RAAC00554                 YLALSFDHRVREAAQAASHEYGAGATGSRLISGNHPEIEGLEAELASWHGAEASLVFSSG
                          **.::  *    :   .    :*:*:.:**   *.       *   :  ::  ::::..:* sp|P22806|BIOF_BACSH      YLANVGVISSVMKAGDTIFSDAWNHASIIDGCRLSKAKTIVYEHADMVDLERKLRQSHGD
dbj|BAB39457.1|           YMANIAALTTLVGSDDLILSDEMNHASIIDGCRLSRAETIIYRHADLLDLEMKLQINTRY
ref|NP_390900.1|          YLANVGVLSSLPEKEDVILSDQLNHASMIDGCRLSKADTVVYRHIDMNDLENKLNETQRY
ref|ZP_01667656.1|        YMANVGIISALAGPGDVIFSDELNHASIIDGCRLARAKVVVYRHADAGHLAECLATTPCA
ref|YP_147981.1|          YTANIGVLTALIGRDDLVFSDKLNHASLIDGIRLSKAACFRYRHIDIDQLESLLKQSPPA
RAAC00554                 YAANVGVLSALVRSDDVVFSDELNHASLIDGCRMTRARVVVYRHADVQHLEQLMRETPCR
                          *  **:. ::::      *  ::**  ****:***  *:::*    . *.*  .*    :   .

sp|P22806|BIOF_BACSH      GLKFIVTDGVFSMDCGIAPLPKIVELAKFYKAYIMTDDAHATGVLGNDGCGTADYFGLKD
dbj|BAB39457.1|           RKRIIVTDGVFSMDGDIAPLPGIVELAKRYDALVMVDDAHATGVLGKDGRGTSEHFGLKG
ref|NP_390900.1|          QRRFIVTDGVFSMDCTIAPLDQIISLAKRYHAFVMVDDAHATGVLGDSGQGTSEYFGV--
ref|ZP_01667656.1|        GRRLIVTDGVFSMDGDIAPLDQIVPLAEQYDALVMVDDAHATGVIGPGGRGTTAYFGLKK
ref|YP_147981.1|          KRKWIVTDAVFSMDGDMAPLEELVELKRRYRAVLLVDEAHSGCVFGPNGEGLLHHFGLEK
RAAC00554                 GQRFVVSDAVFSMDGDIAPIAELIETARLFFAVVILDDAHGVGMLGRRGAGTLENFGIVN
                           : :*:*.******  :**:     ::    . .:    * :::*:**. *::* *    *   **:

sp|P22806|BIOF_BACSH      EIDFT-VGTLSKAIGAEGGFVSTSSIAKNYLLNNARSFIFQTALSPSAIEAAREGISIIQ
dbj|BAB39457.1|           KIDI-EMGTLSKAVGAEGGYIAGSRSLVDYVLNRARPFVFSTALSAGVVASALTAVDIIQ
ref|NP_390900.1|          CPDIV-IGTLSKAVGAEGGFAAGSAVFIDFLLNHARTFIFQTAIPPASCAAAHEAFNIIE
ref|ZP_01667656.1|        RVHI-EMGTLSKALAAEGGYVAGRRELIDYLVNKARSFIFSTALAPATVAAATAALRELA
ref|YP_147981.1|          EEDVIALGTFSKALGSFGAYVTGEPWLVDYLTNSARSLTFTTALPPSVLAANEAAIHIVQ
RAAC00554                 VDDIVYIGTLSKALGAEGGYVAGRKILIEYLVNRARSFIFSTGLSPMVASSARKARSIAE
                           ..  :**:***:.: *.: :      ::::* **.::*  *.:..          .

sp|P22806|BIOF_BACSH      N----EPERRKQLLKNAQYLRLKLEESGFVMKEGETPIISLIIGGSHEAMQFSAKLLDEG
dbj|BAB39457.1|           S----EPERRVRTRAMSQRLYNELTSLGYTVSGGETPILAIICGEPEQAMFLSKELHKHG
ref|NP_390900.1|          A----SREKRQLLFSYISMIRTSLKNMGYVVKGDHTPIIPVVIGDAHKTVLFAEKLQGKG
ref|ZP_01667656.1|        A----RPALVATLQANARYLRDRINEAGFNVASSVTATIPVIVGEADAAVAMARSLKEAG
ref|YP_147981.1|          A----EPKRRERLHALSERFRTKLKRLGFDTGGSETPIVPVIVGPNDRAVAMSEQLQEAG
RAAC00554                 L----EDWRRQKVLSLSSALRTSLQQLGYVVRGGETPIVPVIVGDEHSSLTISRHLMSYG
                                    :        *:      . *.*:. ::  *   :: ::      *     * sp|P22806|BIOF_BACSH      VFIPAIRPPTVPKGSSRLRITVMATHTIEQLDMVISKIK------
dbj|BAB39457.1|           IYAPAIRSPTVPLGTSRIRLTLMATHQEEQMNHVIDVFR------
ref|NP_390900.1|          IYAPAIRPPTVAPGESRIRITITSDHSMGDI--------------
ref|ZP_01667656.1|        LIVSAIRPPTVPPGTCRLRLTVSAAHSREDL--------------
ref|YP_147981.1|          IAAVAIRPPTVPEGTARIRFSITAAMTEEDIDMAVDCI-------
RAAC00554                 IYVPAIRPPSVPEGKCRLRFSLTAAHEMTDVRLVIDVLKDWKPSR
                          :   ***.*:*.   * .*:*:::  :         ::
```

FIG. 9

```
ref|YP_001126681.1|        ------IFLNGEFVTKENAKISVYDHGFLYGDGVFEGIRVYSGNVFRLEEHIDRLYNSAK
ref|YP_148515.1|           ------IFLNGEFVTKENAKISVYDHGFLYGDGVFEGIRVYSGNVFRLEEHIDRLYNSAK
ref|ZP_01171798.1|         ------IFLNGEFVTKENAKISVYDHGFLYGDGIFEGIRVYSGNIFRMKEHMDRLYRSAK
ref|YP_080106.1|           ------IFLNDKLVKKEDAKISVYDHGFLYGDGVFEGTRVYDGNIFRMQEHMDRLYDSAR
ref|YP_001374758.1|        ------IYMNGELVEKEKAVVSVYDHGFLYGDGVFEGIRSYGGNVFCLKEHVKRLYESAK
RAAC00632                  MDVASQVFLDGEFVSSDAASVSVFDHGLLYGDGVFEGIRAYDGNVFRLKPHMDRLYRSAK
                                 :::..::*  .: *  :**:***:*****:***** *..**:*  ::  *:.*** **:

ref|YP_001126681.1|        STMLNIPYTKDEMINHVLETVRRNGYQDAYIRLVVSRGVGDLGLDPYKCKSPQVVIIVEP
ref|YP_148515.1|           SILLDIPYTKEEMIGHVLETIRRNGYQDAYIRLVVSRGVGDLGLDPYKCKTPQIVIIVEP
ref|ZP_01171798.1|         SILLTMPYTEEELTDIIVATVEKNLYEDAYIRVVVSRGVGDLGLDPYNCKKANVVVIVEP
ref|YP_080106.1|           SIMLEIPYPQEELTQHVLKTVEKNGLKDAYIRLVVSRGAGDLGLDPNNCSNPSVIIIVEP
ref|YP_001374758.1|        SILLTIPMTVEEMEKAVVQTLQKNGYADAYIRLIVSRGKGDLGLDPRSCEKPSVIIIAEQ
RAAC00632                  SILLEIPYTQDELTELVCETVRRNHLSSAYIRLVVTRGSGDLGLNPYNCAKARVFIIAEQ
                           **:*  :*   .  :*:    :   *:..:*   .****:::*: ***:*   .*  ..  ::*.* ref|YP_001126681.1|        LALFPKHLYETGIEVVTVATRRNRSDVLSPKVKSLNYLNNVLVKIEAHLANVSEALILND
ref|YP_148515.1|           LALFPKHLYETGIEVVTVATRRNRSDVLSPKVKSLNYLNNVLVKIEAHLANVSEALILND
ref|ZP_01171798.1|         LSIFPKELYETGLEIVTVATRRNRPDVLSPKVKSLNYLNNILVRIEARLANVSEALMLND
ref|YP_080106.1|           LAIFPKHLYETGIDIVTVPTRRNRPDVLSPKVKSLNYLNNILVRIEAHMAGVTEALMLND
ref|YP_001374758.1|        LKLFPQEFYDNGLSVVSVASRRNMPDALDPRIKSMNYLNNVLVKIEAAQAGALEALMLNQ
RAAC00632                  LSMFPKALYEQGIRAITAATRRTRGDVLNPKIKSLNYLNNILIKMEAIHAGANEAIVLNH
                           *  :**:  :*:  *:   :..:**. *.*.*::**:*****:*::**  *.. **::**.

ref|YP_001126681.1|        QGYVAEGSGDNIFIVKNGVVYTPPGYVGALEGITRQAIIEIAEELGYTVKEEPFTRHDVY
ref|YP_148515.1|           QGYVAEGSGDNVFIIKNGVIYTPPGYVGALEGITRQAIIEIAEDLGYTVKEEPFTRHDVY
ref|ZP_01171798.1|         QGYVAEGSADNVFIIKDKCFYTPPGYVGALEGITRNAVMEIARELGYEVKEEPFTRHDVY
ref|YP_080106.1|           QGYVAEGSADNVFIYKNGKLLTPPGYIGALEGITRNAIIEIARELGYEVKEEPFTRHDVY
ref|YP_001374758.1|        QGYVCEGSGDNVFVVKDGKVVTPPSYLGALEGVTRNSVIELCDKLGIPCEERPFTRHDVY
RAAC00632                  EGYVVEGSGENIFLVRDGVLITPPAYLGALEGITRQAVIDLAPALGLEVRQEPFTQHDVY
                           :*** ***.:*:*:  ::    . ***.*:*****:**::::::.   **     .:.****:****

ref|YP_001126681.1|        VADEVFLTGTAAEVISVIKVDGRTIGDGTPGPHTKRLLEEFRRRVIAEGVKV-----
ref|YP_148515.1|           VADEVFLTGTAAEVISVIKVDGRTIGDGTPGPHTKRLLEEFRRRVVEGVKV-----
ref|ZP_01171798.1|         TADEVFLTGTAAEVIAVVKVDGRTIGEGYPGAHTKELLVKFRERVVSEGVKV-----
ref|YP_080106.1|           TAEEVFLTGTAAEVIAVVKVDGRKIGDGKPGVHTNRMLEKFRERVVREGLKV-----
ref|YP_001374758.1|        VADEVFLTGTAAELIPVVKVDAREIGDGKPGEVTKQLTEAFKRLTRERGVRVPG---
RAAC00632                  VADEVFLTGTAAEIVPVVEVDRRAIGHGVPGPVTKRVHAAFQEIVRADGVRIEGARV
                           .:*********::.*::**  * **.* **  *:..  *:..  *:::
```

FIG. 10A

```
ref|NP_243928.1|      MRSDMIKKGIDRAPHRSLLRAAG-VKEE-EMDKPFIGVCNSYIDIIPGHMHLNKFAEVAK
ref|YP_176142.1|      MRSNMIKKGIDRAPHRSLLRAAG-VKEE-DMDKPFIGVCNSYIDIIPGHMHLNKFAEVAK
ref|ZP_01695378.1|    MRSDMIKKGIDRAPHRSLLYAAG-LKTE-DFDKPFIGVCNSYIDIIPGHRHLNKFAEVVK
ref|ZP_01725506.1|    MRSDMIKVGVDRAPHRSLLYATGKVKAK-DLGKPFIGVCNSYIDIIPGHVHLRTFADVVK
RAAC00633             MRSDMIKKGVDRAPHRALLYATG-VKPR-DLSKPFIGVCNSYDIVPGHVHLREFAEVVK
ref|YP_850199.1|      MRSDKIKKGVEQAPARSLLHATGQIKSPGDMDKPFIAICNSYIDIVPGHVHLRELADVAK
                      *:   ::** *:** *:*  :*    ::.**.:::* .:*:*.* ref|NP_243928.1|      EAIREAGGIPFEFNTIGVDDGIAMGHIGMRYSLPSREIICDAAETVINAHWFDGVFFIPN
ref|YP_176142.1|      EAIIEAGGIPFEFNTIGVDDGIAMGHIIGMRYSLPSREIICDAAETVINAHWFDGVFYIPN
ref|ZP_01695378.1|    EAIREAGGVPFEFNTIGVDDGIAMGHIGMRYSLPSRELIADSAETVINAHWFDGVFYIPN
ref|ZP_01725506.1|    EAIIEAGGIPFEFNTIGVDDGIAMGHIGMRYSLPSREIIADSAETVINAHWFDGVFYIPN
RAAC00633             DAIRQAGGVPFEFNTIGVDDGIAMGHICMRYSLASRELIADSAETMINAHWFDGVFFIPN
ref|YP_850199.1|      EAIREAGGIPFEFNTIGVDDGIAMGHIGMRYSLPSREVIADAAETVINAHWFDGVFYIPN
                      :  :****************** *:*.*:*:******:* ref|NP_243928.1|      CDKITPGMLMASVRTNVPSVFVSGGPMEAGRTKDGKNLSLASVFEGVGAFSSGKMTREEL
ref|YP_176142.1|      CDKITPGMLMAAVRTNVPAVFVSGGPMEAGRTKEGKSLSLVSVFEGVGAFSSGKMTREEL
ref|ZP_01695378.1|    CDKITPGMLMAAVRTNVPAVFVSGGPMEAGMAPDGKQLSLTSVFEGVGAHKSGKISYEEL
ref|ZP_01725506.1|    CDKITPGMLMAAVRTNVPSIFVSGGPMEAGTSASGKQLSLTSVFEGVGAHKSGNMSAEEL
RAAC00633             CDKITPGMLMAAVRCNVPAVFVSGGPMEAGRSRTGRPLSLSSVFEGVGQYMSGQISEDDL
ref|YP_850199.1|      CDKITPGMLLASVRTNVPAIFCSGGPMKACLSAHGKALTLSSVFEAVGAFKDGSMSQEDF
                      *********:*:** ***.:* *****:**  :  *: *:* ****.**  .  *.::  :::

ref|NP_243928.1|      LEIEQTACPTCGSCSCMFTANSMNSLMEMLGMALPGNGTIVATSEARHQLIKDAAKHLMN
ref|YP_176142.1|      LEIEQLACPTCGSCSGMFTANSMNSLMEMLGLALPGNGTLVATSTERHNLIKDAAKHLIN
ref|ZP_01695378.1|    KMLETSACPTCGSCSCMFTANSMNSLMEMLGLTPPGNATIVATSEERHRIIREAVGHLMN
ref|ZP_01725506.1|    LDIENNACPTCGSCSGMFTANSMNCLMEMLGVALPGNGTIVATSEERHKLIKEAAKQLIR
RAAC00633             LDLERNACPTCGSCSGMFTANSMNCIMEMLGIALPGNGTLVATSKERHELIYEAAKHLIR
ref|YP_850199.1|      LDMEANACPTCGSCAGMFTANSMNCLMEILGMAVPGNGTTLAVSDARRELIRESAFHLMD
                      :*    *******.: ******** :**.**:: ***.* :*.*  *:::*  :: .*:

ref|NP_243928.1|      LIEKDIRPRDIITKETIDDAFALDMAMGGSTNTVLHTLAIANEAEIE-YDLNRINEVAER
ref|YP_176142.1|      LIEKDIRPRDIVTEETIDDAFALDMAMGGSTNTVLHTLAIANEAEID-YDLTRINEVAER
ref|ZP_01695378.1|    CIKNDIRPRDIVTEEAIDDAFALDMAMGGSTNTVLHTLAIAREAGID-YDLERINKVAER
ref|ZP_01725506.1|    MVKEDIKPRDIITKEAIDDAFALDMAMGGSTNTVLHTLAIANEAEID-YNIEDINKVAER
RAAC00633             MVEQDIRPRDIITREAIDDAFALDMAMGGSTNTVLHIMAIAHEAGID-YSLSDINEIAKR
ref|YP_850199.1|      LVKKDIRPRDIITKDAIDDAFALDMAMGGSTNTVLHTLALANEAGIEDYDLERINDIAKR
                       ::::**:*. :: *****************  :*:*.**  *:   **.:*:* ref|NP_243928.1|      VPYLCKISPASDYSMDDVHHAGGVAAIIKELCEIDGAIHPDRITITGKSIYENVKDAEIT
ref|YP_176142.1|      VPYLCKISPASDYSMDDVHKAGGVAAIMKELIE-MGAVKGDRITITGKSLYENVAHAQIT
ref|ZP_01695378.1|    VPYLAKIMPASDYSMHDVHLAGGISAIVHELCKIEGAIHPGRLTITGKSIYENVKDAEIR
ref|ZP_01725506.1|    VPYLAKIMPASDISMDDINKAGGVSAIINELVSIPGAIHPNRPTVAGVTMGELVKDHHIT
RAAC00633             VPYLAKISPASEYSIQDVHRAGGVSAIIRELCEHTDAVHPDRITVTGKTLYEQVKDAKIL
ref|YP_850199.1|      VPYLSKIAPSSSYSMHDVHEAGGVSAIVKELVDLGGATHPDRITVTGKTIRENVADAKIN
                      **.  *:*. *::*  :  * :.**    . *:: .* *::* *    ..* ref|NP_243928.1|      DDVVIRRKDNPYSPVGGLSILFGNLAPNGAVIKVGAVDPSIQIFEGEAIVYNSQEEAQQG
ref|YP_176142.1|      NTDVIRTKETAYSPVGGLSILYGNLAPDGAVIKVGAVDPSIKTFTGEAIVFNSQEEAQEQ
ref|ZP_01695378.1|    NPEVIRPKENPSPVGGLSILYGNIAPDGAVIKVGAVDPDIHTFTGEAIVFESQEEAQKG
ref|ZP_01725506.1|    NNQVIRTKENFYSAVGGLSVLFGNIAPEGSVIKVCAVDPSIQVFKGQAIVFDSQEAAQEN
RAAC00633             DERVIRPASNPYSREGGLSILFGNLAPDGAVLKVGAVDPDIQRFVGRAICFNSQDEAMEG
ref|YP_850199.1|      NTDVIHPKENPYSPVGGLSMLFGNIAPKGAAIKVCGVDPSVQVFKGEAICFSSHDEAVEA
                      :  **:   ...**  ****:*:**:**.*: :***.***.::   *  *.** :.*:  * :
```

FIG. 10B

```
ref|NP_243928.1|      INNGDVREGHVVVIRYEGPKGGPGMPEMLAPTSAIIGRGLGTKVALITDGRFSGASRGIS
ref|YP_176142.1|      INNGAVKEGQVVVIRYEGPKGGPGMPEMLAPTSAIQGRGLGTKVALITDGRFSGASRGIS
ref|ZP_01695378.1|    IDSGLVHEGHVVVIRYEGPKGGPGMPEMLAPTSSTMGRGLGKTVALITDGRFSGATRGIC
ref|ZP_01725506.1|    IDNGIVKEGHVVVIRYEGPKGGPGMPEMLAPTSAIQGRGLGTKVALITDGRFSGASRGIS
RAAC00633             INSGKVQPGHVVVIRYEGPKGGPGMPEMLAPTSSIVGRGLGREVALITDGRFSGATRGIC
ref|YP_850199.1|      IDNHTVREGHVVVIRYEGPKGGPGMPEMLAPTSSIVGRGLGKDVALITDGRFSGATRGIA
                      *:.   *: *:***********************:* *****  ************:***.

ref|NP_243928.1|      IGHISPEAAEGGPIAFIENGDKIRIDLPNRTIEWLVSDEEIAKRQ-EGWTEPEPKVKK--
ref|YP_176142.1|      IGHISPEAAEGGPIAFVENGDMIKIDLIERTIEWEISEEELAKRR-EGWTEPEPKVKK--
ref|ZP_01695378.1|    VGHISPEAAEGGPIALVENGDRITIDLINRRIELIIVPDEELQRRK-QNWVQPEPKITS--
ref|ZP_01725506.1|    IGHISPEAAEGGPIALVEDGDMIEIDLPNRTINLQVSEEVLAERR-AKLPVFEPKIKR--
RAAC00633             VGHISPEACVGGPIALVEDGDEIETDIPNRAITLKVSDEELAARR-ARYQPPAKEKLT--
ref|YP_850199.1|      VGHISPEAAAGGPIALVHDGDIITIDLFNRTLNVDVSDEVLEERR-KELPKFKAKVKT--
                      :******. ****::.:** * **: :* :     :.:* : *:          :

ref|NP_243928.1|      -GYLARYSKLVTSANTGGVMKI--
ref|YP_176142.1|      -GYLARYSKLVTSANTGGVMKI--
ref|ZP_01695378.1|    -GYLARYSALVTSANTGGVLKI--
ref|ZP_01725506.1|    -GWLARYSKLVTNASTGGVMKI--
RAAC00633             -GYLARYQKLVTSANTGAVLTVDA
ref|YP_850199.1|      -GYLARYTALVTSAHTGGILQI--
                      *:****  ***.* **.:: :
```

FIG. 11A

```
ref|YP_148514.1|        --QGGSTMTKMKVEEQEKARTKAR------MSGSLMLIEALKEEKVEVIFGYPGGAVLPL
gb|AAL99356.1|          ------------------------------MSGSMMLIEALKAEQVEVIFGYPGGAVLPL
ref|YP_001126680.1|     ------------------------------MSGSLMLIEALKAENVEVIFGYPGGAVLPL
ref|YP_001487695.1|     ------------------------------MNGALMLIEALKREKVEVIFGYPGGAVLPI
ref|YP_176141.1|        ------------------------------GSEILLKALASEGVEVIFGYPGGAILPT
RAAC00634               MWRGGNAMPGMSKPADDETLTRSGEGGAMWMKGADMVVEALRREQVEVIFGYPGGAVLPL
                                                      *:  ::::**  * ***********:**

ref|YP_148514.1|        YDELYKAGVFHVLTRHEQGAIHAAEGYARISGKPGVVIATSGPGATNIVTGLTDAMMDSL
gb|AAL99356.1|          YDELYKAGVFHVLTRHEQGAIHAAEGYARISGKPGFVIATSGPGATNIVTGLTDAMMDSL
ref|YP_001126680.1|     YDELYKAGVFHVLTRHEQGAIHAAEGYARISGKPGVVIATSGPGATNIVTGLTDAMMDSL
ref|YP_001487695.1|     YDKIYDSGLFHVLPRHEQGAIHAAEGYARVSGKPGVVIATSGPGATNLVTGIADAMIDSL
ref|YP_176141.1|        YDEIYKLGMNHILARHEQGAIHAAEGYARITQKPGVCIVTSGPGATNVVTGIADAMMDSL
RAAC00634               YDALYQCGIRHVLTRHEQGAIHAAEEGYARVTGKPGVVIATSGPGATNLVTGLADAMMDSI
                        **  :*.  *: *:*.******:****::    ***. *.********:***::***:**:

ref|YP_148514.1|        PLVVFTGQVATSVIGSDAFQEADVVGITMPITKHNYQVRDISELPRIIKEAFHIATTGRP
gb|AAL99356.1|          PLVVFTGQVATSVIGSDAFQEADVVGITMPITKHNYQVRDISELPKIIKEAFHIATTGRP
ref|YP_001126680.1|     PLVVFTGQVATNVIGSDAFQEADVVGITMPITKHNYQVRDISELPKIIKEAFHIATTGRP
ref|YP_001487695.1|     PLVVFTCQVATSVIGSDAFQEADVLGITMPITKHSYQVRNPEELPGVIKEAFHIATTGRP
ref|YP_176141.1|        PMVVITGQVATKVIGTDAFQEADMLGITMPITKHNFQIRSIEELAQTVKEAFHIAVSGRP
RAAC00634               PLVAITGQVAKTVIGTDAFQETSIIGISTPITKHNYQIRHASEIPKVFKEAFHIANSGRK
                        *:*.:*****..***:*****::.::**: *****:*:*   .*::  .******* :**

ref|YP_148514.1|        GPVLIDIPKDITTAEGEFDYDQDVHLPGYQPTTQPNHWQIRRLVEAVSQSKRPVILAGAG
gb|AAL99356.1|          GPVLIDIPKDITTAEGEFDYDEEVCLPGYQPTTQPNHWQIRRLVEAVSQSKRPVILAGAG
ref|YP_001126680.1|     GPVLIDIPKDVTIAEGEFDYNQDVHLPGYQPTTQPNHWQIRRLVEAVSQSKRPVILAGAG
ref|YP_001487695.1|     GPVLIDIPKDVGIEGTFEYDQPIDLPGYQPKVEPNYLQIRKLVEAVSRAKKPVILAGAG
ref|YP_176141.1|        GPVLIDLPKDISEKLGIFDYEEPVHLPGYQPTVKPNKQQIRKLLDKFKEAKRPVLLVGAG
RAAC00634               GPVLIDIPKDVSGEEAWFAYDDPPQLPGYQPTVVPHHMQIRKLMHGLQHAKRPVVLAGAG
                        ****:*::    .  * ::   ******.. *:  ***:*:.    .:*:**:*.*** ref|YP_148514.1|        ILHANASNELRQYAEQQNIPVIHTLLGLGGFPADHPLFLGMAGMHGTYTANMALCECDLL
gb|AAL99356.1|          VLHADAANELRQYAEQQNIPVVHTLLGLGGFPADHPLFLGMAGMHGTYTANMALYECDLL
ref|YP_001126680.1|     VLHANAADELQQYAEQQNIPVAHTLLGLGGFPADHPLFLGMAGMHGTYAANMALYECDLL
ref|YP_001487695.1|     VLHGKASEELRQYVEQQQIPVAHTLLGLGGFPAKHPLFLGMAGMHGTYAANMALHQCDLL
ref|YP_176141.1|        VLHAQASEELTAFARKFQTPVAQTLLGLGAFPGEEELHLGMAGMHGTYAANMALHKSDFL
RAAC00634               VLHARATEKLLAFVEKYQLPVVQTLLGLGSFPASHPLCLGMGGMHGSAAANKALYETDFL
                         :**. *:::*    :...: :: :*....  * *.: : ** : *:* ref|YP_148514.1|        INIGARFDDRVTGNLKYFAPKATVAHIDIDPAEIGKNVPTKIPIVSDAKAALQELIAQQG
gb|AAL99356.1|          INICARFADRVTGNLKYFAPKATVAHIDIDPAEIGKNVPTKIPIVSDAKAALQELIAQQG
ref|YP_001126680.1|     INIGARFDDRVTGNLKYFAPKATVAHIDIDPAEIGKNVPTKIPIVSDAKAALQELIEQQG
ref|YP_001487695.1|     ISTGARFDDRVTGNLNHFAKHAKVAHIDIDPAEIGKNIHTHIPVVGDSKLVLQELIKQDG
ref|YP_176141.1|        INIGSRFDDRLTGALEHFAPEACIAHIDIDPAEIGKNVIVEIPVVGDAKEAIAMLVKGSG
RAAC00634               INLCARFDDRLTCKLEHFAPHAVVAHIDIDPAEIGKNVPTDIPVVGDVGEALSMMLSIDV
                        *.:*:** **:** *::**  .* :*************: ..**:*.*     .*   ::

ref|YP_148514.1|        KPADTAAWLTQLDEWKRRFPLHYEP-EAGTIKPQKLIEMIYEMTNGEAIVTTDVGQHQMW
gb|AAL99356.1|          KPADNAAWLEQLNEWKRRFPLHYEP-EAGTIKPQKLIEMIYELTNGEAIVTTDVGQHQMW
ref|YP_001126680.1|     KPADNAAWLAQLNEWKRRFPLHYEP-EAGAIKPQKLIEMIYEVTGGEAIVTTDVGQHQMW
ref|YP_001487695.1|     KQGESDEWKNQLDQWKEEYPLWYVENEAEGFKPQKLIEYIHQFTKGEAIVATDVGQHQMW
ref|YP_176141.1|        AIDEHDEWRKQVSDWKRDYPLWFHR-DGEVIKPQELIQKLYEHTKGEAIVTTDVGQHQMW
RAAC00634               PAPDAEAWREELLRVKRELPFWWVQ-DGKHIKPQRLISEIARITKGDVVVTTDVGQHQMW
                         :  *  ::  *. *::  *:  *:  :.  *:.:*:********
```

FIG. 11B

```
ref|YP_148514.1|        AAQYYKFNRPHRWVTSGGLGTMGFGLPAAIGAQLADRSATVVSIVGDGGFQMTFQELSVI
gb|AAL99356.1|          AAQYYKFNRPNRWVTSGGLGTMGFGLPAAIGAQLADRSATVVSIVGDGGFQMTLQELSVI
ref|YP_001126680.1|     AAQYYKFNRPNRWVTSGGLGTMGFGLPAAIGAQLADQSATVVSIVGDGGFQMTCQELSVI
ref|YP_001487695.1|     AAQFYPFENADKWVTSGGLGTMGFGLPAAIGAQLADQEATVVAILGDGGFQMTLQELAVI
ref|YP_176141.1|        TAQHFKFNKPNRWITSGGLGTMGFGFPAAIGAQIAEPELPVLAITGDAGFQMTLQEMSIL
RAAC00634               AAQFFPLNQPDRWVTSGGLGTMGFGLPAAIGAHFGQPDKLVVAILGDAGFQMTLQELAVI
                         :**.: ::...:*:**********:*****::.: . *::* **.***** **::::

ref|YP_148514.1|        QELRLPIKIVIVNNQALGMVRQWQELFYDKRYSHSLIPNQPDFVKLAEAYGMPGLRAKTE
gb|AAL99356.1|          RELGLPIKIVIVNNQALGMVRQWQELFYEKRYSHSLIPNHPDFVKLAEPYGIPGLRAKTE
ref|YP_001126680.1|     QELQLPIKVVIVNNQALGMVRQWQELFYDKRYSHSLIPNQPDFVKLAEAYGMPGLRAKTE
ref|YP_001487695.1|     RELNLPVKVIVLNNHSLCMVRQWQEIFYEERYSYSKFSEQPDFVKLSEAYGIKGIRISSD
ref|YP_176141.1|        QELDLPVKIVIVNNASLGMVRQWQQRFHGERYSHSLFPIQPNFAKLAEAYNIKAVKVDKL
RAAC00634               GEHQLPIKVVIVNNSALGMVRQWQELFHGERYSESLLPWQPDFVKLGEAYRIPSARVERD
                          * **:*::::** :********: *: :*** * :. :*:*.**.*.* : . : .

ref|YP_148514.1|        AEAAEVLKQAFAMDGPVLLDFHVRADENVYPMVAPGKGLHEMVGVK-
gb|AAL99356.1|          AESAEVLKQAFAMDGPVLLDFHVRADENVYPMVSPGKGLHEMVGVK-
ref|YP_001126680.1|     AEAAEVLKQAFAIDGPVLLDFHVCADENVYPMVAPGKGLHEMVGVK-
ref|YP_001487695.1|     EEAKEKLEEALTSREPVFIDVNVARDEKVFPMVAPGKGLHEMVGVKP
ref|YP_176141.1|        SMLDEAIAETLAHPGPVLLEVCVAKEENVYPMVCPGTGHHCMEGVEP
RAAC00634               EDLTAALEAFLSEPGPGLLECVVDPNENVYPMVAPGTGIHQMVGVRP
                          :   :: * ::: * :*:*:***.**.* * * **.
```

FIG. 12

```
ref|NP_389472.1|      --IAFLFPGQGSQFIGMGKELYEQVPAAKRLFDEADETLETKLSSLIFEGDAEELTLTYN
ref|ZP_01861659.1|    --IAFVFPGQGSQKAGMGKELSEKFPQVEEYFKKADQRLGFDLSTLIFEGPQDKLTLTEN
ref|YP_147042.1|      --IAFLFPGQGSQTVGMAKDAAEHDDRARAVIAEADERLGFALSKLMFNGPQEELTLTYN
ref|NP_243358.1|      --VAFLFPCQGSQSVGMGSELLSEEK-AKEIFDEADERLGYSLSSIMFEGPEEKLRRTEN
ref|YP_175798.1|      --IAFLFPGQGSQKVGMGATLFAEDSLAKEVLERADKALGFPLSEIIEHGPEEKLKQTAY
RAAC00174             MNVAFVFPCQCAQYVGMGRAIFDEYPVARALLEEADEALGMKLSDIIFEGPEDTLRLTYY
                         :***:*   .   .    ..   :  .: *    ** ::  .*   : *   * ref|NP_389472.1|      AQPALLTTSIAVLEKFKES-GITPDFTAGHSLGEYSALVAAGALSFKDAVYTVRKRGEFM
ref|ZP_01861659.1|    AQPALLTTSIAFLQML-ESEGVKPDYTAGHSLGEYSALVAAGAISFEDGVYAVRKRGEYM
ref|YP_147042.1|      AQPALLTASIALLQ-LVDGAGLKADYVAGHSLGEYTALVAAGAMSFADAVYAVRRRGELM
ref|NP_243358.1|      TQPALLTMSTAVL-SLVREYGIKPDYTAGHSLGEYSALVASGSLTFADAVYAVHHRGLFM
ref|YP_175798.1|      AQPALVTMSTAVLQLFRD-AGIQADFVAGHSLGEYSALVACKSLTFEDAVTLVHQRGTLM
RAAC00174             TQPALLTVSVAVWRALVDRVDIQPLAVAGHSLGEYSALVAAKSISFADAVKLVYQRGKLM
                      :****:*  * *.      :   .: .******:**. :::* *.*   * :**  * ref|NP_389472.1|      NEAVPAGEGAMAAILGMDAEALKQVTDKVTEE-GNLVQLANLNCPGQIVISGTAKGVELA
ref|ZP_01861659.1|    EEAVPAGEGTMAAVLGMGRDQLSEITERISAE-GNHVGLANLNCPGQIVISGSFRGVELA
ref|YP_147042.1|      DEAVPAGEGTMAAVLGMDADALEAVTNEIAAQ-GDPVEPANFNCPGQIVISGSKAGVEKA
ref|NP_243358.1|      EEAVPFGEGAMAAILGMERDELEQVTKRVTE-AGAVVELANLNCPGQIVISGSAEGVEQA
ref|YP_175798.1|      EEAVPQGQGAMAAVLGLNKEELEEVASEIAAD-GEVAELANLNCPGQIVLSGTAKGIEQA
RAAC00174             DEAYPAGQGTMAAVLGLDEEPLREVCKRASEETGEIVELANVNCPGQIVISGAKAAVERA
                      :**  * *:*:*::       :   * :  ..  :   * .  .***::    .:* * ref|NP_389472.1|      SELAKENGAKRATPLEVSGPFHSELMKPAAEKLKEVLDACDIKDADVPVISNVSADVMTE
ref|ZP_01861659.1|    SDLAKEEGAKRVLPLQVSCGPFHSSMMKPAAENFSGVLDEIAIRDAFVPVIANVNAEPMIS
ref|YP_147042.1|      AQLLKERGAKRVIPLEVSGPFHSALMKPAAEKLKAVLDSLVIRDAVIPVVANVTAEPVTK
ref|NP_243358.1|      SEEAKEAGAKRVIPLQVSGPFHSSLMKPAAEKLEAVLADLAIADAAPPVIANVTADLVQK
ref|YP_175798.1|      AVLAKQKGAKRVLPLAVSGPFHSSLMKPAADQFKQALEQAPFANPTVPLIANVTAEVTDA
RAAC00174             SLLAKEAGARRVMPLNVSGPFHSSLMQPAADRLGALLDEIEFADAETPVVANVDGHPRRM
                        :  *: **:*.:** ******* :*:***:.:   *     : :. *::: **  ..

ref|NP_389472.1|      KADIKEKLIEQLYSPVRFEESINKLIAEGVTTFIEIGPGKVLSGLVKKVNRRLKTIAVSD
ref|ZP_01861659.1|    ASEIKERLIQQLYSPVPLVEDTVVKLLDAGVDTFIEIGPGKVLSGLIKKVNRRVNTFSISD
ref|YP_147042.1|      KEDIARLLIEQLYSPVRWEQSVRTLLSLGVDTFVEIGPGKVLSGLVKKIDRNARVYAVND
ref|NP_243358.1|      AADIRSSLIEQVYSPVRWEDTVRRMLELGVDTFVEIGSGNVLSGLVRKVQRRVNVFSVSD
ref|YP_175798.1|      PEVIREQLAEQIYSPVRFEESVRRMIELGVDTFIEIGAGNVLCGLVRKIDRNLRTFAVSD
RAAC00174             ASDLRDALKKQLVMPVRFVDCVLSMKRLGVDCVVFLGPGTVLSGLVRKIDKSLETAHAED
                            :   * :*:     :  :   :        .:*:*.*..::*::: ..     .* ref|NP_389472.1|      PETIE---------------
ref|ZP_01861659.1|    --------------------
ref|YP_147042.1|      LASFEATVAAL---------
ref|NP_243358.1|      RASIE---------------
ref|YP_175798.1|      RESFEKMAAAL---------
RAAC00174             PATLDEVCALLTRGGESGE
```

FIG. 13

```
ref|YP_148513.1|        ------------------------------------------MRRIITMTVNNRPGVLNRITGL
ref|YP_001126679.1|     ------------------------------------------MRRIITMTVNNRPGVLNRITGL
ref|NP_843875.1|        ------------------------------------------MKRIVTATVRNQSGVLNRITGV
ref|NP_243926.1|        ------------------------------------------MKRTITALVNNTSGVLNRITGL
ref|YP_176140.1|        ------------------------------------------MKRTITVLVNNKSGVLNRMTGL
RAAC00635               ------------------------------------------MTPVLSVLVHNKPGVLNRITAL
                                                                    *   ::   *.* .*****:*.:

ref|YP_148513.1|        FTKRHYNIESITVGHTEIEGISRMTFVVNVDDERTAEQIIKQLNKQIDVLKVNDITDQAI
ref|YP_001126679.1|     FTKRHYNIESITVGHTEIDGVSRMTFVVNVDDERIAEQIIKQLNKQIDVLKVSDITDQAI
ref|NP_843875.1|        MTRRHFNIESISVGHTESSDISRMTIVVHVENEQQVEQLIKQLHKQIDVLKVSDITEEAM
ref|NP_243926.1|        FARRHFNIESITVGVTENPTVSRMTFVVIVDNQKNIEQVIKQLHKQVDVLKVKDITDEAI
ref|YP_176140.1|        FARRQYNIDSITVGVTENPTISRMTFVVFVDSMENVEQMIKQLHKQVDVLKIKDITDEAI
RAAC00635               FMRKGFNIQSLTVCITENPEISRMTIVMSDMDEAALEQVIKQLHKQIDVLKVTDLTDQAM
                        :  ::  :**:*::*   **    :****:*:     . **:****:**:****:.*:*::*:

ref|YP_148513.1|        VARELALIKVAAPPAVRQEIYTLIEPFRASIVDVSKDSLVIQVTCEPEKVEALIELLRPY
ref|YP_001126679.1|     VARELALVKVAAAPATRQEIYTLIEPFRASIVDVSKDSLVIQVTGEPEKVEALIELLRPY
ref|NP_843875.1|        IARELALIKVATSVA-RAELYSLIEPFRAAVIDVGKDSIVVQVTCTQEKVEALIELLRPY
ref|NP_243926.1|        VARELALIKVASPQQRGEIAAVVNPFRASIIDIGRESMTVQITGDHQKVETFIDLLRPY
ref|YP_176140.1|        VERELALVRVGATPQQRGEIASLAETFRAQAVDIGKESMTLQITGNNEKIEAFIELVKPY
RAAC00635               VARELALIRVSSPIAERAVIHSLIEPFRANIVDVGRETVTVQVTGDAEKIDALIALLRPY
                        : *****::*  :.    *  : :: :.***  :*:.::::.: *:**     :*::::* *::**

ref|YP_148513.1|        GIKEVARTGTTAFTRGA-------------------
ref|YP_001126679.1|     GIKEVARTGTTAFTRGAQKAGSNQK----------
ref|NP_843875.1|        GLKEIARTGVTAFTR--------------------
ref|NP_243926.1|        GIKELARTGITAFKR--------------------
ref|YP_176140.1|        GIQELARTGVTAVNRSSKVSTDTSR----------
RAAC00635               GIRELARTGLTALPREAASSADPKRAGEAQVLHI
                        *::*:**** **. *
```

FIG. 14

```
ref|YP_148510.1|            ----------IAVLPGDGIGKEVTSGAVEVLKAVGIRFGHEFTFEYGLIGGAAIDEAGTP
ref|YP_001126676.1|         ----------IAVLPGDGIGKEVTSGAVEVLKAVGIRFGHEFTFEYGLTGGAAIDEVGTP
ref|ZP_01171803.1|          ------MKKRIAVLPGDGIGKEVAAGAVEVLQAAGERFGHTFEFSYGKIGGTAIDSTGVP
ref|NP_243923.1|            ------MEKQIAVLPGDGIGPEVTDAAIEVLQAVADRFGHTFSYKKALLGGCAIDEVGTP
RAAC00637                   MKGTDGMTKNIAILPGDGIGREVTAEAVKLIQVVAASRGETWNLEEGLIGGSALDATGSP
ref|NP_926497.1|            ----------IAVLPGDGIGTEIVQVGVAMLEAAARRFDFAFDFEEAPIGGAAIDATGEP
                                      :*****  *:.   .:  ::::...   .  :   . . :** *:* .* * ref|YP_148510.1|            LPEETLRLCRESDAVLLGAVGGPKWDDNPPHLRPEKGLLAIRKQLDLYANLRPVVCYDSL
ref|YP_001126676.1|         LPEETLRLCQQSDAVLLGAVGGPKWDQNPPHLRPEKGLLAIRQQLGLYANLRPVVCYDSL
ref|ZP_01171803.1|          LPDETVELCKSSDAILLGAVGGPRWEKLHPSLRPERGLLKIRKDLNLYANLRPTSYFASV
ref|NP_243923.1|            LPEETLDVCREHADGILLGAVGGPKWDTLPGHLRPEKGLLGLRKGLNLFANLRPVTVYDSL
RAAC00637                   LPEETVRLCRAADAVLLGAVGGPKWDHLPGDKRPEACLLGTRKALEVYANLRPIRTWPGL
ref|NP_926497.1|            LPAATLELCKASDAVFLGAVGGPQWDTLPSDKRPEKALLGLRAGLGLFANLRPARILPQL
                            **    *:  :*: :*.::*******:*:     ***  .** :*   *  ::*****        :

ref|YP_148510.1|            VSASPLKPDLVQGVDFVIVRELTGGIYFGQPSGRV-VENGEEKAVDTLLYKKEEIERIVR
ref|YP_001126676.1|         DSASPLKSDLVQGVDFIIVRELTGGIYFGQPSGRV-VENGEEKAVDTLLYKKEEIERIVR
ref|ZP_01171803.1|          ADSSPLRKEVIEGTDFLMVRELTGGLYFGKPSERA-GNGSEETAVDTLFYKKEEVQRVVR
ref|NP_243923.1|            ADASTLKNDVIDGVDLLIVRELTGGLYFGEPRERR-GEGETEEVVDTLLYTRGEMRRIIR
RAAC00637                   LLASPLKPELVEGVDILVVRELTGGLYFGQPKARL-DGG--EAVVDTLHYTRAEIRRVVK
ref|NP_926497.1|            VAASALKPEVVEGVDILVVRELTGGLYFGIPKGIFPEKKGGRRGVNTMSYSAFEIERIGR
                             :*.*:   :::::*.*:::*******:*** *                *:*:  *.  *:.*:  :

ref|YP_148510.1|            MAFILARGRKKKVTSVDKANVLSSSRLWREVAEEVAKQFPDVTLEHMLVDNAAMQLIRAP
ref|YP_001126676.1|         MAFTLARGRKKKVTSVDKANVLSSSRLWREVAEEVAKQFPDVELEHMLVDNAAMQLIRAP
ref|ZP_01171803.1|          LAFELARGRDGKVTSVDKANVLESSRMWRETAEEIAAQYPDIQLEHMLVDNAAMQIIKNP
ref|NP_243923.1|            KAFELAMVRNKHVTSVDKANVLESSRMWREVANEVAQEFPEVTLEHMLVDNAAMQLIRRP
RAAC00637                   VAFELAKGRQGRLTSVDKANVLESSRVWREVVEEVASEYPGVLVEHLLVDNAAMQIITRP
ref|NP_926497.1|            VAFEAARERRGKLCSVDKANVLEVSQLWREVLVGLAPEYPDVELTHMYVDNCAMQLVRRP
                             **   *    *  ::  ********. *::***.     :*  ::*  : : *: *.*::  * ref|YP_148510.1|            KQFDVIVTENMFGDILSDEASMLSGSLGMLPSASLSASGPSLYEPVHGSAPDIAGMNKAN
ref|YP_001126676.1|         KQFDVIVTENMFGDILSDEASMLSGSLGMLPSASLSEPVHGSAPDIAGMRKAN
ref|ZP_01171803.1|          KQFDVIVTENMFGDILSDEASVLTGSLGMLPSASLSEGGPYLYEPTHGSAPDIEGKGIAN
ref|NP_243923.1|            KQFDVLVTENLFGDILSDEASMVTGSLGMLPSASLTSDGPGLYEPIHGSAPDIAGKGVAN
RAAC00637                   KTFDVIVTENMFGDTLSDEAAVITGSIGMLPSASLGEAGPGLYEPVHGSAPDIAGQGLAN
ref|NP_926497.1|            RQFDTIVTENMFGDILSDEAAMLTGSIGMLPSASLGSGGPGLYEPVHGSAPDIAGQDKAN
                            : .::*****::::::******    **:*****  *  ** ref|YP_148510.1|            PIAAILSAAMMLRLSFGLTAEAEAVEHAVRQALDQGLRTADLAPSGGRIVSTNEM-----
ref|YP_001126676.1|         PIAAILSAAMMLRLSFGLTAEAEAIEHAVQQALTAGLRTADLAQSNGRVVSTDEM-----
ref|ZP_01171803.1|          PVGMILSAAMMLRLSFGMEEEAAAIEKAVSDVLESGIRTADLA-SGGKAASTKVMTEEIK
ref|NP_243923.1|            PLATIASCAMMLKYSFGLHEEAKTIEDAIEAVLKQGYRTADIAKPGEESSSTKAITDAVV
RAAC00637                   PLATFLSVALMMRHSLHLPEAADAIEQAVHGVIERGVRTRDLARSGEAFVKTADVSAMVC
ref|NP_926497.1|            PLAQVLSGAMLLRHSLRQPEAAQAVERAVQTVLEQGYRTGDIAAPCAQIV----------
                            *:.  .  * *:::: *:     * ::* *:    .:  * ** *:*  ..

ref|YP_148510.1|            --------
ref|YP_001126676.1|         --------
ref|ZP_01171803.1|          AALLDN--
ref|NP_243923.1|            EAIQ----
RAAC00637                   EDVKRRLG
ref|NP_926497.1|            --------
```

FIG. 15A

```
ref|YP_148509.1|          ------------KTIIDKIWENHVVYREEGKPDLLYIDLHLVHEVTSPQAFEGLRQKGRK
ref|YP_001126675.1|       ------------KTIIEKIWENHVVYREEGKPDLLYIDLHLVHEVTSPQAFEGLRQNGRK
ref|YP_075945.1|          ---------MSGRTLLDKIWERHVVRREPGKPDLLYIDLHLVHEVTSPQAFEGLRMAGRR
RAAC00638                 MRRREKEARLMGRTLFEKVWDAHVVKELPDGQTLLYIDLHLVHEVTSPQAFAGLRFAGRK
ref|NP_243922.1|          ------------KTIIEKIWDAHTVIGEEGKPSLLYIDLHMVHEVTSPQAFEGLRLAGRP
ref|ZP_01171804.1|        ----------MGKSIVEKIWDRHIVHTETDKPDLLYIDLHLVHEVTSPQAFSGLRMKNRK
                                      ::..:*:*: *  *      .   *****:*****  *   .* ref|YP_148509.1|          VRRPDLTFATMDHNVPTVN-RFVITDEVARNQIAALERNCREFGIPLADLHSEEQGIVHV
ref|YP_001126675.1|       VRRPDLTFATMDHNVPTVN-RFVITDEVARNQIAALERNCREFGIPLADLHSEEQGIVHV
ref|YP_075945.1|          VRRPDLTIATMDHNVPTTDRSLPLTDEIAARQMAALERNCSEFGVRLFDLYSPFQGIVHV
RAAC00638                 VRRPELTFATMDHNVPTVN-PKDVRDAIARKQIETLEQNCREFGVQLAGLDSPFQGIVHV
ref|NP_243922.1|          VRRPDLTFATMDHNVPTVD-RFNIQDQIARKQIETLEANCKEFGIEIAGLDSPNNGIVHV
ref|ZP_01171804.1|        VRRPDKTFATMDHNVPTIN-RGQTDDPVAKKQMTTLEKNCREFGVPLAGMDSPDQGIVHV
                          ****: *:*********   :    : * :*. *:     ***: :  .:  *    .:***** ref|YP_148509.1|          IGPELGLTQPGKTIVCGDSHTSTHGAFGALAFGIGTSEVEHVLATQTLWQHKPKTLQICI
ref|YP_001126675.1|       IGPELGLTQPGKTIVCGDSHTSTHGAFGALAFGIGTSEVEHVLATQTLWQHKPKTLQIRI
ref|YP_075945.1|          IGPELGLTQPGLTIVCGDSHTATHGAFGALAFGIGTSEVEHVLATQCLWQHKPKVMEIRV
RAAC00638                 IGPELGLTMPGKTIVCGDSHTSTHGAFGALAFGIGTSEVEHVLATQCLWQSRPKTMRIQL
ref|NP_243922.1|          IGPELGLTQPGKTIVCGDSHTSTHGAFGALAFGIGTSEVEHVLATQTLWQSKPKTMEVRV
ref|ZP_01171804.1|        IGPELGLTRPGMTIVCGDSHTSTHGAFGSLAFGIGTSEVEHVLATQTLWQSRPKTLKLQI
                          ********  **  ********:******.****************  ***  :**.:.:  :

ref|YP_148509.1|          NGRLGKGVTAKDVILAIIGRYGVGVGTGYIIEFTGEAIRRMSMEERMTICNMSIEAGARA
ref|YP_001126675.1|       NGQLGKGVTAKDVILAIIGRYGVGVGTGYIIEFTGEAIRRMSMEERMTICNMSIEAGARA
ref|YP_075945.1|          NGKLPPGTTAKDLILGIIGQIGTDGATGYVIEYTGEAIRSLSMEGRMTVCNMSIEAGARA
RAAC00638                 NGTLQPGVTAKDVILGLIAKYGVNFGTGHVVEYAGSLIPELSMEQRMTICNMSIEFGARA
ref|NP_243922.1|          TGELAPSVSAKDIILAVIAKYGVDFGTGHVIEFTGEAIRSLSMEERMTICNMSIEAGAKA
ref|ZP_01171804.1|        DGRLESGVTAKDVILYIISRFGIGFGTGHVIEYCGEAVRSMSMEERMTICNMSIEGCARA
                           *  *  ..:*:  :*.:  *  ..**:::*: *. :  :* *:**** :* ref|YP_148509.1|          GLISPDETTFAYLRGRKYAPKGEEFDKAVERWRALASDEGAKYDKTIEIDASTIAPMVTW
ref|YP_001126675.1|       GLTSPDETTFAYLRGRKYAPKGEEFDQAVERWRALASDEGAEYDKTIEIDASTIAPMVTW
ref|YP_075945.1|          GMIAPDFTTFAYLKGRPHAPQGELWEAAVADWRTLASDPDAVYDRVVEFDAGQLAPVVSW
RAAC00638                 GMMAPDETTIAYVQGRRYAPKGADWEACVAAWRELKSDPDAVFDVDVVFDVNDLEPQVTW
ref|NP_243922.1|          GLISPDSVTFEYLRGRPNAPKGEAFDVAIQQWEALATDAGAVYDRVLTMNASETEPMVTW
ref|ZP_01171804.1|        GLVSPDETTFSYIKGRKYAPKDNEWDTSLAHWQALASDPDANYDKEITLDAGFTPPMVSW
                          *:::**..*:  *::   :.    ::  .:  *. * :* .* :*   : ::..  :  *   *:* ref|YP_148509.1|          GTNPAMSTSVDGVVPHPEQFESKTEQNAVRRALEYMGLKPGTPITDIPVQHVFIGSCTNS
ref|YP_001126675.1|       GTNPSMSTSVDGTVPDPEQFESETERNAVRRALEYMGLKPGMSITEIPVQHVFIGSCTNS
ref|YP_075945.1|          GTNPGQVVPVTGRIPDPRDFADPAQRKAAEAALAYMDLEPGTPIQDIRIDRVFIGSCTNG
RAAC00638                 GTNPGQGTGISGVVPDPKDAKSEEEALAIRQALEYMDLKPGTKTSEIPIQHVFIGSCTNA
ref|NP_243922.1|          GTNPAQGTGVSQVVPSPDDAKDENERRAIKQSLAYMGLEPGTPTTETAIQHVFIGSCTNS
ref|ZP_01171804.1|        GTNPSMAAGVDERIPSEADCKTETERTSLERALRYMGLSEGQEISDISIQHVFIGSCTNS
                          ****. .: :*  :*  :  :  :.*.*.* *   * :*  :::*********.

ref|YP_148509.1|          RLSDLRAAASIVKGKKVAPGVRALVVPGSQQVKKQAEAEGLAQIFIDAGFEWRDSGCSAC
ref|YP_001126675.1|       RISDLREAAKIVKGQKVAPGVRALVVPGSQQVKKQAEEEGLAQIFLDAGFEWRDAGCSAC
ref|YP_075945.1|          RIEDLRAAAAVVKGRKVAPGVRAMVVPGSGQVKAQAEAEGLDQIFREAGFEWREAGCSMC
RAAC00638                 RIEDLRLAASIVKGRKVADGVRAVVVPGSKQVKQQAEAEAEGLHEIFLEAGFEWREPGCSAC
ref|NP_243922.1|          RLSDLRTAAELIKGRKVADGVRALVVPGSQQVKRAAEKEGLDEIFKEAGFEWRDSGCSMC
ref|ZP_01171804.1|        RIEDLRQAAEFAAGKKVHPGVRALVVPGSQQAVKEQAEKEGLHHIFIESGFEWRESGCSMC
                          *:.***  **   .   *::*   ****:*****  **  ** ***  .**  ::*****:.*** *
```

FIG. 15B

```
ref|YP_148509.1|         LGMNPDIIPEGEHCASTSNRNFEGRQGKGARTHLVSPVMAAAAAIYGHFVDVRQLEAEPV
ref|YP_001126675.1|      LGMNPDIIPEGEHCASTSNRNFEGRQGKGARTHLVSPAMAAAAAIYGRFVDVRQLEAEPV
ref|YP_075945.1|         LGMNPDILAPGERCASTSNRNFEGRQGKGGRTHLVSPAMAAAAAIAGHFVDVRELLAEGG
RAAC00638                LGMNPDIIPAGERCASTSNRNFEGRQGKGARTHLVSPAMAAAAAIAGHFVDVRELTSEGV
ref|NP_243922.1|         LGMNPDTVPEGERCASTSNRNFEGRQGKGARTHLVSPQMAAAAAIAGHFVDVRTFQSEPQ
ref|ZP_01171804.1|       LSMNNDIVPPGEHCASTSNRNFEGRQGSGARTHLVSPLMAAAAAVNGKFVDVRKTLMEES
                         *.**  *  :. :***********.*.****.****: *:*****      * ref|YP_148509.1|         --
ref|YP_001126675.1|      --
ref|YP_075945.1|         AA
RAAC00638                TA
ref|NP_243922.1|         T-
ref|ZP_01171804.1|       IT
```

FIG. 16

```
ref|YP_148508.1|         -MKPFTIHRGKTAGIDRANIDTDQIIPKQFLKRIERTGFGQFLFYDWRYLSDGTPNPEFE
ref|YP_001126674.1|      -MKPFTIHRGKTAGIDRVNIDTDQIIPKQFLKRIERTGFGQFLFYDWRYLSDGTPNPEFE
sp|Q67MJ3|LEUD_SYMTH     -MRPFTRETGLAVPLDRVNVDTDQIIPKQFLKRIERTGFGQFFFHDWRYLPDGSPNPEFV
RAAC00639                MMEPMVRHEGLVVCMNRVNVDTDQIIPKQFLKRIERDGFGEFLFFDWRYLPDGSPNPDFE
ref|YP_080099.1|         -MEPLKTHNGIAAVLNRINVDTDQIIPKQFLKRIERTGYGRFAFFDWRYLDNGDPNPDFE
ref|YP_001487689.1|      -MEPLVTIIKGKAAVLNRINVDTDQIIPKQFLKRIERTGYGRFAFFDWRYLADGSPNPDFE
                          *.*:   . *  .. ::* *:************** *:*.* *.***** :* ***:* ref|YP_148508.1|         LNRPENEGATILVADENFGCGSSREHAPWALQDYGFRVIIAPSFADIFYNNCLKNGLLPI
ref|YP_001126674.1|      LNRPENEGATILVAGDNFGCGSSREHAPWALQDYGFRAIIAPSFADIFYNNCIKNGLLPI
sp|Q67MJ3|LEUD_SYMTH     LNRPQYAGATILIAGRNFGSGSSREHAPWALSDYGFRAIIAPSFADIFYNNCFQNGLLPV
RAAC00639                LNQPEAQGATILLVDDNFGCGSSREHAVWALRDYGFRVILAPSFADIFYNNCFKNGLLPI
ref|YP_080099.1|         LNRPEYKGASILIAGENFGCGSSREHAPWALDDYGFKIIIAPSFADIFHQNCFKNGMLPI
ref|YP_001487689.1|      LNQPIYEGSSILIAGENFGCGSSREHAPWALDDYGFKIVIAPSFADIFHQNCFKNGMLPI
                         **:*    *::**:..  ***.******* *** ****:  ::********::**:**:**:

ref|YP_148508.1|         RLDKEDVRYLLR-QSERADY-ELTVSLEEQRVFDDEGFSRPFDIDPYRKQLLLKGWDEID
ref|YP_001126674.1|      RLDQEDVRYLLQ-QSERADY-ELTVSLEEQRVFDDEGFSRPFDIDPYRKKLLLKGWDEID
sp|Q67MJ3|LEUD_SYMTH     VLPEEAVAELMR-RAQEPGY-RLTVDLERCVVEDDACFRVDFAIDAFRRHRMLHGLDDIG
RAAC00639                RIPRELYKQLSE-SHARGEWRRMTVDLEQQMAATDHGVTFSFEIDPHKRHMLLRGLDDIG
ref|YP_080099.1|         RLPYEAWKELAEQY-EYQSL-TMTVDLEKQTITDHACRQIAFEVDPHWKEMLLNGYDEIS
ref|YP_001487689.1|      RLDYDVWKTFAASY-ENKGY-EMTVDLEKQQIEDHEGNITPFDVDPHWREMLLNGYDEIS
                            :    :    :          :**.**.       . *    * :*.. :. :*.* *:*.

ref|YP_148508.1|         LTFVYEAHIAAYERRHCP------
ref|YP_001126674.1|      LTFVYESHIAAYEQKHCP------
sp|Q67MJ3|LEUD_SYMTH     LTLQYEDEIAAYEA-RRP------
RAAC00639                ITLQYFADIAAYEASRRPYQFVYA
ref|YP_080099.1|         LTLLLEEEIEQFEKQR--------
ref|YP_001487689.1|      LTLLLEDDIQAFFDKR--------
                         :*:  *  .*  :*   :
```

FIG. 17A

```
gb|ABV27286.1|        ------FVKGLEGVLAAQSSICFIDGAAGRLTYRGIDIHVLAEH-STFEE
RAAC00642             MAAETTFKAGLEDVVSNTSEICFLDGKQGRLLYYGYDIHDLVDGGASFEE
ref|YP_826036.1|      -----TTTAGLEGIIAGESEICYIDGYLGILSYRGFNIHTLADN-AKFEE
gb|AAL17866.1|AF424980_1  -----TVTRGLEGVVATTSSISSII--DDTLTYVGYNIDDLADN-ASFEE
ref|ZP_01859643.1|    -----TATRGLEGVVATTSSISSII--DDTLTYVGYNIDDLTNN-ASFEE
ref|NP_244026.1|      ---------GLEGVVATTSSVSSII--ESVLTYQGYDIDELAEH-ASFEE
                               ***.::: *.:. :   . * * * :*. *.: :.*** gb|ABV27286.1|        TAYFLLFGHLPKQAELDAFTKQLQAEREVPTEIYTLLRTLPPT-ATPMEV
RAAC00642             VVYLLWHGELPNQSELKAFTEELASERALAEPVLDLLKRLPKD-ANAMAV
ref|YP_826036.1|      VIFLLWNGWLPRQAELDALKAALVAERELPGAIVDFLKSAPK--VNTMDL
gb|AAL17866.1|AF424980_1  VIFLLWHRKLPTKSELEELKILLAENAELPKEILDHFKMYPIDKVHPMAA
ref|ZP_01859643.1|    IIYLLWNLKLPTASELDALKKDLAENAALPKEVIEHFKMYPIDKVHPMAA
ref|NP_244026.1|      VIYLLWNGKLPNKVELKELADELANNAEIPQEVIEQMKAYPLDRVHPMGA
                       ::*        . :   *   : :.  :    ::  *   . .* gb|ABV27286.1|        LRTATSALSAYDPDGPDNSDEANVRKGIRLIARMTTLTTAYDRIRRGLEP
RAAC00642             LRTAVSFLGLYDPDDGDESLEANYRKAARLVAKIPTIVTSYERIRQGLDP
ref|YP_826036.1|      LRTAVSMLSLHDAEAQDMSAEANHRKAIRLMSKTATLVTTYDRLRNGKEV
gb|AAL17866.1|AF424980_1  LRSAVSLLGLYDEEADLMDEEANYRKAIRLQAKIPSIVAAFARVRKGLEP
ref|ZP_01859643.1|    LRSAVSLLGLYDEEADVMEEGANFRKAVRLQAKIPTIVTSFARIRSGKEP
ref|NP_244026.1|      LRTAISSLGLYDEEADLMDEAANKRKALKLQACVSTVVTAFSRIREGKEP
                      **:* * *. :*  :    . ** **. :*  ::  .::.:: *:*  *  :

gb|ABV27286.1|        VKPDPSLSMAESFLYGLTGEKPHPSSARVFDVCLILHADHELNASTFAAR
RAAC00642             VQPDPSLSAAANFFYLLRGTKPSEFEEKAFNTALILHADHELNASTFSAR
ref|YP_826036.1|      IPGDPKLSFAANFLYTLTGNRPDEIMERAFDVAMTLHADHELNASTFAAR
gb|AAL17866.1|AF424980_1  VAPRKDLSFAANFLYMLKGKEPEDIAVEAFNKVLVLHADHELNASTFTAR
ref|ZP_01859643.1|    IAPRTDLGFAANFLYMLTGNEPADIEVEAFNKALVLHADHELNASTFTAR
ref|NP_244026.1|      VAPRTDLSFAANFLYMLTGEEPDEIAVDAFNKALVLHADHELNASTFTAR
                      :    .*. * .*:* * * .*      .*:  :  **********:**

gb|ABV27286.1|        VIASTLSDMYAAITCAIGALAGSLHGGANQRVLEMLLEIGELDKVEAYVD
RAAC00642             VTAGTLSDMYSAITSAIGTLKGPLHGGANEQVMRMLLEIGDPSKAITWID
ref|YP_826036.1|      VVAATLSDIYSAITAGIGALKGPLIIGGANQDVIKWLLSLGDEEEAVKAVE
gb|AAL17866.1|AF424980_1  VCVATLSDIYSGVTAAIGALKGPLHGGANEAVMKMLTEIGSLENVEPYIR
ref|ZP_01859643.1|    VCVATLSDVYSGVTAAIGALKGPLHGGANEQVMKMLTEIDSVDNVESVIR
ref|NP_244026.1|      VCVATLSDVYSGITAAIGALKGPLHGGANEQVMAMLTEIGDVENVEPYIR
                      *  ..****:*::.:*..**:*  *.******: *:  *  :...  ::  :

gb|ABV27286.1|        NLFANKKKIMGFGHRVYRTMDPRATVLRKFAKQLGEDVGNTKWYEMAERI
RAAC00642             EALAQKKKIMGFGHRVYRTEDPRATHLRELSKQAGELKGETKWFEMSQAI
ref|YP_826036.1|      NTLARKVKIPGFGHRVYRTDDPRATHLRVLSEELGKRTGHEKLYRLSQRM
gb|AAL17866.1|AF424980_1  EKLAKKEKIMGFGHRVYRKGDPRAKHLREMSKKLTELTGEPHWYEMSTKI
ref|ZP_01859643.1|    EKLANKEKIMGFGIIRVYQQGDPRAKHLKEMSKKLTELRGESKYYEMSTKI
ref|NP_244026.1|      KALDNKQKIMGFGHRVYKNGDPRAKHLREMSKKLTSITGESKWYEMSVKI
                      :   : .* ** *******:  ****. *:  :::: .  *. :  :.:: :

gb|ABV27286.1|        EQLAFARKKLYPNVDFFSAPVFYTLNIPVDLFTPIFACSRISGWVAHTLE
RAAC00642             EKHMLEVKGLHANVDFYSASLYYSLGIPTHLYTPIFACSRISGWTAHVLE
ref|YP_826036.1|      EATVKGIKGLNPNVDFYSASAYYSLGIPIDLYTPIFAVSRMSGWTAHVLE
gb|AAL17866.1|AF424980_1  EAIVTGEKGLPPNVDFYSASIYHSLGIDHDLFTPIFAVSRISGWLAHILE
ref|ZP_01859643.1|    EEIVTSEKGLPPNVDFYSASVYHSLGIDHDLFTPIFAVSRVSCWLAHILE
ref|NP_244026.1|      EEIVTNEKGLLPNVDFYSASVYHSLGIKHDLFTPIFAVSRMSGWLAHILE
                      *       *  .****:**. :::.*.*  .*:***** **:*** ** **
```

FIG. 17B

```
gb|ABV27286.1|            QLRDNRLIRPLALYTG-PEQAEYIPISER
RAAC00642                 QYKNNRLIRPRAEYVG-PTDRKFVPLSER
ref|YP_826036.1|          QYRNNRLIRPRAEYKGNPDGQTWIPIDKR
gb|AAL17866.1|AF424980_1  QYENNRLIRPRADYIG-PGMQKFIPIEQR
ref|ZP_01859643.1|        QYSNNRLIRPRADYIG-PGKQAYVPVEQR
ref|NP_244026.1|          QYSNNRLIRPRAEYVG-PNKRQYVRLEER
                          *  :****** * * *     ::  :.:*
```

FIG. 18A

```
ref|YP_001637294.1|    ----------------------------------------------------
ref|ZP_01516643.1|     ----------------------------------------------------
ref|YP_645264.1|       ----------------------------------------------------
RAAC00727              MCFAREVLRGNSDCGIHRNRKRIGFVLPVYSFSDTRPEFLLGIPGCPKAPQAGAPSCPVR
ref|YP_146876.1|       ----------------------------------------------------
ref|YP_001125008.1|    ---------------------------------------------------- ref|YP_001637294.1|    ------------------WNGFYGPNAGYLIELYERYCADPNSVDEATRAFFAQWAPPSD
ref|ZP_01516643.1|     ------------------WNGFYGPNAGYLLELYERYCADPNSVDEATRAFFAQWTPPDE
ref|YP_645264.1|       ------------------QFYGPNLGYVLELYERYREDPGSVDEETRRFFERWSPP-R
RAAC00727              VEEGFTMANEQPGSVQTFWHQFSGPNLAYLLEQYEQYLADPNAVPEDVRSLFAQYGDPAQ
ref|YP_146876.1|       ------------------WSQFYGPNLGYVIEMYEQYLDDPNSIDPELKQLFEQWGAPVL
ref|YP_001125008.1|    ---------------------------DPDSVDPELKQLFEQWGAPVV
                                                  **.::     : :* ::    * ref|YP_001637294.1|    SAAPAGEAGQP-----------PLDVTRIVGAARLIRYIREL--------------G
ref|ZP_01516643.1|     ITSSETRDGQP-----------PLDVTRIVGAARLIRYIREL--------------G
ref|YP_645264.1|       IEVDGRVAGAA-------------LEAEKYVGAAKYIRSIRDF-------------G
RAAC00727              AVSASPIETQPVFGPQVSAL--SPRTLEAAAKAHQLAQAIRAN-------------G
ref|YP_146876.1|       EEPVSPADDETAKTHQTFRLPETPTIFSKLVAAVKLADSIRHY-------------G
ref|YP_001125008.1|    EEPVSPADPEATQTHQTFRLPETPTVFSKLVAAVKLADSIRHY-------------G
                         .                        . * :    **                  * ref|YP_001637294.1|    HLAARIDPLGSDPPGDPGLELATHGVTQADLAALPAHIVRGPIATQVRNAAEGVERLRQA
ref|ZP_01516643.1|     HLAARIDPLGSDPPGDPGLELATHGVTQADLAALPAHIVRGPIASQVRNAAEGVERLRQA
ref|YP_645264.1|       HSAARLDPLGGEPPGDPALDPAFHGITEEDLERMPSSIVGGPIAERTSNAREAVEELKRI
RAAC00727              HLAADTDPLFA-PEGSPELEASTYGLVEADLASLPASVVGGPIAQTAPTALAAIEALRKA
ref|YP_146876.1|       HLVADTNPLVKKEKKLRRLELDEYDLTEEDLKRIPVAFLCPHAPAHVKNGWDAILHLRKI
ref|YP_001125008.1|    HLAADTNPIVKKEKKLRRLELDEYDLTEEDLKRIPVAFLCPHAPAHVKNGWDAILHLRKI
                       * .*  :*:         *:  :.:.: ** :* .:    . ...  .: *::

ref|YP_001637294.1|    YSGSIGYETDQIQDYL-ERAWIREAAEDRRFFGGLDADRQRELLDRLTEVECFERFLHKT
ref|ZP_01516643.1|     YSGSIGYETDQIQDYR-ERAWIREAAEDRRFFGGLDADRQRELLDRLTEVETFERFLHKT
ref|YP_645264.1|       YCKTTGYDFGHIAHLPEERFWLRDAVESEQFYQRLEGEAARRLLRRLTRVDTFEKFLHRT
RAAC00727              YCSDLGYEFAHLSSRE-ERAWFEDQIENRRFHQPLTLDEAKALYELLARAQLFERFMHKR
ref|YP_146876.1|       YTDKIAFEFSQVHNLE-ERNWLIQQIESGAYYPSLANKERVALLRRLTEVEGFEKFIHRT
ref|YP_001125008.1|    YTDKIAFEFSQVHNLE-ERNWLIQQIESGAYYPSLANKERVALLRRLTEVEGFEKFIHRT
                       *    .::   ::     ** *: :   *.  :.  *   *    *:...: **:*:*:

ref|YP_001637294.1|    FPGQKRFSIEGCDMLIPMIDAIIRNAAVNGTKEVVIGMAHRGRLNVLAHILGKPYSMILT
ref|ZP_01516643.1|     FPGQKRFSIEGCDMLIPMIDAIIRNAAASGTKEVVIGMAHRGRLNVLAHILGKPYSLILT
ref|YP_645264.1|       FLGQKRFSVEGNDMVVPMLDRLIRHAADAGTPEVVMGMAHRGRLNVLAHVLNKPYAKIFG
RAAC00727              FVGQKRFSVEGVDALVPMVDALAKMAVDAGFDHVFIGMAHRGRLNILAHVLKKPYERIFS
ref|YP_146876.1|       YVGQKRFSIEGLDSMVPLLDELVRQAIEHEIDAVNIGMAHRGRLNVLAHVLGKPYEMIFA
ref|YP_001125008.1|    YVGQKRFSIEGLDSMVPLLDELVRQAIEHEIDAVNIGMAHRGRLNVLAHVLGKPYEMIFA
                       : *****:**   *  ::*::* :  : *         * :*********:*** ***  *:
```

FIG. 18B

```
ref|YP_001637294.1|    EFHSPDYTKDTYE---------GWTGDVKYHLG-ARKAYRESG--IAEMPITLAPNPSHL
ref|ZP_01516643.1|     EFHSPDYTKDTYE---------GWSGDVKYHLG-ARKAYRESG--IAEMPITLAPNPSHL
ref|YP_645264.1|       EFQQPERGEQSSVSEMSGE---GWVGDVKYHLG-VRNFHLEEGQEDAKVLINLAPNPSHL
RAAC00727              EFHAGNGMASDEE---LAEYMLGWGGDVKYHMGWTRTFETPNG---HKARYVLSNNPSHL
ref|YP_146876.1|       EFQHAESKNFIPS-EGSVAITYGWTGDVKYHLGAARRLRNQSA---HTMRITLANNPSHL
ref|YP_001125008.1|    EFQHAESKNFIPS-EGAVAITYGWTGDVKYHLGAARRLRNKSA---HTMRITLANNPSHL
                       :  :                ****:*  .*       ..        *:  ***** ref|YP_001637294.1|    EFINPVVEGRARAAQEHRNRPGFPEEDEKESLAILIHGDAAFPGQGIVAETLNLSRLKGY
ref|ZP_01516643.1|     EFINPVVEGRARAAQERRNRPGFPEEDEKESLAILIHGDAAFPGQGIVAETLNLSRLKGY
ref|YP_645264.1|       EHVNPVVSGMTRAAQERRDEAGFPPRQDVDAALSIVLHGDAAFPGEGVAAETLNLYRLPGY
RAAC00727              EFVDPVVEGMTRAAQDDRTRPGQPIQDVIIKAFPILVHGDAAFTGEGVVAETLNFSKIPGY
ref|YP_146876.1|       EVVNPVVLGYTRAAQEDRTKPGVPVQNTDASFAILIHGDAAFPGQGIVAETLNLSQLRGY
ref|YP_001125008.1|    EVVNPVVLGYTRAAQEDRTKPGVPEQKVDASFAILIHGDAAFPGQGVVAETLNLSQLRGY
                       * ::***  *  :****:  *  ..* * :.  ::.*::******.*:*:.***** :: **

ref|YP_001637294.1|    HTGGTIHIIINNQTGFTTDSNDSRSTLYASDLARGLEIPVVHVNADDVEACIAAARMASA
ref|ZP_01516643.1|     HIGGTIHIIINNQTGFTTDSSDSRSTLYASDLARGLEIPVVIIVNADDVEACIAAARMASA
ref|YP_645264.1|       RVGGTIHIITNNQLGFTTEKEDARSTTYASDLAKGYEIPVVHVNADDPEACLAAVSLAYA
RAAC00727              YTGGTVHIIANNHLGFTADPEQGRSTRYASDLAKGYDLPVVHVSADNPEACLRAVRLAFL
ref|YP_146876.1|       TTGGTIHIIANNMIGFTTESYDSRSTTYASDMAKGFEVPIVHVNADDPEACLAAACLAFA
ref|YP_001125008.1|    TTGGAIHIIANNMIGFTTESYDSRSTTYASDMAKGFEVPIVHVNADDPEACLAAASLAFA
                       ::*    :*::   .  *  **:*:*   :::.*.:  ***: *. :* ref|YP_001637294.1|    YREKFQKDFLIDLVGYRRWGHNEGDEPEFTQPKMYERIRNHPTVREIWARELERRGIITR
ref|ZP_01516643.1|     YREKFQKDFLIDLVGYRRWGHNEGDEPEFTQPKMYERIRNHPTVREIWARELERRGIITR
ref|YP_645264.1|       YRQRFHKDFMIDLIGYRRYGHNEGDEPVYTQPVMYEKIRNHPTVREIWARTLEERGVISE
RAAC00727              YRETFQKDIVIDLVGYRRWGHNESDDPAMTQPVMYAKIASHPTVMEIYANELVARGAFTA
ref|YP_146876.1|       YRQRFKKDFVIDLIGYRRFGHNEMDEPMATNPTMYAIINQHPTVRKLYAQKLMEKGIITE
ref|YP_001125008.1|    YRQRFKKDFVIDLIGYRRFGHNEMDEPMATNPLMYSIIHQHPTVRQLYAQKLIDKGIIAE
                       **: *:**::***:****:****  *:*   *:* **   *  .****  :::*. * :  :* ::

ref|YP_001637294.1|    EEAQARVDAVMNRLQQAFEKVRERQRLAASLPPAPPP-PVQPLRRPPIFARPVSAKTLIE
ref|ZP_01516643.1|     EEAQARVNAVMNKLQQAFDKVRERQRLAAELPPAPAPAPSLPPRRPPIFARPVSAKTLIE
ref|YP_645264.1|       GEAEKMAEEMFARMQEIHKNPSE-QLTEEDF---DTEEPHTPLVDIPETA--VEASRLEA
RAAC00727              ADLQKIDQAIDEFLLQAYKFYPE----------IHTPAAITDFSEPTEDAKPVPLEELKE
ref|YP_146876.1|       REVDEMEQEVAERLKIAYERVPK----NEDELDFTMDPPKPVVDRLPEVKTSVAKDVLHR
ref|YP_001125008.1|    REVEEMEQEVAERLKIAYERVPK----NEEELDFTMDPPKPVVDRLPEVKTGVAKDVLHR
                       :  : :: :  .::   ...  :                     .        *   . * ref|YP_001637294.1|    LNEALLDRPEGFTVHPKLERTLQRRRQAIFEESGIDWGHAEALAFASILADGTPIRLTGQ
ref|ZP_01516643.1|     LNEALLDRPEGFTVHPKLERMLQRRRQAIYEENGIDWGHAEALAFASILADGTPIRLTGQ
ref|YP_645264.1|       LNRAMLERPEGFSPNRKLERLFQKNR-GSLER--IDWAHAEALAFASLLEDGIPIRLTGQ
RAAC00727              INRALLETPPDFTVYPKLKRILERRR-DALDCGDIDWAHAEALAFGTILRSGTPIRMSGQ
ref|YP_146876.1|       VNEELLQFPDGFNVFNKLERILKRRSGVFAQNGKVDWAHAEILAFATILQDCVPIRLTGQ
ref|YP_001125008.1|    INEELLEFPADFHVFNKLERILKRRSNVFAQNGKIDWAHAETLAFATILQDGVPIRLTGQ
                       :*. :*:  * .*   **:*  :::.             : :**.*** ***.::*  .* ***::**

ref|YP_001637294.1|    DSERGTFSHRHAVLHDVVTGERFIPLHHIPQARASFAVYNSPLSEASVLGFEYGYSCHAP
ref|ZP_01516643.1|     DSERGTFSHRHAVLHDVVTGERFIPLHAIPQARASFAVYNSPLSEASVLGFEYGYSCHAP
ref|YP_645264.1|       DSERGTFSQRHAVLHDEKTGEEYVPLQNIPQARASFDIHNSPLSEMAVMGFEYGYSVNAP
RAAC00727              DSERGTFGQRHLVLHDANTNARYAPLQHLPGAKASPFVVYNSPLSETAVIGFEYGYSVEAK
ref|YP_146876.1|       DSQRGTFAQRHLVLHDVKTGEEYVPLHHISGAKASFVVYNSPLTEAAVLGYEYGYNVYAP
ref|YP_001125008.1|    DSQRGTFAQRHLVLHDVKTGKEYVPLHHISGAKASFVVYNSPLTEAAVLGYEYGYNVYAP
                       **:****.:**  ****   *     .:  **:  .  :  ****  :*****:* :*:*:****.  *
```

FIG. 18C

```
ref|YP_001637294.1|    DTLVLWEAQFGDFANGAQVIIDQFIVSGHAKWGQNPSLVMLLPHGYEGQGPEHSSARLER
ref|ZP_01516643.1|     DTLVLWEAQFGDFANGAQVITDQFIVSGHAKWCQNPSLVMLLPHGYEGQGPEHSSARLER
ref|YP_645264.1|       DALTLWEAQYGDFANVGQPIIDQFIVSGQAKWGQVSNLVLLLPHGYEGQGPEHSSARLER
RAAC00727              DALVLWEAQYGDFANVGQPLFDNFIVAARSKWGETSGLVLLLPHGFEGQAHEHSSGRVER
ref|YP_146876.1|       ETLVLWEAQFGDFANMAQVMFDQFISSGRAKWGQKSGLVMLLPHGYEGQGPEHSSGRVER
ref|YP_001125008.1|    ETLVLWEAQFGDFANMAQVMFDQFISSGRAKWGQKSGLVMLLPHGYEGQGPEHSSGRIER
                       ::*.*****:*****  .* ::*:**  :.::***: ..**:*****:***. ****.*:**

ref|YP_001637294.1|    FLQLAANDNIRVANCTTAAQYFHLLRYQAASLYADP-KPLIILTPKSLLRHPRSSSSLRD
ref|ZP_01516643.1|     FLQLAANDNIRIANCTTAAQYFHLLRYQATSLYADP-KPLIILTPKSLLRHPRSSSSLRD
ref|YP_645264.1|       FLQLAAGENIRVANPTTAAQYFHLLRAQAI-LKDHK-RPLVLMTPKSLLRHPMAASGLQE
RAAC00727              FLQLAARNNIVVANVTTSAQYFHLLRRQAARLKNP--RPLVIMTPKSLLRNPLAASKPED
ref|YP_146876.1|       FLQLAAENNWTVANLSTAAQYFHILRRQAALLTREEVRPLIIMTPKSLLRHPLAASDAEV
ref|YP_001125008.1|    FLQLAAENNWTVANLSTAAQYFHILRRQAALLKKEEVRPLVLMTPKSLLRHPLASSEAEA
                       ******:*   :** :*:*****:**  **   *        :**:::********:* ::*  .

ref|YP_001637294.1|    LTDHRFQPVLGLGAEAPAPEGVTRLILCSGKVAIDLLS--SAEWE---KTAGRVDVLRLE
ref|ZP_01516643.1|     LTDLRFQPVLGLGAEAPLPEGVTRLILCSGKVAIDLIS--SAEWE---KTAGRADLLRLE
ref|YP_645264.1|       LAEGRFHPVLDDEEARERAGSVERLILCSGKIYTELVG---SDFR---EEAEEVAIARVE
RAAC00727              LTNGRFQPVLHFAKTGEGAQAVRRLILSSGKVGVDLAAEMSKRGE---EACAHVATARVE
ref|YP_146876.1|       FVDGAFSPVLEQPGLGADAGKVERIVFGTGKLMIDLAEQIGKMES---LDWLHI--VRIE
ref|YP_001125008.1|    LVQGAFSPVLEQPGLGVDASKVERIVFGTGKLMIDLAEQIGKMDG---LDWLHV--VRVE
                       :.:  * ***     .  * *::: :**:  :*              .       *:* ref|YP_001637294.1|    LLYPFPAEELRMAMQRYPNLQEVVWLQEEPQNMGAWSFVWPRLQQLLPEGVTLRYVGRAE
ref|ZP_01516643.1|     LLYPFPAEEVQAAIRRYPNLREVVWLQEEPQNMGAWTFVWPRLQTLLPTGVTLRYVGRAE
ref|YP_645264.1|       QLYPFPEGQIREVIAGYPNLRELVWVQEEPENQGPWNFMRPRLQELLPASVKLRYIGRPE
RAAC00727              QLYPFPADRVKDVIASYPNLQEVVWLQEEPENQGPWNFMRPRLQELLPASVKLRYIGRPE
ref|YP_146876.1|       ELYPFPEEAVKDIIARYPNVKELVWVQEEPKNMGAWLYMEPRLRALAPEGVDVSYIGRRR
ref|YP_001125008.1|    ELYPFPEEAVQAIIARYPNVKELVWVQEEPKNMGAWMYMEPRLRAIAPEGVDVSYIGRRR
                       *****  ::    :   **:*:***:****:* *.*  ::  ***: :    : : *:*:

ref|YP_001637294.1|    SASPAEGLHSIHVREQARILREAVAD---
ref|ZP_01516643.1|     SSSPAEGLHSIHVREQARILREAVAN---
ref|YP_645264.1|       RPSPAQGSVSFHRREHAQIVREAFRRDS-
RAAC00727              QGFVAEGSPDVHNRVQAEILAQALANDNH
ref|YP_146876.1|       RASPAEGDPVVHRKEQERIIRCAL-----
ref|YP_001125008.1|    RASPAEGDPVVHRKEQERIIRCAL-----
                         *:*   .*   :  .*: *.
```

FIG. 19A

```
ref|YP_001125365.1|    ------------------------------------------------------QTKTD
ref|YP_147249.1|       --------------------------------------------------------KMD
ref|NP_244828.1|       ------------------------------------------------------QNKTD
ref|YP_895448.1|       --------------------------------------------------------KTD
ref|ZP_01695431.1|     --------------------------------------------------------KTD
RAAC00729              MIYTLYGLSKSVERCGNRLISARGRSARRRMSTVWFAGRIKVRPHLIIKDGIDMDGKTRSD
                                                                                : * ref|YP_001125365.1|    VILIGAGIMSATLGTLLKELAPEWDITVFERLEEAGVESSNEWNNAGTGHAALCELNYTV
ref|YP_147249.1|       VILIGAGIMSATLGTLLKELAPEWDIVVFERLEEAGAESSNEWNNAGTGHAALCELNYTV
ref|NP_244828.1|       VILIGAGIMSATLGSLLKELKPEWEIKVFEKLANAGEESSNEWNNAGTGHAALCELNYTA
ref|YP_895448.1|       VILIGAGIMSATLGSLLKELAPEWEIKVFEKLASAGEESSNEWNNAGTGHSALCELNYTS
ref|ZP_01695431.1|     VILIGAGIMSATLGTLLKELTPDWEITVYEKLAKPAEESSNEWNNAGTGHSALCELNYTP
RAAC00729              VALIGGGIMSATLGTLFRQLAPDWTITVFERLDEVAVESSNEWNNAGTGHSALCELNYTV
                       * *.******:*::.*  *:* * *:*:*   .. ************:***** ref|YP_001125365.1|    EKPDGSIDISKAIKINEQFYVSLQFWAYLVNSGVLRDPKEFIRPLPHMSFVQGEDNVAFL
ref|YP_147249.1|       EKADGSIDIGKAIKINEQFYVSLQFWAYLVNSGILRDPKDFVRPLPHMSFVQGEDNVAFL
ref|NP_244828.1|       EKSDGTIDISKAVKINEQFQISRQFWAYLVSQNLISNPQDFIMPIPHMSLVQGEDNVAYL
ref|YP_895448.1|       EKSDGSIDISKAVKVNEQFQLSRQFWAYLVKSKLIRNPQDFIMPLPHMSLVQGEKNVEFL
ref|ZP_01695431.1|     EKPDGSIDITKAVNVNEQFQLSRQFWSYLVSKGLIHNPQDFIRPIPHMSLVEGEANVAFL
RAAC00729              EQPDGSIDIKAIQVNEQFLVSRQFWSFLVRQGIIEHPRDFIVPVPHMSFVQGETNVAFL
                       *:.:*  ::**  :*  *:: .  ::  .*::*: *:****:*:  :* ref|YP_001125365.1|    KKRYETMVNNPLFKGMEFSDDPKKLAEWIPLMMENRVVNEPIAATRIESGTDVNFGALTR
ref|YP_147249.1|       KKRHETMAANPLFKGMEFTDDPKKLAEWVPLMMEGRVVDEPIAATRIESGTDVNFGALTR
ref|NP_244828.1|       KKRFKALSNIPLFEGMEFSNDPEKLKEWIPLVMEGRTSNEPIAATKIDSGTDVNFGALTR
ref|YP_895448.1|       KNRFEALSKNPLFQGMEFSDAPETLKKWLPLIMEGRTSNEPMAATKIDSGTDVNFGALTR
ref|ZP_01695431.1|     KKRFKALSAHPLFEGMTFSDDPEQLKEWIPLVMEGRTSNEPIAATKSDAGTDVNFGALTR
RAAC00729              KKRHQLLSQHPLFQGMEYSEDPERLREWIPLMMKDRKLDRPIAATWIASGTDVNFGALTR
                       *:*.:  :   *:   :::  *:  * :*::*:*:.*   :.*:*  :********** ref|YP_001125365.1|    KLFEHLKRKNVEIHYRHHVDDIKRTSDGLWELKVRDLDSGAVERHVAKFVFIGAGGGSLH
ref|YP_147249.1|       QLFEHLKRKNVEIRYRHHVEDIKRTSDGLWELKVRNLDTGTVELHAAKFVFIGAGGGSLH
ref|NP_244828.1|       MLFEHLKEQNVEVHYKHSVKDIKRTSDCSWSVKVQEIESGTIEYHTANFVFIGGGGGSLP
ref|YP_895448.1|       MLFDYLQTKNVELNYKHSVENIKRTKNGLWEVKVHDINSGKIEHHTAKFVFIGGGGGSLP
ref|ZP_01695431.1|     ILFDHLERQDVEINYKHAVQDIQRTPEGNWEVKVHDIEHNRIEYHTAKFIFIGACGGSLP
RAAC00729              MLFQYLERECVDVQCGKEVQDLKRTRDGMWQLRVRDVKTGATYEHVSKFVFVGAGGWSLL
                       **::*:  :.*::.  : *.:::**  :* *.:::*::. . . . .: :*:*:*.*.**  **

ref|YP_001125365.1|    LLQKSGIPEGRGIGGFPVSGLFMVCNNPDVVEQHHAKVYGKAKVGAPPMSVPHLDTRFIN
ref|YP_147249.1|       LLQKSGIPEGKGIGGFPVSGLFMVCNNPEVVEQHHAKVYGKAKVGAPPMSVPHLDTRFID
ref|NP_244828.1|       LLQKTGIPESKNIGGFPVSGLFMVCNKQKVVEQHHAKVYGKAKVGAPPMSVPHLDTRYID
ref|YP_895448.1|       LLQKTGIPESKHIGGFPVSGLFMVCKNQKVVEQHHAKVYGKAKVGAPPMSVPHLDTRYID
ref|ZP_01695431.1|     LLQKTGIPESKHIGGFPVSGLFMVCNNPEVINRHHAKVYGKAKVGAPPMSVPHLDTRYID
RAAC00729              LLQKSGIDEGKGIGGFPVSGLFMVCENPEIVRQHRAKVYGKAPVGAPPMSVPHLDSRVIG
                       ****:**  *.: ************:* .::..:*:******* **************:*  *.

ref|YP_001125365.1|    NQKMLLFGPFAGFSPKFLKNGSMLDLFTSVKPHNLLTMLAAGVKNMALTNYLIQQVMLSK
ref|YP_147249.1|       NQKMLLFGPFAGFSPKFLKNGSMLDLFTSIKPHNVLTILAAGVKNMSLTNYLIQQVLLSK
ref|NP_244828.1|       NKKSLLFGPFAGFSPKFLKTGSNFDLIGSVKPYNVFTMLAAGAKEMSLTKYLIQQVMLSK
ref|YP_895448.1|       NKKALLFGPFAGFSPKFLKTGSNLDLIGSVKPNNVLTMLAAGVKEMGLTKYLIQQVMLSH
ref|ZP_01695431.1|     HKKCLLFGPFAGFSPKFLKTGSNLDLIGSVKPNNVVTMLASGAKNVPLVKYLIGQLLLSD
RAAC00729              GREYVLFGPFAGFSPRFLKTGSMLDLLKSVKLHNLSTLLAAGAKNASLTLYLIRQLMLTK
                       ::  :*********:***.**  :**:  *:*  *:  *:**:*.*:   *. *** *::*:.
```

FIG. 19B

```
ref|YP_001125365.1|    EQRMEELREFVPTAKSEEWDVIVAGQRVQVIKDTEAGGKGTLQFGTEVVHAADGSIAALL
ref|YP_147249.1|       EQRMQELREFVPTAKSDEWDIVVAGQRVQVIKDTESGGKGTLQFGTEVVHAADGSIAALL
ref|NP_244828.1|       EKRMAELREFMPNAKSEDWDIVVAGQRVQVIKDTEAGGKGTLQFGTEVVSSADGSIAALL
ref|YP_895448.1|       EKRMEELREFIPNAKSEDWDIVVAGQRVQVIKDTDAGGKGTLQFGTEVVSAADGSIAALL
ref|ZP_01695431.1|     EKRLETLQEFIPDARLEDWDVVVAGQRVQVIKDTEAGGKGTLQFGTEVVTAADGSVAALL
RAAC00729              KQRMDELREFVPTARDEDWRLVVAGQRVQVIKRRP---RGELQFGTEVVSARDGSIAALL
                       ::*:  *:**:*  *:  ::*  ::**********    :* ****** : *:**** ref|YP_001125365.1|    GASPGASTAVHVMLEVITKCFPERMKEWEPKVREMIPSYGVSLMKNERLLHDVQAATAEM
ref|YP_147249.1|       GASPGASTAVIIVMLEVMEKCFPERMNEWRAKVKEMIPSYGESLMKNEALLRQVQASTAEA
ref|NP_244828.1|       GASPGASTAVHVMLEVLEKCFPHHMLEWQPKIKEMIPSYGVSLAENRELFQEIHQSTAEA
ref|YP_895448.1|       GASPGASTAVHVMLEVLEKCFPSRMVEWEGKIKEMIPSYGISLTENPRLFQDLHTSTGRT
ref|ZP_01695431.1|     CASPGASTAVHVMLEVIEKCFPDRKNAWAPKIKEMIPSYGVRLAENPELLHQIHAETAET
RAAC00729              GASPGASVVVSIMLEVIRKCFPDRLPEWENKIREMIPSYGVTLRHRPDLMRSIQAETAEV
                       ******..* :****: ****  :   *  *:******* *  .. *::.:: *..

ref|YP_001125365.1|    LGL---------
ref|YP_147249.1|       LGLN--------
ref|NP_244828.1|       LGLSEKE-----
ref|YP_895448.1|       LGLNEKE-----
ref|ZP_01695431.1|     LGLTEKE-----
RAAC00729              LGLHRMEARTDA
                       ***
```

FIG. 20A

```
sp|P16468|MAOX_BACST    -----AAMNITIRLQFEKDIVSFSDIAAAIGKAGGDIVGIDVISSSKVHTVRDITVSALD
ref|YP_147293.1|        -----AAMNITIRLQFEKDIVSFSDIAAAIGKAGGDIVGIDVISSSKVHTVRDITVSALD
ref|YP_001125416.1|     ------------------------------------------------------------
ref|YP_075148.1|        -----ASMRIIVRLEIENTGSIFSYIATAIGASGGDIVAVDLIQSRRDVVVRDITIAVEN
RAAC00730               MEFQRSGTSLIYRLEIANKGNTFAKVASLVGNAGGDIAAVDVIRVTQDVVVRDVTINVAN
ref|YP_643888.1|        --------SMTLRVEFPHRAGALGRILTTIGDAGGMVGAIDIVRMGQERSIRDITVNARD sp|P16468|MAOX_BACST    TKQCDLIIEALKKIRGVKIVNVSDRTFLMHIGGKIETNSKIPVKTRDDLSRVYTPGVARV
ref|YP_147293.1|        TKQCDLIIEALKKIQGVKIINVSDRTFLMHIGGKIETNSKIPVKTRDDLSRVYTPGVARV
ref|YP_001125416.1|     ------IIEALKKIRGVKIVNVSDRTFLMHIGGKIETNSKIPVKTRDDLSRVYTPGVARV
ref|YP_075148.1|        RAHGDRIVQALAALPGVKVVNVSDRIFLAHLGGKIEVKPRVQVKTRDDLSVVYTPGVADV
RAAC00730               REHGRQIAELLDAEPGTHVVAVSDRTFLVHLGGKLEVVPKIQVKNREDLSRVYTPHVARV
ref|YP_643888.1|        SEHGQRTVRAVGALPEVRVVNVSDRTFLLHLGGKIEVHSKIPVRTRDDLSMAYTPGVARV
                              *  .  :      :::: **   *:***:*.  .::  *:.:*  .* ** * sp|P16468|MAOX_BACST    CTAIAEDPRKAYSLTIKRNTVAVVSDGTAVLGLGDIGPYAAMPVMEGKAMLFKEFAGVDA
ref|YP_147293.1|        CTAIAEDPRKAYSLTIKRNTVAVVSDGTAVLGLGDIGPYAAMPVMEGKAMLFKEFAGVDA
ref|YP_001125416.1|     CTAIAEDPRKAYSLTIKRNTVAVVSDGTAVLGLGDIGPYAAMPVMEGKAMLFKQFAGVDA
ref|YP_075148.1|        CRAIAEDPAKAFTLTIKRNTVAVVTDGTAVLGLGNIGPAAALPVMEGKAMLFKQFAGVDA
RAAC00730               CEAIHEDPSKAFQLTIKRNTVAVVSDGTAVLGLGDIGPYAAMPVMEGKAMLFKQFAGVDA
ref|YP_643888.1|        CRAIAQEPERAFNLTIKRNSVAVVTDGTAVLGLGDIGPYAAMPVMEGKAMLFKEFAGVDA
                        * **  ::* :*: **:** *:****:**.* :******:**** sp|P16468|MAOX_BACST    FPICLDTKDTEEIIQIVKAIAPAFGGINLEDISAPRCFEIEKRLKEELDIPVFHDDQHGT
ref|YP_147293.1|        FPICLNTKDTEEIIQIVKAIAPAFGGINLEDISAPRCFEIEKRLKEELDIPVFHDDQHGT
ref|YP_001125416.1|     FPVCLDTKDTEEIIQIVKAIAPAFGGINLEDISAPRCFEIEARLKEELDIPVFHDDQHGT
ref|YP_075148.1|        FPICLDTTDPDEIVRIVKAIAPAFGGINLEDISSPRCFEIEERLKEELDIPVFHDDQHGT
RAAC00730               FPICLDTKDPDEIVETVKRIAPAFGGINLEDISSPRCFYIEERLKQELDIPVFHDDQHGT
ref|YP_643888.1|        FPVCLDTKDPEEIVRTVKYVAPAFGGINLEDISAPRCFEIEERLKQELDIPVFHDDQHGT
                        ::** .*. ::.   :***********.   *:*********** sp|P16468|MAOX_BACST    AVVLLAGLLNALKIVDKKLEDIKVVLTGIGAAGIACTKILLAAGVRNIIGVDRHGAIHRD
ref|YP_147293.1|        AVVLLAGLLNALKIVDKKLEDIKVVLTGIGAAGIACTKILLAAGVRNIIGVDRHGAIHRD
ref|YP_001125416.1|     AVVLLAGLLNALKIVDKKLEDIKVVLTGIGAAGIACTKILLAAGVRNIIGVDRYGAIHRD
ref|YP_075148.1|        AVVVLAGLMNAARVVGKELADLRVVVCGIGAAGVAISKMLMAAGITNIVGVDRVGIIERG
RAAC00730               AVVMLAGLMNAAKLVGKKLQDLKVVIVGIGAAGVACTKMLLSAGVKNIIGVTLEGILHRG
ref|YP_643888.1|        AVVVLAALINALRIVGKRMEELKVVVCGVGAAGVACAKILLAAGVKNIVGCDRYGVVYRG
                        ***:**.*:**  ::*.*.: :::.**: *:****:* .*:*:*::**  **:*    * : *.

sp|P16468|MAOX_BACST    ETYENPYWQEYAQLTNPDNLKGSLSDVIAGADVFIGVSAPGILKVEDVKKMARDPIVFAM
ref|YP_147293.1|        ETYENPYWQEYAQITNPDNLKGSLSDVIAGADVFIGVSAPGILKVEDVKKMARDPIVFAM
ref|YP_001125416.1|     ETYENPYWQEYAQITNPYNLKGSLSDVIVGADVFIGVSAPGILKVEDVKKMARDPIVFAM
ref|YP_075148.1|        KTYENPMWQWYAEHTNPENRHGTLDDAIEGADAFIGVSAPNVLKVEHVKKMAKDPIVFAM
RAAC00730               KQYDNEIWNWYKEHTNPDNITGTLDDAIVGADVFIGVSGPGVLTVDHIKKMAPDPIVFAM
ref|YP_643888.1|        RGDADTSRGWFAENTNPENIRGTLADAIRGADVFIGVSAPDVLTVEHIESMADEPIVFAM
                          .  :     : : *** *  *:* *.* *.*** .*:*.*:::..  :**** sp|P16468|MAOX_BACST    ANPIPEIDPELAEPYVRVMATGRSDYPNQINNVLCFPGIFRGALDCRAREINEEMKLAAA
ref|YP_147293.1|        ANPIPEIDPELAEPYVRVMATGRSDYPNQINNVLCFPGIFRGALDCRAREINEEMKLAAA
ref|YP_001125416.1|     ANPVPEIDPELAEPYVRVMATGRSDYPNQINNVLCFPGIFRGALDCRAKEINEEMKLAAA
ref|YP_075148.1|        ANPVPEIDPDEAAPYVAVMATGRSDYPNQVNNLLCFPGIFRGALNCRARQINEAMKLAAA
RAAC00730               ANPTPEIEPELAAPHVRVLATGRSDYPNQINNLLCFPGMFKGALAARASTINEEMKLAAA
ref|YP_643888.1|        ANPDPEIRPEIAYGHARIIATGRSDYPNQINNVLCFPGVFRGALDIRARFINEEMKLAAA
                        *** ***  *:.*    :.  ::**********:**:****:.*.***   **  *** ******
```

FIG. 20B

```
sp|P16468|MAOX_BACST    KAIASVVTEDELNETYIIPSVFN-------------------------------
ref|YP_147293.1|        KAIASVVTEDELNETYIIPSVFN-------------------------------
ref|YP_001125416.1|     KAIASVVTEDELNETYIIPSVFN-------------------------------
ref|YP_075148.1|        RAIASVVSDEELHAEYIIPSVFN-------------------------------
RAAC00730               QAIASIIRENELREDYIIPSVFNQAVVQRVADAVADAARRTGVARREVMPKDNY
ref|YP_643888.1|        RAIAGVIPEESLSEDYIIPSVFD-------------------------------
                        :***.:: ::.*   *******:
```

FIG. 21A

```
ref|ZP_01696337.1|     ------------------------GEALLKTIQNIRSLAQKARETGDEAFYLQLKKEI
ref|ZP_02171753.1|     ------------------------GEALFNEVEEIREMTKALRKSYDEANEKELKKRI
RAAC00735              MANDAPLHRDIRVLGDLLGEVLVEQCGRRVFDIVESIRLAAKAFRADPSPETRAALQAAV
ref|YP_001546997.1|    ------------------------QDGVSAFELEEDVRQRTKQRRSDGTLQETQTLTELI
ref|YP_001277075.1|    ------------------------QAGEEEAFRLVEQLRTLGKELRNGEPDRADASLRALA
ref|YP_284976.1|       -SKDEPLRTDIRLLGRILGDTVREQEGESVFDIVERVRQTAVRFARDGDPAARDELAALL
                                                *     :    : :*                * ref|ZP_01696337.1|     TDLNPPERQEVIRAFSTYLQLFNITEQNFRIKRRREYQSEDTDQVQPRSLEDGIETLRKE
ref|ZP_02171753.1|     ENLKSPMRQQVIRAFAIYFHLVNIAEQHHRIRRSRQYRMKRGENIQPSSIEAAIVNIQKE
RAAC00735              SAVEPEHRNDVIHAFSVYFQLVNLAEQNHRLRRHRDYD--RSQQVLRCSFRETMRTLADR
ref|YP_001546997.1|    SQLPVAQLMGLIKAFTHYFGLVNLAESVERLRVLAERDRQNGDAPRSESVELALQELRDR
ref|YP_001277075.1|    SQMTVTDVQTVIKAFNAYFLLVNLAEQMQRVWILRDREQASPTAPRTESIAAAIAEIHAH
ref|YP_284976.1|       DPLPGDTTQAVVRAFSYFQLANIAEDEHHIRRRAHDLAGSPP-REGSLIFALDALSTA
                              :::**   ::  * *::*.  ::              : :   *. :

ref|ZP_01696337.1|     KVPAEMVAELLNSLSLELIITAHPTEATRRTILQIHKRIADLLKALEYAN-TRYEKKVIE
ref|ZP_02171753.1|     KYPETVIQQVLDDSSIELIMTAHPTEATKRTILEIQKRISYILEQFDNPALTEKEREDHE
RAAC00735              GMTADDIESLLREVGIELVLTAHPTEALRRTVLDKHTKIAAFLEDMDDPRKTPRELDVLR
ref|YP_001546997.1|    GITAQQVQDLLDHAEIRPVFTAHPTEAKRRTTLKKHHRIAGAARQLTADTTFQRQRERLL
ref|YP_001277075.1|    NVSAVTVQEWLETARIQPVFTAHPTEARRRTALEKVRRLATLL-DRRSGGLQGFELEENT
ref|YP_284976.1|       AVSPEAIADFFAHVVAPVLTAHPTEVQRQSLIRNHRDLAHLLDQRERLQMTPEEEAEND
                            . :  . :     ::******. :::  :        ::

ref|ZP_01696337.1|     ETILNEITILWQSSEIREKKPSVLDEVKNGLYYFDNVLFDVLPRIHEDLEDYLHESYG-Q
ref|ZP_02171753.1|     ESLINEVTALWHTDELRFKKPTVIDEVKNGLYYFDTTLFDVLPAVHQEIEEQLERYYPDQ
RAAC00735              ERIRTEIVALWQTRSVRKQRITVLDEVRNGLYFLDQILFDVLPRVHQKLEQAVEEQFGRQ
ref|YP_001546997.1|    ESIREEVISLWQSDEVRIIKPTVIDEVKNNLYYFEESLFDMIPQLYRDTEASLRQIYPEH
ref|YP_001277075.1|    LRIREEIVSLWQTDEVRVVKPTVIDEVKNGLFYFESGLFDLIPRLYRELEYALRTAYPDH
ref|YP_284976.1|       LALANAILTLWQSRMLRPVRLKVLDEVKNGITYFKETFFTELPRLYIQATEQLQKRYPEK
                           :   **::  :*   : .*:***:*.: ::.  :*  :*  ::  .  :.  : :

ref|ZP_01696337.1|     RFKVPSYLHFGSWIGGDRDGNPNVTADITWKTLEMQRELVLEKYKKSLTTLRELLSHSSK
ref|ZP_02171753.1|     DFKVPNFIHFGSWIGGDRDGNPFVTPEVTWETLNLQRDLTLRKYEESITELMRRFSQSTT
RAAC00735              LLELPPLIRFGSWMGGDRDGNPNVTSDITWQTLVLHCDLALNKYEQKLRELGRDLSVSVD
ref|YP_001546997.1|    EWRVPAFLRFGSWVGGDRDGNPFVIPSVTVETLKLLMGRSLREHIHSVERLSHRLSQSSR
ref|YP_001277075.1|    EWRVPPLLRYGAWMGGDRDGNPNVTHAVTLQTVRLLRAAAVQRHITTIEELSHRLGQSTR
ref|YP_284976.1|       TWALPPFFRVGSWIGGDRDGNPFVTADILREALRLQSSAALNHYLNEVHELGGELPLSDL
                           :*   :: *:*:********   :    :::     :   ...:      *    : * ref|ZP_01696337.1|     KISASHALLASVES-EENTMPAAKL----WPTKDEIYRRKLTIMIHKLECVGKNNGG---
ref|ZP_02171753.1|     RVDIDPEFIETMEQYEKKYMKKSET----WPVTTEIYRRMLGAIRKRIRQVGKTNTG---
RAAC00735              RAGADEDLLASLGG------ENDEP----YRALINRMLFRLANTRRRLHGERVDGPD---
ref|YP_001546997.1|    QVPISEELAQSL--IHDAPLFPELAQVLERRNPHEPYRQKCSYIHAKLHATLAYVERYEP
ref|YP_001277075.1|    QAPVSEELRASL--ANDAALFPDVADMLTQRNPYELYRQKCTYIREKLLRTLNDANTASL
ref|YP_284976.1|       LVKVTPELLALAEH------STDHS----PQRADEFYRRALSGIYARLAATARALDQFEP
                                                :             :   .    ::

ref|ZP_01696337.1|     ---------------YQSAKELLADLYMIRDSVNQHHPAGHPIKLLRKVIRQVELFGFHLA
ref|ZP_02171753.1|     ---------------YDVAEELLADLRYVRENALKHQLPNQKLKQLNKMIRQVELFGFHLA
RAAC00735              ---------------YASPEAMMEDVERMARSLAHHRGQRMVDAWLRPFLLQLRIFGFHMV
ref|YP_001546997.1|    DWARGGHRPAEGTWYANANQYLADLATMEYSLRTNGAASVADGFLRDIQCSAKVFGLHTA
ref|YP_001277075.1|    DWGRS--DPPPNGAYLRSDDLLADLRVMEQSLRANNAAVVADGALRDLIRQVEVFGLHTA
ref|YP_284976.1|       VRHEIG----HATPYDTPDALRADLKLLANSLKLNGSAKLAGGRLRRLLRGVQIFGFHIA
                             *  ..    *:  :    .   :       *. .    ..:**:*  .
```

FIG. 21B

```
ref|ZP_01696337.1|      SLDIRNHSGEHESALAEVLYNVNIAKDYKNLSEDEKVAVLLKALNDPRPMISIYDTFTPE
ref|ZP_02171753.1|      TLDVRNHSGEHETAIAEILKVVGITEDYKSLDEEEKMTILENALKDPRPLMLLNEDYSEE
RAAC00735               TLDIRQHSGVHEQAVAELLQTAGLVDDYTSLGEEERVRVLSECLASPRPIRNPYHVYSDV
ref|YP_001546997.1|     TLDIRQHSSRHTNALSEIFEYACICDDYASLSQAERTAVLERELANNRPLTPTHLYYSPE
ref|YP_001277075.1|     TLDIRQHSERHTAALAEVLASAGVCADYTALNETERIDLLSREIGNPRPLIPAHLDYSPD
ref|YP_284976.1|        PIDLRQNSDVHARSVAELLAGAGRCPDYEALSEAERIKLLVDEISTPRPLYSPYLNYSEE
                         .:*:*::*   *   :::*::    ..    **   *.:  *:    :*      :      **:          ::

ref|ZP_01696337.1|      TQEVINTFRMIKRAHQTFGERSIQVYLISMAHSVSDVLEVLVLAKEAGLYRVYPSGDIL-
ref|ZP_02171753.1|      TREIFKVFQMIKDAHEEFGQRSIEVYLVSMTQSASDLLEVLVLAKEAGIYRLHADGSV--
RAAC00735               TTEALAVLDCVRRGHETFGPRCVQDYLISMTQCASDLLEVLLLAKESGLFG-WPDGPMAP
ref|YP_001546997.1|     TVEIIETFRTIRAVLSDLNAEAIETYIISMTEGPSDILAVLLLAREAGLY-------QPG
ref|YP_001277075.1|     TVEVIQTFRTIAAILNRLSPEAIETYIVSMTRGASDLLAPLLLAKEAGLF-------RPF
ref|YP_284976.1|        TQGELAIFFAARELRQKYGSAALPNCIISKTDGVSDLLELALLLKESGLLL-----PGAK
                         *     :    :     .   . .:  ::*   :  .   **:*        :*  :*:*:

ref|ZP_01696337.1|      --SEIHIAPLLETIADLRNGAKMLETLFQMPIYRNHLKVRGNLQEVMLGYSDGSKDGGTM
ref|ZP_02171753.1|      -DSNLHVAPLLETVDDLMAGPAIMKRLFEMDIYRTHLGERGDHQEIMLGYSDGSKDGGTL
RAAC00735               PKSDLNVVPLFETIEDLESAAGIMRSLFENPVYRRHLEMRGWQQEIMLGYSDSNKDGGYL
ref|YP_001546997.1|     EHSWLNIVPLFETGADLIAAPEIMHTLLSSEAYRQHLVLRNDVQEIMLGYSDSNKDGGFA
ref|YP_001277075.1|     RFSRLNIAPLFETGADLTCCDTILEACLSLPVYRDHLALRGNLQFVMTGYSDSNKDVGYV
ref|YP_284976.1|        PQLKVNIIPLFETIEDLQKSAATMAGVFAIPAYRELIAGRGDEHEVMLGYSDSNKDGGFL
                         :::  :          :       :          :  *.  .  :*:*:**..  * ref|ZP_01696337.1|      TANWQLYKAQKEIHEMGAKYGIKLKFFHGRGGSLGRGGGPLYSSLLSQPPVTLGDGVKIT
ref|ZP_02171753.1|      TANWKLFEAQAKTHNMAKDYNVRLKFFHGRGGSLGRGGGPLNRSIVSQPAETLGDGVKIT
RAAC00735               TANWSLYMAQKHLIRLAEAYGVRIKFFHGRGGALGRGGGPVEQSILAQPTEALRGHVKIT
ref|YP_001546997.1|     DAHWALYLAQVALAETCFRHRVAMRLFHGRGGAVGRGGGPANRAILGQPPGTVGGRIKIT
ref|YP_001277075.1|     AANWALYQAQRKLRDFGRRYGIHMRLFHGRGGAIGRGGGPANHAILAQPPGSIGNQIKIT
ref|YP_284976.1|        TSGWELYKAEIELARIFGQHGVRLRLFHGRGGSVGRGGGPTYHAILAQPAGAVAGQIRLT
                         :    *   *:  *:         :    :  :::****::**   :::..  ::    . :::* ref|ZP_01696337.1|      EQGEVLSSRYLLRDIAYRSLEQATSTMMCAITEQKQNE-KNGKTPNEEAVRAMDKISEYA
ref|ZP_02171753.1|      EQGEVLSSRYLLGDIAFRNLEQAASALLEASANVYASPGDSCHTRRFQWEEAMEEISKAS
RAAC00735               EQGEVISQRYGHPGIAERSLESSAAAVLVGATREDSEE---WAERHPRWFRLLDRASEIS
ref|YP_001546997.1|     EQGEVISDRYAEPETAYRHQEQIINAVLRSSL---GVS---IAHISQEWHDAMSSLAKVS
ref|YP_001277075.1|     EQGEVIADRYGLPLLAHRHIEQVMNAVLRAGLLQRDDP---PAE----WMQALERLADLS
ref|YP_284976.1|        EQGEVISTKYGNADTGRRNLEVLLAATLE-ASLTDHEN---RVEPAEQFHAVMDELSARA
                         *****::  :*      .   *   *     : :                              :.   . :

ref|ZP_01696337.1|      LEKYQELVFRDPDFLSYFKQATPLNEIGELNIGSRPMSRKGSARFEDLRAIPWVFSWTQS
ref|ZP_02171753.1|      LSKYQSLVFKDPDFLTYFKETTPLNELKELNIGSRPMSRKGSERFEDLRAIPWVFAWTQC
RAAC00735               FRAYRKLVFEHPAFLEYFHRATPIDEIGKMNIGSRPSRRSQSARIEDLRAIPWVFSWTQS
ref|YP_001546997.1|     RKVYRGLVYDHPHFLEYFRNATPITEISRLNIGSRPASRKASDRIEDLRAIPWVFSWMQS
ref|YP_001277075.1|     QRHYRALVYERNDFVPYFHNVTPITEISRLNIGSRPASRRNTGRIEDLRAIPWVFSWMQS
ref|YP_284976.1|        FNAYRGLVYETPGFTTYFRQSTVVSEIASLNIGSRPASRKASERIEDLRAIPWVFSWAQC
                         *:  **:       *   **:.  *   *:    :******    *    :  *:**********:*  *.

ref|ZP_01696337.1|      RQLLPAWYAAGTGLSKYV-EETGN------------------------FKL--LQEMY
ref|ZP_02171753.1|      RQMLPAWYASGTGLAAYGKASFEN------------------------LEL--LQDMY
RAAC00735               RHLLPAWYGFGSAIFAIMREDPRA------------------------LED--LRRMY
ref|YP_001546997.1|     RHTLPGWYGLGSALEHLIQA------DANG------------------LTT--LQGMY
ref|YP_001277075.1|     RHTLPGWYGMGFALFTFVYKGDGIDLDMSGDSGNVTGDGTTDHVGSAIDRLAL--LQEMY
ref|YP_284976.1|        RLMLPGWYGFGAAVEGYLQANPAG------------------------LAT--LRRMV
                         *   **.**.  *  .:                                           :    *: *
```

FIG. 21C

```
ref|ZP_01696337.1|      ASWPFFHATINNLQMALIKAELSTAEEYTRLVKDPEVAGRIFGLIKAEYELTKEMVLKIA
ref|ZP_02171753.1|      QNWPFFHSTINNLQMALMKADLFAAKEYVKLVKDQEMGQRIYGEIEKEFNLTKEMLLKIS
RAAC00735               EVWPFFRTLVDNLQMALAKADMLVAKEYAQLAG--EAGEAVFPLIEEEYARTERAVLDIT
ref|YP_001546997.1|     NDWPFFRTMLDNAQMILSKADMDIAAQYALLVPDQALANEIFGLIKAEYTRTVKWICEVA
ref|YP_001277075.1|     ARWSFFRVMIDNAQMILGKADLHIAARYAELAPDREAAASTFAATRDEYGRTDRMIRQIA
ref|YP_284976.1|        HAWPFFKSLLSNMDMVLAKTDLAIASRYAELVADVELREHIFSRIKAEWALTRQHLLAIL
                         *.**:  :.* :* * *:::   *  .*. *.            ::  *. *:  *  . :  :

ref|ZP_01696337.1|      DQKELLDYTPNIKESVRLRNPYVDPLNLFQVYLISQLRERENKD-EKARHLLMEVLLTIN
ref|ZP_02171753.1|      GSEQLLDFTPNIRDSVHLRNPYVDPLNFLQVDLIEKMR-ESSSE-ERTEELLTEVLLTIS
RAAC00735               GYRQLLDNRPVIRESISLRNPYVDPLSFFQVRLLADLRTDNLSP-EEREAELADALQTIN
ref|YP_001546997.1|     QTNELLDTSPILQHSIKQRNPYVDPLSFVQIELLRRLRTDPDGL-EHSDLEDA-ILLSIN
ref|YP_001277075.1|     RIERLLDNSPVLQHSIQRRNPYIDPMSYLQIELLRRLRAAPDGP-QHAAIEDA-ILLSIS
ref|YP_284976.1|        EQDEFLADNPLLARSLQLRSPYMDPLNHLQVELLKRHRAG-----DTDERLARGIHLTIN
                         .:*    * :  *:  *.**:**:. .*: *:   *          :        :*.

ref|ZP_01696337.1|      GIAAGLRNTG
ref|ZP_02171753.1|      GVAAGLLNTG
RAAC00735               GIAAGLRNTG
ref|YP_001546997.1|     GIAAGLKNTG
ref|YP_001277075.1|     GLAAGLMNTG
ref|YP_284976.1|        GIASGLRNSG
                        *:*:** *:*
```

FIG. 22

```
ref|YP_001378696.1|      ------------------NKLVESADAAVADIRDGATVMVGGFGLCGNPENLIAALHRKG
RAAC00812                MHHGASRLGRMGVRFMRSNKVYESAGAAIADIPNGATLLVGGFGLCGIPMALIQALRDRG
ref|YP_386234.1|         ------------------KVQSSIEKALEGIQDGATLMVGGFGLVGIPEKLILGLREKG
ref|ZP_01723286.1|       ---------------MKDGKVWGSFEEAVADIKDGDMLAVGGFGLCGIPEKAIAALVQKG
ref|NP_391778.1|         ------------------KVLSSSKEAAKLIHDGDTLIAGGFGLCGIPEQLILSIRDQG
ref|ZP_00539373.1|       ---------------MQQGKIYDSFTEATADIFDGATLVVGGFGLCGIPEKSIAALQEQG
                                            *:   *    *  *:*   :  .***** * *    *  .:  :* ref|YP_001378696.1|      VKDLTVISNNCGTTEQGLGILLKARQIRKMVSSYVGENKEFERQYLSGELEVELVPQGTL
RAAC00812                VSDLVCVSNNCGVDDWGLGILLQTRQIRKMVSSYVGENKTFERQFLNGELFVELVPQGTL
ref|YP_386234.1|         VKNLTVISNNCGVDDFGLGILLQNRQIRKMVSSYVGENKEFERQFLSGELEVELTPQGTL
ref|ZP_01723286.1|       TKDLTVVSNNCGVDDWGLGLLLANKQIKKMVASYVGENKIFEQQFLSGELEVELTPQGTL
ref|NP_391778.1|         VKDLTVVSNNCGVDDWGLGLLLANKQIKKMIASYVGENKIFERQFLSGELEVELVPQGTL
ref|ZP_00539373.1|       VKELTVVSNNCGVDDFGLGILLQSRQIKKMVSSYVGENKTFEQQYLSGEIEVDLVPQGTL
                         ..:*. :***. : *:  :::*** ::*.::*.***** ref|YP_001378696.1|      AERIRAGGAGIGGFYTATGVGTQVAEGKETRVIDGREYLLERPLVADFALVYAWKADTWG
RAAC00812                AERIRAGGAGIPAFYTATGVGTSVAEGKEVRTFDGREYVLERAITGDFALIKGWKADKLG
ref|YP_386234.1|         AERIRAGGAGIPAFYTPAGVGTPLAEGREVRSFNGREYLLETGLVADFALVKAWKGDWMG
ref|ZP_01723286.1|       AERLRAGGAGIPGFYTATGVGTPIAEGKEVKVFDGKDYILEKGITADFALVKAWKADKLG
ref|NP_391778.1|         AERIRAGGAGIPGFYTATGVGTSIAEGKEHKTFGGRTYVLERGITGDVAIVKAWKADTMG
ref|ZP_00539373.1|       AERIRAGGAGIPGFYTPTGVGTPIAEGKEQKQFDGKTYLLEECIVGDFALVKAWKADKLG
                         *:***  .*.:**  :*:*   :  .*:  *:**    :..*.*::    * ref|YP_001378696.1|      NLLYRKTTRQFGPMMATAARITIAEVEHVVQPGEIDPDVVHTPSIYVKRLVRGERYEKWI
RAAC00812                NVIYHETERNFNPVMATAAKVTIEVEELVEPGFLDPNFIHTPSIYVHRIVVNPNPIKRI
ref|YP_386234.1|         NLIYNKTSRNFNPMMATAAKVTIAEVEDLLDPGELDPAFIHTPGVYVQRIVLCGNYEKRI
ref|ZP_01723286.1|       NLVYRKTSRNFNPLAAMAGKITIAEVREIVEIGELDPDHIHTPGVFVQRVLLGENYEKRI
ref|NP_391778.1|         NLIFRKTARNFNPIAAMAGKITIAEAEEIVEAGELDPDHIHTPGIYVQHVVLGASQEKRI
ref|ZP_00539373.1|       NLVFRKTSRNFNPLVATAGKVTIAEVEELVEVGELDPNEIHTPAVYVQRIIVGTDYEKRI
                         *:::.:*  *:*.*:  *  *.:.**.*.*.:::  :   :***.::*::::        * * ref|YP_001378696.1|      ERRTVRPR---
RAAC00812                ERRTVRPRPQA
ref|YP_386234.1|         ERRTVR-----
ref|ZP_01723286.1|       ERLTVK-----
ref|NP_391778.1|         EKRTVQ-----
ref|ZP_00539373.1|       ERRTVR-----
                         *: **:
```

FIG. 23A

```
ref|YP_147293.1|       ------------------------------MNITIRLQFEKDIVSFSDIAAAIGKACGDI
sp|P16468|MAOX_BACST   ------------------------------MNITIRLQFEKDIVSFSDIAAAIGKACGDI
ref|YP_001125416.1|    ------------------------------------------------------------
ref|YP_075148.1|       ---------------------------RLASMRIIVRLEIENTGSIFSYIATAIGASGGDI
ref|YP_643888.1|       ---------------------------------------------ALGRILTTIGDAGMV
RAAC00196              MFQSAWLMRMAEPWPETQGEWNVTLTRAGNVRVLFRVRLEAG-AALGEVHGAIVRAGGET ref|YP_147293.1|       VGIDVISSSKVHTVRDITVSALDTKQCDLII-EALKKIQGVKIINVSDRTFLMHIGGKIE
sp|P16468|MAOX_BACST   VGIDVISSSKVHTVRDITVSALDTKQCDLII-EALKKIRGVKIVNVSDRTFLMHIGGKIE
ref|YP_001125416.1|    -------------MRDITVSALDTKQCDLII-EALKKIRGVKIVNVSDRTFLMHIGGKIE
ref|YP_075148.1|       VAVDLIQSRRDVVVRDITIAVENRAHGDRIV-QALAALPGVKVVNVSDRIFLAHLGGKIE
ref|YP_643888.1|       GAIDIVRMGQERSIRDITVNARDSEHGQRIV-RAVCALPEVRVVNVSDRTFLLHLGGKIE
RAAC00196              VAMETRALHADHSVRDITVAV-DTEPDVRAVEQALDEVQGVKRLETLDRTFLVHGGKIA
                            :****:  . :          : .*:    : *: :.    *:**** ref|YP_147293.1|       TNSKIPVKTRDDLSRVYTPGVARVCTAIAEDPRKAYSLTIKRNTVAVVSDGTAVLGLGDI
sp|P16468|MAOX_BACST   TNSKIPVKTRDDLSRVYTPGVARVCTAIAEDPRKAYSLTIKRNTVAVVSDGTAVLGLGDI
ref|YP_001125416.1|    TNSKIPVKTRDDLSRVYTPGVARVCTAIAEDPRKAYSLTIKRNTVAVVSDGTAVLGLGDI
ref|YP_075148.1|       VKPRVQVKTRDDLSVVYTPGVADVCRAIAEDPAKAFTLTIKRNTVAVVTDGTAVLGLGNI
ref|YP_643888.1|       VHSKIPVRTRDDLSMAYTPGVARVCRAIAQEPERAFNLTIKRNSVAVVTDGTAVLGLGDI
RAAC00196              THLKVPVVDRDDLAVVYTPGVARVCEAIRDRRDRAFEFTIRKNTVAVVSDGSAVLGLGNI
                       .: :: *  **: .**  **    :*: :**::*:**::******:* ref|YP_147293.1|       GPYAAMPVMEGKAMLFKEFAGVDAFPICLNIKDTEEIIQIVKAIAPAFGGINLEDISAPR
sp|P16468|MAOX_BACST   GPYAAMPVMEGKAMLFKEFAGVDAFPICLDTKDTEEIIQTVKAIAPAFGGINLEDISAPR
ref|YP_001125416.1|    GPYAAMPVMEGKAMLFKQFAGVDAFPVCLDTKDTFEIIQIVKAIAPAFGGINLEDISAPR
ref|YP_075148.1|       GPAAALPVMEGKAMLFKQFAGVDAFPICLDTTDPDEIVRIVKAIAPAFGGINLEDISSPR
ref|YP_643888.1|       GPYAAMPVMEGKAMLFKEFAGVDAFPVCLDTKDPEEIVRIVKYVAPAFGGINLEDISAPR
RAAC00196              GPEAAMPVMEGKAMLFKRFADVDAFPICLATQDVDEIVETVERMAPSFGGINLEDISSPR
                       ** **:***********. **.*****:**  *  :**:.  *: :**:*********:**

ref|YP_147293.1|       CFEIEKRLKEELDIPVFHDDQHGTAVVLLACLLNALKIVDKKLEDIKVVLTGIGAAGIAC
sp|P16468|MAOX_BACST   CFEIEKRLKEELDIPVFHDDQHGTAVVLLAGLLNALKIVDKKLEDIKVVLTGIGAAGIAC
ref|YP_001125416.1|    CFEIEARLKEELDIPVFHDDQHGTAVVLLAGLLNALKIVDKKLEDIKVVLTGIGAAGIAC
ref|YP_075148.1|       CFEIEERLKEELDIPVFHDDQHGTAVVLAGLMNAARVVGKELADLRVVVCGTGAAGVAI
ref|YP_643888.1|       CFEIERLQELDIPVFHDDQHGTAVVVLAALINALRIVGKRMEFLKVVVCGVGAAGVAC
RAAC00196              CFEIEERLRKRLDIPVFHDDQHGTAVVMLAGLINALKIVNKRMQDVSVVVAGVGAAGVAC
                       *** ::. *************:.*:** ::*.*.: :: **: *:****:* ref|YP_147293.1|       TKILLAAGVRNIIGVDRHGAIHRDETYENPYWQEYAQITNPDNLKGSLSDVIAGADVFIG
sp|P16468|MAOX_BACST   TKILLAAGVRNIIGVDRHGAIHRDETYENPYWQEYAQLTNPDNLKCSLSDVIAGADVFIG
ref|YP_001125416.1|    TKILLAAGVRNIIGVDRYGAIHRDETYENPYWQEYAQITNPYNLKGSLSDVIVGADVFIG
ref|YP_075148.1|       SKMLMAAGITNIVGVDRVGIIERGKTYENPMWQWYAEHTNPENRHGTLDDAIEGADAFTG
ref|YP_643888.1|       AKILLAAGVKNIVGCDRYGVVYRGRGDADTSRGWFAENTNPENIRGTLADAIRGADVFIG
RAAC00196              TKILLAAGVHIVGVDRVGIIERGRHYDNPVKQWYAENTNSENRRGTLEEAVRGADVFIG
                       :*:*:***: :*:* ** * : *.. :.    :*: **. * :*:* ::.: *.* ref|YP_147293.1|       VSAPGILKVEDVKKMARDPIVFAMANPIPEIDPELAEPYVRVMATGRSDYPNQINNVLCF
sp|P16468|MAOX_BACST   VSAPGILKVEDVKKMARDPIVFAMANPIPEIDPELAEPYVRVMATGRSDYPNQINNVLCF
ref|YP_001125416.1|    VSAPGILKVEDVKKMARDPIVFAMANPIPEIDPELAEPYVRVMATGRSDYPNQINNVLCF
ref|YP_075148.1|       VSAPNVLKVEHVKKMAKDPIVFAMANPVPEIDPDEAAPYVAVMATGRSDYPNQVNNLLCF
ref|YP_643888.1|       VSAPDVLTVEHIESMADEPIVFAMANPDPEIRPEIAYGHARIIATGRSDYPNQINNVLCF
RAAC00196              VSGPGILTVGHVKQMARDPIVFAMANPIPEILPEVAAGHVRVMATGRSDYPNQINNVLCF
                       **.*.:*.*  .::.** :********* ***  *:  *    :.. ::*******:*:***
```

FIG. 23B

```
ref|YP_147293.1|        PGIFRGALDCRAREINEEMKLAAAKAIASVVTEDELNETYIIPSVFN----------------
sp|P16468|MAOX_BACST    PGIFRGALDCRAREINEEMKLAAAKAIASVVTEDELNETYIIPSVFN----------------
ref|YP_001125416.1|     PGIFRGALDCRAKEINEEMKLAAAKAIASVVTEDELNETYIIPSVFN----------------
ref|YP_075148.1|        PGIFRGALNCRARQINEAMKLAAARAIASVVSDERLHAEYIIPSVFN----------------
ref|YP_643888.1|        PGVFRGALDIRAREINEEMKLAAARAIAGVIPEESLSEDYIIPSVFD----------------
RAAC00196               PGMFRGALDVRARDITEEMKQAAALAIAECVPEEQLSEQYIIPSPFDPNVVPAVSRAVQA
                        **:*****: **::*.* ** *** ***   :.::.*   ***** *:

ref|YP_147293.1|        ---------------------------
sp|P16468|MAOX_BACST    ---------------------------
ref|YP_001125416.1|     ---------------------------
ref|YP_075148.1|        ---------------------------
ref|YP_643888.1|        ---------------------------
RAAC00196               AAVRSGVARAAAPLELEEEPLYTEM
```

FIG. 24

```
ref|NP_242895.1|    -EEVVIASGVRTPIGRFGGHLKDLKAPTLGALVTSEALHRAGVLNEQVDEVIMGNVLQAG
ref|ZP_01372991.1|  MQDVVIVSAVRTPIASFGGALQGYGAVNLGALVIREAVQRAGIQGKQVDEVIMGNVLQAG
ref|ZP_01666093.1|  MREVVIASAVRTAIGSFNGTLAPFSAPELGSFVIKAALERANVPASAVDEVIMGNVLQAG
ref|YP_360188.1|    MEEVVIVSAVRTPIGSFLGSLAQTPAVDLGALVIKESLNRINLAPRFVDEVIMGNVLQAG
ref|YP_360122.1|    MQEVVILSAVRTAIGKFGGSLKDIPAAELGAIVIKEALVRAQIPPAEVDEVIFGNVLQAG
RAAC00814           MQDVVIAGAVRTPIGTFQGSLSPLSAPDLGAAVIRESLRRAGVEAGAVDEVVMGNVLQAG
                    .:*..*.*.*  *    *  :  ::  *  :      **:.***** ref|NP_242895.1|    LGQNPARQAALQAGLPETVPAMTINKVCGSGLKAVHLASQAIACGDAEIVVAGGMENMSQ
ref|ZP_01372991.1|  LGQNPARQAALKAGLPVETTAQTINVVCGSGLKAVIAAAQAIRAGDAEIVAAGGMESMSD
ref|ZP_01666093.1|  LGQNPARQAALKAGLPVEVPTMTINKVCGSGLKAVNLAAQAIMTGDADIVVAGGMESMTN
ref|YP_360188.1|    LGQNPARQAAIKAGIPQEVPAFTVNKVCGSGLKSVGLAYQAIATGDADIVVAGGMENMSL
ref|YP_360122.1|    QGQNPARQAATKAGIPVDIPAMTVNMVCGSGLRSVSLAATLIAAGEADLIVAGGMENMSA
RAAC00814           VGQNPARQAAMRAGLPEDIPATTVNMVCGSGLKSVMLAAQAIRAGDADVLVAGGMESMSN
                    *********::**:*   .: *:* ******:*    *   *  *:*:::.*****.*:

ref|NP_242895.1|    APYLAVGARNGYRMGHHQLIDSMIHDGLWCAFNDYHMGITAENLCEQYGLSRTELDEFSA
ref|ZP_01372991.1|  AAFLLDQARWGQRMGIIGTLVDSMIKDGLWCAFNEYHMGITAENVAEKYGISRREQDEFAA
ref|ZP_01666093.1|  APYLLDKSRWGYRMGHGKLIDSMTTDGLWCAFNDYHMGITAENIVEKYGVTREEQDQLAF
ref|YP_360188.1|    APYVLPKARTGYRMGHDTLIDSMIKDGLWCAFTDVHMGITAENIAEKYNITREEQDKFAL
ref|YP_360122.1|    APYAIPGARWGTRMGDGKIVDLMIKDGLWDAFYDYHMGITAENLAERYNISREEQDRFAL
RAAC00814           APYLLPGAREGYRMGHREVVDSMIRDCLWCAFCDIHMGVTAFNVANRHGISREDQDRFAL
                    *.:      :* *  ***.  ::*  ** ****.** : ***:****: :::..:* * *.::

ref|NP_242895.1|    WSQEKAVQAIESGRFKDEIVPVDIPQRKGEPIQFDTDEYVKRGTTTETLGALRPAFKKDG
ref|ZP_01372991.1|  WSQAKAVAAMEKGRFKEEIVPVAIPQRKGEPVIFDRDEYPRAGTTVETLAKLKPAFKKDG
ref|ZP_01666093.1|  ESQDKAIKAIASGAFKKEIVPVVIKDKKGD-KIFDTDEYPRAGTTVEKLCALKPAFKKDG
ref|YP_360188.1|    QSQERAIKAIDEGKFKEEIVPVIIPQKKGEPLVFSTDEFPKRGTSLEKLAALKPAFKKDG
ref|YP_360122.1|    ESQRRAEKAIKEGRFRDEIVPVKLPQRKGEPLEFVQDENPRFDTTLEALAKLKPAFKEGG
RAAC00814           QSQMRAKEAMEAGRFKDEIVPVSVPRRKGEPTLVDCDEHPRPDTTYEALAKLKPAFQADG
                    **  :* *: * *:.*** :  : :     ** .:* *  *:***:  .* ref|NP_242895.1|    KVTAGNASGINDGAAAVVVMSKEKAVELGIKPLVTVRANATAGVEPRIMGIGPVPATKKA
ref|ZP_01372991.1|  TVTAGNASGINDAAAACVLMSKEKAAALGIPYLAAIKGYGMAGVDPAIMGVGPVNAVKKA
ref|ZP_01666093.1|  TVTAGNASGINDGAAALVVMSADKAKELGIKPMARIRSYASAGVDPSIMGMGPVPATRKA
ref|YP_360188.1|    TVTAGNASGINDGAAAVVVMSAKKAQELNIKPLAVIRGYAAAGVDPAYMCLGPIPATRKA
ref|YP_360122.1|    TVTAGNASSINDGAAALVIASSKKAESLGTKPMAVIRSWGATGVDPSIMGIGPVGATRKA
RAAC00814           TVIAGNSSGINDGAAAMLVLARDRAEALGVKPMARIVSYASVGLDPSVMGLGPIEATRRA
                    .* *** :* *.* ::   ..:*  *.:   :. ..   *::* :: *.::* ref|NP_242895.1|    LTKAGLTMDDIDLIEANEAFAAQSLAVAKELSFAEDRLNVNGGAIALGHPIGASGTRIFV
ref|ZP_01372991.1|  LQKAGIALDELDLIEANEAFAAQLAVTKELGFPGEKVNVNGGAIALGHIPIGASGTRILV
ref|ZP_01666093.1|  LAKAGLVMDDIDLIEANEAFAAQFLAVGKELGFVKEKVNVHGGAIALCHPIGASGARILV
ref|YP_360188.1|    LKKANLTVSDLGLIEANEAFAAQALAVTKFLELNPEITNVNGGAIALGHPIGASGARILV
ref|YP_360122.1|    LKRAGLTIADIDLVEANEAFAAQALAVAKELELDLSKTNVNGGAIALGHPIGASGARILV
RAAC00814           LGRAGLSVEDLDLIEANEAFAAQALAVARELSFPDDKLNVNGGAIALGHPIGASGARILV
                    *  :*.:  :  ::.:*:*******    *  :    .  :***********::* ref|NP_242895.1|    TLLFELLRRGETYGLATLCIGGGQGVATIIER---
ref|ZP_01372991.1|  TLVHEMKKRRDKLGLATLCIGGGQGIALVVE----
ref|ZP_01666093.1|  TLLHAMELRNVKTGLATLCIGGGQGVATIVERM--
ref|YP_360188.1|    TLLHEMQKRNTKYGLATLCIGGGQGFALVVEKV--
ref|YP_360122.1|    TLLHEMKKSNSRYGLATLCIGGGMGVAAIVEK---
RAAC00814           TLLYELERRGGRFGLATLCIGGGQGVAMVVERMSQ
                    **::  :        **********  *.*  ::*
```

FIG. 25A

```
ref|NP_294183.1|    ------------------------------------------------------------
ref|YP_605214.1|    ------------------------------------------------------------
ref|YP_644483.1|    ------------------------------------------------------------
RAAC00815           MRRDPRGRRSVEHDRERPAHPATGGLRGPVLSLELRRVPREISSVHRRSGGILGRDRRRV
ref|YP_359514.1|    ------------------------------------------------------------
ref|YP_592595.1|    ------------------------------------------------------------ ref|NP_294183.1|    --------------------------------------------KNRVALYYEREDGLKETWS
ref|YP_605214.1|    --------------------------------------------RTALLYEREDGLRETWT
ref|YP_644483.1|    --------------------------------------------RNKAALLWESEDGRREVWT
RAAC00815           GMAAARKDGHRGRASRFSVLSRKLHQRVRKLRGSTSQAPDVRNKVALFFEGEDGERRSVT
ref|YP_359514.1|    --------------------------------------------RNKAALTFECEPGDSKILT
ref|YP_592595.1|    --------------------------------------------RHKAAFIWEGEPGDVRTLT
                                                                  :..*: :*  * *    . :

ref|NP_294183.1|    YGDLTDATARFAAALQDLGVDKGDRVAIYLSNVPEAFIAIHACYRIGAIYSVIFAGFSAS
ref|YP_605214.1|    YGELTDATARFAAALQDLGVAKGDRVAIYLGNVPEAFIAIHACYRIGAIYSVIFAGFSAS
ref|YP_644483.1|    YQQLADEVNRFANVLRELGVGRGDVVAIYMGNIPEVFVSVHACYRIGALYSIIFAGFSTD
RAAC00815           YLQLQDAVSRFAKALKDLGLRQGDVVCVYMQNLIETYVALLACLRIGVLYNTVFAGFSAE
ref|YP_359514.1|    YQELYREVNKFANVLKKLGVQKGDRVTIYMPMIPEAVIAMLACTRIGAPHSVVFGGFSSQ
ref|YP_592595.1|    YQQLWLEVQKFANVLLDLGIKKGDRVAIYMGMVPELPVAMLACARIGATHSVIFGGFSAN
                    * :*    .  :**  . **: :**  * :*:    : *  :::  ** ***. :. :*.***:.

ref|NP_294183.1|    AVRDRLTDAQPKVVVCTDGTLRRGRNIPLKATLDEALEGLEKPT-VIVARRLD-----PF
ref|YP_605214.1|    AVRDRLTDARPKVVICTDATLRRGKVIPLKATLDEALEGLE-IGHVIVARRV----DRES
ref|YP_644483.1|    AVRQRLEDARPKVVVVADATSRRGREVPLKRTLDQALAGIDSVETVVVVPRA----GAET
RAAC00815           ALRERIVRCGAKAVICANGSLRRGRVLRLKETVDRALEGVETVEIVIVYRRLP---DLDT
ref|YP_359514.1|    ALKDRIDDAKAKLLITADGGYRRGSIVELKKNADAALEGETTIEKVVVVKRTGQ----EV
ref|YP_592595.1|    ALVDRITDQQAVAVITQDGSWRRGNEVKLKVAVDEALEKCPTVKHVVVYKRTASA---IN
                    *: :*:   . :: :. *  :     * **       *:*  * ref|NP_294183.1|    LPLGENELDFAELLEKTTRRAAPVSLDANDPGFIIYTSGTTSKPKGLVHSGIGFLTGTYA
ref|YP_605214.1|    ALRGGEH-DFHALLNSTARRADPVPLEANEPGFIIYTSGTTSKPKGLVHAGLGFLAGAYA
ref|YP_644483.1|    ELREGRDRLYGDLVSRAGAWCPPEPMEANEPGFIIYTSGTESRPKGLVHAGLGFLVGTYA
RAAC00815           PMTPGRDLDFESLVERASRDCPPAVLEANEPAFLIFTSGTTGRPKGIVHAGGGFLLGTYA
ref|YP_359514.1|    PMTEGRDYWYHELMADAALYCEPEQCDAEDMLFTLYSSGTTGKPKGIQHTTGGYLVGVHT
ref|YP_592595.1|    -MKEGRDHWWHDLMAKAKDHCPAEPLDAEHPLYILYTSGTTGKPKGIVHTTGGYAVGTYY
                    ..  :  *:  :    ..   :*:.  :::::*** .:***: *:  *:  *.:

ref|NP_294183.1|    NVKWALNLQPDDVYWCTADVGWLTFPIFALVGGLAHGATHVIYEGSIDTPTPERPYQIIE
ref|YP_605214.1|    NVKWALNLCPQDVYWCTADVGWLTFPIFALVGGLAHGATHVIYEGSIDTPTPARPYEIIE
ref|YP_644483.1|    DVKWSMNPQDDDVYWCTADVGWLTFPIWSLVGGLAHGTTMVVYEGALNHPDPGRFYEILE
RAAC00815           YTKYQLDLRPEDVYWNTADIGWLTSHIFVLVGGLALGTTTILYEGALDWPKSGRLYEMIF
ref|YP_359514.1|    TFKYIFDYREEDIYWCTADIGWITGHSYIVYGPLSNGATVVLYEGAPDWPQKDRFWEIIE
ref|YP_592595.1|    TTKMVFDLKEDDTEWCTADIGWVTGHSYIVYGPLQTGATTVMYEGAPNFPDLDRFWALVA
                    * ::   :*  :* ***:**:*   : * * *:* ::***: *    * : ::

ref|NP_294183.1|    RYRADKVFTAPTALRMLRRSGDEALARYDLSPLQLVALVGEPLDPETWHWTHDVLGGGRL
ref|YP_605214.1|    RYGVNKVFTAPTALRMLRRAGDSALAGHDINTLELIALVGEPLDPETWHWTRERLGAGRI
ref|YP_644483.1|    RYRVNKVFTAPTALRMLRGAGERWLEGRDLSALKLVSLVGEPIDPETWHWVREVVGRGEA
RAAC00815           RYRVNKLFSAPTAYRMMMKHGEDIARCYDLSSLELLVSVGEPFNPEAWHWVRRVVGGDVA
ref|YP_359514.1|    KYRVNILYTAPTAIRTEMRWGEKWPKGRDLSSLRLLGTVGEPINPEAWIWYEHIGGGRC
ref|YP_592595.1|    KHKVTVFYTAPTAIRTFMKWGAEYPNRHDMSTLRLLGSVGEPINPEAWMWYRDVIGKDRC
                    :: . .::****  *  :    *       *:..*.*:  ****::**:* *  : :*  .
```

FIG. 25B

```
ref|NP_294183.1|    FVNNTYGQTETGTAWASSMVGLTEGRPGSCGHPLPGYRAAVVHEDGTPCGPNELGSLTLT
ref|YP_605214.1|    FVNNTYGQTETGTAWASSMVGLTPTRPGSCGHPLPGYRARVVREDGQAAAPGELGALTLT
ref|YP_644483.1|    FVNNTYGQTETATGWTSAIVGLTGAKPGSCGIPLPGYVSEVVDECGRPVPPCTPGYLTIT
RAAC00815           VINNTWGQTETGGTPLALLPGAVPMKPGSCGVPFFGHDLAVVDEQGREVPDGVPGYLVIR
ref|YP_359514.1|    PIVDTWWQTETGMIMITPLPGVIPTKPGSATKPFFGVEADVVNDKGEPVPPGQGGYLVLK
ref|YP_592595.1|    PIVDTWWQTETGAIMISPLPGAIATKPGSATKPLPGIIAEVVTRAGEKVPLGSGGFLVIK
                     :*: ****.    : :  *    :***. *: *    **   *      . * *.:

ref|NP_294183.1|    EPFPCLARTVWGDHDRYVETYLSEFPGKYAAADAALLDSDGQLWVTGRLDDVMNVAGHRL
ref|YP_605214.1|    EPFPCLARTVWGDHERYVQTYLADFPGSYAASDAALLDGDGQLWVTGRLDDVMNVAGHRI
ref|YP_644483.1|    EPFPCLARTVWGDHQRYLSTYFERFPGRYFSADACVVDRDGHYWVTGRVDDVINVAGHRL
RAAC00815           RPFPSLARDVYGDRNLYLNAYFSRMPGLYFTGDSAVRDADGHFWVLGRVDDVINVSGHRI
ref|YP_359514.1|    KPWPAMLRTLYGDPERYKNTYWSKFPGWYFTGDGAKKDEDGYFWILGRVDDVINVSGHRI
ref|YP_592595.1|    KPWPSMMRTIYGDPERYKHQYWSDIPGVYFTGDGAREDKDGYFWIMGRVDDVLNVSGHRL
                    .*:*.: *  ::**  :    *   :** * :.*..  * **   *: **:***.**:***:

ref|NP_294183.1|    GTMEMEAALLTHPAVSEAAVVAMPDDIKGAVPVAFVVPRAGIRLDTDLTWLENELADAVV
ref|YP_605214.1|    GTMELEAALITHPAVSEAAVVAQPDEVKGSVPVAFVVPRGDAQVG---PGLEEELAEAIV
ref|YP_644483.1|    GTMEMESALLNHPDVAEAAVIGVPDATKGTVPVAFALLRAGAEPR---PGLREELEQRIV
RAAC00815           STMEMESSLIQHPAVVEAAVVGEPDDVKGQVPVAFVTLERGWEPS---TDLEEELKARVV
ref|YP_359514.1|    GTMEVESALVEHPLVAEAAVIGKSHEVKGQAIAAFVTLKEGVEGT---PELVQELKQFVA
ref|YP_592595.1|    STMEIESALVAHPKVAEAAVVGRPDEMKGQAVSAFVTLESGSKPS---PELKEELRAWVA
                    .***:*::*: ** * ****:.  ..   **.   **.   . .     . * :**    :.

ref|NP_294183.1|    SGVGAIARPGRVVVTPTVPRTRSGKIMRRLLRDLLLTGEVKGDLTSLENPDALE----TV
ref|YP_605214.1|    RGVGPIARPARVIVTPTVPRTRSGKIMRRLLRDLLVSGEVRGDLTSLENPDAIE----VV
ref|YP_644483.1|    ERVGSIARPAAVHIVSALPKTRSGKIMRRLLRELVTEGRVRGDTTALEDPESVS----VL
RAAC00815           ADIGSFARPARVYFVEAMPKTRSGKILRRMLREILQTGEVKGDVTGLEDWEVVERLLHDL
ref|YP_359514.1|    QKICALARPDDIFFTAELPKTRSGKIMRRLLRDIAE-GRALGDTTTLTDPAVIN----KI
ref|YP_592595.1|    KEIGSMAKPDDIRFTDTLPKTRSGKIMRRLLRELATGGDVKGDTTTLEDFTVIA----KL
                    :*.:*:*       : ..  :*:****** :**:**::    * . ** * * :   :       :

ref|NP_294183.1|    RERLGGAAAG
ref|YP_605214.1|    RERLAGG---
ref|YP_644483.1|    EKEL------
RAAC00815           RERAPGGE--
ref|YP_359514.1|    KEQYKD----
ref|YP_592595.1|    KED-------
                    .:
```

FIG. 26

```
ref|YP_147450.1|        MNFSLTKEQQMIKEMVRDFAEKEIAPYAAKWDEEAHFPLDVFRKMGELGLLGLPFPEEYG
ref|YP_001125561.1|     MDFSLTKEQQMIKEMVRDFAEKEIAPYAAKWDEEAYFPREVFRKMGELGLLGLPFPESYG
ref|ZP_01696479.1|      MDFELSKEQIMLQEMVRDFAEKEIEPYAREVDETGKMRMETFQKLGNLGLLGIPFPEKYG
ref|NP_241996.1|        MNFELTKEQQMVRDMVRDFAENEIAPNAIHYDKTAQFPEDVFKKMGELGLLGIPFPEEYG
ref|YP_079308.1|        MNFELTREQQMIRELARDFAKQFIAPHAEHVDRTGEFPIETFKKMGELGLLGIPFPESYG
RAAC00816               MDFDLTSEQKMIRDTVREFAEAEIAPHAAEWDRTEHFPIEVFRKMGELGFLGLPIPEEYG
                        *:*.*: ** *::: .*:**: ** * * _ *.   :  :.*:*:*:**:**:*:**.**

ref|YP_147450.1|        GAGGDTISYAIAVEEIGRACGGTGLSYAAAVSLGASPIYYFGTEEQKQKWLVPMAKGETL
ref|YP_001125561.1|     GAGGDTISYAIAVEEIGRACGGTGLSYAAAVSLGASPIYYFGSEEQKQTWLVPMAKGETL
ref|ZP_01696479.1|      GAGGDTISYCIAVEEIGKACGGTGLSYAANTSLGASPIYYFGTEEQKQKWLVPMAKGEAL
ref|NP_241996.1|        GSGGDTISYALAVEEVGRACGGTGLSYAAAVSLGASPIYYFGTERQKQEHLVPLATGESL
ref|YP_079308.1|        GSCGDTISYALSVEEIGKACGSTGLSYAAAVSLGAAPIYYFGTEEQKQEYLVPLATGRAL
RAAC00816               GAGADMISYCLAVEEIGRACGGTGLSYEAIIVSLACTPILLYGTEEQKQKYLVPMARGEAL
                        *:*.* *.::*:*:*.*** * ...: :*:*.* *:* *.:* ref|YP_147450.1|        GAFGLTEPNAGSDAGGTRTTAVLDGDEYVINGEKCWITNAQYARQVIVTAVTGKDARGKN
ref|YP_001125561.1|     GAFGLTEPNAGSDAGGTRTTAVLDGDEYVINGEKCWITNAQYARQVIVTAVTGKDARGKN
ref|ZP_01696479.1|      GAFGLTEPNAGSDAGGTRTKAVLDGDEWVINGEKCWITNAEYARQVIVTAVTGKRENGRN
ref|NP_241996.1|        GSFGLTEPNAGSDAGGTRTKAVLEGDEYVINGEKCWITNAGYARTVIVTAVTGKDERGKP
ref|YP_079308.1|        GAFGLTEPNAGSDAGGTRTKARSEGDSYVISGEKCWITNAGFARTVIVTAVTGIDDNGKN
RAAC00816               GAFGLTEPGAGSDAGGTRTTAVLEGDEWVITGNKIFNTGGYAKYVVLTAVTDPASRG--
                        *:****.*******.*  ::.*:* : **. :*: *:*****.    .* ref|YP_147450.1|        IITALIVPTDSPGFTIRSNYDKMGVRASNTCELVFENVRVPKENVLGDPQKGFKQFLYTL
ref|YP_001125561.1|     IITALIVPTDSPGFTIRSNYDKMGVRASNTCELVFENVRVPKENVLGDPQKGFKQFLYTL
ref|ZP_01696479.1|      IISAIIVPADAPGVAITSPYEKMGVRGSNTCQIVLENVRVPRENLLGDENKGFSQFLYTL
ref|NP_241996.1|        VISALIVPTGIEGFTISCNYDKMGVRASNTCELVLEDVRVPKENLLGDPTKGFKQFLYTL
ref|YP_079308.1|        IISAIIVPTDSEGFTIKSEYDKMGVRGSNTSQLILDNVRVPKQNLLGSPEKGFKQFLNTL
RAAC00816               -ISAFIVPTDAEGFSVSKPYEKLGMRASNTVELILDHVRVPKENLLGPLNAGFKQFLSTL
                        *:*:***:.  *.::   *:*:*:*.* :::::.**:::*: .* ref|YP_147450.1|        DGGRISIAALAVGIAQAAFEKALQYAKERVQFGQPISKFQAIQFKLADMAMEIELARNMV
ref|YP_001125561.1|     DGGRISIAALAVGIAQAAFEKALQYAKERVQFGQSISKFQAIQFKLADMAMEIELARNMV
ref|ZP_01696479.1|      DGGRISIAALSVGIAQAAFEKALRYAKERMQFGQAISKFQAIQFKLADMAMEIDLARNAV
ref|NP_241996.1|        DGGRISIGALAVGIAQAAFDRALAYANERKQFGQKISSFQAIQFKLADMAMEIELARNMV
ref|YP_079308.1|        DGGRISIAALAVGIAQGAFEAALTYARERKQFGRPISYFQAIQFKLADMAMEIELARNMV
RAAC00816               DGGRVAIAALAVGIARAAFETALAYAKTRVQFGQAISKFQAIQHKLADMAMHIDLARNAV
                        ****:*.**:*.**:.:  .* *  ***** *.******.*:**** * ref|YP_147450.1|        YKAAWLKDQGKPFTKEASFAKLFASEMGFRVCNQAIQIHGGYGYMKEYGVERHLRDIKLM
ref|YP_001125561.1|     YKAAWLKDQGKPFTKEASFAKLFASEMGFRVCNQAIQIHGGYGYMKEYGVERHLRDIKLM
ref|ZP_01696479.1|      YKAAWLKDQGKPFSKEAAYAKLFASEMGFRVCNQAIQIHGGSGYMREYGVERHLRDIKLM
ref|NP_241996.1|        LKAAWLKDQKKPFTKEGAYAKLYASFTAMRTANQAIQIHGGYGYMQEYEVERMLRDAKLL
ref|YP_079308.1|        LKAAWLKDQGRPFTKEAAFAKLYASEMAFRTCNQSIQIHGGYGYMKEYGVERMLRDAKLM
RAAC00816               MKAAWLKDQGRPYTLEASYAKLFASEMCTRTCEQAIQILGGYGYMREYPVERHYRDAKLI
                        ********.*:::  *.::***:***     *..:*:***  ***:** *** ** **:

ref|YP_147450.1|        EIGEGTSEIQRLVIARQLCC
ref|YP_001125561.1|     EIGEGTSEIQRLVIARQLGC
ref|ZP_01696479.1|      EIGEGTSEIQRLVIARKLGC
ref|NP_241996.1|        EIGEGTSEIQRMVIARQLGC
ref|YP_079308.1|        EIGEGTSEIQRLVIARQLG-
RAAC00816               EIGEGTSEIQRLVIARQLGC
                        ***********:****:**
```

FIG. 27

```
ref|NP_241073.1|      -----VLQTIKNHVAIITFNRPDQLNCFNYQMLLDLEQVIQEVKANPAIRTVIFTGAGGK
dbj|BAA75325.1|       -----VLQTIKNHVAIITFNRPDQLNCFNYQMLLDLEQVIQEVKANPAIRTVIFTGAGGK
ref|ZP_00539140.1|    -----------DHVAVIRVDRPERLNCFDYPTLVELKELVATVRREPDIRVVLFTGTG-K
ref|ZP_01696475.1|    -----------QDGIAVMTLNRSEAANALSKEMLSDMHEVLSEIKKDRSTRVVILTGAGEK
RAAC00822             MEQPIVWQKAEDGIAELLLNRPDAMNALNYALLRALEDAVREIAEDRGVRAVIVRGEG-K
ref|ZP_02130394.1|    MEEELVLSQTEDQVLTLTLNRPKVMNSFNFAMLHALKAAVDKARFDPEVRVIIITCAGDR
                           :    :  ..:*..  *.:.    *  :.  :         :   *.::. * * :

ref|NP_241073.1|      SFSAGADLKERRTLDENQVRRNVNKIRSVFNQIEELPQPTIAAINGYALGGGFELALACD
dbj|BAA75325.1|       SFSAGADLKERRTLDENQVRRNVNKIRSVFNQIEELPQPTIAAINGYALGGGFELALACD
ref|ZP_00539140.1|    AFSAGADLKERVTLNETEVRRNVFMIRDVFADIARLPQPTIAAVNGHALGGGFEWMLACD
ref|ZP_01696475.1|    VFCAGADLKERKGMNEEEVLQAVRKIGAVVNETAALPQPVIAALNGSAFGGGLELALACD
RAAC00822             GFCAGADLKERRGLAPHEVRRNVRLTREAFDRVARLPQPTIAVLHGFAFGGGLELALACD
ref|ZP_02130394.1|    AFCAGADLKERATLTPVQVKEFIYTIRNLFTDIENLPKPVIAAVNGIALGGGTELALGCD
                       *.********   :   :*  . :       .   **:*.**.::* *:*** *  *.**

ref|NP_241073.1|      FRLAVPEAKMGLTEVTWAIIPGAGGTQRLPRLIGSQRAKEMILTGRKVAAEEAQRLGIIL
dbj|BAA75325.1|       FRLAVPEAKMGLTEVTWAIISGAGGTQRLPRLIGSQRAKEMILTGRKVAAEEAQRLGIIL
ref|ZP_00539140.1|    FRIIVNGALVGLTETSFGIIPGAGGTQRLPRLIGETRAKEMIFTAKKIDAETAERYGIVS
ref|ZP_01696475.1|    LRIGAREAKYGLTETSLAIIPGAGGTQRLPRLIGVGKAKELIYTARRLTAEEAAAIG-LL
RAAC00822             FRIGSRDLRLGLTETSLAIVPGAGGTQRLARLIGPTWAKWMIFTAARIDAERARELGILL
ref|ZP_02130394.1|    IRLAAETAAMGLTETTLAIIPGAGGTQRLPRLIGKGKAKELIFTGRRVDAQEALDLGMVN
                      :*:       ****.: .*:.********.****   ** :* *. :: *: *    * :

ref|NP_241073.1|      EVCDS-KHLLTEAVRLAEKMSV-NGPLAVIQAKYAIHYGCQTDLHTGLAIEAKAYETIIP
dbj|BAA75325.1|       EVCDS-KHLLTEAVRLAEKMSV-NGPLAVIQAKYAIHYGCQTDLHTGLAIEAKAYETIIP
ref|ZP_00539140.1|    RVVPTVEELMEVCLAFADEMLR-NGPIAIRQAKQAIDQGLDHTLSEGLKLETAAYETVIP
ref|ZP_01696475.1|    EYAVPRAAVIEKAFELAGEMQK-NGPIALRQAKTAIDQGTETGLSAGLKIEELAYNALIP
RAAC00822             EVADTREAAMDAARALARAIAE-NGPVAVRQAKWAIDRGLDVDLSTGLAIEDAAYEGVLP
ref|ZP_02130394.1|    KV-VPGDSLLDAAKDMAAAIRK-NGPIAVTQAKYAINQGMETDLSTGLAIESNAYWITIP
                       .       :  .  :*  :   ***:*: * . *    * ** :*   **   :* ref|NP_241073.1|      TEDRLEALQAFKEKRPPQFKGK
dbj|BAA75325.1|       TEDRLEALQAFKEKRPPQFKGK
ref|ZP_00539140.1|    TEDRLEALRAFAEKRTPQFQGK
ref|ZP_01696475.1|    TEDRLEGLRAFAEKRTPVYKG-
RAAC00822             TSDRLEALAAFAEKRKPHFRGE
ref|ZP_02130394.1|    SKDRLEGLAAFREKRKPVYKGE
                      : ****.* ** *** *  :: *
```

FIG. 28A

```
ref|NP_389098.1|        -----KKTITING--VEMEASEEQTVLQLLNNSSIEVPQVCYHPSLGPIETCDTCIVSIN
ref|YP_091797.1|        MEMAEQKKITING--VEMEASEEQTVLQLLNNSSIEVPQICYHPSLGPIETCDTCIVSIN
ref|YP_001420821.1|     ----------TING--VEMEAPDGQTVLQLLNNSSIDVPHVCYHPSLGPIETCDTCIVNVN
ref|ZP_01171726.1|      -DLPDTYQVKLNGAEVKVAAGDETTILQLLQNSSVEVPNVCYIIPSLGPIETCDTCIVSVN
ref|ZP_01696606.1|      ----------ING--QELAARKGQTILEVANAHDMYIPAICYHPNLGSIQTCDTCFVNVN
RAAC00950               MSVDLKRTFTLDG--SPLTATEGETILQAMLAAGLDFPHICYHPALGPIETCDTCMVEVN
                           :  :*       :  * .  *:*:       .: .* :** .*:****:*.:* ref|NP_389098.1|        GELKRSCSAELKDGDVIDTLSPDVKKAQVIGMDKILYNHELYCTVCDYNNGGCEIHNTVK
ref|YP_091797.1|        GELKRSCSAEVKDCDVIDTLSPDVKKAQVIGMDKILYNHELYCTVCDYNNGGCEIHNTVK
ref|YP_001420821.1|     GELVRSCSAQIKDGDVIDTLSSDVKKAQIIGMDNILHNHELYCTVCDYNNCSCEVHNTVK
ref|ZP_01171726.1|      GELVRSCSTKLNDGDIIDTVSADVKEAQVIGMDRILTNHELYCTVCDYNNGGCEVHNTVK
ref|ZP_01696606.1|      GNLVRACATKVEPCMEVESGSKPVKDAQYEAMSRILKNHELYCTVCDNNNGNCVVHNTAE
RAAC00950               GDLVRACATPVVEGMSVRTKSVAARYARKEAMDRILKNHDLYCTVCDNNNGNCVVHNTTM
                        *:*  *:*::  :   *   :  :   *  .*..** **:****** ***.*  :***.

ref|NP_389098.1|        EMKINHQSIPFDHKPYIIKDESHPFYRYDPDQCILCGRCVEACQDVQVTETLTIDWERKRP
ref|YP_091797.1|        EMKVNHQSIPFDQKPYHKDESNPFYRYDPDQCILCGRCVEACQDVQVTETLTIDWERKRP
ref|YP_001420821.1|     EMKINHQSIPFDQKPYPKDESNPFYRYDPDQCILCGRCVEACQDVQVTETLSIDWERKRP
ref|ZP_01171726.1|      EMKINHQSVPFAQKPYPADNSHPFYRYDPDQCILCGRCVEACQDVQVTETLTIDWEREKP
ref|ZP_01696606.1|      HLEIEHQKYQFEAKPYPPDQSHPFYRYEPDQCILCGRCVEACQDLQVNETLTIDWDREVP
RAAC00950               AMDIDIIQSYPFREKFYEVDMSHPFYRYDPSQCILCGRCVEACQNLQVSEVLSIDWDREIP
                         : .:** .   *    *  * *:*****:*.***********:.*.*.:***:*: * ref|NP_389098.1|        RVIWDNDVPINESSCVSCGHCSTVCPCNAMMEKGMEGEAGYLTGINNETLRPMIEITKGV
ref|YP_091797.1|        RVIWDNDVPINESSCVSCGHCSTVCPCNAMMEKGMEGEAGYLTGIDDETLRPMIEITKGV
ref|YP_001420821.1|     RVIWDQDVPINESSCVSCGHCSTVCPCNAMMEKGMEGEAGYLTGINQETLRPMIDITKGV
ref|ZP_01171726.1|      RVIWDNDVPINESSCVSCGHCSTVCPCNAMLEKGMEGEAGYLTGIAKQTLRPMIEITKNV
ref|ZP_01696606.1|      RVIWDNDVPIDESSCVSCGHCVTVCPCNALMEKSMLGEAGYLTGIPQKVLEPMIDLTKEV
RAAC00950               RVIWDNDVPINESSCVSCGHCVTVCPCNALMEKSMLGKAGFLTGIEPEPLQRMIDVTKAV
                        ***::******* **.:.* *::**  : *. :: * ref|NP_389098.1|        ETGYGSILAISDMESAMRDERIKKTKTVCTYCGVGCSFDVWTKGRDILKVEPQEEAPANG
ref|YP_091797.1|        ETGYGSILAISDMESAMRDERIKKTKTVCTYCGVGCSFDVWTKGRDILKVEPQEEAPANG
ref|YP_001420821.1|     ETGYGSILAISDMESAMRDERIKKTKTVCTYCGVGCSFDIWTKGRDILKVEPQAEAPANG
ref|ZP_01171726.1|      ETGYGSILAISDMEAAMRDERIKKTKTVCTYCGVGCSFDVWTKGREILKVDPQPEAPANG
ref|ZP_01696606.1|      EPGYKEIFAISEMEAAMRKSRIKRTKTVCTYCCVGCSFEIWTKGRHILKVEPQEHAPVNG
RAAC00950               EPGYRAIFAISEIESHMRNSRIKRTKTVCTYCGVGCSFDIWTKDRDILKVEPQMEAPTNQ
                        *.  :**::*: ..*:*******.*::*.*:  :  . ..* ref|NP_389098.1|        ISTCVKGKFGWDFVNSEERLTKPLIREGDHFREAEWEEALLLIASKFTELKEAFGPDSLA
ref|YP_091797.1|        ISTCVKGKFGWDFINSEERLTKPLIREGDHFREAEWEEALTLIASKFTDLKEEFGPDSLA
ref|YP_001420821.1|     ISTCVKGKFGWDFVNSEKRLTKPLIREGDSFREAEWDEAIQLIADKFTDIKEHFGPDALA
ref|ZP_01171726.1|      ISTCVKGKFGWDFVNSEERLTKPLIREGEFFREAEWDEAISLIARRFTEIKNEHGAQAMS
ref|ZP_01696606.1|      ISTCVKGKFGWDFVNSEERLTKPLIRKGEEFVEASWDEALNLIASKLQEIKKQHGPDALG
RAAC00950               ISTCVKGKFGWDFVNSPDRLTKPLIRKGDAFHEVSWDEALDFVAKRLTEIRQQYGDDAIA
                        ************:**  .********:*: *  *.:*:**:  ::* ::  :::.  * :::.

ref|NP_389098.1|        FITSSKCTNEESYLMQKLARGVIGTNNVDNCSRYCQSPATAGLFRTVGYGGDSGSITDIA
ref|YP_091797.1|        FITSSKCTNEESYLMQKLARGIIGTNNVDNCSRYCQSPATAGLFRTVGYGGDSGSIADIA
ref|YP_001420821.1|     FITSSKCTNEESYVMQKLARAVIGTNNVDNCSRYCQSPATAGLFRTVGYGGDSGSITDIE
ref|ZP_01171726.1|      FISSSKCTNEESFLMQKLGRAVIGTNNIDNCSRYCQTPATVGLFRTVGYGGDAGSIRDIQ
ref|ZP_01696606.1|      FIASSKCSNEENYLFQKFARAIIGTNNLDNCSRYCQSPATSGLLRTVGIGGDSGTTRDTQ
RAAC00950               LISSSKCTNEENYLMQKLARAVLHTNNIDNCSRYCQSPATEGLRRTMGYGGDTGSLHDLA
                        :*:****:***.: :::**:.*.::  ***:********:.*** ** **.**:*:: *:
```

FIG. 28B

```
ref|NP_389098.1|         QADLVLIIGSNTSESHPVLSTRIKRAHKLRGQKVIVADIRKHEMAERSDLFVQPRAGSDI
ref|YP_091797.1|         QADLVLIIGSNTSESHPVLSTRIKRAHKLRCQKVIVADIRKHEMAERSDLFVQPRAGSDI
ref|YP_001420821.1|      KAELVLIIGSNTSESHPVLSTRIKRSHKLIIGQKLVVADLRKHEMAERSDVFFQPRAGSDI
ref|ZP_01171726.1|       MSDLVLIIGSNTAESHPVLSTRVKRSHKLGGGQKLIVADLRKHEMADRADLFVQPKAGTDI
ref|ZP_01696606.1|       QADLVVTVGANPAESHPVLATRIKRAHKLHCQKLMVVDLRENELASRANLFIHSKPSTDL
RAAC00950                MADLLIIIGANPAESHPVFSTRMRRAKKKYGQKHIVIDLREHDMAHRADLFVRPNPGTDL
                          :*::  :*:*.:*****::**::*:*   *** :* *:*::::* *:::*.:.....:*:

ref|NP_389098.1|         VWLNAIAKYLIENGKADERFLRERVNGRDEYVKSLAPYTLEYAEEKTGIDQFTLIQMAEM
ref|YP_091797.1|         VWLNAIAKYLIENGKADERFLQERVNGRDEYVKSLTPYTLEYAEEKTGIDQETLIQMAEM
ref|YP_001420821.1|      VWLNAVSKYLLDHDLADTSFLKERVNGLDEFVKSLEPYTMEYAEKHTGVDKDTLIKVARM
ref|ZP_01171726.1|       VWLSAVAKYIIDNGMADEEFLAEKVNCLDEFTKNLEKYTMEYAAEVTGIALEQLIDMAEM
ref|ZP_01696606.1|       IWLNAVTKYILDQGWEDKAFLEARVKGLDKFRASLEKYTLAFAEEKTGISKENLIKMATM
RAAC00950                VLISAVTRYIIDQGWHDADFVRDRVDGFEDFVRSLEPYTLEYAERVTGVPRDTVIQIATM
                          : :.*:::*::::.   *  *:  : :.:  .*  **: :* . **:  : :*:.:* * ref|NP_389098.1|         IGQADSVCALWAMGVTQHIGGSDTSTAISNLLLVTGNYGKPGAGSYPLRGHNNVQGASDF
ref|YP_091797.1|         IGQADSVCALWAMGVTQHIGGSDTSTAISNLLLVTGNYGKPGAGSYPLRGHNNVQGASDF
ref|YP_001420821.1|      IHEAGSVCALWAMGVTQHIGGSDTSTAISNMLLVTGNYGKPGAGSYPLRGHNNVQGASDF
ref|ZP_01171726.1|       IGRAKSVCALWAMGITQHMGGSDASTAISNLLLVTGNYAKPGAGAYPLRGHNNVQGASDF
ref|ZP_01696606.1|       IHEAKSVCILWAMGITQHTCGTDASTAISNLLLVTGNYGRPGTGAYPLRGHNNVQGACDF
RAAC00950                IHEAKSTCICWAMGVTQHKGGSETSTAICNLLLVTGNVGRPGTGAYPLRGHNNVQGAGDM
                         * .* *.* ****:*** *::**** *:******  .:**:*:************ *:

ref|NP_389098.1|         GSMPDRLPGYEKVTDEQVRQKYERVWGVPLPKEPGMTNHEMIEKIHSGQLKAMYVKGEEM
ref|YP_091797.1|         GSMPDRLPGYEKVTDEQVRQKYEQAWGVPLPKEPGMTNHEMIEKIHSGKLKAMYVKGEEM
ref|YP_001420821.1|      GSMPDSFPGYEKVTDEKARKKYEQGWGTDLPKEIGMTNHEMIEGIHSCKLKSMYLKGEEM
ref|ZP_01171726.1|       GSMPNMFPGYQEVADPEIRKKYELAWGTELPGEPGLNNHEMVEGIHAGTLKAMYLKGEDM
ref|ZP_01696606.1|       GTMPAWFPGYEPVEDNEVRERYEKAWGVKLPENPGLDNHQMIGGIKSGKLRGLYLFGEEM
RAAC00950                GCSPVYMPGYERVDDPAVRAKYETAWVVELPTSKGLDNHEMVDAIHEGKLRALIIQGEEM
                         *  *  :***:  *  *   :**  *  . ** . *: **:*: *: * *:.: : **:* ref|NP_389098.1|         GLVDSNINHVHAAYEKLDFFVVQDIFLSRTAEFADVVLPASPSLEKEGTFTNTERRIQRL
ref|YP_091797.1|         GLVDSNINHVHAAYEKLDFFVVQDIFFSRTAEFADVVLPASPSLEKEGTFTNTERRIQRL
ref|YP_001420821.1|      GLVDSNINHVHAAFEKLDFFVVQDIFLSRTAEFADVVLPASPSLEKEGTFTNTERRVQRL
ref|ZP_01171726.1|       GLVDSNINHVHAAFEKLDFFVVQDIFLSRTAEFADVVLPASPSLEKEGTFTNTERRIQRL
ref|ZP_01696606.1|       AIVDSNINFVEEHLEKLDFFVVQDVFFSKTAQFADVILPAAPSLEKEGTFTNTERRIQRF
RAAC00950                ALVDSNSHYVREAFAKLDLLVVIDVFFSKTAEYADVVLAASPSLEKEGTFTNTERRIQRL
                          .:****  :.* .   ***::** *:*:*:**::***:. *:******************;**:

ref|NP_389098.1|         YQVFEPLGESKPDWQIIMEVANKLGAGWLYEHPADIMEEAAKLSPIYAGVTYERLEGYNS
ref|YP_091797.1|         YQVFEPLGESKPDWQIIMEVANKLGADWHYEHPADIMEEAAKLSPIYAGVTYERLEGYNS
ref|YP_001420821.1|      YEVFEPLGDSKPDWQIITDIANRLCADWHYEHPADIMEEAAMLSPLYAGVTYERLEGYNS
ref|ZP_01171726.1|       YQALEPLGDSKPDWQIIMEIANSLGAGWNYTHPSEIMEEASRLMPLYSGVTYERLEGYNS
ref|ZP_01696606.1|       YQVFEPMGESKPDWVIFQELANKMGAQWHYQHPGEIMAEAASLAKYFAGISYERLEGFNS
RAAC00950                YQVFEPLGESRPDWVILRDLANRLGANWTYAHPSEILEEMASLAALMQGVRWDRLEGYRS
                         *:..:*:*:*:*** *: :*** * * **.:*: * : *   *: ::***:.* ref|NP_389098.1|         LQWPVNADGKDSPLLFTERFPFPDGKAILYPVQWTEPKEFGEEYDIHVNNGRLLEHFHEG
ref|YP_091797.1|         LQWPVSADGKDSPLLFTERFPFPDGKAILYPVHWTEPEEFGEEYDIHVNNGRLLEHFHEG
ref|YP_001420821.1|      LQWPVAADGTDSPLLFTDKFPFSDGKAILYPVQWTEPKEFDEEYDIHVNNGRLLEHFHEG
ref|ZP_01171726.1|       LQWPVAEDGQDTPLLYTERFPFEDGRARLVPVDWTKPLEFEEEYDLHINNGRLLEHFHEG
ref|ZP_01696606.1|       QIWPVKKDGTSTPLLYQDRFAFPDGKARLVPVDWEPPFSAGEGFDYHLNNGRLLEQFHEG
RAAC00950                LQWPVEPDGTDTPLLYTNGFPFPNGKARLVPARWIEPTAFEPEYDLHLNNGRMLEHFHEG
                          ***  **  :***:  :  *.*  :*:* * *.  *   :*   :****:**:*****
```

FIG. 28C

```
ref|NP_389098.1|      NLTYKSKGISEKTPEVFLEISPELAAERGIQDGTLVRLTSPFGNVKVKCLITDRVKGKEV
ref|YP_091797.1|      NLTYKSKGISKKTPEVFLEISPELAAERGIQDGTLVRLTSPFGNVKVKCLITDRVKGKEV
ref|YP_001420821.1|   NLTYRSKGISEKTPSVFLEVSPELAEERGLEDGTLVRLTSPYGNVKVKCVITDRVKGKQV
ref|ZP_01171726.1|    NMTYRSKGISEKTPSVFLEVSPELAEERGLESGTLVRLSSPYGNVKVQCHITDRVKGKEV
ref|ZP_01696606.1|    NLTDRSPGTHHKVPEPWLEISPEAASERGIKDGALVRLTSPYGKVKVRAVVTGRVQGKEL
RAAC00950             NLTYRVHGLKEKVPTTYLEVSPELAKERGIETGALVRLISPYGELKLPVVVTDRVKGKQM
                      *:*  :   *: .*.*   :**:*** * ***::  *:**** **:*::*:    :*.**:**::

ref|NP_389098.1|      YLPMNDSG-EAAINLLTGSHADKDTDTPAYKETSAKMEILKHDGISPLPKINHRNGNPQP
ref|YP_091797.1|      YLPMNDSG-EAAINLLTGSHADKDTDTPAYKETSAKMEILKRDGSNPLPKINHRNGNPQP
ref|YP_001420821.1|   YLPMNDSKD-AAINLLTSSYADKDTDTPAYKETSAKMEILKKEGVNPLPKINFRYGNPQP
ref|ZP_01171726.1|    YLPMN-DRGEAAINLLTSSYADKDTDTPAYKEIRAKMEILKAKGEDPLPRINHRYGNPQP
ref|ZP_01696606.1|    YLTMNARKEDEMVNRLTSSYHDRVTHTPNYKEMGVKMEILEEKGKPPLPKVNHRYGNRIP
RAAC00950             YLPMNTSNDEEAINILTSSESDETTHTPAYKELQVRMEVIRPRGESPMTRFNFRMHRPNP
                              :* **.* *. *. *  .:**::.   *  *:.:.*.*   .  * ref|NP_389098.1|      QIGVQVHKKWARKDYIFPGDAVK------
ref|YP_091797.1|      QIGVQVQKKWARKDYIFPGDAVK------
ref|YP_001420821.1|   QIGVRVDRKWARKDYVFPGDAVK------
ref|ZP_01171726.1|    QIGVQVQKKWARKDYIFPGDLVKKEREHG
ref|ZP_01696606.1|    QISVRVEEKWKRDDFIPI-----------
RAAC00950             QSGVRVERKWSRGYVPVAEAAKEKARG-
                      *  .*:*..**  *   .::
```

FIG. 29

```
ref|YP_146314.1|        --------GFAAKRRPIAKYRNGRFVEEEDEIALEFPLTITVNGEEFATIVCTPAHLDEL
ref|YP_001124593.1|     --------GFVAKRRYIVKYRNGQLAEKEDEIALEFPLTVVVNGQEFATIVCTPGHIDEL
ref|NP_391552.1|        -----------TAVRDVWRYEQGEISKVEDRMVTEFPLTVILNGSEFVTLVCTPEHIEEL
RAAC00952               MNGVSRFGGAETRRRFVLRYRSGEYRQEEDVIATEFALTLFVNGEEFSTLVCTPTYAEDL
ref|NP_830405.1|        ----------------IVRYQSGTFSKQLDEIVTESPITIKLNGEEYVTVVCTPNYIEDM
ref|ZP_00739906.1|      ----------------IVRYQSGTFSKQLDEIVTESPITIKLNGEEYVTVVCTPNYIEDM
                                         :  :*..*      :   * :.  *  .:*:  :**.*:  *:**** :  :::

ref|YP_146314.1|        VIGFLASEGAIRTCSDIKGMTIDGERGFAYVELAAGGLPAKQFYAKRFIGSCCGKSRQ-F
ref|YP_001124593.1|     VIGFLASEGVIRVIDDIKAMTIDGERGFVYVELTSDFLPAKQFYAKRFIGSCCGKSRQ-F
ref|NP_391552.1|        VIGFLASEGVIRFQKEIKRFTIDESLGFVYVDLVHPETLDQKDYTKRVIGSCCGKGRH-F
RAAC00952               VYGFLASEGVIRDVDDVESIRVSLWTGTARVQTKSGAVLSPALYNKRYIGSCCGKGRQSF
ref|NP_830405.1|        VIGFLISEGIISSYNDVEELWVQKDNGIVHVKSSKVNPLYQTLYNKRYVTSCCGKGRQGF
ref|ZP_00739906.1|      VIGFLISEGIISSYKDVEELWVQKDNGIVHVKSSKVNPLYQTLYNKRYITSCCGKGRQGF
                        * * *  *     .::: :  :.    *. *.          *   : ***.*:  * ref|YP_146314.1|        YFYNDMKTAKTIVG-GITVKADDCIRLMKALHERSTDFAATGGLHNAALATPDEMVVIRS
ref|YP_001124593.1|     YFYNDAKTAKTIVG-GITVKADDCVCLMKTLHEQSIDFAATGGLHNAALATPDRIVVIRS
ref|NP_391552.1|        YFQQDVKTAKTAVS-QIKISPEACLALMKDMQQGSGTFQDTGGVHNAALCDTEKLLLMRT
RAAC00952               YFQSDALTARPVED-PVSLSADDVFRAMDLLDASSGLFEETGGVHVAALVREGQLVLARA
ref|NP_830405.1|        IFVNDAAKAKDLHDIHVKITPEECFYLMNTLQQSSTTFRQTGGVHNTALCDRNKILLSRM
ref|ZP_00739906.1|      IFVNDAAKAKDLHDIHVKITPEECFHLMNTLQQSSTTFRQTGGVHNTALCDRNNILLSRM
                         * .*  .*:    .  :.:..:.    *.  :.    *    *  ***:*  :**      .:::   * ref|YP_146314.1|        DIGRHNALDKLYGYCLRHQVAMKDKLIVFSGRVSSEVLLKAAKMGVSVLLSKSAPTTLAL
ref|YP_001124593.1|     DIGRHNALDKLYGYCLRHQVAMKDKLIVFSGRVSSEVLLKAAKMGISILLSKSAPTTLAL
ref|NP_391552.1|        DIGRHNALDKLYGHCLLNGMSVRDKLIVFSGRISSEVLLKAAKIGVSIVISKSAPTELAI
RAAC00952               DIGRHNALDKIYGHCLRAGERLSGTAVAFSGRISSEVLLKVAKIGVGVVIARGAPTLLAV
ref|NP_830405.1|        DIGRHNALDKIYGHCLRNDISVKGKIIAFSGRISSEILLKVSKIGCEIVLSKSAPTKLAL
ref|ZP_00739906.1|      DIGRHNALDKIYGHCLRNDISIKGKIIAFSGRISSEILLKVSKIGCEIVLSKSAPTKLAL
                        **********:**:**        :  .. :.***:***.*** .*:*      :::::.*** **:

ref|YP_146314.1|        DLADELGITVVGFLRGQAFNVYTHESRI--------------
ref|YP_001124593.1|     DLAEELGITVVGFLRGQDFNVYTHEKRI-------------
ref|NP_391552.1|        QMAEELNITAIGFVRNGSFNVYTHPERIRE-----------
RAAC00952               DLAEELNITAIGFVRGRAFNVYSHPWRLADAKKAQGAIEGA
ref|NP_830405.1|        QLAHDLGITVVGFIRNESCNIYTHPHRI-------------
ref|ZP_00739906.1|      QLAHDLGITVVGFIRNESCNIYTHPKRI-------------
                        ::*.:*.**.:**:*.    *:*:*   *:
```

FIG. 30

```
ref|YP_148038.1|          --------------IRIAIAGPRGRMGREAVALVQQTDHFELAAVIDRRYDGQNLAEIDGF
ref|YP_001126216.1|       --------------IRIVIAGPRGRMGREAVALVQRTDHFELAAVIDRRYDGQNLADIDGF
ref|NP_242546.1|          --------------IKVAVAGPRGKMGREAVKMIHEADTLELVAVVDSKHDGMLVRQLDGL
ref|YP_175412.1|          --------------RIVIAGPRGNMGQEAVKLCLREESFELVAVVDSKNDGKQLKGLQEF
ref|ZP_01697215.1|        --------------IRIIVAGARGKMGSEAVRLIERTEHFKLVGVVDRTFDGKLFNDVSDY
RAAC00990                 MAKGGERMDKAGGIRVALAGALGRMGQVALEALRREDDIAICGVLVRRADEEAERRLSTY
                                        ::  :**. *.**   *:     . : : : .*:      *      :.

ref|YP_148038.1|          SGVNAPIYTDAARCFAEVKPDVLIDLTTPEAGKRHTELALRYGVRPVVGTTGFTPEDIER
ref|YP_001126216.1|       AGIDAPIYTDAVRCFTEVKPDVLIDLTTPEVGKRHAELALRYGVRPVIGTTGFTPEDIER
ref|NP_242546.1|          PPSDAPVYNELERCLTSQTIDVLVDLTTPAHGKRHMEIALDHGVRPVVGTTGFTDEDITN
ref|YP_175412.1|          QQGDVPVYTDMARCFAEHEPDVLIDLTAPAFGRKHMEVAFEHGVRPVVGTTGFSDEDIRD
ref|ZP_01697215.1|        NGEPVRVYTDPEACLENCPADVWIDLTVPKAGFLHAKTALAHGVRPVVGTTGFTDAELEE
RAAC00990                 G----AVYDDPERLIDTEEPDVWVDLTGPASVVRHVDLALSRGVRAVVGATGYTDEDVRR
                               :  :      :        **  :***  *  . *:   ***.*:*:**::   ::

ref|YP_148038.1|          LTKLAEEKEIGAIIAPNFAVGAVLMMKFARMAAKYFTDVEIIELHHDQKLDAPSGTALKT
ref|YP_001126216.1|       LTELAETNEIGAIIAPNFAVGAVLMMKFARMAAKYFTDVEIIELHHDQKLDAPSGTALKT
ref|NP_242546.1|          LRKKAEEKGIGAIIAPNFAIGAILMMKFAQTAAKYLPDVEIIEMHHDRKLDAPSGTALKT
ref|YP_175412.1|          LTKLAEAKELGAIIAPNFAIGAILMMKFAQTAARYMNDVEIIEQHHDRKLDAPSGTAVKT
ref|ZP_01697215.1|        LKAVSAQKGIGCIIAPNFAIGAVLMMKFAQMAAKYFPDVEIIFLHHDRKKDAPSGTSVKT
RAAC00990                 WDEMARHRQVGAAVCPNFAIGALLMMRFAREAARFLPRAEIIELHHDGKRDKPSGTSLRT
                          :  . :*. :.**:.**::    ::   . * * *  ****::* ref|YP_148038.1|          AQLIAEVRPSKKQGHPNEKETLAGARGAFYDGIPIHSVRLPGFVAHQEVIFGGNGQTLTI
ref|YP_001126216.1|       AQLIAEVRPSKKQGHPDEKETLAGARGAAYDGIPIHSVRLPGFVAHQEVIFGGEGQTLTI
ref|NP_242546.1|          AQLISEVRKAKQQGHPDETEELKGARGADFEGMSIHSVRLPGLVAHQEVLFGGVGQTLKI
ref|YP_175412.1|          AQLIAEVRAPKKQGHEQEREEMAGARGADFDGMKIHSRLPGRVAHQEVLFGGVGQTLSI
ref|ZP_01697215.1|        AQMISEARRKKTQGHPDEKETLQGARGADFEGMHIHSVRLPGLVAHQEVLFGGDGQLLTT
RAAC00990                 KAMM------------------EVEYD-VPIHSVRLPGLVAHQEVIFGGAGEVLTI
                          ::                          . :: : ******  **:* *: *.* ref|YP_148038.1|          RHDSFDRRSFMSGVKLAVETVMHLHTLVYGLEHIL-
ref|YP_001126216.1|       RHDSLDRRSFMSGVKLAVETVMHLHTLVYGLEHIL-
ref|NP_242546.1|          RHDSMNRESFMPGVKLSIETVMGIDTLVYGLENII-
ref|YP_175412.1|          RHDSLNRESFMPGVKLAVEQVVKLSTLVYGLENLI-
ref|ZP_01697215.1|        RHDSMDRASFMSGVKVAVETVMNLNTFVYGLENIL-
RAAC00990                 RHDSLSRESFMPGLILAVRRVMTLRALVYGLDKLLW
                          ****:.* ***.*: :::. *: : ::*****::::
```

FIG. 31

```
ref|YP_704478.1|        --------MTKASVAIVGSGNISTDLLYKLQRSFWLEPRWMIGIDPESEGLARARKLGLE
ref|YP_879906.2|        ----------KAKVAIVGSGNISTDLLYKLLRSDWLEPRWMVGIDPQSEGLARARKLGLE
ref|YP_890165.1|        ---------KKSSVAIVGSGNISTDLLYKLLRSEWLEPRWMIGIDPESEGLARARKLGLE
ref|YP_956012.1|        ---------KKSVAIVGSGNISTDLLYKLLRSEWLEPRWMIGIDPESEGLARARKLGLE
ref|YP_001132791.1|     ---------KLSVAIVGSGNISTDLLYKLLRSEWLEPRWMIGIDPESEGLARARKLGLE
RAAC01029               MGERRGFGLKKLSAAIVGSGNIGTDLMIKLKRSPWIEPRWMIGIDPESDGLRRAREMGLE
                                  .******.*:   *:*** : :. *::* ref|YP_704478.1|        TSAEGVDWLLNQPEKPDLVFEATSAYVHREAAPRYEAAGIRAVDLTPAAVGPAVVPPANL
ref|YP_879906.2|        TTHEGVDWLLAQPEKPDLVFEATSAYVHRDAAPKYEAAGIRAIDLTPAAVGPAVIPPANL
ref|YP_890165.1|        TSAEGVDWLLAQSEKPDLVFEATSAYVHRDAAPRYEEAGIRAIDLTPAAVGPGVVPPANL
ref|YP_956012.1|        TSHEGVDWLLAQSELPDMVFEATSAYVHKAAAPRYAEAGIRAIDLTPAAVGPGVIPPANL
ref|YP_001132791.1|     TSHEGVDWLLARDEKPDMVFEATSAYVHRDAAPRYAEAGIRAIDLTPAAIGPGVIPPANL
RAAC01029               TSADGLKAVLEQGVRPDIVFDATSAKAHVRHAKLLREAGIQAVDLTPAARGPYVIAAVNL
                        *: :*:. :* :   **:**:****  .*   *   ***:*:****** ** *:...**

ref|YP_704478.1|        REHLGAPNVNMITCGGQATIPIVYAVSRVVDVPYAEIVASVASVSAGPGTRANIDEFTKT
ref|YP_879906.2|        RQHLDAPNVNMITCGGQATIPIVYAVSRVVEVPYAEIVASVASVSAGPGTRANIDEFTKT
ref|YP_890165.1|        RDHLDAPNVNMVTCGGQATIPIVHAVSRVVDVPYAEIVASVSSASAGPGTRANIDEFTKT
ref|YP_956012.1|        RAHLDAPNVNMVTCGGQATIPMVYAVSRVVEVPYAEIVASVSSASAGPGTRANIDEFTKT
ref|YP_001132791.1|     REHLDAPNVNMVTCGGQATIPMVHAVSRVVDVPYAEIVASVSSASAGPGTRANIDEFTKT
RAAC01029               EEHLDSPNVNMVTCGGQATVPMVYAVSRVVGVRYAEIVATIASKSAGPGTRANIDEFTQT
                         ..:*:*****:*:*:****** *  ******::::* *************:* ref|YP_704478.1|        TSRGIETIGGAQRGKAIIILNPADPPMIMRDTIFCAIPEDAD---RAAITDSIHRVVADI
ref|YP_879906.2|        TSRGVETIGGAKRGKAIIILNPADPPMIMRDTIFCAIPEDAD---RDAIAQSIHDVVKEV
ref|YP_890165.1|        TSAGVQNIGGAQRGKAIIVLNPAEPPMIMRDTIFCAIPEGA---DHDAITQSIKDVVAEV
ref|YP_956012.1|        TSAGVQNIGGAQRGKAIIILNPAEPPMIMRDTIFCAIPEHA---DHAAITQSIKDVVAEV
ref|YP_001132791.1|     TSAGVEVIGGARRGKAIIILNPADPPMIMRDTIFCAIPEDAD---HAAITQSVKDVVAEV
RAAC01029               TARALEAIGGAKRGKAIIILNPAEPPILMRDTIYCLMEDASP-TTQAKVLESIEQMVRHV
                        *:  .::.****:*****:****:**::*****:*  :  :    :  : :*:. :* .:

ref|YP_704478.1|        QQYVPGYRLLNEPQFDDPSVVSGGQATVTTFVEVEGAGDFLPPYAGNLDIMTAAATKVGE
ref|YP_879906.2|        QSYVPGYRLLNEPQFDDPSLNSGGQALVTTFVEVEGAGDYLPPYAGNLDIMTAAATKVGE
ref|YP_890165.1|        QTYVPGYRLLNEPQFDEPSVVNGGNHLVTTFVEVEGAGDYLPPYAGNLDIMTAAATKVGE
ref|YP_956012.1|        QTYVPGYRLLNEPQFDEPSVVNGGNHVVTVFVEVEGAGDYLPPYAGNLDIMTAAATKVGE
ref|YP_001132791.1|     QTYVPGYRLLNEPQFDEPSVVNGGNHLVTIFVEVEGAGDYLPPYAGNLDIMTAAAAKVGE
RAAC01029               QTFVPGYRLNREPIFQD--------DLVSISIEVEGLGDYLPVYAGNLDIMTAAAVKFGE
                        * :****** .** *::        *:  :**** **:** ***********.*.**

ref|YP_704478.1|        EIAQKLLSV-------
ref|YP_879906.2|        EIAKETLSVA------
ref|YP_890165.1|        EIAKKSAEASLASGAQ
ref|YP_956012.1|        EIAKESL---------
ref|YP_001132791.1|     EIARERVATST-----
RAAC01029               EYARHKMQVASAEEAR
                        * *:.           
```

FIG. 32A

```
ref|YP_519313.1|      ------------------------------------------------MSKKFVYLFREGQASM
ref|ZP_01370069.1|    ------------------------------------------------MSKKFVYLFREGQASM
ref|YP_359304.1|      ------------------------------------------------TKYVYLFHEGRADM
ref|YP_429480.1|      ------------------------------------------------KYVYLFSEGKADM
ref|ZP_01697277.1|    ------------------------------------------------TKFVYLFNEGNSHM
RAAC01041             MSHGELAASARRPMCKRFAGWATRRPRQGGCKMAQVQDVQRDQALTTRWVYSFDQADPKN
                                                                      ::**  *  :. .

ref|YP_519313.1|      RDLLGGKGANLAEMTNIGLPVPPGFTITTEACNDYYALGRNLPEGIWEQIGPALGDIEKA
ref|ZP_01370069.1|    RDLLGGKGANLAEMTNIGLPVPPGFTITTEACNDYYALGRNLPEGLWEQIGPALGDIEKA
ref|YP_359304.1|      KDLLGGKGANLAEMTNIGLPVPPGMTITTEACREYYRLGGKFPEGLMEEVKEKLVYIEEK
ref|YP_429480.1|      RLLLGGKGANLAEMTNIGLPVPQGITITCEACNEYNRLCQQFPEGLEEEVAARLKDLEAI
ref|ZP_01697277.1|    RDLLGGKGANLAEMTNIGLPVPFGFTITTEACNDYYSNGKKISDAVETQMEEALLKLEEK
RAAC01041             RSLLGGKGANLAQMVQWGFPVPPGFTITTEACNEYWARGGKFPKGLLDEVALAILRLERT
                      :  **********. :  *:*** *:* *.:*    * ::.:.  ::    :  :* ref|YP_519313.1|      TGKKFGDKDNPLLVSVRSGAKFSMPGMMDTILNLGLNDETVEGLAASTQNARFAYDSYRR
ref|ZP_01370069.1|    TGKKFGDKDNPLLVSVRSGAKFSMPGMMDTILNLGLNDETVEGLAASTQNARFAYDSYRR
ref|YP_359304.1|      TGKKFGDPQNPLLVSVRSGAKFSMPGMMDTILNLGLNEETVEGLAQNTQNPRFAYDAYRR
ref|YP_429480.1|      NGKKLGDPENPLLVSVRSGAPVSMPGMMDTILNLGLNDNSVKGLAAQTGDERFALDCYRR
ref|ZP_01697277.1|    TGKKLGGNENPLLVSVRSCSVFSMPGMMDTVLNLGLNDTVEAVAKLTGNPRFAYDSYRR
RAAC01041             AGKRFGDAFQPLLVSVRSGAPVSMPGMMDTILNLGLNDLTVRALANQSQDPAFAYDSYRR
                       **::*.   :******:  .****:**:*: :*..:*  : :   ** *.*** ref|YP_519313.1|      FIQMFGDVVLEVEHHEFERILEEAKEKQNVNYDSELTAESLKGVVEGYKRLIQRRTGSPF
ref|ZP_01370069.1|    FIQMFGDVVLEVEHHEFERILEEAKEKQNVNYDSELTAESLKGVVEGYKRLIQRRTGSPF
ref|YP_359304.1|      FIQMFGDVVLEIPKHEFEHILDRQKEKEGVTFDQELSAEALKEVITRYKELVERKTGKPF
ref|YP_429480.1|      FIQMFGNVVLGIEHNDFEAVLEKEKERLGVKFDHELTPDALREVIAEYKDVVKSRSGRDF
ref|ZP_01697277.1|    FIQMFSDVVLGIEVYHFEHLLEQTREQKGYTADPFMTAEDWKDIIAGYKKIVKKHTKQDF
RAAC01041             LIQMFANVVFNVSLEPFEHALRAAKAKHGVERDRDLPADAWKDLVATYLKLFAEHVGQPF
                      :**.:: :   ** *  : :.    * :::.:  : ::   *   :. :      * ref|YP_519313.1|      PLDPMKQLEQAILAVFRSWNNDRAIVYRRINSIPDNIGTAVNVQSMVFGNMGNDSGTGVA
ref|ZP_01370069.1|    PLEPMKQLEQAILAVFRSWNNDRAIVYRRINSIPDNIGTAVNVQSMVFGNMGNDSGTGVA
ref|YP_359304.1|      PSDPMVQLTMAIEAVFKSWNNDRAIVYRRINKIPDDLGTAVNIQSMVFGNMGNDSGTGVA
ref|YP_429480.1|      PQDPREQLYMAIRAVFDSWNNPRAIVYRKINKIPDDLGTAVNVQTMAFGNMGPTSGTGVA
ref|ZP_01697277.1|    PQDPKTQLYLAVNAVFDSWNQRAIVYRRLNKIPDHLGTAVNIQSMVFGNMGDDSGTGVA
RAAC01041             PQDVNVQLELAIEAVFRSWNSPRAIVYRKAHGIPETLGTAVNVQAMVFGNMGDDSGTGVI
                      *  :    **  *: * *.  : . :*** *:*.*** *** ref|YP_519313.1|      FTRNPSTGERVLYGEYLMNAQGEDVVAGIRTPQPIKSLEDENKAIYAQFVETSNSLEAHY
ref|ZP_01370069.1|    FTRNPSTGERVLYGEYLMNAQGEDVVAGIRTPQPIKSLEDENQAIYAQFVKTSNSLEAHY
ref|YP_359304.1|      FTRNPSTGEKVLYGEYLTNAQGEDVVAGIRTPSPISKLKEEMPEVYEQFVSIAKLLESHY
ref|YP_429480.1|      FTRNPSTGEKGIYGEYLINAQGEDVVAGIRTPKPISSLKEEMPEVYRQFEDICQLLEKHY
ref|ZP_01697277.1|    FTRNPSTGERVLYGEYLINAQGEDVVAGIRTPQPIQVLAKDMPEVYRQFVKTSKLLEEHY
RAAC01041             FTRHPSTGEPVLFGEFLANAQGEDVVAGIRTPQPIADLAHTMPHVYESLVALAKQLETRF
                      ***:*****   ::**:* **************.** *    :* .:   .: ** ::

ref|YP_519313.1|      RDMQDIEFTIERGRLYILQTRNGKRTAPAAIRVAVELCREGVISKEEAIARIEPGQLDQL
ref|ZP_01370069.1|    RDMQDIEFTIERGRLYILQTRNGKRTAPAAIRVAVELCREGVISKEEAIARIEPGQLDQL
ref|YP_359304.1|      KNMQDIEFTIERGKLYILQTRNGKRTAQAAVKIAHDMVEEGLITKKEAILMVEPGQLDQL
ref|YP_429480.1|      RDMQDIEFTIEKGKLFILQTRNGKRTAAAAVKIAVDMVNEGLITKEEAVLRVDADQLIQL
ref|ZP_01697277.1|    QDMQDIEFTVERGKLYLLQTRNGKRTAQAAIRIAVEMVKEGILDKKTALLRVDPDQMNQL
RAAC01041             RDMQDVEFTVERGKLFVLQTRSGKRTAQAAVRIAIDMLEEGLIQPFEALLRVDAQHLRQL
                      ::*** :*** :*:*:*: ****. ***** **::: *  :: .**:: :   *:  :: :  **
```

FIG. 32B

```
ref|YP_519313.1|      LHRRMDSEAKLEVIAKGLPASPGAASCKIVFDADEAERLGHTGERVLLVRTETTPDDIHG
ref|ZP_01370069.1|    LHRRMDSEAKLEVIAKGLPASPGAASGKIVFDADEAERLGHTGEKVLLVRTETTPDDIHG
ref|YP_359304.1|      LHRQIDPSAKVEVIAKGLPASPGAASGIVVFDADEAEKLGKEGKKVLLVRTETTPDDIHG
ref|YP_429480.1|      MHRRIDPSAKLEVVAKGLPASPGAASGQVVFDADDAEKMGLDGQKVVLVRTETTPDDIHG
ref|ZP_01697277.1|    LHRRIDGSATKNHLAKGLPASPGAATGTVVFDADEAERLGKEGEKVILVRPETTPDDIHG
RAAC01041             LHRRLQGTDALQVFAKGLPASPGASVGRIVLDADTAVEWAQRGEKVVLVRPETTPEDIHG
                      :**::.         : .**********: * :*.***  *  .   *::***.****.****

ref|YP_519313.1|      ILAAQGILTSRGGMTSHAAVVARHMGKPAVCGCEALRIDYAHNTVTIDGVTYPEGTLFSI
ref|ZP_01370069.1|    ILAAQGILTSRGGMTSHAAVVARHMGKPAVCGCEALRIDYAHNTVTIDGVTYPEGTLFSI
ref|YP_359304.1|      IVAAQGVLTSRGGMTSHAAVVARGMGKPCVCGCEAIKIDYEKKLFTVDNITVKEGDYLSI
ref|YP_429480.1|      IVQAQGVLTARGGMTSHAAVVARGMGKPAVTGCDAIKIDVENKRFFIGDLVVKEGDVIST
ref|ZP_01697277.1|    IVASQAVVTSRGGMTSHAAVVARGMGKACICGCESMKIDLKAKQFTVGDTVVRYGDVITI
RAAC01041             VLAAEGVVTTHGGMTSHAAVVARGIGKPAVCGCDGVHIDFEARQVESNGVVLKEGDVISV
                      ::  ::.::*::************ :**..:  **:.::**     . .  ...  *  :::

ref|YP_519313.1|      DGTTGRVIKGAVPMIDPELSEEFKELLGWADEIRTLKVLANADNPRDAQKARDFGAQGIG
ref|ZP_01370069.1|    DGTTGRVIKGAVPMIDPELSEEFKELLGWADEIRTLKVLANADNPRDAQKARDFGAQGIG
ref|YP_359304.1|      DGSTGRVILGTVPMKDPELSPEFIKLLEWADELKRLEVRANADTPEDAQKAREFGAKGIG
ref|YP_429480.1|      DGSTGNVMLGEVPLIDPQLTGEFETILEWADSFRRLKVRANADTPEDARRSREFGADGIG
ref|ZP_01697277.1|    DGSTGEVMLGEVPMIDPELSGEFKTLLEWADEVRDLGVRANADNPTDAKKSLEFGADGIG
RAAC01041             DGGTGTVYVGEAQMEEAKMADELKELLSIADQVRRLKVRANADTPEDARRAREFGAEGIG
                      ..*  *  . : :.::: *:  :*  **..:  * * ****.* :::  :*.*** ref|YP_519313.1|      LCRTEHMFMDPARIPIVQEMILAQTLPEREVALAKLLPMQEEDFYGILKVMAGFPVTIRL
ref|ZP_01370069.1|    LCRTEHMFMDPARIPIVQEMILAQTLPEREVALAKLLPMQEEDFYGILKVMAGFPVTIRL
ref|YP_359304.1|      LCRTEHMFMGPERLPHVQRMILAETKEEREFALSHLLPMQEEDFYGILKAMEGYPVCIRL
ref|YP_429480.1|      LTRTEHMFMQVDRLPVVQQMILAKTKEERQAALDKLLPMQQGDFYGILKAMEGLPVTIRL
ref|ZP_01697277.1|    LCRTEHMFMDIKRVPIVQEMILAETEEREKALDKLLPMQQGDFEGIFEEMAGHPVTIRL
RAAC01041             LCRTEHMFLSPDRVPLVQRMILATTSAERQAALSKLLPLQVSDFTAIFEAMDGLPVTIRL
                      * ******:     *:* .**  *   :   .:***:*   **  .*::  *   * ref|YP_519313.1|      LDPPLHEFLPNVEELVVDITKLKLQGDREEELNEKEVLLRKVRALSEMNPMLGHRGCRLG
ref|ZP_01370069.1|    LDPPLHEFLPNVEELVVDITKLKLQGDREEELNEKEVLLRKVRALSEMNPMLGHRGCRLG
ref|YP_359304.1|      LDPPLHEFLPSLEELLVETTELRVRGDNPELLAEKEALLKKVKSLHEFNPMLGHRGCRLG
ref|YP_429480.1|      LDPPLHEFLPNIEELLVDVTRLQATNGDSKELEEKQALLREVRARHEFNPMLGHRGCRLG
ref|ZP_01697277.1|    LDPPMHEFLPDKEELLVEVTKLQLTAPESKELEEKEYLLKKVQHLAEFNPMLGHRGCRLG
RAAC01041             LDPPLHEFLPREEELAERLEELRAQGASEDEIAETEQLLRQARYLREANPMMGLRGSRLG
                      **:*  *    .*:     . :  *.:  **:::.:  *  ***:* .* ref|YP_519313.1|      ITFPEIYAMQARAIFQASARLVKEGCEIHPEVMIPLVIHVKELAKLRKVTEEAAQTVMAE
ref|ZP_01370069.1|    ITFPEIYAMQARAIFQAAARLVKEGYEIYPEVMIPLVIHVKELAKLRKVTEEAAQTVMAE
ref|YP_359304.1|      ITYPEVYEMQIRAIFNAAARLTKEGYKVYPEVEIPLTIDVNEMKFFKERIDAIAREVMER
ref|YP_429480.1|      ITYPEIYAMQVRAIFQAVAQLVKEGVKVLPEVEIPLVIHVNELQRLHAMVDEVAAAVKKE
ref|ZP_01697277.1|    VIFPEIYEMQVKAIFYAAAAVLQKGIKVQPEIMIPLVGHVNELKRMRALVTDMANQVMEE
RAAC01041             TVYPEIYDMQMEAIITAAAQAKRRGIAVDLEVMLPLIGSPKELRVLRERMEEIAKRTMER
                      : :**:* ** .**: *  *   :.*  :*: **   :*:  ::     *  ..

ref|YP_519313.1|      QGVTFSYTIGTMIEVPRAALTADEVATAADFFSFGTNDLTQTTLGFSRDDAEGKFLPAYL
ref|ZP_01370069.1|    QGVTFAYTIGTMIEVPRAALTADEVATAADFFSFGTNDLTQTTLGFSRDDAEGKFLPAYL
ref|YP_359304.1|      EGVTFHYTTGTMIELPRAALLADELAEVAEFFSFGTNDLTQITLGFSRDDAEGKFLTHYL
ref|YP_429480.1|      TGVDFDYKVGTMIEMPRACATADEIAREAEFFSFGTNDLTQTTFGFSRDDAEGKFLHQYV
ref|ZP_01697277.1|    KGLKFDYTVGTMIEIPRAALTADQIAEEADFFSFGTNDLTQTTFGFSRDDAEGKFLQQYI
RAAC01041             EGVEFEYRIGTMIEVPRAALTADQIAEDAQFFSFGTNDLTQMTFAFSRDDAEGKFLNVYL
                      *: : *  *****:***.  **:*  *:*********** *:.*********  *:
```

FIG. 32C

```
ref|YP_519313.1|      EQNILEHNPFAVLDRIGVGKLMKMGVQLGREANPGLKVGICGEHGGDPSSIEFCHQIGLN
ref|ZP_01370069.1|    EQNILEHNPFAVLDRIGVGKLMKMGVQLGREANPGLKVGICGEHGGDPSSIEFCHQIGLN
ref|YP_359304.1|      DMKILKENPFIVLDRKGVGKLMKIAVEGGRKTRPDLLVGICGEHGGEPSSVEFCHQIGLD
ref|YP_429480.1|      DEKILKEDPFIVLDRDGVGKFMKMAVELGRSTNPKLEIGICGEHGGEPSSVEFCHQIGLN
ref|ZP_01697277.1|    EQKVLPENPFAVLDQEGVGKLVETGVKLGRQTKPGLKTGICGEHGGEKSSIEFCYKTGLN
RAAC01041             DREILPYNPFETLDTEGVGKLIQWAVEAGRKRRPDLKTGVCGEHGDPASIAFCEDIGLD
                      : ::*  :** .**  ****::: .*: **. .* *  *:******: :*: **  .**:

ref|YP_519313.1|      YVSCSPF--------------------
ref|ZP_01370069.1|    YVSCSPF--------------------
ref|YP_359304.1|      FVSCSPY--------------------
ref|YP_429480.1|      YVSCSPF--------------------
ref|ZP_01697277.1|    YVSCSPY--------------------
RAAC01041             YVSCSPFRIPVARIAAAQAAVRKRMTG
                      :*****:
```

FIG. 33A

```
ref|ZP_01697463.1|    ---IQKAAVIGSGVMCSGIAAHLANTGTPVLLLDIVPNALTEAEKAKGYTLEDKAVRNRF
ref|ZP_01173543.1|    IQQIKKAAVLGSGVMGSGIAAHLANIGIPTLLLDIVPRELNEAEQKKGLTLEDKAVRNRI
ref|NP_244355.1|      -RQTRKVAVIGSGVMGSGIAAHLANVGIPSLLLDIVPNQLTEEEQRKGLTLEDRAVRNRL
ref|YP_148861.1|      VKRIRRAAVLGSGVMGSGIAAHLANVGIPTLLLDIVPRELTKEEEAKGWTLEHKQVRNRL
RAAC01057             MRQIRRAAVIGSGVMGAQIAAHLANVGIPSLLLDLVPQELTAFEQKKGLSLDHPAVRNRL
ref|YP_076839.1|      ---IRKAAVLGAGVMGAQIAAHLANVGTPTLLLDIVPRELTPDEAKKGLTLESPAVRNRL
                         *::.**:*:****. ******:*** ****:**. *. *  ** :*:  ****:

ref|ZP_01697463.1|    SQSALQKLLKQKPAPLTSKKSLALIEAGNLEDDLERLKEADWIIEVVTERLDIKKSVFEK
ref|ZP_01173543.1|    SQGALQKLQKQKPAPLTSKKSLALLEAGNFEDDMESLKDVDWIIEVVVENLDIKKQVFAK
ref|NP_244355.1|      ATLALKKLQKQKPAPLSRKSHVHYIQPGNLEDDVEKLAEVDWIIEVVVENLDVKKQLFEK
ref|YP_148861.1|      ANQALERLLKQKPAPLMSKDNIALIETGNFEDDFHRLAEVDWIIEAVVEKLEVKKEVFAR
RAAC01057             ATEAIRRLNKLSPAPLFRADYAKLITPGNLEDDLHRTCEVDWVIEVIVESLEPKRQLLER
ref|YP_076839.1|      AASALQNLQKLKPSPLYSKDVERLITPGNLEDDLAKVAECDWVVEAVIENLQIKKDLWQR
                       :  *:..* * .*:** .      :.**:***. : : **::*.: * *: *:..: :

ref|ZP_01697463.1|    VERFRRPGTIVSSNTSGISIEAMAEGRSEDFRKHFLGTHFFNPPRYLKLLEVIPTADTDP
ref|ZP_01173543.1|    VDQFRKPGSIVSSNTSGISVNSMAEGRSDDFQKHFIGTHFFNPPRYLKLLEVIPAKTTAP
ref|NP_244355.1|      VDQYRKQGTLVSSNTSGISIEAMAKGRSEDFQAHFLGTHFFNPPRYLKLLEIIPTKKTKP
ref|YP_148861.1|      VDEVRTPGTIVSSNTSGISIAAMAEGRSDDFKKHFLGTHFFNPPRYLKLLEIIPTEHTDP
RAAC01057             IERYWHEGMIVSTNTSGISINAMVEGRSEAFRRHFLGTHFFNPPRYMKLLEVIPGRDTDP
ref|YP_076839.1|      VAAHHRPGMICSSNTSGISIQAMVEGTPESFRRHFLGTHFFNPPRYMKLLEIIPTPDTDP
                      :   *  : *:******:  :*.:* .: *: :******::   * * ref|ZP_01697463.1|    DVTSFMKQFGEDVLGKGVVLAKDTPNFIGNRIGTYGLLVTVREMMKGGYTVGEVDSVTGP
ref|ZP_01173543.1|    EVLSFMKKFGEDVLGKGVVEAKDTPNFIGNRIGTYGLLTTVQEMLKGGYSVGEVDSVTGP
ref|NP_244355.1|      EVTAFMKAFAEDVLGKGVVEGKDTPNFIANRIGTYGLLVTVREMMQGGYSVGEVDSVTGP
ref|YP_148861.1|      DVVAYMKSFGEDVLGKGVVMAKDTPNFIANRIGTYGLLVTVREMMQGGYSVGEVDSVTGP
RAAC01057             AIVEFMRDFGTERLGKGVVLAKDTPNFIANRIGTYGLLVTVEEMQKGGFTVEEVDAITGP
ref|YP_076839.1|      EVVAFMADFGERVLGKGVVMAKDTPNFIGNRIGVYGMMVTLEEMNRLGLTPDEVDALTGK
                       :   :*  *. ******  .******:*****.**::**: .* . * . ***::**

ref|ZP_01697463.1|    VIGRPKSATFRTLDVVGIDTFVHVANNVYEK-TEGEEKEVFKVPAFMHKLVENGWLGSKT
ref|ZP_01173543.1|    LIGRPKSATFRTLDVVGLDTFIHVANNVYEQV-DCKEKEAFEVPAFMKQMLENGWLGSKS
ref|NP_244355.1|      LIGRPKSATFRTLDVVGLDTFLHVAKNV-HDVVDGEEKDVFDPPVFMKKMAENGWIGSKS
ref|YP_148861.1|      LIGRPKSATFRTLDVVGLDTFVHVANNVYENV-EGEEKEAFRVPEFMKTMLENGWLGSKS
RAAC01057             ALGRPKSATFRTLDLVGIDTFVIIVANNVRQNVTDPQEQCRAFEVPEAIQKLVERGWLGEKS
ref|YP_076839.1|      AIGRPKSATFRTLDVVGIDTFCHVADNCRATIPDPEEAKIFVVPEPTRFMVKRGWVGQKA
                       :***********:** ***  ***.*     :*      * ::   :: :.**:*.*:

ref|ZP_01697463.1|    GKGFYEK----KGKEIYELNPETLEYGERTKMKAASLEAARQAKCTANKIKTIVYAD-DR
ref|ZP_01173543.1|    GQGFFKK----EGKEILELNPDTLEYGPRQKLKAASVEMSKQEKGLANKLKALVYAD-DK
ref|NP_244355.1|      GQGFFLKQKGENGSEILELNPSTLEYEKRKKMKAPSIEQAKQAKSLNEKLSILIQAN-DR
ref|YP_148861.1|      GQGFF--VKQG--KDTLELNYVTMQYEPRKKLVTPAVEMAKQAKGAAAKLQTLVYADGDR
RAAC01057             GQGFYKRVKQNGQRQILVLDLDTFEYREQKKIASSALEASKQAKGAAGKAKALLQGG-DR
ref|YP_076839.1|      RQGFFKKEGD----QILTLDLETMEYRPRRKASFPSLEAAKANPDLRSRVRGLVFAK-DK
                       :**:      :* *: *::*  *   .::*  ::        :  ::  . *:

ref|ZP_01697463.1|    AGRLLWNILAPCLVYSAELSGVIADDILAIDQAMKWGFGWKFGPFETWDAIGVEKSVQKM
ref|ZP_01173543.1|    AGQLLWNILSPALLYSAELLGEIADDVISIDKAMKWGFGWQMGPFETWDSIGLEKSVGKM
ref|NP_244355.1|      AGQLLWNLMKPVLIYSAEKVYEIAGDIKAVDDAMKWGFGWFQGPFEMQGPFEMDAIGVASSVQRM
ref|YP_148861.1|      AGTLLWNIIAPTLLYTARLVGEIADDTAAIDQAMKWGFGWEQGPFELWDAIGLEKSVRKM
RAAC01057             YAELAWNIVKRVLVYSAEKLGEIADTIQDIDAAMRWGFNWELGPFELWDALGLVETAERM
ref|YP_076839.1|      AGEFLWAITKRTLLYAARKVGEIADDVVAIDNAMKWGYNWELGPFEMWDAIGLPESIARM
                       .: * :   *:*:*.     **. :  :* **:**:.* **** **::*:  .: :*
```

FIG. 33B

```
ref|ZP_01697463.1|   EEDGLQVPGWVKGMLEKGFTSFYKEENGVVSYYDNGAYKPLPANPKEINLKALKTQGKVL
ref|ZP_01173543.1|   EAEGKEVPAWIKEMLSNGHTSFYKEENGDTSFYKNGEYVPEEENPKNINLKKLKKQKGVI
ref|NP_244355.1|     EEEGATVPSWVKEMLTSGRERFYQ--DG--TFYHHGEAKVIPINGKIIHLKALKPE-RVI
ref|YP_148861.1|     QSEGRDIPSWITDMLADGATSFYKTENGRLFYYAPGGYKTVEENEKVIHIRRLKEARGVI
RAAC01057            RAEGLRLPSWVEDWIAAGHRAFYEEKDGKLTMPVNGKPEPVRVPAGVIDLAALKKAGKVI
ref|YP_076839.1|     EAEGEAVPDWVKE--AARKGGFYRREAGKSFFINKGEYAPVPVSDRVIDIGALRETGRVV
                      .:*  :* *:          **.   *         *      *.:  *:    *:

ref|ZP_01697463.1|   KENAGASLIDIGDGVLLEFHSKSNTIGLDILQMINYAVDEAEKH-YKGIVIGNQGKNFC
ref|ZP_01173543.1|   KKNTGASLLDLGDGVALLEFHSQSNAIGLDIIQMINFAVDEVEKN-YKGLVIGNQGKNFS
ref|NP_244355.1|     TKNSGASLIDLGDDVALLEFHSPNNSIGFDVVQMINKAVDEVEAN-YKGLVIGNQGKNFC
ref|YP_148861.1|     KKNAGASLIDLGDDVALLEFHSPNNAIGADIVQMINEALEEVNRN-YKGLVIGNQGKNFC
RAAC01057            AQNTGASLIDLGDGVACLEFHSQNNAIGPDILTMIEKSVAIAEKD-FAGLVIANQGKNFC
ref|YP_076839.1|     REKKGATLLDMGDGVLLMETHSPKAAIGFDIINMCKVAAEELASGRWKGLVIGARTENFC
                      :: **:*:**.*  :* **  .:** *::  * : :         : *:**. : :**.

ref|ZP_01697463.1|   VGANLALMLMEAQDDNIFELDMVVRQFQNTMMKIKYSQKPVVAAPFAMTLGGGAEVCLHT
ref|ZP_01173543.1|   VGANLAMILMEAQDDNVFELDMVVRHFQQAMMKIKYSTKPVVAAPFAMTLGGGAEICLPA
ref|NP_244355.1|     VGANLMMILMEAQDDNFFEIDMVVRQFQQAMAKIRYSQKPVVSAPFAMTLGGGTEICLPT
ref|YP_148861.1|     VGANLAMMLMEAQDENFFELELAVRQFQQALLKMKYNPKPVVVAPFAMTLGGGAEVSLAA
RAAC01057            VGANLMLILMAAQEGDWDEIDLSIRQFHRAMLALRYSQVPVVAAPHRMTLGGGVEVCLAS
ref|YP_076839.1|     VGANVAIMLMEAQEEEWDELEFMAREFQNAFMALKLAPKEVVVAPYGMTLGGGYELCAVA
                     ****: ::** **: :  *::: *.*:.:  ::    *** **.****** *:.   :

ref|ZP_01697463.1|   AHIQAASETYMGLVETGVGLLPGGGGNKELYIKHLKNIPEGVQFDLQNVVNKVFETIAMA
ref|ZP_01173543.1|   AHIQASMETYMGLVEAGVGLIPGGGGNKELYIKHLECMPNGVEFDLQKVANKVFESIAMA
ref|NP_244355.1|     ASIQASLETYMGLVEVGVGVIPGGGGNKELYLRHLERLPEGANIDLQSIANKTFETIAMA
ref|YP_148861.1|     SRIQAAAETYIGLVEVGVCLIPGGGGNKELYIKRLNSLPRGVDVDYKIAASVFETIAMA
RAAC01057            SRVLPAAETYFGLVEVGVGVIPGGGGCKETARRVAESV--GPEDDLVPALARMFQAIGTA
ref|YP_076839.1|     DRVVAAAESYIGLVEVGVGVIPGAGGNKEMLIRGLEGLPAGAQVDIQPILNRIFETIATA
                      : .: *:*:**** .***::**.**.**        : : :  * :*     *::*. *  .

ref|ZP_01697463.1|   KVSTSAEEARESGFLDRTDGVSFNQDHLIYDAKQAVLRLADAGY-KPPVREKVPVTGESG
ref|ZP_01173543.1|   KVSTSGEEARENNFLGAADGISVNGDHQLYDAKQAVLALHEQGY--PPVRKKIPVVGETG
ref|NP_244355.1|     KVSTSAHEAMENGFLSERDGVVVNGDHLLYQAKQQVIHLHDAGY-RPPARKKIPVVGETG
ref|YP_148861.1|     KVSTSAAEARELGFLNHRDGITMNGDHLLYEAKQAVLSMYEEGY-RPPVRKKVPVAGESG
RAAC01057            KVSTSGAEALAMGWLRETDRVVVNDDLRISAAKAEVLRMAEIGYTAPPKAKEIRVAGRDG
ref|YP_076839.1|     KVATSAREAQEMGYLRKSDVIVVNKDEQLYEAKRVVLALEAAGY-RPPEPALIPAAGPEG
                     :. **  ..:*   *  : .*  :  **    *: :           :..*  * ref|ZP_01697463.1|   YAALLLGAQQMHLSGYISDYDLEIAKKIAFVLSGGKVPFGTKVDEQYLLDLEREAFLSLI
ref|ZP_01173543.1|   YATLLLGAQAMLYSGFISEHDLKIAQKLAYVIAGGKVPYGTEVDEQYLLDLEREAFLSLV
ref|NP_244355.1|     YATMLLGAKSMKFGGMISEHDLKIAEKLAFVIAGGRVAKGTLVDEQYLLDLEREAFLSLV
ref|YP_148861.1|     YAAMLLGAQSMFHSGYISEHDLKIAKKLAYVLAGGKVPYGTEVDFQYLLDLEREAFLSLI
RAAC01057            KATLQMAARSMWNGGYITDYDLHIAYKLAHVLAGGDVPAGSLVSEDYLLDLEREAFLSLC
ref|YP_076839.1|     RAVLELGAYGMFMGGWATEHELFIARKLAYVLTGGNVPAGTLVTEQYLLDLEREAFLSLL
                      *.:  :.*   *  .*  :::::* ** *:*.*::** *. *: * *:************ ref|ZP_01697463.1|   AQPKTQQRMQHMLLKGKPLRN
ref|ZP_01173543.1|   AQPKSQQRMQHMLVKGKPLRN
ref|NP_244355.1|     GEPKSQQRMQHMLMKGKPLRN
ref|YP_148861.1|     GEPKTQARMQHMLVKGKPLRN
RAAC01057            CEPKTIQRMQHMLATGKPLRN
ref|YP_076839.1|     GTKKTQERMAHLLKTGKPLRN
                      . *:  **  **:*  .*****
```

FIG. 34

```
ref|NP_691707.1|         ----------------KARAVDGPHQPFHATEIKRRNLDSHDVLIEIKYSGICHSDIHTA
RAAC00352                MHICFESAEEVEGMQVKARGVLSKESPFHAIKIERRELQPDDVLIEIHYCGICHSDIHSA
ref|YP_829756.1|         -----------------------------IERRDVGPHDVLIGIKFAGICHSDIHTV
ref|YP_947785.1|         -----------------------------IERREVGPNDVHTDTKFAGICHSDIHTV
ref|YP_001221402.1|      ---------------VNAYAATSATDPITKTTIERRDVGPKDVSIDIAYSGVCHSDIHTV
ref|YP_885435.1|         ---------------VSAYAATSATEPLTKTTITRRAVGPHDVAFDIHFAGICHSDIHTV
                                            * **  :  ..**  : *  :.*:******:.

ref|NP_691707.1|         HGEWGEVNYPLVPGHEIAGVVSDVGPEVTKYKVGDRVGVGCMVDSCGECENCRRGEEQYC
RAAC00352                RGEWGEVRYPFVPGHEITGIVSKVGSQVTKFKPGDRVGVGCMVDSCGECENCKRGDEQYC
ref|YP_829756.1|         RGDWGPQQYPLAPGHEIAGIVTDVGSEVTKHAVGDRVGVGCMVNSCRECVNCQKGEEQYC
ref|YP_947785.1|         RGDWGPQQYPLAPGHEIAGIVTEVGSDVTKHHVGDRVGVGCMVNSCKECKNCLAGEEQYC
ref|YP_001221402.1|      RGEWGPIAYPQVVGHEIVGRVTEVGSEVSKHEVGDLVGVGCMVNSCKECEQCKAGQEQYC
ref|YP_885435.1|         KAEWGVPNYPVVPGHEIAGVVTEVGSEVTKYKVGDRVGVGCFVDSCRECDNCKAGLEQYC
                          :.:     . ****.* *:.**.:*:*.    ***:*:  :*   * **** ref|NP_691707.1|         H-QGNVQTYGGVD-KYGEPTQGGYSTHIVVTEDFVLRIPDNIELDVAAPLLCAGITTYSP
RAAC00352                V-KGNIQTYGSVD-RYGQYTMGGYSTHIVVKEDFVLRIPDALPLDKAAPLLCAGITTYSP
ref|YP_829756.1|         L-KGNIGTYGAVD-RDGTITQGGYSTHVVVTEDFVVRIPEGIELDVAAPLLCAGITTYSP
ref|YP_947785.1|         L-KGNVGTYGSVD-RDGTITQGGYSSHVVVNEDFVVTIPEGLDLDVAAPLLCAGITTYSP
ref|YP_001221402.1|      L-KGNIQTYGGTDPADGTITQGGYSEAVVVDEDFVLRVPESLDIEKVAPLLCAGITTYSP
ref|YP_885435.1|         TGTGMVGTYNAID-RDGTPTHGGYSGAIVVDENYVLRIPDSLPLDAAAPLLCAGITTYSP
                             :  **..  *      *   *  ** : *::*:  :*:  :  ::  .************ ref|NP_691707.1|         LNHWNAGPGKKVAVVGMGGLGHMAVKIAHAMGAEVTVLSRTLNKKEDGLEFGAENYYATS
RAAC00352                LRHWQAGPGKEVAVVGLGGLGHMAVKLAKAMGAKVTVLSQSLRKKEDGLRLGAKAYYATS
ref|YP_829756.1|         LHHWGAGPGKKVAVVGLGGLGHMAVKIAHAMGAEVTVLSQSLKKQEDGLKLGADHYYATS
ref|YP_947785.1|         LHHWGAGPGKKVAVVGLGGLGHMAVKIAHAMGAEVTVLSQSLKKMEDGLKLGADHYYATS
ref|YP_001221402.1|      LRHWNAGPGTKVAVVGMGGLGHMAVKIAHAMGAEVTVLSQTLSKKEDGLRLGADRYFATS
ref|YP_885435.1|         LRHWNAGPGKKVAVIGLGGLGHVAVKLAKAMGADVTVLSQSLKKMEDGLRLGASAYYATS
                         *. .:*:*:***:*:*:**.***::* * **.:. *:*** ref|NP_691707.1|         EKETFETLAGSFDLIINTVSAKLDMDAYFSLLNLDGSLVNVGAPAEPLSVNVFSLIGHRR
RAAC00352                DPETFRQLAGRFDLIINTVSAKIPITEYLGLLKTDGALVNVGAPPEPLEVNAFALIAQRR
ref|YP_829756.1|         DENTFSDLAGSFDLIINTVSASIDISSYLQLLTLDGALVNVGAPAEPLPVNAFALIAGRR
ref|YP_947785.1|         DPATFEQLGGTFDLTVNTVSASIDISAYLQLLTLDGTLVNVGAPAEPLPVNVFSLITGRR
ref|YP_001221402.1|      DDATFTELASSFDLIINTVSAKLDMSKYIGLLAIDGTLVNVGAPSEPLEIPAFALIPARR
ref|YP_885435.1|         DPETFDKLAGSFDLILNTVSANLDLGAYLGLLKLDGALVELGLPEHPMEVPAFPLLAQRR
                          :  **  *..  ****:*****.: :    *: **  **:**:* *  .*: :  .*.*:  **

ref|NP_691707.1|         SFAGSLIGGIRETQEMLDFCAEHNIVPKIEVISADQIDEAYTRVLDSDVKYRFVIDVSTI
RAAC00352                TFAGSCIGGIRETQEMLDFCAESGVTPEIEVISADEIDAAWERVLKSDVRYRFVIDISTM
ref|YP_829756.1|         SFAGSMIGGIRETQEMLDFCAEHNLGAEIEVIPAEKINEAYERVLASDVRYRFVIDTATL
ref|YP_947785.1|         RFAGSAIGGIRETQEMLNFCAEHGLGAEIEVIPASKINDAYERVLASDVRYRFVIDVSTI
ref|YP_001221402.1|      SWAGSMIGGIAETQEMLDFCAEHGLVPETELISAEQINEAYERVLKSDVRYRFVIDAKT-
ref|YP_885435.1|         NLTGSMIGGIPETQEMLDFCAEHDVRPEIEIITPDYINEAYERVLASDVRYRFVIDTASL
                          :**  **** ******:****  .: ..:  *:*...  *:  *:  *** ***:******    :

ref|NP_691707.1|         --
RAAC00352                RN
ref|YP_829756.1|         --
ref|YP_947785.1|         --
ref|YP_001221402.1|      --
ref|YP_885435.1|         RS
```

FIG. 35

```
ref|YP_055250.1|        --------MKAALVEQYHEPLAIRDIPEPAHDSDGVVVEVKACGVCRSDWHGWQGEWPGF
ref|YP_134751.1|        --------MRAAVLEEYEEPLAIRDVERPDPDPDGVVAKVDACGVCRSDWHGWVGNWDWF
gb|ABW71834.1|          --------VRAAQIVGYGEPLQVREVPDPAPEPGGVVVAVLATGICRSDWHGWRGDWEWL
RAAC04321               MERERGQAVKAARMVGFREPLVIERVPDPTPGPEDAVIRVEASGICRSDWHGWMGDWTWL
ref|YP_612035.1|        --------MKAVLYETFKELPKLVTVEDPTPDPDGVVIKVEATGLCRSDWHGWMGHDSDI
ref|ZP_01441442.1|      --------MKAVLFETFQEAPKLVTVPDPVPDAHGVVLKVAATGVCRSDWHGWMGHDSDI
                                 ::*.      :   *    :   :   *    .. .*  * * *:*******  *. :

ref|YP_055250.1|        -TGGSLFHIFGHEFVGLVSDIGNNVSRYRVGDRVIVPFTLGCGHCEYCRSGHSNVCP-TV
ref|YP_134751.1|        DYKPPRGHILGHEPSGTVVEVGENVDTVKEGDTVAIPFNFACGHCHECRVGYENLCENHL
gb|ABW71834.1|          GGRIALPRTPGHEIAGEVVAAGPGVRGVRVGDRVTVPFHLACGTCAHCRAGQANLCD-EM
RAAC04321               GLSPQLPITPGHEFGGEIVALGREVRDFQIGDKVTVPFHYACGHCEHCHAGVPNRCD-HV
ref|YP_612035.1|        ----VLPHVPGHEFAGVIVALGKNVRNWTVGDRVTVPFISGGCACSECHAGHQQVCH-NQ
ref|ZP_01441442.1|      ----ELPHVPGHELAGEVAAVGKDVRNWKIGDKVTVPFICGCGSCSECHAGQQQVCL-HQ
                              ***    *:      *    *             ** *  :   . *   *: *   :  * ref|YP_055250.1|        SMPGFSY--DGGFAQYVTVPDADANLVKLPDAVDFTDAAGMGCRLMTAYHGIVEVGQIHP
ref|YP_134751.1|        GL-GFQPGAPGAFAEEVPIPNADINAVKLPDGVDPVEVAGMGCRFMTSYRGMAHQADVSR
gb|ABW71834.1|          EVLGFWR--DGGYAEYVRIPHADFNCVRIPDGVTPLTASAIGCRFMTAFHAVDGQGRVRP
RAAC04321               GIYGFSW--DGSFAEYVVVRNANMNLIRLPEGVDALTAAAVGCRFMTGYHGVMRGG-VRP
ref|YP_612035.1|        QQPGFTH--WGSFAEYVGVRQADLNLVALPQEMDFATAASLGCRFATSFRAVVDQAQTRA
ref|ZP_01441442.1|      EQPGFTH--WGSFAEYVPIHQADLNLVALPEGMGFDTAASLGCRFATSFRAVIDQGKVRA
                                **            *.:*: *   : .*: *   :*:  :      .:..:*** : *.::.:       .

ref|YP_055250.1|        GDWLVVYGAGGVGLSATLVATSAGANVIAVDIADDKLALARKVGAIATINSRE-TDPVEA
ref|YP_134751.1|        GEYVVVQGLGGIGLSAVHIADALGGNVIGVDLMDEKLEMAEEELGAIDTVNAAEEDDVVQA
gb|ABW71834.1|          GEWVAVHGVGGVGLSCVQIASAAGASVVAVDIDPAKLALAEQQGAAHTVDAGAEQDVPAA
RAAC04321               GQWVAVHGAGGVGLSAIQTAYAVGARVIAVDVDDEKLAKAREEGACEVVNA-KNQPVVEA
ref|YP_612035.1|        GQWVAVHGCGGVGLSAVMIAQAVGANVIAIDIDDEKLNLAQFLGAVATINGARVADVPEA
ref|ZP_01441442.1|      GQWVAVHGCGGVGLSAVMIAAAAGANVIGVDLDPVKLALAKEIGAVAAIDG-HEADVPGA
                           *::.*  * *  :*.     * : *. *:.:*:       **   *.: **    .::.        * ref|YP_055250.1|        VRELTDGGADKSVDALGISETLHNAVNSLRSRGTHIQIGMTAE-GPVGDVALTINDLIAK
ref|YP_134751.1|        VRDITDGGAHVSLDALGIEETCQNAIESLRTRGRHVQIGLTTK-EQRGYNSLPTDTIVMN
gb|ABW71834.1|          VREVTGGGAHVSIDALGIRTTVVNSVRSLRKRGRHVQVGLTGA-EDAGEIALPTDLITLG
RAAC04321               IREITKGGAHVSIDALGIRDTVLNSVLSLRKGGRHVQIGLTTS-QEGGFVPLPMDLITSC
ref|YP_612035.1|        VIDLSRGGAHVSLDALGHPLTCFNSIQNLRPRGKHVQVGLMLA-EHST-PSVPMAKVIAK
ref|ZP_01441442.1|      IREITRGGAHVSLDALGHPVTMTNSILCLRPRGKHVQVGLMLG-EHAA-PQVPMPKIVGQ
                          : :::  ***.  *:****    *  ::  **    * *:*:*:       :.   :

ref|YP_055250.1|        EIDFRGSFGMPAVEFRYLLNQVAAGKMKPGQLVTKTIALSEVNDALTAMSTYNTVGTTVI
ref|YP_134751.1|        EIQVQGSSGLPPSKYGEMFRMVENGKLDPGAVITDKIGLEGVSDELAAMTDYETIGIPVV
gb|ABW71834.1|          ELTVVGSHGNPHAAYPRLLSLIESGRLAPQTLVQRTVSLDQAGDVLAAMDAFATSGLTVI
RAAC04321               EIEVVGSLGIPHPDYAGLLALVAEGRLRPRNLVEREVRLEDVNEVFDKMTRFETRGFNMI
ref|YP_612035.1|        ELEILGSHGMQAHRYDAMLDMIASGKLDPRRLVGREISLDAAPSALVKMDQFQSIGATVI
ref|ZP_01441442.1|      ETELLGSHGMQAHRYGAMLDMVASGKLDPARLVGERISLAEAPAALMAMDSFRSVGATVI
                         *:  . **  *        :   ::    :   *::  *   ::   :  *    .    :   *  :  :  ::

ref|YP_055250.1|        TDF
ref|YP_134751.1|        NEF
gb|ABW71834.1|          DRF
RAAC04321               TAF
ref|YP_612035.1|        TTF
ref|ZP_01441442.1|      TRF
                         *
```

```
FIG. 36 ref|YP_917551.1|         ---------VKICGLTEAAGLAAAVDAGARYVGFVFFPKSPRHVTPGTAAEL---AAQVP
ref|ZP_00631342.1|       ---------VKICGLTEAAGLAAAVDAGARYVGFVFFPKSPRHVTPGTAAEL---AAQVP
ref|ZP_00998521.1|       ---------VKICGLSRFEDVAAAARAGAVYGGFVFFPKSPRHVSVESAREL---ATAAP
ref|YP_001259911.1|      MRRKPMALDIKICGLKTPEAVAAALDGGATHIGFIFFPKSPRHITPDAAARL---RAAAT
ref|NP_105797.1|         ---------IKICGLKTDQAMAAALGGGASHVGFIFFAKSPRYVEPAEAGRLR--EAA--
RAAC04349                ---MRSLPLLKICGLRPGDDLSFLRHPAVTHVGVVMVPASRRYVSPDEAGDLVRTAKRLR
                            :*****      ::      .. : *.::.. * *::    *  * ref|YP_917551.1|         ---LGVAKVGLFVNPDDAALDAVLAHVPLDVIQLHGAETPARVAEVKARTGLPVMKAVGV
ref|ZP_00631342.1|       ---LGVAKVGLFVNPDDAALDAVLAHVPLDVIQLHGAETPARVAEVKARTGLPVMKAVGV
ref|ZP_00998521.1|       ---PGLAKVALTVDADDDLIDRITATVPLDMLQLHGTESPDRVAEVRARTGLPVMKAVGL
ref|YP_001259911.1|      G-R--AVTVAVTVDADDEALDEIVKTVRPDMLQLHGGETPERVRFLKERYNLPVMKAFSI
ref|NP_105797.1|         --RCKAVAVAVTVDATDAFLDEIVSAMQPDMLQLHGSEHPERVAELKARYGLPVMKALPL
RAAC04349                ---PDVTTVAVVSGGSREEIGEGARRAGVDVVQLHGGE-PRDVAERLREAGFRVWRAVAF
                            *.:  .        :.         *::****  *   *       .: * :*. .

ref|YP_917551.1|         ADPQD-----LDALWD----YGLVADMLLIDAKPPKDAV--LPGGNGLAFDW-RLLA---
ref|ZP_00631342.1|       ADPQD-----LDALWD----YGLVADMLLIDAKPPKDAV--LPGGNGLAFDW-RLLA---
ref|ZP_00998521.1|       SEAAD-----LAA----IDLYSEVADQLLIDAKPPKEAS--IPGGNGLAFDW-RLLQQ--
ref|YP_001259911.1|      REAGD-----LEAIAP----YRGIADRFLFDAKPPKGSE--LPGGNGISFDW-NLLA--A
ref|NP_105797.1|         SEAAD-----LDRIRP----FIGIADRFLFDAKPPKGSE--LPGGNGVAFDW-RILA--G
RAAC04349                DPGDD-VTSFLDTLRS----HASSADAILFDAKPPSDAKPGVTGGHGRAFDWDRLAEM--
                          *    *         .  **  :*:*****.  :    :.**:* :*** .:

ref|YP_917551.1|         --GRQILKPWLLAGGLTPENVHEAIRLTRAPGVDVSSGVESAPGVKDPDRIRSFI-----
ref|ZP_00631342.1|       --GRQILKPWLLAGGLTPENVHEAIRLTRAPGVDVSSGVESAPGVKDPDRIRSFI-----
ref|ZP_00998521.1|       --RKYWSRPWMLAGGLTPDNVAEAIRLTGARQVDVSSGVEAGRGIKDPERIAGFVAA---
ref|YP_001259911.1|      L-DADI--DYMLSGGLNADNIAEALLKTGAPGIDISSGVECAPGEKDVRLIENFFQAV--
ref|NP_105797.1|         L-DAGV--DYMLSGGLNAANIGDALRLANPPGIDISSGVESAPGVKDPALIEQFFRAVRA
RAAC04349                --ARAFSFDWWVAGGITPENVRDLLRRVRPVGIDVSSGVEVG-GRKDVRRIDQLIQAMEA
                           :  ::**:.. *: : :   . .   :*:***** . * **   *  :.

ref|YP_917551.1|         ---------
ref|ZP_00631342.1|       ---------
ref|ZP_00998521.1|       ---------
ref|YP_001259911.1|      ---------
ref|NP_105797.1|         ---------
RAAC04349                WGHESLSLS
```

FIG. 37A

```
emb|CAD30313.1|        -----IAAPKLKEKVEKFLSGKKKMYINGSFVESASGKTFDTPNPATGERLATVYEGDAE
ref|ZP_01697379.1|     --------------VQHFLQGKKKMFINGQFVESASGKTFDTPNPATGETLATIYEGDKQ
ref|NP_833288.1|       ----------LHEKVEKFLQGTKKLYVNGSFIESASGKTFKTPNPATGETLAVVSEAGRE
ref|NP_979866.1|       ----------LHEKVEKFLQGTKKLYVNGSFIESASGKTFNTPNPATGETLAVVSEAGRE
ref|YP_001375474.1|    ----------LHEKVEQFLQGTKKLYVNGTFVESVSGKTFKTPNPATGETLAIVSEAGRE
RAAC01327              MAVQEVNASALHPDVVEFLKGPKGLFIDGEFVPSLSGKTFKSINPATEEVLVEVAEAEAP
                                  *  .**.* *  ::::* *:  * *****.:  **** * *.  : *.

emb|CAD30313.1|        DIDRAVKAAREAFDRGPWSRMSAAERSRLMYKLADLMEENKEELAQLETLDNGKPIRETI
ref|ZP_01697379.1|     DIDRAVQAARKAFDEGPWPRMNPADRSRLMYKLADLMEEHREALAQLETLDNGKPIRETA
ref|NP_833288.1|       DIHKAVVAARMAFDEGPWSRMSTAERSRLMYKLADLMEEHKEELAQLETLDNGKPIRETM
ref|NP_979866.1|       DIHKAVVAARMAFDEGPWSRMSTAERSRLMYKLADLMEEHKEELAQLETLDNGKPIRETM
ref|YP_001375474.1|    DIIKAVMAARQAFDEGPWSCMSGAERSRLMYKLADLMEEHKNELAQLETLDNGKPIRETL
RAAC01327              DIDRAVKAARRAFESGPWSRMSAAERSRLLYRLADLMEEHKLQLAQLETLDNGKPIRESL
                       **.:** *** **: ***.  *.  *:****:*:*******::   ***************:

emb|CAD30313.1|        NADVPLAIEHMRYYAGWSTKIVGQTIPVNGPYFNYTRHEPVGVVGQIIPWNFPLLMAMWK
ref|ZP_01697379.1|     NADIPLAIEHMRYYAGWTTKITGQTIPVNGPYFNYTRHEPVGVVGQIIPWNFPLLMAMWK
ref|NP_833288.1|       AADIPLAIEHMRYYAGWATKIVGQTIPVSGDYFNYTRHEAVGVVGQIIPWNFPLLMAMWK
ref|NP_979866.1|       AADIPLAIEHMRYYAGWATKIVGQTIPVSGDYFNYTRHEAVGVVGQIIPWNFPLLMAMWK
ref|YP_001375474.1|    AADIPLAIEHMRYYAGWATKIVGQTIPVSGEYFNYTRHEAVGVVGQIIPWNFPLLMAMWK
RAAC01327              NADLPLAIEHIRYYAGWPTKVVGQTIPVAGKYFNYTRHEPVGVVGQIIPWNFPLLMACWK
                        :**:** ::*******:*. ***** ********** emb|CAD30313.1|        LGAALATGCTVVLKPAEQTPLSALYLAELIEEAGFPAGVVNIVPGFGETAGDALVKHPQV
ref|ZP_01697379.1|     MGAALATGCTIILKPAEQTPLSALYLAQLVSEAGFPDGVVNIVPGFGETAGAALVDHPLV
ref|NP_833288.1|       MGAALATGCTIVLKPAEQTPLSALYLAELIEEAGFPKGVINIVPGFGESAGQALVNHPLV
ref|NP_979866.1|       MGAALATGCTIVLKPAEQTPLSALYLAELIEEAGFPKGVINIVPGFGESAGQALVNHPLV
ref|YP_001375474.1|    MGAALATGCTIVLKPAEQTPLSALYLAELFEEAGFPKGVVNIVPGFGEIAGQALVNHPFV
RAAC01327              IGAALAMGCTVVLKPAEQTPLSALYLAKLIQEAGFPPGVVNVVPGFGETAGQALVEHPDV
                       :*** *:::*************:*.. *** :*.:****  *. * emb|CAD30313.1|        DKIAFTGSTEVGKLIMANASKSLKRVTLELGGKSPNIILPDADFSKAIPGALNGVMFNQG
ref|ZP_01697379.1|     DKIAFTGSTEVGKLIMANASKTLKRVTLELGGKSPNIILPDADLSKAIPGALNGVMFNQG
ref|NP_833288.1|       DKIAFTGSTPVGKQIMRQASETLKRVTLELGGKSPNIILPDADLSRAIPGALSGVMFNQG
ref|NP_979866.1|       DKIAFTGSTPVGKQIMRQASETLKRVTLELGGKSPNIILPDADLSRAIPGALSGVMFNQG
ref|YP_001375474.1|    DKIAFTGSTPVGKQIMRQASETLKRVTLELGGKSPNIILPDADLSRAIPAALSGVMFNQG
RAAC01327              NKIAFTGSTEVGKLIMRNAAATLKRVTLELGGKSPNIILPDADMSRAIPGAFMGIMFNQG
                       :******  *  **  :*: :*************.*:***.*:  *:**** emb|CAD30313.1|        QVCCAGSRVFIQKKQYDNVVADMVSHAKSIKQGFGLKADTEMGPLVSSEQQNRVLGYIEK
ref|ZP_01697379.1|     QVCCAGSRVFIQKKHFDNVIADMASHAQSIKQGFGLNKDTEMGPLVSDEQQARVLNYIEK
ref|NP_833288.1|       QVCSAGSRLFVPKKMYDNVMADLVLYSKKLNQGVGLNPETTIGPLVSEEQQKRVMGYIEK
ref|NP_979866.1|       QVCSAGSRLFVPKKMYDNVMADLVLYSKKLNQGAGLSPETTIGPLVSEEQQKRVMGYIEK
ref|YP_001375474.1|    QVCCAGSRLFIPKKMYDNVMADLVLYSKNLTQGAGLDPKTTIGPLVSEEQQQRVMGYIEK
RAAC01327              QVCCAGSRLFVQKKAYDNVVADLVSLAKKIRQGPGLDQGTEMGPLVSDEQEKRVLGYIEK
                       ***.****:*: **  ***:***:* ::.:   **   **. *****.**. **: ****

emb|CAD30313.1|        GLEEGAELLTGGQKPSEQGYFVEPTIFANVEDSMTISKEEIFGPVIAALPYEDIDELIER
ref|ZP_01697379.1|     GLDEGAEIVTGGKKPREEGFFVEPTIFADVRDEMTIAKEEIFGPVIAAMPYESLDEVISR
ref|NP_833288.1|       GIEEGAEVLCGGSNPFDQGYFVSPTVFADVNDEMTIAKEEIFGPVISAIPFNDIDEVIER
ref|NP_979866.1|       GIEEGAEVLCGGSNPFDRGYFVSPTVFADVNDEMTIAKEEIFGPVISAIPFNDIDEVIER
ref|YP_001375474.1|    GIEEGAEVLCGGNKPFDKGYFVAPTVFADVNDEMTIAKEEIFGPVISALPFNDIDEVIER
RAAC01327              GVEEGAEVLVCGGKATDRGYFVQPTTFANVRDDMTIAREEIFGPVVAAMPFEDLDEVIAR
                       *::****::  **  :.  .:*** **:**.*.***:*********:.*:::..***:* *
```

FIG. 37B

```
emb|CAD30313.1|      ANDTNYGLAAGVWTRDVTKAHYIANKLRAGTVWVNCYNVFDAASPFGGYKESGIGREMGS
ref|ZP_01697379.1|   ANCSEYGLAAGVWTENVANAHYIANRLRAGTVWVNCYNVFDAASPFGGYKQSGIGREMGS
ref|NP_833288.1|     ANKSQFGLAAGVWTENVKTAHYVASKVRAGTVWVNCYNVFDAASPFGGFKQSGLGREMGS
ref|NP_979866.1|     ANKSQFGLAAGVWTENVKTAHYVASKVRAGTVWVNCYNVFDAASPFGGFKQSGLGREMGS
ref|YP_001375474.1|  ANKSSFGLAAGVWTENIKNAHYIASKVRAGTVWVNCYNVFDAASPFGGYKQSGLGREMGS
RAAC01327            ANDTEYGLAAGVWTENIRNAHYIASKLKAGTVWVNCYNVFDAAAPFGGYKQSGIGREMGS
                       : :****.::  .*:*.:::**************:**:*::**** emb|CAD30313.1|      YALDNYTEVKSVWIA--
ref|ZP_01697379.1|   YALQNYTEVKSVWIA--
ref|NP_833288.1|     YALNNYTEVKSVWLNLN
ref|NP_979866.1|     YALNNYTEVKSVWLNLN
ref|YP_001375474.1|  YALDNYTEVKSVWVNLN
RAAC01327            YALNNYTEVKDVWISLS
                     ***:******.**:
```

FIG. 38A

```
ref|YP_001125497.1|    ----PACATASLGNYRFADLPDPSKWADCVHCGMCLESCPTYEQTGEEQHSPRGRVHLMK
ref|YP_147384.1|       ------------------------------------------------------------
ref|YP_175672.1|       ---DPPCSPTSKSNYLWNDAPDENKWADCVHCGMCLESCPTYEITGQEQHSPRGRVHLIK
ref|NP_243001.1|       ------------TNYHWSDHPDPNKWADCVHCGMCLEACPTYELTGHEQQSPRGRVHLIK
RAAC01351              MVNEPTAVAAKGSDFRFPDAPEEEKYSVCVHCGFCLEVCPTYQAWGDENHSPRGRVYLIK
ref|YP_001108459.1|    --------------------PQRELIDDCVHCGFCLPSCPTYELWGEEMDSPRGRIYLMK ref|YP_001125497.1|    SVGEGKLDLTPDLLDPIFTCLDCRACTTACPADVDVGGLIEQVRGQLRQAVPLTGWKALV
ref|YP_147384.1|       ------------LLDPIFTCLDCRACTTACPADVDVGGLIEQVRGQLRQAVPLTGWKALV
ref|YP_175672.1|       SVAEGKLEVNEPFIDPVYQCLDCRACTTACPADVDVGGLIEEARGQIRQAMPLTGIKGLV
ref|NP_243001.1|       SVAEGKLEVNEAFADPVFTCLDCRACETACPADVEVGGLIEEARGQIRQALPLSGWKKVV
RAAC01351              ACAEGELPLDESVIDPVFTCLDCRACETVCPSGVQVGALVEEARGQVFYARDAEGKRDPV
ref|YP_001108459.1|    EGLEGE--PMTGSMVGHFDACLGCMACVTACPSGVQYGTLITETRAQV-ERRHERCRWEKL
                           .  . **.*  **  *.**:.*:  *  *: :.*.*:      *           :

ref|YP_001125497.1|    NDFFLKGIFPHPSRLDWLGRLLKLYQQSGLQTVARKTGMLRVMPDHLAEMEAILPKVGTP
ref|YP_147384.1|       SDVFLKGIFPHPSRLDWLGRLLKWYQKSGLQTVARKTGLLRVMPDHLAEMEAILPAVGTP
ref|YP_175672.1|       SKFFLEGLFPHPKRMQSLGGLLKIYQKSGVQKLVRTTRLIRIMPKHLVELEAIMPGMGVP
ref|NP_243001.1|       SHLFLRGLFPYPHRLHALGSLVKVYQKVGIRKAVRKTGLLHLFPEHFADMEAVIPEVSTP
RAAC01351              MRFFLRGVFPRPARLRIIRRLMRFYQKSGLQKLARSTGVLRVLPPQVREMEDVIPEIGRG
ref|YP_001108459.1|    LRAGIFALFPYPRRLRAMRGPLALYQKTGLSKLVKRSGLLRKMPASLRVMESLAPPISRA
                         :.:**  *  *:   :       **: *:.  ..:  :  ::: :*      :*   : *  :.

ref|YP_001125497.1|    VRKKYRNEPLIKAKGETKRTVAILTGCIMDVMFSDINEATIRVLTRNGNDVVIVSDQTCC
ref|YP_147384.1|       VRRKYHQPLIKAKGETKRTVAILTGCVMDVMFSDINEATIRVLTHNGNDVVIVPNQTCC
ref|YP_175672.1|       VRKKYKNENIILAKGEETHTVAFLTGCIMDVMFSDINESTIQVLTRNGNNVTIPKQQTCC
ref|NP_243001.1|       VQKRYRKKSFIKAKGKSKQRVTLLAGCVMDVMFSEVNEATIRVLTRNGNDVSLPKDQTCC
RAAC01351              PAIDVLPET-IAPQGERKATAALFTGCVMDVFFSDVNEATARVLRVNGVEVRVPKDQICC
ref|YP_001108459.1|    PK----LGNRVPARGTRRATVGMITGCVQSAFFPDVNAATARVLSAEGCDVVIPRAQGCC
                         :  .:*    . :  :::**:  ...*.::*  :* :**   :*  :*  :    *  ** ref|YP_001125497.1|    GALHVHAGDRETGRKLAKQNIEAFQ--GVDHVIVNAAGCGAMLKEYPELFRH-DPEWHEK
ref|YP_147384.1|       GALHVHAGDRETGRKLAKQFQHV--DHVIVNAAGCGAMLKEYPELFRH-DPEWHEK
ref|YP_175672.1|       GALHVHAGDRETGRRLAKQNIEAFENAQT--VIVNAAGCGCMLKDYPELFRD-DPKWHEK
ref|NP_243001.1|       GALHVHAGDREMGRRLAKQNMKAFE--NEETIIVNAAGCGSMLQEYPELFREVFREWYER
RAAC01351              GALQVHAGDRDMAREMAKRNIEVFERAGADYVAINAAGCGAALKEYPELFRD-DPAWRDR
ref|YP_001108459.1|    GALSEHTGREEEAVRFARNLLDTFEDAGVEYVVINSAGCGSTLKEYPRLLRD-DPEYAEK
                       ***  :*  .:  ..*:.  ...*:     : :*:****.  *::**.:*.  :   : ::

ref|YP_001125497.1|    AEQFAAKVEDVSKFLYDTGFKAPKAELNVRLTYHDACHLAHGQCIRKEPRAVIESIPGVE
ref|YP_147384.1|       AEQFAAKVEDVSKFLHDTGFKPPKAELNVRLTYHDACHLAHGQGIRQEPRALIESIPGVE
ref|YP_175672.1|       AKAFSAKVQDITKYLYDTGYEKPKSEMKIRLTYHDACHLAHGQGIRQEPRELLHATPGVE
ref|NP_243001.1|       AEAFAEKVDVSKHLYDTGYEKPKGEVRAKVAYHDACHLAHGQNVRQEPRDLLLKISGVE
RAAC01351              AVQFSSRVRDISQLLVEVGFDPPKAELPMAVTYHDACHLFHAQKIRYEPRSLLKSVPGLT
ref|YP_001108459.1|    AERFSARVRDIAELLVELGPVAERHPLPVRAAYHDACHLAHGQGIRSQPRELLRGIPGME
                       *  *: :*.*.::: *  : *         :.: :******* *.* :* :**  ::  :.*:

ref|YP_001125497.1|    MVAMPNADRCCGSAGIYNLTIIPDMAQAVLESKMQNVPQD-VELISMGNPGCMLQMALGVM
ref|YP_147384.1|       MVAMPNADRCCGSAGIYNLTHPEMAQAVLESKMQHVPQE-VELISMGNPGCMLQMALGVM
ref|YP_175672.1|       IVHMPNADRCCGSAGIYNITNPEMAGAVLESKMENVPED-VEMISMGNPGCMLQMAVGVQ
ref|NP_243001.1|       LIPMENADRCCGSAGIYNLTHPKMASRVLEKKMECVPSD-VEMVSMGNPGCMLQMAMGVK
RAAC01351              LCEMPDSDRCCGSAGIYNLTHPAMANELLERKMDDVPEG-VDAIVMGNPGCMMQTRLGVK
ref|YP_001108459.1|    VREINRGELCCGSAGVYNILQPEAAMDLGDRKAENVLDTGAELLISANPGCAMQIRTSLE
                         :    .:  *****:**  :* .*   : : *  . .:  :  .****   :*  .:
```

FIG. 38B

```
ref|YP_001125497.1|    KHGRNQKIVHTVQLLDWAYQKE---
ref|YP_147384.1|       KHGRNQKIVHTVQLLDWAYQKE---
ref|YP_175672.1|       KYGRRQKIVHTVQLLNWAYKRD---
ref|NP_243001.1|       KYGGNQRIIHTVQLLDLAYQQE---
RAAC01351              RRNQPLRVMHTVEVLDLAYRREGSR
ref|YP_001108459.1|    RRGSELAMAHTVEVLDASIRGLGA-
                          :  .   : ***::*:  :  :
```

FIG. 39A

```
ref|YP_147385.1|        ---------------------------------IATNDPHIQALARIV-GEQAILYRKED
ref|YP_001125498.1|     ---------------------------------IATNDPHIRATARIV-GEEAILYRKED
ref|YP_175671.1|        ---------------------------------IKTNDPDILNLAKLVDGPKSILYLKED
RAAC01352               MHDADPARRQAQEPAIARHAHGRSARSRLPEGGIAMRDVHIDRLVETV-GERRCLWRPIIQ
ref|NP_926015.1|        ----------------------------------------QMEQIV-GKSGVVWTPEE
ref|YP_001660274.1|     ---------------------------------IKQLEAIL-GKDGVIRRKDE
                                                         :   ::  *        :     ..:

ref|YP_147385.1|        LMAYDCDGFTVHRHLPRAVVFPNSTEQVAAVVKYCHEHDLPFLARGAGTGLSGGAIPLNG
ref|YP_001125498.1|     LIAYDCDGFTVHRHLPKAVVFPNSTEEVAAVVKYCHEHELPFLARGAGTGLSGGATPLNG
ref|YP_175671.1|        LIAYDCDGFTIHKHLPKAVVFPKNTEEVAKIVNYCASHDLPFLARGAGTGLSGGAIPTNG
RAAC01352               VKAYACDGYTAEEGLPRAVVFPESTDEVARICRYLYENDIPYLPRGAGTGLSGGATPTGG
ref|NP_926015.1|        LLVFECDGLTSYKQRPALAVLPRTTEEVSRVLALCYREGLPFVARGSGTGLSGGALPVEG
ref|YP_001660274.1|     LITYECDGITGYRQRPALVVLPRSTAEIAAVVKLCHDNELAWVARGAGTGLSGGALPLEE
                        :  : *** *    .  * . .*:*..* ::: :    .    :.::.:***** * ref|YP_147385.1|        EVVISLTRMKRLLHVDLENRRAVVEPGFVNLKLTNSVAHRGYYYAPDPSSQYCCTIGGNV
ref|YP_001125498.1|     EVVISLTRMKRLLHVDLENRRAVVEPGFVNLKLTNSVAHRGYYYAPDPSSQYCCTIGGNV
ref|YP_175671.1|        EVIISMVRMKRLISVDLENRRAVVEPGYVNLKLTNMIADKGYYYAPDPSSQSCCTIGGNV
RAAC01352               EVVISLARMNKLLAVDFDNLRAVVQPGLVNLTLTRRVSHADCYYAPDPSSQSVCTIGGNF
ref|NP_926015.1|        CVLVVTARMNRILAVDLDNRQVVVQPGVINNWVTQAVSGAGFYYAPDPSSQSICSIGGNV
ref|YP_001660274.1|     GILIVTARMNQILRVDLDNQRVVVQPGVINNWVTQAVSGAGFYYAPDPSSQIICSIGGNV
                         ::: .**::::  **::*   :.**:** :*  :*. ::   .********   *:****.

ref|YP_147385.1|        AENAGGAHCLKYGVTTNHILGLEVVLPNGEVIEIGGNGVPDPPGYDLLGLLTGSEGTLGI
ref|YP_001125498.1|     AENAGGAHCLKYGVTTNHILGLEVVLPDGEVIEIGGNGVPDPPGYDLLGLLTGSEGTLGI
ref|YP_175671.1|        AENAGGAHCLKYGVTTNHILGLEVVLPNGDIIDINCEGIADVPGYDLLGLLTGSEGTLGI
RAAC01352               AENAGGSHCLKYGVTTNHVVAAKVVLPDGDVIDVGAP-FGDAPGYDLLGLLVGSEGTLGI
ref|NP_926015.1|        AENSGGVHCLKYGVTTNHVLGLKLVLPDGEVVDVGGR-VPETPGYDLAGVFVGSEGTLGI
ref|YP_001660274.1|     AENSGGVHCLKYGVTTNHVMGLKIVLPDGSIIDVGGA-VPEQPGYDLTGLFVGSEGTLGI
                        *: ********::. ::*:*.:::::.  .  :  ****  *::.******** ref|YP_147385.1|        VTKITVRLLKNPEAKQTVLAYFDEVEDASQTVSDIISAGIVPAALEMMDQTAIEAVEAAA
ref|YP_001125498.1|     VTKITVRLLKNPEAKQTVLAYFDEVEDASQTVSDIISAGIVPAALEMMDQTAIEAVEAAA
ref|YP_175671.1|        VTKITVRILKNPEAKQTVLAYFDEVSDGSYAVSDIVSAGIVPAALEMMDKTAIEGVEAAA
RAAC01352               ATEITVRILKKPQALRTALAYFDRVADASDTVTDIIGAGIIPAAIEMMDQLAMQAVDKSN
ref|NP_926015.1|        ATEITLRLLKSAESIRVLLADFAAIEEAGAAVTAIIAAGIVPGGMEIMDNLSINAVEDVV
ref|YP_001660274.1|     ATEITLRILKTPESICVLLADFTSIEAAGQAVADIIKSGMIPAGMETMDNLSINAVEDVV
                        .*:**:*:**..::  **  *    :  ..  :*: *:  :*:*:*...:*:**: :::.*:

ref|YP_147385.1|        FPVGHPKDIAALLLIEVDGISAGIDEQINDILTICRRHEVREVKVAQSEEERARWWANRK
ref|YP_001125498.1|     FPVGHPKDIAALLLIEVDGISAGISEQIDDILTICRRHEVREVKVAESEEERARWWANRK
ref|YP_175671.1|        FPVGHPRDIAALLLIEVDGISAGIDEQINQILDICKRRHEVREVKVAENEQERARWWANRK
RAAC01352               YHVGYPTDIEAVLLIEVDGLAAGVQDEVMARVVEICRRHRVERVRVAQSDAERALWWSSRK
ref|NP_926015.1|        ATDCYPRDAGAILLVEVDGLAVEVEAASARVEALCLEAGARAVRTATDPAERLKLWKGRK
ref|YP_001660274.1|     ATGCYPRDAESVLLVELDGLGVEVTRNKHRVAEICRQNGARNITTANDAETRLKLWKGRK
                        :  *     ::**:*:**:.. :     :     :*.  .:* :.  *       *  *.**

ref|YP_147385.1|        TGFGAMGAISPDYLVQDGVIPRSRLPEVLREIADISRKYGLRIANIFHAGDGNLHPLVLF
ref|YP_001125498.1|     TGFGAMGAISPDYLVQDGVIPRSRLPEVLREIANISRKYGLRIANIFHAGDGNLHPLVLF
ref|YP_175671.1|        TGFGAMGAISADYLVQDGVIPRSKLPEVLERINQISEQFGLRIANIFHAGDGNLHPLVLF
RAAC01352               MAFGAMGRISPDYIVQDGVIPRTRLTEVLQKIDEVSRRYGLKIANVFHAGDGNLHPLILY
ref|NP_926015.1|        AAFAAMGQRAPNYYVQDGVIPRTKLQFVLQQQIELLSEKHGYPVANVFHAGDGNLHPLILY
ref|YP_001660274.1|     AAFAAAGKISPNYFVQDGVIPRTQLVYVLQEIKALSEKYGYKIANVFHAGDGNLHPLILY
                         .*.* *   :.:* ********::*  **..*   :*.:.*  :**:*************:
```

FIG. 39B

```
ref|YP_147385.1|       DASKPGETERALAAGSECLKACAAVGGSITGEHGVGIEKKEEMRFIFTDEEILAQTAIRD
ref|YP_001125498.1|    DASQPGETERALAAGSECLKACAAVGGSITGEHGVGLEKKEEMRFIFSDEEILAQTAIRD
ref|YP_175671.1|       DARIPGETEKALEAGSACLKACDVGGSITGEHGVGIEKMEEMRFVFNEEELAAQTRIRE
RAAC01352              DSRVPGEAERAVRAGSEVLRACVDAGGSITGEHGVGIEKIGEMAYMFSEDEIHAQRAVKS
ref|NP_926015.1|       DGRIAGELEKVELLGGEILKLCVAVGGSISGEHGIGAEKRCYMSDMFTPADLETMQWVRT
ref|YP_001660274.1|    DNKVEGAWEEVEELGGEILKLCVRVGGSLSGEHGIGIDKNCYMPAMFNEIDLETMGYVRD
                       *    *  *..  *.  *: *. .***::****:* :*   *  :*.  ::  :   ::

ref|YP_147385.1|       VFNPKNLLNAGKLFPTPERCVETK------------------------------------
ref|YP_001125498.1|    VFNPKNLLNAGKLFPTPGRCVETKQVSSTVK-----------------------------
ref|YP_175671.1|       VFNPDNLLNGGKLFPSPGRCVEVKK-----------------------------------
RAAC01352              CFDPKGIVNAGKLIPLPGRCVEVKRAREIIEENWQILNSFPDQAAVQARGAFVQEPGREA
ref|NP_926015.1|       VFDPKGLANPTKLFPTPRTCGEAARA----------------------------------
ref|YP_001660274.1|    CFNPKGLANPGKLFPTPRSCGEAANAK---------------------------------
                       *:*..: *  **:* *    * *.

ref|YP_147385.1|       ------
ref|YP_001125498.1|    ------
ref|YP_175671.1|       ------
RAAC01352              STSAQG
ref|NP_926015.1|       ------
ref|YP_001660274.1|    ------
```

FIG. 40A

```
ref|YP_001636557.1|        -------PAGVTITAPITPAYAEILTPEALEFLATLHRRFNTRRLELLARRAERQRAIDA
ref|ZP_01517435.1|         -------PAGVTITAPITPEYAEILTPEALEFLATLHRRFNARRLELLARRAERQRAIDA
RAAC01354                  MAGSYACPQGVQITGEYRPEFAEILTTDALQFIAELERRFGPRRDELRLRKERDERLLA
ref|YP_001374183.1|        ----------VTLAGELLPSYNEILTPEALTFLKELHENFNERRIQLLKKREEKQKRIDA
ref|YP_082630.1|           ----------VTLVGEMLPAYNEILTPEALSFLKELHGNFNERRIELLQKRAEKQKRIDA
ref|ZP_01697170.1|         ---------GITVTGSIHDGYDDILTPEALQFLEQLERHFGERRRELLAYRKKRDEEIKS
                                     :  ..     : :***.:**  *:   *. .*. ** :**  *  :::. : :

ref|YP_001636557.1|        GERPDFLPETAHIRESEWTIAPIPPQIQDRRVEITGPV-DRKMIINALNSGAKVFMADFE
ref|ZP_01517435.1|         GERPDFLPETAHIRESDWTIAPFPPQLNDRRVEITGPV-DRKMIINALNSGAKVFMADFE
RAAC01354                  GEWPDFLPETKEIRESEWTVGPIPADLQDRRVEITGPSSDRKMVINALNSGAKCFMADFE
ref|YP_001374183.1|        GEFPNFLPETAHIRAGNWTIAPLPRDLEDRRVEITGPV-DRKMIINALNSGAHLFMADFE
ref|YP_082630.1|           GEFPKFLEETKHIREADWTIAKLPKDLEDRRVEITGPV-DRKMVINALNSGAHLFMADFE
ref|ZP_01697170.1|         GKLPHFLEETASIRESDWTIAPLPEDLQDRRVEITGPV-DRKMVINALNSGAKIFMACFE
                           *: *.     .::. :*  :::*******  :****: * ** ref|YP_001636557.1|        DANTPTWQNQVEGQINLRDALRRTITYTSPEGKHYALNNNPAILFVRPRGWHLNEKHMLV
ref|ZP_01517435.1|         DANTPTWQNQIEGQINLRDALRRTITYTSPEGKYYALNPNPAILFVRPRGWHLPEKHMLV
RAAC01354                  DACAPSWENVVQGQINMRDAVRRTIEYTSPEGKHYKLNDEVAVLIVRPRGWHLPEKHIRV
ref|YP_001374183.1|        DSSSPTWKNIIEGQINLRDAAKGTISYKSPSGKEYRLGDQTAVLIVRPRGWHLEEKHMQV
ref|YP_082630.1|           DSNSPTWENAIEGQINLRDAVRGTISHKNENGKEYRLNSKTAVLIVRPRGWHLEEKHMQV
ref|ZP_01697170.1|         DATSPTWENIIEGQIHLRDAVNRTITFTGPNGKEYKLADHPAVLIVRPRGWHLEEKHILV
                           *:  :*:*:*  ::*::*  .   ... . * .  *.:*:****** *: * ref|YP_001636557.1|        DGEPISGAIFDFGLYFFHNAQTAIDVQGGPYFYLPKMESHLEARLWNDIFVLAQELRGIP
ref|ZP_01517435.1|         DGEPIAGAIFDFGLYFFHNAQTAIEVQGGPYFYLPKLESHLEARLWNDIFVLAQELRGIP
RAAC01354                  DGRVATGALVDFGLYFYHNAKELLARGTGPYFYLPKMESHLEARLWNDVFNYAQDALGIP
ref|YP_001374183.1|        DGKRMSGSLVDFGLYFFHNAKTLIEKGSGPYFYLPKMESYLEARLWNDVFVFAQKYVGIP
ref|YP_082630.1|           DGKNMSGSLVDFGLYFFHNAKALLEKGSGPYFYLPKMESYLEARLWNDVFVFAQKYIGIP
ref|ZP_01697170.1|         DCKPISGSLTDFGLYFFHNARRLLENSTGPYFYLPKMESHLEARLWNDVFIFAQKYIGIP
                           **.   :*:: ****:*:    :     *******::******.:  . *** ref|YP_001636557.1|        QGTIKATVLIETILAAFEMDEILYELRNHSAGLNCGRWDYIFSCIKKFRNDPNFCLADRA
ref|ZP_01517435.1|         RGTIKATVLIETILAAFEMDEILYELREHSAGLNCGRWDYIFSCIKKFRNDPNFCLADRV
RAAC01354                  RGTIKATVLIETILATFEMDEILYELRDHAAGLNCGRWDYIFSYIKKFRNHPEVILPDRA
ref|YP_001374183.1|        NGTIKATVLLETIHAAFEMDEILYELRDHSAGLNCGRWDYIFSFLKCFRNHKAFLLPDRA
ref|YP_082630.1|           NGTIKATVLLETIHASFEMDEILYELKDHSAGLNCGRWDYIFSFLKAFRNHNEFLLPDRA
ref|ZP_01697170.1|         KGTIKATVLIETIMAAFEMDEILYELKEHSAGLNCGRWDYIFSYIKKLRTNPQFITPDRS
                            .******** ***  *:***********::*:*************  :*  :*.. . .**

ref|YP_001636557.1|        LVTMTTHFMRSYSLLAIKTCHRRGAHAMGGMAAQIPIKNDPVANEAALAKVRADKEREAS
ref|ZP_01517435.1|         LVTMTTHFMRSYSLLAIKTCHRRGAHAMGGMAAQIPIKNDPVANEAALAKVRADKERAN
RAAC01354                  QVTMTVPFMRAYTLLTIRTCHRRKAFAMGGMAAQIPIKNDPKANEEALAKVRADKEREAQ
ref|YP_001374183.1|        QVTMTVPFMRAYSLKVIQTCHRRNAPAMGGMAAQIPIKNNPEANEIAFEKVRVDKEREAL
ref|YP_082630.1|           QVTMTAPFMRAYSLKVIQTCHRRNAPAIGGMAAQIPIKNNPKANEAAFEKVRADKEREAL
ref|ZP_01697170.1|         LVTMTVPFMRAYSLLTIKTCHRRNAPAIGGMAAQIPVKDDPAKNEEAFQKVRADKERAR
                           **. *:*:*  .*:***** *:********:*::.*  ** *:  *.**** ref|YP_001636557.1|        DGHDGTWVAHPGLVPVAMEVFDRLMPTPNQINR-QRDDVQVTAADLLAFGPEKPITEQGM
ref|ZP_01517435.1|         DGHDGTWVAHPGLVPVAMEVFDRLMPTPNQINR-QRDDVHVTAADLLAFGPSEPITEQGL
RAAC01354                  DGHDGTWVAHPGLVPVAMEVFNRLMPTPNQLHR-LREDVQVTAADLVAV-PQGTITEGGL
ref|YP_001374183.1|        DGHDGTWVAHPGLVPVAMEVFNHIMKTPNQIFR-KREELHVTEKDLLEV-PMGTITEEGL
ref|YP_082630.1|           DGHDGTWVAHPGLVPVAMEVFNHIMKTPNQIFR-KREEIHVTEKDLLEV-PVGTITEEGL
ref|ZP_01697170.1|         DGHDGTWVAHPGLVPVALEAFNKEMPEPNQIHSGKQMDFTATADDLLAV-PQGEITEKGT
                           ******************:*.*:: *  ***:      : :..  *   **: .  ***  *:
```

FIG. 40B

```
ref|YP_001636557.1|    RLNINVGIQYLGAWLAGNGCVPVFNLMEDAATAEISRAQIWQWIRSPKGVLEDGRKVTVE
ref|ZP_01517435.1|     RLNINVGIQYLGAWLAGNGCVPVFNLMEDAATAEISRAQIWQWIRSPKGVLADGRKVTVE
RAAC01354              RTNVAVALRYIEAWLRGSGAVPIFNLMEDAATAEISRAQIWQWIHHPKGVLDDGRKVTVE
ref|YP_001374183.1|    RMNISVGIQYIASWLSGRGAAPIYNLMEDAATAEISRAQVWQWIRHEEGKLNDGRKVTFA
ref|YP_082630.1|       RMNISVGIQYIASWLSGRGAAPIYNLMEDAATAEISRAQVWQWIRHEGGKLNDGRNITLE
ref|ZP_01697170.1|     RENIYAGIQYIESWLRGRGAVPISNLMEDAATAEISRTQLWHWIRHPKGVLQDGRKVTIE
                        * *:  ..::*: :** * *..*: *************:*:*:**:    * * ***:*.

ref|YP_001636557.1|    LFRQMLPEELHKVREILG-PAYEDGRYEEAAELFDEITTDPEFVEFLTLPAYERI-
ref|ZP_01517435.1|     LFRQMLPEELAKVREILG-PAYEDGRYGEAAELFDEITTDPNFVEFLTLPAYDRI-
RAAC01354              LFRQILEEELRKLKDEIGEEAYAQSKFPLAAELLDDISTKDDFVDFLTLPGYEHLA
ref|YP_001374183.1|    LVEQLKAEELAKIEKEIGKESFEKGRFVEATKLFTDLVRKDEFEPFLTLPGYEIL-
ref|YP_082630.1|       LMEELKEEELEKIEREIGKEAFKKGRFQEATTLFTNLVRNDEFVPFLTLPGYEIL-
ref|ZP_01697170.1|     LYEQIKAEELERIRREIGEEYYRAGRFEEAVALFDRLVKEDEFIEFLTLPAYELL-
                       * .::  ***  ::.  :*    :   .::  *. *:   :   .:*  *****.*: :
```

FIG. 41A

```
ref|YP_895924.1|        ------------------------------------------DRVVINTTVRELHS
ref|YP_037600.1|        ------------------------------------------DRVVINTTVRELHS
ref|ZP_00235684.1|      -----------------------------------------GDRVVVNTTVRELHS
ref|YP_001646030.1|     ------------------------------------------DQVVVNKTVRELHS
ref|ZP_01724857.1|      ---------------------------------------LEEQVSTNETVRQLHG
RAAC01360               MYPFSSYMTFTRRVSPWDRRHARRRATEMEARMMTIPWFTLKEELGDKLSFGESVRRSHA
                                                                :::    .:**. *.

ref|YP_895924.1|        KDESYHASSLPDVVVFPKTTEEVSTIMKIASEHGTPVVPFGVGSSLEGHVIPYEKGITVD
ref|YP_037600.1|        KDESYHASSLPDVVVFPKTTEEVSTIMKVASEHGTPVVPFGVGSSLEGHVIPYEKGITVD
ref|ZP_00235684.1|      KDESYHASSLPDVVVFPKTTEEVSSIMKVASQHGTAIVPFGVGSSLEGHVIPYEKGITVD
ref|YP_001646030.1|     KDESYHNSSLPDVVVFPKTTEEVRAIMKVASEHKKPVIPFGVGSSLEGHIIPYEKGITVD
ref|ZP_01724857.1|      KDESHHPMSLPDIVVFPRSTADVSAILKVAHAQRVPVVPFGVGSSLEGNAIPIANGISID
RAAC01360               KDESYHPEHLPDAVAYPEETADVVALARFSHAHGVPLVAYGAGSGLEGQVIPVRGGISVD
                        ****:*     ***  *.:*. *  :*   ::  :.:      :  ::..:*..*:      ::* ref|YP_895924.1|        FSLMNKILEIREKDFLVKVQPGVTRSQLNKELKKYGLFFSVDPGADATLGGMAATNASGT
ref|YP_037600.1|        FSLMNKILEIREKDFLVRVQPGVTRSQLNKELKKYGLFFSVDPGADATLGGMAATNASGT
ref|ZP_00235684.1|      FSLMNKILEIREKDFLVRVQPGVTRSQLNKELKKYGLFFSVDPGADATLGGMAATNASGT
ref|YP_001646030.1|     FSLMNKILEIREKDFLVKVQPGVTRSQLNKELKKYCLFFSVDPGADATLGGMAATNASGT
ref|ZP_01724857.1|      FSEMNAILEVRPEDLLVKVQPGVTRQQLKHGLQFIVDPGADATLGGMAATNASGT
RAAC01360               FSRMNRVLEIRPDDFLVCVEPGVTRQQLNDALRPYGLMFPVDPGANASLGGMAATNASGT
                          :**:*  .*:**  *:**.*    *:  :**  *.*****:*:*********** ref|YP_895924.1|        TAVKYGVMRDQVRDLEVVLADGEVIHTGNLAAKSSSGYHLNGVFVGSEGTLGCFTELTLK
ref|YP_037600.1|        TAVKYGVMRDQVRDLEVVLADGEVIHTGNLAAKSSSGYHLNGVFVGSEGTLGCFTELTLK
ref|ZP_00235684.1|      TAVKYGVMRDQVRDLEVVLADGEVIHTGNLAAKSSSGYHLNGIFVGSEGTLGCFTELTLK
ref|YP_001646030.1|     TAVRYGVMRDQVRDLEVVLADGQVIHTGNLAAKSSSGYHLNGIFVGSEGTLGCFTELTLK
ref|ZP_01724857.1|      TAVRYGVMRDQVRDLEVVLADGSVIHTGNLAAKSSSGYHLNGLFVGSEGTLGCFTELTLK
RAAC01360               TAVRYGPMKANVRKLEVVLADGRVIEVGTLAAKSSSGYNLVELFVGSEGTLGLFTKLWLR
                        ***:** *: :**.******** **.*.******** :*********  **:*  *:

ref|YP_895924.1|        VYGIPEHVMAARASFPATNDAVEAVINILQAGIPIARIELVDELSMKQVNHYSETSYREE
ref|YP_037600.1|        VYGIPEHVMAARASFPTINDAVEAVINILQAGIPIARIELVDELSMKQVNHYSETSYREE
ref|ZP_00235684.1|      VYGIPEHVMAARASFPATNDAVEAVINILQAGIPIARIELVDELSMKQVNHYSETSYREE
ref|YP_001646030.1|     VYGIPEHVMAARASFPTINDAVEAVINILQAGIPIARIELVDELSMKQVNHYNETNYREE
ref|ZP_01724857.1|      VYGIPEFVTAGRAVFNTVGDAVSSVTALLQTGISVGRVELVDEASIQQANIYNDTAFSEK
RAAC01360               VYGVPEATLAASAEFATVRFAVDAVCMLIGSGLQLTRCELVTKPYIEIINRQFDTSYTPA
                        ***:**  .  *. * ** ::  :**.:*  ::  :*:  * ***  ::  *  :* :

ref|YP_895924.1|        PTLFLEFHGNEACLKQDVEFTKEIVFDQKCKEVAFETETAARNKLWDARHNLAYAYVHSY
ref|YP_037600.1|        PTLFLEFHGNEACLKQDVEFTKEIVFDHKCKEVAFETETAARNKLWDARHNLAYAYVHSY
ref|ZP_00235684.1|      PTLFLEFHGNEACLKQDIEFTKEIVFDHKCKEVAFETETAARNKLWDARHNLAYAYVHSY
ref|YP_001646030.1|     PTLFLEFHGNEAGLTQDIEFTKEIVFDHKCKEVAFETFTVARNKLWDARHNLAYSYVHSY
ref|ZP_01724857.1|      PTLFLEFHGNEACMHADIAFATEIFEDFHCLSVFFFHDNAGRNKLWEARHSLAYAYMHAH
RAAC01360               PTLFLELSGSQAAVQADMGTVDEILRDAGAARVSVVMDRERQKLWHARHNAAYALMRTY
                        ******: *.:*.:   *:  .**. *  . * .  : *:***.***. **: ::::

ref|YP_895924.1|        PGKKLMSTDVCVPISELAGAIQQAKETLEKNGLVGGILGHVGDGNFHVLLMVDPNDKEEV
ref|YP_037600.1|        PGKKLMSTDVCVPISELAGAIQQAKETLEKNGLVGGILGHVGDGNFHVLLMVDPNDKEEV
ref|ZP_00235684.1|      PGKKLMSTDVCVPISELAGAIQHAKETLDKVGLVGGILGHVGDGNFHVLLMVDPNDKEEV
ref|YP_001646030.1|     PGKKLMSTDVCVPISELAGAIQHAKETLDKVGLVGGILGHVGDGNFHVLTMTNPNDKDEV
ref|ZP_01724857.1|      PGKKLMSTDVCVPISMLAETILYAREQLNTVGLAGGIVGHVGDGNFHALIMLNPDDAEEQ
RAAC01360               PGLSHLSTDVCVPMSKLPEAVDVAETWIERLGIRGGIVCHVGDGNFHVSLMVNPSDPDDL
                        **  .:*******:*  .:  *.  ::   *. :: *: ***:*********. **::*.* ::
```

FIG. 41B

```
ref|YP_895924.1|        EKADEINESIVLYALKRGGTCTGEHGVGIGKRKYQEEEHGAALFVMEKIKKALDPQNILN
ref|YP_037600.1|        EKADKINESIVLYALKRGGTCTGEHGVGIGKRKYQEEEHGAALLVMEKIKKALDPQNILN
ref|ZP_00235684.1|      EKADEINESIVLYALKRGGTCTGEHGVGIGKRKYQEEEHGAALFVMEKIKRALDPQNILN
ref|YP_001646030.1|     KKADEINESIVLYALKRGGTCTGEHGVGIGKQKYQEEEHGAALLVMEKIKKALDPQNILN
ref|ZP_01724857.1|      AKADRFNFHIVQYALLRGGTCTGEHGVGLGKMRYQATEHGSSLAVMKSIKIALDPLNIMN
RAAC01360               GRAYELSHHLVEYALSVGGTCTGEHGVGLGKMKYQKQFHGEALALMQAVKRLFDPADMLN
                         :*  .:.. :* *  *******: :  * :* :*: :*   :** :::* ref|YP_895924.1|        PNKV-----
ref|YP_037600.1|        PNKV-----
ref|ZP_00235684.1|      PNKV-----
ref|YP_001646030.1|     PNKI-----
ref|ZP_01724857.1|      PGKI-----
RAAC01360               PGKLVDGIA
                        *.*:
```

FIG. 42

```
ref|YP_701593.1|     ------------------------QRIEDDEQVPHDIVMPILERIGALGLLVPREYGGSG
ref|YP_885121.1|     ------------------------ERIENEERIPNEIVLPILERIGAFGLLVPREYGGSG
ref|YP_872951.1|     --------RREVEEFVRGPGERYAEQIEAENRVP-ESLWTELRDRGYLRLAAPQEYGGRG
gb|AAQ84159.1|       ------------VERWVEGPGERWAERIEETGEVP-EAVWSELDELGFLRLAAPVEYGGQG
RAAC01408            MMRTLDEWKKDVDAYVAGPARAWSEHIEATGTVP-DALWRELRDAGYLRLAAPPHLGGHG
ref|ZP_02169377.1|   -----------VRQFAAERVAPFVEEMEMNETFP-DALLREMGELGLLGIPVEEEHCGAG
                                                 :.:*    .*::   :     *::.  .**  * ref|YP_701593.1|     LSIAQYLPIIAEFAKVQGALRVIVHVHNSFAH-ALSEIGSDRQKADVLPGTATGRNSVAF
ref|YP_885121.1|     LSIAQYLPIISEFAKVQGGLRVIVHVHNSFAH-ALSEIGNDEQKAAVLHGAATGANSVAF
ref|YP_872951.1|     LQFSKYLELVELFAMSHASLRMIVHVVNGIWR-AIDQLATDEQRKKFVLPQVAGDIRVAF
gb|AAQ84159.1|       LGFTQWMELMEIFSRSHGSLRMIVHVVNCIWR-SMDGHACDEQRKRFVVPSVLGEIKIAF
RAAC01408            LSFTDYLDLLRRFAHTHGSIRVMVHVANSLWR-SLAQKATPEQVERFVKPFVAGDIRVTF
ref|ZP_02169377.1|   MDFTSYITAIHELSKVSATLGVILSVHTSVGTNPIRYYGTADQISRYVPKLASGEWLGAF
                      : ::.::      :   ::    .: :::  *   ...   .:    .  *     :* ref|YP_701593.1|     ALTEPGFGT-GADLGSTAVREGDGYILNGEKWLITNSDIASHFIVFAKTTATD----VSA
ref|YP_885121.1|     ALTEPGHGT-GADLGSSAVRMGDEYEITGEKWLITNSDIATHFIVFAKTAPTE----VSA
ref|YP_872951.1|     TLTEPTAGT-GADIRSTVVRDGDTYYLTGEKHLITFGVRCDYWLLFARVAGTTGKDGTVA
gb|AAQ84159.1|       ALTEPGNGT-GADITTSVVREGDTYYLSGRKHLITFGMRCDYYLLAARVAGSAGHEGTVA
RAAC01408            TLTEPNSGS-GADIKTTARREGDEYVLNGEKWMIIFSDVADYFLLFCRLEGTSGGEGTLA
ref|ZP_02169377.1|   ALSEPGAGSDAASLRTTAKKDGDEYILNGSKAWTTNGGYADTYIVFAKTDPDAGKKGITA
                      :*:**  *:.*.:  :: .:  ** * :.* *   . .  :::  .:           * ref|YP_701593.1|     FLVPRETDGLSIAALPETMGCKGTEHGRVTLDSVRVPATALVGVEGQGNEHLERA-LEIS
ref|YP_885121.1|     FLVPRDTDGLSIEPLPETMGCKGGEHGHIRLACVRVPATALIGAEGEGNQHLERA-LEIS
ref|YP_872951.1|     LMVDRHSPNVVVKEMSPSMGVRGTDHAHLIFRETPVPVANRLGAEGEGLDVAFGGFLTPS
gb|AAQ84159.1|       LLVPRNAPGVSAEDTSRTMGVTGTDHASIVFDRTPVPVDHRLGEEGQGLEVFLGGFLTPS
RAAC01408            LLVPRDAPGLTVELMAPAMGIAGTAHGHLRLRDCRVPVANRLGEEGDGLEVAFRGFLDPS
ref|ZP_02169377.1|   FIVEKDTPGFTVLAKERKMGLLGSSTTGLAFEDCRIHESRRLGEEGQGYTIALSN-LDYG
                      ::* :.:  ..      ** *   ::   :     :* **:*            *  .

ref|YP_701593.1|     RVFIAASSLGTSERALELSIAHAKSRVTFCKPICTRQAIQRYLAEMATDVYALRGILADA
ref|YP_885121.1|     RVFIAASSLGTSERALELSVARAKERVTFGKPIGSRQAIQRYLAEMATDIYALRGLLADA
ref|YP_872951.1|     RISVAMTCVGLARRAQELAVEYAKQRVTFGKRLADRQVIAYALAENATDIEAARQLTLYA
gb|AAQ84159.1|       RISVAMSCVGLAQRAQQLAVDYARSRVTFGKSLTERQAIQFMLAENAADIEAAARQLVLHA
RAAC01408            RTAIGMTCVGAAERALELAADHALRRVTFGCPLAKRQIIQMWLAEMATDIEAARQLVLHA
ref|ZP_02169377.1|   RVGIAAQALGIAEAALEHATDYAKERKQFGKPIAMQQGLAFKLADMATAVEAAKLLTYSA
                     *  :.  .:*  :. * :   *   **:  :  :*   :   **: *: : * : :   * ref|YP_701593.1|     AQKWDAGER-IPAEASMCKLFGLEAVGRVTDRALLIHGGIGYTRAHPIERLYRDARLNWL
ref|YP_885121.1|     AHKWDSGKR-IPAEASMCKLFGLEAVGRVTDRALLIHGGIGYTRAYPVERLYRDARLNWL
ref|YP_872951.1|     ARQWESGAADALTLSSMAKLNAVDMLTRVTDKALQIHGGIGYFQSSPIERVYRDARAQRF
gb|AAQ84159.1|       ARRFEEGADDASMQSSMAKMHAVTMLTTVTDKALQVHGGLGYWKSQKIERVYRDARAQRF
RAAC01408            ARRFDEGHP-ITVEAAMAKMFATEMLQRVTDKALQIHGGPGYFKSSEIERIYRDARMQRF
ref|ZP_02169377.1|   ANRKDQGLT-TGIEASMAKTFASDTAMKVTTEAIQVFGGYGYTKDYPVERFFRDAKVTQI
                     *.: :  *     ::*.*  .      ** .*: :.** **  :  :**.:***:   :

ref|YP_701593.1|     EEGTPTIQYLVTAGRLLD--------------
ref|YP_885121.1|     EEGTPTIQYMVAANELL---------------
ref|YP_872951.1|     EEGTNEIQKTVIARSVL---------------
gb|AAQ84159.1|       EEGPNEVQKAVVFRELLRQAGTVTAGGAR---
RAAC01408            EEGTSEIQKMVIARDVIDKAKRASEGSERRCW
ref|ZP_02169377.1|   YEGTNEIQRIVIAGQLL---------------
                      **.  :*    *      ::
```

FIG. 43

```
ref|YP_146050.1|         ------MDFTLPAEIEFLKENVRKFVREVVEPVAMDIEENDQIPQDIIEKSKEMGLFGLSI
ref|YP_001124307.1|      ------MEFTLPAEIEFLKENVRKFVREVVEPVAMDIEENDHIPEDIIEKSKEMGLFGLSI
RAAC01425                MEVSRVDFTLPSELFEMRRTIRDFVEHEVEPLAMQIEEEDRVPDSVLEKSKELGLFGLSI
ref|NP_691609.1|         ------MNFELDEDIQIIKDNVRNFIQTEVEQVADNIERNNKIPDRIIELSKQMGLFGLSI
ref|YP_360564.1|         ------MDFTISEELQMMVQTVKDFVDNEVDPISQQIDEEDRVPEEIIQKARELGLFGLSI
ref|NP_294646.1|         ------MDFNLPDDLREVQATIRDFMLTRVEDRAQEIEHTNSVPPELIKEAADLGLFGLSI
                               ::* :  ::. :  .:::.*:    *:    : :*:. : :*   ::: : ::******* ref|YP_146050.1|         PEEYGGLG-LSMVGKCAIYEELGKTHNGYTTLIGAHTGIGTVGIVELGTEEQKQRYLPKM
ref|YP_001124307.1|      PEEYGGLG-LSMVGKCAIYEELCKTHNGYTTLIGAHTGIGTVGIVELGTEEQKQRYLPKM
RAAC01425                PEEYGGIG-LSMLGKCVIYEELGKTINGYTTIIGAHNGIGSVGIVEFGTKEQKEKYLPKM
ref|NP_691609.1|         PEQYGGLG-IGMVGKCALYEEIGVTHNGYTTLIGAHTGIGTVGIVEMGNEQQKQKYLPLM
ref|YP_360564.1|         PEEYGGVGSIGMLGKCIIYEQLGRTANGFTTLICAHTGIGTTGIVELGTEEQKRRYLPDL
ref|NP_294646.1|         PEEYGGVG-LSSLCRCAVYEAMGQGHMGFGGMISAHASIGTSGLVKLGNEEQKQRFLPRM
                         **:****:*  :. :*:* :** :*     *: :*.** .**: *:*::*.::**.::**  :

ref|YP_146050.1|         ATGEWIGAFALTEPSAGSNAAAIKTTAVRKGDRYIINGSKHYITNAVDAHVFTVMAVTDP
ref|YP_001124307.1|      ATGEWIGAFALTEPSAGSNAAALKTTAVRKGDRYIINGSKHYITNAVDAHVFTVMAVTDP
RAAC01425                ATGEWIGAFALTEPQAGSNAAAIKTTAVKKGDRYILNGQKIYITNAPYAHVFTVMAVTDP
ref|NP_691609.1|         ASGEKIGAFALTEPEAGSNASALKTSAIKKKDKYILNGTKHYITNATEAEVFTVMAVTDP
ref|YP_360564.1|         ASGKKLAAFALTEPEAGSDAASIRTTAVKKGDRYILNGVKHFITNGPDADVFTIIAVTDK
ref|NP_294646.1|         AAGECIAGFAITEPSSGSDACNIRTKAVKKGDVYVLNGTKHYISNAPIAGLLTVIAITDP
                         *:*:  :..**:***.:**:*. ::* .*::*  * *::**   *  :*:*.   *  ::*::*:**

ref|YP_146050.1|         SKGPKG-ITSFIVE-KDFPGFIVGKVERKMGLRGSHSAELFFDNLEVPAENVLGREGEGY
ref|YP_001124307.1|      SKGPKG-ITSFIVE-KDFPGFTIGNVERKMGLRGSHSAELFFDNLEVPVENVLGKEGEGY
RAAC01425                SKGAKG-ITSFIVE-RDFPGFRVGHIEKKMGLHGSHTAQIFFEDMEVPEENVLGREGEGY
ref|NP_691609.1|         AKGAKG-TSSFIVE-KSNLGFHVGAVEEKMGLKGSHSAEIILDDCEVSVENLLGEEGQGY
ref|YP_360564.1|         SKGAKGGITAFIVE-KNFPGFKVGTIEKKMGLRGSHTSEIILEDCEVPEENVLGNVGEGY
ref|NP_294646.1|         AQGSRG-MSAFLVEPQSTPGVSIGKIDEKMGQKGALSAEVIFEDAEIPAANLLGPENRGY
                         ::*.:* ::::*:**  :.   .:* ::.*** :*: :::::::::: *:.  *:**  ..**

ref|YP_146050.1|         VNALKILANGRAGLAARNLGSCIRLLEYCMEYAEQREQFGKPIIEQQAIQHMLAEMSMLI
ref|YP_001124307.1|      INALKILANGRAGLAARNLGSCIRLLEYCMEYAEQREQFGKPIIEQQAIQHMLAEMSMLI
RAAC01425                VNALKILANGRAGLAARCLGSCEYLLDKSLAFAHERIQFGKPIFEQQTIQHYLAEMALEI
ref|NP_691609.1|         VNALKILTNGRAGLAARNLGSCQKLLDMSTTYAIERQQFGTSIIDHQAVAHMLAEMAVEI
ref|YP_360564.1|         INALKTLAKGRVGLAARCVGSMQKLLELSTRYAQQRVQFGKPISSFQAIQHMLAEMAVDI
ref|NP_294646.1|         REALGILTNGRVGIAARSTGAMQRLLDLSVAHAQTREQFGKPIAEFQAVQFMLAEMEVAT
                          : ::**.*:***  *:     **: .    .*  * ***..* *  :  . **** : * ref|YP_146050.1|         EVLRSTVYRVAWMVDQKMRVVKEAAIAKLFGSEVYNKIADMAVQIHGGLGYMKDYPIERY
ref|YP_001124307.1|      EVLRSTVYRVAWMVDQKMRVVKEAAIAKLFGSEVYNKIADMAVQIHGGLGYMKDYPIERY
RAAC01425                ELLRTFVYRVAWMTDQKMNVLKEAAMLKLYGSEVYNRVADKAVQIHGGLGFIAEYPIERF
ref|NP_691609.1|         EALRALTYKVAWMVDNGENVIKEAAMLKLYGSEVYNRVADKAVQVHGGIGYISDFPVERY
ref|YP_360564.1|         EATRWFAYRVAWLVDQGAKVIKEAAAVKLFASEAYGRVVDKAVQIFGGMGYMKEFPIERY
ref|NP_294646.1|         QTSRVLWQKVAWMVDQGQDVKRMASVAKYHATEMLSQVADKAVQVAGGMGYVKDAPFERF
                         :  *    :***:.*:    *  *:    *  ..:*  .:::.* ***: **:*::  :  *.**:

ref|YP_146050.1|         FRDARTTKIYEGTSEIQRNIIASELRKEYGKVRA---
ref|YP_001124307.1|      FRDARITKIYEGTSEIQRNIIANELRKEYGKVR---
RAAC01425                YRDARITRIYEGTSEIQKNIIAAQLHKEYERTKADA
ref|NP_691609.1|         YRDARITRIYEGTSEIQKNIIAGQLKKHY-------
ref|YP_360564.1|         YRDARTTRIYEGTSEIQKNIIASQILKE--------
ref|NP_294646.1|         YRDQRLLRIYEGTSEIQKVIIAAEL-----------
                         :** *: :*********: *** ::
```

FIG. 44

```
ref|YP_902570.1|      ----------------IIIAPDSYKGSLSAVEVAEAMARGIVSVFPDAEIVSLPVADGGEG
ref|ZP_01667660.1|    ----------------VVLAPDSFKGSVSALGVANAVANGVRAVFPDAEIIKVPIADGGEG
ref|YP_429281.1|      ----------------IVIAPDSFKESLSAPEVAAAIAQGIHRVLPEVETVNVPMADGGEG
ref|YP_076319.1|      ----------------IIVAPDSFKGSLTALKAAEAMRQGVLDAMPDAEVVALPMADGGEG
ref|YP_001629366.1|   ----------------IIIAPDSFKESLSAPDAAAAIERGVKQAFPGARTLCVPMADGGEG
RAAC01517             MTHVTSIGAKGEAPHILLAPDSFKGSLTAREAAEAMAEGVSRACPSAQLALVPIADGGEG
                                      :::****:* *::*  .* *: .*:   *  ..   :*:****** ref|YP_902570.1|      TVEALVAATSGRFVCQEVSGPLGEPVMARWGILGDGATAVIEMAAASGLPLVAPERRNPL
ref|ZP_01667660.1|    TVEALVTATGGQIVTREVVGPLGEPVMAHWGVLGDCDTAVIEMAAASGLTLVPKEKRDPR
ref|YP_429281.1|      LTATLVAATGGREMTATVTGPLGEPVQASWGILGDGITAVVEMAQASGLPLVPREKRNPL
ref|YP_076319.1|      TTQALVAATGGQLVEAEVTGPLGEPVRAAFGLLGDGDTAVIEMAAASGLLLVPPERRDPK
ref|YP_001629366.1|   TVAAVLAATGGQWRTTPVSGALGFPMQAAWGWLDDS-TAVIEMAAAAGLEQTPPERRDPL
RAAC01517             TLAAIATSTRARWLSTEVTAASGQPKQGRFLALPDG-TAVVECAEAVGLPEALRSGADVW
                       ::  ::* .:          * .. *:*  . :  * *. ***:*  * * **  . .  :

ref|YP_902570.1|      RASTCGTGELIRAALDAGLRRLIVGIGGSATNDGGAMARALGVRFLDADGTELPEGGAA
ref|ZP_01667660.1|    ITTTYGTGQLIKAVLDRGIRKIIIGIGGSATNDGGTGMAKALGARFLDASGQELPPGGAA
ref|YP_429281.1|      VTTTYGTGELIHQALEAGCRRLIVGIGGSATNDGGAGMARALGVKLLDAEGADIPPCAGG
ref|YP_076319.1|      VTTTYGTGELIRAALDRGVRRILVGIGGSATNDGGVGMAQALGGRFLKADGSPVDRGGAA
ref|YP_001629366.1|   RASSGGVGELLRAALDAGARRIILGLGGSATNDGGAGMLAALGVRFLDANGLDLPPGGAA
RAAC01517             RRTTVGVGEMIRHALETGHRRIAVALGGSATNDAGVGMLAALGVRLLDDAGQDVPPVPAE
                       ::  *.*::::  .*: * *:: :.:*******.*.**  *** ::*.  *  :    .

ref|YP_902570.1|      LARLARVDLDGLDPRLVETSLQVACDVTNPLCGENGASVIYGPQKGATPEMVRELDRALE
ref|ZP_01667660.1|    LARLAKIDLSGLDERLRTTTILVACDVDNPLCGPRGASAVYGPQKGATPEMVKELDAALK
ref|YP_429281.1|      LERLERIDIQGLDPRVKEVEILVACDVDNPLCGPRGASAVYGPQKGATPEMIPRLDAALA
ref|YP_076319.1|      LLELERIDLSGLDPRLKGVELMVACDVDNPLTGPRGAAAVYGPQKGATAEDVALLDRALT
ref|YP_001629366.1|   LQQLARIDVQGLDPRLAGVQIDIASDVDNPLCGPQGASHTFGPQKGASPEQVALLDRSLA
RAAC01517             FHRVARVDVSGLDERLRGAEMLAVCDVDNPLTGENGATTVFGPQKGVSTHDVPRLDEALA
                       :  .: ::*:.*** *:  . :  .. * *.: :*.:...  :    :* ref|YP_902570.1|      HYSQVVEQAIARNVSDQAGSGAAGGLGAGLRYFTNASLLPGVKIVLDAVGFAEALKT-AD
ref|ZP_01667660.1|    NFAAVATVATGKDVADYPGAGAAGGLGAGLLFFTGAQLRPGVEIVLETTGFASLVAT-AD
ref|YP_429281.1|      RLADIVARDLKVDVRELPGAGAAGGLGAGLVAFLGATLRRGIELVIEAVNLDGILAAGAD
ref|YP_076319.1|      RLADVMVRDLGRDVRNLPGAGAAGGLMGFLGARLRPGIDVVMEVTGLRRQLQG--AA
ref|YP_001629366.1|   RLADVCARDLGRDMRDAPGAGAAGGLGYAAHAFLNARFRPGVELVAELGKLAQAMEG--AA
RAAC01517             HLAARCEAAFGCKAADLPGAGAAGGLGFALY-LLGAARVSGIDFVLDAVGFDHALER-AA
                          . :   .   . : .*:*******  . :.*  *:..* :     :   * ref|YP_902570.1|      LVITGEGCSDAQTAHGKAPLGVARLARNGGVPVICLSGGLGAGAEQLLEHGTDALLGIVS
ref|ZP_01667660.1|    LVITGEGRTDFQTAYGKAPVGVAKVAKQYGVPVVCLSGGLGDGADDVLAQGVDALMSVVP
ref|YP_429281.1|      LVITGEGEINRQTAYGKVPAGVGKVAAKYGIPVVALVGSIGEGASAVYDHGIQGFMSIVP
ref|YP_076319.1|      LLLTGEGRTDGQTLAGKVPLGLARAAAPCGVPVVVISGAVTDDADALLEQGVAALLSTAP
ref|YP_001629366.1|   LAFTGEGRMDAQTLRGKTPAGVARIARRAGVPVVALGSLGEGYQDLHAGGITAAFSLAP
RAAC01517             LVLTGEGRTDAQTAHGKAVAGVARRAKARGVPVFCISGAIGPGAERLYDHGVSALFATAP
                       *  :****  :  ** **.  *:* *  *:**  *  *:**. : *.:      *:  ..  ..

ref|YP_902570.1|      CPMPLED------------------------
ref|ZP_01667660.1|    QPMALDE------------------------
ref|YP_429281.1|      RPVPL--------------------------
ref|YP_076319.1|      GPVTLDE------------------------
ref|YP_001629366.1|   GPVSLQQ------------------------
RAAC01517             GPIALDEAMANAKALLAAAAENAVRAWLAGRP
                       *:..*
```

FIG. 45

```
ref|ZP_01666747.1|        --TVRLDIVTPERLAYSDDVNMVIARATDGDIGILPGHAPLIAGLEIAPLRI-LKDDGEK
ref|ZP_01188594.1|        --TIRLEVVTPEKVVFSEPVNILIAPAIDGEIGILPKHTPLVTGLKTGVMRVK-KDGEEV
pdb|2QE7|H                MATVQVDIVTPERKVFQGEADIVIARGVEGELGVMAGHIPLVTPLKTAPVRIKQGD-KET
sp|P22480|ATPE_BACPF      MSTIRVNVVTPDGKVYDGDVDMVVVRTVEGELGILPKHIPLVAPLTVGAVRLKKGN-SEE
RAAC00449                 MLTVPLEIVTPERIVLSMDVRMVILRGGDGEIGILPRHMPLATAVKPCLVRIRLADDRQD
ref|YP_521144.1|          --TFTLRVVSPEGNVLKEEAEFVVLPGGNGEIGILPNHAPLISSIEIGVIRYTV-NGKVE
                            *.  : :*:*:    . .  . :::       :*::*::. * **  : :    :*     :

ref|ZP_01666747.1|        RIA-VCCGFIEVRPDKVTVLAGCAELPEEIDVKRAEAARERAE---ARL-KYREGIDVAR
ref|ZP_01188594.1|        KIS-ISEGFMEVKPDEINVIVRTAELPHEIDVERARDALKRAE---KRLNSRNDRIDRAR
pdb|2QE7|H                LTA-VSGGFLEVRPDKVNILADTAELPEEIDVERAKKAKARHETILKRL--DKTDKDYLR
sp|P22480|ATPE_BACPF      QVA-VSGGFVEVRPDQVTILAEAAELPSAIDVDRARAAK---------------------
RAAC00449                 VVP-VSGGFVEVLPEKITILADTAELPEEIDVDRALRAKDRAE---KRLQAAVDEEEADR
ref|YP_521144.1|          KIA-TSGGFVEVSDNKVTILADTAEPGEKVDLDRALAAK---------------------
                          :.    . :   :::.::.  **       :*:.**   * ref|ZP_01666747.1|        AEQALKRALMRLSVAEYHKKM-----------
ref|ZP_01188594.1|        ARAAFERAIARLKA------------------
pdb|2QE7|H                HKRALERAEVRLQ-------------------
sp|P22480|ATPE_BACPF      -----ERAESRL--------------------
RAAC00449                 ARQALTRAELRLQAVEEHKRLNGFLHASVPSA
ref|YP_521144.1|          -----ERAEKRL--------------------
                                 
```

FIG. 46A

```
sp|P23630|DCDA_BACSU      ------------------------------------------------------------
ref|NP_390219.1|          ------------------------------------------------------------
ref|YP_001421740.1|       ------------------------------------------------------------
ref|YP_079644.1|          ------------------------------------------------------------
ref|YP_001487298.1|       ------------------------------------------------------------
RAAC01555                 MFWLLPRYAPGLTQFAVAHVDGARIYLCLNLYSGPVHRSCRRASCKRETIGVDGVKSEHL sp|P23630|DCDA_BACSU      ------------QNQHGHLEIGGVDALYLAEKYGTPLYVYDVALIRERAKSFKQAFISAG
ref|NP_390219.1|          ------------QNQHGHLEIGGVDALYLAEKYGTPLYVYDVALIRERAKSFKQAFISAG
ref|YP_001421740.1|       ------------QNKLGHLEIGGVDALYLAEHYGTPLYVYDVALIRERAKSFKQAFIDAD
ref|YP_079644.1|          ------------QNERGHLEIGGVDVLSLAERYGTPLYVYDVALIRERARKFQKAFKEAG
ref|YP_001487298.1|       ------------QNELGHLEIGGVDAVSLAETYGTPLYVYDVALIRERAKSFQKAFIEEE
RAAC01555                 LDVRPRVDAHFPRDEKGHLLIGGVSAVDLVAQFGTPLIAYDEGLIRDTIRAFHRVFQDEG
                                      :::  ***  ****..:  *.    :****  .**  .***:    :  *::.*  .

sp|P23630|DCDA_BACSU      LKAQVAYASKAFSSVAMIQLAEEEGLSLDVVSGGELYTAVAAGFPAERIHFHGNNKSREE
ref|NP_390219.1|          LKAQVAYASKAFSSVAMIQLAEEEGLSLDVVSGGELYTAVAAGFPAERIHFHGNNKSREE
ref|YP_001421740.1|       LKAQVAYASKAFSSVAMIQLAEQEGLSLDVVSGGELFTAVAAGFPADRIHFHGNNKSEEE
ref|YP_079644.1|          LKAQVAYASKAFSSVAMIQLAEQEGLSLDVVSGGELFTAIKAGFPAERIHFHGNNKSPEE
ref|YP_001487298.1|       LTAQVAYASKAFSSIAMFQLAKEEGLSLDVVSGGELHTAICAGFPVEKIHFHGNNKSRDE
RAAC01555                 VPYQISYASKAFCTMAICQLAHEEGLGIDVVSGGELYTALAAGVPASKLHMHGNNKTPEE
                          :  :.******.::*:  *.:*.:******.:  **.*..::*:*****:  :* sp|P23630|DCDA_BACSU      LRMALEHRIGCIVVDNFYEIALLEDLCKETGHSIDVLLRITPGVEAHTHDYITTGQEDSK
ref|NP_390219.1|          LRMALEHRIGCIVVDNFYEIALLEDLCKETGHSIDVLLRITPGVEAHTHDYITTGQEDSK
ref|YP_001421740.1|       LKMALDHQIGCIVVDNFYEISLLAELCRKSGRTMDVLLRITPGVEAHTHDYITTGQEDSK
ref|YP_079644.1|          LAMALEHQIGCIVLDNFHEIAITEDLCKRSGQTVDVLLRITPGVEAHTHDYITTGQEDSK
ref|YP_001487298.1|       LKMALENEIGCIVVDNFYEMKLLEELGQELSKQVKVLLRITPGVEAHTHDYITTGQEDSK
RAAC01555                 LEYAEESGIGAVIVDNFDEIDLLADILQETGRTVDVLVRVAPGVEAHTHDYISTGQQDSK
                          *  *::  .:::* *:   ::  .:  .:*.**:*::**:*:*****:*:*** sp|P23630|DCDA_BACSU      FGFDLHNGQTERAIEQVLQSEHIQLLGVHCHIGSQIFDTAGFVLAAEKIFKKLDEWRDSY
ref|NP_390219.1|          FGFDLHNGQTERAIEQVLQSEHIQLLGVHCHIGSQIFDTAGFVLAAEKIFKKLDEWRDSY
ref|YP_001421740.1|       FGFDLHNGQIEKAIEQVLQSDHIRLLGVHCHIGSQIFDTAGFVLAAEKIFAKLNEWRESF
ref|YP_079644.1|          FGFDLHNGQVEQAIEQVLRSSAFKLLGVHCHIGSQIFDTAGFVLAADKIFEKLAEWRETY
ref|YP_001487298.1|       FGFDLHNGQADEAVKRVLESEVIELLGVHCHIGSQIFDTAGFVLAADKIFLKLNEWRESF
RAAC01555                 FGFDLASHQVEEAFSRLKEVERARVIGVHAHIGSQIFDVEGFRLLADRMAGVYEDGLRRF
                          *****  .  *  :.*..::    .   ..:::***.********.  **  *  *:::      :    :

sp|P23630|DCDA_BACSU      SFVSKVLNLGGGFGIRYTEDDEPLHATEYVEKIIEAVKENASRYGFDIPEIWIEPGRSLV
ref|NP_390219.1|          SFVSKVLNLGGGFGIRYTEDDEPLHATEYVEKIIEAVKENASRYGFDIPEIWIEPGRSLV
ref|YP_001421740.1|       GFVSEVLNLGGGFGIRYTEEDEPLHPAVYVEKIIEAVKENAALHAFDIPEIWIEPGRSLV
ref|YP_079644.1|          SFIPEVLNLGGGFGIRYTKDDEPLAADVYVEKIIEAVKANAEHFGFDIPEIWIEPGRSLV
ref|YP_001487298.1|       GFISTVLNLGCGFGIRYTEEDEPLPATEYVEKIIQAVKENVARYEFDMPEIWIEPGRSLV
RAAC01555                 GLPFSVLNLGGGFGIPYTDEDAP-PVADLVRGVIRAAKAAFAARGMDVPVLWIEPGRSIV
                          .:    *******  .:*  *          *.  :*.*.*          :*:*  :*******:* sp|P23630|DCDA_BACSU      GDAGTTLYTVGSQKEVPGVRQYVAVDGGMNDNIRPALYQAKYEAAAANRIGEAHDKTVSI
ref|NP_390219.1|          GDAGTTLYTVGSQKEVPGVRQYVAVDGGMNDNIRPALYQAKYEAAAANRIGEAHDKTVSI
ref|YP_001421740.1|       GDAGTTLYTIGSQKFVPGTRKYAAVDGGMSDNIRPALYQAKYEAVSANRIGEHHDKTVSI
ref|YP_079644.1|          GDAGTTLYTIGSQKEVPGIRKYVAIDGGMSDNTRPALYEAKYEAAVANRMNDACHDTASI
ref|YP_001487298.1|       GDAGTTLYTIGSSKHVPGIRDYVAVDGGMSDNIRPALYQAKYEAASANKMSQSHDQTVSI
RAAC01555                 GPAGVTLYRVGSRKVIPGVRNYVAIDGGMTDNPRLALYGAKYHACYANRAADPPDRPWSV
                          *  **.***  :**  *  :**  *.*:****.**  *** ***.*  **:    :  . .  *:
```

FIG. 46B

```
sp|P23630|DCDA_BACSU     AGKCCESGDMLIWDIDLPEVKEGDLLAVFCTGAYGYSMANNYNRIPRPAVVFVENGEAHL
ref|NP_390219.1|         AGKCCESGDMLIWDIDLPEVKEGDLLAVFCTGAYGYSMANNYNRIPRPAVVFVENGEAHL
ref|YP_001421740.1|      AGKCCESGDMLIWDIDLPEVKEGDLLAVFCTGAYGYSMANNYNRIPRPAVVFVEDGEAHL
ref|YP_079644.1|         AGKCCESGDMLIWDLEIPEVRDGDVLAVFCTGAYGYSMANNYNRIPRPAVVFVEDGEAQL
ref|YP_001487298.1|      AGKCCESGDMLIWDIDLPELSQGDLLAVFCTGAYGYSMSNNYNRIPRPAVVFVEDGEAQL
RAAC01555                AGKCCESGDMLIWDLPLPDPQPGDLLAVFATGAYTYAMASHYNRIPKPAVVFCRDGEARL
                         ************:  :*:   :.** *:*:.:***:*  .:*:* sp|P23630|DCDA_BACSU     VVKRETYEDIVKLDLPFK
ref|NP_390219.1|         VVKRETYEDIVKLDLPFK
ref|YP_001421740.1|      VIRRETYEDIVKLDLPFK
ref|YP_079644.1|         VIQRETYEDIVKLDLPLK
ref|YP_001487298.1|      VVERESYADMVKLDLP--
RAAC01555                VARRETWADVARLDVPLR
                         *  .**::  *:..:**:*
```

FIG. 47A

```
ref|YP_001420375.1|    MFQYEELNKQFIGGRWRDGSSRNVLENRNPYTQKVITSFQKATSDDVDAAYRAAALAKQE
ref|NP_388616.1|       MFQYEELNKQFIGGKWQEGSSPNVLENKNPYTQKTFTTFRKATADDVDEAYRAAALAKKK
ref|YP_077980.1|       MIQITDLNRQYIGGEWRDGQSESVLADLNPFTHKTIASFRKATREDVDAAYKAALEAKKK
ref|NP_241871.1|       MFNIQDLNKQYIDGEWRDGKSPRVLRDRNPYNQEVLAEFQIATDSDVDAAYHAALKAQNE
ref|NP_693628.1|       -----QLDSQYINGVWKDGNGKATIQNTNPYSGEVIATYRAASLQDLDDAYETAQEVQKA
RAAC01575              MLDLRQLSRQYIAGEWRDGRSSRVHRDLNPFDGSTVAEIRLATVEDIDQAYRAAAEAQKV
                            :*. *:* * *::*  .  . : **:  ...: : *: .*:* **.:*  .:

ref|YP_001420375.1|    WDKVNPFKKRAILEKAVSFIEEHEEAIIYLIMEELGGTRLKAEFEIGLVKNMIKEAATFP
ref|NP_388616.1|       WDAVNPFEKRTILEKAVTYIEENEEAIIYLIMEELGGTRLKAAFEIGLVKNIIKEAATFP
ref|YP_077980.1|       WDGVNPYEKRAILEKAAAYIEDNREAIVFLIMEELGGTRLKAAFEIDLVVNMIKEAAGFP
ref|NP_241871.1|       WATVNPYRKREILERAVTYIEEHEEEIVAIIIDELGGTRLKAAFEIGLVKNMIKEASTFP
ref|NP_693628.1|       WAKENPITVQRIMDKAVTYMEENHEEIVDIIIQEIGGTRLKAEFEIGLVTNMIKEASSFP
RAAC01575              WAQVNPFERQAVMERALQIWEGYRDEVISLVADEIGGTFIKAAIEFELVKNFLREAATYP
                       *    **    :  ::::*    *  .: :: ::  :*:* : :*: ** *:::**:  :* ref|YP_001420375.1|    VRMEGKILPSTIDGKENRLYRIPAGVVGVISPFNFPFFLSMKSVAPALGAGNGVVLKPHE
ref|NP_388616.1|       IRMEGKILPSTIDGKENRLYRVPAGVVGVISPFNFPFFLSMKSVAPALGAGNGVVLKPHE
ref|YP_077980.1|       LKMEGKILPSPVDGKENRIYRIPAGVVGVISPFNFPFFLSVKSVAPALGAGNGVVLKPHE
ref|NP_241871.1|       LRMEGKILPSTENGKENRLYRVPAGVVGVISPFNFPFFLSVKSVAPALGAGNGVVLKPHE
ref|NP_693628.1|       MRMSGSILPSPIDGKENRVYRVPVGVVGVISPFNFPFFLSMKSVAPALATGNAVVLKPHE
RAAC01575              LRMEGRLLPATIPGKENRLLRLPAGVVGILSPFNFPMCLSMRALAPAIACGNGVVLKPHE
                       ::*.* ::.  ***: *:*.**::**: :::*:. .******* ref|YP_001420375.1|    ETPICGGTLIAKIFEAAGVPDGLLNVIVTDIGEIGDSFVEHPVPRIISFTGSTGVGSYIG
ref|NP_388616.1|       ETPICGGTLIAKIFENAGIPAGLLNVVVTDIAEIGDSFVEHPVPRIISFTGSTKVGSYIG
ref|YP_077980.1|       ETPICGGTLIAKIFEEAGLPKGLLNVVVTDIGEIGDSFVEHPIPRIISFTGSTKVGSYIG
ref|NP_241871.1|       ETPITGGTLIAKIFEEAGVPKGLLNVVVTEIDEIGNAFVEHPIPRIISFTGSTNVGSHIG
ref|NP_693628.1|       HTAITGGTMIAKIFEEAGLPKGVLQVVTTEISEIGDRFVDHPVPAAISFTGSTKVGKHIG
RAAC01575              EAAITGGALLAKVFEEAGVPKGLVNIVVADVAEIGDAFLEHPIPRIISFTGSTAVGRHIA
                        .:.* **::**:** **:* *:::::.:::  ***: *::**:*  ******** ** :*.

ref|YP_001420375.1|    QLAVKHFKKPLLELGGNSALIVLEDADLEYAVNAAVFSRFTHQGQICMSANRVLVHTSVY
ref|NP_388616.1|       QLAMKHFKKPLLELGGNSAFIVLEDADIEYAVNAAVFSRFTHQGQICMSANRVLVHSSIY
ref|YP_077980.1|       QLAIKHFKKPLLELGGNSALIVLEDADLEYAVNAATFSRFTHQGQICMSANRILVQKEVY
ref|NP_241871.1|       QLAVKHFKKPLLELGGNSAFLIFADADLDYAVQAATFSRFTHQGQICMSANRIFVQRDVY
ref|NP_693628.1|       EVASRNLKEVHLELGGNSALIVLEDADVDYAVSAGVFSRFTHQGQICMSANRIIVHEDVY
RAAC01575              EVAGRHLKRVTLELGGNSALIVLDDADLDLAVDAAVFSRFTHQGQICMCANRVIAVKDVY
                       ::*  :::*.  ********:::: *::  **.*..**********.*::. ..:* ref|YP_001420375.1|    DKFTELYEAKVSSLKVGDPMDPDTVIGPLINERQAEGLRRSVEKAIEEGAVPVLSGRFSG
ref|NP_388616.1|       DKFLELYQAKVESLKVGDPMDPDTIIGPLINSRQTDGLMKTVEQAIEEGAVPVKLGGFNG
ref|YP_077980.1|       PEFLKLFSQKVSGLKTGDPLDPETVIGPVINERQAEHLRKSIEKGIEEGATPLLKGDIKG
ref|NP_241871.1|       DEFVERYVTKVASLKVGDPRDPETVIGPVMNSRQAETLKQAIESGIAAGAKPVLHGAISG
ref|NP_693628.1|       DEFVQKYADKVKTLTCGDPADSSTIIGPLINERQVQNTVNLIEKGVEEGAHPLVRGQVNG
RAAC01575              ERFLGKFVERVSKLKMGSPRDPETVIGPLINRRQVERLLAVVDASIEQGARVAYRGPVDG
                       .*   :   : :* *. *.* *..:***::* .:       :: .:     * ..* ref|YP_001420375.1|    TVAEPVILKDVKPEMSIAKEELFGPAVCIMTFETEDEAVSIANATPFGLSGAVHTANVER
ref|NP_388616.1|       TIVEPTILKDVKPFMSIAKEELFGPVVSFMKFDSEDEAVDIANETPFGLSGAVHTSNLER
ref|YP_077980.1|       NLVEPTILADVTPDMSVAKEELFGPVVCVMPFETEADAVEIANDTPFGLSGAVHTGNVES
ref|NP_241871.1|       NMVEPTILIDASPEMAIAQEELFGPVVCVIPFDTEEEAVEMANDTKYGLSGAIHTANVER
ref|NP_693628.1|       NVVEPVIFTEVTPDMQIANEEFFAPVVAIMKVSSEEQAIAYANASSYGLSGAVHTSDVNR
RAAC01575              NVVGPVVLADVGPEMACAKEEMFGPVVAVMPVEDEEEAVRAANDSEYGLTGAVITRDVER
                       .:.  *.::   :. *  * * *:**:*.*.*..:.  .  :*:    ** : :**:**:  * :::
```

FIG. 47B

```
ref|YP_001420375.1|    GVEFAKRIETGMIHVNDTTINDEPNVAFGGEKQSGLGRLNGEWSLEEFTTLKWISVQHEK
ref|NP_388616.1|       GVAFAKRIETGMIHVNDTTINDEPNVAFGGEKQSGLGRLNGEWSLEEFTTLKWISVQHEK
ref|YP_077980.1|       GVAIAKQIETGMIHVNDTTINDEPHVAFGGEKQSGIGRLNGEWSLDEFTTLKWISVQHQK
ref|NP_241871.1|       GVEIAKRIQTGMIHVNDITINDEPIVAFGGEKHSGLGRLNGEWSLEEFTTLKWVSVHYSQ
ref|NP_693628.1|       GAEVAKQLESGMIHINDGTINDEPNVAFGGVKNSGVGRLNGEWSLEAFTTKWISIQHTK
RAAC01575              GVRIAMQVETGMFHVNDGTVNDEPLVAFGGEKGSGVGRYNGQWGIDEFTTLKWISIQRER
                       *. .* :::: **:*:** *:**** ***** * **:** **:*.:: *** **:*::  :

ref|YP_001420375.1|    RQFP-
ref|NP_388616.1|       RSFP-
ref|YP_077980.1|       RSFP-
ref|NP_241871.1|       RVFP-
ref|NP_693628.1|       RQFP-
RAAC01575              RQYPI
                       *  :*
```

FIG. 48

```
ref|YP_001126012.1|   ------------------------VLNEEGTVVQPEYRERITKELTMVYRHLIRTRTF
ref|ZP_01860561.1|    MTQSRDRGEEMEEQFPIK------RIIDNDGTLLG-DKDPGITEQLAKEFYRHMVRIRTF
ref|ZP_01171269.1|    ------------------------MIDENGNEVS--GTSGFDTEIALEFYRQLVRIRVF
dbj|BAB40585.1|       -----------EHQFPK------IQIVDENGNIVDSKYEDKLTPEFIKELYERLMFVRTF
ref|NP_241079.1|      ---------------------------------------VLSMYKQMINCREF
RAAC01657             MLAEHDRAERLMETAKAEGLYEEIHLLKEDGTLAG--AVDDIPPEVMVAMYRHMVFARAF
                                                            :*.::: *  *  * ref|YP_001126012.1|   DRKCVSLQRQGRIGTYVPYEGQEACQVGSALAINDEDWMFPTYRDHGAMMTFGRSLVNTL
ref|ZP_01860561.1|    DKKAISLQRQGRIGTYAPFEGQFASQVGSSAALKEDDWMFPSYRDHIGAAMTFGHSLRNIL
ref|ZP_01171269.1|    DRKAVSLQRQGRIGTYAPFEGQEAAQIGSAMALEESDWMFPTYRDHGAALAFGHSMRNVL
dbj|BAB40585.1|       DRKAISLQRQGRLGTYAPFEGQEAAQVGSALALEKDDWLFPTYRDHAATITFGHKLSTVF
ref|NP_241079.1|      DEKALKLQRQGRIGTYASFKGQEACQIGGALALRPTDWLFPTYRDHAAISTHGQPWHRIF
RAAC01657             DRKAIALQRQGRIGTYAPFEGQEAAQVASAMALAPEDFVFPSYRDHAATMVLGQSPANVL
                      *.*.:  ******:***..::****.*:...  **    *::**:****.*  . *:    :

ref|YP_001126012.1|   LYWKGRTEGCVPPEGKKIVPPSVPIATQLPHAAGAACAEKWKGTKNAVIVYFGDGATSEG
ref|ZP_01860561.1|    LFWKGRNEGCVPPQGKKIFPPGIPIATQLPHAAGAAYAEMRKGTKNAAIVYFGDGATSEG
ref|ZP_01171269.1|    LFWNGRNEGCIPPEGKNIFPPGIPIATQTPHAAGAAYAEKRKGTKKAAIVYFGDGATSEG
dbj|BAB40585.1|       LYWNGRVEGCVPPEGKKIFPPAVPIATQLPHATGAAMAEKYKGTKNAAIVYFGDGATSEG
ref|NP_241079.1|      LYWMGHMDGSLSPDDRNILPPAVPIATQMLHAVGTAWADKLKGNPHVSLVFFGDGATSEG
RAAC01657             LYWSGRVEGIRSPEGRHILPPSVPIATHVLHAVGAAWASRYRKESAVSTAYFGDGATSEG
                      *:*   *:  :*   .*::..*.:::  .*:* *.   :  .  ::********* ref|YP_001126012.1|   DFHEGLNFASVFNAPVVFFNQNNQYAISVPITRQMRSKTIAQKALAYDIPGVRIDGNDVF
ref|ZP_01860561.1|    DFHEGLNVASVLNAPVVFFNQNNGFAISVPIKKQMKTKTIAQKALAYDTPGVRIDGNDIF
ref|ZP_01171269.1|    DFHEGLNFASIVKAPVVFFNQNNQYAISVPLSKQMNTKTIAQKSLAYDIPGVRVDGNDVF
dbj|BAB40585.1|       DFHEGLNFASVFKAPVVFFNQNNSFAISVPIHKQMNSKTIAQKSVAYGIPGIRLDGNDIF
ref|NP_241079.1|      DFHEALNFAGVYQTPTIFFCQNNGYAISVPFEKQSASKTIKQRSVAYDMRGERVDGNDIF
RAAC01657             DFHEALNFAGVFHLPVLFFCQNNGYAISVPFSRQSASRTIAQRAIAYDIVGVRVDGNDAF
                      **..*.:  : *.: *  :*       ::**  *:::**.:  *  *:****  * ref|YP_001126012.1|   AVYFQTAEALERARHGGGPTLIEAVTWRYGAHTTSDDPSRYRDQEESKKRRET-TDPIKR
ref|ZP_01860561.1|    AVYFETLKALERARNGEGPTLIEAVTWRYGAHTTADDPTKYRDQSESDERRKL-CDPIAR
ref|ZP_01171269.1|    AVYRETKKALERAREGGGPTLIEAVTWRYGAHTTADDPAKYRDQQESSVLRGK-IDPILR
dbj|BAB40585.1|       AVYFYTKEALDRARNGEGPTLIEAVTWRYGAHTTADDPTKYRNQEESLERREK-YDPILR
ref|NP_241079.1|      AVYLTVKRAIFQARKGRGPTLIEAVTTRFGSHTTADDAKKYRDQEEIERTWKEMQDPLTR
RAAC01657             AVYRAVKEARSRALHGLGPTLIEAVTFRMGAHTTADDPTRYRDQKAVVEAWQK-RDPIVR
                      ***   .*  .:*  .* *********  *  *:*::. :**:*:.         **: * ref|YP_001126012.1|   VVRLMQREGWWNEQWANQVQEEVNAEIEQAVAEMERYPKANASDMFDYVFAEPTWTIA--
ref|ZP_01860561.1|    LQRYMERQGWWDQEWADSVQKEYTAEMDQAVEELESYPEADPKVIFDYVFEKPTWTIS--
ref|ZP_01171269.1|    MERWLKNKDLYDENWAKRAESEAAAEIDLAIAEMEAYPPADPADIFDHVFAELIWPL---
dbj|BAB40585.1|       VERLMKNKGIWDEKWAASVEEKASQTIEEAVKEMEAFPAPDVNDLFDHVFEKPTW-----
ref|NP_241079.1|      LKAYIQAKGWLSEEEEAQMKAKTRETIDEELSMAEQYPKPSISQMFEIIVYENQPWYV---
RAAC01657             LRLYLESQKLWSESDEAKLQDEVKARVEAAVEEALSIAPPDMEMMFDHVYAEEPWHLAAE
                      :   ::   .:.         :   ::    :            ... :*::*:  :   * ref|YP_001126012.1|   -------------
ref|ZP_01860561.1|    -------------
ref|ZP_01171269.1|    -------------
dbj|BAB40585.1|       -------------
ref|NP_241079.1|      -------------
RAAC01657             REEYRRTREGVSV
```

FIG. 49

```
ref|YP_001126011.1|     -TKSLTLVQAVNDALRIMLKERDDVVLLGEDVGRNGGVFRATDGLLQEFGEERVIDTPLS
ref|NP_693798.1|        -TKQLTLIQAITDGMRTMLHEREEVVVLGEDVGKNGGVFRATDGLQEEFGEKRVFDTPLS
dbj|BAB40586.1|         ----LTLVQAVTDGLRTMLKEKKEVIVLGEDVGKNGGVFRATDGLQEEFGEDRVIDTPLS
ref|ZP_00539126.1|      ----MTLVQAVTDALRTKLTDDETTLVLGEDVGKNGGVFRATDGTQEEFGEDRIIDTPLS
ref|NP_241080.1|        -SQQQTMLQAINQTLDDLLATNDDVMLIGEDIGTNGGVFRATDGLYEKYGKDRVVDTPLA
RAAC01658               MSRMLNLVQAINEALDLKLADDPRVVLLGEDIGKNGGVFRATDGLLEKYGEERVIDTPLA
                            .::**:.:  :    *     .::****:* **********  :::*:.*:.****:

ref|YP_001126011.1|     EAGFTGAAIGMALNGFRPVVEIQFLGFIYPAYEQIMTHAARMRSRTRGHFTVPLVIRAPY
ref|NP_693798.1|        EAGIIGSSIGMAINGLLPVAEIQFSGFIYPAYEQIMTHATRMRYRTKGVFTVPLVIRAPY
dbj|BAB40586.1|         EAGIVGVSIGMAINGMLPVAEIQFLGFIYPAYEQIMTHASRIRMRTMSKFHVPLVIRAPY
ref|ZP_00539126.1|      EAGIVGTSIGLAVNGFKPIVEIQFLGFIYPAYEQIMTHVSRIRMRTMCRYCVPMVIRAPY
ref|NP_241080.1|        ESGIIGSAIGLAMNGKRPIVEIQFLAFIYPGFEQLISHAARMRYRTRGQYNVPMVIRTPY
RAAC01658               ESAIIGTSIGMAVNGLIPVPEIQFLAFIFPALDQLFSHVARMRYSQGQFPVPMTIRTPY
                        *:.: * :**:*:**  *: **** .**:*. .*:::*.:*:* *: . . **:.**:**

ref|YP_001126011.1|     GAGVRAPEIHSDSTEALFTHMPGVKVVCPSSPYDAKGLLIAAIEDPDPVLFLEPMRNYRA
ref|NP_693798.1|        GAGVRAPEIHSDSMEALFTHMPGIKVVCPSSPYDAKGLLISAIEDPDPVLFLEPLKLYRA
dbj|BAB40586.1|         GAGVRAPEIHSDSVETLFTHMPGIKVVCPSTPYDAKGLLIAAIEDPDPVLFMESMKLYRS
ref|ZP_00539126.1|      GAGIRAPEIHSDSTEALFTSMPGLKVVCPSTPYDAKGLLIAAIEDPDPVLFLESMRSYRA
ref|NP_241080.1|        GAGIRGPELHSESVEAFFAHTPGLKVVAPSNPYDAKGLLTAATSDPDPVIFLEDTKLYRA
RAAC01658               GAGIHGPELHAESVESFFAHTPGLKVVVPSGPYDAKGLLISAIEDPDPVVFLEPTKLYRA
                        ***::.**:*::* *:.:*   **:***  ** ********  :*  .*****:*:*    : **:

ref|YP_001126011.1|     FREDVPEGKYTVDIGKGKKLREGEDVTVIAWGAMVPVAMKAAEAAAK-KGIDADVIDLRT
ref|NP_693798.1|        VRGEVPEEKYEIEIGKGKYLREGDDVTVIAWGAMVPVAMKAAEQ--AAEKGITCEVIDLRT
dbj|BAB40586.1|         SREDVPEGKYTVDIGKARKVRDGKDVSIFAWGAMVPVATKAAEEMEK-KGVTCDVIDLRT
ref|ZP_00539126.1|      FKEPVPSEAYTIEIGKANCITEGQDVTLIAWGGMVQVAQKAATE-AATRGISCEVIDLRT
ref|NP_241080.1|        FKEDVPNTLYEIPLGQAKVVQEGEDVTVIAWGGMVREALQAAKEAEKAHGWSCEIIDLRT
RAAC01658               FREEVPEGLYRVPIGKAKRVREGEDVSVFAWGSMLHTALKVAEAIERERGWTCDVIDLRT
                         :   **.  *  : :*:..  : :*.::*.*:  *  :.*       :*  .::***** ref|YP_001126011.1|     LYPLDKDMIAESVQKTGRTVIVQEAHATGGLANDILAVINDTSFFYQKAPAERVTGFDVP
ref|NP_693798.1|        LYPIDRAIIAESVQKTGRCVVVHEAPATGGLGNDIISIVNDTSFLYMKSPIERVTGADVH
dbj|BAB40586.1|         LYPLDKDAIAESVQKTGRVVIVHEAHTCGVSNDVMAVINDTAFLYLKAPIERVTGFDVP
ref|ZP_00539126.1|      LYPLDRETISASVQKTGRAVIIHEAQATGGLGNDLLALINDTSFLYLRAPVARVTGFDVP
ref|NP_241080.1|        IAPIDRETIIESVKKTGRAIIIHEAHKTAGLGGEITALINEEALIYLKAPVKRIAGFDIP
RAAC01658               LYPLDRDAIVESVQKTGRAVVVHEAHKTAGLGAEIVSLINEEALLYLRAPIKRIAGFDVP
                        : *:*:    *  **:****  :::**  *.*:.  ::   :::*:  :::*   ::*   *:** *:

ref|YP_001126011.1|     VPFFAHEDDYLPTPARVLHAIEKVM--
ref|NP_693798.1|        VPFWALEEHNIPTPARVMDAINQVINF
dbj|BAB40586.1|         VPFFTLEEHYLPNTGRVVKAIEKVIHF
ref|ZP_00539126.1|      VPLFALEDHYIPTPTRVLEAIQRTVDF
ref|NP_241080.1|        VPQFLSENQYLPTIERMFRGIEETVSF
RAAC01658               VPFFALEDEYMPTEARIRAGIEETITF
                        **  :   *:. :*.   *:   .*:..:
```

FIG. 50

```
ref|YP_001125402.1|    -----------MPTFQAFVVNKTEAEFTAGVETLSMDDLPEGDVVVRVHYSSVNYKDGLA
ref|YP_147282.1|       -----------MSAFQAFVVNKTETEFTAGVQTISMDDLPEGDVVVRVHYSSVNYKDGLA
ref|ZP_01859257.1|     --------------TFKALVVNKTEEDFSVNIEPLTFEDLPQGDVTIRVHYSSVNYKDGLA
ref|YP_001420249.1|    ---------------FKALVVDQREDRFSVSVRELAVQDLPEGEVLIKVCYSGVNYKDSLA
ref|NP_388913.1|       ------------TLFQALQAEKNADDVSVHVKTISTEDLPKDGVLIKVAYSGINYKDGLA
RAAC01669              MRSRPPKEVHDMTTFRAHMVEQDGNAHRAGVRELTLDQLPEGEVLTRVRYSSVNYKDGIC
                                    *:*    .::    . :. :: ::**:. *  ::* **.:****.:.

ref|YP_001125402.1|    SIPDGKIVKTYPFVPGIDLAGIVVSSNDARFREGDEVIATGYEIGVTHFGGYSEYARLHG
ref|YP_147282.1|       SIPDGKIVKTYPFVPGIDLAGVVVSSQHPRFREGDEVIATGYEIGVTHFGGYSEYARLHG
ref|ZP_01859257.1|     SIPNGKVVQSYPFVPGIDLAGVVTSSDDDRYKEGDKVIVTSYELGVSHYGGYSEYARVPG
ref|YP_001420249.1|    AIPDGKIVTSYPFVPGIDLAGIVVSSDDARFKEGDKVIATSYGIGVSRFGGYSGMARIPA
ref|NP_388913.1|       GKAGGNIVREYPLILGIDAAGTVVSSNDPRFAEGDEVIATSYELGVSRDGGLSEYASVPG
RAAC01669              SQPASRLVTRYPMVLGIDLAGEVVESRDARFRPGDPVICTSYDLGTGHFCGFSEYARVPA
                          . ..:*  **::  ***  **  .. *    . *:  ** ** *.* :*. : ** *  * :  .

ref|YP_001125402.1|    DWLVPLPKGLTLREAMAIGTAGFTAALSIHRLEELGLVPERGPVLVTGATGGVGSLAVSM
ref|YP_147282.1|       DWLVPLPKGLTLKEAMAIGTAGFTAALSTHRLEEHGLTPERGPVLVTGATGGVGSLAVSM
ref|ZP_01859257.1|     DWVVPLPDNLTLKEAMVFGTAGFTAALSIHQLENSGLRPENGPVLVTGATGGVGSMAVAM
ref|YP_001420249.1|    DWIVPLPEGLTLKEAMTIGTAGFTAALSVQRLEENHAAPEKGKVLVTGATGGVGSFAVSI
ref|NP_388913.1|       DWLVPLPQNLSLKEAMVYGTAGFTAALSVHRLEQNGLSPEKGSVLVTGATGGVGGIAVSM
RAAC01669              DWVVPLPDGLSLRDAMVLGTAGFTAALSLYRMEQNGVSPAMGAMLVTGATGGVGATGIAI
                       **:****..*:*::**. **********: ::*:    *  * :*********.  .:::

ref|YP_001125402.1|    LAKRGYTVAASTGKATEHDYLRALGAKEVLTRED---VTAERIRPL--DKQRWAAAVDPV
ref|YP_147282.1|       LSKRGYTVEASTGKTAEHDYLRALGAKEVLTRED---VTAERIRPL--DKQRWAAAVDPV
ref|ZP_01859257.1|     LAKRNYHVTASTGKESEHEYLKSLGAKEIVSREE---VAPEKIRPI--GKQRWAGAVDPV
ref|YP_001420249.1|    LSTLGYEVEASTGKEDESGYLKSLGAKTVIHRDE---VYNGTLKPM--QKQKWAAAVDPV
ref|NP_388913.1|       LNKRGYDVVASTGNREAADYLKQLCASEVISRED---VYDGTLKAL--SKQQWQGAVDPV
RAAC01669              AKRAGYRVVASTRKDEAAEWLKTLGADDVVRPDA--LLLQEGESYLN-VKTRYAGVIDPV
                         .* * ***    :     :*: ***. ::  :       :            * ::  ...:*** ref|YP_001125402.1|    GGRTLATVLSRIRYGGAVAVSGLTGGVEVPTTVHPFILRGVSLLGIDSVYCPMDLRLRIW
ref|YP_147282.1|       GGRTLATVLSRIRYGGAVAVSGLTGGAEVPTTVHPFILRGVSLLGIDSVYCPMDVRLRIW
ref|ZP_01859257.1|     GGKTLASVLSNTKYGGAVAVSGLTGGVEVPTTVHPFILRGVNLLGIDSVYCPKELRETLW
ref|YP_001420249.1|    GGEPLASVLSQIQYGGSVAVSGLTAGTKLPATVFPFILRGVSLLGIDSVFCPMETRKKTW
ref|NP_388913.1|       GGKQLASLLSKIQYGGSVAVSGLTGGGEVPATVYPFILRGVSLLGIDSVYCPMDVRAAVW
RAAC01669              SGKYVPHLLQRLEYGGVIAISGYTGGPDFTASVFPFLRRQAAIIGIDSVWLDMETRREIW
                        .*. :. .:*.. .*** :*:**  *.*   ...::*.**:  *  .  ::*****:      :  *         * ref|YP_001125402.1|    EQLASDLKPD----LEQIVHEISLHELPGALARILRGELRGRTVVRL
ref|YP_147282.1|       ERLAGDLKPD----LFRIAQEISLAELPQALKRILRGELRGRMVVRL
ref|ZP_01859257.1|     NRMADDLKP---DGLGEIENEVTLEELPRTLSAILQGKTRGRTVVKI
ref|YP_001420249.1|    QRLADDFKPADLEAF--IQKEITLEELPDTLPALLKGEARGRTIVTI
ref|NP_388913.1|       ERMSSDLKP--DQLLTIVDREVSLEETPGALKDILQNRIQGRVIVKL
RAAC01669              RRLAGPWKPS-DEALRQIGHDITLDDLDSALKQILAGRMQGRAVVNL
                        .:::.  **        :   : .:::*  :    :*    :*    ..  :** :* :
```

FIG. 51A

```
ref|ZP_01696606.1|        ----------EEATFSIRINGQELAARKG--QTILEVANAHDMYIPAICYHPNLGSIQTC
ref|ZP_01171726.1|        --------------TYQVKLNGAEVKVAAGDETTILQLLQNSSVEVPNVCYHPSLGPIETC
RAAC01678                 MIDIRTEAQAEARTVQLEIDGKEVTVERG--ASVLDAILSTGQEHPHVCYHPALGPIETC
ref|YP_146312.1|          ----------EAQMVTVTINGRAYRAKPG--MTILEVVNEHGLPHPQVCYTPELGAIQTC
ref|YP_001124591.1|       ----------ETRTVTVTINGRPYHVKQG--MTILETVNEHGLPHPQVCYTPELGAIQTC
ref|ZP_01696079.1|        ----------ETKSIHITIDGRDYEARPG--EKIIDVINRNDIFHPQICYYPEVDPIQTC
                                     :  ::*     .  *    .::       .   :**  *  :..*:**

ref|ZP_01696606.1|        DTCFVNVNGNLVRACATKVEPGMEVESGSKPVKDAQYEAMSRILKNHELYCTVCDNNNGN
ref|ZP_01171726.1|        DTCIVSVNGELVRSCSTKLNDGDIIDTVSADVKEAQVIGMDRILTNHELYCTVCDYNNGG
RAAC01678                 DTCIVEIDGKLMRACSTPVEDGMAVRTKSVAARYARKEAMDRILKNHELYCTVCDNNNGN
ref|YP_146312.1|          DTCIAEVNGTLLRACATPVEDGMVVELGSPRAKAAQKEAMDRLLENHLLYCTVCDNNNGN
ref|YP_001124591.1|       DTCIAEVNGTLLRACSTLVEDGMVVELSSPRAKVVQKEAMDRLLENHLLYCTVCDNNNGN
ref|ZP_01696079.1|        DTCIAEVNGELMRTCSTVAEDGMVVRLSDDRSEAARHEAMDRILANHLLYCTVCDNNNGN
                          ***:. ::*  :*:*:*:*   :  *  :         . *.*:* ** ******* ***.

ref|ZP_01696606.1|        CVVHNTAEHLEIEHQKYQFEAKPYP--PDQSHPFYRYEPDQCILCGRCVEACQDLQVNET
ref|ZP_01171726.1|        CRVHNTVKEMKINHQSVPFAQKPYP--ADNSHPFYRYDPDQCILCGRCVEACQDVQVTET
RAAC01678                 CVLHNTVMQMGVEHQAYPFTPKPYE--VDMSNPFYRYDPQQCILCGRCVEACQNLQVSEV
ref|YP_146312.1|          CKLHNTAEMMQIEHQTYPYRPKVDPSEVDMSHPFYRYDPNQCIACGQCVEACQNLQVNET
ref|YP_001124591.1|       CKLHNTTEMMQIEHQTYPYRPKVDPSEVDMSHPFYRYDPNQCIACGQCVEACQNLQVNET
ref|ZP_01696079.1|        CIVHNTTEKMGIEHQKYPFTPKTDASGVDYSNPFYRYDPNQCIACGRCVEACQNLQVNET
                          *  :***.   :  ::**    :  *     *  *:*****:*:*** **:****:.**.*.

ref|ZP_01696606.1|        LTIDWDREVPRVIWDNDVPIDESSCVSCGHCVTVCPCNALMEKSMLGEAGYLTGIPQKVL
ref|ZP_01171726.1|        LTIDWEREKPRVIWDNDVPINESSCVSCGHCSTVCPCNAMLEKGMEGEAGYLTGIAKQTL
RAAC01678                 LSIAWDREVPRVIWDNDVPINESSCVSCGHCVTVCPTNALMEKSMLGEAGFLTGIEKPTL
ref|YP_146312.1|          LSIDWEAERPRVVWDGGVPINESSCVSCGQCVTVCPCNALMEKSMLGEAGFLTGLDKDVL
ref|YP_001124591.1|       LSIDWEAERPRVVWDGGVPINESSCVSCGHCVTVCPCNALMEKSMLGEAGFMTGLDQDVL
ref|ZP_01696079.1|        LSIDWEAERPRVIWDNGVPINESSCVSCGHCVTVCPCNALMEKSMLGEAGYLTGLEEDLL
                          *:* *: *  *:..*:** :   ::**.* **:::   * ref|ZP_01696606.1|        EPMIDLTKEVEPGYKEIFAISEMEAAMRKSRIKRTKTVCTYCGVGCSFEIWTKGRHILKV
ref|ZP_01171726.1|        RPMIEITKNVETGYGSILAISDMEAAMRDERIKKTKTVCTYCGVGCSFDVWTKGREILKV
RAAC01678                 DKMIDITKKVEPGYSSIFVVSEIEHEMREARIRKTKTVCTYCGVGCAFDVWTKDRHILKV
ref|YP_146312.1|          NPMIDFVKEVEPNYTSIFAISEIEAAMREQRIKKTKTVCTFCGVGCSFEVWTKGRKILKI
ref|YP_001124591.1|       KPMIDFVKEVEPNYTSIFAISEIEAAMRQQRIKKTKTVCTFCGVGCSFEVWTKGRKILKI
ref|ZP_01696079.1|        DPMIDLVKKVEPGYGSIFAISEIEASMREQRTKKTKTVCTFCGVGCTFEVWTKGRKILKI
                           **::.*:**..*  .*::*::*  **. * ::*:*****:*****:*:*:***.*.***:

ref|ZP_01696606.1|        EPQEHAPVNGISTCVKGKFGWDFVNSEERLTKPLIRKGEEFVEASWDEALNLIASKLQEI
ref|ZP_01171726.1|        DPQPEAPANGISTCVKGKFGWDFVNSEERLTKPLIREGEFFREAEWDEAISLIARRFTEI
RAAC01678                 EPQMEAPVNQISTCVKGKFGWDFVNSPDRLTKPLVRKGDRFVEVSWDEALDVIERRIKEI
ref|YP_146312.1|          QPVSEAPVNAISTCVKGKFGWDFVNSEERLTKPLIRKGDVFVESTWDEALDLVAEKLGAI
ref|YP_001124591.1|       QPVSEAPVNAISTCVKGKFGWDFINSEERLTKPLIRKGDTFVESTWEEALDLVAEKLGAI
ref|ZP_01696079.1|        EPKHEGPVNAISTCIKGKFGWDFVNSDKRLTKPLVRKGDKFVETSWDEALSVVASRLKEI
                          :*   ..*.* **:****:  **** :****:*:.   * *::*.::  ::  * ref|ZP_01696606.1|        KKQHGPDALGFIASSKCSNEENYLFQKFARAIIGTNNLDNCSRYCQSPATSGLLRTVGIG
ref|ZP_01171726.1|        KNEHGAQAMSFISSSKCTNEESFLMQKLGRAVIGTNNIDNCSRYCQTPATVGLFRTVGYG
RAAC01678                 QAKHGYDAVAFISSSKTTNEENYLMQKLARAVMHTNNIDNCSRYCQSPATEALRRTMGLG
ref|YP_146312.1|          KRQYGGNAIGFISSSSKISNEENYLMQKLARQVFETNNVDNCSRYCQSPATDGLFRTVGMG
ref|YP_001124591.1|       KQQYGGNAIGFISSSSKISNEENYLMQKLARQVFETNNVDNCSRYCQSPATDGLFRTVGMG
ref|ZP_01696079.1|        HSQYGKDAVGFISSSKVTNEENYLMQKLARQVFETNNVDNCSRYCQSPATDGLLRTVGMG
                          :  ::*   *:*:**:*** :***.:**:.:*::  :: ***:*******.*  .* **:* *
```

FIG. 51B

```
ref|ZP_01696606.1|      GDSCTIRDIQQADLVVTVGANPAESHPVLATRIKRAHKLHGQKLMVVDLRENELASRANL
ref|ZP_01171726.1|      GDAGSIRDIQMSDLVLIIGSNTAESHPVLSTRVKRSHKLGGQKLIVADLRKHEMADRADL
RAAC01678               GDTGSIKDLELADLVLIVGANPAEAHPVLSTRLRRAQKKRGQKHIVADVRRNIMATRADL
ref|YP_146312.1|        GDSGTIHDIATAGLVIIIGANPAEGHPVLATRVKRAHKLFGQKLIVADLRRNEMAERADL
ref|YP_001124591.1|     GDSGTIYDIASAGLVIIIGANPAEGHPVLATRVKRAHKLFGQKLIVADLRRNEMAERADL
ref|ZP_01696079.1|      GDSGTIKDIASAGLVITVGANPAEAHPVLATRIKRAHKLHGQKLIVADMRKNEMAERADL
                        **.*.*  *.   :.**. :*:*..*:.**.:*::*   ***  :*.*.*..:  :* **:* ref|ZP_01696606.1|      FIHSKPSTDLIWLNAVTKYILDQGWEDKAFLEARVKGLDKFRASLEKYTLAFAEEKTGIS
ref|ZP_01171726.1|      FVQPKAGTDIVWLSAVAKYIIDNGMADEEFLAEKVNGLDEFTKNIEKYTMEYAAEVTGIA
RAAC01678               FIQPRQGTDLVWLSAVTKYIIDQGRIIDEAFLRDRVNGFDEYVQSLEKFTLDYASEICGLR
ref|YP_146312.1|        FIRPKQGTDQVWLMAVTKYIIDQGWHDEAFIRERVHFFEEFKQLLEKYTLDYAEQVTGIA
ref|YP_001124591.1|     FIRPKQGTDQVWLMAVTKYIIDQGWHDESFIRERVHFFDEFKQLLEKYTLDYAEQITGIA
ref|ZP_01696079.1|      FIHPNQGTDQVWLMAVTKYIIDQGWHDENFIAEKVNFFDEFKETLEKYTLDYAEKMTGIP
                        *::..  .** :** **:***:*:*   *: *:   :*: ::::      ***:*: *  :  *:

ref|ZP_01696606.1|      KENLIKMATMIHEAKSVCILWAMGITQHTCGTDASTAISNLLLVTGNYGRPGTGAYPLRG
ref|ZP_01171726.1|      LEQLIDMAEMIGRAKSVCALWAMGITQHMGGSDASTAISNLLLVTGNYAKPCAGAYPLRG
RAAC01678               KEELVRVAEMIMEAKRVAVCWAMGVTQHRGGSDTSTAICNLLLVTGNVARPGTGAYPLRG
ref|YP_146312.1|        KADLIRIAEMIHEADGTCVLWGMGVTQNTGGSDTSAAISNLLLATGNYGRPGAGAFPLRG
ref|YP_001124591.1|     KTDLIRIAEMIHEADGTCVLWGMGVTQNTGGSDTSAAISNLLLATGNYGRPGAGAFPLRG
ref|ZP_01696079.1|      KETLIQIAEMIHQADGTCILWGMGVTQNTGGSDTSAAISNLLLATGNYTRPGTGAYPLRG
                          *:  :* **  .*  ..  *.::    *: ::* :* .  :: :**** ref|ZP_01696606.1|      HNNVQGACDFGTMPAWFPGYEPVEDNEVRERYEKAWGVKLPENPGLDNHQMIGGIKSGKL
ref|ZP_01171726.1|      HNNVQGASDFGSMPNMFPGYQEVADPEIRKKYELAWGTELPGEPGLNNHEMVEGIHAGTL
RAAC01678               HNNVQGAGDMGCAPPPFLPGYERVDNEEQRRKWEKLWGVELPTTPGLNNHQMVDAIHEGKL
ref|YP_146312.1|        HNNVQGACDMGSLPAWLPGYQHVTDDEARAKFEQAYGVRIDAKPGLDNIQMLEAAERGEL
ref|YP_001124591.1|     HNNVQGACDMGSLPSWLPGYQHVTDDAARTKFEKVYGVRIDAKPGLDNIQMIEAAERGDL
ref|ZP_01696079.1|      HNNVQGACDMGTLPGWLPGYQHVEDDAAREKFEKAYGVKISNKPGLNNIEMLHAIAAGQL
                        *******  *:*       *:***: * :       *  ::*   :*..:    ***:*   :*:  .     *  * ref|ZP_01696606.1|      RGLYLFGEEMAIVDSNINFVEEHLEKLDFFVVQDVFFSKTAQFADVILPAAPSLEKEGTF
ref|ZP_01171726.1|      KAMYLKGEDMGLVDSNINHVHAAFEKLDFFVVQDIFLSKTAEFADVVLPASPSLEKEGTF
RAAC01678               KAMYLCGEDMAVVDSNANYVEDAFRKLEFFVVQDVFLSKTAQFADVVLPACPSLEKEGTF
ref|YP_146312.1|        KAMYIVGEDMALVDCNANHVQETLAKLDFVVVQDIFLSKTAQFADVILPAAPSLEKEGTF
ref|YP_001124591.1|     KAMYIIGEDMALVDCNANHVQDTLAKLDFVVVQDIFLSKTAQFADVILPAAPSLEKEGTF
ref|ZP_01696079.1|      KAMYIIGEDMALVDSDANHVSEELSNLDFLVVQDVFFSKTAQYADVILPAAPSLEKEGTF
                        :..:*: **:*.:**.: *.*    : :*:*.****:*:**::*.*.******** ref|ZP_01696606.1|      TNTERRIQRFYQVFEPMGESKPDWVIFQELANKMGAQWHYQHPGEIMAEAASLAKYFAGI
ref|ZP_01171726.1|      TNTERRIQRLYQALEPLGDSKPDWQIIMEIANSLGAGWNYTHPSEIMEEASRLMPLYSGV
RAAC01678               TNTERRIQRLYRVLEPLGDAKPDWEIIQMVANRFGAHWNYTSAREIFEEMASAADLFRGA
ref|YP_146312.1|        TNTERRIQRFYQALEPLGDSKPDWWIIQEIAKRLGADWNYAGPKEIMDEIASLAPLYSQA
ref|YP_001124591.1|     TNTERRIQRFYQALEPLGDSKPDWWIIQEIAKRLGADWNYAGPSEIMDEIASLAPLYSQA
ref|ZP_01696079.1|      TNTERRVQRLYQALPALGESKPDWWIIQEVAKRLGADWNYSHPCEIFAEMASLTPLFAQA
                        ******:**:**:..:   ..:.:****  *:   :**  :**   :::   . **: *  .     :

ref|ZP_01696606.1|      SYERLEGFNSQIWPVKKDGTSTPLLYQDRFAFPDGKARLVPVDWEPPFSAGEGFDYHLNN
ref|ZP_01171726.1|      TYERLEGYNSLQWPVAEDGQDTPLLYTERFFFEDGRARLVPVDWTKPLEFEEEYDLHINN
RAAC01678               SYDRLEGYGSLQWPVLPDGTDTPLLYTDGFAFPDKKARLYPVDWTPPIEVGEEYDLELNN
ref|YP_146312.1|        HYDRLEGWNSLCWG-SHDGADTPLLYKERFNFPDGKARFALADWVEPVQYPEEYDLLVNN
ref|YP_001124591.1|     HYDRLEGWNSLCWGSY-DGADTPLLYKERFNFPDGKARFALADWVEPVQYPEEYDLLVNN
ref|ZP_01696079.1|      DYDKLEGWNSFLWGSL-DGANTPLLYKDGFPFPDGKARFALTDWVKPAEFPEQYDLHINN
                        .*::***:.*   *     **  *.****  :   *   *   :  *:*   .**   *  .  * :*   :**
```

FIG. 51C

```
ref|ZP_01696606.1|      GRLLEQFHEGNLTDRSPGIHHKVPEPWLEISPEAASERGIKDGALVRLTSPYGKVKVRAV
ref|ZP_01171726.1|      GRLLEHFHEGNMTYRSKGTSEKTPSVFLEVSPELAEERGLESGTLVRLSSPYGNVKVQCH
RAAC01678               GRLLEHFHEGNMTSRVPGIHEKVPETFVEISPELAKERGVQDGALVRLVSPYGSIKVRVA
ref|YP_146312.1|        GRLLEHFHEGNLTYKSKGIEHKFPEVFVEVSPELAKERGIEDGALVRLISPYGRVKVRVL
ref|YP_001124591.1|     GRLLEHFHEGNLTYKSKGTQRKFPDIFVEVSPELAKERGISDGALVRLISPYGRVKVRVL
ref|ZP_01696079.1|      GRMLEQFHEGNLTNKSEGIESKVPGVFVEVSPELAKERNLDTGDLVRVTSPFGSLQLHVL
                        **:**:*****:*  :  **   *  *    ::*:***  *.**.:.  *  ***:  **:*  ::::

ref|ZP_01696606.1|      VTCRVQGKELYLT-MNARKEDEMVNRLTSSYHDRVTHTPNYKEMGVKMEILEEKGKPPLP
ref|ZP_01171726.1|      ITDRVKGKEVYLP-MNDRGE-AAINLLTSSYADKDTDTPAYKEIRAKMEILKAKGEDPLP
RAAC01678               VTDRVSGKHVYVP-LLSHADEEAVNRLTSSDHDTATYTPAYKEMRVRMEVIQSCGEPPIK
ref|YP_146312.1|        VTDRVRGNELFLP-MHSTANESAINILTGPATDRRTNTPAYKQARVRMEVIERSGKTPLP
ref|YP_001124591.1|     VTDRVRGNELFLP-MHSTANESAINILTGPQTDHRTNTPAYKQARVRMEVLERSGETPLP
ref|ZP_01696079.1|      VTDRVQGKELYLP-MHSTEKESAINFLTGPIYDKRQSTPAFKQTKVKMELIRKGGESPLP
                        :*.** *:.:::.  :    .  :* **..  *    ** :*:   .:**::.  *: *:

ref|ZP_01696606.1|      KVNHRYGNRIPQISVRVEEKWKRDDFIPI----------
ref|ZP_01171726.1|      RINHRYGNPQPQIGVQVQKKWARKDYI------------
RAAC01678               RGNFRLGKPNPQPGVNVEQKWARKDYVPLVTDRALVKEG
ref|YP_146312.1|        RTNPRFKKRHPQNGVEVERKWRRSDYVPLTEENKGVTIG
ref|YP_001124591.1|     CTNPRFQKRHPQNGVEVERKWRRRDYVPLTEAEKEVKIG
ref|ZP_01696079.1|      KSNHRDKKRNPTRGVEVERKWQREGYQPL----------
                         *  *   :  *  .*.*:.** *  .:
```

FIG. 52A

```
ref|YP_001211085.1|    MPSVKIYDTTLRDGAQAEGISFSVEDKIKIALRLDKMGFHYIEGGWPGSNPKDLEFFKKI
ref|YP_001111663.1|    -----MYDTTLRDGTQGEGVSLSAEDKVKIALRLDEMGFQYIEGGWPGSNPKDMEFFQKI
ref|YP_431081.1|       ---ILIYDTTLRDGSQGEGISLSVEDKLKIASRLDRLGVDYIEGGWPWANPKDMEFFLRA
ref|NP_213242.1|       ----VYIYDTTLRDGSQMEGVSFSLEDKIRIAEKLDDFGTHYIEGGWPYANPKDNLFFQKA
RAAC01685              MSYVYLLDTTLRDGTQGEGVSLTVADKLKIAEKLDDLGVAYIEGGFPGANPKDEEFFRAA
ref|YP_001547204.1|    ---IFLYDTTLRDGTQREGLSLSLADKLKIARELDRFGMHYIEGGWPGSNPKDAAFFAEA
                          :.*******:* **:*::  **::** .** :*. *****:* :****  **

ref|YP_001211085.1|    RHCPLRHARLAAFGSTRKAGAAAENDASVKAIIDSGVQVATIFGKSWDFHVFKALGVTLE
ref|YP_001111663.1|    QQYSLRNAQVTAFGSTCRPGVEPHEDANINCLLEAGAKIATIFGKCWDFHVTKALNTTLE
ref|YP_431081.1|       REVIWRQARLVAFGRTRKPGQAAAEDANLLAIKRAGVKVATIFGKSWDLHVTAALGTTLA
ref|NP_213242.1|       KKMNFKNAKLTAFGSTRRPNKKVSEDPQVFSLIKAETPVVTIFGKSWDLHVTDALKTTLE
RAAC01685              KSLHLKHAKLTAFGSTRRPGVRVEDDASVRAVLDASTPVVAIVGKAWDFHVTEALRIDLD
ref|YP_001547204.1|    AKMEWKHAKIAAFGSTRRANSKPETDANLKALLDANTPVVTLVGKSWTLHVTEVLETTLE
                         :.*::.*** * :..      *..: .:   :  ..:..:**.* :**  .*   * ref|YP_001211085.1|    ENLAMIRETVAYLKSRGLEVIYDAEHFFDGCKANPAYALETIRAAAESGASAVVLCDTNG
ref|YP_001111663.1|    FNLRMVRESVAYLKSKGLMVFFDGEHFFDGYKANADYALSVLKAAVQGGAATVILCDTNG
ref|YP_431081.1|       ENLAMIGDSVAFLVDQGLEVIYDAEHFFDGFKANPDYALETLKAAAKAGASWIVLCDTNG
ref|NP_213242.1|       ENLNMIYETVFYLKRYVDEVIFDAEHFFDGYKSNPEYALQVLEAALKGGADWVVLCDTNG
RAAC01685              ENLAMIRDTVQYLKQHGREVIFDAEHFFDGFKRNRAYALATVRAAWEAGVDWVALCDTNG
ref|YP_001547204.1|    ENLAMIRDSVALMKAHGKEVIYDAEHFFDGYRADNDYALATIKAAAEAGADWIVLCDTNG
                       *** *: ::*   :    *::*.**** :  *  .:..**  :.*.   : ****** ref|YP_001211085.1|    GTLPAEVKELVEKARSVL-GVPVGIHAHNDGELAVANTLAAVQAGAEQVQGTVNGYGERC
ref|YP_001111663.1|    GSMPQEIQRAVTHVVEELPGVELGIHAHNDGEMAVANSIMAVQAGVSQVQGTVNGLGERC
ref|YP_431081.1|       GCLPWEIEEAVARVRQEI-QVPVGIHAHNDGDLAVANTLAAVTAGCRQVQGTINGFGERC
ref|NP_213242.1|       GTLPHEIYEITKKVKERFKDANVGIHAHNDSETAVANSLMAVLAGARQVHGTINGIGERT
RAAC01685              GSMPHEIHEMVTQVIQEVP-VQVGIHTHNDCELAVANSLAAVQAGARMVHGTINGIGERC
ref|YP_001547204.1|    GSLPDWISAVVQRVKGKIN-TQLGIHTHNDSELAVANSLAAIVGGCRQVQGTINGYGERC
                       *  :*   :   .  :.   .   :*:* : ****:: *: .*   *:: *** ref|YP_001211085.1|    GNANLCSVIPNLTLKCG-IFTIP-REKLVHLTDLSHFVSEVANISPNPHQPFVGASAFAH
ref|YP_001111663.1|    GNANLCSIIPNLALKMG-YSTIPA-ENLVYLTELSRYVYELANLNPIANQPFVGESAFAH
ref|YP_431081.1|       GNADLCSVMPNLELKMG-YQCLPP-GQLAFLTEVSRYVSEIANVVPAGNQPFVGYSAFAH
ref|NP_213242.1|       GNANLCSIIPNLQLKLG-FDVIP-QENLKKLTELANFVAEIINMPLPRNMPYVGESAFAH
RAAC01685              GNANLASIIPNLELKLG-YPCLPSRDHLRLLTPVARFVGEVCNLVAHSYQPFVGHSAFAH
ref|YP_001547204.1|    GNANLISIIPNLQLKMGMFCVLP--DQLQRLTELSRTVSEIANLNPDEHAAYVGNSAFAH
                       ***:*  *::*  *        :*   :*   ** ::.  *  *:  .: *** ref|YP_001211085.1|    KGGVHVSALLKDSRTYEHISPGEVGNRRRVLVSELSGMSNLLYKYKELNLDIERQSPEGK
ref|YP_001111663.1|    KGGIHVSALMKEPGTYEHMNPEAVGNVRRVLMSELAGISNLLYKYKELHL--DKSSPEGR
ref|YP_431081.1|       KGGIHVSAVLKAPDTYEHIRPQQVGNERRVLMSDQAGASNLRCKAEEMGL--ELNPERER
ref|NP_213242.1|       KGGVHASAVLKNAKTYEHINPELVGNKRKITVSDLAGRSNLVHKLKEFGIEIDPKSPELK
RAAC01685              KGGIHVSAIQRDPETYEHIPPELVGNERRVLLSELSGVSNVLAQAQAFGIPTEGRETELR
ref|YP_001547204.1|    KGGIHVAAVAKVEHSYQHIEPVQVGNRKRVVISELSGRGNIKMRAEEELGV---ESTGLER
                       ***:*.:*: :   :*:*: *  ***  :*: :* .*:   : : : :          :

ref|YP_001211085.1|    RILEDIKKLESQGFQFEDAEGSFELLVRKTNHGYRDPFILEALRLLVEIKEN-TPAYSEA
ref|YP_001111663.1|    QVLEKLKNMEHGGYQFEAAEGSLELMLRKAMNGYREPFQLESMRLILEMREE-NPIHSEA
ref|YP_431081.1|       GIIEGIKELERQGYQFEGADASLELFLRKTTGEYRQQFEVEYVKALVEKRAG-QEAISEA
ref|NP_213242.1|       KLIDKIKELEKEGYHFEAAEASLELLIKRHFGLVKDYFDFDAYRVLIAKRRDDSLPTSEA
RAAC01685              RLLERIKQMEHMGYQFEGAEASQELLFRRVLNDFTPPFKVLAVRVDTDVQRQ-GEATSQA
ref|YP_001547204.1|    GVLERVKLLESKGFQFEAAEGSFELLVRRAAADYAAPFKLLDVVTIVEQRRG-VEMQAEA
                       ::: :*  *:  *::** *:.* **:..:    *                       ::*
```

FIG. 52B

```
ref|YP_001211085.1|    IIKMRVGDRVVHTAAEGNGPVNALDNALRKALYDFYPCIGSMHLTDYKVRVLEEKDGTGA
ref|YP_001111663.1|    VIKLKVGDQVVHTAAEGNGPVHALDNALRKALETFYPEVAGMRLSDYKVRVLEEKACTEA
ref|YP_431081.1|       TVKLRVGDQVVHTAAEGNGPVNAMDNALRKALEEVFPAIRHMRLTDYKVRVLDEKDATSA
ref|NP_213242.1|       TVRLSVEGVEEHTASLGNGPISALDRALRKALEEFYPNLKELQLIDYKVRIINESAGTSA
RAAC01685              IIKLEVDGEIVHTVSEGNGPVNALDAVLRKALAPHRPEIRRMHLTDYKVRVLDEKDATAA
ref|YP_001547204.1|    TVKLQIGEEIYHTAASGNGPVNALDQAMRKALLSRYPELAEVHLVDYKVRILDSESATGA
                       ::: :     .: **: *:* .:****   * :  ::* ****:::.. .* * ref|YP_001211085.1|    AVRVHIQTGDGKRSWGTVGVSRNIIEASWQALADSTSYGL------------
ref|YP_001111663.1|    RVRVLIETGDGKKTWGTVGVSTNIIEASWQALADSMAYGL------------
ref|YP_431081.1|       RVRVLIESRDGSNSWNTVGVSTNIIEASWEALLDSMEYAL------------
ref|NP_213242.1|       KVRVLIESTDGKRKWGTVGVSENVIEASWIALRDSIVYKL------------
RAAC01685              RVRVLIESTDGEHVWRTVGVSENVIAASWEALVDSIQYYLALVVPSQALVEA
ref|YP_001547204.1|    TTRVLIEAAMGDERWTTVGCSENIIEASWQALVDSLELPLVRARSNQPVL--
                       .** *::   *.. * *** * *:* *** ** **:   *
```

FIG. 53

```
ref|ZP_00539127.1|      ----------------RILDDAGQ-VTDTSKTDLLTKDLSLALFTHMNRIRTFDRKAINL
ref|YP_074240.1|        ----------------RILQADGT-LLEP-VPAFLSVDQLKDVYRKMVYLRVFDQRCLNL
ref|YP_001127228.1|     ----------------QILDENGN--GDEAKIAAFSDEWLLDAYRAMRRARVVDERLLRM
ref|YP_149070.1|        FDPDKLP-----VEIVRILDENGN--GDEEKLAAFSDEWLLRAYREMRRARVIDERLLRM
RAAC01745               MDDVQVYRFTGDTKPDQVLNEAGE---MVGELPENAADLALEWYPFMIFCRKFDERAQLL
ref|NP_241079.1|        ----------------QVLTPKGE--CQYEGSEFLDKTFVLSMYKQMINCREFDEKALKL
                                          ::*    *                :  *    *.*.:    :

ref|ZP_00539127.1|      QRQGRLGTYAPFEGQEAAQVGSAYALQ-DKDWVFPTYRDHGATLTFG-ADMVRTFLYWNG
ref|YP_074240.1|        QRQGRMGTFAPFSCQEASQVGSAYLLRPDRDWIFPTYRDHGAMHVMG-VPLVNILRYFMG
ref|YP_001127228.1|     QRQGRIGTYAPFSGQEAAQIGSVLALQ-KDDWIFPSYREVAVCLTHG-MPLEQFFHYVRG
ref|YP_149070.1|        QRQGRIGTYAPFSGQEAAQIGSALALH-KDDWIFPSYREVAVCLMHG-MPLEQFFHYVQG
RAAC01745               QRQGRLGTYAPFRGQEAAQIASFAVLR-PSDWVFPTYRELAGMMYHG-LEPVHALLKSRG
ref|NP_241079.1|        QRQGRIGTYASFKGQEACQIGGALALR-PTDWLFPTYRDHAAISTHG-QPWHRIFLYWMG
                        ***::.*.* ****.*:..  *:  ::**.  .  *  .  .  :     * ref|ZP_00539127.1|      RVEGCVATDELHIFPPAVPIATQIPHAVGAAWAEKRKGSTQVAVAYFGDGATSEGDFHEG
ref|YP_074240.1|        DEQGSHAPQGVNAFPISIPIATQLLHAVGAAWAGRIKGEDTVAVGYAGDGGTSPGDFHEA
ref|YP_001127228.1|     RLSGKRMPEELNIFPTQIIIAAQTLHAVGCAWATKLKGESHVSVAYFGDGATSEGDFHEA
ref|YP_149070.1|        RLSGKRMPEGVNIFPTQIIIAAQTLHAVGCAWASKLKGEPHVSVAYFGDGATSEGDFHEA
RAAC01745               HPDAGRMPEEIHMAPPQIAIAAQILHAVGAGWACKLQEKDDIAVAYFGDGATSEGDFHEG
ref|NP_241079.1|        HMDGSLSPDDRNILPPAVPIATQMLHAVGTAWADKLKGNPHVSLVFFGDGATSEGDFHEA
                         .. .: :   *  : **:*  ****.** : :. ::: : ***.** *****.

ref|ZP_00539127.1|      MNFASVFQAPVTLFNQNNGYAISVPIQKQMIISETIAQKALAYGMPSVRIDGNDVFAVYFT
ref|YP_074240.1|        LNFAAVFNVPVIFFIQNNRYAISTPNSRQFKTPTIAQRALGYDIAGVRVDGQDVLAVLAV
ref|YP_001127228.1|     MNFAAVYNVPVIFFCQNNQYAISVPYAKQTASRTIAQKALAYGMKGVLVDGNDVLAVYET
ref|YP_149070.1|        MNFAAVYNVPVIFFCQNNQYAISVPYRKQTASRTIAQKALAYGMKGVLVDGNDVLAVYET
RAAC01745               MNFASVMRLPVVFFCQNNQYAISVPVHRQMASPTIAQKAIAYGMEGLRVDGNDAFAVYQA
ref|NP_241079.1|        LNFAGVYQTPTIFFCQNNGYAISVPFEKQSASKTIKQRSVAYDMRGERVDGNDIFAVYLT
                        :***.*  . *.::* *** ****.*  :*  :   ** *:::.*.:  .:**:* :**  .

ref|ZP_00539127.1|      MQKALERARSGGGPTLIEAVTWRFGAHTTADDPSKYRDQ---ER-SRDRVDPLERLEAFM
ref|YP_074240.1|        MHEAIERARSGGGPTLVESVTFRYGPHTTSDDPKRYRSQEELEE-W-QARDPIERLRLYL
ref|YP_001127228.1|     MKQAVEAARRGEGPMLIEALTYRLGPHTTADDPTKYRHPEEVET-W-RRKDPLHRLRVLL
ref|YP_149070.1|        MKQAVEAARRGEGPMLIEALTYRLGPHTTADDPTKYRRPEEVET-W-RAKDPLRRLRLLL
RAAC01745               MCYAVERARRGDGPTLIEAVTYRLGPHTTADDPGRYRDAVDVER-WAAAKDPLVRLRLWL
ref|NP_241079.1|        VKRAIEQARKGRGPTLIEAVTTRFGSHTTADDAKKYRDQEEIERTWKEMQDPLTRLKAYI
                        :  *:* ** *** * ** *: :* *.***:**. :**   *     **: **. :

ref|ZP_00539127.1|      KEQGFYDEQEIETIRSRHQEEVEAAVKTMESFPPPDVNDLFDHTFATLPDDL--------
ref|YP_074240.1|        VSQGQWSDSDDEALWTAAREQVAAAVAEAEAMPRPSVDDLFDYLYAEPTPNLVRQKEYLK
ref|YP_001127228.1|     ERRGLWTDAKEEEFVAKVNEEVTAAYEAAVASESGSIADVFDYVYSEAPKLLA-------
ref|YP_149070.1|        ERRGLWTEAQEDALVAQVNDEVTAAYEAAIASKSGSIVDAFDCVYSEAPKLLA-------
RAAC01745               TRQGLWDDERQAACEEEAEARVRQAVADMEAYPHKSLEEAARHVYAEVPEALALHLAKRG
ref|NP_241079.1|        QAKGWLSEEEEAQMKAKIRETIDEELSMAEQYPKPSISQMFEHVYENQP-----------
                         :*    :            . :             .: :   :  .

ref|ZP_00539127.1|      -----------
ref|YP_074240.1|        AYLAKKEGGAR
ref|YP_001127228.1|     -----------
ref|YP_149070.1|        -----------
RAAC01745               KEAR-------
ref|NP_241079.1|        -----------
```

FIG. 54

```
ref|ZP_00539126.1|         ----TLVQAVTDALRTKLTDDETTIVLGEDVGKNGGVFRATDGLQEEFGEDRIIDTPLSE
RAAC01746                  MPKWTMIEAIRDALAIALRDDPRVLVFGEDVGKNGGVFRATDGLQAEFGEARVADTPLAE
ref|YP_149069.1|           MAELTMIEAINEAMRQEMERDPRIIVLGEDVGENGGVFRATDGLLAQFGEGRVFDTPLAE
ref|YP_001127227.1|        MAELTMIEAINEAMRQEMERNSRVTVLGEDVGENGGVFRATDGLLEQFGSGRVFDTPLAE
ref|YP_001125046.1|        MAQMTMVQAITDALRIELKNDPNVLIFGEDVGVNGGVFRATECLQAEFGEERVFDTPLAE
ref|NP_833691.1|           MAQMTMIQAITDALRVEMKNDPNVLVFGEDVGVNGGVFRATEGLQAEFGEDRVMDTPLAE
                               *:::*:  :*:     :   :   :::***.*****:   :**. *: ****:* ref|ZP_00539126.1|         AGIVGTSIGLAVNGFKPIVEIQFLGFIYPAYEQIMTHVSRIRMRTMGRYGVPMVIRAPYG
RAAC01746                  KAIVGTAVGLAMAGMKPVAEIQFLGFAYEAMDQIAAQLARIRFRTQGRFTAPAVIRAPYG
ref|YP_149069.1|           SGIIGTSIGLAINGMRPIAEIQFLGFVYQAMDQLAAQAARIRFRSAGRFSCPIVVRSPYG
ref|YP_001127227.1|        SGIIGTSIGLAINGMRPIAEIQFLGFVYQAMDQLAAQAARIRFRSGGRFSCPIVVRSPYG
ref|YP_001125046.1|        SGTGGLAVGLALQGFRPVPEIQFFGFVYEVMDSISGQMARIRYRTGGRYHMPITVRSPFG
ref|NP_833691.1|           SGIGGLAVGLALEGFRPVPEIQFFGFVYEVMDSISGQLARMRYRSGGGRWTAPVTVRSPFG
                             .* *  ::***:  *::*:  **:   *   .  :    : :*:*  *:  **:  *   .:*:*:* ref|ZP_00539126.1|         AGIRAPEIHSDSTEALFTSMPGLKVVCPSTPYDAKGLLIAAIEDPDPVLFLESMRSYRAF
RAAC01746                  GGVRTPELHSDSLEALFAHTPGLVVVTPSRPYDAKGLLLSAIRSPDPVVFLEPIRLYRAF
ref|YP_149069.1|           GGVRTPELHSDALEALFTHSPGLKVVMPSNPYDAKGLLISAIRDEDPVLFLEPMKLYRAF
ref|YP_001127227.1|        GGVRTPELHSDALEALFTHSPGLKVVMPSNPYDAKGLLISAIRDDDPVLFFEPMKLYRAF
ref|YP_001125046.1|        GGVHTPELHSDSLEGLVAQQPGLKVVIPSTPYDAKGLLISAIRDNDPVIFLEHLKLYRSF
ref|NP_833691.1|           GGVHTPELHADSLEGLVAQQPGLKVVIPSTPYDAKGLLISAIRDNDPVIYLEHMKLYRSF
                             .*:::***:*:*: *.*.: *   ****:...  ***:::*  ::  **:* ref|ZP_00539126.1|         KEPVFSEAYTIEIGKANCITEGQDVTLIAWGAMVQVAQKAATEAATRGISCEVIDLRTLY
RAAC01746                  REEVPEGDYQVPLGRAAVRREGSDVTLVAWGPTVPVAESAAAQVASRGISCEVLDLRTLA
ref|YP_149069.1|           RMEVPEEPYTIPLGQARVVKEGDDVTIIAWGATVPLAAKVAAEMQAKGVNAEVIDLRCLQ
ref|YP_001127227.1|        RMEVPEEPYTIPLGQARIVKEGDDVTILTWGATVPLVAKLADEMRMRGVDAEVIDLRCLQ
ref|YP_001125046.1|        RQEVPEGEYTIPIGKADTKREGKDITIIAYGAMVHESLKAAAELEKEGISAEVVDLRTVQ
ref|NP_833691.1|           RQEVPEGDYTIDLGKADIKREGTDVSVIAYGAMVHAALKAAEELEKEGISLEVVDLRTVQ
                             :  **.  *  :  *:* :*    ** *:::::::*. *    . * :  .*:.  **:***  :

ref|ZP_00539126.1|         PLDRETISASVQKTGRAVIIHEAQATGGLGNDLLALINDTSFLYLRAPVARVTGFDVPVP
RAAC01746                  PLDRSALKASVEKTGRAVIVHEAVRYAGLGAEIAASIMDLAFYHLRAPIERVAGLDTPYP
ref|YP_149069.1|           PLDIDTIITSVEKTGRVMIVHEAVKTGGFGAEVAALISERALFSLSAPIVRIAGYDTPYP
ref|YP_001127227.1|        PLDIDTIIASVEKTGRVMIVHEAVKTSGFGAEVAALISERALFSLSAPIVRIAGYDTPYP
ref|YP_001125046.1|        PLDETIIGSVEKTGRAIVVQFAQRQAGIAANVVAEINERAILSLEAPVLRVAAPDTVYP
ref|NP_833691.1|           PLDIETIIASVEKTGRVVVVQEAQKQAGIAANVVAEINDRAILNLEAPVVRVAAADTVFP
                             *  .::    :**.::::    .*:.  ::    *    *  **:   *:: *. * ref|ZP_00539126.1|         LFALEDHYIPTPTRVLEAIQRTVD-
RAAC01746                  PPALEDAWLPSVTRVVEAIERVMED
ref|YP_149069.1|           VPSVEDDWLPNAERTAEGIETLL--
ref|YP_001127227.1|        VPSVEDDWLPNPARIVEGIETLM--
ref|YP_001125046.1|        FAQAESVWLPNFKDVIETAKKVM--
ref|NP_833691.1|           FSQAESVWLPNIIKDIVEAVNKVM--
                             *. ::*.   : *   :   :
```

FIG. 55

```
emb|CAJ88521.1|       ----------QYEIYLNGMTGAVPRLPTDLTRLEELAERR--LGPGPVGYVAGSAGDGSA
ref|NP_625066.1|      ----------QYEIYLNGMTGAVPRLPTDLTRLEELTERR--LGPGPFGYVAGSAGDGST
ref|NP_828658.1|      ----------QYEIYLNGMTGAVPRLPTDLTRLEELTEQR--LGPGPVGYVAGGAGNGST
ref|YP_001104836.1|   ------------------------------SMEE---HARAVLPANAYGYVAGNAGVGAT
RAAC01748             MKRMNIGNEAQFQIYQMRLTGQYGGDPLCISMEDWVARAREVLSPEAFWYLAGGSGRGET
ref|YP_658557.1|      ------------------------------VSFSDLREEAFEEMSWKAKAYVHGGAGTEET
                                                      :  :    .   :    .  *: *.:*   :

emb|CAJ88521.1|       ARANRAALDRRRIVPRMLRDVHRRDLSVEVLGRPLPAPLALAPVGVLSIMHPDAEPAAAR
ref|NP_625066.1|      ARANRAALARRRIVPRMLRDVHERDLRVEVLGRSLPAPLALAPVGVLSIMHPEAEPAAAR
ref|NP_828658.1|      ARANRSALDRRRIVPRMLRDVHERDLSVEVLGRTLPAPLALAPVGVLSIMHPDAESAAAR
ref|YP_001104836.1|   GRANRQAFDQWRLVPRMLRGATRRDLTVSLFGQRLAAPVLLAPIAAQTVVHPEGELAAVR
RAAC01748             MRANEEAFAKWRIVPRVFRDVSVRDLSIELFGERLPYPVLLAPIGVQSILHADGEVAAVR
ref|YP_658557.1|      FERNKD-FSRWRIIPRMLRGVADRDLSTTVLGNEHSYPLMITPLGVQSLLHDDGEIATAR
                       . *.   : : *:.*.:..   *   ::*.   .  *:  ::*:..  ::::* :.* *:.* emb|CAJ88521.1|       AAAAQGVPYILSSASSTPMEQVAEAMGDAERWFQLYWPKDREVARSFLERARAAGYSALF
ref|NP_625066.1|      AAAAQGVPYILSSASSTPMEEVAEAMGDAERWFQLYWPKDREVARSFLDRARAAGYTALF
ref|NP_828658.1|      AAAAQGVPYILSSASSTPMERVAEAMGDAERWFQLYWAKDREVTRSFLNRAKAAGYTALF
ref|YP_001104836.1|   GAADAGVPFVLSTGASHPLEDVAAAAGGQPRWFQLYWPAHRAVCESLVRRAEASGYSALV
RAAC01748             GAAKVGLPYIVSSASTMPLETIAEKAPGATLWFQLYWSRDRDVAQSFVRRAEAAGCKALV
ref|YP_658557.1|      ACAEMDVPFVLSSLSSATMEDVAEALGDTPKWFQYYWASDRDVATSFLDRAETAGYDAIV
                      ..*  .:*:::*: :: ..:* :*      .  *** **. .*  . *:: **:.:*  *:.

emb|CAJ88521.1|       VTLDTPLLSWRPRDLDQAYLPFLHGVGTANYFSDPAFRAGLAKPVHEDPNAAVMHFVGMF
ref|NP_625066.1|      VTLDTPLLSWRPRDLDQAYLPFLHGVGTANYFSDPAFRAGLAKPVHEDPNAAVMHFVGMF
ref|NP_828658.1|      VTLDTPLLAWRPRDLDQAYLPFLHGVGTANYFTDPAFRAGLAKPVHEDPNAAVMHFVSMF
ref|YP_001104836.1|   LTVDSPSFGYRPADLDNGYLPFLNGAGIANFVSDPPEFQGGL--PSDAGEREVVEHWARVF
RAAC01748             VTLDTPMMAWREDRLERAYLPFLLGEGLGNYLSDPAFRAKLRRPPEEDPASAILLWTQIF
ref|YP_658557.1|      VTVDAPTLGWRDRLLEKGYYPFLEGEGIGNYFSDPAFRDSLARPPEEDPEAAVDRFLSIF
                      :*:*:*   :.:*    *:..* *** * * .*:.:** *:   *  *  .. .:  :* emb|CAJ88521.1|       SDPAKTWPDLAFLRENWDGPIVLKGVLHPDDARMAADAGMDGVVVSNHGGRQVAGSVAAA
ref|NP_625066.1|      SDPAKSWPDLAFLRENWDGPIVLKGVLHPDDARLAADAGMDGVVVSNHGGRQVAGSVAAA
ref|NP_828658.1|      ADPGKTWPDLEFLRENWDGPIVLKGILHPDDARRAASAGMDGVVVSNHGGRQVAGSVAAA
ref|YP_001104836.1|   ANPGLTWDDLPWLRSLTGLPIVIKGVLHADDARRAVELGADGLVVSNHGGRQLDGSVASL
RAAC01748             GHPGLTCDDLDWLRETTDLPLLLKGILHPDDAEEAFRRGADGIIVSNHGGRQVDGAVPSL
ref|YP_658557.1|      GDASLTWDDLAFVREQTDLPIIIKGVLHPDDARRAVEAGADAVQVSTHGGRQVDGSIAAI
                      ....  :  **  ::*.   .  *:::*:**.***.  *    * *.:  **.*****:  *:.:.:

emb|CAJ88521.1|       DALPRVVEAAGDRLTVLFDSGVRTGDDVFKALALGARAVLLGRPYAYGLGLDGQAGVEHV
ref|NP_625066.1|      DALPRVAEAVGDRLTVLFDSGVRTGDDVFKALALGARAVLLGRPYVYGLGLDGRPGVEHV
ref|NP_828658.1|      DALPRVVEAAGDRLTVLFDSGIRTGDDIFKALALGARAVLVGRPYAYGLGLDGQAGVEHV
ref|YP_001104836.1|   DALPAVRAAVGDGVPVLLDSGVRTGSDVVKALALGADAVLYGRPVVYGLALDGQEGVSHV
RAAC01748             DALVAIRERVGREKVVLMDGGVRRGSDVVKALALGANAVLVGRLYAYGLAVDGERGVETV
ref|YP_658557.1|      EALPEIAEAVGDETTVLFDSGIRRGAQAFKALALGADTVLLGRPFAYGLAHSGQEGVEQV
                      :**   :    .*    **:*.*:* *   : .*****  :    :.*. .*. **. * emb|CAJ88521.1|       IRCLLAELDLTLALSGHSSPAT---------
ref|NP_625066.1|      IRCLLAELDLTLALSGHASPAT---------
ref|NP_828658.1|      VRCLLAEFDLTLALSGHAGPGTL--------
ref|YP_001104836.1|   LRCLLAELDLALALTGSGAVSEITADLLA--
RAAC01748             LRYLLADFDLTMALSGHRSLSTLDVRALARA
ref|YP_658557.1|      LENTLSQIDLTMGLAGIDDVDDIDRSAV---
                      :.   *:::**::.*:*
```

FIG. 56A

```
sp|P41009|ATPB_BACCA    MTRGRVIQVMGPVVDVKFENGHLPAIYNALKIQHKARNENEVDIDLTLEVALHLGDDTVR
prf||1211283A           MTRGRVIQVMGPVVDVKFENGHLPAIYNALKIQHKARNENEVDIDLTLEVALHLGDDTVR
sp|Q9LA80|ATPB_GEOTH    MTRGRVIQVMGPVVDVKFENGHLPAIYNALKIQHKARNENEVDIDLTLEVALHLGDDTVR
ref|YP_149211.1|        MTRGRVIQVMGPVVDVKFENGHLPAIYNALKIQHKARNENEVDIDLTLEVALHLGDDTVR
pdb|2QE7|D              MNKCRIIQVMGPVVDIQFESGQLPDIYNAITIE---RPQGGT---LTVEAAVHLGDNVVR
RAAC00450               MNKGYVVQVMGPVVDVRFPEGQLPAINNALRID----YEGDLPVHLTLEVALHLGDNVVR
                         *.:* ::********:* .*:** * **: *:       :.      **:*.*:****:.**

sp|P41009|ATPB_BACCA    TIAMASTDGLIRGMEVIDTGAPISVPVGEVTLGRVFNVLGEPIDLEGDIPADARRDPIHR
prf||1211283A           TIAMASTDGLIRGMEVIDTGAPISVPVGQVTLGRVFNVLGEPIDLEGDIPADARRDPIHR
sp|Q9LA80|ATPB_GEOTH    TIAMASTDGLIRGMEVIDTGAPISVPVGEVTLGRVFNVLGEPIDLEGDIPADARRDPIHR
ref|YP_149211.1|        TIAMASTDGLIRGMEVIDTGAPISVPVGEVTLGRVFNVLGEPIDLEGDIPADARRDPIHR
pdb|2QE7|D              CVAMASTDGLVRGLEAVDTGAPISVPVGKATLGRVFNVLGEPIDEQGEVNAEER-HPIHR
RAAC00450               TIAMSSTDGLVRGVEVVDTGQPISMPVGPGTLGRIFNVLGETIDERGPVDAPER-WPIHR
                         ::::*.:* *:* :*: .* : *  * **** sp|P41009|ATPB_BACCA    PAPKFEELATEVEILETGIKVVDLLAPYIKGGKIGLFGGAGVGKTVLIQELIHNIAQEHG
prf||1211283A           PAPKFEELATEVEILETGIKVVDLLAPYIKGGKIGLFGGAGDGKTVLIQELIHNIAQEHG
sp|Q9LA80|ATPB_GEOTH    PAPKFEELATEVEILETGIKVVDLLAPYIKGGKIGLFGGAGVGKTVLIQELIHNIAQEHG
ref|YP_149211.1|        PAPKFEELATEVEILETGIKVVDLLAPYIKGGKIGLFGGAGVGKTVLIQELIHNIAQEHG
pdb|2QE7|D              PAPEFEELSTADEILETGIKVIDLLAPYAKGGKIGLFGGAGVGKTVLIQELINNVAQEHG
RAAC00450               PAPAFGDLTTKTEIFETGIKVVDLLAPYVKGGKVGLFGGAGVGKTVLIQELIHNIAKEHG
                        *** * .:*:* :**:** :*** *******:*:*:*** sp|P41009|ATPB_BACCA    GISVFAGVGERTREGNDLYHEMKDSGVISKTAMVFGQMNEPPGARMRVALTGLTMAEYFR
prf||1211283A           GISVFAGVGERTREGNDLYHEMKDSGVISKTAMVFGQMNEPPGARMRVALTGLTMAEYFR
sp|Q9LA80|ATPB_GEOTH    GISVFAGVGERTREGNDLYHEMKDSGVISKTAMVFGQMNEPPGARMRVALTGLTMAEYFR
ref|YP_149211.1|        GISVFAGVGERTREGNDLYHEMKDSGVISKTAMVFGQMNEPPGARMRVALTGLTMAEYFR
pdb|2QE7|D              GLSVFAGVGERTREGNDLYHEMKDSGVISKTSMVFGQMNEPPGARLRVALTGLTMAEYFR
RAAC00450               GYSVFAGVGERTREGNDLYHEMKESGVLDKTCMVFGQMNEPPGARLRVALSGLTLAEYFR
                        * ******************:*:: **********::*:**** sp|P41009|ATPB_BACCA    DEQGQDVLLFIDNIFRFTQAGSEVSALLGRMPSAVGYQPTLATEMGQLQERITSTAKGST
prf||1211283A           DEQGQDVLLFIDNIFRFTQAGSEVSALLGRMPSAIGYQPTLATEMGQLQERITSTAKGSI
sp|Q9LA80|ATPB_GEOTH    DEQGQDVLLFIDNIFRFTQAGSEVSALLGRMPSAVGYQPTLATEMGQLQERITSTAKGSI
ref|YP_149211.1|        DEQGQDVLLFIDNIFRFTQAGSEVSALLGRMPSAVGYQPTLATEMGQLQERITSTAKGSI
pdb|2QE7|D              DREGQDVLLFIDNIFRFTQAGSEVSALLGRMPSAVGYQPTLATEMGQLQERITSTKKGSI
RAAC00450               DVEQRDVLFFIDNIFRFTQAGSEVSALLGRMPSAVGYQPTLATEMGQLQERIASTVRGSI
                        *  : :***:*****************:******.**************** **:  **

sp|P41009|ATPB_BACCA    TSIQAIYVPADDYTDPAPATTFSHLDATTNLERNVAEMGIYPAVDPLASTSRALAPEIVG
prf||1211283A           TSIQAIYVPADDYTDPAPATTFSHLDATTNLERKLAEMGIYPAVDPVSTSRALAPEIVG
sp|Q9LA80|ATPB_GEOTH    TSIQAIYVPADDYTDPAPATTFSHLDATTNLERKLAEMGIYPAVDPLASTSRALAPEIVG
ref|YP_149211.1|        TSIQAIYVPADDYTDPAPATTFAHLDATTNLERKLAEMGIYPAVDPLASTSRILSPAVVG
pdb|2QE7|D              TSIQAVYVPADDYTDPAPANTFTHLDATTVLERRIADMGLYPAVDPLASTSRALQPDIVG
RAAC00450               *****:************* **:****** ***:.*:**:******.**** *  :**

sp|P41009|ATPB_BACCA    EEHYQVARKVQQTLQRYKELQDIIAILGMDELSDEDKLVVHRARRIQFFLSQNFHVAEQF
prf||1211283A           EEHYQVARKVQQTLERYKELQDIIAILGMDELSDEDKLVVHRARRIQFFLSQNFHVAEQF
sp|Q9LA80|ATPB_GEOTH    EEHYQVARKVQQTLQRYKELQDIIAILGMDELSDEDKLVVHRARRIQFFLSQNFHVAEQF
ref|YP_149211.1|        EEHYQVARKVQQTLQRYKELQDIIAILGMDELSDEDKLVVHRARRIQFFLSQNFHVAEQF
pdb|2QE7|D              EEHYRVARGVQQVLQRYNDLQDIIAILGMDELSDEDKLIVARARKIQRFLSQPFHVAEVF
RAAC00450               EEHYQVARGVQAVLQRYRELQDIIAILGMDELTDEDRLIVSRARKIQNFLSQPFFVAEVF
                        ****:***.** .*:**:.:***********:***:*:*:***:** ****.*:***.*
```

FIG. 56B

```
sp|P41009|ATPB_BACCA    TGQPGSYVPVKETVRGFKEILEGKYDHLPEDRFRLVGRIEEVVEKAKAMG--
prf||1211283A           TGQPGSYVPVKETVRGFKEILEGKYDHLPEDRFRLVGRIEEVVEKAKAMG--
sp|Q9LA80|ATPB_GEOTH    TGQPGSYVPVKETVRGFKEILEGKYDHLPEDRFRLVGRIEDVVEKAKAMG--
ref|YP_149211.1|        TGQPGSYVPVKETVRGFKEILEGKYDHLPEDAFRLVGRIEEVVEKAKAMG--
pdb|2QE7|D              TGMPGKYVPVKETVRGFKEILEGKHDNLPEEAFYMVGTIDEAVEKAKK----
RAAC00450               TGTPGKYVPVKDTVRSFKEILEGKHDDIPETYFRYCGAIEDVIEKARKDGYA
                        ** **.*****:***.********:*.:**   *   * *::.:***:
```

FIG. 57A

```
ref|YP_001125323.1|      ---DVFNARSSFEVNGKKYNYYRLQALEEAGIGRVSRLPYSIKVLLESVLRQVDGRVITK
ref|YP_147200.2|         ---DVFNTRSSFEVNGKKYNYYRLQALEEAGIGQVSRLPYSIKVLLESVLRQVDGRVITK
ref|YP_091630.1|         -----FQSRKTFTVQGKTYSYYSLKALEDQGIGNVSKLPYSIKVLLESVLRQVDGRVITE
ref|ZP_02170376.1|       ----LYQAKKQFEVNGKTYHYYDLKAIEEAGIGNVSKLPYSIRVLLESVLRQHDGRVIKQ
RAAC01759                MGANLFQAKQTLTVGGKSYTYYRLDALQEQGVADISRLPISIKILLESVLRQYDGRVITE
ref|YP_001546865.1|      -----FGAKATLTVGDRSLVYYRLNKLEEDGIAAVSKLPFSIKVLLEAMLRNNDGFAVTK
                              :  ::  : * .:.   ** *. :::  *:. :*:** **::***::**: **  .:.:

ref|YP_001125323.1|      EHVENLAKWGTPEMKDIDVPFKPSRVILQDFTGVPAVVDLASMRKAMADLGGDPYEINPE
ref|YP_147200.2|         EHVENLAKWGTPEMKDIDVPFKPSRVILQDFTGVPVVVDLASMRKAMADLGGDPYEINPE
ref|YP_091630.1|         EHVENLAKWGTAELKDIDVPFKPSRVILQDFTGVPAVVDLASLRKAMASVGGDPDKINPE
ref|ZP_02170376.1|       EHVDNLAKFGSGELAAIDVPFKPARVILQDFTGVPAVVDLASLRKAMADFGGDPKETNPA
RAAC01759                EHVRELANWNAANPAKSEVPFKPARILLQDFTCVPVVVDLAAMRTAMHKLGGNPKRINPL
ref|YP_001546865.1|      QDVENMARWNAANPEKIEVPFKPARVILQDFTGVPAVVDLAAMRAAMAQQGGDPQRINPL
                         :.*  ::*.:.: :    :*****:*::****.***::*   . :*  *** ref|YP_001125323.1|      IPVDLVIDHSVQVDRYGSDDALEYNMDLEFQRNAERYKFLKWAQKAFDNYRAVPPATGIV
ref|YP_147200.2|         IPVDLVIDHSVQVDRYGSDDALEYNMDLEFKRNAERYKFLKWAQKAFDNYRAVPPATGIV
ref|YP_091630.1|         IPVDLVIDHSVQVDKAGTEDALTVNMDLEFQRNAERYKFLSWAKKAFNNYQAVPPATGIV
ref|ZP_02170376.1|       IPVDLVVDHSLQVDKFGAADSLMFNMEREFERNLERYKFLNWAQKSLDNYRAVPPATGIV
RAAC01759                IPVDLVIDHSVQVDAFGSKEALEFNIAKEFERNEERYRFLRWAQTAFDNFRAVPPGMGIV
ref|YP_001546865.1|      VPVDLVIDHSVQIDQFGSKMALFFNAEREFERNAERYEFLKWGQQAFDNFSVVPPETGIV
                          :**:*:*:*    *:  :*   *  : *. *.:  :::*: .* * ref|YP_001125323.1|      HQVNLEYLASVVHAVEGENGEYEAFPDTLVGTDSHTTMINGIGVLGWGVGGIEAEACMLG
ref|YP_147200.2|         HQVNLEYLASVVHAVEGENGEYEAFPDTLVGTDSHTTMINGLGVLGWGVGGIEAEAGMLG
ref|YP_091630.1|         HQVNLEYLANVVHAVE-EDGEIVTYPDTLVGTDSHTTMINGIGVLGWGVGGIEAEACMLG
ref|ZP_02170376.1|       HQVNLEYLANVVQEEE-QDGELVAFPDSLVGTDSHTTMINGLGVLGWGVGGIEAEAGMLK
RAAC01759                HQVNLEYLARVVQERT-VDGEQVVFPDSLVGTDSHTTMINGVGVLGWGVGGIEAEACMLG
ref|YP_001546865.1|      HQVNLEYLAKVVQVFT-EEGELVALPDSLVGTDSHTTMINGLGVVGWGVGGIEAEAVMLG
                         ******* :     :  . :**********:.********* ref|YP_001125323.1|      QPSYFPVPEVVGVRLTGKLPDGSTATDLALKVTQVLRKKGVVGKFVEFFGPGVATLPLAD
ref|YP_147200.2|         QPSYFPVPEVIGVRLTGKLPDGATATDLALKVTQVLRKKGVVGKFVEFFGPGVATLPLAD
ref|YP_091630.1|         QPSYFPVPEVIGAKLVGKLPNGTTATDLALKVTQVLREKGVVGKFVEFFGPGVAELPLAD
ref|ZP_02170376.1|       QPSYFPVPEVVGLKFTGKMPEGATATDLALKVTQILRQANVVGKFVEFFGPGLSDMTLAD
RAAC01759                QPLYFVQPEVIGFKLTGKLPEGATATDLALTVVNMLRKKGVVGKFVEFYGAGLSNISVAD
ref|YP_001546865.1|      QPIYMLLPEVIGFKVTGQLPEGATATDLALTVTELLRKKGVVGKFVEFYGPGVANMALSD
                         **  *:   ***:* :..:*:*:*******.*.::: .******:*.*:  ..::* ref|YP_001125323.1|      RATIANMAPEYGATCGFFPVDAEALDYLRLTGRDEHHIQVVEAYCKANGLFYTPDAPEPT
ref|YP_147200.2|         RATIANMAPEYGATCGFFPVDAEALDYLRLTGRDEHHVQVVEAYCKANGLFYTPDAPEPV
ref|YP_091630.1|         RATIANMAPEYGATCGFFPVDEEALEYMRLTGRDEEHINVVKEYCRQNGLFYTPDQEDPV
ref|ZP_02170376.1|       RATISNMAPEYGATCGFFPVDEETLNYMRFTGRSEELVKLVETYTKANDMYYTPDKEDPE
RAAC01759                RATIANMAPEYGATMGFFPIDQATLDYLRLTGRDESLIQLVEAYAKQGMFRTDDMPDPV
ref|YP_001546865.1|      RATIANMAPEYGATMGFFPVDQETIHFLRSTGRSDELADLVEAYSKAQGLFLDANSPEAE
                         ****:******** ****:*  ::.::*  ***.:    .:*: *  : :..:    : :.

ref|YP_001125323.1|      FTDVVEINLSEIETNLSGPKRPQDLIPLSKMKQSFREAVKAPQGNQGFGLTEADLEREIT
ref|YP_147200.2|         FTDVVEINLSEIETNLSGPKRPQDLIPLSKMKQSFRDAVKAPQGNQGFGLTEADLEREIT
ref|YP_091630.1|         FTDIVEIDLSKVEANLSGPKRPQDLIPLTDMKETFHKHLASPAGNQGFGLNASEADKEIK
ref|ZP_02170376.1|       FTEVIELDLGTIEPNLSGPKRPQDLIPLSQMKKEWRKALTAPVGNQGFGLEAAEADRSVD
RAAC01759                FTDTLELDLGSIQPTMAGPKRPQDKIFLSDMKNNFEAALEKPVSEGGGFGLAD-QRDKTAL
ref|YP_001546865.1|      YTDTVHLDLSTIVPSVAGPKRPQDRVELQNTKASFQKSLTAPIAERGFALSTEKAENTAT
                         :*:  :..::*.  :   ..::*******     : * .  *    :  :  *  .: **.*    . :..
```

FIG. 57B

```
ref|YP_001125323.1|   VTL-NGEQVSMKTGAVVIAAITSCTNTSNPYVLVAAGLVAKKAVEKGLQVPKYVKTSLAP
ref|YP_147200.2|      VEL-NGEQVKLKTGAVVIAAITSCTNTSNPYVLVAAGLVAKKAVEKGLQVPKYVKTSLAP
ref|YP_091630.1|      FKLENGEEAVMKTGAIAIAAITSCTNTSNPYVLIGAGLVAKKAVELGLKVPNYVKTSLAP
ref|ZP_02170376.1|    VKHPDGRTSQLKTGAVTIAAITSCTNTSNPHVMIGSGLLAKNAVDKGLEVPAYVKTSLAP
RAAC01759             VQYPDGHKDELHHGAVVIAAITSCTNTSNPSVMLGAGLLAKKAVEKGLKTPRYVKTSLAP
ref|YP_001546865.1|   VQN-NGHSATIGHGAVVIASITSCTNTSNPSVMLGAGLLAKKAVEKGLTVAPYVKTSLAP
                         :*.   :  :.:********** *::.::::   .. ******** ref|YP_001125323.1|   GSKVVTGYLRDSGLLPYLQQLGFNVVGYGCTTCIGNSGPLAPELEKALAESDLLVTSVLS
ref|YP_147200.2|      GSKVVTGYLRDSGLLPYLEQLGFNIVGYGCTTCIGNSGPLAPELEKALAESDLLVTSVLS
ref|YP_091630.1|      GSKVVTGYLVNSGLLPYMRELGFNIVGYGCTTCIGNSGPLAPEIEKAVAENDLLITSVLS
ref|ZP_02170376.1|    GSKVVTGYLEDAGLMPYLDKLGFNLVGYGCTTCIGNSGPLPDEVEQAISENDLTVSSVLS
RAAC01759             GSRVVTDYLERSGLLEPLSKLGFDVVGYGCTTCIGNSGPLPEEVAKAIQENDLLVSAVLS
ref|YP_001546865.1|   GSRVVSSYLEQAELIEPLEALGFHVVGYGCTTCIGNSGPLPEPVAAAVQEGELVAAAVLS
                      ::.**  : *:  :   * :******** *.  :   *: *.:*  ::*** ref|YP_001125323.1|   GNRNFEGRIHPLVKGNYLASPPLVVAYALAGTVDIDLLNEPIGKDKDGNDVYFRDIWPSM
ref|YP_147200.2|      GNRNFEGRIHPLVKGNYLASPPLVVAYALAGTVDIDLLSEPIGKGKDGSDVYFRDIWPSM
ref|YP_091630.1|      GNRNFEGRIHPLVKGNYLASPPLVVAYALAGTVDIDLKNEPIGVKDGQNVYFNDIWPTM
ref|ZP_02170376.1|    GNRNFEGRIHPLVKANYLASPPLVVAYALAGTVDIDFETEPLGQDKEGNDVFFRDIWPSN
RAAC01759             GNRNFEGRIHSLVRANYLASPPLVVAYAIAGTVDIDLVNEPIGKDENGNDVFLRDIWPSN
ref|YP_001546865.1|   GNRNFEGRINPLVKAAYLASPPLVVAYALAGTINLDLATEPLGNDKEGNPVYLRDIWPSQ
                      *********:.**:. *************:***.::*:  .**:* .::*. *::.****:

ref|YP_001125323.1|   EEVKEVVKRAVDPELFRKEYERVFDGNPRWNAIETTDEPLYQWDEQSTYIQNPPFFEGLS
ref|YP_147200.2|      EEVKDVVKRAVDPELFRKEYERVFDGNPRWNAIETTDEPLYQWDENSTYIQNPPFFEGLS
ref|YP_091630.1|      DEINSVVKQTVTPELFRKEYERVFDDNERWNAIETTDEALYKWDEESTYIQNPPFFENMS
ref|ZP_02170376.1|    EEIHKSMQEAVDPKLFKREYKRVFDDNERWNALETPDGDLYEFDEESTYIQNPPFFENLS
RAAC01759             EEIQAVIRQIINPEMFKKEYESVFNRNERWNKLDVPKGELYEWDPNSTYIQEPPFFEGLS
ref|YP_001546865.1|   SEIQETVRKAIKPEMFTQQYGNVFAGSDAWKRVQAPTGNIYAWNNDSTYIQHPPFFQDLQ
                      .*::  ::.  : *::*  **  .  *: ::.. :*  :*****.****:::.

ref|YP_001125323.1|   PDVRKVEPLTGLRVVGKFGDSVTTDHISPAGSIGKSTPAGQYLISKGVEPKDFNSYGSRR
ref|YP_147200.2|      PEVRKVEPLTGLRVVGKFGDSVTTDHISPAGSIGKNTPAGQYLISKGVDPKDFNSYGSRR
ref|YP_091630.1|      VEPGTVEPLKGLRIVGKFGDSVTTDHISPAGAIGKDTPAGKYLQEKGVSPRDFNSYGSRR
ref|ZP_02170376.1|    PDPKDVEKLSGLRAVGKFGDSVTTDHISPAGAIAKNSPAGRYLMEKGLEPKDFNSYGSRR
RAAC01759             EEVPDIQEIQGARVLAYLGDSVTTDHISPAGSIAPSSPAGQYLQSKGVKPHEFNSYGSRR
ref|YP_001546865.1|   PEPAPIGDITGARVLALLGDSVTTDHISPAGSIAKNSPAAKYLIDNGVDPQDFNSYGARR
                         :    :  * *  :. :************:*.  .:**.:**  .:*::*:****:**

ref|YP_001125323.1|   GNHEVMMRGTFANIRIRNQIAPGTEGGYYTYWPTGEVMSIYDACMKYQDGTGLVVVAGK
ref|YP_147200.2|      GNHEVMMRGTFANIRIRNQIAPGTEGGYYTYWPTGEVMSMYDACMKYQDGTGLVVIAGK
ref|YP_091630.1|      GNHEVMMRGTFANIRIKNQIAPGTEGGYYTYWPTGEVMSIYDACMKYKEDGTGLVVIAGK
ref|ZP_02170376.1|    GNHEVMMRGTFANIRIKNQLAPGTEGGYYTHWPTGDVMAIYDACMQYEEEGTGLLVMAGK
RAAC01759             GNHEVMMRGTFANIRIRNKVAPGTEGGYYTYFPTGEVMPIYDAAMKYKADGTPLVVIAGK
ref|YP_001546865.1|   GNHEVMMRGTFANIRLKNLLLNGVEGGYTLYFPTGEQQSIYDASMAYQASGTPLVILAGK
                      ***************::*   :  *.*** ::*:  .:***.* *: ** *:::*** ref|YP_001125323.1|   DYGMGSSRDWAAKGTFLLGIKTVIAESFERIHRSNLVLMGVLPLQFKEGENAETLGLTGK
ref|YP_147200.2|      DYGMGSSRDWAAKGTFLLGIKTVIAESFERIHRSNLVLMGVLPLQFKEGNAETLGLTGK
ref|YP_091630.1|      DYGMGSSRDWAAKGTNLLGIKTVIAESFERIHRSNLVLMGVLPLQFKEGNAETLGLTGK
ref|ZP_02170376.1|    DYGMGSSRDWAAKGTNLLGIKTVIAESFERIHRSNLVLMGVLPLQFKSGENADTLGLTGE
RAAC01759             EYGTGSSRDWAAKGTYLLGVKVVIAESYERIHRSNLVGMGVLPLEFIDGQNAETLGLTGR
ref|YP_001546865.1|   EYGTGSSRDWAAKGTYLLGVKVVIAESYERIHRSNLVGMGVLPLQYRAGESAASLGLKGD
                      :** ********** ***:*  *****:******** ******::   :.*  .:***.*
```

FIG. 57C

```
ref|YP_001125323.1|      EVFEVQ-IDESVKPRDLVKVTATNPDTGEKKEFEVIVRFDSEVEIDYYRHGGILQMVLR-
ref|YP_147200.2|         EVFDIH-IDENVKPRDLVKVTATNPDTGEKKEFEVIVRFDSEVEIDYYRHGGILQMVLR-
ref|YP_091630.1|         ETIEV-DVSESVRPRDLVQVKAIAED-GTVKSFEAVVRFDSEVEIDYYRHGGILQMVLRN
ref|ZP_02170376.1|       EHFDVH-VDNDVQPRQEIKVTATDSD-GKGTEFHVIARFDSEVEIDYYRHGGILQMVLRN
RAAC01759                EVYTIKGLSNDLKPRQTVTVEVTRED-GSSFTFQALVRLDSDIEVDYYRNGGILQTVLRN
ref|YP_001546865.1|      ESFSVEGINDDLQARSELTVRAVRPD-GSELSFQAVVRIDTPVEVEYYKNGGILHTVLRQ
                          *   :  :.:.::.*. : * .   * *     *...:.*:*: :*::::: * ref|YP_001125323.1|      -------
ref|YP_147200.2|         -------
ref|YP_091630.1|         KMKQ---
ref|ZP_02170376.1|       -------
RAAC01759                FMREQHA
ref|YP_001546865.1|      LAK----
```

FIG. 58

```
ref|ZP_02015336.1|    MRAAILREYGEPLDIHEVPDPEPGPDGAVVRVTACGVCRSDWHAWAGHGEWADDRVP-RG
ref|YP_136548.1|      MRAAVIEEHGEPLTIQDVPYPEPQPDQVVIETEACGVCRSDWHAWQGDWEWFGIQTG-PG
ref|YP_055250.1|      MKAALVEQYHEPLAIRDIPEPAHDSDGVVVEVKACGVCRSDWHGWQGE--WPGFTGCSLP
gb|ABW71834.1|        VRAAQIVGYGEPLQVREVPDPAPEPGGVVVAVLATGICRSDWHGWRGDWEWLGGRIA-LP
RAAC01762             MKAARLHAFHTPFAIETVPDPEPGPEDAIVRVRAAGVCRSDLHIWQGELAWVGIRPQ-LP
ref|NP_102793.1|      MKAVVFEKFGEAPTIQTVPDPKPAADGVVIKVEATGLCRSDWHGWMGHD--DGITL---P
                       ::*.  .   . :. :* *    .  .::  .  * *:****  * * *.    .

ref|ZP_02015336.1|    QVL---GHEPAGEVVTVGDSVDRFAPGDRVVVPFSLGDGTCPRCRQGHGNVCDDGRALGF
ref|YP_136548.1|      QIL---GHEPAGVVADVGADVEQFSEGDRVTVPFHLGDGSCQYCQRGHANICETSMPLGF
ref|YP_055250.1|      HIF---GHEFVGLVSDIGNNVSRYRVGDRVIVPFTLGCGHCEYCRSGHSNVCPTVSMPGF
gb|ABW71834.1|        RTP---GHEIAGEVVAAGPGVRGVRVGDRVTVPFHLACGTCAHCRAGQANLCDEMEVLGF
RAAC01762             ITL---GHEFGEVVAVGRNVRRFVAGDRVTVPFHNGCCRCPQCQSGRSNLCDEFGFYGA
ref|NP_102793.1|      HVP---GHELAGVVAAGKQVSRWKAGDRVTVPFAVGCGRCFECSSGNHQVCEHQTQPGF
                              ***       *   *       **  *  . *    *      *  . ::*         * ref|ZP_02015336.1|    EPEA-PGAFAERVAVPDADYNLVERPPWLDATAAAALGCRYMTAYHALAERAGLDGGEWL
ref|YP_136548.1|      LEAA-PGAFAEAFPVREADFNCVTLPDAVDFTEMAGLGCRFMTAYHALTDRATLRPGDAV
ref|YP_055250.1|      SYDG---GFAQYVTVPDADANLVKLPDAVDFTDAAGMGCRLMTAYHGIVEVGQIHPGDWL
gb|ABW71834.1|        WRDG---GYAEYVRIPHADFNCVRIPDGVTPLTASAIGCRFMTAFHAVDGQGRVRPGEWV
RAAC01762             TYDG---CFAEYVRVPNADFNLIHLPDEVDFVTAAAMGCRYMTCFHAVMR-GRVQPGEWV
ref|NP_102793.1|      TGWG---SFAEYVGIEHADTNLVRLPDEMEYATAASLGCRFVTSFRAIVDQGRVKPGEWV
                           .:*:   .  .** *:  *   :    ::.:*** :*.::.:   . :   *: :

ref|ZP_02015336.1|    AVHGCGGVGLSAVQLGDALGARIVAVDVDDDALSLARDLGADETVNPNDLDEETVPDRVR
ref|YP_136548.1|      AIHGCGGVGLSAVHIADALGAEPIAVDVQDRKLDRARDLGAAATIN--AAEADNVPGEVH
ref|YP_055250.1|      VVYGAGGVGLSATLVATSAGANVIAVDIADDKLALARKVGAIATIN--SRETDPV-EAVR
gb|ABW71834.1|        AVHGVGGVGLSCVQIASAAGASVVAVDIDPAKLALAEQQGAAHTVD--AGAEQDVPAAVR
RAAC01762             AVHGAGGVGLSAIQAAHAIGAQVIAVDIDDDKLEKARTEGAAVTIN--SRREERVFKAIK
ref|NP_102793.1|      AVHGCGGVGLSAIMIASSMGANVIALDLTDEKLEFARKIGAVATIN--ASTTPNVVKAVK
                      .::* ******.   . :  ** :*:*:    *  *.  **  *::    *   ::

ref|ZP_02015336.1|    NLTDGGADVSVDALGIAETCRNSVRSVRPRGTHVQVGLTTEAERGEVSLPTDWMTRWEVS
ref|YP_136548.1|      AVTDGGADVAIDALGIAETCRNAVGSLGKQGTHVQVGLTTDDEAGEIPLPVDTMTLQEID
ref|YP_055250.1|      ELTDGGADKSVDALGISETLHNAVNSLRSRGTHIQIGMTAEGPVGDVALTINDLIAKEID
gb|ABW71834.1|        EVTGGGAHVSIDALGIRTTVVNSVRSLRKRGRHVQVGLTGAEDAGEIALPIDLITLGELT
RAAC01762             QVTRGGAHVSIDALGLAETVFNSVRCLRKGGRHVQVGLTSSSEQGMVALPVDIMTTGEIE
ref|NP_102793.1|      QIANGGAHMSMDALGHPTTSFNSIANLRRRGRHVQVGL-MLGEHARPQVPMDKIIAFELE
                       ::   ***. ::****    * *::   :   * *:*:*:      .  :. ::   *:

ref|ZP_02015336.1|    FVGSRGMPPTSYDDLFALVEATDVDPAALVSEELALSEVSERLAAMGEYDARGVEVVTDF
ref|YP_136548.1|      FHGSYGMPPVRYDELFRLIDAGTLDPSQIVGETLALEDVPATLSSMGEYETVGIPVIDEF
ref|YP_055250.1|      FRGSFGMPAVEFRYLLNQVAAGKMKPGQLVTKTIALSEVNDALTAMSTYNTVGTTVITDF
gb|ABW71834.1|        VVGSHGNPHAAYPRLLSLIESGRLAPQTLVQRTVSLDQAGDVLAAMDAFATSGLTVIDRF
RAAC01762             FIGSFGNPHVAFDGLLRLVAAGRLRPKALVERVSLAELNDVFHRMLRFETKGFNVITAF
ref|NP_102793.1|      ILGSHGMQAYRYQAMMDMIRNGKLKPELLVGKKISLDHAPAALMAMGGFEGIGIGVVTKF ref|ZP_02015336.1|    -
ref|YP_136548.1|      -
ref|YP_055250.1|      -
gb|ABW71834.1|        -
RAAC01762             A
ref|NP_102793.1|      -
```

FIG. 59

```
ref|YP_190012.1|     MKTRAAVLYEMGAKKPYKESKPLKIEYLELDNPSEHEVLIKIHAAGLCHSDLSVINGNRP
ref|YP_252288.1|     MKTRAAVLYEMEASQPYKESKPLKIESLELEDPHEHEVLLKIHAAGLCHSDLSVINGSRP
ref|YP_300327.1|     MKTRAAVLREMGKDAPYTESHPLTIETLELQGPQSNEVLIKICAVGLCHSDLSVINGSRP
ref|NP_693723.1|     MQVKTAVLRTQGADSPYKESKPIKIETLELDAPQLGEVLIQIKAASLCHSDLSVINGSRP
ref|ZP_01227084.1|   --TRAAVLRRSPVEGPYATSRPLSIETVELAPPGDGEVLVRIKAAGLCHSDLSVIDGVRP
RAAC01763            MQTRAAVLMEMGARPPYASTRPLRLFTLFLEPPGPGEVLIRVRAAGLCHSDLSVIEGARP
                       :*         ::*: :*  :**   *    ***::: *:.*********:* ** ref|YP_190012.1|     RPLPMALGHEASGEVIKVGKAVTRVSEGDHVVCTFIPSCGKCIPCKEGRPALCENGAISN
ref|YP_252288.1|     RPLPMALGHEATGEVLKVGSSVTRVKEGDHVVCTFIPSCGKCIPCKEGRPALCENGAKAN
ref|YP_300327.1|     RPMPMVLGHEAAGEIIEVGENVAEFEVGDHIVCTFIPSCGHCIPCREGRPALCENGAAAN
ref|NP_693723.1|     RPLPMALGHEASGVVVEVGEGVTYLEPGDHTVCVFVPSCGHCVPCKEGRPALCEPGADSN
ref|ZP_01227084.1|   RPTPMVLGHEAAGIVETVGAGVDDLAPGDHVVMVFVPSCGIICSPCAEGRPALCEPGNARN
RAAC01763            RPMPMALGHEAAGEVVELGEGVTDLAPGDHVVCAFVPSCGHCAPCQEGRPALCEPGAEAN
                      .*****:*  :  :*  *  . ***:* .*:****:*  ***** *    * ref|YP_190012.1|     EKGEMLEGGMRLSND-EGKVYHHLGISGFAEYSVVSENSIVKTDKKIPFERAAAFGCAII
ref|YP_252288.1|     EKGEMLEGGIRLSNE-DCQVYHHLGVSGFAEHAVVSENSIVKISNEIPFERAAVFGCAVI
ref|YP_300327.1|     EKGEMLEGGFRYESDRDEVMHHHELGVSGFADYAVVSTNSIVKVDKKIPFEKVAIFGCAVI
ref|NP_693723.1|     TAGTLISGGTRLHAD-GEAINHELGVSAFSEFAVVSRNSLVKVKKDIPFEKLALFGCAVI
ref|ZP_01227084.1|   GEGTLLSGERRLSCE-GEPVHHHLGVSAFAERSVLSRRSLIKIDPELPLEIAALFGCAVL
RAAC01763            GRGTLLSGARRLRLG-GQPVHHHLGVSAFSDYAVVSRRSLVRIDPSLPFEHAALFGCAVM
                       * ::.*  *           : ****:*.*::  :*:*  .*::::.  .:*:*  * **** ref|YP_190012.1|     TGIGAVVNTAQIRSGSNVAVVGLGGIGLNAIIGAKLAGANEIIALDINEDKFELAKQFGA
ref|YP_252288.1|     TGIGAVMNTAQIRPGSNVAVVGLGGIGLNAIIGAKLAGANEIIALDINEDKFDLAKQFGA
ref|YP_300327.1|     TGIGAVINTARINAGSTVAVVGLGGIGLNAILGARLAGASEIIALDINEEKFALAKSLGA
ref|NP_693723.1|     TGVGAVVNTANVKLGSTVAIVGLGGIGLSALLGAVAAGASRIIAVDINENKLKQAKELGA
ref|ZP_01227084.1|   TGVGAVVNTGRVKAGETVAVVGLGGVGLSAILGAVAAGASRIIAVDLQADKLDMAKTIGA
RAAC01763            TGVGAIVNTARVPVGASVGIVGLGGVGLAALLGAVASSARHIAAIDVNPEKLAFARELGA
                     **:**::**..:  * .*:.:*****:**  *:**   :.* .*  *::*:  *:  :**

ref|YP_190012.1|     TATFNSSDKDIDEQIKEYIPGGVEYAFETAGVVPAMKVAYQITKRGGTTVTTGLPNPKDN
ref|YP_252288.1|     TATFNSSDDDIDEQIKEYVPGGVEYAFETAGVVPAMQVAYRITKRGGTTVTTGLPHPKDE
ref|YP_300327.1|     TAVFNSGEAHTIEDIKQYTQGGVDYAFETAGVVPAMDVAYQITRRGGMTTTTGLPDPKHQ
ref|NP_693723.1|     TDVFNSTEETVIQQIKEATDGGVNYAFETACAVPAMEVAYGITKRGGTTVTTGLPHPEHQ
ref|ZP_01227084.1|   TDIFNAGEAGVADAVRAATGGGVDHAFEMAGSARALELAFAITRRGGATVTAGLTPPTAT
RAAC01763            THTYDARDPGVIDKVRADSAGGLEYVFETAGSVAAMKTAFMVTRRGGTTVTTGLPDPRHE
                     *   :::  :      : ::      :::. **  . *:. *: :*:*** *.:*.*  * ref|YP_190012.1|     FSFPQVTLAAEERTIKGSYVGSCVPDRDIPRFVNLYNQGRLNIDSLISEVITLDEINEGF
ref|YP_252288.1|     FSFPQVTLAAEERTVKGSYVGSCVPDRDIPRFVSLYKQGRINTDPIISEVITLDDINEGF
ref|YP_300327.1|     FSFPQVTLAAEERTIKGSYVGSCVPDRDIPRFINLYHQGRLPVNELLTDTLPLEHINEGF
ref|NP_693723.1|     FSFPYVTLTAEEKTLKGSYVGSCVPDRDIPRYMNLFKQDRLPVDKLMTDFISLDEINEGF
ref|ZP_01227084.1|   MALSPLKLVAEERTLKGSYVGSCIPSRDIPRYIALYRGGRLPVDRLLTSRGTLDDINEGF
RAAC01763            WSVPQVLLAAEERTIRGSYVGSCIPSRDIPRFISLFQQGKLPVDRLVSDVIDLDHINEGF
                      :..  :  *.*:::*****:*.*****:: *.  :* ::  *:::.   *:.***** ref|YP_190012.1|     DRLSNGEVGRIIMKM---
ref|YP_252288.1|     DKLASGDVGRIIVKM---
ref|YP_300327.1|     DRLARGEAARLVVKM---
ref|NP_693723.1|     DKLAKGDSSRIIIKM---
ref|ZP_01227084.1|   DALAAGRTVRIIVV-----
RAAC01763            DRLAAGEAVRIVVRMSGA
                     * *:  *   * ::
```

FIG. 60

```
ref|ZP_01860323.1|    -LTIAMPKGRIFDEALELLRQAGYNLPPEFDDSRKLIIEVP--EEKLTFILAKPMDVPTY
ref|ZP_01171654.1|    LLTIAMPKGRIFEEAAELLRQAGEDLPPEFDDSRKLTTDV--EEERFQFILAKPMDVPTY
ref|NP_244450.1|      MLTVAMPKGRIFDEAVGLLRKAGYNLPAEFEASRKLIVDVP--EENMRFILAKPMDVPTY
ref|YP_080823.1|      -LTIAMPKGRIFEEAADMLRKACYQLPEEFDDSRKLIIQVP--EENLRFILAKPMDVTTY
ref|YP_148929.1|      MLTIAMPKGRIFEEAVELLRRADYALPPEFTESRKLVIDVP--EENMRFILAKPMDVVTY
RAAC01767             MLTVAMAKGRTLDDVVPLWEEAGIPYPRDWDESRALVFEIPWRDWTLRYLLAKPADVPTY
                       :.***  ::: .    : ..*.    * ::  ** *:..::     :   : ::**  ** ref|ZP_01860323.1|    VEHGVADLGIAGKDVMLEEERDVYELLDLKISACYLAVAGLP-GTKMNEVAPK-IATKYP
ref|ZP_01171654.1|    VEHGVADLGIAGKDVMLEEERDIYELLDLKISACYLAVAGIP-GTKMNEVAPK-VATKYP
ref|NP_244450.1|      VEHGVADVGVAGKDVMLEEERDVYEVDLKISECYLAVACLPNYEKKHDLNPK-VASKYP
ref|YP_080823.1|      VEHGVADVGIAGKDVLLEEERDVYEVLDLNISKCRLAVAGLP-ETAADTVAPR-VATKYP
ref|YP_148929.1|      VEHGVADLGIAGKDVLMEEERDVYELLDLHISRCHLAVAGMP-GAKMNEIAPR-VATKYP
RAAC01767             VAYGVADLGIVGNDILLEQEREMYELLDLGVARCKLCVAGRE---EERRHAPRRVATKYP
                       *  :****:*:.*:*:::*::**  ::  *  *.***           *: :*:*** ref|ZP_01860323.1|    TIASSYFREQGEQVEIIKLNGSIELAPMIGLADRIVDIVSTGRTLKENGLVEYEKIVDIT
ref|ZP_01171654.1|    NVAAAYFREQGEQVEIIKLNGSIELAPLIGLSDRIVDIVSTGRTLKENGLVEYEQIVGIT
ref|NP_244450.1|      HLATRYFKEQGEQVEIIKLNGSIELAPLIGLADRIVDIVSTGRTLRENGLVELEKMMTIT
ref|YP_080823.1|      NVASSYFREQGEQVEIIKLNGSIELAPLIGLAGRIVDIVSTGQTLRENGLVETEKICDIT
ref|YP_148929.1|      NIASTYFREQGEQVEIIRLNGSIELAPLIGLADRIVDIVSTGRTLRENGLVELERIAEVT
RAAC01767             KLADRYFRSQGHQVEIVPLAGSIELASVIGLTDRIFDLVQTGETLRANGLVVFDEVLDIS
                      :*   **:.**.****: * ******.:***:.**.*:*.**.**:  ****    :.:   ::

ref|ZP_01860323.1|    SRLIVNPVSYRMKDERIDELAERLREVVS-------
ref|ZP_01171654.1|    SRLIVNPVSYRIKDKRISEIVDKLSRVVNEQAA---
ref|NP_244450.1|      SRLIVNPVSYRMKDERIDEMVERL------------
ref|YP_080823.1|      SRLIVNPVSYRMKDAVIDEMASRLSLIVEGEKA---
ref|YP_148929.1|      SRLIVNPASYRLNGGDIERLVDRLAAVI--------
RAAC01767             ARLVANRSSYRMKHREISACLERLEAAVARRNAYAP
                      :**:.*  ***::     *.   .:*
```

FIG. 61

```
ref|NP_388333.1|        ------------------------IADEFQQTAAEDDEQGRFPAEKIQKLRDAGYTALTLP
ref|YP_001375327.1|     ------------------------FQERECELRELGSFPFENINELKDIGYTTLTLP
ref|NP_691214.1|        ------------KRIQLLK---NTVAPFNERAQKHDKDVSFPFENYKDLQSIGYPSLTIP
ref|ZP_01170331.1|      ------KAAGEADKYEQMK---ELSAIFKERSRSKENRGSFPHRNILDLKASGYTSLTVP
ref|YP_076186.1|        ---------------RRFVALAGELADRFAGRAALHDRENSFPFENFAELRASGYVRLTVP
RAAC01797               MYDIYGEAALPADVRERLRITRDLAQAFHERAPEHDRAGDFPFENIEDLKASGYVRWTVP
                                                 *         .   **  .:  .*:   **    *:* ref|NP_388333.1|        ASHGGGGISVYDMLLFQERLARGDAPTALSIGWHLSVIGELGEGNSWDEDVFAFVAKEV-
ref|YP_001375327.1|     KDCGGQEISLYDFVLYQEKIAEGDATALSIGWHLGIVKELTENQSWKPDMFAWFCEEV-
ref|NP_691214.1|        KEYGGAGITLDELLTYQEIIAQADGSTALSIGWHMGIMKYLGENKIWNEDVYSTVANDVI
ref|ZP_01170331.1|      ADRGGKGISLLEMIRLQEKLAEGDGSTALAIGWHMGITKNLGEKRKWDDELFSFLCREIL
ref|YP_076186.1|        VEWGGEGANLTETLLAQERLAQGDGATALGTGWHLAVVGKLAETRAWPPAATARIFREVA
RAAC01797               VEYGGLGLSLEEMLMHQEVLAKGDGSTALAIGWHVGILLHLRETGAFPDELFRMVCESVV
                         . **       .: :  :  ** :*..*..***.****:.:    *  *  :      . ..:

ref|NP_388333.1|        QNGAVINRAATEAKTGSPTRGGRPGTHAVKKDGKWAVNGRKTFTTMSQALDYFLVTAWIE
ref|YP_001375327.1|     KKGALFNRAATERKTGSPTRGGRPETLAVKKGEKWIINGRKTFTTMAPMLDYFIISASIE
ref|NP_691214.1|        QNGALLNNAATEPATGSPTRGGKPETHAIKQGNKWIMNGRKTFTTLSPILTYFVVSATID
ref|ZP_01170331.1|      -DGKLINSAATERQTGSPTRGGRPQTTAVLKGGNWVISGRKTFTTMAPALDYFIVSAFIP
ref|YP_076186.1|        GRGALINSAASEVETGSPSRGGRPTTTARRAPGGWLLTGRKSFTSLAPVLDYAVVSASFE
RAAC01797               KEGALINSCATEPATGSPSRGGKPETTAVKVPGGYRITGRKTFSTLSPALTWIMVTATVA
                          * ::*  .*:*  ****:***:*  *  *         :  :.***:*:::: * : ::*  .

ref|NP_388333.1|        DKQTTGVFLIHKDDPGLSIEETWDMMAMRATGSHDLVLNEVMLDENKLVEL----LQGPR
ref|YP_001375327.1|     GREEIGEFVVPRAQKGVSIEETWDSVAMRGTASHDLVLRNVEISDKYFTDIKG----SQS
ref|NP_691214.1|        ETGEVGNFLIKRDRPGVNVEETWDSIAMRGSGSHDLVLENVHLDEENLVEILS-----NK
ref|ZP_01170331.1|      SEDKTGNFLVPREAEGLSIEETWDSVSMRGTGSHDLVLDEVSIDKTFLAEILG------Q
ref|YP_076186.1|        GSDGGGWFLVQTGSPGVTVVETWDALCMRATGSHDLVLEDVFVEDGDLLETFG--RGNTC
RAAC01797               DEDVVGQFLVRK--EDVEIVETWDTLGMRATGSHDIVLKDVFVPEERVIVIQR--PGVQA
                             *  *::      .: : ****  :.**.:.***:**  :*  :  .  .

ref|NP_388333.1|        GAKP------NGWLLHIPAIYLGVAQAARDYAVQFASEYSPNSLNGPIKNVPAVQQRTGE
ref|YP_001375327.1|     KPKG------VGWLLHIPACYLGIAQAARNYALRFAESYQPNSLKHPISSLPNIRRLVGE
ref|NP_691214.1|        KRKP------AGWLLHIPACYLGIAQAAQKEAVQFAMNYSPNSIEGTISDLPNVKQKMGD
ref|ZP_01170331.1|      DKKA------NGWLLHIPAVYLGIAQAAQDYAAGFAKSYSPNSIQGTISDIPSVQQKIGE
ref|YP_076186.1|        QVGTG---DGAGWALHIPAVYLGIARAAHGFAVEYARTRRPNSLPGPIADQPHIQALLGQ
RAAC01797               ERRP----DGSGWLLHIPACYLGIALAARDFALEYAATYRPNTLPHPIAEVPHVEQKLGE
                                   ** *****  ***:* **:  *  :*   **::  .*  *   :.    *:

ref|NP_388333.1|        MELELLNARHFLFHIAQLYD--DPVRRPHLTSELGAAKHIVTNAALSVVDKAMRIVGAKS
ref|YP_001375327.1|     LELELMQARMFLYQIAKKYDEV--DDKQSLQAELAAAKYIATNAAISVVDKAMRIVGAKS
ref|NP_691214.1|        LELLLMESKHFLHSIAQQWDNGDENIRVAMGPELGAAKLSVTNKAVHAVDLAMRIVGAKS
ref|ZP_01170331.1|      IELELMRAREFLYAAADRWDRAAENERESMQPLLGAVKLAVTNAALTVADLAIRVVGARS
ref|YP_076186.1|        NEIDLLAARSALYTVADRWD-AEPERRGELVPLLGAAKVLAVNLALQIVDRAMRVAGIAG
RAAC01797               MELKLLAARTLLYDLARRFDAASPEERVKLQPQFGAVKTLATNAANQVVDLAMRVVGGRS
                         *: *: ::   *.  *  :*       :  :  :.*.*   ..* *   .*  *:*:.*   .

ref|NP_388333.1|        LERTNPLQRYYRDVRAGLHNPPMDDAV-------------------
ref|YP_001375327.1|     LSEKNPLHRYYLNVRAGLHNPPMDDV--------------------
ref|NP_691214.1|        LSEKNNLQRYYRDVRAGLHNPPMDDM--------------------
ref|ZP_01170331.1|      LSEQNPLQQYYLDIRAGLHNPPMDDM--------------------
ref|YP_076186.1|        LFRQLPLERLYRDVRAGLHNPPMEDAV-------------------
RAAC01797               LSRALPLERYYRDVRAGLHNPMDDVVYRNLAKAALARRAAGQAGR
                         *  .    *.:  *  ::**********:*
```

FIG. 62A

```
ref|NP_242876.1|            ---------AIYTRQFLAGEWIEGASTQTITNYNPYTGEKIHEIKGASLDDLDQAYRAAK
RAAC01900                   MSSTTSVKYAQWNKLYLGGEWRSGTSSRTVTVRNPYNQEVLAEFPLASVEDIDQAYRKAQ
ref|NP_691405.1|            ---------YENLNKNFISGEWRDGQGETTYEVKNPYNDEVLQEIKMASKEDIDEAYKSAE
ref|YP_001420375.1|         ---------QYEELNKQFIGGRWRDGSSRNVLENRNPYTQKVITSFQKATSDDVDAAYRAAA
ref|NP_388616.1|            ---------QYEELNKQFIGGKWQEGSSPNVLENKNPYTQKTFTTFRKATADDVDEAYRAAA
ref|NP_241871.1|            ------------NKQYIDGEWRDGKSPRVLRDRNPYNQEVLAEFQIATDSDVDAAYHAAL
                                      .: :: *.* .* .    ***. : :   *: .*:* **: * ref|NP_242876.1|            NAQKEWEQTLPAQKQEVLEKAAALLAERKDEVIERLVNEAGSSIIKASIEWGATLQTIKV
RAAC01900                   AAQQGWAEESAFTRAEVMERAASILAQRKDEIVRYLVEETCSSQLKASIEVDASIGDIKL
ref|NP_691405.1|            QAKKKWAKFNPFERSSIMEKAVQIIDARREFFVNHLIREGGSSHLKANVEIDFVIAITRE
ref|YP_001420375.1|         LAKQEWDKVNPFKKRAILEKAVSFIEEHEEAIIYLIMEELGGTRLKAEFEIGLVKNMIKE
ref|NP_388616.1|            LAKKKWDAVNPFEKRTILEKAVTYIEENEEAIIYLIMEELGGTRLKAAFEIGLVKNIIKE
ref|NP_241871.1|            KAQNEWATVNPYRKREILERAVTYIEEHEEEIVAIIIDELGGTRLKAAFEIGLVKNMIKE
                             *::   *            .  :  ::*:*.   :   ..: .:   * *.: :** .*  .        :

ref|NP_242876.1|            AATFPLRMECKTLPSNIPGKENRIYRSAKGV1GVISPFNFPLVLAMRSVAPALATGNAVV
RAAC01900                   AAEYAHKMTAVILPSAIPGKENRVYRTPVGVVGAITPWNWPFYLSIRVVAPALATGNAIV
ref|NP_691405.1|            AASFPLRMSGEIVPSLIPGKENRIYRSPLGVVGVIGPFNFPMYLAMRSVAPALAVGNGVV
ref|YP_001420375.1|         AATFPVRMEGKILPSTIDGKENRLYRIPAGVVGVISPFNFPFFLSMKSVAPALGAGNGVV
ref|NP_388616.1|            AATFPIRMEGKILPSTIDGKENRLYRVPAGVVGVISPFNFPFFLSMKSVAPALGAGNGVV
ref|NP_241871.1|            ASTFPLRMECKILPSTENGKENRLYRVPAGVVGVISPFNFPFFLSVKSVAPALGAGNGVV
                            *:  :. :*   .  *:   :   **:*.*  *:*:*:  *:::  ***...:* ref|NP_242876.1|            LKCSSDAPITSGLLIAELFEEAGLPKGVLNVVVGKAAEIGDAFVTHPIPKLISFTGSTEV
RAAC01900                   LKADSQTPITGGLLVADLFEQAGLPPGLLSVVVADLDEIGDAMVEHPVPRVISFTGSTAA
ref|NP_691405.1|            LKPDDQTAVTGGILLAKVFEEAGLPKGVFNVVVPNIEDIGDAFVEHPIPRLISFTGSTPV
ref|YP_001420375.1|         LKPHEETPICGGTLIAKIFEAAGVPDGLLNVIVTDIGEIGDSFVEHPVPRIISFTGSTGV
ref|NP_388616.1|            LKPHEETPICGGTLIAKIFENAGIPAGLLNVVVTDIAEIGDSFVEHPVPRIISFTGSTKV
ref|NP_241871.1|            LKPHEETPITGGTLIAKIFEEAGVPKGLLNVVVTEIDEIGNAFVEHPIPRIISFTGSTNV
                            **   .:::.: .* *:*.:** **:* *::.*:*  .  :**:::* **:*::******* .

ref|NP_242876.1|            GRHIAQLAARELKETALELCGNNVMIVLDDADIEKAAEKAAVGKFLHQGQICMALNRIIV
RAAC01900                   GRHIAEVAARSLRKVALELGGNNVFIVLDDADVDQAVAAAAFGKYLHQGQICIATNRMIV
ref|NP_691405.1|            GRHIGEICGRNIKKVALELGGNNPLVVLEDAKVENAVNSALFGKFMHNGQICMAINRIIV
ref|YP_001420375.1|         GSYIGQLAVKHFKKPLLELGGNSALIVLEDADLEYAVNAAVFSRFTHQGQICMSANRVLV
ref|NP_388616.1|            GSYIGQLAMKHFKKPLLELGGNSAFIVLEDADIEYAVNAAVFSRFTHQGQICMSANRVLV
ref|NP_241871.1|            GSHIGQLAVKHFKKPLLELGGNSAFLIFADADLDYAVQAATFSRFTHQGQICMSANRIFV
                             * :*.::. : ::: ****. :::: .::  *.  *  ..:: *:**:: ::* ref|NP_242876.1|            DASIYDSFVEVFKEKVSQLQTGNPAEPATLIGPLINYKQIGRIQQLVKESVAQGAVKVLE
RAAC01900                   HRKVYDEFVEKFMAATEKVKVGDPADPETVICPLINERQAKRIMGLIDESLKMGARLVLE
ref|NP_691405.1|            HKDIYEEFVEKFVEKAKKIKVGNPSEKDNLIGPLINRQAIDRILEQIESAKEQGAEVVLE
ref|YP_001420375.1|         HTSVYDKFTELYEAKVSSLKVGDPMDPDTVIGPLINERQAEGLRRSVEKAIEEGAVPVLS
ref|NP_388616.1|            HSSIYDKFLELYQAKVESLKVGDPMDPDTIIGPLINSRQTDGLMKTVEQAIEEGAVPVKL
ref|NP_241871.1|            QRDVYDEFVERYVTKVASLKVGDPRDPETVIGPVMNSRQAETLKQAIESGIAAGAKPVLH
                            . ..:*:.* *  :  . .::.*:*  :   ..:*  *::* :              :...   ** * ref|NP_242876.1|            GHVQGNLMSPTILSEVTNDMPVAKEEIFGPIAPIIKAKDEAEAIAIANDSPYGLSGSIFT
RAAC01900                   GKLEGLLMYPYIIADVTNDMPIAKNEIFGPVAAILPVDSEEEAVNIANESDYGLSGAVFT
ref|NP_691405.1|            GKVEGNVMHPYILTG-SNDVATAQNEMFGPVATIISAESDEEEAIRIANDTPFGLSGAVHA
ref|YP_001420375.1|         GRFSGTVAEPVILKDVKPEMSIAKEELFGPAVCIMTFETEDEAVSIANATPFGLSGAVHT
ref|NP_388616.1|            GGFNGTIVEPTILKDVKPFMSIAKEELFGPVVSFMKFDSEDEAVDIANETPFGLSGAVHT
ref|NP_241871.1|            GAISGNMVEPTILIDASPEMAIAQEELFGPVVCVIPFDTEEEAVEMANDTKYGLSGAIHT
                            *  ..*  :   * ** .  .  :. *::*:***  . .:    . :: **: :** :  :*****:::.:
```

FIG. 62B

```
ref|NP_242876.1|        GSLHRGVQVAKQIDTGMIHVNDQPVNEEAHISFGGEKDSGIGRFGGEWVLDKFTTVKWIS
RAAC01900               GDLERGIRVAQRIVTGMIHVNDQTVNVESNVPFGGEKASGIGRYCGEWGIEEFTTLKWIS
ref|NP_691405.1|        GSPERGVEVAKQITSGMVHVNDQSVNDEPLIAFGGEKASGLGRFGGKWSLEEFTTVQWIS
ref|YP_001420375.1|     ANVERGVEFAKRIETGMIHVNDTTINDEPNVAFGGEKQSGLGRLNGEWSLEEFTTLKWIS
ref|NP_388616.1|        SNLERGVAFAKRIETGMIHVNDTTINDEPNVAFGGEKQSGLGRLNGEWSLEEFTTLKWIS
ref|NP_241871.1|        ANVERGVEIAKRIQTGMIHVNDITINDEPIVAFGGEKHSGLGRINGEWSLEEFTTLKWVS
                        .. .**: .*::* ::**  .:* *. :.*** :**  *:* :::***:*:* ref|NP_242876.1|        IQEKERVYPF-
RAAC01900               VQKEPRVYPFS
ref|NP_691405.1|        VQTEERENPF-
ref|YP_001420375.1|     VQHEKRQFPY-
ref|NP_388616.1|        VQHEKRSFPY-
ref|NP_241871.1|        VHYSQRVFPY-
                        ::  . * *:
```

FIG. 63

```
ref|NP_390790.1|        ---RKKVSVIGAGFTGATTAFLIAQKELADVVLVDIPQLENPTKGKALDMLEASPVQGFD
ref|YP_080204.1|        --KRNKVSVIGAGFTGATTAFLTAQKELADVVLVDIPQLENPTKGKALDMLEASPVQGFD
sp|Q59202|MDH_BACIS     -IKRKKISVIGAGFTGATTAFLLAKKELGDVVLVDIPQAENPTKGKALDMLESSPVLGFD
ref|ZP_02170616.1|      -IKRRKITVVGGGFTGTTTALMTAQKELGDVVLIDIPKMEDPTKGKALDMMEASPVQGFD
ref|NP_693087.1|        -LKRRKISVIGSGFTGATTALMVAQKELGDVVLVDIPDMEDPTKGKALDMAEAAPVQGFD
RAAC01939               MLERKKISVIGAGFTGATTAFLLAAKELGDVVLLDIPSLENPTKGKALDMLEAMPVLCSD
                         * *::*:*.**:*::  * *.:*. *:*********  *:  ** * * ref|NP_390790.1|        AKITGTSNYEDTAGSDIVVITAGIARKPGMSRDDLVSTNEKIMRSVTQEIVKYSPDSIIV
ref|YP_080204.1|        ANITGTANYEDTAGSDIVVITAGIARKPGMSRDDLVATNEKIMRSVTKEVVKYSPDCIII
sp|Q59202|MDH_BACIS     ANIIGTSNYEETADSDIVVITAGIARKPGMSRDDLVQTNQKVMKSVTKEVVKYSPNSIII
ref|ZP_02170616.1|      SKITGTSDYKDTAGSDIVVITAGIPRKPGMSRDDLVSTNAGIMKSVTQEIVKYSPDCYII
ref|NP_693087.1|        AKITGTSNYADTEGSDLVITTAGIARKPGMSRDDLVNTNANIMKSVTKEIVHYSPNTTIV
RAAC01939               ARVVGTSNYEDTAGSDLVIITAGLPRKPGMSRDDLVNTNANIVKSVTEQVVRHSPDACLI
                        :.: **::*  :* .**:****:.*********** .::****:::*:**:    ::

ref|NP_390790.1|        VLTNPVDAMTYAVYKESGFPKERVIGQSGVLDTARFRTFVAEELNLSVKDVTGFVLGGHG
ref|YP_080204.1|        VLTNPVDAMTYAVYKESGFPKERVIGQSGVLDTARFRTFVAQELNLSVKDITGFVLGGHG
sp|Q59202|MDH_BACIS     VLTNPVDAMTYTVYKESGFPKHRVIGQSGVLDTARFRTFVAQELNLSVKDITGFVLGGHG
ref|ZP_02170616.1|      VLTNPVDAMTYTVFKESGFPKNRVIGQSGVLDTARFNTFVAEELNVSVEDVTGFVLGGHG
ref|NP_693087.1|        VLTNPVDAMTYTVFKESGLPKERVIGQSGILDTARFRTFVAEELNLSVKDVTGFVLGGHG
RAAC01939               VLSNPVDAMTYVAYKTSGFPKQRVIGQAGVLDTARFNTFVAMELGVSVEDVHGFVLGVHG
                        :******..:* : *****:*:****.    .:::* *** ref|NP_390790.1|        DDMVPLVRYSYAGGIPLETLIPKERIDAIVERTRKGGGEIVNLLGNGSAYYAPAASLTEM
ref|YP_080204.1|        DDMVPLVRYSYAGGIPLETLLPKDRIDAIVERTRKGGGEIVNLLGNGSAYYAPAASLTEM
sp|Q59202|MDH_BACIS     DDMVPLVRYSYAGGIPLEKLIPKERLEAIVERTRKGGGEIVNLLGNGSAYYAPAASLVEM
ref|ZP_02170616.1|      DDMVPMLRYSFAGGIPLEKLIDKERLEAIVERTRKGGGEIVNLLGNGSAYYAPAASIVQM
ref|NP_693087.1|        DDMVPLIRYSYAGGIPLEKLIPQERLDAIVQRTRTGGGEIVNLLGNGSAYYAPAASLTVM
RAAC01939               DDMVPLVRYANVGGVPLEKLLPKERIDAIVERTRNGGGEIVSLMGNASAYYAPAASLLQM
                        ***:::  .  ***. *:  ::*:*:*.****** .*: *******:  * ref|NP_390790.1|        VEAILKDQRRVLPTIAYLEGEYGYEGIYLGVPTIVGGNGLEQIIELELTDYERAQLNKSV
ref|YP_080204.1|        VEAILKDQRRVLPTIAYLEGEYGYEGIYLGVPTIIGGNGLEQIIELELTETEKSQLDKSV
sp|Q59202|MDH_BACIS     VEAIVKDQRRVLPTIAYLEGEYGFEGIYLGVPTILGGNGLEQIIELELTDEEKAALEKSA
ref|ZP_02170616.1|      VEAILKDKKRILPTIAYLEGEYGYSDLYLGVPTVIGGDGIEQVFELDLNDDEKAALDKSV
ref|NP_693087.1|        AEAILKDQRRVLPTIAYLEGEYGYQDIYLGVPTILGGEGIEEIIELDLTKEEKAQLDKSA
RAAC01939               AESILKDKRRVLPATAYLEGEYGYRDLTLGVPTVLGKGGIERILELELLPEEKAALDKSA
                        .*:*:**::*:**:*********: .: ******::*  *:*.::****:*    *:: *:**.

ref|NP_390790.1|        ESVKNVMKVLS
ref|YP_080204.1|        ESVKNVMKVLS
sp|Q59202|MDH_BACIS     ESVRNVMKAL-
ref|ZP_02170616.1|      ASVKKVMEIL-
ref|NP_693087.1|        DSVKNVLNVL-
RAAC01939               ESVRRLISVLS
                        **:.::. *
```

FIG. 64

```
ref|YP_001126997.1|    ------------------------------------------------FTKMHGLGNS
ref|YP_148810.1|       ------------------------------------------------FTKMHGLGNS
ref|YP_001488092.1|    -----------------------------------------------QFTKMHGLGNN
ref|NP_391097.1|       ------------------------------------------------RFTKMHGLGNS
ref|NP_244279.1|       ----------------------------------------------MKFTKMHGLGNS
RAAC01996              MSEMVSLAVRFRISTAANDYIIQGITQVCNESFHRWPDFFNRAQGGVGMQFFKMHALGNN
                                                                       *  * * ref|YP_001126997.1|    YIYVDLFRETLPEEDLPAIARSVADVHTGIGSDGLILICPSEQAPVKMRIFNSDGSEGKN
ref|YP_148810.1|       YIYVDLFRETLPEEELPAIARSVADVHTGIGSDGLILICPSEKAPVKMRIFNSDGSEGKN
ref|YP_001488092.1|    YIYVNQMKEQLPEEKLSEIAIQVSSIYTGIGSDGMILICPSDVAPVKMRIFNNDGSEGKN
ref|NP_391097.1|       YIYVNQFEEQLPEEKLSEIAIQVSSVYTGIGSDGMILICPSDQAPVKMRIFNNDGSEGKN
ref|NP_244279.1|       YIYVDCFKELLKEEELPALAVAVADKNKGIGSDGMILICPSDRAPVKMRVFNNDGSEAKN
RAAC01996              YVFVDTARTTLPTDDLPSLARRVSDVRRGIGSDGLILVTPSDSADVGMRIWNADGSEAES
                         *  *       *   *    *  *  *:   *****:**: **: *  **::* ****.:.

ref|YP_001126997.1|    CGNGLRCVAKYAYEHGIVRDRSFLIETLSGLVEAEVTVE-NGEVTSVTIDMGEPRLRRSA
ref|YP_148810.1|       CGNGLRCVAKYAYEHGIVSDRTFLIETLSGLVEARVAV-ADGEVTSVTVDMGEPRLERSA
ref|YP_001488092.1|    CGNGLRCVAKYVYEHQIVTDTTFQIETLSGLVEATVHVQ-DDHVHLVTVDMGKPRFEKEA
ref|NP_391097.1|       CGNGLRCVAKYAYEHKLVEETSFLIETLSGLVKAEVQVE-NGKVNVVTVDMGEPRLTKSE
ref|NP_244279.1|       CGNGLRCVAKFAFEHGYVKETSFDVETLGGLVKATVHPNDNGLVDTVTVNMGEPRLGRAQ
RAAC01996              CGNGLRCVARYAYERGLVDATHFSIETKAGVVAAQVHLDVEGRVRLVTIDMGEARFGTEA
                       *********: :*:    *  :** .*:* *       :  *  **::**:.*:

ref|YP_001126997.1|    IPM--TGPE-AEQVVAESFAIDGREYEITAVSMGNPHVIFYVDDIEKAPVTTLGPVVEKD
ref|YP_148810.1|       IPM--LGPE-AERVVAEPFAIAGGEYEITAVSMGNPHVIFYVDDIQKAPVTTLGPLVEKD
ref|YP_001488092.1|    MPM--LGEP-ASTTINEPLDFGTTTLNGTAVSMGNPHIVFYLEDIEKAPLDTLGPIIEKH
ref|NP_391097.1|       LPM--LDGG-EEHTINETMAFGEVELTGTAVSMGNPHIVFPIADIEQAPLTTLGPVIEKD
ref|NP_244279.1|       IPM--LGEE-AAEVVAEPFTIGEKEYRLTAVSMGNPHAIMFIDTIEDAPVEQVGPLLEKH
RAAC01996              VPY----RG-ADRGEDVRVEAGGARYTGTLVSMGNPHFVTLVDRVDDVDVERVGRVIESH
                       :*                           *  ******  :   ::.. :  :* ::*..

ref|YP_001126997.1|    ARFPEGVNVEFVEVVSERELHFRVWERGSGVTQACGTGACAAVVASVLNGKTARGVETVV
ref|YP_148810.1|       PRFPEGVNVEFVEVVNERELHFRVWERGSGVTQACGTGACAAVVASVLNGKTARGEETVV
ref|YP_001488092.1|    DMFPEGVNVEFVEVVSETELHFRVWERGSGITQACGTGACAAVSTIVNGQAKKETDMTV
ref|NP_391097.1|       PRFPEGINVEFVETVNEQELHFRVWERGSGITQACGTGACAAVASVLNGVSKRNQDITV
ref|NP_244279.1|       EAFPDWVNVEFVQVVSPTEIHFRVWERGSGITQACGTGACAAVVASVLNGFTQKGQEVTV
RAAC01996              PDFPERVNVEFVSVLAPDEIDFRVYERGSGVTFACGTGACASVAALAKKGLVRN--RVTV
                         : :***..:    *:.*:*:* ********:..:    :*    . .* ref|YP_001126997.1|    HLAGGDLTITWGHDGKVRMTGPAETVCTGVYY-
ref|YP_148810.1|       HLAGGDLTIVWGHDGRVRMTGPAETVCTGVYY-
ref|YP_001488092.1|    HLAGGDLIIRWKDNEHVLMTGPAETICDGTFY-
ref|NP_391097.1|       HLAGGDLVINWKDNGHVMMTGPAETVCEGVYF-
ref|NP_244279.1|       HLLGGDLTISWLENGDVLMTGAAETICEGTY--
RAAC01996              HLLGGDLDIEIRDDGHVWMTGEAHWVCEGTYYA
                       ** ****  .  :  *  ***  *  *:*.:
```

FIG. 65

```
ref|NP_390723.1|         ------------------------------------------------NREFYFRRLHSL
ref|YP_001422141.1|      ------------------------------------------------NREFYFRRLHSL
ref|YP_080139.1|         ------------------------------------------------NREFVYRRLHSL
ref|ZP_01171785.1|       ------------------------------------------------NREFFNRRLHSL
ref|NP_243959.1|         ------------------------------------------------NREFFNRRLHSL
RAAC02025                MPNGWRRASRWPAVFCTCTAIPPRVHTVFSFGGLKGGTQVAVAQAAQHNREFFWRRLHTL
                                                                         **  **:* ref|NP_390723.1|         LGVIPVGIFLIQHLVVNQFAARGAEAFNSAAHFMDSLPFRYALEIFIIFLPLIYHAVYGV
ref|YP_001422141.1|      LGVIPVGIFLIQHLVVNQFAARGADAFNKAAGFMDSLPFRYALEIFIIFLPLIYHAVYGV
ref|YP_080139.1|         LGVIPVGIFLIQHLVVNHFAASGEEAFNNAAHFMENLPFRYALEIFVIFLPLIYHAVYGV
ref|ZP_01171785.1|       LGVIPVGLFLVQHLVVNHFATGGEESFNKAAHFMEQLPFRYVLETVVIFLPLLFHAIYGL
ref|NP_243959.1|         LGVIPIGIFLIQHFVVNHFATAGASAFNQAAHFMESLPFRYALEIFIIFIPILYHAIYGL
RAAC02025                SGVIPVGLFLLEHLFTNATALGGAAAFNEAVQAIQSLPLLHVIEFVFIFLPITYHGVFGL
                         ****:*:**::*...*   *   * :**.*.   ::.**: :..* ..**:*: :*.::*:

ref|NP_390723.1|         YIAFTAKNNAGQYSYMRNWLFVLQRVTGIITLIFVSWHVWETRIAAQMGAEVNFDMMANI
ref|YP_001422141.1|      YIAFTAKNNAGHYSYFRNWMFVLQRVTGILTLIFVSWHVWQTRIAAQMGAEVNFDMMANI
ref|YP_080139.1|         YIAFTAKNNANRFGFFRNWMFVLQRITGIITLIFVSWHVWETRIAAQMCAEVNFDMMADI
ref|ZP_01171785.1|       YIAFTAKNNAGRFGFFRNWMFLLQRVSGVVTLTFITWHVWETRVAAAFGADVNFQMMENI
ref|NP_243959.1|         YIAFQAKNNTSHYGYFRNWMFLLQRISGVFLLIFIAWHVWETRIQAAFGAEVNYDMMADI
RAAC02025                YVAFVSGYNANRYSFSRNVMFVLQRVTGIITFVFIIFHLWTTRFS---GNAPSFDMVHEL
                         *:**  :  *:.::.: ** :*:***::*:. ::*: :*:* **.    *    .::*: ::

ref|NP_390723.1|         LSSPAMLGFYIVGVLSTIFHFSNGLWSFAVTWGITVTPRSQRISTYVTLIIFVALSYVGL
ref|YP_001422141.1|      LSSPFMLGFYIVGVLSVIFHFSNGLWSFAVTWGITVTPRSQRISTYVTLIIFLALSYVGL
ref|YP_080139.1|         LSSPIMLGFYIVGVLSTIFHFSNGLWSFAVTWGITVSPRSQRIATFVTMGVFVVLSYVGL
ref|ZP_01171785.1|       LSNPFMFWFYIVGVISTIFHFANGLWSFAVSWGITVTPRSQRLSTYVTIAIFIALSIVGI
ref|NP_243959.1|         LSNPFMLVFYILGVVSATFHFANGLWSFFVSWGITVSPRSQQIMTYVTVAIFFALTFVGI
RAAC02025                VTDNAYFAFMIVGVIAATFHFSNGLWSFAIHWGITVGRRAQRITAWVTMIMFVVLAAVGV
                         ::.   : * *:**::. ***:****** : ***** *:* * ::**: :*..*: **:

ref|NP_390723.1|         KAIFAF----
ref|YP_001422141.1|      KAIFAF----
ref|YP_080139.1|         RAILAF----
ref|ZP_01171785.1|       RAITAF----
ref|NP_243959.1|         RAILAF----
RAAC02025                ASLIAFRMNV
                         ::  **
```

FIG. 66

```
ref|YP_149212.1|        -----SLRDIKTRINATKKTSQITKAMEMVSTSKLNRAEQNAKSFVPYMEKIQEVVANVAL
emb|CAA30654.1|         -----SLRDIKTRINATKKTSQITKAMEMVLTSKLNRAEKR-EIVRPYMEKIQEVVANVAL
ref|YP_001127389.1|     -----SLRDIKTRINSTKKTSQITKAMEMVSTSKLNRAEQNAKSFVPYMEKMQEVVANVAL
ref|YP_001488540.1|     -----SLRDIKSRITSTKKSSQITKAMQMVSAAKLNRAENNAKSFVPYMEKIQEVVAAIAT
pdb|2QE7|G              -----MREIKRRIRSVKNTRQITKAMKMVAAAKLRRAQETAENARPYADKIKEVISSIAA
RAAC00451               MAQNSMRDIRRRIKSVRNTAQITKAMEMVAAAKLRRVQDAVQQSKPYLSKMQEMLANLSL
                             :*:*:  **  :.:::  ******:**   ::**.*.:.      :     ** .*::*::: ::

ref|YP_149212.1|        GAGGASHPMLVSRPVKKTGYLVITSDRGLAGAYNSNVLRLVYQTIQKRHASPDEYAIIVI
emb|CAA30654.1|         AAR-ASHPMLVSRPVKKTGYLVITSDRGLAGAYNSNVLRLVYQTIQKRHASPDEYAIIVI
ref|YP_001127389.1|     GAGGASHPMLISRPVKKTGYLVITSDRGLAGAYNSNVLRTVYQTIQARHSSPDEYAIIVI
ref|YP_001488540.1|     GTS-AKHPMLLSRPVKKTGYLVITSDRGLAGPFNSSILRAAYQTIQSRHQSADEYAVIVI
pdb|2QE7|G              GTKDFSHPMLEARPVKKTGYMVITSDRGLAGPYNANILRLVSKTIEERHQSKDEYVIFAV
RAAC00451               SARLVKHPLLAVRPVRRIGYLVITADRGLAGPYNAQVVRAAMQEFCKRDKGS--YAIYTV
                        .:    .*:*  ***:: **:***:******.:*:..::*  . :   *.. .  *.: .:

ref|YP_149212.1|        GRVGLSFFRKRNMPVILDITRLPDQPSFADIKEIARKTVGLFADGTFDELYMYYNHYVSA
emb|CAA30654.1|         GRVGLSFFRKRNMPVILDITRLPDQPSFADIKEIARKTVGLFADGTFDELYMYYNHYVSA
ref|YP_001127389.1|     GRVGLNFFRKRNMPVILDITRLPDQPSFADIKEIANKAVGLFADGTFDELYMYYNHYVSA
ref|YP_001488540.1|     GKIGRDFFKKRGIPVISEVTGLGDEVAFADIKELASSTVQMFSDEAFDELYMFYNHFVSA
pdb|2QE7|G              GRKGRDFFKKRGYPVVEEVTGISDTPSLTEIQDIAQSAIGMFADETFDKLTIFYNEFVSP
RAAC00451               GKRGRNFFQRRGLPIAAEVVDLPDTPTYHSVRHLAENIVAAYEREEFDELYFIYNEFINA
                        *:   * .**::*.  *:   ::.  :  *   :   .::.:* .  :    **:*  :  **.::..

ref|YP_149212.1|        IQQEVTERKLLPLTDLAE----NKQ--RTVYEFEPSQEEILDVLLPQYAESLIYGALLDA
emb|CAA30654.1|         IQQEVTERKLLPLTDLAE----NKQ--RTVYEFEPSQEEILDVLLPQYAESLIYGALLDA
ref|YP_001127389.1|     IQQDVTERKLLPLTDLAD----NQQ--RTMYEFEPSQEEILDVLLPQYAFSLIYGALLDA
ref|YP_001488540.1|     ISQEVTEKKLLPLTDISAAATPNKR--SASYEFEPSEEEILEVLLPQYAESLIFGALLDS
pdb|2QE7|G              IVQRPVEKQLLPLTS-EEVLDGPVS----AYEYEPDSESVLEVLLPKYAETLIYSALLDA
RAAC00451               AVQRPVVRKVLPLASLGENVQGPRR----NYLFEPDEESVLAALLPRYAETLVYQAVLDA
                         * . :::***:.          * :**..*.:*  .***:***:**:   *:**:

ref|YP_149212.1|        KASEHAARMTAMKNATDNANELIRTLTLSYNRARQAAITQEITEIVAGANALQ
emb|CAA30654.1|         KASEHAARMTAMKNATDNANELIRTLTLSYNRARQAAITQEITEIVAGANALQ
ref|YP_001127389.1|     KASEHAARMTAMKNATDNAHELIRTLTLSYNRARQASITQEITEIVAGANALQ
ref|YP_001488540.1|     KASEHAARMTAMKSATDNAKELIDSLTLSYNRARQAAITQEITEIVGGAAALE
pdb|2QE7|G              KASEFGARMTAMGNATDNATEMLETLTLQFNRARQAAITQEIAEIVAGANALR
RAAC00451               KASEHAARMNAMGNATDNALELIEKLTLSLNRARQAAITTQIAEIVGGAEALK
                        ****..***.**  ***** *::  .***.  ******:**  :*:***.**  **.
```

FIG. 67A

```
ref|YP_148525.1|          ----------------IIVVGGGLAGLMATIKIAEAGVPVELFSLVPVKRSHSVCAQGGIN
ref|YP_001126690.1|       ----------------IIVVGGGLAGLMATIKIAEAGVPVELFSLVPVKRSHSVCAQGGIN
ref|YP_092553.1|          ----------MSNSSIIVVGGGLAGLMATIKAAEAGTNVKLFSIVPVKRSHSVCAQGGIN
ref|NP_243958.1|          ----------------VIVVGGGLAGLMATIKVAEAGVPVELFSLVPVKRSHSVCAQGGIN
emb|CAA69872.1|           ----------MAKQSVIVVGGGLAGLMATIKSAEAGVPVHLFSLVPVKRSHSVCAQGGIN
RAAC02026                 MLTRAWEGIDVANTSIIVVGGGLAGLMTTIKVAEAGVPVKLFSLVPVKRSHSVCAQGGIN
                                          :******** :* ****. *.*:*********** ref|YP_148525.1|          GAVNTKGEGDSPWEHFDDTVYGGDFLANQPPVKAMCEAAPGIIYMLDRMGVMFNRTPEGL
ref|YP_001126690.1|       GAVNTKGEGDSPWEHFDDTVYGGDFLANQPPVKAMCEAAPGIIYMLDRMGVMFNRTPEGL
ref|YP_092553.1|          GAVNTKGEGDSPWEHFDDTVYGGDFLANQPPVKAMCEAAPSIIHLLDRMGVMFNRTPEGL
ref|NP_243958.1|          GAVNTKGEGDSPWEHFDDTVYGGDFLANQPPVKAMCDAAPGIIHLMDRMGVMFNRTAEGL
emb|CAA69872.1|           GAVNTKGEGDSPWEHFDDTVYGGDFLANQPPVKAMCEAAPGIIHLMDRMGVMFNRTPEGL
RAAC02026                 GAVNTKGEGDSPWEHFDDTIYGGDFLANQPPVLGMCEAAPAIIYLMDRMGVMFNRTPEGL
                          *****************:******** .:*.::.:********.* ref|YP_148525.1|          LDFRRFGGTQHHRTAYAGATTGQQILYALDEQVRRHEVAGLVTKYEHWEFLGVVLDDEQI
ref|YP_001126690.1|       LDFRRFGGTQHHRTAYAGATTGQQILYALDEQVRRHEVAGLVTKYEHWEFLGVVLDDEQI
ref|YP_092553.1|          LDFRRFGGTQHHRTAYAGATTGQQLLYALDEQVRRFEVEGLVSKYEGWEFLGAVLDDDNT
ref|NP_243958.1|          LDFRRFGGTQHHRTAFAGATTGQQLLYALDEQVRRHETSGLVTKYEGWEFISAIIDDEGI
emb|CAA69872.1|           LDFRRFGGTKHHRTAFAGATTGQQLLYALDEQVRRHEAAGLVTKYENWEFLSVVLDDDGV
RAAC02026                 LDFRRFGGTKHHRTAFAGASTGQQLLYALDEQVRRYEVAGLVEKYEGWDFLGAVIDDEQI
                          *********:*****:***:****:*********  *** *** *:*: .::*:

ref|YP_148525.1|          CRGIVAQDLRSMEIKAFPADAVILATGGPGIIFGKSTNSVINTGSAASIAYQQGVYYANG
ref|YP_001126690.1|       CRGIVAQDLRSMEIKAFPADAVILATGGPGIIFGKSTNSVINTGSAASIAYQQGVYYANG
ref|YP_092553.1|          CRGIVAQNLTTMEIESFRSDAVIMATGGPGIIFGKSTNSMINTGSAASIVYQQGAYYANG
ref|NP_243958.1|          CRGITAQNLKTSEFQSFSADAVIYAAAKLYEQGVYYANG
emb|CAA69872.1|           CRGITAQNLRSMEIVTFASDAVILATGGPGIIFGKTTNSVINTGTAASAVYQQGVHYANG
RAAC02026                 CRGIVAQDLRSMEIHYFRADAVVMCTGGNGLIFGKSTNSMINTGSAASELYQQGVKYANP
                          **.:*  : *: *  :*:: * *:**:*.****  *:. * ref|YP_148525.1|          EFIQIHPTAIPGDDKLRLMSESARGEGGRIWTYKDGKPWYFLEEKYPAYGNLVPRDIAAR
ref|YP_001126690.1|       EFIQIHPTAIPGDDKLRLMSESARGEGGRVWTYKDGKPWYFLEEKYPAYGNLVPRDIAAR
ref|YP_092553.1|          EFIQIHPTAIPGDDKLRLMSESARGEGGRVWTYKDGKPWYFLEEKYPAYGNLVPRDIATR
ref|NP_243958.1|          EFIQIHPTAIPGDDKLRLMSESARGEGGRVWTYKDGKPWYFLEEKYPAYGNLVPRDIATR
emb|CAA69872.1|           EFIQIHPTAIPGDDKLRLMSESARGEGGRIWTYKDGKPWYFLEEKYPAYGNLVPRDIATR
RAAC02026                 EMIQVHPTAIPGDDKLRLMSESARGEGGRVWTYKDGKPWYFLEEWYPEYGNLVPRDIATR
                          *::*******************:**********  **********:* ref|YP_148525.1|          EIFHVCVDLKLGINGENMVYLDLSHKDPKELDVKLGGIIEIYEKFMGEDPRKVPMKVFPA
ref|YP_001126690.1|       EIFHVCVDLKLGINGENMVYLDLSHKDPKELDVKLGGIIEIYEKFMGEDPRKVPMKVFPA
ref|YP_092553.1|          EIFDVCVRQKLGINGENMVYLDLSHKDPKELDIKLGGIIEIYEKFMGDDPRKLPMKIFPA
ref|NP_243958.1|          EIFHVCVDLKLGINGENMVYLDLSHKDPKELDIKLGGIIEIYEKFMGDDPRKVPMKIFPA
emb|CAA69872.1|           EIFHVCVDQKLGINGENMVYLDLSHKDPKELDVKLGGIIEIYEKFMGDDPRKIPMKIFPA
RAAC02026                 AIHKVCVEMGLGVDGQNMVYLDLTHIPADVLDRKLGNILDIYEKFVGDDPRKVPMKIFPA
                           *..*** .    .*:*******:* .*: *.*::*****.*:**:*:*** ref|YP_148525.1|          VHYSMGGLWVDYDQMTNIKGLFAAGECDYSIHGANRLGANSLLSAIYGGMVAGPNAVRYI
ref|YP_001126690.1|       VHYSMGGLWVDYDQMTNIKGLFAAGECDYSIHGANRLGANSLLSAIYGGMVAGPNAVRYI
ref|YP_092553.1|          VHYSMGGLWVDYDQMTNIPGLFAAGECDYSMHGGNRLGANSLLSAIYGGMVAGPKAVEYI
ref|NP_243958.1|          VHYSMGGMWIDYDQMTNIPGLFAAGECDYSQHGANRLGANSLLSAIFGGMVAGPKAVEYM
emb|CAA69872.1|           VHYSMGGMWVDYNQMTNIPGLFAAGECEYQYHGANRLGANSLVSAIYGGMVAGPKAVEYI
RAAC02026                 VIYSMGGLWVDYDQMTNIPGLFAAGEADYQYHGANRLGANSLVSCIYGGMIAGPNAVRWA
                          * *****:*:**:***** *******  *  **.********:*.*:****:***:**  :
```

FIG. 67B

```
ref|YP_148525.1|         RGLEKSADAMPSTLYDSYVKREQEKWENILAMDGTENAYVLHKELGEWMTANVTIVRYND
ref|YP_001126690.1|      RGLEKSADALPSTLFDSYVKQEQEKWENILSMDGTENAYVLHKELGEWMTANVTIVRYND
ref|YP_092553.1|         QGLETSAEDLSSSVFDAYVKKEEEKWADIMKMDGNENAYVLHKELCEWMTDNVTVVRYND
ref|NP_243958.1|         NGLEKSAESMPSSLFEGELKKEQEKFDDILKMDGKENAYVLHKELGEWMTDNVTVVRYND
emb|CAA69872.1|          RGLKKSADDIRPDVFDRYRKAQEDKFEGLLNMNGSENAYVLHKELGEWMTDNMTVVRYND
RAAC02026                KNLRKSADSLPESLFEQYRRKYEQEFEEILKLDGDENPYQLHRELGKWMTDHVTVVRYND
                         ..*..**: :   :::     :   ::::   ::  ::* **.* :*:***  :: *:***** ref|YP_148525.1|         RLLKTDEKIQELMERYKNISVTDTSRWSNQGATFIRQLYNMLQLARVITLGAYHRNESRG
ref|YP_001126690.1|      RLLKTDEKIQELMERYKNISVTDTAKWSNQGATFIRQLYNMLQLARVITLGAYNRNESRG
ref|YP_092553.1|         KLLKTDEKIQELAERYRNININDTAKWSNQGAVFTRQLHNMLQLARVITLGAYNRNESRG
ref|NP_243958.1|         KLLKTDEKIQELMERYKNIDINDTAKWSNQGASFTRQLDGMLKLARVITLGAYNRNESRG
emb|CAA69872.1|          RLEATINKIKELKERYKKININDTSRWNNAGAAFTRQLWNMLELAEAMTLGALLRNESRG
RAAC02026                KLKETDAKIQELQERWKRIKMSDTSRWFNQVAQFTRELKNMLIMARAITIGALMRNESRG
                         :*    *   :  **::.*.:.**::*.*   * * *:* .**  :*..:*:   **** ref|YP_148525.1|         AHYKPEFPERNDEEWLKTTMARYTPD--GPAFHYEDVDVSLIKPRKRDYSKKKEEVK-
ref|YP_001126690.1|      AHYKPEFPERNDKEWLKTTMARYTPD--GPSFHYEDVDVSLIKPRKRDYSKKKEEVK-
ref|YP_092553.1|         AHYKPDFPFRNDEEWLKTTMAKHAGDFEAPKFHYEDVDVSLIAPRKRDYSKKKVA---
ref|NP_243958.1|         AHYKPDFPERNDEEFLKTTKAKFNPETLAPEFEYEEVDVSLIEPRKRDYSQKKQ----
emb|CAA69872.1|          AHYKPDFPNRNDEEFLKTTKATWTPD--GPQISYEDVDVSLIPPRIRDYSKDK-----
RAAC02026                AHYKPEFPERDDENFLKTTIAEYTPD--GPKISYFDVDVSLIKPRKRNYAVSKEATKE
                         *****:**:*:*:::**** *    :  .* : **:*****  **  *:*:  .*
```

FIG. 68

```
ref|YP_080136.1|        ----------------KTIKFIITRQDTSDSNPYQEEFEIPYRPNMNVISALMEIRRNPV
ref|NP_243957.1|        -----------------VRFIITRQDDPDSSPYEEEFQVPYRQNMNVISALMEIRRNPV
ref|YP_148524.1|        ----------------KTVRLIITRQDRPDSAPYEEEFVIPYRPNMNVISALMEIRRNPV
ref|ZP_01697535.1|      ----------------KTVTFIIQRQDNPESEPYDETFEVPYRPNMNVISALMEIRRNPV
emb|CAA69873.1|         MAETEAAVKQK---SGKKVKFIITRQDDPNSQPYTEEFELDYRPNMNVISALMEIQRNPV
RAAC02027               MSTTAEAVQQAQADSGRKVHLITERQDTPDSEPYWEEFEVPYRPGMNVIACLMEIQRNPV
                         : ** *** .:* ** * * : ** .****:****:****

ref|YP_080136.1|        NAKGEKTSPIAWDMNCLEEVCGACSMVINGKPRQSCTALIDQLEQPIRLEPMKTFPVVRD
ref|NP_243957.1|        NSKGETSTPVAWEMNCLEEVCGACSMVINGKPRQSCTALVDQLEQPIRLEPMKTFPVVRD
ref|YP_148524.1|        NAKGEKTTPVAWEMNCLEEVCGACSMVINGKPRQACAALIDKLEQPIRLEPMRTFPVIRD
ref|ZP_01697535.1|      NAKGEKTTPVVWEMNCLEEVCGACSMVINGKPRQACSALVDKLQQPIRLAPMRTFPVVRD
emb|CAA69873.1|         NQKGEHTAPVCWESNCLEEVCGACSMVINGKPRQACAALIDQLEQPVRIEPMRTFPVVRD
RAAC02027               NKKGEPVAPVTWEMNCLEEVGACTMVINNKPRQACSALVDKLQQPIRIRPMRTFPVVRD
                        * ***  :*: *: ********** :****.****:*:**:*:**:*: **:****:**

ref|YP_080136.1|        LQVDRSRMFDSLKKVKAWVPIDGTYDLGPGPRMPERRRQWAYELSKCMTCGVCLEACPNV
ref|NP_243957.1|        LVIDRSRMFDSLKKVKAWIPIDGTYDLGPGPRMAESKRQWAYELSKCMTCGVCLEACPNV
ref|YP_148524.1|        LVIDRSRMFDALKRVKAWIPIDGTYDLGPGPRMPERKRQWAYELSKCMTCGVCLEACPNV
ref|ZP_01697535.1|      LQIDRGRMFDSLKKVKAWIPIDGTYDLGEGPRMPEKKRQWAYELAKCMTCGVCLEACPNV
emb|CAA69873.1|         LVIDRSRMFNALKRVKAWIPIDGTYDLGPGPRMPEKKRQWAYELSKCMTCGVCLEACPNV
RAAC02027               LVVDRSRMFEALKRIKAWIPIDGTHDLGPGPRMSSEEQQIAYELSRCFTCGACVEACPNV
                        * :.*::::* :***.: ****::*:* .:**** ref|YP_080136.1|        NDKTNFMGPAPLSQVRLFNTHPTGAMNKSERLEAIMGDGGLAECGNSQNCVQSCPKGIPL
ref|NP_243957.1|        NSKSEFIGPAPLSQVRLFNAHPTGEMNKEERLQAIMGDGGLANCGNSQNCVQSCPKGIPL
ref|YP_148524.1|        NSKSNFIGPAPLSQVRLFNAHPTGAMHKAERLRAIMGDGGLANCGNSQNCVQSCPKGIPL
ref|ZP_01697535.1|      NSRSNFIGPAPLSQVRLFNAHPTGHMNRDERLEAIMGDGGLANCGNSQNCVQACPKGIPL
emb|CAA69873.1|         NEKTDFIGPAAISQVRLFNAHPTGAMNADERLDALMEDGGIEGCGNSQNCVRACPKGIPL
RAAC02027               NDKTSFIGPFAISQARLFNMHPTGKMNKEERLQALMGEGGIFECGNAQNCVEVCPKGIPL
                        *.::.*:  .:.** ** *:   *** *:* ::   *:**. ***** ref|YP_080136.1|        TTSIAALNRDTTVQA-------
ref|NP_243957.1|        TTSIAALNRSATLQS-------
ref|YP_148524.1|        TTSIAALNRETT----------
ref|ZP_01697535.1|      TTSIAALNRETT----------
emb|CAA69873.1|         TTSIAEMNRDTTKRMFKRWL--
RAAC02027               TTSIAVMNREVTYRAIGAWLRK
                        *****  :**..:*
```

FIG. 69

```
ref|YP_001124579.1|    -MNFDFTPEQEMLRQTVRKFVDKEIMPYIKEWDERGEFDRNIFKRLAELNLMGVCIPEQY
ref|YP_146298.1|       -MNFDFTPEQEMLRQTVRKFVDKEIMPYIKEWDERGEFDRNIFKRLAELNLMGVCIPEEY
ref|ZP_01697399.1|     -MHFELTEEQELLKKTVRNFVDKEIMPFIREWDENHHFETGLLKKLADLGLMGVCIPEKY
RAAC02040              MMDFSLSQEQMAVRDVVRKFVDEEILPHIREWDEKQHFEPGVLRRLAELGLMGVCIPEKY
ref|NP_691785.1|       -MDFHFSEEQQLLRKTVRDFTDKEIMPYISEWDRNGKFDPTLLNKLAELGLMGVCIPEQY
ref|ZP_01723229.1|     -MNFDMSTEHEMLRKTVRQFVDEEIIPYTAKWDAEGGFDAKIWSRLAELGLMGVCVPEQY
                        *.*  ::  *:    ::..**.*.*:**:*.*  :**  .   *:   :  :**:*.***::* ref|YP_001124579.1|    GGMGMDYNSLAIVCEELERGDTAFRTAVSVHTGLNSLTLLQWGTEEQKQKYLIPQARGEK
ref|YP_146298.1|       GGMGMDYNSLAIVCEELERGDTAFRTAVSVHTGLNSLTLLQWGTEEQKQKYLVPQARGEK
ref|ZP_01697399.1|     GGSGMDYNALAIVCEELERGDTAFRTAVSVHTGLNSLTLLQWGTEAQKQKYLVPQAKGEK
RAAC02040              GGAGMDYNTLAIVCEELERGDIAFRTAVSVHTGLNSLTLLQWGTEEQKQKYLVPQAKGEK
ref|NP_691785.1|       GGSGMDYNSLAIVCEELERGDTAFRTAVSVHTGLNSMTLLQWGNEQQKQKYLIPQAKGEK
ref|ZP_01723229.1|     GGSGMDYNSLAIVCEELERGDTAFRTAVSVHTGLNSMTLMQWGTEDQKQRYLIPQAKGVR
                       ** *****:*********** **************:**:***.* ***:**:***:*  :

ref|YP_001124579.1|    IGAFGLTEPNAGSDVASIQTTAVRDGDDYILNGQKTWISLADIADHFLVFAYT-DKSKKH
ref|YP_146298.1|       IGAFGLTEPNAGSDVASIQTTAVRDGDDYILNGQKTWISLADIADHFLVFAYT-DKSKKH
ref|ZP_01697399.1|     IGAFGLTEPGAGSDVAGIGTTAEKDGDFYILNGQKTWISLCDVADHFLVFAYT-DKAKKH
RAAC02040              IGAFGLTEPNAGSDVAAMRTTAVRDGDSYILNGSKIWISLADVADHFLVFAYT-DRSKKH
ref|NP_691785.1|       IGAFGLTEPGAGSDVAALQSTAVKQGDHYILNGQKTWISLCDIADHFIVFAYTKDRSEKH
ref|ZP_01723229.1|     IGAFGLTEPGAGSDVAAMSTTAVRDGDHYVINGQKTWISLCDIADHFIIFAYT-DKSKRH
                       *******.**.:  :  ::**  *::**.*  ****.*:**::** *:::* ref|YP_001124579.1|    RGISAFIVERTMPGFSSRPIKGKLGIRSGNTGELFFDNVRVPKENLLGEEGEGFKIAMSA
ref|YP_146298.1|       RGISAFIVERTMPGFSSRPIKGKLGIRSGNTGELFFDNVRVPKENLLGEEGEGFKIAMSA
ref|ZP_01697399.1|     HGISAFIVERTMPGFSSKAIKCKLGIRAGNTGELFFDNVRVPKENLLGEEGEGFKIAMSA
RAAC02040              HGITAFIVERGWEGFSTRSIKGLKGIRAGNTGELFFDHVRVPIENRLGEEGEGFKIAMSA
ref|NP_691785.1|       KGISAFIVERSWEGFSSKAIKGKHGIRSGNTGEIFFDHIKVPKENLLGEEGEGFKIAMSA
ref|ZP_01723229.1|     HGISAFIVERSMAGFSTSKAIKGKYGIRAGNTGELFFEDLRVPVENRLGVEGEGFKIAMSA
                       ::**    :::.** *:***:::::   ******** ref|YP_001124579.1|    LDNGRFTVAAGAVGLIMACLEASVKYCHERKTFGKEIGRHQLVQQMIARMEAGLQISRLL
ref|YP_146298.1|       LDNGRFTVAAGAVGLIMACLEASVKYCHERKTFGKEIGRHQLVQQMIARMEAGLQISRLL
ref|ZP_01697399.1|     LDNGRFTVAAGACGLIQACLEASVKYCHERKTFGHEIGKHQLVQQMIAKMEAGYQMSRLL
RAAC02040              LDNGRFTVAAGACGCIAACLEASVKYCHERETFGQPIGKHQLVQQMIAKMAANLDISRLL
ref|NP_691785.1|       LDNGRFTVAAGAVGQIMACIEASVKYCHERETFGKEIGKHQLVQQMIAKMEAGYQMSKLL
ref|ZP_01723229.1|     LDNGRFTVAAGAVGLIQACLEASVKYCHERETFGKPIGEHQLVGQMIANMEAGYQMSRLL
                       ***********  *  *  **:***********:***: **.****  ****.*  *.  ::*:**

ref|YP_001124579.1|    VYKVGFLKNEGRRCTRETSLAKWIACDYANQAADDAVQVHGAYGYSNEYPVERYLRNSKA
ref|YP_146298.1|       VYKVGFLKNEGRRCTRETSLAKWIACDYANQAADDAVQIHGAYGYSNEYPVERYLRNSKA
ref|ZP_01697399.1|     VFRAGELKNQGKRNTRETSLAKWQACDFANEAANDAVQIHGAYGYSSEYPVERYLRNSKA
RAAC02040              VYRAGWLKNQCLPNTRETSLAKWVACDAAWEAASDAVQIHGAYGYSNEYPVERYLRNAKA
ref|NP_691785.1|       VYRAGELKNQGKRNTRETSLAKWQACDFANKAADDAVQIHGAYGYSDEYPVERFLRNSKA
ref|ZP_01723229.1|     VYRVGELKNKGVRNTRETSLAKWQACDFANKAADDAVQIHGAYGYSDEYPVARYLRNSKA
                       *::.* ***:*  ********* *** *  :**.****:******.**** *:***:**

ref|YP_001124579.1|    PVIYEGTREIHTIMQAEYVLGYRKDKPLRKTLPAWRPDE
ref|YP_146298.1|       PVIYEGTREIHTIMQAEYVLGYRQDKPLRKTLPAW----
ref|ZP_01697399.1|     PVIYEGTREIHTIMQAEYVLGYRTDKPLSKMLPAWPFTE
RAAC02040              PVIYEGTREIHTILQAEYALGYRRDKPLSRRLPAWPFEE
ref|NP_691785.1|       PVIYEGTREVHTIMQAEYVLGYREDKLLNQMLPAW----
ref|ZP_01723229.1|     PVIYEGTREIHTIMQADYVLGRRQDKPLANRLPXWPFEE
                       *********:***:**:*.**  *  **  .  ** *
```

FIG. 70A

```
ref|NP_391000.1|        ---------VEELVYRSNLIGSDRTVCNWGGGNTSMKTTEKDFRGREIEVMWVKGSGSDL
ref|YP_080655.1|        ---------LAELVYRSNLIGADRSVCNWGGGNTSMKTTEKDFRGRDIEVMWVKGSGSDL
ref|NP_242416.1|        -------TGLDELVYRSNLIGSDRAVCNWGGGNTSMKTVEKDFRGREIAVMWVKGSGSDL
ref|YP_173878.1|        ---------LDELVYRSNLIGADRSVCNWGGGNTSMKTTEIDFRGNEVDVMWVKGSGSDL
RAAC02181               MIVTQEITALQQLVDRSRRLGADRSICNWGGGNTSAKTTMLDHMGREIRVMWVKGSGSDL
ref|YP_644452.1|        ------LSPLEELAYRSNLLGSDRAVANYGGGNTSMKLRQEDHAGREIDVLWVKGSGSDL
                                : :*. **. :*:**::.*:******  *     *. *.::  *:******** ref|NP_391000.1|        ATMKAHNFSGLKLDDIRPLIKRDQMPDEEMVDYLSHCMTDSKHPRPSIETLLHAFLPYKH
ref|YP_080655.1|        ATMSAGQFTGLRLDDIRPLMERSSMTDEEMTAYLSHCMMDGKHPRPSIETLLHAFLPFPH
ref|NP_242416.1|        ATMGAKNFTGLNLEDIRPLIEREEMSDEEMVEYLGHCMIDRNHPRPSIETLLHAFLPFKH
ref|YP_173878.1|        ATMGANNFTGLRLDDVLPLKEREAMTDEEMVAYLGHCLIDPRHPRPSIETLLHAFLPFKH
RAAC02181               AEATEKSFTALRLDEVLPLMERDAMTDEEMVDYLAHCMVEAKHPRSSIETLLHAFIPHTH
ref|YP_644452.1|        ATIRPEQFTGLRLAEILPLMERDSMTDEEMVSYLARCQLAPDMPRSSIETLLHAFIPHPH
                         *   .*:.*.* ::  ** :*. *.**. .:*  :    .*******:*. * ref|NP_391000.1|        VDHTHPDAIISICCADNGKQIAEDIYGNRFVWVPYVRPGFTLSKMIAEGVANNPHAELVL
ref|YP_080655.1|        VDHTHPDAIISICCCDNGKEIAEEIYGSRFVWVPYVRPGFALSKMIAEGVKNNPNAELVL
ref|NP_242416.1|        VDHTHPDAIISICCADNGKEIAKNLFGDRFVWVPYVRPCFSLSKLIAEGVQKNPHAELVL
ref|YP_173878.1|        VDHTHPDAIISLCCAENGRELAEELFGDRFVWVPYIRPGFALSKMIAEQVDANPKAELVL
RAAC02181               VDHTHPDSIIAICTSTNGREVAKEIFGDRAVWVPYLRPGFALSKLVAEAVRANPQCECVL
ref|YP_644452.1|        VDHTHPDAVNMLCCAANGEELARECFGDEAVWIPYLRPGFDLSKKVAAAVRGNPRARFVL
                        *******::  :*  . **..::*.:  :*.. **:**:**** ***  :*  *  **... **

ref|NP_391000.1|        MEKHGLVTWGETSETCYQKTISIIQEAEQYINDRINQHEVFGGKRYQPLPEDKRKQILAG
ref|YP_080655.1|        MEKHGLVTWGETSKESYDQTIAVIRFAEAYIKSRSEDHQPFGGQMVEPLAPEERKRILAD
ref|NP_242416.1|        MEKHGLVVWGETAKESYDRTISVINEAEAYIRSRINESVIFGGGKYTALAKEERMSMLAN
ref|YP_173878.1|        MEKHGLVVWGETAKESYDRTISVINEAEQFIEKKRGKNAPFGGAATAGLKKEERQALLAN
RAAC02181               MEKHGLITWGETSEACYANTVRIIGEAAEYLEAKQRGRVAFGGVKHPALFQEERRRIAVQ
ref|YP_644452.1|        LAKHGLVTWGETAEESYARTVEAVNRAAEFVFRRASRTEAFGGCRRLDPPPEEERRRLLAA
                        : ****:.****::   .* .*:   : .*   ::  :     ***          ::*   : .

ref|NP_391000.1|        IMPVIRGAVSEE-KKMILSYDDHDDVLEFVNSVQAFALSQIGAACPDHLVHTKRVPLYID
ref|YP_080655.1|        ILPVIRGAVSGE-KRMLVTWCDADDVLEFANSRRAPSLSQVGAACPDHLVHTKRVPAYIP
ref|NP_242416.1|        VMPVIRGAVSDE-KKMIVTFDDGDDVLEFVNSVDAARLSQVGAACPDHLVHTKMKPLFVK
ref|YP_173878.1|        IMPVLRGAVAHNGRNMIVTYDDSDPILEFVNSKEAKELSQIGAACPDHLVHTKRLPLFID
RAAC02181               ILPFVRGIVSER-QGAILSFDDSPEFLEFAGSHDAPSLSQVGAACPDHLVHTKRRPLFVD
ref|YP_644452.1|        VLPALRGELSSRGGPKILRADTSPDVTGFVCGRDSGELSQVGAACPDHLVHTKVRPLWVD
                        ::* :** ::  .    ::       . *.  . :   ***:**********  * ::

ref|NP_391000.1|        WNPETQDVIIKLADLIKSGVETFTSEYQAYFTRNQQ----DGDQIFESAPRVILIPGIGMV
ref|YP_080655.1|        WNPAEQDTEALVDRIKTEIAGFKESYAAYFQRNRH----EGDFMFEPAPRVMLIPGIGMV
ref|NP_242416.1|        WDPSMNDINQLIAAIKDGISSFKEEYKSYFERNKN----EGDVMFEPAPRVLLIPGIGMV
ref|YP_173878.1|        WVPDASDEEGLKQAVLNGIAAYKEDYIRYFERNRR----EGDTMFEPSPRVLLIPGIGLI
RAAC02181               WSPSE-GVDALKEKLKAGLTAYRDDYTAYYERNVD----LDVPMHDPFPRILLIPGLGVI
ref|YP_644452.1|        FDPASEGVDALERRLREGVRRYRERYEEYTRRNRARVGRGDEQMHDPNPRVVLISGVGLV
                        : *   ..  *    :  * *:  **  *  ::   .  **:**.*:*::

ref|NP_391000.1|        NTGKSYAMSKVSGALYRRAIAVMKGATALGQFVSLHENESYHVEYWPLELYKLTLAPPEA
ref|YP_080655.1|        TAGKSLAMAKVSRDLYRRAIAVMKGTEVLGNFVSLNEEESYNVEYWPLELYKLTLAPPEA
ref|NP_242416.1|        NTGKNVTMARVSGALYHRAIAVMKGDVTALGTFVSLNENESYNIEYWPLELYKLSLAPAEA
ref|YP_173878.1|        SSGKAVENAKVSRALYERAIAVMRGTNALGSFVSLNEAESYEIEYWPLELYKLSLAPKEA
RAAC02181               GTGKNKKMANIALDLYRRAIEVMRGATAIGEFVSLDEKESFDVFYWPLELYKLTLAPPEK
ref|YP_644452.1|        AAGRDLKAATLARDLYHRAISVIRGASSVDRFVSLDEEESYRVEYWPLELYKLTLAPPPK
                         :*:    :   :: **.*** *::*:    :. ****.* **: :**********:***
```

FIG. 70B

```
ref|NP_391000.1|    EFSRKVALITGGAGGIGSAACRRFAAEGGHVIVADLNIEGAQKIAGEINDAYGKGRAMAV
ref|YP_080655.1|    EFSRKIAFVTGGAGGIGSEACRRLALEGAHVVVADINIEGAEKTAAEINDQYGAERAYAV
ref|NP_242416.1|    EFSRKVAFVTGGAGGIGSETCRQFVAEGAHVVVADLNLEGAEKVVSEINEQYGTDRALAV
ref|YP_173878.1|    TFSRKVAFVTGGAGGIGSETSRQFAAQGAHVVLADLNLERAEEVAAEINGQFGAGRALAL
RAAC02181           ELSRKVAYITGGAGGIGSATARRLAEEGAHVVIADLAADAARRLAEELCADHGPGTAIGV
ref|YP_644452.1|    ELAGRVALVTGGAGGIGSAVAERLHEAGACVVVADLDGEGASEVASRL----GP-EGLAV
                    ::  ::* :********    ..::   *. *::**:  :  *  . . .:    * .  ..:

ref|NP_391000.1|    KMDVTKEEDVQSAFERAALAYGGIDIVVNNAGLATSSPFDETSLKEWNLNMNVLGTGYFL
ref|YP_080655.1|    RMDVTKEEEVQTAFEEIALKYGGIDLLVNNAGLATSSPLDETTLEEWNLNMNVLGTGYFL
ref|NP_242416.1|    KMDVTSEEQVQAAFKQASLTYGGIDIVVNNAGLATSSPFDETTLDEWNLNMNVLGTGYFL
ref|YP_173878.1|    KMDVTDEQAVKQAFADVARTYGGVDIVVNNAGLATSSPFDETTLQEWQLNLDVLATGYFL
RAAC02181           ALDVTQEDAVVRSIEEAILAYGGIDLFVSNAGLASSAPVTETSLAEWNKNVAVLGTGYFL
ref|YP_644452.1|    RADVTSEEEVARAFRAAALAYGGVDVVISNAGLASSAPLEETSLDLWRRNHAVLSEGYFL
                     ***.*: *   ::      ***:*:..:*****:*:*. **:*  *.  *  **. ****

ref|NP_391000.1|    VAREAFKQMKHQNRGGSMVFVGSKNSVYAGKNASAYSSSVKALETHLARCIAAEGGEFGIR
ref|YP_080655.1|    VAREAFKQMKKQGSGGSMVFVGSKNSVYAGKNASAYSSAKALEVHLARCIAAEGGPYGIR
ref|NP_242416.1|    VAREAFKQMKVQGTGGNMVFIGSKNSVYAGKNATAYSSAKALETHLARCIAAEGGPFGIR
ref|YP_173878.1|    VARQAFAQMKEQGTGGSMVFIGSKNSVYAGKNASAYSAAKAMEAHLARCIAAEGGTYGIR
RAAC02181           TSREAFRVMVEQGRGGAVVFVTSKNAVYAGKDASAYSAAKAMENHLARCLAVEGGPHGIR
ref|YP_644452.1|    VSREAFALLKRQGIGGSIVFVGSKNALAAGRNAAAYSSAKAAELHLARCLAEEGGPHGIR
                    .:*:**   :   *.  :: *::  ::*:*:. * *****:* * ,* ref|NP_391000.1|    VNSVLPDAVLQGSAIWGSSWREERAAAYGIEPDQLEEHYRKRTALLVNIYPEDIAEAIAF
ref|YP_080655.1|    ANSVLPDAVLQGSAIWDSKWREERAAAYGIEPDRLEEHYRKRTALSVNIYPADIAEAIAY
ref|NP_242416.1|    VNSVLPDAVLQGSAIWGSRWRQERATAYGIEPDQLEEHYRKRTTLLVNVYPGDIAAAILF
ref|YP_173878.1|    VNTVLPDAVLQGSAIWDSAWREERAAAYGIAADELEDHYKKRTTLGVHIFPADIAEAVLF
RAAC02181           VNIVMPDAVLQGSNIWNSAWREERARAYGIAPEELEDYYRRRTILGVNILPEDIAEAILF
ref|YP_644452.1|    VNTVNPDAVLQGSRIWDSAWREERARAYGIEPGELEEYYRNRTALKTNVYPEDVAEAVLH
                    .* * ********  **.* **:*** **** . .**::*:.** *  .:: * *:* *: .

ref|NP_391000.1|    FAS-SKAEKTTGCMITVDGGVPAAFTR
ref|YP_080655.1|    FAS-EKTAKTTGCMLTVDGGVPAAFSR
ref|NP_242416.1|    FAS-SKAEKTTGCMLTVDGGVPAAFTR
ref|YP_173878.1|    FAS-SKSEKTTGCMLTVDGGVPAAFPR
RAAC02181           FCS-PRSAKTTGCMLTVDGGVAAAFPR
ref|YP_644452.1|    FASGRRSGKSTGNVLNVDGGVREAYPR
                    *.*   ::  :*** ::.***** *:.*
```

FIG. 71

```
ref|YP_001487576.1|    -FEYHCQTNIMMGNGQSKEIGSIVEDLVLPG--AKVMIVTDSCVRNAGLVQPIEAYLQEA
RAAC02222              MFSYSIQTHIEFGDG---AVEHLPEHLVARGFGRRLLIVTDPGLVRAGVADRIAGLLSRA
ref|ZP_02211990.1|     LFSFELPTKIIYGAN---CLDNLCVEL-KENKGKKPIIITDKGVENAGILKKITDLLDKD
ref|NP_744947.1|       -FKFLLPSKIVMEPG---LRERTGEHLRQLGLAR-VLIVTDAGVKAAGLLDSVYASLDKA
ref|YP_001343716.1|    ---YFLPTRNVFGEN--AVEEVGTLMKSLG-GNNPLIVTDAFLAKNGMADQLAAVLSNA
ref|YP_633768.1|       -------TRIVFGAG---ALLRLPAQAQRLGIQRPLL-VTDAGVVKAGLAARVADVLNTA
                              :.       .         : :**  :   *:   :   *.

ref|YP_001487576.1|    GYSVFVFDQVSPNPRDNECLAGAELFRKEQASAVIAIGGGSPMDTAKAIALLGPN-GGIP
RAAC02222              GFVPRVFAEVRPNPDETVCLAGRGAFFEHRADGVVAVGGGSSLDAGKAIALLARQ-GGTP
ref|ZP_02211990.1|     DFPYVIYAGVEANPKDVNVEEGAKIARENDCDCIIAVGGGSPIDCAKSVGVLLAHNDTEI
ref|NP_744947.1|       GIAYEEVADIKANPRSDDINHTAQRYRGTGIDGLLAVGGGSAMDAAKAISLLLTH-DGRI
ref|YP_001343716.1|    GLKPVIFGGAEPNPTDKNVEEGIVFYNEHGCDSIISLGGGSSHDCAKGIGLIASN-GGRI
ref|YP_633768.1|       GLACEVFDRVEPNPTERDVFAGLEAYRSHSCDGIVALGGGSALDAGKLIQLLTTH-EPPL
                         .  **  .           .  ::::****. * .* .::    :

ref|YP_001487576.1|    EDYKSGKK----AYANLSPLICIPTTAGTGSEVTRSSVITLAASHKKITLKHALLRPTIA
RAAC02222              SDYALNRR----PYGPPAPVCAVPTTAGTGSEVTRSAVITERGTHRKLTLKHEYLRPPLA
ref|ZP_02211990.1|     KKYEGKTA----ATKPLPLFITIPTTSGTGSEITFSSVITDTKNKYKMTVKSKYTAAKVA
ref|NP_744947.1|       EDYEGSFT----LTHAIPPIVAIPTTAGTGSEVTCFSVITDTARHFKMNVLDYRIGPVLA
ref|YP_001343716.1|    QDYEGVDR----SHNAMVPLMAVNTTAGTASEITRFCIITDTARKVKMAIVDWRITPQIA
ref|YP_633768.1|       SRYDDAKGGDQYVRDDLPPLIAIPTTAGTGSEVGRSGVVTLEDTGRKTVIFSPYLLPRAA
                       . *                  : :.**:    ::*    *  :    . * ref|YP_001487576.1|    ILDPALTLTVPKSITAATGVDALVHAIEGYSCKVTNPISKAMGASAMETIVKYLPAAYKD
RAAC02222              VCDPTLTASLPPDVTAHTGVDALVHAIEGSTCKGAHPIARAYAREALGLIYRALPKAIKA
ref|ZP_02211990.1|     ICDPVLTLSVPPAVTAATGMDALTHAIEAYTATCSEPIADAVSLYAIELIYNNLKTAVFE
ref|NP_744947.1|       LLDSHITDTLPPSIAAATGMDALTHAIEAYTCRVANPISDGLALHAIRLISQHLKAAVQE
ref|YP_001343716.1|    VNDPLLMKGMPPSLTAATGMDALTHAIEAYVSTAANPLTDAAALMATTMIQQYLPKAVAN
ref|YP_633768.1|       ICDPELTLGLPPGITAATGMDAFTHCLEAYLANGFHPLADAVAIDGIYRVGRSLETAVRD
                        : *. :    :*  ::*   ::.*.:*.   .   .*::. .    .: :  . *   * ref|YP_001487576.1|    GSDLEARYKM-QEGSLLAGLCFGSADVAAVHCLAEALGSLYDTPHGIANAVFLPYVMQFN
RAAC02222              G-DPASRHDM--LLGSLLAGLAFGSTDVASVHCLAEALGSLYETPHGLANAVMLLPTLRYN
ref|ZP_02211990.1|     GDNLQARSAM-LMGSMLAGIGFSHSDVASVHCISEALGGMFDLSHGVCNAVLLPHVMEYN
ref|NP_744947.1|       PDNQAAREQM-LVASLIAGMAFGNADVGSVHCISEAIGGMYDTPHGVGNAIFLPFVEFGHN
ref|YP_001343716.1|    GDYMKARDKM-AYAQYLAGIAFNNASLGYVHAMAHQLGGFYNLPHGVCNAILLPYVEEFN
ref|YP_633768.1|       GKDLAARTDM-MVAAMEGAMAFQKG-LGACHALAHALTPVSNVIHIGLANAIVLPVVMEFN
                       :*   *       ..: *    :.  *.::. .  : : :.*    .* ref|YP_001487576.1|    AAENKVLHAELAKIMSFADKTDSDDVATQKLIDGMYTFTK--NLGIP-VLKDLSYVKEED
RAAC02222              LPCAVEPYAWIARAMGLAREEDGAERAAEALLAGLRTWLE--SLDIP-KLRDLPGVRPSD
ref|ZP_02211990.1|     KDYCVAKYARVAKAM-GFEFK-SDDEGADLAVKAVQQLAL--DVKLP-LFSEL-NVEPKD
ref|NP_744947.1|       RDADIVRHAQVAYAL-GIDPTLSPVDAAEEAAVGHLFQMSK--DLGIP-RFAEVKGVREED
ref|YP_001343716.1|    LIGNLNRFRDIAKAMGENIDGLCTDDAALKAIGAIRRLSK--QVGIP-ANLQLLGVKPED
ref|YP_633768.1|       RAVCTARLARVAVAL-GDTTQAREEVLAGNAIDRVRKL-N--AAVGIPSRLRD-AGVQEKD
                         :*   :             :          :    :*   :   *. .* ref|YP_001487576.1|    FEKMAELAEQNGSTSSNVRTVTKADYLDILKAAF--
RAAC02222              FDRLAELAYENTSTPSNPRPMAVSDYRAVLEMAYAD
ref|ZP_02211990.1|     FDILADKSAINISTESNPRPMSKEDYLNVLNNAY--
ref|NP_744947.1|       FPTIAEKSKQNFSDASNAKAMSVEAYHDIITTAY--
ref|YP_001343716.1|    FDVMAENAMKDVCMLTNPRKATKQQVIEIFQRAY--
ref|YP_633768.1|       LERIAEKAFQDASHLSNPRKVSQADLLALAREAY--
                       :  :*: :   :. .:*  :        :   *:
```

FIG. 72A

```
ref|ZP_01869175.1|      ---------------------------------------------------NNFTFNL
ref|ZP_00989613.1|      ---------------------------------------------------NNFNFQL
ref|YP_146053.1|        -------------------------------------------------------FWL
RAAC02274               MGRTRSTNTRSSSTYTRRSCTSSKTAIGIPLCCPTGPDAIDFCEVVRRMPYIRSGFQFMA
ref|YP_001276414.1|     ------------------------------------------------------FEYHM
ref|YP_001211401.1|     ---------------------------------------------------------FWT
                                                                                 :

ref|ZP_01869175.1|      RTVVHSGASSIEA---IPTLFKAKGAQRVLLVSDKGLESLGFVERLASLFS--------T
ref|ZP_00989613.1|      KTIVHAQENGIEN---IPSLFGRLGAQRVVLFSDKGLESLGFVEQFSALFVNEKVNQPGY
ref|YP_146053.1|        RTAIYTGSNTRAL---VPDLFRGLGAKRVLLLSDRGLEQAGVVEKVASLFDLTT-----H
RAAC02274               RTTITNGVGSRVF---LPETVRGLCCKRAFVVTDPGIVRAGLLDKILELFDLVP------
ref|YP_001276414.1|     RTRLMYKTGLARD--FANEVVQ-LGVQRALLVADPGVVQAGLLDRVREGLE---------
ref|YP_001211401.1|     SGTIITGRGSLKR--IADEAKG-LGATRVLIVTDPVLLKTGLIERVKEA--LAP------
                                       :  .    * *.::.:*  :   *.:::.

ref|ZP_01869175.1|      EEKVKLAGIYTDIEADASCLDINRALEFAKQVNADSILALGGGSVIDASKGIKYGLEHK-
ref|ZP_00989613.1|      EQAVQLVGVYTDIAPDATCDNINAAIEFANSVNADAILSVGGGSVIDASKGVKYAFHKQ-
ref|YP_146053.1|        GVGPELVGIFLDIRQDAESECVNEAVRYARAVGADALLAVGGGSVLDTAKGVKYALFKG-
RAAC02274               -TPVTIAGVFDRVEQDAKAHIINEAARAYRECAADSLIALGGGSVLDTVKGIKWMVSRG-
ref|YP_001276414.1|     -GSITVAGAFTDVPPDSSVATVEQGAAVARDAGADVLIAVGGGSAIDTAKAMRILLTEG-
ref|YP_001211401.1|     -AGLE-TGIFSGVEPEPRLQIVTECLKAVKEGGYDLIVAVGGGSSMDVSKAASVLMTN--
                              .*  :     :   .  *  :::****  :*. *.       . .

ref|ZP_01869175.1|      ---LDDIRDAIQGGGRLEVGPD---VKPFSIPHIGVPTTAGTGAEASPIAVFYNEREQVK
ref|ZP_00989613.1|      ---IDDIRTVIAGGGHIDVWPN---NEDIRVPHIAVPTTAGTGAEASPIAVFYNEHENIK
ref|YP_146053.1|        ---LRDIKEAIPGGLRYESFPQ---AQFMPIPHIAIPTTAGTGSEVSPIAVIYNEELRLK
RAAC02274               ---LTDIRPALIGN-VLEMWPE---AQPIFIPHVALPTTAGTGAEASPIAVVFHDDLGVK
ref|YP_001276414.1|     -----GTLYDYQGA---NLL-----TRPLF-PMIATPTTAGTGSEVTPVAVIRDEQAEQK
ref|YP_001211401.1|     ----PGTINDYLGV---NLI-----PRP-GIPVIAVPTTAGTGSEVTPIAILSDVEEQLK
                               .    *   :      . *  ::.*******:*.:*:*:. .       * ref|ZP_01869175.1|      ASLVVSGLECDIAVLDPELTVSLPAALTVSTGMDALTHAIEALASPLSNTFTDAYATQAC
ref|ZP_00989613.1|      ASLVASGLEADIAILDPTVTTKLPAHLTRSTAMDALTHAVEAIVSPMSNAFTDAYGIQAA
ref|YP_146053.1|        TNIINPFINADVAVLDPDLTVGLPPKVTAFTGMDALTHAIEALASPMATALTDACALQAI
RAAC02274               VNLINPFINADIAILDPELTVGLPPSITAFTGFDALTHAIEGFFSPQANPETDAYAIQSA
ref|YP_001276414.1|     LFFLSPYLGPELAILDPEMTRTLPPRLTAATGMDALSHAIETFVGVGANPITDSLAIQAI
ref|YP_001211401.1|     KGVVSPYLLPRVAIVDPELTVTMPPAITAATGMDALTHAVESYISVNATPITDILALEAI
                         .: . :   :*::.** :*  :*. :*  *.:***:**:*    :...:**  .::

ref|ZP_01869175.1|      RLILNNLPQVLQSPQNVAARCELLQASTMAISAFYSS----LGGIPIHNCAHAFGAVAHI
ref|ZP_00989613.1|      KLIIENLPLALKEPENLTARGNLLQASTMAISAFYSS----LGGIPIHNCAHAFGAISHI
ref|YP_146053.1|        RLIRDYLPEAVRDGGDIRARLEMLHASLLGITAFSFA----LNAIPVHNFAHAYGAMFRI
RAAC02274               RMIFENLPKAVANGQDLTARANMLMASTMAIISFSLA----LNAIPVHNMAHAFGAKFGI
ref|YP_001276414.1|     DMISNYLRAATHNGEDMEARGNMLIAAAIAGIAFSTT-GIGVNTGIIHAASHTVGAAYHV
ref|YP_001211401.1|     RLIALNLRTAVANGQDIEARSNMSMASLLAGIAFANA-----GVGAVHALAYPLGAQFHV
                         :*  *   .   ::  **   :: *:  :.  :*  :       :*  :*. **   :

ref|ZP_01869175.1|      PHGDANSVLLPVVIEALPEFYLPSINKLAAVFGI-SPSLTDA-EKHQEVVHSLRAFQALV
ref|ZP_00989613.1|      PHGDANTVLVPVVIEALPEFYMPNAAKLAQAFSV-DTTGTDE-MVYQRVLDFLNNFQTSV
ref|YP_146053.1|        PHGLANAVFLPVVMEAIPELYLPKAKLIAQALGIYDHGQGNE-ALLVKSIERIRQLRDDI
RAAC02274               PHGLANAVLLPNVMAAMPAFYRARTREFMAAIGLDAPSDPD--AALESFIQRIRDLRQQV
ref|YP_001276414.1|     HHGTANSILLPHGMRFNAPVVPNRMVRIARAMGVNAGGRSEEDVIADG-IAAVAKLAADC
ref|YP_001211401.1|     PHGVANAVLLPYVMESNLLGALPRFKTMALAMGEKVEDLSDR-LAADKFNEAIKLLAADI
                         ** **::::*    :       :      . :              :    :   :
```

FIG. 72B

```
ref|ZP_01869175.1|      NATQSFAKWNLDDNKKAQIVSGIEKDISFQFY----------------
ref|ZP_00989613.1|      GAMKRFSSWDFDAQEKSNIAEAIEKDICFQFYPISKQTIETI------
ref|YP_146053.1|        GLPADFADYPMTEEQFAATIPAVASDPAAISFPMPPELIRAIGERV--
RAAC02274               GLPATFADYQLDKRQLGKMVDLVHADPSGVVYRLPDAIIQRVTREVAS
ref|YP_001276414.1|     GLPTRLRDVGVPEDALPALAEGTLMDGAIMSNPRPVEYEDALAILR--
ref|YP_001211401.1|     RIP---------------------------------------------
```

FIG. 73A

```
ref|YP_001636911.1|    --------LPHYDLYIDGAWQPAENGQTFTVYDPATSQPIATCASATHSDVDRAVRAARAA
ref|ZP_01514632.1|     --------LPHYDLYINGAWQPASSKQTFTVFDPANGQPLATCASASPTDVDRAIAAARSA
ref|YP_001274650.1|    --------LPCYGLYIDGSWVDAEGGTM-PVNEPALGRPMARVARGSAADVDRAVAAAREA
ref|YP_001546552.1|    --------LRSFGLYIDGAWVAASDAASETLYNPATGEPVAQVARATIHDIDRAVGAARKS
ref|YP_146052.1|       ---THVQVHHFPLFIDGQWQPATSGETFHVYNPATGEVVATVAKATADDVDRAVKAARKA
RAAC02275              MVMTSVRLPEYGMFIDGEYTPAESGEMFEVVNPATGQPCARVAKSDARDVDRAVRSARRA
                                   :  : ::*:*  :  *   .   : :**  ..  *  * .   *:***: :** :

ref|YP_001636911.1|    FDHGPWPHTSPAQRAEILHAIADALEARNFELAEIESRDAGVPIRKTTYNDITLGLEILR
ref|ZP_01514632.1|     FDHGPWPHTSPARRAEILIIALADALEARNFELAEIESRNAGVPLRKTTYNDITLGIEILR
ref|YP_001274650.1|    FDRGPWPHTPGHERARVLNATADLIEEHTAEFAELETRNLGAPLRKTTFVDIPWSVEHLR
ref|YP_001546552.1|    FDIGSWAQMRPVDRAKTIEAIADLLEENTDELAELETLNGGATLRKSSWLDIPVGIEHLR
ref|YP_146052.1|       FDETDWKAMKPKERARVLNAIAQAIAANAQELAYLEAISSGGTIRRISSIDILQTVDLFQ
RAAC02275              FESGEWSRAKPHERAQVLLRFADEIVAHAQEIAFLEILTSGATVRRVSNADLLLIVDLLQ
                       *:  *      **. :  :*: :   *:* :*    * .:*: :  *:    :: ::

ref|YP_001636911.1|    GCAEMARKHPY-EPLPWNDLPSVSWNFVWREPIGVCAQIIPWNYAFCMAAWKLGPALATG
ref|ZP_01514632.1|     GCAEMARKHPY-EPLPWNDLPSVSWNFVWREPIGVCAQIIPWNYAFCMAAWKLGPALATG
ref|YP_001274650.1|    VFAELATIHPY-EPLPWTDVPSVSWNFVWREPIGVCGQIVPWNYPLLMTIWKIAPALAAG
ref|YP_001546552.1|    YFADLARQHPM-QTLPYIDFPSPSANAVWREPIGVCGQIIPWNYPFLMAIWKIGPALAAG
ref|YP_146052.1|       TMANIVQEYPFSETLPIPPFPGPAHNFVWREPIGVCAAITPWNLPLMIASWKIAPALAAG
RAAC02275              QTARFAQAYEYAKTLPLRPFPQPSHNQVWREPVGVCAGITAWNYPLILAMWKLAPALAMG
                        * :.  :    :.**   .*  :  * ***:*. * . .:  :: :.**** * ref|YP_001636911.1|    NTVVFKPSSLAPLSTLAIFQTIHDLNLLPKGVINLVLGPGGDVGEYLVTHPAVDKVAFTG
ref|ZP_01514632.1|     NTVVFKPSSLAPLSTLAIIQAIHELNLLPKCVVNLVLGPCGEVGEYLVAHPDVDKVAFTG
ref|YP_001274650.1|    NTIVLKPASYTPLTALRLTQLIHEAGLLPRGVLNVVTGPGAEVGDALARHPGVDKVSFTG
ref|YP_001546552.1|    NSLVLKPASLTPVTALRMAELIHEADLLPHGVFNVVTGPGGLVGERLTSHPAVDKIAFTG
ref|YP_146052.1|       NTIVVKPASYTPLSTLKLAEIISSF-VPP-GVINVVAGPGADVGEALVRHPQVDKVAFTG
RAAC02275              NSIVLKPASNTPLSTLKLAELAAKA-GLPKGVFNVVTGPGSSVGEALVTHPEVDKIAFTG
                       *::*.**:*  :*:::*  : :   .       *  **.:* *.  : *.   *:*:*** ref|YP_001636911.1|    STEVGRKIMALAAPHIKRVTLELGGKNAMLILPDADLDLVVDGVLWGAFYHSGQLCEAGS
ref|ZP_01514632.1|     STEVGRKIMALAAPHTKRVTLELGGKNAMIILPDADLDLVVDGVLWGAFYHSGQLCEAGS
ref|YP_001274650.1|    STETGRHIMRLASDTIKRLTLELGGKSPSLVMPDADLELATDGVLFGVFFNGGQSCEAGT
ref|YP_001546552.1|    STEVGRRIAEVAGRNLKRVTLELGGKSPVVVLPNADLDLAVDGAIWAAFMHSGQSCEAGT
ref|YP_146052.1|       STEVGRRIMALAAETVKNVTLELGGKSPNILLEDADLDLAVPGSLFGVFLHSGQLCESGT
RAAC02275              STEVGKRIMQLAAQGVKRVTLELGGKSPATVLPDADLDLATPGILFGVFLHAGQVCECGT
                       *** *::*  :*.  :*.: ********..  ::: :***:*.   *  :: * :.** **.*:

ref|YP_001636911.1|    RLLVPHALHDTLVERLVERVRGMRIGDPMDLETDIGPLISERQREKVEYYIAVGREEGAT
ref|ZP_01514632.1|     RLLVPHALHDTLVSRLVERVRTMRIGDPMDLETDIGPLISEQQRAKVERYIAIGREEGAT
ref|YP_001274650.1|    RCLVPESLHDEFLERLVTRARSLRIGDPLDLETDLGPLVSEAQCRIVEEYIEVCKNEGAR
ref|YP_001546552.1|    RLLLPDSLHDQFVERMVARVEQLVLGDPLDLTTDLGPLVSAAQKRAVEAYIELGIQEGAT
ref|YP_146052.1|       RLFVPDRLHDEVVERLVALTKTLQIGHPLDPATDVGPVISKRQKETVLSYIEAGKQEGAT
RAAC02275              RVIVHEDIYEEVVNRLAEMASQLKLGNPLDDKVGMGPIISESQMNTILSYIESGKAEGAR
                       *  ::   . :::  ..:*:.       .   : :*.*:*       ..:**::  *   :    **  *  *** ref|YP_001636911.1|    VVIGGGRPIGEAFANGHYVEPTIFTGVRPEMRIAREEIFGPVLSVIAYDEIGEAIRIAND
ref|ZP_01514632.1|     VVIGGRRPPDEARAKGYYVEPTIFTGVRPEMRIAREEIFGPVLAVIAYEEVSEAIKIAND
ref|YP_001274650.1|    LVTGGRRVRVPGFERGPFVEPTIFTNVLNGTRLAQEEIFGPVLSVIPYRTVTEAIELANA
ref|YP_001546552.1|    LRCGGVGIDDPNLANGHFVRPTIFTNVHNQMRIAQEEIFGPVLSVIRYHTVGEAITLAND
ref|YP_146052.1|       IVCGGHEVEVPGCEGCHFVAPTIFSNVTNDMKIAQEEIFGPVLSIIRYHDVEEAVTMAND
RAAC02275              LVCGGQRATGGGLDAGYFVQPTIFADVDNRMKIAQEEIFGPVLAVMKARDVDEAVRLAND
                       :  **        *  :* ****:.*   ::*:**********::    :   **: :**
```

FIG. 73B

```
ref|YP_001636911.1|    SIYGLAASVWSRDLQHALSVVRRIRAGTVWINEHHVLNPRAPFGGYRQSGFGREMGRYGL
ref|ZP_01514632.1|     SIYGLAASVWSRDLQQALAVAKRIRAGTVWINEHHVLNPQAPFGGYRQSGFGREMGRYGL
ref|YP_001274650.1|    SRYGLGAAVWSRDLQGAIEVAKRIRTGTVWINDHHIILPRAPFGGYKQSGIGREHGIYGL
ref|YP_001546552.1|    TNYGLAASVWSRDLQDAQEVARAIRAGTVWINDHHLINAKAPFGGYKDSGIGRELGPNAL
ref|YP_146052.1|       TIYGLAAGVWTRDVNKAYAIAGRLQAGVVWINDWHMLRNDAPFGGYKQSGIGREMGKYSL
RAAC02275              TVYGLAGGVWTRDLNQAYRIAREIRAGTIWVNDWHMFRSDAPFGGYKMSGFGREIGPYAL
                       : *...:**:: *  :.  :::*.:*:*: *::   ****: :*** *  .* ref|YP_001636911.1|    DEYTEVKHIHVDLMQRRQGRLWWDTLLPE--
ref|ZP_01514632.1|     DEYTEVKHIHVDLMQRRQGRLWWDTLLPE--
ref|YP_001274650.1|    MAYTELKHIHVDLMQKRTGRVWWDVLIP---
ref|YP_001546552.1|    DAYSEIKHIHTDLTQERTRRIWVDIVTP---
ref|YP_146052.1|       DAYTQLKHVHTSMVPELGKRKWYQVL-----
RAAC02275              DEYTQLKHVHASFVHELENRHWYSIVLPDRA
                       *:::*:*:..:  .    *  *  . :
```

FIG. 74

```
pdb|1W85|A              ---------------------------------QFPT--FQILNEEGEVVNEEAMPELSDE
sp|P21873|ODPA_BACST    ---------------------------------QFPT--FQILNEEGEVVNEEAMPELSDE
ref|YP_146911.1|        ---------------------------------QFPT--FQILNEEGEIVNEEAMPELSDE
ref|YP_001421036.1|     ---------------------------------------QILNAEGEVVNKDAMPDLSDD
ref|NP_243521.1|        ------------------------------LEKVEGQFET--FQILNEEGEVVNEAAMPDLSDE
RAAC02426               ------------------------------MTMLSQVVARFEIPYVQIVDENGNVVNPDLVPELSDD
                                                                **::  :*::**    :*:***:

pdb|1W85|A              QLKELMRRMVYTRILDQRSISLNRQGRLGFYAPTAGQEASQIASHFALEKEDFILPGYRD
sp|P21873|ODPA_BACST    QLKELMRRMVYTRILDQRSISLNRQGRLGFYAPTAGQEASQIASHFALEKEDFILPGYRD
ref|YP_146911.1|        QLKELMRRMVYTRILDQRSISLNRQGRLGFYAPTAGQEASQIASHFALEKEDFILPGYRD
ref|YP_001421036.1|     QLKELMRRMVYIRILDQRSISLSRQGRLGFYAPTAGQEASQIASHFALEQDDFILPGYRD
ref|NP_243521.1|        QLQELMKRMVYTRIWDQRAISLNRQGRLGFYAPVAGQEASMLGSQFALDKEDWILPGYRD
RAAC02426               DLRELMKRMVFTRIWDQRAIRLSRQGRLGFYAPVSGQEASMIGSEFATKKEDFLLPGYRD
                        :*:*:*:  *:* *.********.:*** :.*.**  .::*::****** pdb|1W85|A              VPQIIWHGLPLYQAFLFSRGHFHGNQIPEGVNVLPPQIIIGAQYIQAAGVALGLKMRGKK
sp|P21873|ODPA_BACST    VPQIIWHGLPLYQAFLFSRGHFHGNQIPEGVNVLPPQIIIGAQYIQAAGVALGLKMRGKK
ref|YP_146911.1|        VPQIIWHGLPLYQAFLFSRGHFHGNQIPEGVNVLPPQIIIGAQYIQAAGVALGLKMRGKK
ref|YP_001421036.1|     VPQLIWHGLPLHQAFLFSRGHFKGNQMPEGVNALSPQIIIGAQIIQTAGVALGLKKRGKK
ref|NP_243521.1|        TPQIVFHGLPLYQAFLYSRGHFECGQIPDGVNVLMPQIIGAQIVQAAGVAMGLKRKGKQ
RAAC02426               IPQLYFHGYPLHQLFLYSRGHQLGGKVPEGVNCMVPQIIIGAQIVQAAGVGLAFKLRGEK
                         :**: :** **:*  **:****     *  :****    *:** :* *::: *  :

pdb|1W85|A              AVAITYTGDGGTSQGDFYEGINFAGAFKAPAIFVVQNNRFAISTPVEKQTVAKTLAQKAV
sp|P21873|ODPA_BACST    AVAITYTGDGGTSQGDFYEGINFAGAFKAPAIFVVQNNRFAISTPVEKQTVAKTLAQKAV
ref|YP_146911.1|        AVAITYTGDGGTSQGDFYEGINFAGAFKAPAIFVVQNNRFAISTPVEKQTIAKTLAQKAV
ref|YP_001421036.1|     AVAITYTGDGGASQGDFYEGMNFAGAFKAPAIFVVQNNRYAISTPVEKQSSAQTIAQKAV
ref|NP_243521.1|        NVAITYTGDGGASQGDFYEGMNFAGAYNSPAIFVVQNNRFAISVPVEKQSAAKTIAQKAV
RAAC02426               RVAVTYTGDGGSSQGDFYEGMNFAGAMNLPVVFFVQNNQYAISVPRELQTRAQTLAQKAI
                         **:*******.*******:******   :**:****::***.*  *:  *::*:****:

pdb|1W85|A              AAGIPGIQVDGMDPLAVYAAVKAARERAINGEGPTLIETLCFRYGPHTMSGDDPTRYRSK
sp|P21873|ODPA_BACST    AAGIPGIQVDGMDPLAVYAAVKAARERAINGEGPTLIETLCFRYGPHTMSGDDPTRYRSK
ref|YP_146911.1|        AAGIPGIQVDGMDPLAVYAAVKAARERAINGEGPALIETLCFRYGPHTMSGDDPTRYRSK
ref|YP_001421036.1|     AVGITGVQVDGMDALAVYAATAEARQRAINGEGPTLIETLTFRYGPHTMSGDDPTKYRTK
ref|NP_243521.1|        AAGIEGIQVDGMDVLAVYAATKQARERALAGDGPTLIETLCYRYGPHTMAGDDPTRYRSS
RAAC02426               AAGIPGVQVDGMDVLAVYHVMHEALERARNGEGPTMIEAVTFRYGPHTMSGDDPTRYRTK
                        *.** *:****** ****     *  :** *:**::**  :******.*****:**:.

pdb|1W85|A              ELENEWAKKDPLVRFRKFLEAKGLWSEEEENNVIEQAKEEIKEAIKKADETPKQKVTDLI
sp|P21873|ODPA_BACST    ELENEWAKKDPLVRFRKFLEAKGLWSEEEENNVIEQAKEEIKEAIKKADETPKQKVTDLI
ref|YP_146911.1|        ELENEWAKKDPLVRFRKFLEAKGLWSEEEENRVIEQAKEDIKEAIKKADETPKQKVTDLI
ref|YP_001421036.1|     EIENEWEQKDPLVRFRKFLENKGLWSEEEENKVIEQAKEEIKQAIKKADGESKPKVTELI
ref|NP_243521.1|        DLDDEWEKKDPLVRFRKFLEGKGLWSEEQENEVVEKAKEDIKAAIKKADAAPKQKVTDLI
RAAC02426               DVQEEWEKKDPLIRFRKYLEEKGLWSQEEEAYIEEAKETVNNALKEADAAEKMTIPGLI
                        ::::** :****:****:**  *****:* *:  :****  ::  *:***    *  :. **

pdb|1W85|A              SIMFEELPFNLKEQYEIYKEKES-
sp|P21873|ODPA_BACST    SIMFEELPFNLKEQYEIYKEKES-
ref|YP_146911.1|        SIMFEELPANLKEQYEIYKEKES-
ref|YP_001421036.1|     ENMFEEPTFNLKEQLEIYKAKES-
ref|NP_243521.1|        GFMFEEAPQHLREQLEEYTAKES-
RAAC02426               DSMFEELTPTLKRQRAEFAGEEAN
                         ****  .  *:.*   :  :*:
```

FIG. 75

```
sp|P21874|ODPB_BACST    ---------------------------------------------------MAQMTMVQAI
pdb|1W85|B              ---------------------------------------------------AQMTMVQAI
ref|YP_001125046.1|     ---------------------------------------------------MAQMTMVQAI
ref|YP_146912.1|        ---------------------------------------------------MAQMTMVQAI
ref|ZP_01696304.1|      ---------------------------------------------------MAQLTMIQAI
RAAC02427               --------------------------------------------MPARRRTDMAQMTMIQAI
                                                                                ::*** sp|P21874|ODPB_BACST    TDALRIELKNDPNVLIFGEDVGVNGGVFRATEGLQAEFGEDRVFDTPLAESGIGGLAIGL
pdb|1W85|B              TDALRIELKNDPNVLIFGEDVGVNGGVFRATEGLQAEFGEDRVFDTPLAESGIGGLAIGL
ref|YP_001125046.1|     TDALRIELKNDPNVLIFGEDVGVNGGVFRATEGLQAEFGEERVFDTPLAESGIGGLAVGL
ref|YP_146912.1|        TDALRIEMRNDPNVLVFGEDVGVNGGVFRVTEGLQAEFGEERVFDTPLAESGIGGLAIGL
ref|ZP_01696304.1|      TDALRTELKNDENVLVFGEDVGVNGGVFRATEGLQKEFGKDRVIDTPLAESGINGLAIGL
RAAC02427               THALDLELARDERVLVFGEDVGKNGGVFRATEGLQQKYGPNRVFDTPLAESGIIGLANGL
                        *.**   *:  .* .:** *.***  ::*  ::****  * ** sp|P21874|ODPB_BACST    ALQGFRPVPEIQFFGFVYEVMDSICGQMARIRYRTGGRYHMPITIRSPFGGGVHTPELHS
pdb|1W85|B              ALQGFRPVPEIQFFGFVYEVMDSICGQMARIRYRTGGRYHMPITIRSPFGGGVHTPELHS
ref|YP_001125046.1|     ALQGFRPVPEIQFFGFVYEVMDSISGQMARIRYRTGGRYHMPITVRSPFGGGVHTPELHS
ref|YP_146912.1|        ALQGFRPVPEIQFFGFVYEAMDAICGQMARIRYRTGGRYHVPITIRSPFGGGVHTPELHS
ref|ZP_01696304.1|      ALQGFRPVPEIQFFGFVFETMDSIHGQMARYRFRTGGDLKMPITIRAPFGGGVHTPEMHA
RAAC02427               AIQGFRPVPEIQFGFVFEAFDQIAGQLARTRYRTGGRYTAPVTIRSPFGGGVHTPEMHA
                        *:************:*..:*  * **:**  *:****    *:*:*:**********:*:

sp|P21874|ODPB_BACST    DSLEGLVAQQPGLKVVIPSTPYDAKGLLISAIRDNDPVIFLEHLKLYRSFRQEVPEGEYT
pdb|1W85|B              DSLEGLVAQQPGLKVVIPSTPYDAKGLLISAIRDNDPVIFLEHLKLYRSFRQEVPEGEYT
ref|YP_001125046.1|     DSLEGLVAQQPGLKVVIPSTPYDAKGLLISAIRDNDPVIFLEHLKLYRSFRQEVPEGEYT
ref|YP_146912.1|        DSLEGLVAQQPGLKVVIPSTPYDAKGLLISAIRDNDPVIFLEHLKLYRSFRQEVPEGEYT
ref|ZP_01696304.1|      DSLEGLMAQTPGIKVVIPSTPYDAKGLLISAIRDNDPVVFLEHMKLYRSFREEVPEEEYT
RAAC02427               DSLEGLFVQTPGIKVVIPSTPYDAKGLLLSAIRDPDPVIFLEHMKLYRSFRQEVPEDDYT
                        ******..* **:***************:***** ****:****:*******:****  :**

sp|P21874|ODPB_BACST    IPIGKADIKREGKDITIIAYGAMVHESLKAAAELEKE-GISAEVVDLRTVQPLDIETIIG
pdb|1W85|B              IPIGKADIKREGKDITIIAYGAMVHESLKAAAELEKE-GISAEVVDLRTVQPLDIETIIG
ref|YP_001125046.1|     IPIGKADIKREGKDITIIAYGAMVHESLKAAAELEKE-GISAEVVDLRTVQPLDIETIIG
ref|YP_146912.1|        IPIGKADIKREGKDITIIAYGAMVHESLKAAAELEKE-GISAEVVDLRTVQPLDIETIIG
ref|ZP_01696304.1|      IPLGKADVKREGKDISIIAYGAMVHESLKAADELEKE-GYSAEVVDLRTVSPLDVETIVA
RAAC02427               IPLGVANVVREGKHATVIAYGAMVHVALKAAEQWSKEKGLEAEVIDLRTVNPIDIDTIVA
                        **:*  *::  ****.  ::********  :****  :  .** *  .***:*****.*:*::**:.

sp|P21874|ODPB_BACST    SVEKTGRAIVVQEAQRQAGIAANVVAEINERAILSLEAPVLRVAAPDTVYPFAQAESVWL
pdb|1W85|B              SVEKTGRAIVVQEAQRQAGIAANVVAEINERAILSLEAPVLRVAAPDTVYPFAQAESVWL
ref|YP_001125046.1|     SVEKTGRAIVVQEAQRQAGIAANVVAEINERAILSLEAPVLRVAAPDTVYPFAQAESVWL
ref|YP_146912.1|        SVEKTGRAIVVQEAQRQAGIAANVVAEINERAILSLEAPVLRVAAPDTVYPFAQAESVWL
ref|ZP_01696304.1|      SVEKTNRAIVVQEAQRQAGVAANVVAEINERAILSLEAPVLRVTAPDTVYPFSQAEGVWI
RAAC02427               SVKKTNRATVVQEAQRSAGAAAAEIVAQINENAIYYLEAPVLRATPPDTVYPFGMIEDEWL
                        **:**.*********.** **::**:***.**  ******.::.*******.  *. *:

sp|P21874|ODPB_BACST    PNFKDVIETAKKVMN-
pdb|1W85|B              PNFKDVIETAKKVMN-
ref|YP_001125046.1|     PNFKDVIETAKKVMN-
ref|YP_146912.1|        PNFKDVIETAKKVIN-
ref|ZP_01696304.1|      PTYKDILEKAKETLT-
RAAC02427               PTPEYVLKTLDKVMSL
                        *. : :::. .:.:.
```

FIG. 76A

```
sp|P11959|DLDH1_BACST      MVVGDFAIETETLVVGAPGGYVAAIRAAQLGQKVTIVEKGNLGGVCLNV
pdb|1EBD|A                 --------ETETLVVGAPGGYVAAIRAAQLGQKVTIVEKGNLGGVCLNV
ref|YP_001125048.1|        MVVGDFAIETETLVVGAPGGYVAAIRAAQLGQKVTIVEKANLGGVCLNV
ref|YP_146914.1|           MVVGDFAIETETLVVGAPGGYVAAIRAAQLGQKVTIVEKGNLGGVCLNV
ref|YP_001486601.1|        MVVGDFPIETDTLVIGAPGGYVAAIRAAQLGQKVTIVEKGTLGGVCLNV
RAAC02429                  MVVGDIVEEVEVLVIGAPGGYVAAIRAAQLGKSVTIVDKAELGGVCLNR
                           *.:.:*******.:.**:*, ******* sp|P11959|DLDH1_BACST      GCIPSKALISASHRYEQAKHSEEMGIKAENVTIDFAKVQEWKASVVKKLT
pdb|1EBD|A                 GCIPSKALISASHRYEQAKHSEEMGIKAENVTIDFAKVQEWKASVVKKLT
ref|YP_001125048.1|        GCIPSKALISAGHRYEQAKHSEEMGIKAENVTVDFSKVQEWKASVVKKLT
ref|YP_146914.1|           GCIPSKALISAGHRYEQAKHSEEMGIKAENVTVDFSKVQEWKASIVKKLT
ref|YP_001486601.1|        GCIPSKALINAGHRFENAKHSEDMGIKAENVTVDFTKVQEWKASVVNKLT
RAAC02429                  GCIPSKALTSAAHHYEAAKESPFPGIETT-ATFDFKKVQEWKQSVVKKMT
                           *********.*.*::* **.*   **::  .*. **** *:.*:*:* sp|P11959|DLDH1_BACST      GGVEGLLKGNKVEIVKGEAYFVDANTVRVVNGDSAQTYTFKNAIIATGSR
pdb|1EBD|A                 GGVEGLLKGNKVEIVKGEAYFVDANTVRVVNGDSAQTYTFKNAIIATGSR
ref|YP_001125048.1|        GGVEGLLKGNKVEIVKGEAYFVDANTVRVVNGDSAQTYTFKNAIIATGSR
ref|YP_146914.1|           GGVEGLLKGNKVDIVKGEAYFVDANTVRVVNGDSAQTYTFKNAILATGSR
ref|YP_001486601.1|        GGVQGLLKGNKVDSNSVRVMDENSAQTYTFKNAILATGSR
RAAC02429                  SGVQQLLKGNKVNVIHGEAFFTKPNEVRVMQENGSQRLQFQHCILATGSR
                           .: ***:::*:*...* ***::  ..:*  *::.*:***** sp|P11959|DLDH1_BACST      PIELPNFKFSNRILDSTGALNLGEVPKSLVVIGGGYIGIELGTAYANFGT
pdb|1EBD|A                 PIELPNFKFSNRILDSTGALNLGEVPKSLVVIGGGYIGIELGTAYANFGT
ref|YP_001125048.1|        PIELPNFKFSNRILDSTGALNLGEIPKSLVVIGGGYIGIELGTAYANFGA
ref|YP_146914.1|           PTELPNFKFSGRILDSTGALNLGEIPKSLVVIGGGYIGIELGTAYANFGA
ref|YP_001486601.1|        PIELPTFKYTDRVINSTGALALKEVPKKLVVIGGGYIGTELGTAYANFGT
RAAC02429                  PIELKNLPLGKRVIDSTGALSLDHVPKRLVVVGGGYIGIELGQTFAKFGS
                           ****  .:    *:::***** *  .:** ***:****** ***  ::*:**:

sp|P11959|DLDH1_BACST      KVTILEGAGEILSGFEKQMAAIIKKRLKKKG-VEVVTNALAKGAEEREDG
pdb|1EBD|A                 KVTILEGAGEILSGFEKQMAAIIKKRLKKKG-VEVVTNALAKGAEEREDG
ref|YP_001125048.1|        KVTILEGAGEILSGFEKQMAAIIKRRLKKKG-VDIVTNALAKGAEEREDG
ref|YP_146914.1|           KVTILEGAGEILSGFEKQMVSIIKRRLKNKG-VEVVTNALAKGAEERADG
ref|YP_001486601.1|        EVVILEGGDEILPGFEKQMSSLVKRNLKKKGNVEIHTNALAKGVEEKSDG
RAAC02429                  QVTIIEGLDSILALFDKQMVRLVEKNLKKYN-VQIETNALAQGVEETEDG
                           :*.*:**  ..**. *:***  ::::.**:  . *::  *****:*.**   **

sp|P11959|DLDH1_BACST      VTVTY-EANGETKTIDADYVLVTGRRPNTDELGLEQIGIKMTNRGLIEV
pdb|1EBD|A                 VTVTY-EANGETKTIDADYVLVTGRRPNTDELGLEQIGIKMTNRGLIEV
ref|YP_001125048.1|        VTVTY-EANGETKTVDADYVLVTGRRPNTDELGLEQVGIKMTDRGLIEV
ref|YP_146914.1|           VTVTY-EANGETKTIDADYVLVTGRRPNTDELGLEQIGIKMTNRGLIEV
ref|YP_001486601.1|        VTVTFEVK-GEEKTVDADYVLVTGRRPNTDELGLEQVGVELTDRGVVKT
RAAC02429                  VKLTYKDKDGNEKTIEADYVLVTGRRPNTDEIGLQDAGIELTDKGLVKV
                           *.:*:   *: **:******************:**:: *:::*:*:::.

sp|P11959|DLDH1_BACST      DQQCRTSVPNIFAIGDIVPGPALAHKASYEGKVAAEAIAGHPSAVDYVAI
pdb|1EBD|A                 DQQCRTSVPNIFAIGDIVPGPALAHKASYEGKVAAEAIAGHPSAVDYVAI
ref|YP_001125048.1|        DQQCRTSVPNIFAIGDIVPGPALAHKASYEGKVAAEAIAGHPSVVDYVAI
ref|YP_146914.1|           DQQCRTSVPNIFAIGDIVPGPALAHKASYEGKVAAEAIAGHPSVVDYIAI
ref|YP_001486601.1|        DKQCRTSVSNIYAIGDIVDGPPLAHKASYEGKIAAEAIAGEPAEIDYLGI
RAAC02429                  DQQCRTTNPNVFAIGDIVPGPALAHKASYEGKVAAEVIAGKPSIVDYRCI
                           *:****:  .*::*****  **.*********:***.***.*:  :**   *
```

FIG. 76B

```
sp|P11959|DLDH1_BACST      PAVVFSDPECASVGYFEQQAKDEGIDVIAAKFPFAANGRALALNDTDGFL
pdb|1EBD|A                 PAVVFSDPECASVGYFEQQAKDEGIDVIAAKFPFAANGRALALNDTDGFL
ref|YP_001125048.1|        PAVVFSDPECASVGYFEQQAKDEGIDVITAKFPFAANGRALALNDTDGFL
ref|YP_146914.1|           PAVVFSDPECASVGYFEQQAKEEGIDVITAKFPFAANGRALSLNDTDGFL
ref|YP_001486601.1|        PAVVFSEPELATVGYTEAEAKEEGIDIVAAKFPFAANGRALSLDATDGFM
RAAC02429                  PSVVFSDPEMASVGLTEEEAKKEYGQVAVGRFPYAANGRATALNATDGFI
                           *:****:**  *:**   *  :**.*   ::   ..:**:***** :*: ****:

sp|P11959|DLDH1_BACST      KLVVRKEDGVIIGAQIIGPNASDMIAELGLAIEAGMTAEDIALTIHAHPT
pdb|1EBD|A                 KLVVRKEDGVIIGAQIIGPNASDMIAELGLAIEAGMTAEDIALTIHAHPT
ref|YP_001125048.1|        KLVVRKEDGVVIGAQIIGPNASDMIAELGLAIEAGMTAEDIALTIHAHPT
ref|YP_146914.1|           KLVVRKEDGVVIGAQIIGPNASDMIAELGLAIEAGMTAEDIALTIHAHPT
ref|YP_001486601.1|        KMITRKEDGLVIGAQIAGVGASDMISELSLAIEAGVTAEDIAMTIHAHPT
RAAC02429                  KLVANKENGVLVGAQVVGVEASNIIAELGLAIEMSATLEDIALTIHAHPT
                           *::..**:*:::***:  *   **:*:.**   . *  **:***** sp|P11959|DLDH1_BACST      LGEIAMEAAEVALGTPIHII--
pdb|1EBD|A                 LGEIAMEAAEVAL---------
ref|YP_001125048.1|        LGEIAMEGAEVALGTPIHII--
ref|YP_146914.1|           LGEIAMEAAEVALGTPIHII--
ref|YP_001486601.1|        LGEITMETAEVAIGSPIHIVK-
RAAC02429                  LGEMVMEAAEVGLGEPIHIIKG
                           ***:.** ***.:
```

FIG. 77A

```
ref|YP_001127390.1|     MSIRAEEISALIKQQIENYESQIQVSDVGTVIQIGDGIARVHGLDNVMSGELVEFANGVM
ref|YP_149213.1|        MSIRAEEISALIKQQIENYESQIQVSDVGTVIQVGDGIARAHGLDNVMSGELVEFANGVM
pdb|2QE7|A              MSIRPEEISALIKKQIENYEADLEVVEVGTVIQVGDGIARVHGLEKVMAGELLEFENGVM
ref|YP_361340.1|        MNLRPEEIGSIIKQQIENYQVQVEVSSVGTVIQVGDGIARVYGLEDCMASELLEFPGGVL
RAAC00452               MSIRPDEISALIKQQIEQFEVKAEVRDTGTVLSVGDGIARLYGLDNVMAGELVEFESGVY
ref|YP_001356688.1|     --LQADEISSIIKERIEDFELKIDVEETGKVISFGDGVAKVFGLNNVMAGEMLEFDNGDK
                          ::.:.::::**::: . :* ..*.*:..***:*: .**:. *:.*::** .* ref|YP_001127390.1|     GMALNLEENNVGIVILGPYTGIKEGDEVRRTGRIMEVPVGEALIGRVVNPLGQPVDGLGP
ref|YP_149213.1|        GMALNLEENNVGIVILGPYTGIKEGDEVRRTGRIMEVPVGEALIGRVVNPLGQPVDGLGP
pdb|2QE7|A              GMAQNLEEDNVGVVILGPYTEIREGTQVKRTGRIMEVPVGEALLGRVVNPLGQPLDGRGP
ref|YP_361340.1|        GMALNLEEDNVGCVILGPYTHIKEGDTVKRTGRVVSVPVGEALIGRVVNPLGQPLDGKGP
RAAC00452               GMALNLEEDNVGVVLGSVQGIREGEQVRRTGRLVTVPVGPQLLGRVVNALGQPIDNKGP
ref|YP_001356688.1|     GMALNLEETNVGVVVLGRGEGIREGSSVKRLGQLLKAPVGEALVGRVINAIGEPIDGKGP
                        *** **** *** *:**     *:** *:* *:::.*** *:***:*.:*:*:*. **

ref|YP_001127390.1|     VETTETRPIESPAPGVMDRKSVHEPLQTGIKAIDALVPIGRGQRELIIGDRQTGKTAVAI
ref|YP_149213.1|        VETTETRPIESPAPGVMDRRSVHEPLQTGIKAIDALVPIGRGQRELIIGDRQTGKTSVAI
pdb|2QE7|A              IETAEYRPIESPAPGVMDRKSVHEPLQTGIKAIDSMIPIGRGQRELIIGDRQTGKTTIAI
ref|YP_361340.1|        IVTDKFRPVERIAPGVITRKSVHEPLQTGIKAIDSMIPIGRGQRELIIGDRQTGKTAIAI
RAAC00452               IEATEYRPVESPAPGVIVRRSVHEPLETGIKAIDSMVPIGRGQRELIIGDRQTGKTAIAL
ref|YP_001356688.1|     IEATEYRYVEEKAPGIMARKSVHEPLQTGIKAIDALVPIGRGQRELIIGDRQTGKTTVAI
                        : : :  *  :*  ***:: *:******:****::.:******:*********::*:

ref|YP_001127390.1|     DTILNQKGQDMICIYVAIGQKESTVRTVVETLRKHGALDYTIVVTASASQPAPLLFLAPY
ref|YP_149213.1|        DTIINQKDQNMICIYVAIGQKESTVRTVVETLRKHGALDYTIVVTASASQPAPLLFLAPY
pdb|2QE7|A              DTIINQKGQDVICIYVAIGQKQSTVAGVVETLRQHDALDYTIVVTASASEPAPLLYLAPY
ref|YP_361340.1|        DTIINQKNTDVICIYVAIGQKASTVAKVVQTLKDHGAMDYTIVVSATASDPAPLLYLAPY
RAAC00452               DTIINQKGKDVKCIYVAIGQKQSTVAQVVETLRRYGAMFYTVVVASASEPAPLLFLAPY
ref|YP_001356688.1|     DTIINQKGQDVVCIYVAVGQKQSTVAQVVKKLEEHGAMDYTIVVNAGASEPAALQFLAPY
                        *:*. :: ***:* * :.*. ..*::  * :.* :**** ref|YP_001127390.1|     AGVSMGEYFMYKGKHVLVVYDDLSKQAAAYRELSLLLRRPPGREAYPGDVFYLHSRLLER
ref|YP_149213.1|        AGVAMGEYFMYKGQHVLVVYDDLSKQAAAYRELSLLLRRPPGREAYPGDIFYLHSRLLER
pdb|2QE7|A              AGCAMGEYFMYKGKHALVVYDDLSKQAAAYRELSLLLRRPPGREAYPGDVFYLHSRLLER
ref|YP_361340.1|        AGCAMGEEFMEQGKHVLVVYDDLSKQAAAYRELSLLLRRPPGREAYPGDVFYLHSRLLER
RAAC00452               AGCAMAEYYLYNGQHALVVYDDLSKQAAAYREMSLLLRRPPGREAYPGDVFYLHSRLLER
ref|YP_001356688.1|     TGVTIGEYFRDNGKHALIVYDDLSKHAVAYREMSLILRRPPGREAYPGDVFYLHSRLLER
                        :*  ::.*  :  :*:*.*:******.*  **:**:****:*************.****

ref|YP_001127390.1|     AAKLSDAKGAGSLTALPFVETQAGDISAYIPTNVISITDGQIFLQSDLFFSGVRPAINAG
ref|YP_149213.1|        AAKLSDAKGGGSLTALPFVETQAGDISAYIPTNVISITDGQIFLQSDLFFSGVRPAINAG
pdb|2QE7|A              AAKLSDEKGGGSLTALPFIETQAGDVSAYIPTNVISITDGQIFLESDLFYSGVRPAVNVG
ref|YP_361340.1|        AAKLSDEYGGGSLTALPIIETQAGDVSAYIPTNVISITDGQIYLESDLFYAGVRPAVNVG
RAAC00452               AAKLNDEHGGGSLTALPFIETQAGDVSAYIPTNVISITDGQIFLESDLFFAGVRPAINVG
ref|YP_001356688.1|     AAKLNDKLGAGSLTALPIIETQAGDVSAYIPTNVISITDGQIFLESDLFNAGIRPAINVG
                        ****.* .*.****::***:************:*:****  :*:***:*.* ref|YP_001127390.1|     LSVSRVGGAAQIKAMKKVSGTLRLDLAAYRELEAFAQFGSDLDKATQAKLARGARTVEVL
ref|YP_149213.1|        LSVSRVGGAAQIKAMKKVAGTLRLDLAAYRELEAFAQFGSDLDKATQAKLARGARTVEVL
pdb|2QE7|A              ISVSRVGGAAQIKAMKKVAGTLRLDLAQYRELQAFAQFGSDLDKATQAKLNRGERTVEIL
ref|YP_361340.1|        LSVSRVGGAAQIKAMKQVAGSLRLDLAQYRELAAFAQFGSDLDKATLARLTRGERLVELL
RAAC00452               SSVSRVGSAAQTKAMKKVAGTLKLDLAQYRELQAFTQFGSDLDKATQDTLRRGERMTELL
ref|YP_001356688.1|     ISVSRVGGAAQIKAMKQVAGTLRLDLAQYRELEAFAQFASDLDEASRKQLERCMRMVEIL
                        ******.***.***:.*:*:****.****.****.****:*:   .  *   * :*
```

FIG. 77B

```
ref|YP_001127390.1|      KQDLHQPIPVEKQVAIIYALTRGFLDDIPVEDVRRFEKEFFLWLDQNGQHLLEHIRTTKD
ref|YP_149213.1|         KQDLHQPIPVEKQVLIIYALTRGFLDDIPVEDVRRFEKEFYLWLDQNGQHLLEHIRTTKD
pdb|2QE7|A               KQDEHKPMPVEEQVISIYAVTNGFMDDIPVEDVRRFEEELLSFMRANKDSLLDHIRQTGE
ref|YP_361340.1|         KQDQYKPMPVEEQVMAIFAAVNGYLDDLPVEKVRPFEAEFLKFMRANYPQIGEEIRTKGV
RAAC00452                KQPQYHPLTFDRQVASLWTGVNGYLDDIPVEAVQKFEREWLAFLDREYPQVFQQMQERKS
ref|YP_001356688.1|      KQPPYSPLPVEKQVVIIYAGANGFLDDIEVSAIGKFFYELYSFIEAKYPQIFELIRERKA
                         **  : *:..:.**   :::  ..*::**: *. :  ** *    ::  :   : : ::

ref|YP_001127390.1|      L-PNE-----EDFNKAIEAFKKTFV-
ref|YP_149213.1|         L-PNEDD-----LNKAIEAFKKTFV-
pdb|2QE7|A               L-PDTKEL-----DAAIEEFKKGFTP
ref|YP_361340.1|         LTDELTSR----LKSAIEEFKKTF--
RAAC00452                LEDDTIEL----MKEAMAKFKPTFVP
ref|YP_001356688.1|      LDDEIKEL----LNKAIEEFKASF--
                         *  :        . *:  **  *
```

FIG. 78

```
ref|YP_644829.1|       ---MESRTIAVLEGDQTGQELLEEALRVLDPGVTGLELEFRRFDLSLENRRRTENRVVHE
RAAC02433              MTDMGKPTIIVMEGDQTGQELLEEALRVLSPDVTGYEIEIRKFDLSLENRRRTQNAVVHE
ref|YP_001542913.1|    ---MSKPTIVVLEGDQTGQEELLEESLRVLDPAVTGVDIELKRYDLSLESRRATNNQIVLE
ref|YP_356005.1|       ------PTITVLEGDQTGQELLEEALRILDPAVTGVTVTFKHFDLSLDNRRATKNKVVYE
emb|CAO90974.1|        ------PTIVVMHGDQTGEELLLEALRVLQPSIIRQPLNFADVDLSLAQRRQSNNQVVHE
ref|YP_001656571.1|    ------PTIVVMHGDQTGEELLLEALRVLQPSIIRQPLNFADFDLSLAQRRQSNNQVVHE
                             ** *:.***:* *:**:*.*  :     :  :  ** . ::* :* * ref|YP_644829.1|       AAAAMRECGYGIKAATITPERAGDVGSPNALLRKDINGTVIVRTGRRIPGVNPLPGVHAP
RAAC02433              AAEAMRDTGLGLKAATITPEEKGDVGSPNAILRKEINGTVIVRTGRRIPGIAPPVGVYSP
ref|YP_001542913.1|    AAQQAMKEAGFGLKAATITPEKAGDVGSPNAILREQINGTVIVRTGRRIPGVRPVGGAYAP
ref|YP_356005.1|       AAESMKSTGLGLKAATITPAIKGDVGSPNAILRDQVDGTVIVRTGRRIPGIRPSGGAYAP
emb|CAO90974.1|        AAEATLKTGLALKAATITPEIKGDVGSPNAILREAMNSQVILRIGRRIPGIRPIGGVYSP
ref|YP_001656571.1|    AAEATLKTGLALKAATITPEIKGDVGSPNAILREAMNSQVILRIGRRIPGIRPIGGVYSP
                       **  :  . * .:*****  ****:.  ::.  **:*  ******: *  *.::* ref|YP_644829.1|       ISVVRMAVDDAYGAEEWREG-EGPDEVAYRTEKISRRVCRGVAEFAFIHARRMRAKVFGG
RAAC02433              ISVIRMAVDDAYGAKEWREQLENGDEVAYRTEKTSRSVCRGVAKYAFQHARRMHAKVFGG
ref|YP_001542913.1|    ISVIRMAVDDAYGAKEWREG-EGDNEVAYRTEKITRGTCRAVSEYAFMHARRMKAKVFGG
ref|YP_356005.1|       ISVVRMAVGGSYGAQESR-QGTGLDEVASRTFSTTRRNCHAVAEFAFRHAQKLGVKVFGG
emb|CAO90974.1|        IAIVRMAVDDAYGAKEWRETTATGDEIAYRTSRISRATSRAVAEFTFQHAKKTGARVFGG
ref|YP_001656571.1|    IAIVRMAVDDAYGAKEWRETTATGDEIAYRTSRISRATSRAVAEFTFQQAKKTGARVFGG
                       *::**..:*:* *       :*:* **. *:*  .:.*:::::* :*::  ..**** ref|YP_644829.1|       PKWTVSPVYEGMLKEEMDRAAEKNPDVRYEPQLIDATYALLLSTYGEPLVIPTLNRDGDC
RAAC02433              PKYTVSPVYEGMLKEEMDAAAKEYPDVRYEPQLIDATYALLLARAGFALVIPALNRDGDC
ref|YP_001542913.1|    PKYTVSPIYEGMLKEEMDAAAKRYADVRYEPQLIDATYALLLTNSGDPMVIPALNRDGDC
ref|YP_356005.1|       PKFTVSPVYEGMLKEEMDAAAERFPDVVYEPQLIDATYALLLTNGGDGMVIPSLNRDGDC
emb|CAO90974.1|        PKFTVSATYEGMFKEELDAAAQRHPEVRYQPLLIDATFALLLQTDGEALVIPALNRDGDL
ref|YP_001656571.1|    PKFTVSATYEGMFKEELDAAAQRHPEVRYQPLLIDATFALLLQTDGEALVIPALNRDGDL
                       :*. **:*:* **:. .:* *:* ***:**    *:  :*:**** ref|YP_644829.1|       LSDMVLQMFGSIAGAESLLIALDEE-ERPQTVMAEAPHGTAPSLEGKNIANPMAMILAGA
RAAC02433              LSDLVLQMFGTIAGSESLLLSLDES-FQPKVVMAEAPHGTAPNLFRKNMANPMAMILAGA
ref|YP_001542913.1|    LSDLVLQMFGTIAGAESLLLAFDKD-FKVNVVMAEAPHGTAPSLEGKNVANPMAMILASA
ref|YP_356005.1|       LSDFVLQMFGSIAGAESLLLSFDES-WTPAVVMAEAPHGTAPSLQGKNIANPMAMILAGG
emb|CAO90974.1|        LSDFVLQLYGSIAGAESLVLGFDEETLAVKTIMAEAPHGTAPALEGKNIANPMAMILASA
ref|YP_001656571.1|    LSDFVLQLYGSIAGAESLVLGFDEETLAVKTIMAEAPHGTAPALEGKNIANPMAMILAAA
                       ***:***::*:***:***:::.*:.    .:********** * **:**********..

ref|YP_644829.1|       ALLGFFEDEQAGRVSRAIYESTFETVLDGVKTADLGGSATTTEFTDEVIRHVRNKLEVWS
RAAC02433              ALLNYIQDKDAHTVSRAIYEATLESIVDGIRTADLGGHIATTEFTDEVIRRVRTKLEVWS
ref|YP_001542913.1|    ALLDYIDTPQANMAARAISEATLEAVYDGVRTADLGGHTTTSDFTDEVIRRVKTKMEVWP
ref|YP_356005.1|       ALLRYTNHPDARRAARAISESVFEAVQQGFSTPDLGGSCTTTEFTDEVIRRVASKLEVWQ
emb|CAO90974.1|        ALLGYIETSEARKASRAIYESVFETIHEGKKTPDLGGQMTMSEFTDEVIRRVVSKLEVWS
ref|YP_001656571.1|    ALLGYIETNEARKASRAIYESVFETIHEGKKTPDLGGQMTMSEFTDEVIRRVVSKLEVWS
                       ***  :::    :*   .:*** *:..**: *   *.****  *  ::*******:*  .*:*** ref|YP_644829.1|       ------
RAAC02433              TFGDAV
ref|YP_001542913.1|    SLGN--
ref|YP_356005.1|       TLG---
emb|CAO90974.1|        ALG---
ref|YP_001656571.1|    ALG---
```

FIG. 79A

```
ref|YP_644476.1|      ------------------DDFWASLTSRMPRRLDYETLYEGFSWDLPRPYNIGTDVCDR
RAAC02438             MPCHREMKGAIEHEEVVLMDDLWT-VDGDDLRKLPYGAMYAKFRWPTPDRLNIAEWACRR
ref|ZP_01015586.1|    ---------------------------------WAALRRAFRWTVPDGFNMADACCDS
ref|ZP_02191297.1|    ---------------------------------YEAVRERFRWRIPQRYNIGVDVCDR
ref|ZP_01549387.1|    ---------------------------------YDDLSGRFKWEIPDRFNIGVAICDD
ref|ZP_01850519.1|    ---------------------------------YEAFRSGFRWRIPERYNIAVDVCDR
                                                       : .    *  *   *:.    * ref|YP_644476.1|      HAWE-PGRLALIHDRGDGTAEKW-TFRELKLASDRFANAL-RGLGVERGDRVAVLLSQTP
RAAC02438             HARVCPDAPAIWYDVDGGSAEMW-TFGHLWRTTSRLAWALLRGLGVPTGGRVAILLPQSP
ref|ZP_01015586.1|    WARDEPGRVAVTHV--GHETRDW-TFGELKDASDRLAGAFADA-GVGRGDRVGVLLGQSP
ref|ZP_02191297.1|    HADAGAG-TALIHIAADGAVVEH-SFTELKRQSNRLA-NVLTAAGLQRGDRVGILMPQRP
ref|ZP_01549387.1|    WAAREPNREALVYTDEDGSATSY-TYDDLRRLSNQLA-NLLTARGVQPGDRIGVLMPQRP
ref|ZP_01850519.1|    WAAADPQRPALLDVSADGRVETW-SFAALREASDRFANAL-RALGIARGDRVAVLLPQSP
                       *   .   *:    . .   :: *    : .::*   . . *: *.*:.:*: * * ref|YP_644476.1|      QLPVAHIAVYKLGAVTVPLFALFGEDALRFRLSDSGARVIVTDEEHFEVAASLREELEEL
RAAC02438             QLAAAHLASYAIGAIAVPLFTLFGTDALRYRLQDSGATVVVTDSEQANRIMDIRADLPDL
ref|ZP_01015586.1|    ETLIAHLATWKRGGISIPLFSLFGPDALAFRLADSGTKAVVTDAAGAEKLAAVRGELPDL
ref|ZP_02191297.1|    ETAIAHIAAHKAGMVSVPLFTLFGEDALAYRLGDCAAAALVTDRDSLPKIEAIRDHLPSL
ref|ZP_01549387.1|    ETAFAHIAALKLGAISIPLFTLFGEEALEYRLKDSGAKVVITDASGAAKLATIRDRLPEL
ref|ZP_01850519.1|    AVLIAHLAVYKLGAVALPLAVVFGPDALLHRLGDSGAKAVVTHAGGVAKLLPLRDALPEL
                        **:*    * :::   :  :. *...   .::*.     :*   * .* ref|YP_644476.1|      EHVVLTGGGRAGALGFDDLVRE--ASPF-FRPVETGPDDPAIIIYTSGTTGSPKGALHGH
RAAC02438             EHVIVTDARVPGTQFWDDVLAL--ASSAEYHPMDASPDDPAVLIYTSGTTGSAKGALHGH
ref|ZP_01015586.1|    AQVFAVGGGT-GRDFWAEVEA-----ASPVDPVPVGAEDPAVIIYTSGTTGPPKGALHAH
ref|ZP_02191297.1|    KLILVADTAKNGSGWRALDLALDAASDA-FTPVDTSADDPAVIIYTSGTTGQPKGALHAH
ref|ZP_01549387.1|    TTVLCADEDVPWAESLHHHMA--GHEGT-FHPFDTGPDDPAIIIYTSGTTGQPKGALHGH
ref|ZP_01850519.1|    ALVVSTDG--PGDGALGFAALLEAAAPA-LAPVETGPDDPALMIYTSGTTGPPKGALHGH
                       :.  ..              .       *.   ...:*::****   ***.* ref|YP_644476.1|      RILLGHLPGVSLPHDLAPRRGDLFWTPADWAWIGGLFDVLFPALHWGLPVLSCRMRRFDP
RAAC02438             RILLGHLPGVSLPHDFAPQPGDVFWTPADWAWIGGLYDVLLPALCWGVPVVAHRIRKFDP
ref|ZP_01015586.1|    RFLIGHLPSVELHHEGFPHPGDVGWTPADWAWIGGLMDMAMPCLYHGVRLVSCRMRKFDA
ref|ZP_02191297.1|    RVLLGHLPGVEFPQEFFPAPGDRFWTPADWAWIGGLLDVLLPSLHHGIPVVAHRFAKFDP
ref|ZP_01549387.1|    RVLLGHLPGVEMSHDLLGQPGDRIWTPADWAWIGGLLDVLMPALYLGVPVVACRFRKFTA
ref|ZP_01850519.1|    RVLLGHLPGFAMMHDFMPRPGDRMWTPADWAWAGGLLNALLPSLHHGVAVVARKAEKFEP
                      *.*:****.. : ::       **  ******* *** :  :*.*  *: ::: :  :* .

ref|YP_644476.1|      ERAFDLMERWGVRNVFLPPTALKMMRAVGSPRSR-WRLELETLACGGEPLGEFSLAWARE
RAAC02438             ERAFALMERWRVRNAFMPPTSLKMMRHITDPRSR-WHLILRTLATGGEPLGAELLSWARE
ref|ZP_01015586.1|    DEAYRLIADQRVRNLFLPPTALKLMRQAEVPED----VDIRTIGSGGEALGADLLAWAQD
ref|ZP_02191297.1|    EAAFDLIARHRVRNSFLPPTALKLMRQVPDPLARHALA-MRSIGSGGETLGTELLEWGRS
ref|ZP_01549387.1|    EAAFQLLQDQKIRNTFLPPTALKMMRQVEAPEKRWRFT-LRSVASGGETLGAELIDWGRR
ref|ZP_01850519.1|    EEALRLIADHAVANAFVPPTALRMLRTVARPRARFDLSRLRTLASAGEMLGPETFAWARD
                      :  *  *:    : *  *:***:*:::*        *      :.::. .** **  : : *.:

ref|YP_644476.1|      ELGLPINEFYGQTECNLVLSNCSAIMPIKPGSMGRPVPGHRVAIIDAEGRELPPGEVGEV
RAAC02438             ALGLSIHEFYGQTECNLVVANCSACFQPKPGSMGRPVPGHDVAVIDENGHVVSPGVIGEI
ref|ZP_01015586.1|    ALGVTINEFYGQTECNLVLASCAGSMAVKPGSMGQAVPGHEVAVIDAEGQVVAPGTVGEI
ref|ZP_02191297.1|    VFGLTINEFYGQTECNLVVGNCASILPVRPGSMGKPVPGHEVAIVDANGIPLPASETGAI
ref|ZP_01549387.1|    TFGLTINEFYGQTECNMIVSSCARLMEARPGIMGRPVPGHHVSVVSDKGEELPAGTLGNI
ref|ZP_01850519.1|    ALGLTVNEAYGQTECNLVLASCAALGLARAGSTGKPVPGHRVAVIRPDGTAADPDEIGQI
                      :*:..::* *******:::..*:       :.*  *:.****  *::  .*   .. *  :
```

FIG. 79B

```
ref|YP_644476.1|     AVLRPDPVMMLGYWNNERATEAKFVG---DWLRTGDLATRDGEGYFRFVGRDDDVITSSG
RAAC02438            AVRRPHPVMFIGYWNRPEETAAKFVG---DWLKTGDLGRMDEEGYLWFVGRADDVITSAG
ref|ZP_01015586.1|   AVKRPDPVMFLGYWNLPEKTAAKFTG---DWMRTGDLGVCDEDGYFTYVSRDDDVITSAG
ref|ZP_02191297.1|   AVKRGDPVMFLGYWNNPQATDAKFTGPDKQWMLTGDLGRQDEDGYLEYVGRDDDVITSAG
ref|ZP_01549387.1|   AVKRPDPVMFLNYWNNMEATEKKFAG---DWLLTGDTGIKDDTCWIRFVGRDDDVITSSG
ref|ZP_01850519.1|   AVARPDPVMFLGYWRDEAATARKFLG----DWMTTGDQGRVDADGYVEFVGRDDDVITSSG
                     ** *  *::..      *  **  *   :*: ***    *   *:  :*.* *****:* ref|YP_644476.1|     YRIGPAEIEETLVKHPRVLMAAAVGRPDPVRGEVVKAFVVLREG-EGDFALAEELKELVR
RAAC02438            YRIGPVEIEEAALQHSAVVMAAAVGTPDPVRGEVVKLFVKLREGVPANECLTAELQNWVK
ref|ZP_01015586.1|   YRIGPTEIETCLTGHPDVVMAAAVGVPDETRGEVVKAYVVLRDCA-ATEGLADRLIQRVR
ref|ZP_02191297.1|   YRIGPGEIEDCLTAHPSVALAAVIGVPDPLRTEALKACVVLADGVAPSDSLKAEIQNHVK
ref|ZP_01549387.1|   YRIGPGEIEDCLIKHPAVAMAGVVGKPDSQRTEIVKAYIVLKKGFEPTDKLAGEIADFVK
ref|ZP_01850519.1|   YRIGPGEIEDCLLRHPAVALAAAVCKPDPVRTEIVKAFVVLRPGFAASAALATEIQDFVR
                     *****  ***         *. * :*..:*  **   *  * :*   :  *      *    .: : *:

ref|YP_644476.1|     RRLGAHEYPREVEFVPELPLTATGKIRRNVLRARE--------------
RAAC02438            ERVGAHSYPREIEFVDELPLTPSGKVRRRALREREYAQKGVPLEGKRG
ref|ZP_01015586.1|   EKVSPHVAPRIVEFVDDLPMTATGKIMRRSLRD---------------
ref|ZP_02191297.1|   RRLAAHEYPRIVEFVDSLPMTTTGKIMRRVLRERHAAE----------
ref|ZP_01549387.1|   TRLAAHEYPREVAFVDALPLTTTGKVIRRELRAR--------------
ref|ZP_01850519.1|   RHLSAHEYPREIAFRSSLPLTTTGKIIRRVLRD---------------
                     ::..*   **  :*    **:*.:**:  *. **
```

FIG. 80A

```
ref|YP_147804.1|        ------------------------------------------------SSVTETKTLKNFI
ref|YP_001125954.1|     ------------------------------------------------SSVTETKTLKNFI
ref|YP_001125911.1|     --------------------------------------------------------LKNYI
ref|YP_147740.1|        --------------------------------------------------------LKNYI
ref|NP_243178.1|        ----------------------------------------------ANLATGEKLKNFI
RAAC02441               MAAQRTTRSCPRTRRSSSCTGRPMTPRGMQRRWNRLQNEGEGKMIIRTSSVSVAGHLRNWI
                                                                        *:*:* ref|YP_147804.1|        GGQWVASTSGKEEVVPNPATGEVLAKVPLSSREELDAAVAAAKEAFREWRKVPVPRRARI
ref|YP_001125954.1|     GGQWVASTSGKEEIVPNPATGEVLAKVPISSREELDAAVAAAKEAFREWRKVPVPRRARI
ref|YP_001125911.1|     GGQWVESRSAKTEAVPNPATGEVLAYVPISTREDLDRAVAAAKEAFKTWSKTPVPRRARI
ref|YP_147740.1|        GGQWVESRSGKTEAVPNPATGEVLAYVPISSREELDEAVRAAKEAFKTWRKTPVPRRARI
ref|NP_243178.1|        GGQWVESDSGKTEAVPNPATGEILAHVPISNREDLDRAVSVAKEAFKTWGKTPVPRRARV
RAAC02441               GGAWRDAEASEYLDVFDPATAEVIAQVPLSTQQDVEMAVAAAAEAFREWSKTPVPRRARI
                        ** *     :  :.:     * :***.*::* **:*.:::::  **  .* ***: * *.*******:

ref|YP_147804.1|        LFRYQQLLVEHWDELARLVTLENGKVYEDAYGEVQRGIECVEFAAGIPTLMMGQQLPDIA
ref|YP_001125954.1|     LFRYQQLLVEHWEELARLVTLENGKVYEDAYGEVQRGIECVEFAAGIPTLMMGQQLPDIA
ref|YP_001125911.1|     LFKYQQLLVEHWEELARLVTLENGKSYNEAYGEIQRGIECVEFAAGAPTLMMGRQLPSIA
ref|YP_147740.1|        LFKYQQLLVEHWEELARLVTLENGKSYNEAYGEVQRGIECVEFAAGAPTLMMGRQLPDIA
ref|NP_243178.1|        LFKYQQLLVENWEELARLVTLENGKSYKEAYGEVQRGIECVEFAAGAPSLMMGKQLPDIA
RAAC02441               FFRYQQLLVDHWDELARLIVRENGKSYKDAYGEVQRAIENVEFAASAPTLLMGEQLANIA
                        :*:******::*:*****:. **** *::****:**.** *****.  *:*:**.**..**

ref|YP_147804.1|        TDIESGMYRYPLGVVAGITPFNFPMMVPCWMFPLAIACGNTFVLKPSERTPMLANRLAEL
ref|YP_001125954.1|     TGIESGMYRYPLGVVAGITPFNFPMMVPCWMFPLAIACGNTFVLKPSERTPLLANRLAEL
ref|YP_001125911.1|     TGIESGMYRYPIGVVGGITPFNFPMMVPCWMFPLAIACGNTFVLKPSERTPMLANRLAEL
ref|YP_147740.1|        TGIESGMYRYPIGVVGGITPFNFPMMVPCWMFPLAIACGNTFVLKPSERTPMLANRLAEL
ref|NP_243178.1|        TNIESGMYRYPIGVVGGITPFNFPMMVPCWMFPLAIACGNTFVLKPSERTPLLANRLAEL
RAAC02441               TSLDSGMYRYPLGVVAGITPFNFPMMVPCWMFPLAIVCGNTFVLKPSERTPLLAQRLAEL
                        *.::*****:*.*****************.***********::***** ref|YP_147804.1|        FTEAGLPPGVLNIVHGAHEVVGGILEHKDIKAVSFVGSQPVAEYVYKTAAAHGKRVQALA
ref|YP_001125954.1|     FTEAGLPAGVLNIVHGAHEVVNGILEHKDIKAVSFVGSQPVAEYVYKTAAAYGKRVQALA
ref|YP_001125911.1|     FKEAGLPDGVLNIVHGAHDVVNGLLEHPDVKAISFVGSQPVGEYVYKTAAAHGKRVQALT
ref|YP_147740.1|        FKEAGLPDGVLNIVHGAHDVVNGLLEHPDVKAISFVGSQPVGEYVYKTAAAHGKRVQALT
ref|NP_243178.1|        FTEAGLPEGVLNIVHGAHDVVNGLLEHPDVKAISFVGSQPVAEYVYKTASQHGKRVQALA
RAAC02441               LEEAGLPSGVLNIVHGAREVVQGLIEHPTVRAISFVGSQPVAAYVYREAAAHGKRVQALA
                        : ***** ********** :** ::** ::*:********. ***: *: :*******:

ref|YP_147804.1|        GAKNHSIVMPDADLDMAVTNIINAAFGSAGERCMACSVVVAVGDIADELVRRLKEAADRI
ref|YP_001125954.1|     GAKNHSIVMPDADLDMAVTNIINAAFGSAGERCMACSVVVAVGDIADELVERLKKAADRI
ref|YP_001125911.1|     GAKNHSIVMPDADLKVAVREIINAAFGSAGERCMAASVVVAVGDIADELVERLVAANEI
ref|YP_147740.1|        GAKNHSIVMPDADLNVAVREIINAAFGSAGERCMAASVVVAVGEIADELVEKLVAANEL
ref|NP_243178.1|        GAKNHSIVMPDADLDGAVNQIVNAAYGSAGERCMAAAVVVAVGEVAEPLMEKLQKAVNEI
RAAC02441               GAKNETIVMPDADLDEATPQTISAAFGSAGERCMACSVVVAVGSIADRLVEGLKSAADQI
                        *****:*********.  *:  :.**:*********.:*****.:*: *   *  *.:.:

ref|YP_147804.1|        QIGNGLDKGVFLGPVIRESHKERTIKYIEIGEKEGALLVRDGRRDSATSGQGYFIGPTIF
ref|YP_001125954.1|     QIGNGLDQGVFLGPVIRESHKERTIKYIEIGEREGALLVRDGRRDAATSGKGYFVGPTIF
ref|YP_001125911.1|     KIGNGLEESVFLGPVIREAHKQRTVNYIELGEKEGAILVRDGRKDAAVQGECYFIGPTIF
ref|YP_147740.1|        KIGNGLEESVFLGPVIREAHKQRTVKYIELGEKEGAILVRDGRKDAAVQDNGYFIGPTIF
ref|NP_243178.1|        TIGNGLDDDVFLGPVIRESHKQKTENYIELGEKEGATLVRDGRKDNVSKD-GYFLGPTLF
RAAC02441               RIGNGLDEDVLLGPVIRAEHRDRTLQYIDLGIQEGAVLVRDGRQDRVDAN-GYFVGPTIF
                         *****:.. *:***** *::* :*** :* :*** ******:*   .   .***:***:*
```

FIG. 80B

```
ref|YP_147804.1|       DHVKPGMTIWTDEIFAPVLSVVRARDLDEAIEIANRSEFANGACIYTDSAKAIRQFREEI
ref|YP_001125954.1|    DIIVKPGMTIWTDEIFAPVLSVVRARDLDEAIEIANRSEFANGACIYTDSAKAIRQFREEI
ref|YP_001125911.1|    DRVTTDMTIWKDEIFAPVLSIVRVSTLDEAIEVANKSPFANGACIYTRDGGNVRKFRDEI
ref|YP_147740.1|       DRVTTDMTIWKDEIFAPVLSIVRVETLDEAIEVANKSPFANGACIYTRDGGNVRKFREEI
ref|NP_243178.1|       DNVTTEMTIWKEEIFAPVLSVVRVESLDEAIQLTNQSEFANGACLYTTNGSSVRKFREEI
RAAC02441              DHVRPSMKIWQDEIFAPVLSVVRVGTLDEAIALANRSRFANGACIFTNSASAIRKFREEI
                       *.*  . *.** :********:**.  *****  ::*:* ******::*  ..  :*:**:**

ref|YP_147804.1|       DAGMLGVNVAVPAPMAFFPFSGYKNSFYGDLHANGRDGVEFYTRKKMVTAR-
ref|YP_001125954.1|    DAGMLGVNVAVPAPMAFFPFSGYKNSFYGDLHANGRDGVEFYTRKKMVTAR-
ref|YP_001125911.1|    DAGMLGVNLGVPAPMAFFPFSGWKNSFYGDLHANGMDGVEFYTRKKMLTAR-
ref|YP_147740.1|       DAGMLGVNLGVPAPMAFFPFSGWKNSFYGDLHANGMDGVEFYTRKKMMTSR-
ref|NP_243178.1|       DAGMLGINLGVPAPMAFFPFSGWKNSFYGDLIIANGTDGVEFYTRKKMITAR-
RAAC02441              DAGMLGVNIGVPAPMAFFPFSGWKDSFYGDLHANGKDGVAFYTRRKMITARV
                       ******:*:.************:*:********** *** ****:**:*:*
```

FIG. 81

```
ref|YP_001125956.1|      -------ELLVFNRVIYGRDTFREVGRQAKALGTKALIVSDPVMENIGLVARCEQYLREAG
ref|YP_147805.1|         -------ELLVFSRVVYGRDTFAEVGPQAKALGTKALIVSDPVMEKIGLVARCEQYLQQVG
RAAC02442                MSRVFGEFKVPEAVYAGRGALQMLPQASSSLGKRALIVTDEVMERLGYVAQMQRMLAEAG
ref|NP_831941.1|         -------EFRMPKSVLYGRNSLEKLGEQSKKLGKRAFIVTDTIMEKLGYVEKCMQQLNKKG
ref|ZP_01169177.1|       -------FRVPESIFYGRGSFENLGSQAALKGKKALIISDNVMDQLGYVTEGRALLEVAG
ref|ZP_01695873.1|       -------FRTPQTILYGKQAFEKIGEEAARRGKKALIVTDKIMAGLGNADACQHILQEAG
                                : *.: :  *: ::   :    :   *.:*:*::*  :*  :*  .     *    * ref|YP_001125956.1|      LPLATYTRVDTEPTDVHVKEALDVCRSEQCDVIVAIGGGSSIDAAKAVAVMMTNEGTISD
ref|YP_147805.1|         MTFAKYTGVDTEPTDVHVKEALDVCRSEQCDVIIALGGGSSIDAAKAVSVMMTNEGTISD
RAAC02442                VQADVFAEVNTEPTDVHVETGVRAFLQHGCDHLIALGGGSAIDAAKGISVMAVHEGYIGD
ref|NP_831941.1|         ITVSTYNKVDAEPTNIHVLEALSLCKEEKCDFIIGIGGGSCIDAAKAVAVLYTNGGEVED
ref|ZP_01169177.1|       VQSEVYLGIASEPTDKYVSEALDLFKSEQCDLVISIGGGSCIDTAKAIAVLAVNGGSIGD
ref|ZP_01695873.1|       VKSAVYAGVNSEPVDHYVSEALALFQQESCDLLVSLGGGSCIDTAKAVAVVATNGGYIGD
                              :     :   :**.: :*    .:        ..   ::.:.:**.::*:  .:   *   :  * ref|YP_001125956.1|      YVGNAKMFTKKPVPLIAIPTTAGTGSEVTKVTVIIDTKTDVKMMISQPALLPAVAIVDPL
ref|YP_147805.1|         YVGNQKRFTEKPLPLIAIPTTAGTGSEVTKVTVIIDTKMDVKMMISQPALLPAVAIVDPL
RAAC02442                YMGGRRTFDKAPYPVIAIPTTAGTGSEVTSVTVITNTKDDVKMMIRQPALLPKVAIVDPQ
ref|NP_831941.1|         YVQKDIKIENKPLPLTAIPTTSGTGSEVTSVAVITNKKTDVKMMMKHPSFIPKVAIIDPV
ref|ZP_01169177.1|       YLGGKKLAQQTPVPHIAIPTTAGTGSEATDVTVITNTFNNVKMMIKQPAFLPDAAIVDPL
ref|ZP_01695873.1|       YMGARKIAEKPPVAHIAVPTTAGTGSEATDATIITNTANDVKMMIKQPAFMPAVAIVDPV
                          *:        :  * .  **:***:*****.*..::*  :.     :****: :*:::* .**:**

ref|YP_001125956.1|      LTVSCPPSVTAATGVDALCHSIEAYISRRAHPVTDVLALSAIEAIIGHLRRAYENGQDIE
ref|YP_147805.1|         LTVSCPPSVTAATGVDALCHAIEAYISRRAHPVTDALALSAIEAIVGHLRRAYENGQDIE
RAAC02442                LTVSSPPHVTASSGVDALCHAIEAFISRRSHPLTDALATDAAKKIVTYLERAYNDGQDLE
ref|NP_831941.1|         LTSSLPPQITAATGIDALCHAIEAYISKFSQPLTDVLALSAIESIMKYLRIAYEDGRNME
ref|ZP_01169177.1|       LTVSSPKNITAATGIDALSHAIEAYLSKKAHPMTDTMAISAMKLIAENILTAYNDGGNLD
ref|ZP_01695873.1|       LSKSSPKSVTAATGVDALSHAIEAYISRRAHPLTDTLALSAMRLIIPNLKSAYEDGENME
                          *:  *  *   :**::***.*:***:*:  ::*:**.:*  .*    *   :   **::*  :::

ref|YP_001125956.1|      AREKMAIAAMKAGMAFSNASVTLVIIGMSRPIGALFHVPHGVSNAMLLPGVLEFTKESAIE
ref|YP_147805.1|         AREKMAIAAMKAGMAFSNASVTLVHGMSRPIGALFHVPHGVSNAMLLPGVLEFTKDSAIE
RAAC02442                AREGMAIAALEAGMAFTNSSVCLVHGMSRPIGALFHVPHGFANAMLLPTVLEFRLDDYAP
ref|NP_831941.1|         AREAMMIASLQAGIAFSNASVTLVHGMSRPVGALFHVPHGISNAILLPTVLEFTKTSAMK
ref|ZP_01169177.1|       ARERMSLGSLQAGMAFSNASVCLVHGMSRPIGALFHVPHGISNAMLLPAVLEFSQEACVE
ref|ZP_01695873.1|       ARDAMALGSLQAGMAFSNASVCLVHGMSRPIGALFHVPHGVSNAMLLPAVLEFSKSVCLE
                          **:  *  :.::::*: ****:******..::* ** ref|YP_001125956.1|      RLAVIARLINPQLKDVSNAEAADALVEEVKQLCRDLHIPNMKTWGIDKTAFDKAVDKMAA
ref|YP_147805.1|         RLAVIVRTIKPPLKDVSDTEAAEALVEEVKQLCRDLHIPNMKTWGIDKTAFDKVVDKMAA
RAAC02442                RLALLARALNPELSGASDGEAAAWVVRRVKTLAERLQIPNLKTWGIERDAFERALDKMAN
ref|NP_831941.1|         RLAKTGRSLNKDLYSNSDEEVADYTLGEIKKLCFDLRIPNLKEYGIDEIEFENAISKMAS
ref|ZP_01169177.1|       RLADIGRIFRPDTVSGDGVKAAEIAVQSVKELCRKLNIPNLKEWGIDGEAFEKAVGKMAA
ref|ZP_01695873.1|       RLADICKIFSPEAKDLSGKEAADLAVRAVKQLCLDLNIPNLRGWGIPQQPFESATNKMAS
                          ***  :  :                ...:.*      :  :* *. *.*:: :        *: .:.*** ref|YP_001125956.1|      DALASGSPSNNPRVPTHEEIVALYHICYDYRYD---------
ref|YP_147805.1|         DALASGSPANNPKVPTHEEIVALYHYCYDYQYDTKTVSS---
RAAC02442                DALASGSPANHPVVPSHEEIVQLYRQAYDATWDAAPMESLTK
ref|NP_831941.1|         DAIESGSPANNPRVPSYDEIKELYRECFN-------------
ref|ZP_01169177.1|       DAIDSGSPANNPKVPSQLELEELYHICYDYHFSSA-------
ref|ZP_01695873.1|       DALASGSPQNNPRVPSQKEIEDLYLVCYD-------------
                          **: **** *:* **:  *:  **    .::
```

FIG. 82A

```
ref|YP_723673.1|         --------KVLVSDSIDQNGINILS--QVAQVDIKIGLPVEELVKIIPEYDGLMIRSGTK
ref|ZP_01623360.1|       --------KVLVSDSIDPAGIDILS--QVAQVDVKTGLPAEELVKIISEYDALMIRSGTR
ref|YP_686117.1|         --------KVLVTDPISEEGIKILKSEPGVQVDIETRLTKEQLIEKIKDYNALIIRSETQ
ref|YP_001111391.1|      --------KVLVMDGVSEQGLAPLRQHTDIEVVIGEKMTEDQLVEVIGEYDAMIVRSATK
RAAC02630                MVRENMATKILVTDDISQAGIDILSGLQGAEVVVRTNLAPDELKEAIADADALVVRSQTR
ref|ZP_01695367.1|       ---------ILVTDKVSEEGLKKLYAHKDFIVEHQPGIAPEDLKATIGQYDGLIVRNQTK
                                  :**  *  :.   *: *        *       :. ::*    * :  :.:::*. *:

ref|YP_723673.1|         VTKEIIEAADKLKIIGRAGVGVDNVDVQAATRKGIVVVNSPEGNTIAAAEHALAMMLSMS
ref|ZP_01623360.1|       VTQEIIEAGVQLKIIGRAGVGVDNVDVAAATRAGIVVVNSPEGNTIAAAEHALAMMLSLS
ref|YP_686117.1|         VTKEVIAAGKNLKIIGRAGVGIDNVDVPAATEKGIIVANAPEGNTIAACEHTLSMMLAMS
ref|YP_001111391.1|      VTPRVVEAAKLKVIGRAGVGVDNVDIDRNAATNKGIVVVNAPDGNTIAAAEHTMAMMLGLA
RAAC02630                VTRDVTESAKKLKVIGRAGVGVDNIDLEAATRRGILVINAPDGNTIAAAEHTFAMMISLA
ref|ZP_01695367.1|       VTKDIIEASGNLRVIARAGVGVDNIDVDAATRKGIIVVNSPGGNTISATEHTLAMMLSLS
                         **   ::  :.  .:*::*.*****:**:*    ***  **:*  *:*  ****:*  **:::**:.::

ref|YP_723673.1|         RHVPEANQSIINAQWDRKKFVGVEVYKKTLGVVGLGKIGSHVAKVAKAMGMKILAYDPFI
ref|ZP_01623360.1|       RYIPEANQSVKSGKWDRKKFIGVEVYKKTLGIVGLGKIGSHVAAAAKAMGMKLLAFDPYI
ref|YP_686117.1|         RNIPQANASLKSGKWERSKFMGVEVMNKTLGIIGLGRIGGEITKRARSFGMEVLAYDPFT
ref|YP_001111391.1|      RKVPAACGKLKNGIWDKKAFLGVELRGKTLGVIGLGRIGTAVAKRAQAMEMNIVAYDPYI
RAAC02630                RHIPAAHRDLLQGNWNRKKWIGVELRGKTLAVLGMGRIGTEVAKRAKAFGMTVLGYDPFL
ref|ZP_01695367.1|       RNIPQAHKSAAAGKWEREKFKGVELFKKTLGIIGTGKIGTEVAKRAKAFGMAVLGYDPYL
                         *  :*  *   .    . *::. : ***:   ***.::* *:**   ::  *:::  *  ::.:**:

ref|YP_723673.1|         SEERAEQLGCSLVDLDLLVQESDYITLHIPKTDETYHSINAETFAKMKPTARIINCSRGG
ref|ZP_01623360.1|       SQERADQLSCRLVDLELLLQESDYITLHMPKTKDTYHMIDAKAFEKMKPTARIINCARGG
ref|YP_686117.1|         TAERAQQIGARLTTLDEIYEKADFITVHTPLTPSTKHMVSTAQFEKMKKGVRIINCARGG
ref|YP_001111391.1|      SEDHARKMAVEIVTLQELFKRADFITIHMPKTKETYHMINEEALELMKDGVRIINCARGG
RAAC02630                TEERAQSLGVKRCDLDTAIREADFITVHTPLTKETHHMIDAGRIAQMKEGVRIINCARGG
ref|ZP_01695367.1|       TEERAAKLGIKKATLDEIAAQADFITLHTPLMKETKHLINEAFLAKTKKGVRIINCARGG
                         : ::*  ::.     *:   .:*:**:* *   .*  *  :.     *  .***:* ref|YP_723673.1|         IIDEVALSKALKEGKIAGAALDVYENEPLEVESPLRDLGQKIVMTPHLGASTAEAQVNVA
ref|ZP_01623360.1|       IIDEAALVEALKQGQIAGAAIDVYENEPLEAESPLRALDQKLVLTPHLGASTEEAQVNVA
ref|YP_686117.1|         IIDEAALLEAIKSGKVAGAALDVFEKEP-PVCSPLLEQ-PNIIVTPHLGASTAEAQINVA
ref|YP_001111391.1|      IVDEEALYKFMEAGKVAGAALDVFETEPC-TDNPLLKL-DNFIATPHLGASTQEAQINVA
RAAC02630                IIDEVALAEALEAGRVAGAAIDVFEQEPLPMDHPLRRC-PNVVLTPHLGASTVEAQENVA
ref|ZP_01695367.1|       LVDEQALLQALQEGRVAGAALDVFENEP-DITPGLLEL-PNVTVTPHLGASTREAQVRVA
                         ::**  **  :  :: *:****:**:* **      *   :.. ******** *** .**

ref|YP_723673.1|         IDVAEQIRDVLLGLPARSAVNIPGMYPDTLKKLKPYLRLAETLGNLVSQLAGGRIDFLNV
ref|ZP_01623360.1|       VDVAEQIRDVLLGLPARSAVNIPGLYPDALEKLKPYLQLAETLGNLVSQLAGGRVDFLDV
ref|YP_686117.1|         ITAEQVLNAFKGLPVTTAINIPIMKPEVMEKVKPFLPLAEQLGKFAAQITDGQIKEAIV
ref|YP_001111391.1|      VDVAEEIVAALRGDLVKNAVNMPSMSPKLLAKIRPFLDLAEKLGTFQAQMLDGRIEKVEV
RAAC02630                IQVAEEIVQVLRDDTFEHAVNLPSLSQRQKERLAPYLALAEQLGLFAAQLAQGAPSSMTV
ref|ZP_01695367.1|       ADVSDEIIHIFESEEIRNAINMPQTSGENRERMEPFLLLGEQVAQLGIQLLDEAPEKIEI
                         :::::      :   . .    *:*:*        :: *:*  *.*  :.   *:     .  :

ref|YP_723673.1|         RLEGDLAGGDSKPVVVGALKGLLSQALRERVNYVNAFIEAKERGIRVVETRDDSVRDYTG
ref|ZP_01623360.1|       RLQGELATNKSQPVVVASLKGLLSQALRERVNYVNASIEAKERGIHVIETRDASANDYTG
ref|YP_686117.1|         SYNGEIAQKDVTLVTVAVLKGLLDVKLGEPVNYVNAKHIAKDRSINVAETKLAETGDYTN
ref|YP_001111391.1|      VYSGELAKYDVNPVTTILLKGLLDPILQENVNFVNATLVARNRGISVVQTTKENGEDYHN
RAAC02630                RYAGDAADPDGGYLTRTVLKGFFSFQYNGEVNYVNALRYAEDAGLRVQEVRESRGRVYTN
ref|ZP_01695367.1|       TYAGELLDEDTKLLTRTIIKGILARHLGSTVNLVNALHLLKEQGLTYNLQRNAAFKGFSN
                         *:       :      :.   :**::        **  ***    .: ..:                :.
```

FIG. 82B

```
ref|YP_723673.1|      SLHLEAKGSLGEHNVRGSLLGKDEIRITNIDGFPINVPPSPYMLLTLHRDMPGIIGKIGS
ref|ZP_01623360.1|    SLHLEAKGSLGTHSVTGALLGSSEMRITNIDGFPINVPPTHHMLFTLHRDMPGIIGKIGS
ref|YP_686117.1|      LITLTLKTDKGETRVSGTIFGKSDARIVEIQGYRVDAVPSGTMIVTRHQDRPGVIGKVGM
ref|YP_001111391.1|   LITVYIYTDKGRRMLSCTLFQGNDPRIVNIDGFRINAATQGHMLVVPHIDKPGIVGKVGT
RAAC02630             EVEISVATDNGTHRVTGTVLGEYGPRIVELDGYPIDTPIQGILIYTRHEDRPGMIGRIGT
ref|ZP_01695367.1|    YLELALYKKGKQVNIGASIINGFGGRIVKLNDYRVDLRPEQHLLYTRHLDIPGMIGQVGS
                        : :        .       : .:::       **.:::.: ::      ::    * * **::*::* ref|YP_723673.1|      LLGSFNVNIASMQVGRKIVRGDAVMVLSVDDPLPEEILTEILKEPGIRNAYTVAL
ref|ZP_01623360.1|    LLGSFNVNIASMQVGRKIVRGEAVMVLSIDDPLPEGLLSEIMKVPGIR-------
ref|YP_686117.1|      ILGKLNINISGMVVGRDAVRGDAVMILTVDDEVPAATLKQM--------------
ref|YP_001111391.1|   VVGDMAINIAGMQVGRIELGGKAIMVMMVDNTLPTNALEQLATIDGILEVKMVSL
RAAC02630             LLGDRDINIACMQVGRRETGGEAVMLLSVDKRVPQDVIDEIAKHPGIRLVRAIEL
ref|ZP_01695367.1|    ILGSNDTNIGTMQVGRKEIGGEAIMVLTLDKTASRQVLDQLKEVIGIKAVQTLEL
                      ::*.    **. * ***    *.*:*::  :*.   .     :  ::
```

FIG. 83

```
ref|YP_009822.1|         ------------------MNRIAVIGVGNVGMAFAYAAAIKRLANDIVLIDANAARAEG
RAAC02644                --MTIR-------------LTRIVIIGVGSVGTATAYTLYLRERASEVVLIDADMQKAEG
ref|NP_782567.1|         --------------------KISIIGSGFVGSTTAYALMMEGLASEIVIVDINKEKAKG
sp|Q892U0|LDH_CLOTE      --------------------KISIIGSGFVGSTTAYALMMEGLASEIVIVDINKEKAKG
ref|YP_590559.1|         --------------------RIAVVGLGNVGASFAFALLQRRLAAEIVLIDANHKKAEG
ref|ZP_01514103.1|       -------------------RTGKVGVVGTGMVGTSFAYALMQRSLASELVLTDIDRARAEG
                                              ::  ::*   *  **   *::         *  ::*::*  :   :*:* ref|YP_009822.1|         ESMDLADAMALVGPVQIRSGGYEQCEGARIVVVTAGAKQMPGQSRLDLVRVNAGITRDIL
RAAC02644                EALDMQHGSIYCGGTKIRAGTYEDCATADIVIVTAGVAQRPGQSRIDLLVKNIQVIQDIS
ref|NP_782567.1|         EAMDLSHGVSFVKPVDIIAGDYEDTKDSDIVIITAGAGPKPGETRLDLINKNYELFKGLV
sp|Q892U0|LDH_CLOTE      EAMDLSHGVSFVKPVDIIAGDYEDTKDSDIVIITAGAGPKPGETRLDLINKNYEIFKGIV
ref|YP_590559.1|         EAMDLNHAVPFGAATRIWAGEYADCRGAAVTVITAGAAQRPGETRLQLLDRNLAIFQQIV
ref|ZP_01514103.1|       EAMDLNHGLPFVRPMRIYAGDYADLADADLIVIAAGANQRPGETRLDLLGRNAAIFRDMI
                         *::*:  ..           *  :*  *   :      : :  :::**.    **::*::*:    *     :  : :

ref|YP_009822.1|         TAVMQYADDPLYIMATNPVDVLTHVARTVTGVAPGRVIGSGTVLDSARFRGHVAEILGVD
RAAC02644                FKLKQYGFNGILIVASNPVDILSYVAWYISGLPSERVIGSGTVLDSLRFRYYLGRELGVD
ref|NP_782567.1|         PEVVKYSPKSILLVVSNPVDILTYVTYKLSGFPQERVIGSGTVLDTSRFRYLLGEHFKID
sp|Q892U0|LDH_CLOTE      PEVVKYSPKSILLVVSNPVDILTYVTYKLSGFPQERVIGSGTVLDTSRFRYLLGEHFKID
ref|YP_590559.1|         PEVVKHNPDGLLLIATNPVDIISYASYKISGLPAHRVLGSGTILDTARFRYLLGQHFSVD
ref|ZP_01514103.1|       PAILAANHDGIIVVATNPVDILTTIAAQIAGSDANRVIGSGTILDTARFRYLLGQHYGVD
                              :      .  : ::.:****:::   :   ::*       :::  ***  :..    :* ref|YP_009822.1|         VRGVHAHIVGEHGDSEVALWSRANVSGIPVAEMCARRGIAYDAAFREKALGHVRHAAYEI
RAAC02644                PGSVHAQVLGEHGDTQVHIWSSLNVGGVQVPISERIRGVED---------HTRRAAYEL
ref|NP_782567.1|         VRNVHTYILGEHGDSEIAAWSLTNIAGISVEDYCKDICKGCEGNFKNRIPEEVKNAAYEV
sp|Q892U0|LDH_CLOTE      VRNVHTYILGEHGDSEIAAWSLTNIAGISVEDYCKDICKGCEGNFKNRIPEEVKNAAYEV
ref|YP_590559.1|         ARSVHGLILGEHGDTEVPIWSLANIAGIRLREYCRLHSLPYDEHVFDTIFTDTRDAAYKI
ref|ZP_01514103.1|       PRSVHAYIVGEHGDSELALWSLANIAGVRLVDFVGANGQGYDQAALDAILEQTRNAAYEI
                          .**   ::*****:::   **  *:.*:  :                      ...:  ***::

ref|YP_009822.1|         IGRKGATGYGIGMSLCRIVEAILHDEHSVLTVSCPVAGHYGLGDVSLSLPCVIGSDGIEE
RAAC02644                IEHKGYTNYGIALVLDAICEAILQDKHTVLTVSTKVAEYHGVSDVYLSVPCVIGVRGIER
ref|NP_782567.1|         LERKGYTSYAIALAVRRIVEAIIRDEDSILTVSTLLRGEYGINDIYMGIPSVIGETGIKR
sp|Q892U0|LDH_CLOTE      LERKGYTSYAIALAVRRIVEAIIRDEDSILTVSTLLRGEYGINDIYMGIPSVIGETGIKR
ref|YP_590559.1|         IERKGATYYAVAVGLMQIVESIVRDQKTVLTTSTLVEGAYGINDVYLSLPTIVGAKGVVQ
ref|ZP_01514103.1|       IKRKRATYYAIGLGLLAIAEAVLRDQHTVMTVSSLMTGQYGVTDIAISLPTIVGRDGAEE
                         :  :*   *  *.: :   :   * *::::*:..:::*.*   :   :*: *: :..*  ::*    *   .

ref|YP_009822.1|         VLDAPIAEDEQAALAASARVL--------------
RAAC02644                VIEVPMSDMEERVFQESAKHLYNATREAIRIIGWRES
ref|NP_782567.1|         VLEVKLSKDEEKQLKESAEVL--------------
sp|Q892U0|LDH_CLOTE      VLEVKLSKDEEKQLKESAEVL--------------
ref|YP_590559.1|         VLTPDLSEEELAKLQHSAEVL--------------
ref|ZP_01514103.1|       VLNLPLSDHEVALFQRSANLL--------------
                         *:    ::. *   :  **. *
```

FIG. 84A

```
ref|YP_001124710.1|        ----------------SFAER--VRQLEESWKNEERWKGVVRPYSAEDVIKLRGSLDIEH
ref|YP_146529.1|           ----------------SFAER--VRQLEESWKNEERWKGIVRPYSAEDVIKLRGSLDIEY
ref|YP_893868.1|           -----------------------KLQESWELDTRWKGITRPYSAEDVIRLRGSIDIEH
ref|NP_843617.1|           -----------------------KLQESWELDTRWKGITRPYSAEDVIRLRGSIDIEH
ref|NP_977551.1|           -----------------------KLQESWELDTRWKGITRPYSAEDVIRLRGSIDIEH
RAAC02702                  ----------------MTYFKTAAELEQHWKTDPRWKGVERAYTAEDVIRLRGSVHIEH
                                           :*::  *:  :  ****: *.*:*****:****:.**:

ref|YP_001124710.1|        TLARRGAEKLWKLLNTEDYVHALGALTGNQAVQQVKAGLKAIYLSGWQVAADANLAGHMY
ref|YP_146529.1|           TLARRGAEKLWKLLHTEDYVAALGALTGNQAVQQVKAGLKAIYLSGWQVAADANLAGQMY
ref|YP_893868.1|           TLARRGAEKLWASLHTEDYINALGALTGNQAMQQVKAGLKAIYLSGWQVAADANLSGHMY
ref|NP_843617.1|           TLARRGAEKLWASLHTEDYINALGALTGNQAMQQVKAGLKAIYLSGWQVAADANLSGHMY
ref|NP_977551.1|           TLARRGAEKLWASLHTEDYINALGALTGNQAMQQVKAGLKAIYLSGWQVAADANLSGHMY
RAAC02702                  TLAQMGAEKLWRGLHEDGFIRALGALTGNQAVQQVKAGLKAIYVSGWQVAADANLAEHMY
                           ***: ******   *: :.:: **********:**********:**********:  **

ref|YP_001124710.1|        PDQSLYPSNSVPHVVKRINQALQRADQIQYLEGSGDVDYFVPIVADAEAGFGGQLNVFEL
ref|YP_146529.1|           PDQSLYPSNSVPHVVKRINQALQRADQIQYLEGSGDVDYFVPIVADAEAGFGGQLNVFEL
ref|YP_893868.1|           PDQSLYPANSVPAVVKRINQTLQRADQIQHMEGSGDTDYFVPIVADAEAGFGGQLNVFEL
ref|NP_843617.1|           PDQSLYPANSVPAVVKRINQTLQRADQIQHMEGSGDTDYFVPIVADAEAGFGGQLNVFEL
ref|NP_977551.1|           PDQSLYPANSVPAVVKRINQTLQRADQIQHMEGSGDTDYFVPIVADAEAGFGGQLNVFEL
RAAC02702                  PDQSLYPSNSVPSLVRRINNALLRADQIQTAEGKGDIDWMVPIVADAEAGFGGPLNVFEL
                           *****:**  :*:***::* **** .** *::************  **** ref|YP_001124710.1|        MKAMIEAGAAGVHFEDQLSSEKKCGHLGGKVLLPTQTAVRNLIAARLAADVMGVPTVLIA
ref|YP_146529.1|           MKAMIEAGAAGVHFEDQLSSEKKCGHLGGKVLLPTQTAIRNLIAARLAADVMGVPTVLIA
ref|YP_893868.1|           MKGMIEAGASGVHFEDQLSSEKKCGHLGGKVLLPTQTAVRNLISARLAADVMGVPTIIVA
ref|NP_843617.1|           MKGMIEAGASGVHFEDQLSSEKKCGHLGGKVLLPTQTAVRNLISARLAADVMGVPTIIVA
ref|NP_977551.1|           MKGMIEAGASGVHFEDQLSSEKKCGHLGGKVLLPTQTAVRNLISARLAADVMGVPTIIVA
RAAC02702                  MKMMIEAGAAGVHFEDQLSSEKKCGHMGGKVLIPTSHAVRNLTAARLAADVLGVPTVIVA
                           **  ******:**************:*****:**. *:***  ********:****::*
```

FIG. 84B

```
ref|YP_001124710.1|    RTDANAADLITSDIDPRDQQFITGERTTEGFYRTRAGLDQAIARGLAYAPYADLIWCETS
ref|YP_146529.1|       RTDANAADLITSDIDPRDQAFITGERTPEGFYRTRAGLDQAIARGLAYAPYADLIWCETS
ref|YP_893868.1|       RTDADAADLITSDIDPVDKAFITGERTPEGFYRTKAGLDQAIARGLAYAPYADLVWCETS
ref|NP_843617.1|       RTDADAADLITSDIDPVDKAFITGERTPEGFYRTKAGLDQAIARGLAYAPYADLVWCETS
ref|NP_977551.1|       RTDADAADLITSDIDPVDKAFITGERTPEGFYRTKAGLDQAIARGLAYAPYADLVWCETS
RAAC02702              RTDANGAFLITSDVDDRDARFITGERTPEGFYRFRGGLEAAIARGLAYAPYADMIWCETS
                       ****:.* *****:*   *  ******.*****  :.**: *************:.****

ref|YP_001124710.1|    EPNLDEARRFAEAIHEQFPGKLLAYNCSPSFNWKKKLDDETIAKFQQELGKMGYKFQFVT
ref|YP_146529.1|       EPNLDEARRFAEAIHEKFPGKLLAYNCSPSFNWKKKLDDETIAKFQQELGKMGYKFQFVT
ref|YP_893868.1|       EPNLEDAKRFADAIHKEHPGKLLAYNCSPSFNWKQKLDEKTIASFQKEIASYGYKFQFVT
ref|NP_843617.1|       EPNLEDAKRFADAIHKEHPGKLLAYNCSPSFNWKQKLDEKTIASFQKEIASYGYKFQFVT
ref|NP_977551.1|       EPNLEDAKRFAEAIHKEHPGKLLAYNCSPSFNWKQKLDEKTIASFQKEIASYGYKFQFVT
RAAC02702              EPNIEEAKRFAEAIKAEFPDKLLAYNCSPSFNWRKKLDPKTIEEFQEIIASFGYKFQFVT
                       ***::*:*::   :..*.**********: .  .:  :.. ******* ref|YP_001124710.1|    LAGFHALNYSMFELARGYKDRGMAAYAELQQAEFAAEKYGYTATRHQREVGTGYFDEVAQ
ref|YP_146529.1|       LAGFHALNYSMFELARGYKERGMAAYAELQQAEFAAEKYGYTATRHQREVGTGYFDEVAQ
ref|YP_893868.1|       LAGFHSLNYGMFELARGYKERGMAAYSELQQAEFAAEKHGYSATRHQREVCTGYFDEVAQ
ref|NP_843617.1|       LAGFHSLNYGMFELARGYKERGMAAYSELQQAEFAAEKHGYSATRHQREVGTGYFDEVAQ
ref|NP_977551.1|       LAGFHSLNYGMFELARGYKERGMAAYSELQQAEFAAEKHGYSATRHQREVGTGYFDEVAQ
RAAC02702              LAGFHALNYSMFELAYGYNQRGMGAYSDLQQQEFAAEARGYTATRHQREVGTGYFDEVAQ
                       ***:*.*** ::.*.::*  *  :***************** ref|YP_001124710.1|    VI----------------------
ref|YP_146529.1|       VI----------------------
ref|YP_893868.1|       VI----------------------
ref|NP_843617.1|       VI----------------------
ref|NP_977551.1|       VI----------------------
RAAC02702              VVSGGLSSTTALTGSTEEEQFVEA
                       *:
```

FIG. 85A

```
ref|ZP_02080303.1|   --MRNVEKYTTQYFMPPVPCYDWTKKEYVEKAPIWCSVDLRDGNQALIVPMSLEEKLEFF
ref|YP_520543.1|     --MKNVDNYRRGYFMPPVKSLKWAEKEYITTPPTWCSVDLRDGNQALVVPMSLEEKLEYY
RAAC04058            MDMNNVNKYTRQYFLPPEPCFDWVHKDHVDRPPIWCSVDLRDGNQALIVPMNLEEKLAYF
ref|ZP_01966380.1|   -NMKVVTKYQRQYYMPPMKCMKWAEKEYVDKAPIWCSVDLRDGNQALVIPMSLEQKIEFF
ref|ZP_02073747.1|   LNMKNFEHYKRGYYMPPEKSVKWVEKEYIDKAPIWCSVDLRDGNQALIVPMNLDEKLEFF
ref|ZP_02039587.1|   --MKNFEKYERSYFMPPVPCYDWVKKDHIEKPPVWCSVDLRDGNQALIEPMSLEEKIEFF
                       .*. :*    *::**   . .*..*::.  .* **********: **.*::*: ::

ref|ZP_02080303.1|   KFLVEIGFKEIEVGFPAASETEYEFLRTLIERDMIPEDVTVQVLTQAREHIIRRTFEALE
ref|YP_520543.1|     HMLLKIGFKEIEVGFPAASETEYAFLRTLIEQNLIPEDVTIQVLTQSRDHIIEKTFKALV
RAAC04058            QLLVEIGFKEIEVGFPAASDTEFEFVRTLIERDLVPSDVTIQVLTQSRDHIIERTFEAIR
ref|ZP_01966380.1|   KLLVKIGFKEIEVGFPAASETEYTFVRTLIEQNLIPDDVTIQVLTQAREHIIRKTFEAVK
ref|ZP_02073747.1|   KELVRIGFKEIEIGFPAASETEYEFCRTLIEKNMIPDDVTIQVLTQARPHIIKKTFEAID
ref|ZP_02039587.1|   QMLLDVGFKQIEVGFPAASETEYQFLRTLIEQNMIPEDVTIQVLTQAREHIIKRTFEAVK
                      : *: :***:**:*****:**: * *****:::::*.***:*****:* ***.:**:*:

ref|ZP_02080303.1|   GCPRAIVHLYNSTSVAQREQVFRKSKEEIIRIAVDGAKLLQKISSEMGSDFRFEYSPESF
ref|YP_520543.1|     GVKKAVVHLYNSTSVAQREQVFKMSREEIVEIAVSGARLLKKYAAETEGNFQFEYSPESF
RAAC04058            GAKRAIVHLYNSTSVAQREQVFRADKDEIVNIAVTGAEQIRDLARTTPGNFFFQYSPESF
ref|ZP_01966380.1|   GAPKAIVHLYNSTSVAQREQVFKSKEEILKIAVDGAKLLKELADETEGNFQFEYSPESF
ref|ZP_02073747.1|   GAKHAIVHLYNSTSYAQRTQVFKKSKEEILQLAVDGAKLLNQMAEEHGVNYPFEYSPESF
ref|ZP_02039587.1|   GAPHAVIHLYNSTSVAQREQVFKKNKEEIKKIAVDGAILLNELAKETEGNFTFEYSPESF
                     *  :*::*:***  * *:  .:: .:   :..  :    :: *:****** ref|ZP_02080303.1|   TGTEMEFARDICNAVLDVWKPTPEKKVIINLPVTVEHSMPHVYACQVEYMCKHLDYRDSV
ref|YP_520543.1|     TGTEMEFALEICNQVLDVFEPTPENKVIINLPATVSLSMPHVYASQIEYMSEHLKYRDNV
RAAC04058            TGTELDFALEICNAVLDVWKPTPDRKVIINLPATVELSMPHVYASQIEYMGKRLARRDAI
ref|ZP_01966380.1|   TGTEPEYALEVCNAVLDVWQPTPENKAIINLPVTVELSMPHVYASQIEYMSENMKYRENV
ref|ZP_02073747.1|   TGTEIDYALDVCNAVIKEWKPTPDRKVIINLPATVEMSLPHVYASQIEYMSEHLIDRENV
ref|ZP_02039587.1|   QGTEVDYALEVCNAVLRVWEPSRERKVIINLPTTVENAMPHVFASQVEYMSKHLYNREHV
                      ***  ::* ::** *:    ::*: :.*.*****.**. ::***:*.:*** :.:  *: :

ref|ZP_02080303.1|   VVSLHPHNDRGCGVADCELGLLAGADRIEGTLFGNGERTGNADIVTLALNMFSQGVDPKL
ref|YP_520543.1|     ILSLHPHNDRGTAVADAELGLLAGGQRIEGTLFGNGERTGNVDIVTLALNLFSHGVDPGL
RAAC04058            VLSVHPHNDRGTGVAAAELAMLAGAERLEGTLFGNGERTGNVDIVTLALNLYSHGIDPGL
ref|ZP_01966380.1|   ILSQHPHNDRGCGVADSELGLLAGADRVEGTLFGNGERTGNVDVVTLAMNMFAQGVDPEL
ref|ZP_02073747.1|   ILSLHPHNDRGCGVADAELGILAGADRIEGTLFGNGERTGNVDIITLAMNMFTHGVDPEL
ref|ZP_02039587.1|   LLSLHPHNDRGSGVSDAELGILAGADRIEGTLFGNGERTGNVDIITVAMNMYSQGVDPGL
                      ::* ******* .*: ..:*.:*:.************.*::*:*:*:::*:** * ref|ZP_02080303.1|   NFEDMPSTVALYEKVTGMHVYDRQPYGGKLVFAAFSGSHQDAIAKGMKWREEKECDHWTV
ref|YP_520543.1|     NFASMLEITAKYEALTRMKVHDRQPYGGKLVFAAFSGSHQDAITKGIKWREEHECHYWNV
RAAC04058            DFSNLPAIQARVEALTKMQVSRRHPAGELVFTAFSGSHQDAIAKGMKWREEKSPEHWTV
ref|ZP_01966380.1|   DFSDMPHICEVYEACTGMKVDERSPYSGALVFAAFSGSHQDAIAKGMHWRDEKDPNRWTV
ref|ZP_02073747.1|   DLSDIPKLTELYERVTNMHVYERSPYTGKLVFAAFSGSHQDAIAKGMKYRKDQGDGMWTV
ref|ZP_02039587.1|   DFSNMSEISETYERLTRMQVSPRQPYAGELVFTAFSGSHQDAIAKGMAWREEKQCQTWSV
                     ::  .:      *  *  *:*  *  ** * *:******:: :*.::    *.* ref|ZP_02080303.1|   PYLCIDPKDIGREYEGDVIRINSQSGKGGIGYLLEQKYGFVLPPKMREDFGYAVKNVSDH
ref|YP_520543.1|     PYLLIDPQDIGREYEGDVIRINSQSGKGGIAYMLEQHYALDLPAKMREAFGYKVKNVSDN
RAAC04058            PYLPIDPKDIGREYEGDIIRINSQSGKGGIGYVLEQSHGFDLPPKMREQLGYAVKRVSDR
ref|ZP_01966380.1|   PYLPIDPTDVGRNYDADVIRINSQSGKGGVGYILETKYGLNLPPKMREAMGYAAKAVSDH
ref|ZP_02073747.1|   PYLPLNPEDIGRKYDGDVIRINSQSGKGGIGYILQSKYGFDLPPKFREDLGYTVKDVSDK
ref|ZP_02039587.1|   PYLPLDPKDVGRRYETDVIRINSQSGKGGVNYILKQSFGISLPQKMREEVGYLVKDVSDK
                     *** ::* *:**.*: *:***********: *:*  ...:* *:** .** .* ***.
```

FIG. 85B

```
ref|ZP_02080303.1|    QHKELQPEEVYEIFRREYLNI-NDKISLVDFHFVR-NDCIH-AAVIVKIGGVEKEIKGDG
ref|YP_520543.1|      LHKELMPEEIKDIFFKEYVNI-ENPIKFLNFHFLN-HDDFQ-TTVTLEFKGEIQELSGEG
RAAC04058             EQKELSADEIAEIFMREFVNL-GQPLDLVELTGTDARGSHR-VRATVVWQGETVEIEGAG
ref|ZP_01966380.1|    CHKELHPDEIFNLFKSTFENV-VEPYSIDEVHFQQ-KDGGITTQVTSTFNGKTITTEATG
ref|ZP_02073747.1|    AHKELSATEVLDIFQSTYVNI-ENPVRMLECHFVQ-GDGI-STEITIMKYGEKKVYHGKG
ref|ZP_02039587.1|    AHKELTPDWVYHIFEDHYIHV-KTIFTVDFCHFKQ-EDGI-LAEATIHHAGSDRVINGMG
                      :***  .  :  .:*     :  ::          .  :      .     *     *     . * ref|ZP_02080303.1|    NGRLDAVSNAIKENLGIQYQDLTYTEHALEQGSKSRAAAYVGITGKDGRITWGVGVDSDI
ref|YP_520543.1|      DGRLDAISNALQARLGLSYSNLIYKEHALELGSKSQAVSYVGVTGPDGVIHWGCGIETDT
RAAC04058             NGRLDALCHALEEGLGIRVANLTYKEHALEVGSGSRAVAYISVDDEEGNTHFGCGVDTDI
ref|ZP_01966380.1|    NGRLDAVSNALKKAYEMKFTLVTYQEHALEKSSSSKAIAYVGIQKPDGTLSWGAGVDPDI
ref|ZP_02073747.1|    NGRLDAVSNAIKKHFDIDFKIICYEEHALQVGSNSQAVAYVGLEGKDGTVTWGAGIKDDI
ref|ZP_02039587.1|    NGRLDAVSNAIKHYFDIDYELAFYEEHSMTKGSSSKAVAYVGVICNK-KRYWGVGIDADI
                      :*****::.*::        :         * **::  .* *:* :*:.:   .    :*  *:. **

ref|ZP_02080303.1|    ITASVKALFSAINR--------------
ref|YP_520543.1|      FTSSVKALISAINTMIKDSA--------
RAAC04058             MEASAKALVSAVNRMLAHRAEMAVPVSK
ref|ZP_01966380.1|    IRASIDALVTAIN---------------
ref|ZP_02073747.1|    IDASVYALISAINR--------------
ref|ZP_02039587.1|    IKASVEALVVAVNKI-------------
                      :  :*    **.  *:*
```

FIG. 86A

```
ref|YP_001125182.1|    ------------------------------------------------------------MNI
ref|YP_147061.1|       ------------------------------------------------------------MNI
ref|ZP_01171540.1|     ------------------------------------------------------------MNI
ref|NP_692464.1|       ------------------------------------------------------------MNI
ref|YP_001375719.1|    ------------------------------------------------------------MNI
RAAC02843              MSRFPVCVFIVSTGQDVVKRAAKFYPDRWHKVGRRHGNVCPVFLCAVSVGGQRRTDIVNI
                                                                                   :**

ref|YP_001125182.1|    HEYQAKEILRSYGVSVPNGRVAFTVDEAVEAAKALGTSVCVVKAQIHAGGRGKAGGVKVA
ref|YP_147061.1|       HEYQAKEILRSYGVSVPNGRVAFTVDEAVEAAKELGAPVCVVKAQIHAGGRGKAGGVKVA
ref|ZP_01171540.1|     HEYQGKEVLRKYGVTVPNGKVAFTVEEAVEAAKELGTEVVVVKAQIHAGGRGKAGGVKVA
ref|NP_692464.1|       HEYQGKQVLREYGVKVPNGYVAYTVDEAVQAAEKLGTSVNVVKAQIHAGGRGKAGGVKVA
ref|YP_001375719.1|    HEYQGKAILRSYGVSVPNGKVAFTVEEAVEAAKFLGTDVCVVKAQIHAGGRGKAGGVKVA
RAAC02843              HEYQAKAILAEFGVKVPRGKVAFTVEEAVEAAKELG-GKAVVKAQIHAGGRGKAGGVKVS
                       ****.*.:* .:**.**.* **:**:***.**: **  ******************:

ref|YP_001125182.1|    KSLEEVRTYASELLGKVLVTHQTGPEGKEVKRLLIEEGCDIQKEYYIGLVVDRATSRVVL
ref|YP_147061.1|       KSLEEVRTYASELLGKVLVTHQTGPEGKEVKRLLIEEGCDIQKEYYIGLVVDRATSRVVL
ref|ZP_01171540.1|     KNLDEVRTYASEILGKTLVTHQTGPEGKEVKRLLIEEGCDIQKEYYVGLVVDRATSRVVL
ref|NP_692464.1|       KSLDEVRTYADEILGKTLVTHQTGPEGKEVKRLLIEEGCDIQKEYYVGLVLDRATSRVVM
ref|YP_001375719.1|    KNLEEVRTYAENILGSTLVTHQTGPEGKEVKRLLIEEGCDIKKEYYVGLVLDRATSQVVL
RAAC02843              KSLEEVEANARELLGKRLVTHQTGPQGRIVRRLLIEELTNIQKEYYIGLVLDRSQGRLVM
                       *.*:**.: * .:**. ********:*: *:****** :*:****::*:*** .:*:

ref|YP_001125182.1|    MGSEEGGTEIEEVAAKTPEKIFKEYVDPAVGLQAFQARRLAFNINIPKKLVNQAVKFMMG
ref|YP_147061.1|       MGSEEGGTEIEEVAAKTPEKIFKEYVDPAVGLQAFQARRLAFNINIPKHLVNQAVKFMMG
ref|ZP_01171540.1|     MASEEGGTEIEEVAEKTPEKIFKEEIDPVIGLTAFQARRIAFNINIPGKLVNQAAKFMLA
ref|NP_692464.1|       MASEEGGTEIEEVAEATPEKIFKEVIDPVVGLTPFQARRLAFNINTPEDLLGKAVKFMSG
ref|YP_001375719.1|    MASEEGGTEIEEVAEKTPEKIFKEYIDPAVGLQGFQARRIAFHINIPKELVGQAVKFMMG
RAAC02843              MASQEGGVEIEEVAAKHPEKIFRETIDPLTGLTPFQANNLAYKLELPQDAVKKAAQFMMA
                       *.*:***.******  *****:*  ** **  ***..:*::::::*  .  :*.:** .

ref|YP_001125182.1|    LYQVFVDKDCSIAEINPLVVTGDGKVMALDAKLNFDSNALYRHPDIMEYRDLDEEDPKEV
ref|YP_147061.1|       LYQVFVDKDCSIAEINPLVVTGDGKVMALDAKLNFDSNALYRHPDILEYRDLDEEDPKEV
ref|ZP_01171540.1|     LYNAYIEKDCSIAEINPLVVTGDGKVMALDAKLNFDSNALYRQKDILEYRDLEEEDPKEI
ref|NP_692464.1|       LYDAFVAKDCSIAEINPLVTTGDGEVLALDAKLNFDDNALYRIKDIQDLRDFEEEDEKEI
ref|YP_001375719.1|    LYRVFIEKDCSIAEINPLVTTGDGKVMALDAKLNFDSNALYRHKDILELRDLDEEDPKEI
RAAC02843              LYNAYVAKDCSIAEINPLVLTAEGDIIALDAKLNFDDNALYRHPEIVSLRDEDEEDPKEI
                       **..::.***********.*.::.:*********** ***:  :*  .**.:*** **:

ref|YP_001125182.1|    EASKYDLNYIALDGNIGCMVNGAGLAMATMDIIKYYGGEPANFLDVGGGASEEKVTEAFK
ref|YP_147061.1|       EASKYDLNYIALDGNIGCMVNGAGLAMATMDIIKYYGGEPANFLDVGGGASEEKVREAFK
ref|ZP_01171540.1|     EASKYDLSYISLDGNIGCMVNGAGLAMATMDIVKHYGGDPANFLDVGGGATAEKVTEAFK
ref|NP_692464.1|       QASKYDLSYVSLDGNIGCMVNGAGLAMSTMDIIKHYGGDPANFLDVGGGATAEKVTEAFK
ref|YP_001375719.1|    EASKYDLNYIPLDGNIGCMVNGAGLAMATMDIIKHYHGDPANFLDVCGGATAEKVTEAFK
RAAC02843              EASKYGLSYIALDGNIGCMVNGAGLAMATMDTIKYYGGEPANFLDVGGGASEEKVTAAFK
                       :****.*.*:.**************.* :*:* *:******.:  * *** ref|YP_001125182.1|    IILSDPNVKGIFVNIFGGIMKCDVIASGIVAATKQVGLTLPLVVRLEGTNVELGKKILQE
ref|YP_147061.1|       IILSDPNVKGIFVNIFGGIMKCDVIASGIVAATKQVGLTLPLVVRLEGTNVELGKKILQE
ref|ZP_01171540.1|     IILSDPNVKGIFVNIFGGIMKCDVIAEGVVEAAKQVGLKVPLVVRLEGTNVDLGKKILAE
ref|NP_692464.1|       IILSDKNVKGIFVNIFGGIMKCDVIAEGVVEATKQIGLEIPLVVRLEGTNVDAGKKILDE
ref|YP_001375719.1|    IILSDKNVKGIFVNIFGGIMKCDVIAEGVVEAGKELPLVVRLEGTNVELGKKILNE
RAAC02843              IILSDPKVKGILVNIFGGIMKCDVIANGVVAAAKQVGLDKPLVVRLEGTNVEAGKKILNE
                       *****.:****:******************.*:* *:**.**  *********** *
```

```
FIG. 86B
ref|YP_001125182.1|     SGLNITAAESMADGAQKIVELV
ref|YP_147061.1|        SGLNIIAAESMADGAQKIVELV
ref|ZP_01171540.1|      SDIDIIAADSMSDGAEKIVSLV
ref|NP_692464.1|        SGLNITTATSMADGAEKIVAAV
ref|YP_001375719.1|     SGLNIVAAESMADGAQKIVSLV
RAAC02843               SGLKLVAADSLADAAQKIVALV
                        *.:.: :* *::*.*:*** *
```

FIG. 87

```
ref|YP_147062.1|        MSVFVNKDTKVIVQGITGSQGLFHTKQMIEYGTNIVGGVTPGKGGTEVEGVPVFDTVSEA
ref|YP_001125183.1|     MSVFVNKDTKVIVQGITGSQGLFHTKQMIEYGTNIVGGVTPGKGGTEVEGVPVFDTVSEA
ref|NP_243335.1|        MSILINKDTKVIVQGITGATGLFHTKQAVEYGTNIVGGVTPGKGGTEVEGIPVFDTVSQA
ref|YP_079003.1|        MSVFINKDTKVIVQGITGSTALFHTKQMLEYGTKIVGGVTPGKGGTEVEGVPVFNTVEEA
ref|ZP_01171539.1|      MSVFINKDTKVIVQGITGSTALFHTKQMLEYGTQIVGGTTPGKGGMEVEGVPVFNTVQEA
RAAC02844               MSILVNKETRVITQGITGSAGLFHTQQALAYGTKVVGGTSPGKGGTKVEGLPVFNTVEEA
                        ::::*: *: .***:* : *:*.:** :*:*:.:* ref|YP_147062.1|        VERTGANASVIYVPPAFAADAIMEAVDAGLDLVVCITEGIPVLDMVKVKRYMEGKKTRLI
ref|YP_001125183.1|     VEKTGANASVIYVPPAFAADAIMEAVDAELDLVVCITEGIPVLDMVKVKRYMEGKKTRLI
ref|NP_243335.1|        VEATGANASVIYVPPAFAADAIMEAVDAELDLAICITEGIPVMDMVKVKRYMEGKKTRLV
ref|YP_079003.1|        VKQTGANASVIYVPAAFAADAIMEATDAELDLVICITEHIPVLDMVKVKRYMEGKKTRLI
ref|ZP_01171539.1|      VKETGATASVIYVPAAFAADAILEAVDAELDLAICITEHIPVLDMVKVKRYMEGKKTRLV
RAAC02844               VRETGANASVIYVPPAFAADAIMEAVAAGIELVVCITEGIPILDMVKVKRYMEGKKTRLI
                        *. ***.*******.******:**. * ::*.:**** **:.*****************:

ref|YP_147062.1|        GPNCPGVITPEECKIGIMPGYIHKKGHVGIVSRSGTLTYEAVHQLTQAGIGQSTAVGIGG
ref|YP_001125183.1|     GPNCPGVITPEECKIGIMPGYIHKKGHVGIVSRSGTLTYEAVHQLTQAGIGQSTAVGIGG
ref|NP_243335.1|        GPNCPGVITPEECKIGIMPGYIHKKGHVGVVSRSGTLTYEAVHQLSTAGIGQSTAVGIGG
ref|YP_079003.1|        GPNCPGVITPEECKIGIMPGYIHKKGHVGVVSRSGTLTYEAVHQLSEAGVGQSTAVGIGG
ref|ZP_01171539.1|      GPNCPGVITPDECKIGIMPGYIHTKGHVGVVSRSGTLTYEAVHQLTQAGIGQSTAVGIGG
RAAC02844               GPNCPGVITPNECKIGIMPGYIHTPGKIGVVSRSGTLTYEAVYQLTQLGLGQSTAVGIGG
                        ********:**********. *::*:*********::: *:********** ref|YP_147062.1|        DPVNGTNFIDVLKAFNEDEETYAVIMIGEIGGTAEEEAAEWVKANMTKPVVGFIGGQTAP
ref|YP_001125183.1|     DPVNGTNFIDVLKAFNEDDETYAVIMIGEIGGTAEEEAAEWVKANMTKPVVGFIGGQTAP
ref|NP_243335.1|        DPVNGTNFIDVLKLFNEDPDTYAVIMIGEIGGTAEEEAAEWIKANMTKPVVGFIGGQTAP
ref|YP_079003.1|        DPVNGTNFIDVLKAFNEDPDTHAVIMIGEIGGTAEEEAAEWVKANMTKPVVGFIGGKTAP
ref|ZP_01171539.1|      DPVNGTNFIDVLKAFNEDPETKAVIMIGEIGGTAEEEAAEWVKANMTKPVVGFIGGRTAP
RAAC02844               DPVNGTNFVDVLKMFNDDPDTEAVIMIGEIGGSAEEEAAEWIKANMKKPVVGFIAGATAP
                        ******:  ::  :* ******:***:.*****.* *** ref|YP_147062.1|        PGKRMGHAGAIISGGKGTAAEKIKKMTECGIKVAETPAVIGETLISVLKERGLYEKCKT
ref|YP_001125183.1|     PGKRMGHAGAIISGGKGTAAEKIKKMNECGIKVAETPAVIGETLISVLKERGLYEKCKT
ref|NP_243335.1|        PGKRMGHAGAIISGGKGTAAEKIKTLESCGVKVAETPSVMGETLISVLKEQGLLEKC--
ref|YP_079003.1|        PGKRMGHAGAIISGGKGTADEKIKTMNACGIEVAETPSVMGETLIKVLKEKGLYETCKT
ref|ZP_01171539.1|      PGKRMGHAGAIISGGKGTADEKIRVMNECGIQVADTPSVMGETLIKVLKEKGLFDECKT
RAAC02844               PGRRMGHAGAIVSGGSGTAQSKIEKMKACGIRVAPTPSEMGSTLYQVLEERGLLERCKS
                        **:********:***.***. **. :  **::** **: :.**  .**::** * : *
```

FIG. 88

```
ref|YP_001127392.1|      --------------------------RKFAWGPLMGVMKQREEHIANEIDQAEKRRQEA
ref|YP_149215.1|         --------------------------RKFAWQPLMNIMKQREEHIANEIDQAEKRRQEA
ref|YP_001488543.1|      --------------------------KKFALKPLLGIMKQREDYIGNEISSAEQKHVQA
ref|YP_093437.1|         --------FNAGTMLFQLVAMLILLALKKYALGPLLNIMKEREDYITGEISSAEKKNEEA
ref|YP_521149.1|         --------------------------RRFAWNPLINMMEERRSQIEANIANAEKERLQA
RAAC00454                MFQVGGIFQVGTFIFSVISFLIVFFIIQRFAFKPLARMLEQRRIHIETQISEAEKSREEA
                                                   :::*  **  ::::*.  *  :* .**: . :* ref|YP_001127392.1|      EKLLEEQRELLKQSRQEAQTILENARKLAEEQKEQIVASARAEAERVKEAAKQEIEREKE
ref|YP_149215.1|         EKLLEEQRELMKQSRQEAQALIENARKLAEEQKEQIVASARAEAERVKEVAKKEIEREKE
ref|YP_001488543.1|      EKLLEEQRVLLKEAREESHTLIENAKKIGEKQKEEIIQAARQESERLKDSARTEIVKEKE
ref|YP_093437.1|         KKLIEEQQALLKEAREESQSLIENAKKIGEQQKDEIIKAARQEAERMKESARSEIVKERD
ref|YP_521149.1|         EQIKREYQEEMRKARQEAQEVIAKATKLSEQRAAEILAAAHGEAKIKQSALADIERERD
RAAC00454                ERLLAEQQRLLEEARKEARNLLDQARIRADEQAREIVQKAFEEAARILEESRQAIVRERD
                          ::: *  :  :.::*:*::  ::   :*     .:::   :*:  *.  *:  ::  :     *  :*::

ref|YP_001127392.1|      QAMAALREQVASLSVLIASKVIERELTEQDQRKLI------------
ref|YP_149215.1|         QAMAALREQVASLSVLIASKVIEKELTEQDQRKLI------------
ref|YP_001488543.1|      QAVAALREQVASLSVLIASKVIERELDEQAQEKLIQEYLKEAGE---
ref|YP_093437.1|         QAVTALREQVASLSVMIASKVIEKELDEQAQFKLIQDYLKEVGE---
ref|YP_521149.1|         RAIAQVQAQVADLSVAVAEKIIRKNLDVRGQEDMIEQFIQEVGELPC
RAAC00454                EALAAVTKRVAELSVELTTKLLRDHVTAELHKELVAEAESKLGELVC
                          .*:: :   :**.*** :: *::. .:  . :...::
```

FIG. 89

```
ref|YP_001421255.1|    --MNVGNISTAMITPFDSKGNVDFQKLSTLIDYLLKNGTDSLVVAGTTGESPTLSTEEKI
ref|NP_389559.1|       --MNFGNVSTAMITPFDNKGNVDFQKLSTLIDYLLKNGTDSLVVAGTTGESPTLSTEEKI
ref|YP_091490.1|       --MNFGNIATAMVTPFDKNENIDFQKLSKLIDYLLNNGTDSLVVAGTTGESPTLSEEEKV
ref|YP_001125250.1|    ----FGNIVTAMVTPFDRKGNLDLAKTTELVNYLLDNGTDALVVAGTTGESPTLTAEEKV
ref|ZP_02169638.1|     --MSFGTVLTAMVTPFDDQGMINYDQLEVLINHLIENGSDGLVVGGTTGESATLSIEEKA
RAAC02920              MRMDFGSLITAMVTPFDATGALDEGRLRRLVDHLIETGTTAVVVCGTTGESPTLSHAEKL
                         .*.:  ***:****    ::   :    *::*:..*:  .:** ******.**:  **

ref|YP_001421255.1|    ALFEFTVKEVNGRVPVIAGTGSNNTKDSIKLTKKAEEAGVDCVMLVTPYYNKPSQEGMYR
ref|NP_389559.1|       ALFEYTVKEVNGRVPVIAGTGSNNTKDSIKLTKKAEEAGVDAVMLVTPYYNKPSQEGMYQ
ref|YP_091490.1|       ALIQYSVKEAAGRAPIIAGTGSNNTKASIKLTKKAEEAGADAVMLVTPYYNKPSQEGMYR
ref|YP_001125250.1|    ALFRHVVNVVNGRVPVIAGTGTNDTRASIELTKRAEETGVDAVMLVAPYYNKPNQEGLYQ
ref|ZP_02169638.1|     ALYQQSVRIADGRVPIIAGTGMNDTYATAELTIRAERVGVDGIMLVAPYYNKPSQKGLYE
RAAC02920              RLFDATLRAVDGRIPVIAGTGTNSTKDSIELTLEAARLGVQAVMLVTPYYNRPSQEGLYM
                         *     :.  .  ** *:***** *.*   : :**  .* . *.: :*:**:*.*:*:* ref|YP_001421255.1|    HFKAIAEETSLPVMLYNVPGRTVASLAPETAIRLA-EIPNISAIKEASGDLDAITKIIAE
ref|NP_389559.1|       HFKAIAAETSLPVMLYNVPGRTVASLAPETTIRLAADIPNVVAIKEASGDLEAITKIIAE
ref|YP_091490.1|       HFRAIAEETSLPVMLYNVPGRTAASLAPETTIRLA-EIPNIIAIKEASGDLDAITKIVAE
ref|YP_001125250.1|    HFKAIAESTSLPVMLYNVPGRTSVNLAPETVIRLA-AIPNIVAVKEAGGNLDAMAEIIEQ
ref|ZP_02169638.1|     HFQTIAEKTSLPVMVYNVPGRTAVNILPETVIELA-KIENITSVKEASGNLDQVTMIVAN
RAAC02920              HFASIAESTTLPVMLYNVPGRTGVNLQPQTALQLA-AIPNVVALKEASGDFSQILRIAAE
                       **  :**  .*:****:******  .: *:*.:.**  * *: ::***.*::. :   *   :

ref|YP_001421255.1|    TPEDFYVYSGDDGLTLPTLAVGGRGVVSVASHIVGSDMQQMIKNYTNGQTATAALIHQKL
ref|NP_389559.1|       TPEDFYVYSGDDALTLPILSVGGRGVVSVASHIAGTDMQQMIKNYTNGQTANAALIHQKL
ref|YP_091490.1|       TPEDFAVYSGDDSLTLPALSVGARGIVSVASHIIGPEMQEMIKHYTEGNTAQAALIHQKL
ref|YP_001125250.1|    TPDDFLLYSGDDSLTLPVLAIGGAGVVSVASHIIGNEMQQMIRAFQAGDHQKAAALHRKW
ref|ZP_02169638.1|     TPDDFTVYSGDDSLTLPSLAVGADGIVSVSSHIIGKHMQQMVRYYKDGQVGEAALLHQKL
RAAC02920              KPDDFLLYSGDDKFTLPMLAIGAAGVVSVAGHVVGRQIRTMMDLFWQGQVDEAAYWSARL
                       .*:**  :***** :*** *::*.  *:***:.*:   *   .:: *:     *:    **   :

ref|YP_001421255.1|    LPIMKELFKAPNPAPVKTALQLKGLDVGSVRLPLIPLNEDERLSLSSVISEL--------
ref|NP_389559.1|       LPIMKELFKAPNPAPVKTALQLRGLDVGSVRLPLVPLTEDERLSLSSTISEL--------
ref|YP_091490.1|       LPLMKGLFAAPNPSPLKTALQLKGLDVGSVRLPLIPLNEDERLRLSSLMNGL--------
ref|YP_001125250.1|    VPLMKGLFAAPSPVPVKTALQLRGLDVGPVRLPLVPLTEQERSELSRLLSAL--------
ref|ZP_02169638.1|     LPIMRGMFIAPSPAPVKTALDMTGLDVGGVRLPLVPLTEEERKTLESIV----------
RAAC02920              LPIFEAMFMEASPAPVKEALSILGIDVGSVRSPLVPASKALREHLYTLLNALGVIEPSA
                       :*::. :*   ..* *:* **.: *:*** ** **:*  .:  *     :
```

FIG. 90A

```
ref|NP_844736.1|       ---------------------------------------------------IKRVKNHIN
ref|NP_832053.1|       ---------------------------------------------------IKRVKNHIN
ref|YP_001375026.1|    ---------------------------------------------------IKRVKNHIN
ref|NP_691737.1|       ---------------------------------------------------KHMQNYIN
ref|YP_175305.1|       ---------------------------------------------------VKTVKNWID
RAAC02924              ---------------------------------------------------MRRLQNYVN
                                                                          : ::* ::

ref|NP_844736.1|       GEWVESTGTEVEAVPNPATGKIIAYVPLSPKEDVEKAVEAAKAAYETWSKVPVPNRSRQL
ref|NP_832053.1|       GEWVESTGTEVEAVPNPATGKIIAYVPLSPKEDVEKAVEAAKAAFETWSKVPVPNRSRNL
ref|YP_001375026.1|    GEWVESTGTEVEAVPNPATGKIIAYVPLSPKEDVERAVEAAKNAYETWSKVPVPNRSRML
ref|NP_691737.1|       GKWVDAKSGKQEVIPNPATGETIATVTISDVEDVDMAVAAAKEVFPEWSDIPVPNRTRYL
ref|YP_175305.1|       GAWVEASTADTEVVPNPATGEAIAYVPLSGERDVEQAVASAKRAYETWKTVPVPERTRYM
RAAC02924              GTWVEVESEHAVPVYNPATGEVIAETPLSTHVDVARAVEGAKRAFASWSRVPVVKRARVV
                        * **:      .  : *****: ** ..:*   **  ** .** .:  *. :** :*:* :

ref|NP_844736.1|       YKYLQLLQENKEELAKIITLENGKTLTDATGEVQRGIEAVELATSAPNLMMGQALPNIAS
ref|NP_832053.1|       YKYLQLLQENKDELAKIITLENGKTLTDATGEVQRGIEAVELATSTPNLMMGQALPNIAS
ref|YP_001375026.1|    YKYLQLLQENKDELSKIITLENGKTLKDASGEVQRGIEAVELATSAPNLMMGQALPNIAG
ref|NP_691737.1|       LDYWKLLQDNKEELAKIITLENCKSLRDAQGEVQRGIEVVELATSTPSMMMGDALPSIAK
ref|YP_175305.1|       FAYLEQLKKNREQLAQLITLENKTIKDARGEVQRGIECVELATSTPTMMMGDALPDIAS
RAAC02924              FDFLAKLKAERDAIAKMITTEHGKSYLDAQAEVDRGIEGIEHALSAPTLMMGESLAEVSE
                         : *:  ::: :::::** *:**: :**.**:**** :* * *:*.:***:*..::

ref|NP_844736.1|       GIDGSIWRYPIGVVAGITPFNFPMMIPLWMFPLAIACGNTFVLKTSERTPLLAERLVELF
ref|NP_832053.1|       GIDGSIWRYPIGVVAGITPFNFPMMIPLWMFPLAIACGNTFVLKTSERTPLLAERLVELF
ref|YP_001375026.1|    GIDGSIWRYPLGVVAGITPFNFPMMIPLWMFPLAIACGNTFVLKTSERTPLLAERLVELF
ref|NP_691737.1|       GIDGSIWRYPLGVVAGITPFNFPMMVPLWMFPLAIACGNTFVLKTSERTPILAERLVELF
ref|YP_175305.1|       GIDGSIWRYPLGVVAGITPFNFPMMVPLWMFPLAIAAGNTFVLKTSERTPLLAEQLVSLM
RAAC02924              GLEQTYYRYPLGVVASITPFNFPAMIPLWVMCGWAVVTCNALILKPSEQTPMTTLRLVEMF
                        *::  :  :****.****.****** *:***::  *:. **::::**.**:**:   : :**.::

ref|NP_844736.1|       YEAGFPKGVLNLVQGGKDVVNSILENKDIQAVSFVGSEPVARYVYETGTKHGKRVQALAG
ref|NP_832053.1|       YEAGFPKGVLNLVQGGKDVVNSILENKDIQAVSFVGSEPVARYVYETGTKHGKRVQALAG
ref|YP_001375026.1|    YEAGFPKGVLNLVQGGKEVVNSILENKEIQAVSFVGSEPVARYVYETGTKYGKRVQALAG
ref|NP_691737.1|       YEAGFPKGVLNLVHGGKEVVNRFLTHPDIEAVSFVGSEPVAKHVYQTGTAHGKRVQALAG
ref|YP_175305.1|       HEVGLPRGVLNLVNGGKAVVNGLLNHPDVEAISFVGSEPVARYVYETGTANGKRVQALAG
RAAC02924              HEAGLPPGVLQAVNGGKEAVDAILSHPEIVAVNFTGSTRTAAYVYETAARHHKRVQAFAG
                        :*.*:* ***:  *:*** .*:  :*   : :: *:.*.**  .*  :**:*.:      *****:**

ref|NP_844736.1|       AKNHAIVMPDCNLEKTVQGVIGSAFASSGERCMACSVVAVVDEIADEFIDVLVAETKKLK
ref|NP_832053.1|       AKNHAIVMPDCNLEKTVQGVIGSAFASSGERCMACSVVAVVDEIADEFIDVLVAETKKLK
ref|YP_001375026.1|    AKNHAIVMPDCNLEKTVQGVIGSAFGSSGERCMACSVVAVLDEIADEFIDALVSETRKLK
ref|NP_691737.1|       AKNHAVVMPDCDVEKTIQGVLGAASACSVVAVVDDIADEFLEKLVKETKKLR
ref|YP_175305.1|       AKNHAVVLADCELDKTVQGVIGAAFASSGERCMACSVVAVVEEVADAFIEKLTAETKKLT
RAAC02924              AKNHAIVLEDAVLEPTIDGILRAAFHNGGQRCMATSVVVAVGSVADEVVERLAEGARRMK
                        *****:*: *. :: *::*:: :** ..:****  ***..:  .:**  .:: *. ::::

ref|NP_844736.1|       VGDGFHEDNYVGPLIRESHKERVLGYINSGVADGATLLVDGRKIKEEVGEGYFVGATIFD
ref|NP_832053.1|       VGDGFNEDNYVGPLIRESHKERVLGYINSGVADGATLLVDGRKINEEVGEGYFVGATIFD
ref|YP_001375026.1|    VGDGFHEENYVGPLIRESHKERVIGYINSGVADGASLLVDGRQIKEDVEGCYFVGATIFD
ref|NP_691737.1|       VGDGMDDSNFIGPVIRESHKERVLSYIDSGVDEGAHLLVDGRKIKEETPDGYYVGATIFD
ref|YP_175305.1|       VGNGKNDEHFVGPLIRQSHKDKVVKYIEQGVEQGAELLVDGRNATSEE-AGYYLGATLFD
RAAC02924              IGHGFEEGVDVTPLIRKEHRDRVRAYVDFAAMS-ARLVVDGRPAIDEHPEGFYLGPCLLD
                        :*.* .: :  :*:**:.*:::* *::... . * *:**** .::  *:::*. ::*
```

FIG. 90B

```
ref|NP_844736.1|      GVNQEMKIWQDEIFAPVLSIVRVKDLEEGIKLTNQSKFANGAVIYTSNGKHAQTFRDNID
ref|NP_832053.1|      GVNQEMKIWQDFIFAPVLSIVRVKDLEEGIKLTNQSKFANGAVIYTSNGKHAQTFRDNID
ref|YP_001375026.1|   GVNQNMKTWQDFIFAPVLSIVRVRDLEEGIQLTNQSKFANGAVIYTSSGKHAQTFRDHID
ref|NP_691737.1|      HVTQDMKIWQDEIFAPVLSVVRVSDLEEGIRVTNQSKFANGAVIYTNSGKSAQQFRNRID
ref|YP_175305.1|      HVTPFMTIWQEFLFAPVLSIVRVRDLEEATALTNRSRFANGAVIYTSSGKAAQHFRNAID
RAAC02924             GVTPEMRVWQEELFGPVLSVVRARDLDEAIAIANRSRYANGAILYTQSGKAAQVFRDRID
                       *.  :*  :**:*:*.****:**.  **:*.*   ::*:*::****::**..**  ** **:  **

ref|NP_844736.1|      AGMIGVNVNVPAPMAFFAFAGNKASFFGDLGTNGTDGVQFYTRKKVVTERWF
ref|NP_832053.1|      AGMIGVNVNVPAPMAIFAFAGNKASFFGDLSTNGTDGVQFYTRKKVVTERWF
ref|YP_001375026.1|   AGMIGVNVNVPAPMAFFAFAGNKASFYGDLGTNGKDGVQFYTRKKVVTERWF
ref|NP_691737.1|      AGMIGVNVNVPAPMAFFSFAGNKASFYGDLGTNGKDGVQFYTRKKVVTERWF
ref|YP_175305.1|      AGMVGINVNVPAPMAFFSFAGNKASFFGDLGTNGRDGIQFYTRKKVVTERWF
RAAC02924             AGMVGINVNVPLPVAFFPFGGHKDSFYGVTGENGKELVQFFTRRKVVSTRWF
                      ***:*:*****  *:***.*.*:*  **:*     . ** :  :**:**:***:  ***
```

FIG. 91A

```
ref|YP_148646.1|        ----------DLIAPERYNLTSEMERHAAADPDRIALKWESEQGETKEITYGRLMARANQ
ref|ZP_01859600.1|      ----------DLLSPERYNLISEVEKFAGEQ-GKKAAIIWKSEQGEEKEITYENLIKNANK
ref|YP_001376529.1|     ----------ELLAFPSYNLVTEIEKYMNEK-DKLALIWQDEKGARREVTYFELIKGANK
ref|YP_038694.1|        ----------ELLAFPSYNLVSEIEKYTGDK-EKLALIWQDDKGNRREVTYAELMKGANK
ref|ZP_01696063.1|      ---------SDLIAFQTYNIAEEIEKYARDP-HKVALIWEDKEGMHREVTYKELIENANR
RAAC02926               MEPSQTAAFAELLAPDVFNIASAILDRDESR---RALVWRSEAGAKRTLTYGELRRESLR
                                      :*::*  :*:   :       *: *... *  :** .*   : :

ref|YP_148646.1|        IGNAFLSHGLEKGDKVLVMMPRLIETYEVYIGALKAGLVVIPSSEMLRTKDLQYRLVHSE
ref|ZP_01859600.1|      IGNAFINNGLEKGDVVLVMIPRLIEAYETYVAALKAGMVVIPSSEMLRAKDLKYRIEHGD
ref|YP_001376529.1|     IGNAFIKSGLQKGDKLLIMMPRLIEAYMTYIGAIKAGFVVIPSSEMLRKKDIEYRIQHGE
ref|YP_038694.1|        IGNAFIKSGLQKGDKLLIMMPRLIEAYMTYIAAIKAGFVVIPSSEMLRKKDIEYRIGHGE
ref|ZP_01696063.1|      TGHVFLESGLKKGDTILVMVPRIVEAYEVYLAAMKCGIVLLPASEMLRTKDLDYRIEAGD
RAAC02926               LAQSLHDLGLRKGDRVLVLMPRRPETYAVYLAILSLGAVVLPGSELLMPNDIAYRLRHAE
                         . :  :  . **.***  :*:::**  *:*  .*:.  :. * *:*:*.**:*   :* **:    .:

ref|YP_148646.1|        AKAVVAYAPYTDEFAPIDGIERLTKF--VIGEP-RDGWIPLEDAMAKESETLEAADTSRD
ref|ZP_01859600.1|      VKAVVCYFPYTFQFDELEESSGL--MKFVVGAE-KEGWLSLDSLKNESSDELALADTGRE
ref|YP_001376529.1|     VKAIISYEPYISQFEGIEGMDS--LQKFVLSEKEVDGWANLNTALETESDVLDIVKTDKE
ref|YP_038694.1|        VKAIVSYEPYIGQFDDIEAMES--LQKFVLSEQSVDGWINLKTALETESDMLEMAKTDKE
ref|ZP_01696063.1|      VKGVVAHYSCTEQFKEVRGIDHLKKF--VIGEP-EQGWAFLDEKKKAAPCELEIAKTSKD
RAAC02926               AKGVIAHAALAERAEAAIAEAPWVQLRVVVEGP-REGWLAYDDLVRGAPREWDVVPTRRD
                         .*.::.:  .    :     .**     :**    .  . *  ::

ref|YP_148646.1|        DMAFLSYTSGTTGNPKGVVHCHGWAYAHLRTAAKNWLCIEEGDLVWATAGPGWQKWIWSP
ref|ZP_01859600.1|      DMAFLSYTSGTTGNPKGVVHTHGWAYAHLRTAAKKWLSIEEGDTVWATAGPGWQKWIWSP
ref|YP_001376529.1|     DMVFLSYTSGTTGNPKGVVHTHGWAYAHLRTSAPNWLGIEEND1VWATASPGWQKWIWSP
ref|YP_038694.1|        DMVFLSYTSGTTGNPKGVVHTHAWAYAHLRTSAPNWLGIEENDVVWATASPGWQKWIWSP
ref|ZP_01696063.1|      DIAILSYTSGTTGNPKGVIHTHSWGYAHLRTAAPNWLGIQKGDRVWATAAPGWQKWVWSP
RAAC02926               DLAFLSYTSGTTGYPKGVMHVHGWAYAHWHIAAKRWLGIEPDDVVWATAGPGWAKWIWSP
                        *:.:******* **:* *.*.***   :* .** *: .* ***.* :* ref|YP_148646.1|        FLSVLGSGATGFVYYGRFEPETYLQLLEKYNINVLCCTPTEYRLMAKVPDIGRYHLSHLH
ref|ZP_01859600.1|      FLSVLGSGATGLVYQGKFEPDTYLQMLEDYQVNVLCCTPTEYRLMAKVDDLGKYHLQHLH
ref|YP_001376529.1|     FLATLGSGATGFVYHGKFEPKTYLQLLDENQVNVLCCTPTEYRLMAKVENLQQYNLKALH
ref|YP_038694.1|        FLATLGSGATGFVYHGKFEPKTYINLLDDNKVNVLCCTPTEYRLMAKVENISEYNLEALH
ref|ZP_01696063.1|      FLSVLCSGAIGFVYNGRFDPEKYLSLLDEYEINVLCCTPTEYRLMAKVDDLSQYHLKSLR
RAAC02926               FVATLMSCATGFHYGGRFDAETFLRLIDDEAVNVLCATPTEYRMMAKVDGLDRFRLSSLR
                        *::.* ***  *: * *:*:...:*  ::::  :****.******:**** .:  ..:.*.  *:

ref|YP_148646.1|        SAVSAGEPLNREVIDTFAKHFGVEVRDGYGQTENTLLVGVMKGMPIKPGSMGKPTPGNRV
ref|ZP_01859600.1|      SAVSAGEPLNREVIDAFQKIIFNVDVRDGYGQTENTLLVGIMKGMELKPGSMGKPTPGNRV
ref|YP_001376529.1|     SAVSAGEPLNREVIETFQKHFQVTVRDGYGQTENTLLIGVMKGMEIRPGSMGKPTPGNQV
ref|YP_038694.1|        SAVSAGEPLNREVIETFQKHFHITVRDGYGQTENTLLVGVMKGMDIRPGSMGKPTPGNHV
ref|ZP_01696063.1|      SAVSAGEPLNREVIDVFQNHFGITIRDGYGQTESTLLVGYSLDTPLRPGSMGKPFPGNEV
RAAC02926               QAVSAGEPLNREVIDTFRRHFQVTVRDGYGQTENTLLVATCVDTEVRPGSMGLPTVEGAV
                        .************:.*  .  :  :****.*:.    _  ::****** *    . * ref|YP_148646.1|        EIIDENGEPCPPGQVGDIAVHIETPALFKYYYKDPERTAMQFRGDYYITGDKARKDEDGY
ref|ZP_01859600.1|      EIIDEDGKPCSPGEVGDIAVHVDTPALFKNYYKDPERTAMQFRGDYYITGDKAKKDEDGY
ref|YP_001376529.1|     EIINEEGHPVSVGEVGDIAVHIDTPALFKQYYKDDERTAMQFRGDYYITGDKAKKDEDGY
ref|YP_038694.1|        DIVDEEGMPVRVGEVGDIAVHIETPALFKQYYKDDERTAMQFRGDYYITGDKAKKDEDGY
ref|ZP_01696063.1|      EIVNDDGKPCKLGETGDIAVERDTPALFKGYYKEPERTAKQYRGDYFITGDRARKDEDGY
RAAC02926               DIVDDEGRPLPPGQVGDIAVRRDFPALFRGYYKDDERTEAQFRGAWYITGDRAEKDEDGY
                         :*::::* *   *:.****** : ****: ***: *** *:** ::****:*.******
```

FIG. 91B

```
ref|YP_148646.1|         FWFEGRGDDIIISAGYTIGPFEVEDALVKHPAVKECAVVASPDEVRGHVVKAFVVLRD--
ref|ZP_01859600.1|       FWFEGRGDDIIISSGYTIGPFEVEDALVKHPSVKECAVVASPDEVRGNIVKAFVVLRD--
ref|YP_001376529.1|      FWFEGRGDDIIISSGYTIGPFEVEDALVKHPYVRECAVVASPDEIRGSVVKAFIVLRD--
ref|YP_038694.1|         FWFEGRGDDIIISSGYTIGPFEVEDALVKHPYVRECAVVASPDEIRGSVVKAFIVLRE--
ref|ZP_01696063.1|       FWFEGRRDDIIISSGYTIGPFEVEDALVKHPYVKECAVVASPHEIRGSIVKAFVVLKD--
RAAC02926                LWFSGRADDIIISAGYTIGPFEVEDALVKHPLVRECAAVSSPDEVRGAIVKAFVVLKDAN
                          **.** ******:***************** *:***.*:**.*:** :****:**::

ref|YP_148646.1|         ------GVDKDD--------PSLIPALQEHVKQLTAPYKYPRKIEFVDDLPKTASGKIRR
ref|ZP_01859600.1|       ------GVSPED--------PDLVKSLQDHVKELTAPYKYPRKIEFIEELPKTTSGKIRR
ref|YP_001376529.1|      ------NVQF----------KEDTLIPLLQEHVKTLTAPYKYPRKIEFVDELPKTISGKIRR
ref|YP_038694.1|         ------NIEK----------NEETLIPILQQHVKELTAPYKYPRKIEFVDELPKTISGKIRR
ref|ZP_01696063.1|       ------GISEN--------LPGLVKELQNHVKQLTAPYKYPRAIEFIKELPKTASGKIRR
RAAC02926                ---LHRELASDGE-----RREALVRELQEHVKRITAPYKYPRAIEFVEDLPKTTSGKIRR
                            :           *:  :* :****** *:.:** **** ref|YP_148646.1|         VELRERE-------------
ref|ZP_01859600.1|       IELRQNERKTVQK-------
ref|YP_001376529.1|      VELRKQEMELRLK-------
ref|YP_038694.1|         IELRKQE-------------
ref|ZP_01696063.1|       VELRQQEWNR----------
RAAC02926                VELREREWKRHRKLNEEQGG
                         :***:.*
```

FIG. 92A

```
ref|YP_146227.1|        -----------NYINGEWKEPSTGQFAPVINPATGETIAEVAMSGPNDIDEAVQAAKEAQ
dbj|BAB39706.1|         ------------------------------------SGPNDIDEAVQAAKEAQ
ref|YP_001124476.1|     -----------LNFINGKWQPALSGQWAPVINPANGETIGEVALSAAADVDAAVKAAKAAQ
ref|ZP_01695767.1|      --------EKYLNYIDGEWCEPSTGKFAPVVNPANGKTLGEVAQSAEPDLDRAVQAAKSAQ
RAAC02986               MRRMHRFEPCLNFIGGRWREPKTGQYGDNVNPANGEVLGVWARSGPDDLDDAVRAAREAQ
ref|ZP_01723231.1|      -----------NYIGGKWSTHSHLQSIAVTNPANGEQLATIPLSTSNEVDEAVVAAKQAQ
                                       *   ::* ** **: **

ref|YP_146227.1|        KQWALVPAPKRAEILYKVGMLLKERKEQLARMLTMEMGKVIEEARGEVQEGIDMAFYMAG
dbj|BAB39706.1|         RQWALVPAPKRAEILYKVGMLLKERKEQLARLLTMEMGKVIEEARGEVQEGIDMAFYMAG
ref|YP_001124476.1|     KKWALVPAPKRADVLYKVGLLLKERKEQLARLLTMEMGKVIEEARGEVQEGIDMAFYMAG
ref|ZP_01695767.1|      SVWRLVPAPERANYLYKVGELLKQRKEQIARTLTSEMGKVIDEARGEVQEAIDMAFYMAG
RAAC02986               AAWRLVPAPERAKVLRRVADLLRDRKDEIARTLTMEMGKVIEEARGEVQEAIDMAEYMAG
ref|ZP_01723231.1|      KSWALVPAPKRAEFLYAIGQKMKEKKEYLATVLTKEMGKVIEEARGEVQEGIDMAYYMAG
                         * *****:**. *  :.   :::*: :*  ** *****:********.**** ****

ref|YP_146227.1|        EGRRLFGDTTPSELKDKFAMSVRVPVGVVGIITPWNFPIAIATWKSFPAIVAGNAVVWKP
dbj|BAB39706.1|         EGRRLFGDTTPSELKDKFAMSVRTPVGVVGIITPWNFPIAIATWKSFPAIVAGNAVVWKP
ref|YP_001124476.1|     EGRRLFGDTTPSELKDKFAMSVRVPVGVVGIITPWNFPIAIATWKSFPAIVAGNAVVWKP
ref|ZP_01695767.1|      EGRRQFGDTVPSELQNKFAMSIRVPVGIAGLITPWNFPIAIASWKSLPALVTGNAVIWKP
RAAC02986               EGRRLFGQTTPSELPDKFAMSVRVPVGVVGIITPWNFPIAIASWKSLPAIVAGNAVVWKP
ref|ZP_01723231.1|      EGRRLFGETTPSELANKFAMSVRAPIGVVALITPWNFPVAIATWKSFPAIVAGNTFIWKP
                        ** :*.**  :***:*.:*:*...:*****:*:*::*:::* ref|YP_146227.1|        APETPIMAQELARIFEEAGLPPGVFHVVHGDGPTVGNALVEHPDVKVISFTGSNEVGRMI
dbj|BAB39706.1|         APETPIMAQELARIFEEAGLPPGVFHVVHGDGPTVGNALVEHPDVKVISFTGSNEVGRMI
ref|YP_001124476.1|     ALETPFMARELAAIFTEAGLPDGVFNVVHGDGPTAGNALVEHPDVPVISFTGSNEVGRQI
ref|ZP_01695767.1|      ATETPATACAFVKIYEEAGLPKGLVNLVHGSGSVIGEAMVEHPGIGLISFTGSNEVGRKI
RAAC02986               AEETPLTARAFVEVYQEAGLPAGVLNVVFGDGPVVGEAMLHHPGIDVISFTGSTETGRHI
ref|ZP_01723231.1|      SNETPMMACEMGKIFEEVGLPDGVANIVFGTGPTVGTALIEHPDVKVISFTGSTTTGSKV
                        : ***  *   :  ::  *.***  *: ::*.* *.. * *::.**.: :*****. .*  :

ref|YP_146227.1|        AEKCGRLLKKVSLEMGGKNAVIVMDDADLTLAVDGIIWSAFGTSGQRCTACSRVIVHERV
dbj|BAB39706.1|         AEKCGRLLKKVSLEMGGKNAVIVMDDADLTLAVDGIIWSAFGTSGQRCTACSRVIVHERV
ref|YP_001124476.1|     AEKCGRLLKKVSLEMGGKNAVIVMDDADLTLAVDGIVWSAFGTSGQRCTACSRVIVHERV
ref|ZP_01695767.1|      NERAGGLLKRTSLEMGGKNAVIVMDDADLDLAVDGILWGAFGTSGQRCTATSRVIVHKKI
RAAC02986               ASRAGANLKRVSLEMGGKNAITVLADADLDLAVDAILWSAYCTSCQRCTAASRVIVEREA
ref|ZP_01723231.1|      AELGGKHLKKISLEMGGKNAVIVMDDADLQLATEGILWSAFGTAGQRCTACSRVIVHKDV
                         .  *  **:: ********: *: **** **.:.*:*.:**:****** *****..

ref|YP_146227.1|        KQELERRLLEAVKTLKIGNGLDETVKVGPVIHEEALQKIDRYVRIGVEEGAKLLVGGYIL
dbj|BAB39706.1|         KQEFERRLLEAVKTLKIGNGLDETVKVGPVIHEEALQKIDRYVRIGVEEGAKLLVGGYIL
ref|YP_001124476.1|     KQELEWRLLEAVKTLKIGDGLDETVKVGPVIHEEALQKIERYVHIGREEGAKLLVGGHIL
ref|ZP_01695767.1|      KDALEEKLIRRTAELKIGDGLDETVAVGPVINTEALNRIHQYVETGKKEGARLLTGGRIL
RAAC02986               EEALLARLLPRVQALRVGDGLDPAVNVGPVIHEEALAKIDRYVRLGVDEGARLLTGGRRL
ref|ZP_01723231.1|      KEQLENRLLDEMQKLTIGNGLDEGVKIGPVINKAALEKINHYVQIGKQEGATLLAGGRIL
                        ::  : :*:    *   * :*:***   * :**:  :*.:**. *  * .** * ref|YP_146227.1|        REGDYARGFYYAPTIFTDVTPNMRIAREEIFGPVVSIISVRSLDEAIAVNNSVDYGLSSA
dbj|BAB39706.1|         REGDYARGFYYAPTIFTDVTPNMRIAREEIFGPVVSIISVRSLDEAIAVNNSVDYGLSSA
ref|YP_001124476.1|     SDGDYARGFYYAPTIFTDVTPDMRIAREEIFGPVVSIISVRSLDEAIAVNNCVDYGLSSA
ref|ZP_01695767.1|      P----GKGYYYAPTVFTDVSPEMVIAQEEIFGPVVSIIPVASLEEAIVVNNSVTFGLSSG
RAAC02986               TEGPLARGFYYAPTVFAGVRPDMRIAQEEIFGPVLCVMAVDSFEEAIRVNNGVRYGLSAS
ref|ZP_01723231.1|      NEPPYDNGFYYEPTLFTNVKPDMIIAQEEIFGPVVSLIEVASLEEAIEVNNGVKFGLSSS
                        .*:** **:*:.* *:* **:*******:.:: * *::*** *** * :*** ..
```

FIG. 92B

```
ref|YP_146227.1|       IFTRDVNNVFRAMRDLDTGIVYVNAGTTGAEIHLPFGGTKGTGNGHRDSGVAALDVFTEW
dbj|BAB39706.1|        IFTRDVNNVFRAMRDLDTGIVYVNAGTTGAEIHLPFGGTKGTGNGHRDSGVAALDVFTEW
ref|YP_001124476.1|    IFTRDVNNVFRAMRDLDTGIVYVNAGTTGAEIHLPFGGTKGTGNGHRDSGVAALDVFTEW
ref|ZP_01695767.1|     IFTKDVNKAFQAMRDLDTGIVYINAGTTGAEIHLPFGGTKGTGNGHRDSGPAALDVYTEW
RAAC02986              IFTRDVNRVFRAMRDLDTGIVYVNAGTTGAEIHLPFGGTKATGNGHRDSGQAALDVFTEW
ref|ZP_01723231.1|     IFSQNVNTIFRAQRDLDTGIVYINAGTTGAEIHLPFGGIKGTGNGHRDSGVAALDVYTEW
                       :::   *:* ******:*************.***** :* ref|YP_146227.1|       RSIYVDFSGKLQRAQIDTD
dbj|BAB39706.1|        RSIYVDFSGKLQRAQIDTD
ref|YP_001124476.1|    RSIYVDFSGKLQRAQIDTD
ref|ZP_01695767.1|     KAVYVDFSGKLQRAQIDNN
RAAC02986              KTVYVDYSGRLQRAQIDNN
ref|ZP_01723231.1|     KSIYVDYSGKLQRAQID--
                       :::***:**:*******
```

FIG. 93

```
ref|YP_001127080.1|    ------------------------------------------AYREVKERLRGSIAPVVT
ref|YP_148885.1|       ------------------------------------------AYHEAKERLRGSIAPVVT
ref|YP_001374290.1|    ------------------------------------------------KLRGSIAPIIT
ref|NP_693789.1|       ------------------------------------------------IKKRLRGSIAPVIT
RAAC03010              MVAGRDGGHGLGTQRSRRTVRDDGRACGWVYQMRLRGGRVMGAEKDVYSRLRGSIVPMVT
ref|YP_144223.1|       ---------------------------------------------------RGSIPPLPT
                                                                          ****  *:  * ref|YP_001127080.1|    PFDEEGNVDLTTLTSLIDWHIKSGTHGISVTGTSGEPSSLTLDERKQVMETAKKAVAGRV
ref|YP_148885.1|       PFDEEGNVDFAALAALIDWHIESGTHGISVTGTSGEPSSLTLEERKQVMETAKKAVAGRV
ref|YP_001374290.1|    PFDESGAIDFQTFENLIHWHIESGSHGISVTGTTGEPSSLKVEERVKVMETAAKAINGRV
ref|NP_693789.1|       PFKVNGDIDFKKQSELIEFQIENGTHAISVTGTSGEPSSLTTEERVQVMENAIKTINGRI
RAAC03010              PFLEDGSFDFKSYRELIEWQIESGSHGISCAGTTGEPSSLTIEEREYLFEVTMDAVRGRV
ref|YP_144223.1|       PFRR-GRLDEEALRRLVERVVQGGSHGVSVGGTTGEPGTQTLEERKRAIEVVLDQVAGRV
                       **   *  *      *:.    ::.:*.:*  **:***.:   :**   :*   .  :  **:

ref|YP_001127080.1|    PFVPGTGSTNHAETIELTKFAQEIGADAAMVIVPYYNRPSQQALYKHFKAVAESV-DIPI
ref|YP_148885.1|       PFVPGTGSTNHAETIELTKFAQEIGADAAMVIVPYYNRPSQQALYKHFKAVAEAV-DIPI
ref|YP_001374290.1|    PFAPCTGSTNHEETLYLTKKAQEIGADAALVIVPYYNKPSQHALYKHFKTVADSV-DIPI
ref|NP_693789.1|       PFAPGTGSTNHDETMYVTKKAEEMCADAAMVIVPYYNKPNQEALYDHFKTVADSV-DIPI
RAAC03010              PVVLGTGSTNHAEALRLTKTAERLGADAALVIVPYYNRPSQEGLYRHFRAIADSV-DIPI
ref|YP_144223.1|       PVIPGTGALRLEETLELTRFAKEAGAQGAMVIVPYVVKPNQEGLYRYTAEVARTVPDFPL
                       *.  ***: .  *::  :*: *: . **:.*:******  :*.*..** :*   :*  :*  *:*:

ref|YP_001127080.1|    IVYNIPGRTAVNLEVKTLARLVEDCPNIIGVKESNKDFEHVNRVLWHCGRDFLLFSGIEL
ref|YP_148885.1|       IVYNIPGRTAVNLEVKTLARLAEDCPNIIGVKESNKDFEHVNRVLWHCGRDFLLFSGIEL
ref|YP_001374290.1|    IIYNIPGRTAVNLQVETIAKLNQDCPNIIGIKESNKDFEHINRVLLHCGRDFLLFSGIEL
ref|NP_693789.1|       IIYNIPGRTAQNMEVKTMARLVKDCPNIVGAKESNKDFEHVNRVLLNCGRDFLLFSGIEL
RAAC03010              ILYNIPGRTGVNLEPATMARLKRDCRNIIGVKESNKDFEQVTRVFQACGRDFLVYSGIEL
ref|YP_144223.1|       LIYNIPGRAGVEIAPKTVGRLRRDFPNIVGLKHSSKDLEYLSHLFLEAGRDFLVFCGLES
                       ::*******:. ::   *:.:*  .*  **:* *.*.**:*  :.:::  .*****::.*:* ref|YP_001127080.1|    LCYPMLAIGGAGSISATANVVPQKVAELHDAWFDGDVKRAQDLHFELMELNDVLFIETNP
ref|YP_148885.1|       LCYPMLAIGGAGSISATANVVPHKVAELHDAWFEGDIKRAQDLHFELMELNDVLFIETNP
ref|YP_001374290.1|    LCYPMLAIGGAGHISATANVAPKQVAEVYNAWNECDIKRALTLHYELMPLNDVLFKDTNP
ref|NP_693789.1|       LCYPMLAIGGAGSISATANVEPKKVAEMHNAWEEGDIKRAQDLHFELMNLNDVLFKDTNP
RAAC03010              LCYPMLALGGAGHLSATANLMPREVARLYDLVQAGKWHEAIDLHFQLVDINEALFWETNP
ref|YP_144223.1|       LTLPMMSLGAVGTIAATANWLPKEVALLCEKALAGDYQGARELHFILLEANEAIFWDTNP
                       *  **::*..* :***  *:**    *::**    : .   *. .*   **:.*:   *:..:* :*** ref|YP_001127080.1|    GPVKAALGMLGKITPKLRLPLDLPSEEHQEQIRRTLVKYGLL
ref|YP_148885.1|       GPVKAALGMMGKITPKLRLPLDLPSEEHQQQIRRTLVKYGLL
ref|YP_001374290.1|    APVKAALGMMGKIKPVLRLPMDVPSQELQDEIRDVLKNY---
ref|NP_693789.1|       APVKAALGMMGMIEPVLRRPMGLPSDALQEEIRDTLVKYGKI
RAAC03010              GPVKACLAMMGKIRPVVRPPLALPGEEMTAKLRGVLTSYGLI
ref|YP_144223.1|       IPLKTVLSWMGLLEKEWRPPLGPTTPEVEERLRRMAERYGLL
                       *:*: *. :*  : *    * *:  .     * *:        *
```

THERMOPHILIC AND THERMOACIDOPHILIC METABOLISM GENES AND ENZYMES FROM ALICYCLOBACILLUS ACIDOCALDARIUS AND RELATED ORGANISMS, METHODS

CROSS-REFERENCE TO RELATED APPLICATIONS

This application is a divisional of U.S. patent application Ser. No. 12/380,551, filed Feb. 26, 2009, now U.S. Pat. No. 8,728,803, issued May 20, 2014, which application claims the benefit of the filing date of U.S. Provisional Patent Application Ser. No. 61/032,339, filed Feb. 28, 2008, for "THERMOPHILIC AND THERMOACIDOPHILIC METABOLISM GENES AND ENZYMES FROM *ALICYCLOBACILLUS ACIDOCALDARIUS* AND RELATED ORGANISMS, METHODS," the disclosure of each of which is hereby incorporated herein in its entirety by this reference.

GOVERNMENT RIGHTS

This invention was made with government support under Contract Number DE-AC07-99ID13727 and Contract Number DE-AC07-05ID14517 awarded by the United States Department of Energy. The government has certain rights in the invention.

(long sequence listing—with parent (Filed with Request to Transfer CRF))

STATEMENT ACCORDING TO 37 C.F.R. §1.821(c) or (e)—SEQUENCE LISTING SUBMITTED AS PDF FILE WITH A REQUEST TO TRANSFER CRF FROM PARENT APPLICATION

Pursuant to 37 C.F.R. §1.821(c) or (e), a file containing a PDF version of the Sequence Listing has been submitted concomitant with this application, the contents of which are hereby incorporated by reference. The transmittal documents of this application include a Request to Transfer CRF from the parent application.

TECHNICAL FIELD

The present invention relates generally to biotechnology. More specifically, embodiments of the present invention relate to isolated and/or purified polypeptides and nucleic acid sequences encoding polypeptides from *Alicyclobacillus acidocaldarius* and methods for their use.

BACKGROUND

Enzymes have a great deal of potential for production of useful chemicals in industrial processes. However, industrial processes typically occur at extremes of temperature, pH, salt, etc., to which most of the well-studied enzymes and organisms are not well suited.

BRIEF SUMMARY OF THE INVENTION

Embodiments of the invention relate to purified and/or isolated nucleotide sequences of the genome of *Alicyclobacillus acidocaldarius*, or a homologue or fragment thereof. In one embodiment of the invention, the nucleotide sequence is selected from at least one of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 or a homologue or fragment thereof. In another embodiment of the invention, the homologue is selected from the group consisting of a nucleotide sequence having at least 80% sequence identity to at least one of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566.

Embodiments of the invention may further relate to an isolated and/or purified nucleic acid sequence comprising a nucleic acid sequence encoding a polypeptide selected from the group consisting of a polypeptide having at least 90% sequence identity to at least one of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565.

Embodiments of the invention also relate to isolated and/or purified polypeptides coded for by a nucleotide sequence comprising a nucleotide sequence of the genome of *Alicyclobacillus acidocaldarius*, or a homologue or fragment thereof. In one embodiment, the nucleotide sequence comprises a nucleotide sequence selected from the group consisting of a nucleotide sequence having at least 80% sequence identity to at least one of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566.

In another embodiment of the invention, the nucleotide sequence comprises a nucleotide sequence selected from at least one of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 or a homologue or fragment thereof. In still another embodiment, the polypeptide comprises an amino acid sequence of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565. In yet another embodiment, the polypeptide comprises an amino acid sequence selected from the group consisting of a polypeptide having at least 90% sequence identity to at least one of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565.

In embodiments of the invention, the polypeptides may be acidophilic and/or thermophilic. In further embodiments, the polypeptides may be glycosylated, pegylated, and/or otherwise post-translationally modified.

Embodiments of methods include methods of altering metabolism in a cell, the methods comprising providing a recombinant, purified, and/or isolated nucleotide sequence comprising a nucleotide sequence selected from the group consisting of a nucleotide sequence having at least 90% sequence identity to at least one of the sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 and/or a recombinant, purified, and/or isolated polypeptide selected from the group consisting of a polypeptide having at least 90% sequence identity to at least one of the sequences of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 to the cell.

Further embodiments of methods include placing a cell producing or encoding a recombinant, purified, and/or isolated nucleotide sequence comprising a nucleotide sequence selected from the group consisting of a nucleotide sequence having at least 90% sequence identity to at least one of the sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 and/or a recombinant, purified, and/or isolated polypeptide selected from the group consisting of a polypeptide having at least 90% sequence identity to at least one of the sequences of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 in an environment comprising temperatures at or above about 25, 30, 35, 40, 45, 50, 55, 60, 65, 70, 75, 80, 85, 90, and/or 95 degrees Celsius and/or a pH at, below, and/or above 8, 7, 6, 5, 4, 3, 2, 1, and/or 0.

These and other aspects of the invention will become apparent to the skilled artisan in view of the teachings contained herein.

BRIEF DESCRIPTION OF THE SEVERAL VIEWS OF THE DRAWINGS

FIGS. 1A and 1B depict a sequence alignment between SEQ ID NO:1 (RAAC00079) and ref|YP_074710.1|, ref|YP_359514.1|, ref|YP_516748.1|, ref|YP_643635.1|, and ref|YP_144514.1| (SEQ ID NOS:3-7, respectively), which all have the function assigned to SEQ ID NO:1 in Table 1. Amino acids conserved among all sequences are indicted by a "i" and generally conserved amino acids are indicated by a ":".

FIG. 2 depicts a sequence alignment between SEQ ID NO:18 (RAAC00455) and gb|ABE97159.1|, ref|NP_693902.1|, ref|YP_521150.1|, ref|ZP_01725542.1|, and ref|ZP_01666741.1| (SEQ ID NOS:20-24, respectively), which all have the function assigned to SEQ ID NO:18 in Table 1. Amino acids conserved among all sequences are indicted by a "i" and generally conserved amino acids are indicated by a ":".

FIGS. 3A and 3B depict a sequence alignment between SEQ ID NO:35 (RAAC00461) and ref|YP_361350.1|, ref|NP_244632.1|, ref|ZP_00538452.1|, ref|YP_001127398.1|, and ref|YP_149222.1| (SEQ ID NOS:37-41, respectively), which all have the function assigned to SEQ ID NO:35 in Table 1. Amino acids conserved among all sequences are indicted by a "*" and generally conserved amino acids are indicated by a ":".

FIG. 4 depicts a sequence alignment between SEQ ID NO:52 (RAAC00481) and ref NP_905294.1|, ref|ZP_01666099.1|, ref|YP_360429.1|, ref|YP_754604.1|, and ref|YP_384529.1| (SEQ ID NOS:54-58, respectively), which all have the function assigned to SEQ ID NO:52 in Table 1 Amino acids conserved among all sequences are indicted by a "*" and generally conserved amino acids are indicated by a ":".

FIG. 5 depicts a sequence alignment between SEQ ID NO:69 (RAAC00529) and ref|YP_146903.1|, ref|YP_001125035.1|, ref|YP_001646604.1|, ref|YP_001375911.1|, and ref|ZP_01696300.1| (SEQ ID NOS:71-75, respectively), which all have the function assigned to SEQ ID NO:69 in Table 1. Amino acids conserved among all sequences are indicted by a "*" and generally conserved amino acids are indicated by a ":".

FIG. 6 depicts a sequence alignment between SEQ ID NO:86 (RAAC00552) and ref|YP_001376041.1|, dbj|BAB39458.1|, ref|NP_846569.1|, ref|YP_896466.1|, and ref|ZP_00238879.1| (SEQ ID NOS:88-92, respectively), which all have the function assigned to SEQ ID NO:86 in Table 1. Amino acids conserved among all sequences are indicted by a "*" and generally conserved amino acids are indicated by a ":".

FIG. 7 depicts a sequence alignment between SEQ ID NO:103 (RAAC00553) and ref|YP_001646745.1|, ref|YP_001376045.1|, ref|NP_833836.1|, ref|ZP_00739346.1|, and ref|YP_085454.1| (SEQ ID NOS:105-109, respectively), which all have the function assigned to SEQ ID NO:103 in Table 1. Amino acids conserved among all sequences are indicted by a "*" and generally conserved amino acids are indicated by a ":".

FIG. 8 depicts a sequence alignment between SEQ ID NO:120 (RAAC00554) and reflYP_147981.1l, reflNP_390900.1l, reflZP_01667656.1l, splP22806lBIOF_BACSH, and dbjlBAB39457.1l (SEQ ID NOS:122-126, respectively), which all have the function assigned to SEQ ID NO:120 in Table 1. Amino acids conserved among all sequences are indicted by a "*" and generally conserved amino acids are indicated by a ":".

FIG. 9 depicts a sequence alignment between SEQ ID NO:137 (RAAC00632) and reflYP_001126681.1l, reflYP_148515.1l, reflZP_01171798.1l, reflYP_001374758.1l, and reflYP_080106.1l (SEQ ID NOS:139-143, respectively), which all have the function assigned to SEQ ID NO:137 in Table 1. Amino acids conserved among all sequences are indicted by a "*" and generally conserved amino acids are indicated by a ":".

FIGS. 10A and 10B depict a sequence alignment between SEQ ID NO:154 (RAAC00633) and reflNP_243928.1l, reflZP_01695378.1l, reflZP_01725506.1l, reflYP_176142.1l, and reflYP_850199.1l (SEQ ID NOS:156-160, respectively), which all have the function assigned to SEQ ID NO:154 in Table 1 Amino acids conserved among all sequences are indicted by a "*" and generally conserved amino acids are indicated by a ":".

FIGS. 11A and 11B depict a sequence alignment between SEQ ID NO:171 (RAAC00634) and reflYP_001126680.1l, reflYP_001487695.1l, reflYP_148514.1l, gblAAL99356.1l, and reflYP_176141.1l (SEQ ID NOS: 173-177, respectively), which all have the function assigned to SEQ ID NO:171 in Table 1. Amino acids conserved among all sequences are indicted by a "*" and generally conserved amino acids are indicated by a ":".

FIG. 12 depicts a sequence alignment between SEQ ID NO:188 (RAAC00174) and reflYP_175798.1l, reflNP_243358.1l, reflNP_389472.1l, reflZP_01861659.1l, and reflYP_147042.1l (SEQ ID NOS:190-194, respectively), which all have the function assigned to SEQ ID NO:188 in Table 1 Amino acids conserved among all sequences are indicted by a "*" and generally conserved amino acids are indicated by a ":".

FIG. 13 depicts a sequence alignment between SEQ ID NO:205 (RAAC00635) and reflYP_148513.1l, reflNP_243926.1l, reflYP_001126679.1l, reflYP_176140.1l, and reflNP_843875.1l (SEQ ID NOS:207-211, respectively), which all have the function assigned to SEQ ID NO:205 in Table 1. Amino acids conserved among all sequences are indicted by a "*" and generally conserved amino acids are indicated by a ":".

FIG. 14 depicts a sequence alignment between SEQ ID NO:222 (RAAC00637) and reflNP_243923.1l, reflYP_148510.1l, reflZP_01171803.1l, reflYP_001126676.1l, and reflNP_926497.1l (SEQ ID NOS:224-228, respectively), which all have the function assigned to SEQ ID NO:222 in Table 1. Amino acids conserved among all sequences are indicted by a "*" and generally conserved amino acids are indicated by a ":".

FIGS. 15A and 15B depict a sequence alignment between SEQ ID NO:239 (RAAC00638) and reflNP_243922.1l, reflYP_148509.1l, reflYP_001126675.1l, reflZP_01171804.1l, and reflYP_075945.1l (SEQ ID NOS:241-245, respectively), which all have the function assigned to SEQ ID NO:239 in Table 1. Amino acids conserved among all sequences are indicted by a "*" and generally conserved amino acids are indicated by a ":".

FIG. 16 depicts a sequence alignment between SEQ ID NO:256 (RAAC00639) and splQ67MJ3lLEUD_SYMTH, reflYP_148508.1l, reflYP_001126674.1l, reflYP_080099.1l, and reflYP_001487689.1l (SEQ ID NOS:258-262, respectively), which all have the function assigned to SEQ ID NO:256 in Table 1. Amino acids conserved among all sequences are indicted by a "*" and generally conserved amino acids are indicated by a ":".

FIGS. 17A and 17B depict a sequence alignment between SEQ ID NO:273 (RAAC00642) and reflYP_826036.1l, gblABV27286.1l, gblAAL17866.1lAF424980_1, reflZP_01859643.1l, and reflNP_244026.1l (SEQ ID NOS:275-279, respectively), which all have the function assigned to SEQ ID NO:273 in Table 1. Amino acids conserved among all sequences are indicted by a "*" and generally conserved amino acids are indicated by a ":".

FIGS. 18A-18C depict a sequence alignment between SEQ ID NO:290 (RAAC00727) and reflYP_001637294.1l, reflZP_01516643.1l, reflYP_645264.1l, reflYP_146876.1l, and reflYP_001125008.1l (SEQ ID NOS:292-296, respectively), which all have the function assigned to SEQ ID NO:290 in Table 1. Amino acids conserved among all sequences are indicted by a "*" and generally conserved amino acids are indicated by a ":".

FIGS. 19A and 19B depict a sequence alignment between SEQ ID NO:307 (RAAC00729) and reflYP_001125365.1l, reflYP_147249.1l, reflZP_01695431.1l, reflNP_244828.1l, and reflYP_895448.1l (SEQ ID NOS:309-313, respectively), which all have the function assigned to SEQ ID NO:307 in Table 1. Amino acids conserved among all sequences are indicted by a "*" and generally conserved amino acids are indicated by a ":".

FIGS. 20A and 20B depict a sequence alignment between SEQ ID NO:324 (RAAC00730) and reflYP_075148.1l, splP16468lMAOX_BACST, reflYP_147293.1l, reflYP_643888.1l, and reflYP_001125416.1l (SEQ ID NOS:326-330, respectively), which all have the function assigned to SEQ ID NO:324 in Table 1. Amino acids conserved among all sequences are indicted by a "*" and generally conserved amino acids are indicated by a ":".

FIGS. 21A-21C depict a sequence alignment between SEQ ID NO:341 (RAAC00735) and reflZP_01696337.1l, reflZP_02171753.1l, reflYP_284976.1l, reflYP_001546997.1l, and reflYP_001277075.1l (SEQ ID NOS: 343-347, respectively), which all have the function assigned to SEQ ID NO:341 in Table 1. Amino acids conserved among all sequences are indicted by a "*" and generally conserved amino acids are indicated by a ":".

FIG. 22 depicts a sequence alignment between SEQ ID NO:358 (RAAC00812) and reflZP_00539373.1l, reflYP_386234.1l, reflYP_001378696.1l, reflZP_01723286.1l, and reflNP_391778.1l (SEQ ID NOS:360-364, respectively), which all have the function assigned to SEQ ID NO:358 in Table 1. Amino acids conserved among all sequences are indicted by a "*" and generally conserved amino acids are indicated by a ":".

FIGS. 23A and 23B depict a sequence alignment between SEQ ID NO:375 (RAAC00196) and reflYP_147293.1l, splP16468lMAOX_BACST, reflYP_643888.1l, reflYP_075148.1l, and reflYP_001125416.1l (SEQ ID NOS:377-381, respectively), which all have the function assigned to SEQ ID NO:375 in Table 1. Amino acids conserved among all sequences are indicted by a "*" and generally conserved amino acids are indicated by a ":".

FIG. 24 depicts a sequence alignment between SEQ ID NO:392 (RAAC00814) and reflYP_360188.1l, reflZP_01666093.1l, reflNP_242895.1l, reflYP_360122.1l, and ref|ZP_01372991.1| (SEQ ID NOS:394-398, respectively), which all have the function assigned to SEQ ID NO:392 in Table 1. Amino acids conserved among all sequences are indicted by a "*" and generally conserved amino acids are indicated by a ":".

FIGS. 25A and 25B depict a sequence alignment between SEQ ID NO:409 (RAAC00815) and ref|YP_644483.1|, ref|NP_294183.1|, ref|YP_359514.1|, ref|YP_605214.1|, and ref|YP_592595.1| (SEQ ID NOS:411-415, respectively), which all have the function assigned to SEQ ID NO:409 in Table 1. Amino acids conserved among all sequences are indicted by a "*" and generally conserved amino acids are indicated by a ":".

FIG. 26 depicts a sequence alignment between SEQ ID NO:426 (RAAC00816) and ref|YP_147450.1|, ref|YP_001125561.1|, ref|ZP_01696479.1|, ref|NP_241996.1|, and ref|YP_079308.1| (SEQ ID NOS:428-432, respectively), which all have the function assigned to SEQ ID NO:426 in Table 1. Amino acids conserved among all sequences are indicted by a "*" and generally conserved amino acids are indicated by a ":".

FIG. 27 depicts a sequence alignment between SEQ ID NO:443 (RAAC00822) and ref|ZP_00539140.1|, ref|ZP_02130394.1|, ref|NP_241073.1|, ref|ZP_01696475.1|, and dbj|BAA75325.1| (SEQ ID NOS:445-449, respectively), which all have the function assigned to SEQ ID NO:443 in Table 1. Amino acids conserved among all sequences are indicted by a "*" and generally conserved amino acids are indicated by a ":".

FIGS. 28A-28C depict a sequence alignment between SEQ ID NO:460 (RAAC00950) and ref|YP_001420821.1|, ref|ZP_01696606.1|, ref|ZP_01171726.1|, ref|NP_389098.1|, and ref|YP_091797.1| (SEQ ID NOS:462-466, respectively), which all have the function assigned to SEQ ID NO:460 in Table 1. Amino acids conserved among all sequences are indicted by a "*" and generally conserved amino acids are indicated by a ":".

FIG. 29 depicts a sequence alignment between SEQ ID NO:477 (RAAC00952) and ref|YP_146314.1|, ref|YP_001124593.1|, ref|NP_830405.1|, ref|ZP_00739906.1|, and ref|NP_391552.1| (SEQ ID NOS:479-483, respectively), which all have the function assigned to SEQ ID NO:477 in Table 1. Amino acids conserved among all sequences are indicted by a "*" and generally conserved amino acids are indicated by a ":".

FIG. 30 depicts a sequence alignment between SEQ ID NO:494 (RAAC00990) and ref|YP_148038.1|, ref|YP_001126216.1|, ref|NP_242546.1|, ref|ZP_01697215.1|, and ref|YP_175412.1| (SEQ ID NOS:496-500, respectively), which all have the function assigned to SEQ ID NO:494 in Table 1. Amino acids conserved among all sequences are indicted by a "*" and generally conserved amino acids are indicated by a ":".

FIG. 31 depicts a sequence alignment between SEQ ID NO:511 (RAAC01029) and ref|YP_001132791.1|, ref|YP_890165.1|, ref|YP_704478.1|, ref|YP_956012.1|, and ref|YP_879906.21 (SEQ ID NOS:513-517, respectively), which all have the function assigned to SEQ ID NO:511 in Table 1. Amino acids conserved among all sequences are indicted by a "*" and generally conserved amino acids are indicated by a ":".

FIGS. 32A-32C depict a sequence alignment between SEQ ID NO:528 (RAAC01041) and ref|YP_359304.1|, ref|ZP_01697277.1|, ref|YP_519313.1|, ref|ZP_01370069.1|, and ref|YP_429480.1| (SEQ ID NOS:530-534, respectively), which all have the function assigned to SEQ ID NO:528 in Table 1. Amino acids conserved among all sequences are indicted by a "*" and generally conserved amino acids are indicated by a ":".

FIGS. 33A and 33B depict a sequence alignment between SEQ ID NO:545 (RAAC01057) and ref|YP_148861.1|, ref|YP_076839.1|, ref|NP_244355.1|, ref|ZP_01697463.1|, and ref|ZP_01173543.1| (SEQ ID NOS:547-551, respectively), which all have the function assigned to SEQ ID NO:545 in Table 1. Amino acids conserved among all sequences are indicted by a "*" and generally conserved amino acids are indicated by a ":".

FIG. 34 depicts a sequence alignment between SEQ ID NO:562 (RAAC00352) and ref|NP_691707.1|, ref|YP_829756.1|, ref|YP_947785.1|, ref|YP_001221402.1|, and ref|YP_885435.1| (SEQ ID NOS:564-568, respectively), which all have the function assigned to SEQ ID NO:562 in Table 1. Amino acids conserved among all sequences are indicted by a "*" and generally conserved amino acids are indicated by a ":".

FIG. 35 depicts a sequence alignment between SEQ ID NO:579 (RAAC04321) and gb|ABW71834.1|, ref|YP_055250.1|, ref|YP_612035.1|, ref|YP_134751.1|, and ref|ZP_01441442.1| (SEQ ID NOS:581-585, respectively), which all have the function assigned to SEQ ID NO:579 in Table 1 Amino acids conserved among all sequences are indicted by a "*" and generally conserved amino acids are indicated by a ":".

FIG. 36 depicts a sequence alignment between SEQ ID NO:596 (RAAC04349) and ref|YP_917551.1|, ref|ZP_00631342.1|, ref|YP_001259911.1|, ref|NP_105797.1|, and ref|ZP_00998521.1| (SEQ ID NOS:598-602, respectively), which all have the function assigned to SEQ ID NO:596 in Table 1. Amino acids conserved among all sequences are indicted by a "*" and generally conserved amino acids are indicated by a ":".

FIGS. 37A and 37B depict a sequence alignment between SEQ ID NO:613 (RAAC01327) and emb|CAD30313.1|, ref|ZP_01697379.1|, ref|YP_001375474.1|, ref|NP_833288.1|, and ref|NP_979866.1| (SEQ ID NOS:615-619, respectively), which all have the function assigned to SEQ ID NO:613 in Table 1. Amino acids conserved among all sequences are indicted by a "*" and generally conserved amino acids are indicated by a ":".

FIGS. 38A and 38B depict a sequence alignment between SEQ ID NO:630 (RAAC01351) and ref|YP_001125497.1|, ref|YP_175672.1|, ref|NP_243001.1|, ref|YP_147384.1|, and ref|YP_001108459.1| (SEQ ID NOS:632-636, respectively), which all have the function assigned to SEQ ID NO:630 in Table 1. Amino acids conserved among all sequences are indicted by a "*" and generally conserved amino acids are indicated by a ":".

FIGS. 39A and 39B depict a sequence alignment between SEQ ID NO:647 (RAAC01352) and ref|YP_147385.1|, ref|YP_001125498.1|, ref|YP_175671.1|, ref|NP_926015.1|, and ref|YP_001660274.1| (SEQ ID NOS:649-653, respectively), which all have the function assigned to SEQ ID NO:647 in Table 1. Amino acids conserved among all sequences are indicted by a "*" and generally conserved amino acids are indicated by a ":".

FIGS. 40A and 40B depict a sequence alignment between SEQ ID NO:664 (RAAC01354) and ref|YP_001636557.1|, ref|ZP_01517435.1|, ref|ZP_01697170.1|, ref|YP_001374183.1|, and ref|YP_082630.1| (SEQ ID NOS:666-670, respectively), which all have the function assigned to SEQ ID NO:664 in Table 1. Amino acids conserved among all sequences are indicted by a "*" and generally conserved amino acids are indicated by a ":".

FIGS. 41A and 41B depict a sequence alignment between SEQ ID NO:681 (RAAC01360) and ref|ZP_01724857.1|, ref|ZP_00235684.1|, ref|YP_895924.1|, ref|YP_037600.1|, and ref|YP_001646030.1| (SEQ ID NOS:683-687, respectively), which all have the function assigned to SEQ ID NO:681 in Table 1. Amino acids conserved among all sequences are indicted by a "*" and generally conserved amino acids are indicated by a ":".

FIG. 42 depicts a sequence alignment between SEQ ID NO:698 (RAAC01408) and ref|YP_872951.1|, gb|AAQ84159.1|, ref|YP_701593.1|, ref|YP_885121.1|, and ref|ZP_02169377.1| (SEQ ID NOS:700-704, respectively), which all have the function assigned to SEQ ID NO:698 in Table 1. Amino acids conserved among all sequences are indicted by a "*" and generally conserved amino acids are indicated by a ":".

FIG. 43 depicts a sequence alignment between SEQ ID NO:715 (RAAC01425) and ref|YP_146050.1|, ref|YP_001124307.1|, ref|YP_360564.1|, ref|NP_691609.1|, and ref|NP_294646.1| (SEQ ID NOS:717-721, respectively), which all have the function assigned to SEQ ID NO:715 in Table 1. Amino acids conserved among all sequences are indicted by a "*" and generally conserved amino acids are indicated by a ":".

FIG. 44 depicts a sequence alignment between SEQ ID NO:732 (RAAC01517) and ref|YP_902570.1|, ref|YP_076319.1|, ref|YP_001629366.1|, ref|ZP_01667660.1|, and ref|YP_429281.1| (SEQ ID NOS:734-738, respectively), which all have the function assigned to SEQ ID NO:732 in Table 1. Amino acids conserved among all sequences are indicted by a "*" and generally conserved amino acids are indicated by a ":".

FIG. 45 depicts a sequence alignment between SEQ ID NO:749 (RAAC00449) and ref|ZP_01666747.1|, pdb|2QE7|H, sp|P22480|ATPE_BACPF, ref|ZP_01188594.1|, and ref|YP_521144.1| (SEQ ID NOS:751-755, respectively), which all have the function assigned to SEQ ID NO:749 in Table 1. Amino acids conserved among all sequences are indicted by a "*" and generally conserved amino acids are indicated by a ":".

FIGS. 46A and 46B depict a sequence alignment between SEQ ID NO:766 (RAAC01555) and ref|YP_079644.1|, sp|P23630|DCDA_BACSU, ref|NP_390219.1|, ref|YP_001421740.1|, and ref|YP_001487298.1| (SEQ ID NOS:768-772, respectively), which all have the function assigned to SEQ ID NO:766 in Table 1. Amino acids conserved among all sequences are indicted by a "*" and generally conserved amino acids are indicated by a ":".

FIGS. 47A and 47B depict a sequence alignment between SEQ ID NO:783 (RAAC01575) and ref|NP_241871.1|, ref|YP_077980.1|, ref|YP_001420375.1|, ref|NP_388616.1|, and ref|NP_693628.1| (SEQ ID NOS:785-789, respectively), which all have the function assigned to SEQ ID NO:783 in Table 1. Amino acids conserved among all sequences are indicted by a "*" and generally conserved amino acids are indicated by a ":".

FIG. 48 depicts a sequence alignment between SEQ ID NO:800 (RAAC01657) and dbj|BAB40585.1|, ref|NP_241079.1|, ref|YP_001126012.1|, ref|ZP_01171269.1|, and ref|ZP_01860561.1| (SEQ ID NOS:802-806, respectively), which all have the function assigned to SEQ ID NO:800 in Table 1. Amino acids conserved among all sequences are indicted by a "*" and generally conserved amino acids are indicated by a ":".

FIG. 49 depicts a sequence alignment between SEQ ID NO:817 (RAAC01658) and ref|NP_241080.1|, dbj|BAB40586.1|, ref|YP_001126011.1|, ref|NP_693798.1|, and ref|ZP_00539126.1| (SEQ ID NOS:819-823, respectively), which all have the function assigned to SEQ ID NO:817 in Table 1. Amino acids conserved among all sequences are indicted by a "*" and generally conserved amino acids are indicated by a ":".

FIG. 50 depicts a sequence alignment between SEQ ID NO:834 (RAAC01669) and ref|YP_001125402.1|, ref|YP_147282.1|, ref|ZP_01859257.1|, ref|NP_388913.1|, and ref|YP_001420249.1| (SEQ ID NOS:836-840, respectively), which all have the function assigned to SEQ ID NO:834 in Table 1. Amino acids conserved among all sequences are indicted by a "*" and generally conserved amino acids are indicated by a ":".

FIGS. 51A-51C depict a sequence alignment between SEQ ID NO:851 (RAAC01678) and ref|ZP_01696606.1|, ref|YP_146312.1|, ref|ZP_01171726.1|, ref|YP_001124591.1|, and ref|ZP_01696079.1| (SEQ ID NOS:853-857, respectively), which all have the function assigned to SEQ ID NO:851 in Table 1. Amino acids conserved among all sequences are indicted by a "*" and generally conserved amino acids are indicated by a ":".

FIGS. 52A and 52B depict a sequence alignment between SEQ ID NO:868 (RAAC01685) and ref|YP_431081.1|, ref|YP_001211085.1|, ref|YP_001111663.1|, ref|YP_001547204.1|, and ref|NP_213242.1| (SEQ ID NOS:870-874, respectively), which all have the function assigned to SEQ ID NO:868 in Table 1. Amino acids conserved among all sequences are indicted by a "*" and generally conserved amino acids are indicated by a ":".

FIG. 53 depicts a sequence alignment between SEQ ID NO:885 (RAAC01745) and ref|YP_001127228.1|, ref|YP_149070.1|, ref|ZP_00539127.1|, ref|NP_241079.1|, and ref|YP_074240.1| (SEQ ID NOS:887-891, respectively), which all have the function assigned to SEQ ID NO:885 in Table 1. Amino acids conserved among all sequences are indicted by a "*" and generally conserved amino acids are indicated by a ":".

FIG. 54 depicts a sequence alignment between SEQ ID NO:902 (RAAC01746) and ref|YP_149069.1|, ref|YP_001127227.1|, ref|ZP_00539126.1|, ref|YP_001125046.1|, and ref|NP_833691.1| (SEQ ID NOS:904-908, respectively), which all have the function assigned to SEQ ID NO:902 in Table 1. Amino acids conserved among all sequences are indicted by a "*" and generally conserved amino acids are indicated by a ":".

FIG. 55 depicts a sequence alignment between SEQ ID NO:919 (RAAC01748) and ref|NP_828658.1|, emb|CAJ88521.1|, ref|NP_625066.1|, ref|YP_001104836.1|, and ref|YP_658557.1| (SEQ ID NOS:921-925, respectively), which all have the function assigned to SEQ ID NO:919 in Table 1. Amino acids conserved among all sequences are indicted by a "*" and generally conserved amino acids are indicated by a ":".

FIGS. 56A and 56B depict a sequence alignment between SEQ ID NO:936 (RAAC00450) and pdb|2QE7|D, sp|Q9LA80|ATPB_GEOTH, ref|YP_149211.1|, sp|P41009|ATPB_BACCA, and prf||11211283A (SEQ ID NOS:938-942, respectively), which all have the function assigned to SEQ ID NO:936 in Table 1. Amino acids conserved among all sequences are indicted by a "*" and generally conserved amino acids are indicated by a ":".

FIGS. 57A-57C depict a sequence alignment between SEQ ID NO:953 (RAAC01759) and ref|ZP_02170376.1|, ref YP_001546865.1|, ref|YP_001125323.1|, ref|YP_147200.2|, and ref|YP_091630.1| (SEQ ID NOS:955-959, respectively), which all have the function assigned to SEQ ID NO:953 in Table 1. Amino acids conserved among all sequences are indicted by a "*" and generally conserved amino acids are indicated by a ":".

FIG. 58 depicts a sequence alignment between SEQ ID NO:970 (RAAC01762) and gb|ABW71834.1|, ref|ZP_02015336.1|, ref|YP_055250.1, ref|YP_136548.1|, and ref|NP_102793.1| (SEQ ID NOS:972-976, respectively), which all have the function assigned to SEQ ID NO:970 in Table 1. Amino acids conserved among all sequences are indicted by a "*" and generally conserved amino acids are indicated by a ":".

FIG. 59 depicts a sequence alignment between SEQ ID NO:987 (RAAC01763) and ref|YP_300327.1|, ref|NP_693723.1|, ref|YP_190012.1|, ref|YP_252288.1|, and ref|ZP_01227084.1| (SEQ ID NOS:989-993, respectively), which all have the function assigned to SEQ ID NO:987 in Table 1. Amino acids conserved among all sequences are indicted by a "*" and generally conserved amino acids are indicated by a ":".

FIG. 60 depicts a sequence alignment between SEQ ID NO:1004 (RAAC01767) and ref|ZP_01860323.1|, ref|NP_244450.1|, ref|YP_148929.1|, ref|YP_080823.1|, and ref|ZP_01171654.1| (SEQ ID NOS:1006-1010, respectively), which all have the function assigned to SEQ ID NO:1004 in Table 1. Amino acids conserved among all sequences are indicted by a "*" and generally conserved amino acids are indicated by a ":".

FIG. 61 depicts a sequence alignment between SEQ ID NO:1021 (RAAC01797) and ref|YP_076186.1|, ref|NP_691214.1|, ref|ZP_01170331.1|, ref|NP_388333.1|, and ref|YP_001375327.1| (SEQ ID NOS:1023-1027, respectively), which all have the function assigned to SEQ ID NO:1021 in Table 1. Amino acids conserved among all sequences are indicted by a "*" and generally conserved amino acids are indicated by a ":".

FIGS. 62A and 62B depict a sequence alignment between SEQ ID NO:1038 (RAAC01900) and ref|NP_691405.1|, ref|NP_242876.1|, ref|NP_241871.1|, ref|YP_001420375.1|, and ref|NP_388616.1| (SEQ ID NOS:1040-1044, respectively), which all have the function assigned to SEQ ID NO:1038 in Table 1. Amino acids conserved among all sequences are indicted by a "*" and generally conserved amino acids are indicated by a ":".

FIG. 63 depicts a sequence alignment between SEQ ID NO:1055 (RAAC01939) and ref|NP_390790.1|, ref|ZP_02170616.1|, ref|NP_693087.1|, ref|YP_080204.1|, and sp|Q59202|MDH_BACIS (SEQ ID NOS:1057-1061, respectively), which all have the function assigned to SEQ ID NO:1055 in Table 1. Amino acids conserved among all sequences are indicted by a "*" and generally conserved amino acids are indicated by a ":".

FIG. 64 depicts a sequence alignment between SEQ ID NO:1072 (RAAC01996) and ref|NP_244279.1|, ref|YP_001126997.1|, ref|YP_148810.1|, ref|YP_001488092.1|, and ref|NP_391097.1| (SEQ ID NOS:1074-1078, respectively), which all have the function assigned to SEQ ID NO:1072 Table 1. Amino acids conserved among all sequences are indicted by a "*" and generally conserved amino acids are indicated by a ":".

FIG. 65 depicts a sequence alignment between SEQ ID NO:1089 (RAAC02025) and ref|NP_390723.1|, ref|YP_080139.1|, ref|YP_001422141.1|, ref|ZP_01171785.1|, and ref|NP_243959.1| (SEQ ID NOS:1091-1095, respectively), which all have the function assigned to SEQ ID NO:1089 in Table 1. Amino acids conserved among all sequences are indicted by a "*" and generally conserved amino acids are indicated by a ":".

FIG. 66 depicts a sequence alignment between SEQ ID NO:1106 (RAAC00451) and pdb|2QE7|G, ref|YP_001127389.1|, ref|YP_149212.1|, ref|YP_001488540.1|, and emb|CAA30654.1| (SEQ ID NOS:1108-1112, respectively), which all have the function assigned to SEQ ID NO:1106 in Table 1. Amino acids conserved among all sequences are indicted by a "*" and generally conserved amino acids are indicated by a ":".

FIGS. 67A and 67B depict a sequence alignment between SEQ ID NO:1123 (RAAC02026) and ref|YP_148525.1|, ref|YP_001126690.1|, emb|CAA69872.1|, ref|YP_092553.1|, and ref|NP_243958.1| (SEQ ID NOS:1125-1129, respectively), which all have the function assigned to SEQ ID NO:1123 in Table 1. Amino acids conserved among all sequences are indicted by a "*" and generally conserved amino acids are indicated by a ":".

FIG. 68 depicts a sequence alignment between SEQ ID NO:1140 (RAAC02027) and emb|CAA69873.1|, ref|YP_148524.1|, ref|YP_080136.1|, ref|NP_243957.1|, and ref|ZP_01697535.1| (SEQ ID NOS:1142-1146, respectively), which all have the function assigned to SEQ ID NO:1140 in Table 1. Amino acids conserved among all sequences are indicted by a "*" and generally conserved amino acids are indicated by a ":".

FIG. 69 depicts a sequence alignment between SEQ ID NO:1157 (RAAC02040) and ref|ZP_01697399.1|, ref|YP_001124579.1|, ref|YP_146298.1|, ref|NP_691785.1|, and ref|ZP_01723229.1| (SEQ ID NOS:1159-1163, respectively), which all have the function assigned to SEQ ID NO:1157 in Table 1. Amino acids conserved among all sequences are indicted by a "*" and generally conserved amino acids are indicated by a ":".

FIGS. 70A and 70B depict a sequence alignment between SEQ ID NO:1174 (RAAC02181) and ref|NP_391000.1|, ref|YP_080655.1|, ref|YP_173878.1|, ref|NP_242416.1|, and ref|YP_644452.1| (SEQ ID NOS:1176-1180, respectively), which all have the function assigned to SEQ ID NO:1174 in Table 1. Amino acids conserved among all sequences are indicted by a "*" and generally conserved amino acids are indicated by a ":".

FIG. 71 depicts a sequence alignment between SEQ ID NO:1191 (RAAC02222) and ref|YP_001487576.1|, ref|ZP_02211990.1|, ref|YP_001343716.1|, ref|NP_744947.1|, and ref|YP_633768.1| (SEQ ID NOS:1193-1197, respectively), which all have the function assigned to SEQ ID NO:1191 in Table 1. Amino acids conserved among all sequences are indicted by a "*" and generally conserved amino acids are indicated by a ":".

FIGS. 72A and 72B depict a sequence alignment between SEQ ID NO:1208 (RAAC02274) and ref|YP_146053.1|, ref|ZP_01869175.1|, ref|ZP_00989613.1|, ref|YP_001276414.1|, and ref|YP_001211401.1| (SEQ ID NOS: 1210-1214, respectively), which all have the function assigned to SEQ ID NO:1208 in Table 1. Amino acids conserved among all sequences are indicted by a "*" and generally conserved amino acids are indicated by a ":".

FIGS. 73A and 73B depict a sequence alignment between SEQ ID NO:1225 (RAAC02275) and ref|YP_146052.1|, ref|YP_001546552.1|, ref|YP_001636911.1|, ref|ZP_01514632.1|, and ref|YP_001274650.1| (SEQ ID NOS: 1227-1231, respectively), which all have the function assigned to SEQ ID NO:1225 in Table 1. Amino acids conserved among all sequences are indicted by a "*" and generally conserved amino acids are indicated by a ":".

FIG. 74 depicts a sequence alignment between SEQ ID NO:1242 (RAAC02426) and ref|NP_243521.1|, pdb|1W85|A, sp|P21873|ODPA_BACST, ref|YP_

001421036.1|, and ref|YP_146911.1| (SEQ ID NOS:1244-1248, respectively), which all have the function assigned to SEQ ID NO:1242 in Table 1. Amino acids conserved among all sequences are indicted by a "*" and generally conserved amino acids are indicated by a ":".

FIG. 75 depicts a sequence alignment between SEQ ID NO:1259 (RAAC02427) and ref|ZP_01696304.1|, sp|P21874|ODPB_BACST, ref|YP_001125046.1|, pdb|1W85|B, and ref|YP_146912.1| (SEQ ID NOS:1261-1265, respectively), which all have the function assigned to SEQ ID NO:1259 Table 1. Amino acids conserved among all sequences are indicted by a "*" and generally conserved amino acids are indicated by a ":".

FIGS. 76A and 76B depict a sequence alignment between SEQ ID NO:1276 (RAAC02429) and ref|YP_001125048.1|, sp|P11959|DLDH1_BACST, ref|YP_146914.1|, ref|YP_001486601.1|, and pdb|1EBD|A (SEQ ID NOS:1278-1282, respectively), which all have the function assigned to SEQ ID NO:1276 in Table 1. Amino acids conserved among all sequences are indicted by a "*" and generally conserved amino acids are indicated by a ":".

FIGS. 77A and 77B depicts a sequence alignment between SEQ ID NO:1293 (RAAC00452) and pdb|2QE7|A, ref|YP_361340.1|, ref|YP_001127390.1|, ref|YP_149213.1|, and ref|YP_001356688.1| (SEQ ID NOS:1295-1299, respectively), which all have the function assigned to SEQ ID NO:1293 in Table 1. Amino acids conserved among all sequences are indicted by a "*" and generally conserved amino acids are indicated by a ":".

FIG. 78 depicts a sequence alignment between SEQ ID NO:1310 (RAAC02433) and ref|YP_001542913.1|, ref|YP_644829.1|, ref|YP_356005.1|, emb|CA090974.1|, and ref|YP_001656571.1| (SEQ ID NOS:1312-1316, respectively), which all have the function assigned to SEQ ID NO:1310 in Table 1. Amino acids conserved among all sequences are indicted by a "*" and generally conserved amino acids are indicated by a ":".

FIGS. 79A and 79B depict a sequence alignment between SEQ ID NO:1327 (RAAC02438) and ref|YP_644476.1|, ref|ZP_02191297.1|, ref|ZP_01549387.1|, ref|ZP_01850519.1|, and ref|ZP_01015586.1| (SEQ ID NOS:1329-1333, respectively), which all have the function assigned to SEQ ID NO:1327 in Table 1. Amino acids conserved among all sequences are indicted by a "*" and generally conserved amino acids are indicated by a ":".

FIGS. 80A and 80B depict a sequence alignment between SEQ ID NO:1344 (RAAC02441) and ref|YP_147804.1|, ref|YP_001125954.1|, ref|YP_001125911.1|, ref|YP_147740.1|, and ref|NP_243178.1| (SEQ ID NOS:1346-1350, respectively), which all have the function assigned to SEQ ID NO:1344 in Table 1. Amino acids conserved among all sequences are indicted by a "*" and generally conserved amino acids are indicated by a ":".

FIG. 81 depicts a sequence alignment between SEQ ID NO:1361 (RAAC02442) and ref|YP_001125956.1|, ref|YP_147805.1|, ref|ZP_01169177.1|, ref|ZP_01695873.1|, and ref|NP_831941.1| (SEQ ID NOS:1363-1367, respectively), which all have the function assigned to SEQ ID NO:1361 in Table 1. Amino acids conserved among all sequences are indicted by a "*" and generally conserved amino acids are indicated by a ":".

FIGS. 82A and 82B depict a sequence alignment between SEQ ID NO:1378 (RAAC02630) and ref|ZP_01695367.1|, ref|YP_723673.1|, ref|YP_686117.1|, ref|YP_001111391.1|, and ref|ZP_01623360.1| (SEQ ID NOS: 1380-1384, respectively), which all have the function assigned to SEQ ID NO:1378 in Table 1. Amino acids conserved among all sequences are indicted by a "*" and generally conserved amino acids are indicated by a ":".

FIG. 83 depicts a sequence alignment between SEQ ID NO:1395 (RAAC02644) and ref|NP_782567.1|, sp|Q892U0|LDH_CLOTE, ref|YP_590559.1|, ref|ZP_01514103.1|, and ref|YP_009822.1| (SEQ ID NOS:1397-1401, respectively), which all have the function assigned to SEQ ID NO:1395 in Table 1. Amino acids conserved among all sequences are indicted by a "*" and generally conserved amino acids are indicated by a ":".

FIGS. 84A and 84B depict a sequence alignment between SEQ ID NO:1412 (RAAC02702) and ref|YP_001124710.1|, ref|YP_146529.1|, ref|NP_977551.1|, ref|YP_893868.1|, and ref|NP_843617.1| (SEQ ID NOS:1414-1418, respectively), which all have the function assigned to SEQ ID NO:1412 in Table 1. Amino acids conserved among all sequences are indicted by a "*" and generally conserved amino acids are indicated by a ":".

FIGS. 85A and 85B depict a sequence alignment between SEQ ID NO:1429 (RAAC04058) and ref|ZP_02080303.1|, ref|YP_520543.1|, ref|ZP_01966380.1|, ref|ZP_02039587.1|, and ref|ZP_02073747.1| (SEQ ID NOS:1431-1435, respectively), which all have the function assigned to SEQ ID NO:1429 in Table 1. Amino acids conserved among all sequences are indicted by a "*" and generally conserved amino acids are indicated by a ":".

FIGS. 86A and 86B depict a sequence alignment between SEQ ID NO:1446 (RAAC02843) and ref|YP_001125182.1|, ref|YP_147061.1|, ref|ZP_01171540.1|, ref|NP_692464.1|, and ref|YP_001375719.1| (SEQ ID NOS:1448-1452, respectively), which all have the function assigned to SEQ ID NO:1446 in Table 1. Amino acids conserved among all sequences are indicted by a "*" and generally conserved amino acids are indicated by a ":".

FIG. 87 depicts a sequence alignment between SEQ ID NO:1463 (RAAC02844) and ref|YP_147062.1|, ref|YP_001125183.1|, ref|YP_079003.1|, ref|NP_243335.1|, and ref|ZP_01171539.1| (SEQ ID NOS:1465-1469, respectively), which all have the function assigned to SEQ ID NO:1463 in Table 1. Amino acids conserved among all sequences are indicted by a "*" and generally conserved amino acids are indicated by a ":".

FIG. 88 depicts a sequence alignment between SEQ ID NO:1480 (RAAC00454) and ref|YP_001127392.1|, ref|YP_521149.1|, ref|YP_149215.1|, ref|YP_001488543.1|, and ref|YP_093437.1| (SEQ ID NOS:1482-1486, respectively), which all have the function assigned to SEQ ID NO:1480 in Table 1. Amino acids conserved among all sequences are indicted by a "*" and generally conserved amino acids are indicated by a ":".

FIG. 89 depicts a sequence alignment between SEQ ID NO:1497 (RAAC02920) and ref|YP_001421255.1|, ref|NP_389559.1|, ref|YP_001125250.1|, ref|ZP_02169638.1|, and ref|YP_091490.1| (SEQ ID NOS:1499-1503, respectively), which all have the function assigned to SEQ ID NO:1497 in Table 1. Amino acids conserved among all sequences are indicted by a "*" and generally conserved amino acids are indicated by a ":".

FIGS. 90A and 90B depict a sequence alignment between SEQ ID NO:1514 (RAAC02924) and ref|YP_001375026.1|, ref|YP_175305.1|, ref|NP_844736.1|, ref|NP_691737.1|, and ref|NP_832053.1| (SEQ ID NOS:1516-1520, respectively), which all have the function assigned to SEQ ID NO:1514 in Table 1. Amino acids conserved among all sequences are indicted by a "*" and generally conserved amino acids are indicated by a ":".

FIGS. 91A and 91B depict a sequence alignment between SEQ ID NO:1531 (RAAC02926) and ref|YP_148646.1|, ref|ZP_01696063.1|, ref|ZP_01859600.1|, ref|YP_001376529.1|, and ref|YP_038694.1| (SEQ ID NOS:1533-1537, respectively), which all have the function assigned to SEQ ID NO:1531 in Table 1. Amino acids conserved among all sequences are indicted by a "*" and generally conserved amino acids are indicated by a ":".

FIGS. 92A and 92B depict a sequence alignment between SEQ ID NO:1548 (RAAC02986) and ref|YP_146227.1|, ref|YP_001124476.1|, ref|ZP_01695767.1|, dbj|BAB39706.1|, and ref|ZP_01723231.1| (SEQ ID NOS: 1550-1554, respectively), which all have the function assigned to SEQ ID NO:1548 in Table 1. Amino acids conserved among all sequences are indicted by a "*" and generally conserved amino acids are indicated by a ":".

FIG. 93 depicts a sequence alignment between SEQ ID NO:1565 (RAAC03010) and ref|YP_001127080.1|, ref|YP_148885.1|, ref|YP_001374290.1|, ref|NP_693789.1|, and ref|YP_144223.1| (SEQ ID NOS:1567-1571, respectively), which all have the function assigned to SEQ ID NO:1565 in Table 1. Amino acids conserved among all sequences are indicted by a "*" and generally conserved amino acids are indicated by a ":".

DETAILED DESCRIPTION OF THE INVENTION

Embodiments of the invention include genes and associated proteins related to the metabolism of the thermoacidophile *Alicyclobacillus acidocaldarius*. Coding sequences for genes related to these processes were determined from sequence information generated from sequencing the genome of *Alicyclobacillus acidocaldarius*. These genes and proteins may represent targets and/or elements of transformation systems or vectors for metabolic engineering of *Alicyclobacillus acidocaldarius* or other organisms. Non-limiting examples of nucleotide sequences found within the genome of *Alicyclobacillus acidocaldarius*, and amino acids coded thereby, associated with metabolism are listed in Table 1. Metabolism proteins may be, without limitation, of the following classes: (S)-2-hydroxy-acid oxidases, [acyl-carrier-protein] S-malonyltransferases, 1,3-propanediol Dehydrogenases, 2-isopropylmalate Synthases, 3-hydroxybutyryl-CoA dehydratases, 3-isopropylmalate Dehydratases, 3-isopropylmalate Dehydrogenases, 3-oxoacid CoA-transferases, 8-amino-7-oxononanoate Synthases, Acetaldehyde dehydrogenases (acetylating), Acetate-CoA ligases, Acetolactate synthases, Acetyl-CoA C-acetyltransferases, Aconitate hydratases, Alcohol dehydrogenases, Alcohol dehydrogenases (NADP+), Aldehyde dehydrogenases, Aldehyde dehydrogenases (NAD+), ATP phosphoribosyltransferases, ATP synthase alpha chains, ATP synthase B chains, ATP synthase beta chains, ATP synthase C chains, ATP synthase epsilon chains, ATP synthase gamma chains, Biotin synthases, Branched-chain-amino-acid transaminases, Butyryl-CoA dehydrogenases, Citrate (Si)-synthases, Dethiobiotin synthases, Diaminopimelate decarboxylases, Diaminopimelate epimerases, Dihydrodipicolinate reductases, Dihydrodipicolinate synthases, Dihydrolipoyl dehydrogenases, Dihydroxy-acid dehydratases, Enoyl-CoA hydratases, FdhD proteins (fdsC), Formate dehydrogenases, Glycerate kinases, Glycine hydroxymethyltransferases, Isocitrate lyases, Lactaldehyde reductases, Lactate 2-monooxygenases, L-lactate dehydrogenases, Malate dehydrogenases, Malate dehydrogenases (acceptor), Malate dehydrogenases (oxaloacetate-decarboxylating), Malate synthases, Malonate-semialdehyde dehydrogenases (acetylating), Methylmalonate-semialdehyde dehydrogenases (acylating), N-acetyldiaminopimelate deacetylases, Oxoglutarate dehydrogenases (succinyl-transferring), Phosphoenolpyruvate carboxylases, Phosphoglycerate dehydrogenases, Phosphoribosylanthranilate isomerases, Pyruvate dehydrogenases (acetyl-transferring), Pyruvate phosphate dikinases, Succinate dehydrogenase cytochrome b558 subunits, Succinate dehydrogenase flavoprotein subunits, Succinate dehydrogenase iron-sulfur proteins, Succinate-CoA ligases (ADP-forming); and others.

Embodiments of the invention relate in part to the gene sequences and/or protein sequences comprising genes and/or proteins of *Alicyclobacillus acidocaldarius*. Genes and proteins included are those that play a role in metabolism. Intracellular enzyme activities may be thermophilic and/or acidophilic in nature and general examples of similar genes are described in the literature. Classes of genes, sequences, enzymes and factors include, but are not limited to, those listed in Table 1.

TABLE 1

*Alicyclobacillus acidocaldarius* genes related to metabolism

| Reference | Gene Sequence | Protein Sequence | Function |
| --- | --- | --- | --- |
| RAAC00079 | SEQ ID NO: 1 | SEQ ID NO: 2 | Acetate-CoA ligase |
| RAAC00455 | SEQ ID NO: 18 | SEQ ID NO: 19 | ATP synthase C chain |
| RAAC00461 | SEQ ID NO: 35 | SEQ ID NO: 36 | Glycine hydroxymethyltransferase |
| RAAC00481 | SEQ ID NO: 52 | SEQ ID NO: 53 | 3-hydroxybutyryl-CoA dehydratase |
| RAAC00529 | SEQ ID NO: 69 | SEQ ID NO: 70 | N-acetyldiaminopimelate deacetylase |
| RAAC00552 | SEQ ID NO: 86 | SEQ ID NO: 87 | Biotin synthase |
| RAAC00553 | SEQ ID NO: 103 | SEQ ID NO: 104 | Dethiobiotin synthase |
| RAAC00554 | SEQ ID NO: 120 | SEQ ID NO: 121 | 8-amino-7-oxononanoate Synthase |
| RAAC00632 | SEQ ID NO: 137 | SEQ ID NO: 138 | Branched-chain-amino-acid transaminase |
| RAAC00633 | SEQ ID NO: 154 | SEQ ID NO: 155 | Dihydroxy-acid dehydratase |
| RAAC00634 | SEQ ID NO: 171 | SEQ ID NO: 172 | Acetolactate synthase |
| RAAC00174 | SEQ ID NO: 188 | SEQ ID NO: 189 | [acyl-carrier-protein] S-malonyltransferase |
| RAAC00635 | SEQ ID NO: 205 | SEQ ID NO: 206 | Acetolactate synthase |
| RAAC00637 | SEQ ID NO: 222 | SEQ ID NO: 223 | 3-isopropylmalate Dehydrogenase |
| RAAC00638 | SEQ ID NO: 239 | SEQ ID NO: 240 | 3-isopropylmalate Dehydratase |
| RAAC00639 | SEQ ID NO: 256 | SEQ ID NO: 257 | 3-isopropylmalate Dehydratase |
| RAAC00642 | SEQ ID NO: 273 | SEQ ID NO: 274 | Citrate (Si)-synthase |
| RAAC00727 | SEQ ID NO: 290 | SEQ ID NO: 291 | Oxoglutarate dehydrogenase (succinyl-transferring) |
| RAAC00729 | SEQ ID NO: 307 | SEQ ID NO: 308 | Malate dehydrogenase (acceptor) |
| RAAC00730 | SEQ ID NO: 324 | SEQ ID NO: 325 | Malate dehydrogenase (oxaloacetate-decarboxylating) |
| RAAC00735 | SEQ ID NO: 341 | SEQ ID NO: 342 | Phosphoenolpyruvate carboxylase |
| RAAC00812 | SEQ ID NO: 358 | SEQ ID NO: 359 | 3-oxoacid CoA-transferase |

TABLE 1-continued

*Alicyclobacillus acidocaldarius* genes related to metabolism

| Reference | Gene Sequence | Protein Sequence | Function |
|---|---|---|---|
| RAAC00196 | SEQ ID NO: 375 | SEQ ID NO: 376 | Malate dehydrogenase (oxaloacetate-decarboxylating) |
| RAAC00814 | SEQ ID NO: 392 | SEQ ID NO: 393 | Acetyl-CoA C-acetyltransferase |
| RAAC00815 | SEQ ID NO: 409 | SEQ ID NO: 410 | Acetate-CoA ligase |
| RAAC00816 | SEQ ID NO: 426 | SEQ ID NO: 427 | Butyryl-CoA dehydrogenase |
| RAAC00822 | SEQ ID NO: 443 | SEQ ID NO: 444 | 3-hydroxybutyryl-CoA dehydratase |
| RAAC00950 | SEQ ID NO: 460 | SEQ ID NO: 461 | Formate dehydrogenase |
| RAAC00952 | SEQ ID NO: 477 | SEQ ID NO: 478 | FdhD protein (fdsC) |
| RAAC00990 | SEQ ID NO: 494 | SEQ ID NO: 495 | Dihydrodipicolinate reductase |
| RAAC01029 | SEQ ID NO: 511 | SEQ ID NO: 512 | Acetaldehyde dehydrogenase (acetylating) |
| RAAC01041 | SEQ ID NO: 528 | SEQ ID NO: 529 | Pyruvate, phosphate dikinase |
| RAAC01057 | SEQ ID NO: 545 | SEQ ID NO: 546 | Enoyl-CoA hydratase |
| RAAC00352 | SEQ ID NO: 562 | SEQ ID NO: 563 | Alcohol dehydrogenase (NADP+) |
| RAAC04321 | SEQ ID NO: 579 | SEQ ID NO: 580 | Alcohol dehydrogenase |
| RAAC04349 | SEQ ID NO: 596 | SEQ ID NO: 597 | Phosphoribosylanthranilate isomerase |
| RAAC01327 | SEQ ID NO: 613 | SEQ ID NO: 614 | Aldehyde dehydrogenase (NAD+) |
| RAAC01351 | SEQ ID NO: 630 | SEQ ID NO: 631 | (S)-2-hydroxy-acid oxidase |
| RAAC01352 | SEQ ID NO: 647 | SEQ ID NO: 648 | (S)-2-hydroxy-acid oxidase |
| RAAC01354 | SEQ ID NO: 664 | SEQ ID NO: 665 | Malate synthase |
| RAAC01360 | SEQ ID NO: 681 | SEQ ID NO: 682 | (S)-2-hydroxy-acid oxidase |
| RAAC01408 | SEQ ID NO: 698 | SEQ ID NO: 699 | Butyryl-CoA dehydrogenase |
| RAAC01425 | SEQ ID NO: 715 | SEQ ID NO: 716 | Butyryl-CoA dehydrogenase |
| RAAC01517 | SEQ ID NO: 732 | SEQ ID NO: 733 | Glycerate kinase |
| RAAC00449 | SEQ ID NO: 749 | SEQ ID NO: 750 | ATP synthase epsilon chain |
| RAAC01555 | SEQ ID NO: 766 | SEQ ID NO: 767 | Diaminopimelate decarboxylase |
| RAAC01575 | SEQ ID NO: 783 | SEQ ID NO: 784 | Aldehyde dehydrogenase (NAD+) |
| RAAC01657 | SEQ ID NO: 800 | SEQ ID NO: 801 | Pyruvate dehydrogenase (acetyl-transferring) |
| RAAC01658 | SEQ ID NO: 817 | SEQ ID NO: 818 | Pyruvate dehydrogenase (acetyl-transferring) |
| RAAC01669 | SEQ ID NO: 834 | SEQ ID NO: 835 | Alcohol dehydrogenase |
| RAAC01678 | SEQ ID NO: 851 | SEQ ID NO: 852 | Formate dehydrogenase |
| RAAC01685 | SEQ ID NO: 868 | SEQ ID NO: 869 | 2-isopropylmalate Synthase |
| RAAC01745 | SEQ ID NO: 885 | SEQ ID NO: 886 | Pyruvate dehydrogenase (acetyl-transferring) |
| RAAC01746 | SEQ ID NO: 902 | SEQ ID NO: 903 | Pyruvate dehydrogenase (acetyl-transferring) |
| RAAC01748 | SEQ ID NO: 919 | SEQ ID NO: 920 | Lactate 2-monooxygenase |
| RAAC00450 | SEQ ID NO: 936 | SEQ ID NO: 937 | ATP synthase beta chain |
| RAAC01759 | SEQ ID NO: 953 | SEQ ID NO: 954 | Aconitate hydratase |
| RAAC01762 | SEQ ID NO: 970 | SEQ ID NO: 971 | Alcohol dehydrogenase |
| RAAC01763 | SEQ ID NO: 987 | SEQ ID NO: 988 | Alcohol dehydrogenase |
| RAAC01767 | SEQ ID NO: 1004 | SEQ ID NO: 1005 | ATP phosphoribosyltransferase |
| RAAC01797 | SEQ ID NO: 1021 | SEQ ID NO: 1022 | Butyryl-CoA dehydrogenase |
| RAAC01900 | SEQ ID NO: 1038 | SEQ ID NO: 1039 | Aldehyde dehydrogenase |
| RAAC01939 | SEQ ID NO: 1055 | SEQ ID NO: 1056 | Malate dehydrogenase |
| RAAC01996 | SEQ ID NO: 1072 | SEQ ID NO: 1073 | Diaminopimelate epimerase |
| RAAC02025 | SEQ ID NO: 1089 | SEQ ID NO: 1090 | Succinate dehydrogenase cytochrome b558 subunit |
| RAAC00451 | SEQ ID NO: 1106 | SEQ ID NO: 1107 | ATP synthase gamma chain |
| RAAC02026 | SEQ ID NO: 1123 | SEQ ID NO: 1124 | Succinate dehydrogenase flavoprotein subunit |
| RAAC02027 | SEQ ID NO: 1140 | SEQ ID NO: 1141 | Succinate dehydrogenase iron-sulfur protein |
| RAAC02040 | SEQ ID NO: 1157 | SEQ ID NO: 1158 | Butyryl-CoA dehydrogenase |
| RAAC02181 | SEQ ID NO: 1174 | SEQ ID NO: 1175 | Lactaldehyde reductase |
| RAAC02222 | SEQ ID NO: 1191 | SEQ ID NO: 1192 | 1,3-propanediol Dehydrogenase |
| RAAC02274 | SEQ ID NO: 1208 | SEQ ID NO: 1209 | Alcohol dehydrogenase |
| RAAC02275 | SEQ ID NO: 1225 | SEQ ID NO: 1226 | Aldehyde dehydrogenase (NAD+) |
| RAAC02426 | SEQ ID NO: 1242 | SEQ ID NO: 1243 | Pyruvate dehydrogenase (acetyl-transferring) |
| RAAC02427 | SEQ ID NO: 1259 | SEQ ID NO: 1260 | Pyruvate dehydrogenase (acetyl-transferring) |
| RAAC02429 | SEQ ID NO: 1276 | SEQ ID NO: 1277 | Dihydrolipoyl dehydrogenase |
| RAAC00452 | SEQ ID NO: 1293 | SEQ ID NO: 1294 | ATP synthase alpha chain |
| RAAC02433 | SEQ ID NO: 1310 | SEQ ID NO: 1311 | 3-isopropylmalate Dehydrogenase |
| RAAC02438 | SEQ ID NO: 1327 | SEQ ID NO: 1328 | Acetate-CoA ligase |
| RAAC02441 | SEQ ID NO: 1344 | SEQ ID NO: 1345 | Malonate-semialdehyde dehydrogenase (acetylating) |
| RAAC02442 | SEQ ID NO: 1361 | SEQ ID NO: 1362 | 1,3-propanediol Dehydrogenase |
| RAAC02630 | SEQ ID NO: 1378 | SEQ ID NO: 1379 | Phosphoglycerate dehydrogenase |
| RAAC02644 | SEQ ID NO: 1395 | SEQ ID NO: 1396 | L-lactate dehydrogenase |
| RAAC02702 | SEQ ID NO: 1412 | SEQ ID NO: 1413 | Isocitrate lyase |
| RAAC04058 | SEQ ID NO: 1429 | SEQ ID NO: 1430 | 2-isopropylmalate Synthase |
| RAAC02843 | SEQ ID NO: 1446 | SEQ ID NO: 1447 | Succinate-CoA ligase (ADP-forming) |
| RAAC02844 | SEQ ID NO: 1463 | SEQ ID NO: 1464 | Succinate-CoA ligase (ADP-forming) |
| RAAC00454 | SEQ ID NO: 1480 | SEQ ID NO: 1481 | ATP synthase B chain |
| RAAC02920 | SEQ ID NO: 1497 | SEQ ID NO: 1498 | Dihydrodipicolinate synthase |
| RAAC02924 | SEQ ID NO: 1514 | SEQ ID NO: 1515 | Methylmalonate-semialdehyde dehydrogenase (acylating) |
| RAAC02926 | SEQ ID NO: 1531 | SEQ ID NO: 1532 | Acetate-CoA ligase |
| RAAC02986 | SEQ ID NO: 1548 | SEQ ID NO: 1549 | Aldehyde dehydrogenase (NAD+) |
| RAAC03010 | SEQ ID NO: 1565 | SEQ ID NO: 1566 | Dihydrodipicolinate synthase |

The present invention relates to nucleotides sequences comprising isolated and/or purified nucleotide sequences of the genome of *Alicyclobacillus acidocaldarius* selected from the sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 or one of their fragments.

The present invention likewise relates to isolated and/or purified nucleotide sequences, characterized in that they comprise at least one of: a) a nucleotide sequence of at least one of the sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 or one of their fragments; b) a nucleotide sequence homologous to a nucleotide sequence such as defined in a); c) a nucleotide sequence complementary to a nucleotide sequence such as defined in a) or b), and a nucleotide sequence of their corresponding RNA; d) a nucleotide sequence capable of hybridizing under stringent conditions with a sequence such as defined in a), b) or c); e) a nucleotide sequence comprising a sequence such as defined in a), b), c) or d); and f) a nucleotide sequence modified by a nucleotide sequence such as defined in a), b), c), d) or e).

Nucleotide, polynucleotide, or nucleic acid sequence will be understood according to the present invention as meaning both a double-stranded or single-stranded DNA in the monomeric and dimeric (so-called in tandem) forms and the transcription products of the DNAs.

Aspects of the invention relate to nucleotide sequences in which it has been possible to isolate, purify or partially purify, starting from separation methods such as, for example, ion-exchange chromatography, by exclusion based on molecular size, or by affinity, or, alternatively, fractionation techniques based on solubility in different solvents, or starting from methods of genetic engineering such as amplification, cloning, and subcloning, it being possible for the sequences of the invention to be carried by vectors.

Isolated and/or purified nucleotide sequence fragment according to the invention will be understood as designating any nucleotide fragment of the genome of *Alicyclobacillus acidocaldarius*, and may include, by way of non-limiting example, a length of at least 8, 12, 20, 25, 50, 75, 100, 200, 300, 400, 500, 1000, or more, consecutive nucleotides of the sequence from which it originates.

Specific fragment of an isolated and/or purified nucleotide sequence according to the invention will be understood as designating any nucleotide fragment of the genome of *Alicyclobacillus acidocaldarius*, having, after alignment and comparison with the corresponding fragments of genomic sequences of *Alicyclobacillus acidocaldarius*, at least one nucleotide or base of different nature.

Homologous isolated and/or purified nucleotide sequence in the sense of the present invention is understood as meaning an isolated and/or purified nucleotide sequence having at least a percentage identity with the bases of a nucleotide sequence according to the invention of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%, this percentage being purely statistical and it being possible to distribute the differences between the two nucleotide sequences at random and over the whole of their length.

Specific homologous nucleotide sequence in the sense of the present invention is understood as meaning a homologous nucleotide sequence having at least one nucleotide sequence of a specific fragment, such as defined above. The "specific" homologous sequences can comprise, for example, the sequences corresponding to the genomic sequence or to the sequences of its fragments representative of variants of the genome of *Alicyclobacillus acidocaldarius*. These specific homologous sequences can thus correspond to variations linked to mutations within strains of *Alicyclobacillus acidocaldarius*, and especially correspond to truncations, substitutions, deletions and/or additions of at least one nucleotide. The homologous sequences can likewise correspond to variations linked to the degeneracy of the genetic code.

The term "degree or percentage of sequence homology" refers to "degree or percentage of sequence identity between two sequences after optimal alignment" as defined in the present application.

Two amino-acids or nucleotidic sequences are said to be "identical" if the sequence of amino-acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2:482 (1981), by the homology alignment algorithm of Neddleman and Wunsch, *J. Mol. Biol.* 48:443 (1970), by the search for similarity method of Pearson and Lipman, *Proc. Natl. Acad. Sci.* (U.S.A.) 85:2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would be used by one of skill in the art. The definition by itself does not need the help of any algorithm, the algorithms being helpful only to achieve the optimal alignments of sequences, rather than the calculation of sequence identity.

From the definition given above, it follows that there is a well-defined and only one value for the sequence identity between two compared sequences, which value corresponds to the value obtained for the best or optimal alignment.

In the BLAST N or BLAST P "BLAST 2 sequence," software, which is available at the website ncbi.nlm.nih.gov/gorf/bl2.html, and habitually used by the inventors and in general by the skilled person for comparing and determining the identity between two sequences, gap cost, which depends on the sequence length to be compared, is directly selected by the software (i.e., 11.2 for substitution matrix BLOSUM-62 for length>85).

Complementary nucleotide sequence of a sequence of the invention is understood as meaning any DNA whose nucleotides are complementary to those of the sequence of the invention, and whose orientation is reversed (antisense sequence).

Hybridization under conditions of stringency with a nucleotide sequence according to the invention is understood as meaning hybridization under conditions of temperature and ionic strength chosen in such a way that they allow the maintenance of the hybridization between two fragments of complementary DNA.

By way of illustration, conditions of great stringency of the hybridization step with the aim of defining the nucleotide fragments described above are advantageously the following.

The hybridization is carried out at a preferential temperature of 65° C. in the presence of SSC buffer, 1×SSC corresponding to 0.15 M NaCl and 0.05 M Na citrate. The washing steps, for example, can be the following: 2×SSC, at ambient temperature followed by two washes with 2×SSC, 0.5% SDS at 65° C.; 2×0.5×SSC, 0.5% SDS; at 65° C. for 10 minutes each.

The conditions of intermediate stringency, using, for example, a temperature of 42° C. in the presence of a 2×SSC buffer, or of less stringency, for example, a temperature of 37° C. in the presence of a 2×SSC buffer, respectively, require a globally less significant complementarity for the hybridization between the two sequences.

The stringent hybridization conditions described above for a polynucleotide with a size of approximately 350 bases will be adapted by a person skilled in the art for oligonucleotides of greater or smaller size, according to the teachings of Sambrook et al., 1989.

Among the isolated and/or purified nucleotide sequences according to the invention, are those that can be used as a primer or probe in methods allowing the homologous sequences according to the invention to be obtained, these methods, such as the polymerase chain reaction (PCR), nucleic acid cloning, and sequencing, being well known to a person skilled in the art.

Among the isolated and/or purified nucleotide sequences according to the invention, those are again preferred that can be used as a primer or probe in methods allowing the presence of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566, one of their fragments, or one of their variants such as defined below to be diagnosed.

The nucleotide sequence fragments according to the invention can be obtained, for example, by specific amplification, such as PCR, or after digestion with appropriate restriction enzymes of nucleotide sequences according to the invention, these methods in particular being described in the work of Sambrook et al., 1989. Such representative fragments can likewise be obtained by chemical synthesis according to methods well known to persons of ordinary skill in the art.

Modified nucleotide sequence will be understood as meaning any nucleotide sequence obtained by mutagenesis according to techniques well known to a person skilled in the art, and containing modifications with respect to the normal sequences according to the invention, for example, mutations in the regulatory and/or promoter sequences of polypeptide expression, especially leading to a modification of the rate of expression of the polypeptide or to a modulation of the replicative cycle.

Modified nucleotide sequence will likewise be understood as meaning any nucleotide sequence coding for a modified polypeptide, such as defined below.

The present invention relates to nucleotide sequence comprising isolated and/or purified nucleotide sequences of *Alicyclobacillus acidocaldarius*, characterized in that they are selected from the sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 or one of their fragments.

Embodiments of the invention likewise relate to isolated and/or purified nucleotide sequences characterized in that they comprise a nucleotide sequence selected from: a) at least one of a nucleotide sequence of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 or one of their fragments or one of their fragments; b) a nucleotide sequence of a specific fragment of a sequence such as defined in a); c) a homologous nucleotide sequence having at least 80% identity with a sequence such as defined in a) or b); d) a complementary nucleotide sequence or sequence of RNA corresponding to a sequence such as defined in a), b) or c); and e) a nucleotide sequence modified by a sequence such as defined in a), b), c) or d).

Among the isolated and/or purified nucleotide sequences according to the invention are the nucleotide sequences of SEQ ID NOS:13-17, 30-34, 47-51, 64-68, 81-85, 98-102, 115-119, 132-136, 149-153, 166-170, 183-187, 200-204, 217-221, 234-238, 251-255, 268-272, 285-289, 302-306, 319-323, 336-340, 353-357, 370-374, 387-391, 404-408, 421-425, 438-442, 455-459, 472-476, 489-493, 506-510, 523-527, 540-544, 557-561, 574-578, 591-595, 608-612, 625-629, 642-646, 659-663, 676-680, 693-697, 710-714, 727-731, 744-748, 761-765, 778-782, 795-799, 812-816, 829-833, 846-850, 863-867, 880-884, 897-901, 914-918, 931-935, 948-952, 965-969, 982-986, 999-1003, 1016-1020, 1033-1037, 1050-1054, 1067-1071, 1084-1088, 1101-1105, 1118-1122, 1135-1139, 1152-1156, 1169-1173, 1186-1190, 1203-1207, 1220-1224, 1237-1241, 1254-1258, 1271-1275, 1288-1292, 1305-1309, 1322-1326, 1339-1343, 1356-1360, 1373-1377, 1390-1394, 1407-1411, 1424-1428, 1441-1445, 1458-1462, 1475-1479, 1492-1496, 1509-1513, 1526-1530, 1543-1547, 1560-1564, and 1577-1581, or fragments thereof and any isolated and/or purified nucleotide sequences, which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the at least one of the sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 or fragments thereof. Such homologous sequences can comprise, for example, the sequences corresponding to the genomic sequences of *Alicyclobacillus acidocaldarius*. In the same manner, these specific homologous sequences can correspond to variations linked to mutations within strains of *Alicyclobacillus acidocaldarius* and especially correspond to truncations, substitutions, deletions and/or additions of at least one nucleotide. As will be apparent to one of ordinary skill in the art, such homologues are easily created and identified using conventional techniques and publicly available computer programs such as BLAST. Accordingly, each homologue referenced above should be considered as set forth herein and fully described.

Embodiments of the invention comprise the isolated and/or purified polypeptides coded for by a nucleotide sequence according to the invention, or fragments thereof, whose sequence is represented by a fragment. Amino acid sequences corresponding to the isolated and/or purified polypeptides that can be coded for according to one of the three possible reading frames of at least one of the sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566.

Embodiments of the invention likewise relate to the isolated and/or purified polypeptides, characterized in that they comprise a polypeptide selected from at least one of the amino acid sequences of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 or one of their fragments.

Among the isolated and/or purified polypeptides, according to embodiments of the invention, are the isolated and/or purified polypeptides of amino acid sequence SEQ ID NOS: 8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1215-1219, 1232-1236, 1249-1253, 1266-1270, 1283-1287, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, and 1572-1576, or fragments thereof or any other isolated and/or purified polypeptides that have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with at least one of the sequences of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 or fragments thereof. As will be apparent to one of ordinary skill in the art, such homologues are easily created and identified using conventional techniques and publicly available computer programs such as BLAST. Accordingly, each homologue referenced above should be considered as set forth herein and fully described.

Embodiments of the invention also relate to the polypeptides, characterized in that they comprise a polypeptide selected from: a) a specific fragment of at least 5 amino acids of a polypeptide of an amino acid sequence according to the invention; b) a polypeptide homologous to a polypeptide such as defined in a); c) a specific biologically active fragment of a polypeptide such as defined in a) or b); and d) a polypeptide modified by a polypeptide such as defined in a), b) or c).

In the present description, the terms polypeptide, peptide and protein are interchangeable.

In embodiments of the invention, the isolated and/or purified polypeptides according to the invention may be glycosylated, pegylated, and/or otherwise post-translationally modified. In further embodiments, glycosylation, pegylation, and/or other post-translational modifications may occur in vivo or in vitro and/or may be performed using chemical techniques. In additional embodiments, any glycosylation, pegylation and/or other post-translational modifications may be N-linked or O-linked.

In embodiments of the invention any one of the isolated and/or purified polypeptides according to the invention may be enzymatically or functionally active at temperatures at or above about 25, 30, 35, 40, 45, 50, 55, 60, 65, 70, 75, 80, 85, 90, and/or 95 degrees Celsius and/or may be enzymatically or functionally active at a pH at, below, and/or above 8, 7, 6, 5, 4, 3, 2, 1, and/or 0. In further embodiments of the invention, glycosylation, pegylation, and/or other post-translational modification may be required for the isolated and/or purified polypeptides according to the invention to be enzymatically or functionally active at a pH at or below 8, 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

Aspects of the invention relate to polypeptides that are isolated or obtained by purification from natural sources, or else obtained by genetic recombination, or alternatively by chemical synthesis and that they may thus contain unnatural amino acids, as will be described below.

A "polypeptide fragment" according to the embodiments of the invention is understood as designating a polypeptide containing at least 5 consecutive amino acids, preferably 10 consecutive amino acids or 15 consecutive amino acids.

In the present invention, a specific polypeptide fragment is understood as designating the consecutive polypeptide fragment coded for by a specific fragment nucleotide sequence according to the invention.

"Homologous polypeptide" will be understood as designating the polypeptides having, with respect to the natural polypeptide, certain modifications such as, in particular, a deletion, addition, or substitution of at least one amino acid, a truncation, a prolongation, a chimeric fusion, and/or a mutation. Among the homologous polypeptides, those are preferred whose amino acid sequence has at least 80% or 90%, homology with the sequences of amino acids of polypeptides according to the invention.

"Specific homologous polypeptide" will be understood as designating the homologous polypeptides such as defined above and having a specific fragment of polypeptide according to the invention.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following. As will be apparent to one of ordinary skill in the art, such substitutions are easily created and identified using standard molecular biology techniques and publicly available computer programs such as BLAST. Accordingly, each substitution referenced above should be considered as set forth herein and fully described. Examples of such substitutions in the amino acid sequences of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 may include those isolated and/or purified polypeptides of amino acid sequence SEQ ID NOS:8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1215-1219, 1232-1236, 1249-1253, 1266-1270, 1283-1287, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, and 1572-1576. These equivalent amino acids may be determined either by depending on their structural homology with the amino acids that they substitute, or on results of comparative tests of biological activity between the different polypeptides, which are capable of being carried out.

By way of non-limiting example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine, etc., the reverse substitutions naturally being envisageable under the same conditions.

In a further embodiment, substitutions are limited to substitutions in amino acids not conserved among other proteins that have similar identified enzymatic activity. For example, one of ordinary skill in the art may align proteins of the same function in similar organisms and determine which amino acids are generally conserved among proteins of that function. One example of a program that may be used to generate such alignments is available at the web site charite.de/bioinf/strap/ in conjunction with the databases provided by the NCBI. Examples of such polypeptides may include, but are not limited to, those found in amino acid sequence SEQ ID NOS:8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1215-1219, 1232-1236, 1249-1253, 1266-1270, 1283-1287, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, and 1572-1576.

Thus, according to one embodiment of the invention, substitutions or mutations may be made at positions that are generally conserved among proteins of that function. In a further embodiment, nucleic acid sequences may be mutated or substituted such that the amino acid they code for is unchanged (degenerate substitutions and/or mutations) and/or mutated or substituted such that any resulting amino acid substitutions or mutations are made at positions that are generally conserved among proteins of that function. Examples of such nucleic acid sequences may include, but are not limited to, those found in are the nucleotide sequences of SEQ ID NOS:13-17, 30-34, 47-51, 64-68, 81-85, 98-102, 115-119, 132-136, 149-153, 166-170, 183-187, 200-204, 217-221, 234-238, 251-255, 268-272, 285-289, 302-306, 319-323, 336-340, 353-357, 370-374, 387-391, 404-408, 421-425, 438-442, 455-459, 472-476, 489-493, 506-510, 523-527, 540-544, 557-561, 574-578, 591-595, 608-612, 625-629, 642-646, 659-663, 676-680, 693-697, 710-714, 727-731, 744-748, 761-765, 778-782, 795-799, 812-816, 829-833, 846-850, 863-867, 880-884, 897-901, 914-918, 931-935, 948-952, 965-969, 982-986, 999-1003, 1016-1020, 1033-1037, 1050-1054, 1067-1071, 1084-1088, 1101-1105, 1118-1122, 1135-1139, 1152-1156, 1169-1173, 1186-1190, 1203-1207, 1220-1224, 1237-1241, 1254-1258, 1271-1275, 1288-1292, 1305-1309, 1322-1326, 1339-1343, 1356-1360, 1373-1377, 1390-1394, 1407-1411, 1424-1428, 1441-1445, 1458-1462, 1475-1479, 1492-1496, 1509-1513, 1526-1530, 1543-1547, 1560-1564, 1577-1581 or fragments thereof.

The specific homologous polypeptides likewise correspond to polypeptides coded for by the specific homologous nucleotide sequences such as defined above and thus comprise in the present definition the polypeptides, which are mutated or correspond to variants that can exist in *Alicyclo*-

*bacillus acidocaldarius*, and that especially correspond to truncations, substitutions, deletions, and/or additions of at least one amino acid residue.

"Specific biologically active fragment of a polypeptide" according to an embodiment of the invention will be understood in particular as designating a specific polypeptide fragment, such as defined above, having at least one of the characteristics of polypeptides according to the invention. In certain embodiments the peptide is capable of behaving as at least one of the types of proteins outlined in Table 1.

The polypeptide fragments according to embodiments of the invention can correspond to isolated or purified fragments naturally present in *Alicyclobacillus acidocaldarius* or correspond to fragments that can be obtained by cleavage of the polypeptide by a proteolytic enzyme, such as trypsin or chymotrypsin or collagenase, or by a chemical reagent, such as cyanogen bromide (CNBr). Such polypeptide fragments can likewise just as easily be prepared by chemical synthesis, from hosts transformed by an expression vector according to the invention containing a nucleic acid allowing the expression of the fragments, placed under the control of appropriate regulation and/or expression elements.

"Modified polypeptide" of a polypeptide according to an embodiment of the invention is understood as designating a polypeptide obtained by genetic recombination or by chemical synthesis as will be described below, having at least one modification with respect to the normal sequence. These modifications may or may not be able to bear on amino acids at the origin of specificity, and/or of activity, or at the origin of the structural confolination, localization, and of the capacity of membrane insertion of the polypeptide according to the invention. It will thus be possible to create polypeptides of equivalent, increased, or decreased activity, and of equivalent, narrower, or wider specificity. Among the modified polypeptides, it is necessary to mention the polypeptides in which up to 5 or more amino acids can be modified, truncated at the N- or C-terminal end, or even deleted or added.

The methods allowing the modulations on eukaryotic or prokaryotic cells to be demonstrated are well known to a person of ordinary skill in the art. It is likewise well understood that it will be possible to use the nucleotide sequences coding for the modified polypeptides for the modulations, for example, through vectors according to the invention and described below.

The preceding modified polypeptides can be obtained by using combinatorial chemistry, in which it is possible to systematically vary parts of the polypeptide before testing them on models, cell cultures or microorganisms, for example, to select the compounds that are most active or have the properties sought.

Chemical synthesis likewise has the advantage of being able to use nonnatural amino acids, or nonpeptide bonds.

Thus, in order to improve the duration of life of the polypeptides according to the invention, it may be of interest to use nonnatural amino acids, for example, in D form, or else amino acid analogs, especially sulfur-containing forms, for example.

Finally, it will be possible to integrate the structure of the polypeptides according to the invention, its specific or modified homologous forms, into chemical structures of polypeptide type or others. Thus, it may be of interest to provide at the N- and C-terminal ends molecules not recognized by proteases.

The nucleotide sequences coding for a polypeptide according to the invention are likewise part of the invention.

The invention likewise relates to nucleotide sequences utilizable as a primer or probe, characterized in that the sequences are selected from the nucleotide sequences according to the invention.

It is well understood that the present invention, in various embodiments, likewise relates to specific polypeptides of *Alicyclobacillus acidocaldarius*, coded for by nucleotide sequences, capable of being obtained by purification from natural polypeptides, by genetic recombination or by chemical synthesis by procedures well known to a person skilled in the art and such as described in particular below. In the same manner, the labeled or unlabeled mono- or polyclonal antibodies directed against the specific polypeptides coded for by the nucleotide sequences are also encompassed by the invention.

Embodiments of the invention additionally relate to the use of a nucleotide sequence according to the invention as a primer or probe for the detection and/or the amplification of nucleic acid sequences.

The nucleotide sequences according to embodiments of the invention can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least 8 nucleotides, preferably of at least 12 nucleotides, and even more preferentially of at least 20 nucleotides.

Other amplification techniques of the target nucleic acid can be advantageously employed as alternatives to PCR.

The nucleotide sequences of the invention, in particular the primers according to the invention, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); and the TMA technique (Transcription Mediated Amplification).

The polynucleotides of the invention can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al., as well as by Stone et al. in 1996.

In the case where the target polynucleotide to be detected is possibly an RNA, for example, an mRNA, it will be possible to use, prior to the employment of an amplification reaction with the aid of at least one primer according to the invention or to the employment of a detection procedure with the aid of at least one probe of the invention, an enzyme of reverse transcriptase type in order to obtain a cDNA from the RNA contained in the biological sample. The cDNA obtained will thus serve as a target for the primer(s) or the probe(s) employed in the amplification or detection procedure according to the invention.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

Embodiments of the invention also comprise the nucleotide sequences utilizable as a probe or primer according to the invention, characterized in that they are labeled with a radioactive compound or with a nonradioactive compound.

The unlabeled nucleotide sequences can be used directly as probes or primers, although the sequences are generally labeled with a radioactive isotope ($^{32}P$, $^{35}S$, $^{3}H$, $^{125}I$) or with a nonradioactive molecule (biotin, acetylaminofluorene, digoxigenin, 5-bromodeoxyuridine, fluorescein) to obtain probes that are utilizable for numerous applications.

Examples of nonradioactive labeling of nucleotide sequences are described, for example, in French Patent No. 7810975 or by Urdea et al. or by Sanchez-Pescador et al. in 1988.

In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The invention, in various embodiments, likewise comprises the nucleotide sequences according to the invention, characterized in that they are immobilized on a support, covalently or noncovalently.

According to another advantageous mode of employing nucleotide sequences according to the invention, the latter can be used immobilized on a support and can thus serve to capture, by specific hybridization, the target nucleic acid obtained from the biological sample to be tested. If necessary, the solid support is separated from the sample and the hybridization complex formed between the capture probe and the target nucleic acid is then detected with the aid of a second probe, a so-called detection probe, labeled with an easily detectable element.

Another aspect of the present invention is a vector for the cloning and/or expression of a sequence, characterized in that it contains a nucleotide sequence according to the invention.

The vectors, according to the invention, characterized in that they contain the elements allowing the integration, expression and/or the secretion of the nucleotide sequences in a determined host cell, are likewise part of the invention.

The vector may then contain a promoter, signals of initiation and termination of translation, as well as appropriate regions of regulation of transcription. It may be able to be maintained stably in the host cell and can optionally have particular signals specifying the secretion of the translated protein. These different elements may be chosen as a function of the host cell used. To this end, the nucleotide sequences according to the invention may be inserted into autonomous replication vectors within the chosen host, or integrated vectors of the chosen host.

Such vectors will be prepared according to the methods currently used by a person skilled in the art, and it will be possible to introduce the clones resulting therefrom into an appropriate host by standard methods, such as, for example, lipofection, electroporation, and thermal shock.

The vectors according to the invention are, for example, vectors of plasmid or viral origin. One example of a vector for the expression of polypeptides of the invention is Baculovirus.

These vectors are useful for transforming host cells in order to clone or to express the nucleotide sequences of the invention.

The invention likewise comprises the host cells transformed by a vector according to the invention.

These cells can be obtained by the introduction into host cells of a nucleotide sequence inserted into a vector such as defined above, then the culturing of the cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as plants cells, such as *Arabidopsis* sp., and animal cells, in particular the cultures of mammalian cells (Edwards and Aruffo, 1993), for example, Chinese hamster ovary (CHO) cells, but likewise the cells of insects in which it is possible to use procedures employing baculoviruses, for example, Sf9 insect cells (Luckow, 1993).

Embodiments of the invention likewise relate to organisms comprising one of the transformed cells according to the invention.

The obtainment of transgenic organisms, according to the invention, of expressing one or more of the genes of *Alicyclobacillus acidocaldarius* or part of the genes may be carried out in, for example, rats, mice, or rabbits according to methods well known to a person skilled in the art, such as by viral or nonviral transfections. It will be possible to obtain the transgenic organisms expressing one or more of the genes by transfection of multiple copies of the genes under the control of a strong promoter of ubiquitous nature, or selective for one type of tissue. It will likewise be possible to obtain the transgenic organisms by homologous recombination in embryonic cell strains, transfer of these cell strains to embryos, selection of the affected chimeras at the level of the reproductive lines, and growth of the chimeras.

The transformed cells, as well as the transgenic organisms according to the invention, are utilizable in procedures for preparation of recombinant polypeptides.

It is today possible to produce recombinant polypeptides in relatively large quantity by genetic engineering using the cells transformed by expression vectors according to the invention or using transgenic organisms according to the invention.

The procedures for preparation of a polypeptide of the invention in recombinant form, characterized in that they employ a vector and/or a cell transformed by a vector according to the invention and/or a transgenic organism comprising one of the transformed cells according to the invention are themselves comprised in the present invention.

As used herein, "transformation" and "transformed" relate to the introduction of nucleic acids into a cell, whether prokaryotic or eukaryotic. Further, "transformation" and "transformed," as used herein, need not relate to growth control or growth deregulation.

Among the procedures for preparation of a polypeptide of the invention in recombinant form, the preparation procedures employing a vector, and/or a cell transformed by the vector and/or a transgenic organism comprising one of the transformed cells, containing a nucleotide sequence according to the invention coding for a polypeptide of *Alicyclobacillus acidocaldarius*.

A variant according to the invention may consist of producing a recombinant polypeptide fused to a "carrier" protein (chimeric protein). The advantage of this system is that it may allow stabilization of and/or a decrease in the proteolysis of the recombinant product, an increase in the solubility in the course of renaturation in vitro and/or a simplification of the purification when the fusion partner has an affinity for a specific ligand.

More particularly, the invention relates to a procedure for preparation of a polypeptide of the invention comprising the following steps: a) culture of transformed cells under conditions allowing the expression of a recombinant polypeptide of a nucleotide sequence according to the invention; b) if need be, recovery of the recombinant polypeptide.

When the procedure for preparation of a polypeptide of the invention employs a transgenic organism according to the invention, the recombinant polypeptide is then extracted from the organism.

The invention also relates to a polypeptide that is capable of being obtained by a procedure of the invention such as described previously.

The invention also comprises a procedure for preparation of a synthetic polypeptide, characterized in that it uses a sequence of amino acids of polypeptides according to the invention.

The invention likewise relates to a synthetic polypeptide obtained by a procedure according to the invention.

The polypeptides according to the invention can likewise be prepared by techniques that are conventional in the field of the synthesis of peptides. This synthesis can be carried out in homogeneous solution or in solid phase.

For example, recourse can be made to the technique of synthesis in an homogeneous solution described by Houben-Weyl in 1974.

This method of synthesis consists in successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

Recourse may also be made to the technique described by Merrifield.

To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids that are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The invention additionally relates to hybrid polypeptides having at least one polypeptide according to the invention, and a sequence of a polypeptide capable of inducing an immune response in man or animals.

Advantageously, the antigenic determinant is such that it is capable of inducing a humoral and/or cellular response.

It will be possible for such a determinant to comprise a polypeptide according to the invention in glycosylated, pegylated, and/or otherwise post-translationally modified form used with a view to obtaining immunogenic compositions capable of inducing the synthesis of antibodies directed against multiple epitopes.

These hybrid molecules can be formed, in part, of a polypeptide carrier molecule or of fragments thereof according to the invention, associated with a possibly immunogenic part, in particular, an epitope of the diphtheria toxin, the tetanus toxin, a surface antigen of the hepatitis B virus (Patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984.

The hybrid nucleotide sequences coding for a hybrid polypeptide as well as the hybrid polypeptides according to the invention characterized in that they are recombinant polypeptides obtained by the expression of the hybrid nucleotide sequences are likewise part of the invention.

The invention likewise comprises the vectors characterized in that they contain one of the hybrid nucleotide sequences. The host cells transformed by the vectors, the transgenic organisms comprising one of the transformed cells as well as the procedures for preparation of recombinant polypeptides using the vectors, the transformed cells and/or the transgenic organisms are, of course, likewise part of the invention.

The polypeptides according to the invention, the antibodies according to the invention described below and the nucleotide sequences according to the invention can advantageously be employed in procedures for the detection and/or identification of *Alicyclobacillus acidocaldarius*, in a sample capable of containing them. These procedures, according to the specificity of the polypeptides, the antibodies and the nucleotide sequences according to the invention that will be used, will in particular be able to detect and/or to identify *Alicyclobacillus acidocaldarius*.

The polypeptides according to the invention can advantageously be employed in a procedure for the detection and/or the identification of *Alicyclobacillus acidocaldarius* in a sample capable of containing them, characterized in that it comprises the following steps: a) contacting of this sample with a polypeptide or one of its fragments according to the invention (under conditions allowing an immunological reaction between the polypeptide and the antibodies possibly present in the biological sample); and b) demonstration of the antigen-antibody complexes possibly formed.

Any conventional procedure can be employed for carrying out such a detection of the antigen-antibody complexes possibly formed.

By way of non-limiting example, one method brings into play immunoenzymatic processes according to the ELISA technique, by immunofluorescence, or radioimmunological processes (RIA) or their equivalent.

Thus, the invention likewise relates to the polypeptides according to the invention, labeled with the aid of an adequate label, such as, of the enzymatic, fluorescent or radioactive type.

Such methods comprise, for example, the following acts: deposition of determined quantities of a polypeptide composition according to the invention in the wells of a microtiter plate, introduction into the wells of increasing dilutions of serum, or of a biological sample other than that defined previously, having to be analyzed, incubation of the wells of the microtiter plate, introduction into the wells of the microtiter plate of labeled antibodies directed against pig immunoglobulins, the labeling of these antibodies having been carried out with the aid of an enzyme selected from those that are capable of hydrolyzing a substrate by modifying the absorption of the radiation of the latter, at least at a determined wavelength, for example at 550 nm, detection, by comparison with a control test, of the quantity of hydrolyzed substrate.

The polypeptides according to the invention allow monoclonal or polyclonal antibodies to be prepared, which are characterized in that they specifically recognize the polypeptides according to the invention. It will advantageously be possible to prepare the monoclonal antibodies from hybridomas according to the technique described by Kohler and Milstein in 1975. It will be possible to prepare the polyclonal antibodies, for example, by immunization of an animal, in particular a mouse, with a polypeptide or a DNA, according to the invention, associated with an adjuvant of the immune response, and then purification of the specific antibodies contained in the serum of the immunized animals on an affinity column on which the polypeptide, which has served as an antigen, has previously been immobilized. The polyclonal antibodies according to the invention can also be prepared by purification, on an affinity column on which a polypeptide according to the invention has previously been immobilized, of the antibodies contained in the serum of an animal immunologically challenged by *Alicyclobacillus acidocaldarius*, or a polypeptide or fragment according to the invention.

The invention likewise relates to mono- or polyclonal antibodies or their fragments, or chimeric antibodies, characterized in that they are capable of specifically recognizing a polypeptide according to the invention.

It will likewise be possible for the antibodies of the invention to be labeled in the same manner as described previously for the nucleic probes of the invention, such as a labeling of enzymatic, fluorescent or radioactive type.

The invention is additionally directed at a procedure for the detection and/or identification of *Alicyclobacillus acidocaldarius* in a sample, characterized in that it comprises the following steps: a) contacting of the sample with a mono- or polyclonal antibody according to the invention (under conditions allowing an immunological reaction between the antibodies and the polypeptides of *Alicyclobacillus acidocaldarius* possibly present in the biological sample); and b) demonstration of the antigen-antibody complex possibly formed.

The present invention likewise relates to a procedure for the detection and/or the identification of *Alicyclobacillus acidocaldarius* in a sample, characterized in that it employs a nucleotide sequence according to the invention.

More particularly, the invention relates to a procedure for the detection and/or the identification of *Alicyclobacillus acidocaldarius* in a sample, characterized in that it contains the following steps: a) if need be, isolation of the DNA from the sample to be analyzed; b) specific amplification of the DNA of the sample with the aid of at least one primer, or a pair of primers, according to the invention; and c) demonstration of the amplification products.

These can be detected, for example, by the technique of molecular hybridization utilizing a nucleic probe according to the invention. This probe will advantageously be labeled with a nonradioactive (cold probe) or radioactive isotope.

For the purposes of the present invention, "DNA of the biological sample" or "DNA contained in the biological sample" will be understood as meaning either the DNA present in the biological sample considered, or possibly the cDNA obtained after the action of an enzyme of reverse transcriptase type on the RNA present in the biological sample.

A further embodiment of the invention comprises a method, characterized in that it comprises the following acts: a) contacting of a nucleotide probe according to the invention with a biological sample, the DNA contained in the biological sample having, if need be, previously been made accessible to hybridization under conditions allowing the hybridization of the nucleotide probe with the DNA of the sample; and b) demonstration of the hybrid formed between the nucleotide probe and the DNA of the biological sample.

The present invention also relates to a procedure according to the invention, characterized in that it comprises the following acts: a) contacting of a nucleotide probe immobilized on a support according to the invention with a biological sample, the DNA of the sample having, if need be, previously been made accessible to hybridization, under conditions allowing the hybridization of the nucleotide probe with the DNA of the sample; b) contacting of the hybrid formed between the nucleotide probe immobilized on a support and the DNA contained in the biological sample, if need be, after elimination of the DNA of the biological sample that has not hybridized with the nucleotide probe, with a nucleotide probe labeled according to the invention; c) demonstration of the novel hybrid formed in act b).

According to an advantageous embodiment of the procedure for detection and/or identification defined previously, this is characterized in that, prior to act a), the DNA of the biological sample is first amplified with the aid of at least one primer according to the invention.

Embodiments of methods include methods of altering secondary metabolism in a cell, the methods comprising providing a recombinant, purified, and/or isolated nucleotide sequence comprising a nucleotide sequence selected from the group consisting of a nucleotide sequence having at least 90% sequence identity to at least one of the sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 and/or a recombinant, purified, and/or isolated polypeptide selected from the group consisting of a polypeptide having at least 90% sequence identity to at least one of the sequences of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 to the cell.

Further embodiments of methods include placing a cell producing or encoding a recombinant, purified, and/or isolated nucleotide sequence comprising a nucleotide sequence selected from the group consisting of a nucleotide sequence having at least 90% sequence identity to at least one of the sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 and/or a recombinant, purified, and/or isolated polypeptide selected from the group consisting of a polypeptide having at least 90% sequence identity to at least one of the sequences of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 in an environment comprising temperatures at or above about 25, 30, 35, 40, 45, 50, 55, 60, 65, 70, 75, 80, 85, 90, and/or 95 degrees Celsius and/or a pH at, below, and/or above 8, 7, 6, 5, 4, 3, 2, 1, and/or 0.

The present invention provides cells that have been genetically manipulated to have an altered capacity to produce expressed proteins. In particular, the present invention relates to Gram-positive microorganisms, such as *Bacillus* species having enhanced expression of a protein of interest, wherein one or more chromosomal genes have been inactivated, and/or wherein one or more chromosomal genes have been deleted from the *Bacillus* chromosome. In some further embodiments, one or more indigenous chromosomal regions have been deleted from a corresponding wild-type *Bacillus* host chromosome. In further embodiments, the *Bacillus* is an *Alicyclobacillus* sp. or *Alicyclobacillus acidocaldarius*.

Additional embodiments, include methods of modulating metabolism at temperatures at or above about 25, 30, 35, 40, 45, 50, 55, 60, 65, 70, 75, 80, 85, 90, and/or 95 degrees Celsius and/or at a pH at, below, and/or above 8, 7, 6, 5, 4, 3, 2, 1, and/or 0 via providing a recombinant, purified, and/or isolated nucleotide sequence comprising a nucleotide sequence selected from the group consisting of a nucleotide sequence having at least 90% sequence identity to at least one of the sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 and/or a recombinant, purified, and/or isolated polypeptide selected from the group consisting of a polypeptide having at least 90% sequence identity to at least one of the sequences of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 to a cell.

In embodiments of the invention any one of the isolated and/or purified polypeptides according to the invention may be enzymatically or functionally active at temperatures at or above about 25, 30, 35, 40, 45, 50, 55, 60, 65, 70, 75, 80, 85, 90, and/or 95 degrees Celsius and/or may be enzymatically or functionally active at a pH at, below, and/or above 8, 7, 6, 5, 4, 3, 2, 1, and/or 0. In further embodiments of the invention, glycosylation, pegylation, and/or other post-translational modification may be required for the isolated and/or purified polypeptides according to the invention to be enzymatically or functionally active at a pH at or below 8, 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

The invention is described in additional detail in the following illustrative examples. Although the examples may represent only selected embodiments of the invention, it should be understood that the following examples are illustrative and not limiting.

EXAMPLES

Example 1

Modulating or Altering Metabolism Using Nucleotide and Amino Acid Sequences from *Alicyclobacillus acidocaldarius*

Provided in SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 are a nucleotide sequence isolated from *Alicyclobacillus acidocaldarius* and coding for the polypeptides of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565, respectively. The nucleotide sequences of SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOS:2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, and 1566 produce the polypeptides of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565. The polypeptides of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 are then isolated and/or purified. The isolated and/or purified polypeptides of SEQ ID NOS:1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 are then each demonstrated to have one or more of the activities provided in Table 1.

The isolated and/or purified polypeptides of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, and 1565 are demonstrated to have activity as at least one of a (S)-2-hydroxy-acid oxidase, [acyl-carrier-protein] S-malonyltransferase, 1,3-propanediol Dehydrogenase, 2-isopropylmalate Synthase, 3-hydroxybutyryl-CoA dehydratase, 3-isopropylmalate Dehydratase, 3-isopropylmalate Dehydrogenase, 3-oxoacid CoA-transferase, 8-amino-7-oxononanoate Synthase, Acetaldehyde dehydrogenase (acetylating), Acetate-CoA ligase, Acetolactate synthase, Acetyl-CoA C-acetyltransferase, Aconitate hydratase, Alcohol dehydrogenase, Alcohol dehydrogenase (NADP+), Aldehyde dehydrogenase, Aldehyde dehydrogenase (NAD+), ATP phosphoribosyltransferase, ATP synthase alpha chain, ATP synthase B chain, ATP synthase beta chain, ATP synthase C chain, ATP synthase epsilon chain, ATP synthase gamma chain, Biotin synthase, Branched-chain-amino-acid transaminase, Butyryl-CoA dehydrogenase, Citrate (Si)-synthase, Dethiobiotin synthase, Diaminopimelate decarboxylase, Diaminopimelate epimerase, Dihydrodipicolinate reductase, Dihydrodipicolinate synthase, Dihydrolipoyl dehydrogenase, Dihydroxy-acid dehydratase, Enoyl-CoA hydratase, FdhD protein (fdsC), Formate dehydrogenase, Glycerate kinase, Glycine hydroxymethyltransferase, Isocitrate lyase, Lactaldehyde reductase, Lactate 2-monooxygenase, L-lactate dehydrogenase, Malate dehydrogenase, Malate dehydrogenase (acceptor), Malate dehydrogenase (oxaloacetate-decarboxylating), Malate synthase, Malonate-semialdehyde dehydrogenase (acetylating), Methylmalonate-semialdehyde dehydrogenase (acylating), N-acetyl-diaminopimelate deacetylase, Oxoglutarate dehydrogenase (succinyl-transferring), Phosphoenolpyruvate carboxylase, Phosphoglycerate dehydrogenase, Phosphoribosylanthranilate isomerase, Pyruvate dehydrogenase (acetyl-transferring), Pyruvate, phosphate dikinase, Succinate dehydrogenase cytochrome b558 subunit, Succinate dehydrogenase flavoprotein subunit, Succinate dehydrogenase iron-sulfur protein, and Succinate-CoA ligase (ADP-forming).

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and that fall within the limits of the appended claims and their legal equivalents.

All references, including publications, patents, and patent applications, cited herein are hereby incorporated by reference to the same extent as if each reference were individually and specifically indicated to be incorporated by reference and were set forth in its entirety herein.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and that fall within the limits of the appended claims and their legal equivalents.

BIBLIOGRAPHIC REFERENCES

Barany, F., 1991, PNAS USA, 88:189-193.
Buckholz, R. G., 1993, Yeast systems for the expression of heterologous gene products. Curr. Op. Biotechnology 4:538-542.
Burg, J. L. et al., 1996, Mol. and Cell. Probes, 10:257-271.
Chu, B. C. F. et al., 1986, NAR, 14:5591-5603.
Duck, P. et al., 1990, Biotechniques, 9:142-147.
Edwards, C. P., and Aruffo, A., 1993, Current applications of COS cell based transient expression systems, Curr. Op. Biotechnology 4:558-563.
Guateli, J. C. et al., 1990, PNAS USA, 87:1874-1878.
Houben-Weyl, 1974, in Methoden der Organischen Chemie, E. Wunsch Ed., Volume 15-I and 15-II, Thieme, Stuttgart.
Innis, M. A. et al., 1990, in PCR Protocols, A guide to Methods and Applications, San Diego, Academic Press.
Kievitis, T. et al., 1991, J. Virol. Methods, 35:273-286.
Köhler, G. et al., 1975, Nature, 256(5517):495-497.
Kwoh, D. Y. et al., 1989, PNAS USA, 86:1173-1177.
Luckow, V. A., 1993, Baculovirus systems for the expression of human gene products. Curr. Op. Biotechnology 4:564-572.
Matthews, J. A. et al., 1988, Anal. Biochem., 169:1-25.
Merrifield, R. D., 1966, J. Am. Chem. Soc., 88(21):5051-5052.
Miele, E. A. et al., 1983, J. Mol. Biol., 171:281-295.
Olins, P. O., and Lee, S. C., 1993, Recent advances in heterologous gene expression in E. coli. Curr. Op. Biotechnology 4:520-525.
Rolfs, A. et al., 1991, In PCR Topics, Usage of Polymerase Chain reaction in Genetic and Infectious Disease, Berlin: Springer-Verlag.
Sambrook, J. et al., 1989, In Molecular Cloning: A Laboratory Manual. Cold Spring Harbor, N.Y.: Cold Spring Harbor Laboratory Press.
Sanchez-Pescador, R., 1988, J. Clin. Microbiol., 26(10): 1934-1938.
Segev D., 1992, in "Non-radioactive Labeling and Detection of Biomolecules," Kessler C. Springer-Verlag, Berlin, New-York: 197-205.
Urdea, M. S., 1988, Nucleic Acids Research, 11:4937-4957.
Walker, G. T. et al., 1992, NAR 20:1691-1696.
Walker, G. T. et al., 1992, PNAS USA, 89:392-396.
White, B. A. et al., 1997, Methods in Molecular Biology, 67, Humana Press, Totowa, N.J.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09222094B2). An electronic copy of the "Sequence Listing" will also be available from the USPTO upon request and payment of the fee set forth in 37 CFR 1.19(b)(3).

What is claimed is:

1. An expression vector comprising an isolated polynucleotide encoding a polypeptide having at least 90% sequence identity to SEQ ID No. 392.

2. The expression vector of claim 1, wherein the expression vector comprises a polynucleotide having at least 90% identity to SEQ ID No. 393.

3. The expression vector of claim 1, wherein the encoded polypeptide has Acetyl-CoA C-acetyltransferase enzymatic activity.

4. An expression vector comprising an isolated polynucleotide encoding a polypeptide having at least 95% sequence identity to SEQ ID No. 392.

5. The expression vector of claim 4, wherein the encoded polypeptide has Acetyl-CoA C-acetyltransferase enzymatic activity.

6. The expression vector of claim 4, wherein the expression vector comprises a polynucleotide having at least 95% identity to SEQ ID No. 393.

7. A method of modulating or altering metabolism in a cell, the method comprising:
providing the expression vector of claim 3 to the cell and expressing the encoded polypeptide in the cell.

8. The method according to claim 7, further comprising glycosylating, or otherwise post-translationally modifying the encoded peptide in the cell.

* * * * *